US008568363B2

(12) United States Patent
Boyden et al.

(10) Patent No.: US 8,568,363 B2
(45) Date of Patent: Oct. 29, 2013

(54) FROZEN COMPOSITIONS AND METHODS FOR PIERCING A SUBSTRATE

(75) Inventors: Edward S. Boyden, Cambridge, MA (US); Daniel B. Cook, Seattle, WA (US); Roderick A. Hyde, Redmond, WA (US); Eric C. Leuthardt, St. Louis, MO (US); Nathan P. Myhrvold, Bellevue, WA (US); Elizabeth A. Sweeney, Seattle, WA (US); Lowell L. Wood, Jr., Bellevue, WA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 512 days.

(21) Appl. No.: 12/586,072

(22) Filed: Sep. 15, 2009

(65) Prior Publication Data
US 2010/0143243 A1 Jun. 10, 2010

Related U.S. Application Data

(63) Continuation-in-part of application No. 12/290,671, filed on Oct. 31, 2008, and a continuation-in-part of application No. 12/290,683, filed on Oct. 31, 2008, and a continuation-in-part of application No. 12/290,685, filed on Oct. 31, 2008, and a continuation-in-part of application No. 12/290,686, filed on Oct. 31, 2008, and a continuation-in-part of application No. 12/290,690, filed on Oct. 31, 2008, and a continuation-in-part of application No. 12/290,691, filed on Oct. 31, 2008, and a continuation-in-part of application No. 12/290,684, filed on Oct. 31, 2008, and a continuation-in-part of application No. 12/290,670, filed on Oct. 31, 2008, and a continuation-in-part of application No. 12/290,664, filed on Oct. 31, 2008, and a continuation-in-part of application No. 12/290,659, filed on Oct. 31, 2008, now Pat. No. 8,409,376, and a continuation-in-part of application No. 12/290,658, filed on Oct. 31, 2008, and a continuation-in-part of application No. 12/290,665, filed on Oct. 31, 2008, and a continuation-in-part of application No. 12/290,677, filed on Oct. 31, 2008, and a continuation-in-part of application No. 12/290,687, filed on Oct. 31, 2008, and a continuation-in-part of application No. 12/290,676, filed on Oct. 31, 2008, and a continuation-in-part of application No. 12/383,264, filed on Mar. 20, 2009, now Pat. No. 8,545,856, and a continuation-in-part of application No. 12/383,263, filed on Mar. 20, 2009, and a continuation-in-part of application No. 12/383,260, filed on Mar. 20, 2009, and a continuation-in-part of application No. 12/383,265, filed on Mar. 20, 2009, and a continuation-in-part of application No. 12/383,851, filed on Mar. 27, 2009, and a continuation-in-part of application No. 12/383,863, filed on Mar. 27, 2009, and a continuation-in-part of application No. 12/383,821, filed on Mar. 27, 2009, now Pat. No. 8,545,857, and a continuation-in-part of application No. 12/383,829, filed on Mar. 27, 2009, and a continuation-in-part of application No. 12/384,202, filed on Mar. 31, 2009, and a continuation-in-part of application No. 12/384,201, filed on Mar. 31, 2009, and a continuation-in-part of application No. 12/384,212, filed on Mar. 31, 2009, now Pat. No. 8,545,806, and a continuation-in-part of application No. 12/384,215, filed on Mar. 31, 2009, and a continuation-in-part of application No. 12/384,216, filed on Mar. 31, 2009, and a continuation-in-part of application No. 12/384,218, filed on Mar. 31, 2009, and a continuation-in-part of application No. 12/384,214, filed on Mar. 31, 2009, and a continuation-in-part of application No. 12/586,076, filed on Sep. 15, 2009, and a continuation-in-part of application No. 12/586,074, filed on Sep. 15, 2009, and a continuation-in-part of application No. 12/586,070, filed on Sep. 15, 2009, and a continuation-in-part of application No. 12/586,073, filed on Sep. 15, 2009, and a continuation-in-part of application No. 12/586,077, filed on Sep. 15, 2009, and a continuation-in-part of application No. 12/586,075, filed on Sep. 15, 2009, and a continuation-in-part of application No. 12/586,071, filed on Sep. 15, 2009.

(51) Int. Cl.
*A61M 5/00* (2006.01)
*A61K 9/14* (2006.01)
*A61K 9/00* (2006.01)

(52) U.S. Cl.
USPC .............. 604/173; 424/489; 424/400; 604/20

(58) Field of Classification Search
None
See application file for complete search history.

(56) References Cited

U.S. PATENT DOCUMENTS

| | | | |
|---|---|---|---|
| 1,433,628 | A | 10/1922 | Knaust |
| 2,182,952 | A | 12/1939 | Todd et al. |

(Continued)

FOREIGN PATENT DOCUMENTS

| | | |
|---|---|---|
| CA | 992756 A | 7/1976 |
| GB | 2439092 A | 12/2007 |

(Continued)

OTHER PUBLICATIONS

RxList, "Nystatin", accessed from http://www.rxlist.com/nystatin-and-triamcinolone-acetonide-drug.htm, accessed on Mar. 10, 2012, pp. 1-3.*

(Continued)

*Primary Examiner* — Michael G Hartley
*Assistant Examiner* — Lance E Rider

(57) ABSTRACT

Certain embodiments disclosed herein relate to compositions, methods, devices, systems, and products regarding frozen particles. In certain embodiments, the frozen particles include materials at low temperatures. In certain embodiments, the frozen particles provide vehicles for delivery of particular agents. In certain embodiments, the frozen particles are administered to at least one biological tissue.

25 Claims, 218 Drawing Sheets

(56) References Cited

U.S. PATENT DOCUMENTS

| | | |
|---|---|---|
| 3,089,775 A | 5/1963 | Lindall |
| 3,276,880 A | 10/1966 | Torr |
| 3,491,170 A | 1/1970 | Roe, Jr. |
| 3,500,242 A | 3/1970 | Young |
| 3,551,535 A | 12/1970 | Henderson et al. |
| 3,733,158 A | 5/1973 | Ruekberg |
| 3,787,302 A | 1/1974 | Ijichi et al. |
| 3,808,097 A | 4/1974 | Fowler et al. |
| 3,868,997 A | 3/1975 | Pogers |
| 3,889,002 A | 6/1975 | Clausi et al. |
| 3,911,601 A | 10/1975 | Maheu |
| 3,914,441 A | 10/1975 | Finney et al. |
| 4,016,264 A | 4/1977 | Clark |
| 4,102,765 A | 7/1978 | Fey et al. |
| 4,146,029 A | 3/1979 | Ellinwood, Jr. |
| 4,152,231 A | 5/1979 | St. Clair et al. |
| 4,207,360 A | 6/1980 | Padovani |
| 4,297,379 A | 10/1981 | Topalian et al. |
| 4,312,850 A | 1/1982 | Dietl et al. |
| 4,394,370 A | 7/1983 | Jefferies |
| 4,442,082 A | 4/1984 | Sanjurjo |
| 4,512,160 A | 4/1985 | Arias Mas |
| 4,590,043 A | 5/1986 | Sanjurjo |
| 4,603,051 A | 7/1986 | Rubenstein et al. |
| 4,637,905 A | 1/1987 | Gardner |
| 4,704,873 A | 11/1987 | Imaike et al. |
| 4,712,920 A | 12/1987 | Ames et al. |
| 4,861,714 A | 8/1989 | Dean, Jr. et al. |
| 4,907,415 A | 3/1990 | Stewart, Jr. et al. |
| 4,921,720 A | 5/1990 | Davis |
| 4,951,197 A | 8/1990 | Mellinger |
| 4,958,014 A | 9/1990 | Shirokaze |
| 4,962,091 A | 10/1990 | Eppstein et al. |
| 4,981,625 A | 1/1991 | Rhim et al. |
| 5,006,338 A | 4/1991 | Luenemann |
| 5,008,116 A | 4/1991 | Cahn |
| 5,049,328 A | 9/1991 | Meyer et al. |
| 5,072,596 A | 12/1991 | Gilbertson et al. |
| 5,090,208 A | 2/1992 | Aono et al. |
| 5,102,983 A | 4/1992 | Kennedy |
| 5,114,957 A | 5/1992 | Hendler et al. |
| 5,126,156 A | 6/1992 | Jones |
| 5,132,101 A | 7/1992 | Vogel et al. |
| 5,158,760 A | 10/1992 | Phillips et al. |
| 5,216,890 A | 6/1993 | Ban et al. |
| 5,219,746 A | 6/1993 | Brinegar et al. |
| 5,231,015 A | 7/1993 | Cummins et al. |
| 5,283,985 A | 2/1994 | Browning |
| 5,283,989 A | 2/1994 | Hisasue et al. |
| 5,307,640 A | 5/1994 | Fawzy et al. |
| 5,315,793 A | 5/1994 | Peterson et al. |
| 5,328,517 A | 7/1994 | Cates et al. |
| 5,341,608 A | 8/1994 | Mains, Jr. |
| 5,352,673 A | 10/1994 | Dennis |
| 5,365,699 A | 11/1994 | Armstrong et al. |
| 5,375,432 A | 12/1994 | Cur |
| 5,390,450 A | 2/1995 | Goenka |
| 5,394,705 A | 3/1995 | Torii et al. |
| 5,433,654 A | 7/1995 | Clark, Jr. et al. |
| 5,436,039 A | 7/1995 | Miura et al. |
| 5,438,071 A | 8/1995 | Clauss et al. |
| 5,444,986 A | 8/1995 | Hino |
| 5,599,223 A | 2/1997 | Mains Jr. |
| 5,631,023 A | 5/1997 | Kearney et al. |
| 5,632,150 A | 5/1997 | Henzler |
| 5,656,317 A | 8/1997 | Smits et al. |
| 5,690,940 A | 11/1997 | Joo |
| 5,707,667 A | 1/1998 | Galt et al. |
| 5,725,579 A | 3/1998 | Fages et al. |
| 5,745,377 A | 4/1998 | Power et al. |
| 5,753,234 A | 5/1998 | Lee et al. |
| 5,764,493 A | 6/1998 | Liao |
| 5,785,581 A | 7/1998 | Settles |
| 5,877,819 A | 3/1999 | Branson |
| 5,883,078 A | 3/1999 | Seelich et al. |
| 5,931,721 A | 8/1999 | Rose et al. |
| 5,954,640 A | 9/1999 | Szabo |
| 5,962,018 A | 10/1999 | Curtis et al. |
| 5,976,505 A | 11/1999 | Henderson |
| 6,080,329 A | 6/2000 | Dobry |
| 6,092,235 A | 7/2000 | Santa Cruz et al. |
| 6,129,290 A | 10/2000 | Nikkanen |
| 6,130,206 A | 10/2000 | Carter |
| 6,192,693 B1 | 2/2001 | Kloppenberg et al. |
| 6,203,406 B1 | 3/2001 | Rose et al. |
| 6,241,704 B1 | 6/2001 | Peterson et al. |
| 6,248,063 B1 | 6/2001 | Barnhill et al. |
| 6,270,723 B1 | 8/2001 | Laugharn, Jr. et al. |
| 6,284,283 B1 | 9/2001 | Costantino et al. |
| 6,311,639 B1 | 11/2001 | Stickney |
| 6,349,549 B1 | 2/2002 | Angus et al. |
| 6,350,185 B1 | 2/2002 | Robins et al. |
| 6,366,206 B1 | 4/2002 | Ishikawa et al. |
| 6,379,324 B1 | 4/2002 | Gartstein et al. |
| 6,383,329 B1 | 5/2002 | Agarwala et al. |
| 6,436,422 B1 | 8/2002 | Trogolo et al. |
| 6,464,570 B1 | 10/2002 | Shaw et al. |
| 6,464,999 B1 | 10/2002 | Huo et al. |
| 6,500,187 B1 * | 12/2002 | Petersen ............... 606/167 |
| 6,569,458 B1 | 5/2003 | Gombotz et al. |
| 6,623,457 B1 | 9/2003 | Rosenberg |
| 6,659,844 B2 | 12/2003 | Shaw |
| 6,678,669 B2 | 1/2004 | Lapointe et al. |
| 6,695,686 B1 | 2/2004 | Frohlich et al. |
| 6,705,194 B2 | 3/2004 | Geskin et al. |
| 6,712,237 B2 | 3/2004 | Medina et al. |
| 6,713,083 B1 | 3/2004 | McGregor et al. |
| 6,726,693 B2 | 4/2004 | Weber et al. |
| 6,732,424 B2 | 5/2004 | Nadicksbernd |
| 6,764,493 B1 * | 7/2004 | Weber et al. ............ 606/131 |
| 6,807,717 B2 | 10/2004 | Daehn |
| 6,838,089 B1 | 1/2005 | Carlsson et al. |
| 6,845,631 B1 | 1/2005 | Hallin et al. |
| 6,875,984 B2 | 4/2005 | Kakibayashi et al. |
| 6,991,515 B2 | 1/2006 | Akedo |
| 7,033,249 B2 | 4/2006 | Spalteholz et al. |
| 7,040,962 B2 | 5/2006 | Makino et al. |
| 7,075,658 B2 | 7/2006 | Izatt et al. |
| 7,140,954 B2 | 11/2006 | Johnson et al. |
| 7,143,967 B2 | 12/2006 | Heinrich et al. |
| 7,284,390 B2 | 10/2007 | Van Meter et al. |
| 7,350,374 B1 | 4/2008 | Tashlitsky |
| 7,421,872 B2 | 9/2008 | Indlekofer |
| 7,442,112 B2 | 10/2008 | Yoon |
| 7,547,292 B2 | 6/2009 | Sheldrake et al. |
| 7,666,778 B2 | 2/2010 | Young |
| 7,917,298 B1 | 3/2011 | Scher et al. |
| 7,922,565 B2 | 4/2011 | Knisel et al. |
| 8,128,872 B2 | 3/2012 | Lentz et al. |
| 8,256,233 B2 | 9/2012 | Boyden et al. |
| 8,292,698 B1 | 10/2012 | Shih et al. |
| 2001/0025495 A1 | 10/2001 | Newman et al. |
| 2001/0038338 A1 | 11/2001 | Kadwell et al. |
| 2002/0002474 A1 | 1/2002 | Michelson et al. |
| 2002/0068510 A1 | 6/2002 | Okazawa et al. |
| 2002/0082543 A1 | 6/2002 | Park et al. |
| 2002/0098534 A1 | 7/2002 | McCaskey-Feazel et al. |
| 2002/0107199 A1 | 8/2002 | Walker |
| 2002/0111362 A1 | 8/2002 | Rubinfeld et al. |
| 2002/0169411 A1 | 11/2002 | Sherman et al. |
| 2003/0003105 A1 | 1/2003 | Gerber |
| 2003/0012741 A1 | 1/2003 | Furlan et al. |
| 2003/0041602 A1 | 3/2003 | Williams, III et al. |
| 2003/0049320 A1 | 3/2003 | Bhagwatwar et al. |
| 2003/0065535 A1 | 4/2003 | Karlov et al. |
| 2003/0072814 A1 | 4/2003 | Maibach et al. |
| 2003/0104764 A1 | 6/2003 | Preising |
| 2003/0127054 A1 | 7/2003 | Hebrank |
| 2003/0135201 A1 | 7/2003 | Gonnelli |
| 2003/0147995 A1 | 8/2003 | Koss et al. |
| 2003/0166594 A1 | 9/2003 | Blum et al. |
| 2003/0181826 A1 * | 9/2003 | Smith et al. ............ 600/581 |
| 2003/0181863 A1 | 9/2003 | Ackley et al. |
| 2003/0207655 A1 | 11/2003 | Jackson |

(56) References Cited

U.S. PATENT DOCUMENTS

| | | |
|---|---|---|
| 2004/0026617 A1 | 2/2004 | Gregori et al. |
| 2004/0029774 A1 | 2/2004 | Gamay |
| 2004/0049150 A1 | 3/2004 | Dalton et al. |
| 2004/0076319 A1 | 4/2004 | Fauver et al. |
| 2004/0092920 A1 | 5/2004 | Rozenshpeer |
| 2004/0093240 A1 | 5/2004 | Shah |
| 2004/0106904 A1 | 6/2004 | Gonnelli et al. |
| 2004/0176732 A1 | 9/2004 | Frazier et al. |
| 2004/0180846 A1 | 9/2004 | Huang et al. |
| 2004/0193019 A1 | 9/2004 | Wei |
| 2004/0244508 A1 | 12/2004 | Keskinen et al. |
| 2004/0254525 A1 | 12/2004 | Uber, III et al. |
| 2004/0260234 A1 | 12/2004 | Srinivasan et al. |
| 2005/0019380 A1 | 1/2005 | Hoon et al. |
| 2005/0057366 A1 | 3/2005 | Kadwell et al. |
| 2005/0059940 A1 | 3/2005 | Weber et al. |
| 2005/0086961 A1 | 4/2005 | McKay |
| 2005/0107006 A1 | 5/2005 | Makino et al. |
| 2005/0107832 A1 | 5/2005 | Bernabei |
| 2005/0193451 A1 | 9/2005 | Quistgaard et al. |
| 2005/0271733 A1 | 12/2005 | Burkoth et al. |
| 2006/0045881 A1 | 3/2006 | Molldrem |
| 2006/0123801 A1 | 6/2006 | Jackson |
| 2006/0123819 A1 | 6/2006 | Choe et al. |
| 2006/0129326 A1 | 6/2006 | Braconnier et al. |
| 2006/0153927 A1 | 7/2006 | Xu |
| 2006/0166233 A1 | 7/2006 | Wu et al. |
| 2006/0177564 A1 | 8/2006 | Diaz et al. |
| 2006/0178688 A1 | 8/2006 | Freeman et al. |
| 2006/0182738 A1 | 8/2006 | Holmes |
| 2006/0190195 A1 | 8/2006 | Watanabe et al. |
| 2006/0195269 A1 | 8/2006 | Yeatman et al. |
| 2006/0200369 A1 | 9/2006 | Batch et al. |
| 2006/0202385 A1 | 9/2006 | Xu et al. |
| 2006/0228465 A1 | 10/2006 | Zurecki |
| 2006/0258986 A1 | 11/2006 | Hunter et al. |
| 2007/0013910 A1 | 1/2007 | Jiang et al. |
| 2007/0020273 A1 | 1/2007 | Arlen et al. |
| 2007/0112598 A1 | 5/2007 | Heckerman et al. |
| 2007/0113639 A1 | 5/2007 | DiFoggio et al. |
| 2007/0161964 A1 | 7/2007 | Yuzhakov |
| 2007/0178811 A1 | 8/2007 | Sundaram et al. |
| 2007/0196437 A1 | 8/2007 | Hamaker et al. |
| 2008/0031934 A1 | 2/2008 | MacPhee et al. |
| 2008/0039773 A1 | 2/2008 | Py |
| 2008/0085286 A1 | 4/2008 | Kalkum et al. |
| 2009/0011087 A1 | 1/2009 | Rabault et al. |
| 2009/0062737 A1 | 3/2009 | Sun |
| 2009/0062783 A1 | 3/2009 | Sun |
| 2009/0232849 A1 | 9/2009 | Gallez et al. |
| 2009/0317759 A1 | 12/2009 | Groman |
| 2010/0111854 A1 | 5/2010 | Boyden et al. |
| 2010/0133195 A1 | 6/2010 | Gane et al. |
| 2011/0150765 A1 | 6/2011 | Boyden et al. |
| 2011/0277679 A1 | 11/2011 | Good et al. |

FOREIGN PATENT DOCUMENTS

| | | |
|---|---|---|
| WO | WO 00/09670 | 2/2000 |
| WO | WO 2007/149868 A2 | 12/2007 |
| WO | WO 2009/113856 A1 | 9/2009 |

OTHER PUBLICATIONS

Wissner-Gross, A., et al., "Diamond Stabilization of ice multilayers at human body temperature", 2007, Physical Review E, 76, pp. 1-4.*
Waterquality, Water Quality Information for Consumers, accessed from http://waterquality.cce.cornell.edu/bottled.htm, accessed on Mar. 14, 2012, pp. 1-5.*
NASA Tech Brief, "Tools Made of Ice Facilitate Forming of Soft, Sticky Materials", 1969, pp. 1-2.*
Definition from Hutchinson Unabridged Encyclopedia with Atlas and Weather guide; "Polymers"; The Hutchinson Unabridged Encyclopedia with Atlas and Weather guide; total of 3 pages; located at: http://www.credoreference.com/entry/heliconhe/polymers; © 2010 Helicon Publishing/RM.
Definition from the Crystal Reference Encyclopedia; "Horse"; The Crystal Reference Encyclopedia; total of 1 page; located at: http://www.credoreference.com/enty/cre/horse; Crystal Semantics Ltd.
Babicki, A. et al.; "Evaluation of using fibrin tissue adhesive (Beriplast) and preparations of thrombin and adrenalin in injection hemostatis methods for gastric and duodenal ulcer hemorrhage. Randomized, prospective clinical trial"; Wiad Lek; 1997; pp. 2:383-7; 50 Suppl 1 Pt; PubMed (Abstract Only).
Belitsky, Rosalind B. et al.; "Evaluation of the Effectiveness of Wet Ice, Dry Ice, and Cryogen Packs in Reducing Skin Temperature"; Physical Therapy; Jul. 1987; pp. 1080-1084; vol. 67, No. 7.
Currie, L. A. et al.; "Long range transport of biomass aerosol to Greenland: Multi-spectroscopic investigation of particles deposited in the snow"; Journal of Radioanalytical and Nuclear Chemistry; 2005; pp. 399-411; vol. 263, No. 2; Akadémiai Kiadó, Budapest.
Escámez, Maria José et al.; "An in Vivo Model of Wound Healing in Genetically Modified Skin-Humanized Mice"; The Journal of Investigative Dermatology; Dec. 6, 2004; pp. 1182-1191; vol. 123; The Society for Investigative Dermatology, Inc.
Kennedy, Muiris T. et al.; "Hypertonic saline reduces inflammation and enhances the resolution of oleic acid induced acute lung injury"; BMC Pulmonary Medicine; Jul. 8, 2008; pp. 1-7; vol. 8, Issue 9; BioMed Central Ltd.
Lin, Hwai-Jeng et al.; "Endoscopic injection with fibrin sealant versus epinephrine for arrest of peptic ulcer bleeding: a randomized, comparative trial"; Journal of Clinical Gastroenterology; 2002, pp. 218-221; vol. 35, Issue 3; PubMed (Abstract Only).
"Martian Snowflakes"; exo.net; printed on Nov. 14, 2011; 11 pages; located at http://www.exo.net/~pauld/Mars/4snowflakes/martiansnowflakes.html.
"Precursor"; AudioEnglish.net; printed on Nov. 14, 2011; 2 pages; located at http://www.audioenglish.net/dictionary/precursor.htm.
Rifkin, Barry R. et al.; "Osteoid Resorption by Mononuclear Cells in vitro"; Cell and Tissue Research; 1980; pp. 493-500; vol. 210; Springer-Verlag.
"Snow"; wikipedia.org; printed on Nov. 14, 2011; 18 pages; located at http://en.wikipedia.org/wiki/Snow.
Bertie, J. E. et al.; "Transformations of Ice II, Ice III, and Ice V at Atmospheric Pressure"; The Journal of Chemical Physics; bearing a date of Feb. 15, 1963; pp. 840-846; vol. 38, No. 4; Journal of Chemical Physics.
Buck, Christopher B. et al.; "Carrageenan Is a Potent Inhibitor of Papillomavirus Infection"; PLoS Pathogens; bearing a date of Jul. 2006; pp. 0671-0680; vol. 2, Issue 7; PLoS Pathogens.
Clements, Harry F.; "Life and the Wonders of Water"; Harold L. Lyon Arboretum Lecture Number Seven; bearing a date of Apr. 21, 1976; pp. 1-34; Harold L. Lyon Arboretum, University of Hawaii, Honolulu, Hawaii.
Definition from Dorland's Illustrated Medical Dictionary "Nanoparticle"; bearing a date of 2007; total of 1 page; Elsevier; located at: www.credoreference.com/entry/ehsdorland/nanoparticle.
Goodman, J. M.; "Liquid Nitrogen Therapy of Warts and Other Skin Lesions"; Canad. M. A. J.; bearing a date of Mar. 19, 1960; pp. 628-630; vol. 82.
Hansen, T. C. et al.; "Modelling Ice Ic of Different Origin and Stacking-Faulted Hexagonal Ice Using Neutron Powder Diffraction Data"; Physics and Chemistry of Ice: Proceedings of the 11th International Conference on the Physics and Chemistry of Ice held at Bremerhaven; 2006; pp. 1-8.
KidsHealth.org; "Dehydration"; Internet Archive WayBackMachine; bearing a date of 2002, pp. 1-5; located at: http://replay.waybackmachine.org/20021117135207/http://endoflifecare.tripod.com/juvenilehuntingtonsdisease/id51.html.
Minaev, V. S. et al.; "Polymorphous-Crystalloid Nature of Vitreous and Liquid $H_2O$"; Journal of Optoelectronics and Advanced Materials; bearing a date of Mar. 2004; pp. 103-112; vol. 6, No. 1.
Moffatt, Stanley et al.; "Uptake characteristics of NGR-coupled stealth PEI/pDNA nanoparticles loaded with PLGA-PEG-PLGA triblock copolymer for targeted delivery to human monocyte-derived dendritic cells"; International Journal of Pharmaceutics; bearing a date of 2006; pp. 143-154; vol. 321; Elsevier B.V.

(56) References Cited

OTHER PUBLICATIONS

Oeschger, H. et al.; "Atmospheric $CO_2$ Content in the Past Deduced from Ice-Core Analyses"; Annals of Glaciology; bearing a date of 1982; pp. 227-232; vol. 3; © International Glaciological Society.

Want, Roy; "RFID: A Key to Automating Everything"; Scientific American; bearing a date of Jan. 2004, printed on Feb. 21, 2004; pp. 1-10; vol. 290, No. 1; Scientific American.

Kidshealth.org; "Dehydration"; bearing a date of 2002; located at: http://endoflifecare.tripod.com/juvenilehuntingtonsdisease/id51.html; printed on Mar. 17, 2011; pp. 1-5.

Butler, A.R. et al.; "Therapeutic Uses of Inorganic Nitrite and Nitrate: From the Past to the Future"; Circulation; bearing a date of 2008; pp. 2151-2159; vol. 117; Journal of the American Heart Association.

Schmidt, A.I. et al.; "Exposure to carbon dioxide and helium reduces in vitro proliferation of pediatric tumor cells"; Pediatric Surgical Int. bearing a date of 2006; pp. 72-77; vol. 22; Springer-Verlag.

Oeschger, H. et al.; "Atmospheric $CO_2$ Content in the Past Deduced From Ice-Core Analyses"; Annals of Glaciology; bearing a date of 1982; pp. 227-232; vol. 3; International Glaciological Society.

Edwards, R. et al.; "Iron in East Antarctic snow: Implications for atmospheric iron deposition and algal production in Antarctic waters"; Geophysical Research Letters; bearing a date of 2001; 1 page; vol. 28; No. 20; American Geophysical Union (Abstract only).

Uauy, C. et al.; "A NAC Gene Regulating Senescence Improves Grain Protein, Zinc, and Iron Content in Wheat"; Science; bearing a date of Nov. 24, 2006; pp. 1298-1301; vol. 314; No. 1298; American Association for the Advancement of Science.

Abnet, Christian C. et al.; "Zinc Concentration in Esophageal Biopsy Specimens Measured by X-Ray Fluorescence and Esophageal Cancer Risk"; Journal of the National Cancer Institute, bearing a date of Feb. 15, 2005; pp. 301-306; vol. 97, No. 4; Oxford University Press.

Herman, F. A. et al.; "Total Mineral Material, Acidity, Sulphur and Nitrogen in Rain and Snow at Kentville, Nova Scotia"; Tellus; bearing a date of 1957; pp. 180-183; vol. IX, No. 2.

Berman, S. et al.; "Tracking stem cells using magnetic nanoparticles"; WIREs Nanomedicine and Nanobiotechnology; Jul./Aug. 2011; pp. 343-355; vol. 3; John Wiley & Sons, Inc.

Bourgeois, Jocelyne C..; "Seasonal and interannual pollen variability in snow layers of arctic ice caps"; Review of Palaeobotany & Palynology; 2000; pp. 17-36; vol. 108; Elsevier Science B.V.

Clinical Trial; Pharmaceutical Medicine Dictionary; 2001; one page; located at: http://www.credoreference.com/entry/pmd/clinical_trial retrieved online on Sep. 18, 2011.

eco-usa.net; "Benzene"; eco-usa.net; pp. 1-4; printed on Oct. 24, 2011; located at: http://www.eco-usa.net/toxics/chemicals/benzene.shtml; Information is excerpted from: "Toxicological Profile for Benzene, 2005 Draft for Public Comment"; Agency for Toxic Substances and Disease Registry, United States Public Health Service.

Kluz, K. et al.; "Application of ice-air jet blasting in treatment of sensitive surfaces"; Int. J. Abrasive Technology; May 30, 2007; pp. 59-77; vol. 1, No. 1; Inderscience Enterprises Ltd.

Mayo Clinic; "Impacted wisdom teeth"; mayoclinic.com special in association with cnn.com; Health/Library; Apr. 21, 2006; printed on Oct. 3, 2011; 4 pages; located at http://premium.asia.cnn.com/HEALTH/library/DS/00679.html.

MIStupid; "Composition of Air"; MIStupid.com; pp. 1-2; printed on Oct. 3, 2011; located at: http://mistupid.com/chemistry/aircomp.htm.

Pacini, E. et al.; "Pollen carbohydrates and water content during development, presentation, and dispersal: a short review"; Protoplasma; published Aug. 31, 2006; pp. 73-77; vol. 228; Springer-Verlag.

Sasaki, A. et al.; "Bisphosphonate Risedronate Reduces Metastatic Human Breast Cancer Burden in Bone in Nude Mice"; Cancer Research; Aug. 15, 1995; pp. 3551-3557; vol. 55; American Association for Cancer Research.

Shaw, G. et al.; "Chemical Studies on the Constitution of Some Pollen and Spore Membranes"; Grana Palynologica; published 1964; printed on Oct. 23, 2011; pp. 247-252 (& cover information, 2 pages); vol. 5, No. 2; Taylor & Francis Informa Ltd.

Taylor, C. H.; "Cancer"; 1915; p. 64; Lea & Febiger.

Toshiyuki, O. et al.; "Dermabrasion Technique for Peri-implant Soft Tissue Management in the Mandible Reconstructed by Free Osteocutaneous Flap"; Science Links Japan; 2004; pp. 1-2; Nippon Koku Inpuranto Gakkaishi; printed on Oct. 3, 2011; located at http://sciencelinks.jp/j-east/article/200424/000020042404A0800133.php.

Warts; Black's Medical Dictionary, $42^{nd}$ Edition; 2010; one page; retrieved on Sep. 18, 2011; located at: http://www.credoreference.com/entry/blackmed/warts; A & C Black Publishers Ltd.

Wilhardt, M. et al.; "National PBM Drug Monograph Papain-Urea (Accuzyme®) and Papain-Urea-Chlorophyllin Copper Complex Sodium (Panafil®)"; 10 pages; Jan. 2004; located at: http://www.vapbm.org or http://vaww.pbm.med.va.gov.

Gorman et al.; Effects of Topical Nitroglycerin and Flurbiprofen in the Rat Comb Burn Model; Annals of Plastic Surgery; May 1999; 1 page (abstract only); Lippincott Williams & Wilkins, Inc.

Ito et al.; "Evaluation of self-dissolving needles containing low molecular weight heparin (LMWH) in rats"; International Journal of Pharmaceutics; bearing a date of 2008; available online Aug. 6, 2007; pp. 124-129; vol. 349; Elsevier B. V.

Nagourney, Eric; "Vital Signs: Sensations; A Needle on Ice to Ease the Pain"; The New York Times; Oct. 16, 2001; 2 pages; located online at : http://www.nytimes.com/2001/10/16/health/vital-signs-sensations-a-needle-on-ice-to-ease-the-pain.html ; The New York Times Company.

Ali et al.; "Lid for a Vacuum Line Cooling Trap"; J. Chem. Educ.; bearing a date of Jun. 1995; p. 549; vol. 72, No. 6.

"Dell Precision™ Workstation 650"; Product brochure, bearing a date of Nov. 2002; pp. 1-2; Dell Computer Corporation.

He et al.; "A Virtual Prototype Manufacturing Software System for Mems"; International Workshop on Micro Electromechanical Systems, bearing a date of 1996; pp. 122-126; IEEE.

Henry et al.; "Microfabricated Microneedles: A Novel Approach to Transdermal Drug Delivery"; Journal of Pharmaceutical Sciences; bearing a date of Aug. 1998; pp. 922-925; vol. 87, No. 8; American Chemical Society and American Pharmaceutical Association.

McAllister et al.; "Microfabricated Microneedles for Gene and Drug Delivery"; Annual Review of Biomedical Engineering; bearing a date of 2000; pp. 289-313; Annual Reviews.

McAllister et al.; "Microfabricated Needles for Transdermal Delivery of Macromolecules and Nanoparticles: Fabrication Methods and Transport Studies"; Proceedings of the National Academy of Sciences USA; bearing a date of Nov. 25, 2003; pp. 13755-13760; vol. 100, No. 24; The National Academy of Sciences of the USA.

Van Baare et al.; "Microbiological Evaluation of Glycerolized Cadaveric Donor Skin"; Transplantation; bearing a date of Apr. 15, 1998; pp. 1-7 (966-970); vol. 65, No. 7; Williams & Wilkins.

"A Guide to Snowflakes"; SnowCrystals.com; printed on May 19, 2012; 10 pages; located at http://www.its.caltech.edu/~atomic/snowcrystals/class/class.htm.

Berleant, Daniel; "New Plant Paradigms (Part X: Power Plants, Greening the Desert, Phyto-Terraforming, and Recommendations)"; Lifeboat News: The Blog; Sep. 19, 2010; 3 pages; located at http://lifeboat.com/blog/2010/09/new-plant-paradigms-part-x-power-plants-greening-the-desert-phyto-terraforming-and-recommendations.

"Bullet"; definition of Bullet; dictionary.reference.com; printed on May 19, 2012; 4 pages; located at http://dictionary.reference.com/browse/bullet.

Campo et al.; "Super-exchange interactions enhanced through spin delocalisation in $K_2FeCl_5 \cdot H_2O$"; Scientific Highlights; bearing a date of 2002; pp. 18-19; located at http://www.unizar.es/icma/depart/termomag/lineas/h11.pdf.

"Cryonomic Dry Ice Cleaning Technology"; Cryonomic; bearing a date of 2006; ; 2 pages; located at http://www.cryonomic.ro/produse.php?lang=en&p_id=2.

"Fixative"; definition of Fixative; TheFreeOnlineDictionary.com; printed on May 19, 2012; 2 pages; located at http://www.thefreedictionary.com/fixative.

"Freeze"; definition of Freeze; American Heritage Dictionary; printed on May 19, 2012; 6 pages; located at http://www.answers.com/topic/freeze.

(56) References Cited

OTHER PUBLICATIONS

"Freeze-Dry"; The Penguin English Dictionary; bearing a date of 2000, 2003; 2 pages; Penguin Books.

Gromball, F.; "Nanometer-Scale Height Measurements in Micromachined Picoliter Vials Based on Interference Fringe Analysis"; ACM Digital Library (US Patent & Trademark Office); bearing a date of 2000; 1 page; located at http://dl.acm.org/citation.cfm?id=877015.

Minnery, John; "Kill Without Joy! The Complete How to Kill Book"; bearing a date of 1992; cover page, publication information, and p. 149; Paladin Press.

"Robot"; definition of Robot; TheFreeOnlineDictionary.com; printed on May 7, 2012; 3 pages; located at http://www.thefreedictionary.com/robot.

Ryalls, Charles Wager; Transactions of the National Association for the Promotion of Social Science; Glasgow Meeting, 1874; bearing dates of 1874 and 1875; 2 pages; Longmans, Green, and Co., London (best copy available).

Tamai et al.; "Percutaneous injection of a low-concentration alkaline solution targeting hepatocellular carcinoma"; Oncol. Rep.; bearing a date of Jul.-Aug. 2000; pp. 719-23; vol. 7, No. 4; located at http://www.ncbi.nlm.nih.gov/pubmed/10854532 (abstract only—1 page).

Wiseman, John "Lofty"; "The Ultimate Survival Guide"; bearing dates of 1986, 1993, 2004; cover page, copyright page and p. 140; Harper-Collins Publishers Inc.

Adams et al.; "Update in Vitamin D"; J Clin Endocrinol Metab; bearing a date of Feb. 2010; pp. 471-478; vol. 95, No. 2; The Endocrine Society.

Armstrong et al.; "Vasodilator Therapy in Acute Myocardial Infarction. A Compassion of Sodium Nitoprusside and Nitroglycerin"; Circulation, Journal of the American Heart Association; bearing a date Dec. 1975; pp. 1118-1122 and 1 cover-page.; vol. 52; American Heart Association; Dallas, TX.

"Dynamite"; Classic Encyclopedia 1911; located at: http://1911encyclopedia.org/Dynamite; printed on May 5, 2012; pp. 1-2.

Holmes et al.; "Nitroglycerin: The Explosive Drug"; Journal of Chemical Education; bearing a date of Sep. 1971; pp. 573-576; vol. 48, No. 9.

Leroux et al.; "Biodegradable Nanoparticles—From Sustained Release Formulations to Improved Site Specific Drug Delivery"; Journal of Controlled Release; bearing a date of 1996; pp. 339-350; vol. 39; Elsevier Science B. V.

Murray, Benjamin J.; "Enhanced Formation of Cubic Ice in Aqueous Organic Acid Droplets"; Environmental Research Letters; published May 30, 2008; pp. 1-7; vol. 3; IOP Publishing Ltd.

Nomura et al.; "Interaction of Water with Native Collagen"; Biopolymers; bearing a date of 1977: pp. 231-246; vol. 16; John Wiley & Sons, Inc.

Overholt et al.; "Photodynamic Therapy with Porfimer Sodium for Ablation of High-Grade Dysplasia in Barrett's Esophagus; International, Partially Blinded, Randomized Phase III Trial (CME)": Gastrointestinal Endoscopy; bearing a date of 2005; pp. 488-498; vol. 62, No. 4; The American Society for Gastrointestinal Endoscopy.

Vogl et al.; "Colorectal Carcinoma Metastases in Liver: Laser-Induced Interstitial Thermotherapy—Local Tumor Control Rate and Survival Data"; Radiology; bearing a date of 2004; pp. 450-458; vol. 230, No. 2; RSNA.

Al-Amoudi A. et al.; "Amorphous solid water produced by cryosectioning of crystalline ice at 113 K"; J. Microsc.; Aug. 2002; pp. 146-53; vol. 207 (Pt 2); (Abstract Only).

Barnes, Piers R.F. et al.; "Distribution of soluble impurities in cold glacial ice"; Journal of Glaciology; Jun. 2004; pp. 311-324(14); vol. 50, No. 170; (Abstract Only).

Chen, Si et al.; "In-situ Observations of Snow Sublimation using Scanning Electron Microscopy"; 66th Eastern Snow Conference; 2009; pp. 5-9.

"Clathrate"; Merriam-Webster; accessed Jan. 3, 2012; pp. 1-3; located at http://www.merriam-webster.com/dictionary/clathrate.

Fischer, Ralf G. et al.; "Levels and Pattern of alkyl nitrates, multifunctional alkyl nitrates, and halocarbons in the air over the Atlantic Ocean"; Journal of Geophysical Research; bearing a date of 2000; pp. 14,473-14,494; American Geophysical Union; (Abstract Only).

Hervig, Mark et al.; "First confirmation that water ice is the primary component of polar mesospheric clouds"; Geophysical Research Letters; Mar. 15, 2001; pp. 971-974; vol. 28, No. 6; American Geophysical Union.

Law, Marcus; "A 100-year-old Mystery: Nitrate Tolerance"; HKPJ; Jul.-Sep. 2003; p. 117; vol. 12, No. 3.

McFeeters, Roger F.; "Single-Injection HPLC Analysis of Acids, Sugars, and Alcohols in Cucumber Fermentations"; J. Agric. Food Chem.; 1993; pp. 1439-1443; vol. 41, No. 9.

Melville, Kate; "The incredible noise of snow flakes!"; scienceagogo.com; Mar. 16, 2000; pp. 1-3; located at http://www.scienceagogo.com/news/20000216171241data_trunc_sys.shtml.

Miedaner, Markus Maria; "Characterization of inclusions and their distribution in natural and artificial ice samples by synchrotron cryo-micro-tomography (SCXRT)"; bearing a date of May 15, 2007; 121 pages.

Painter, Thomas H. et al.; "Detection and Quantification of Snow Algae with an Airborne Imaging Spectrometer"; Applied and Environmental Microbiology; Nov. 2001; pp. 5267-5272 plus cover page; vol. 67, No. 11; American Society for Microbiology.

Platt, Ulrich F. et al.; "Measurement of Nitrate Radical Concentrations in Continental Air"; Environ. Sci. Technol.; 1984; pp. 365-369; vol. 18, No. 5; American Chemical Society.

Raman, Chandrashekar et al.; "Modeling small-molecule release from PLG microspheres: effects of polymer degradation and nonuniform drug distribution"; Journal of Controlled Release; bearing a date of Dec. 7, 2004; pp. 149-158; vol. 103; Elsevier B.V.

Singh, Manmohan et al.; "Charged polylactide co-glycolide microparticles as antigen delivery systems"; Expert Opin. Biol. Ther.; 2004; pp. 483-491; vol. 4, No. 4; Ashley Publications Ltd.

Ansiaux, R. et al.; "Use of botulinum toxins in cancer therapy"; Expert Opinion in Investig. Drugs; bearing a date of 2007; pp. 209-218; vol. 16, No. 2; Informa UK Ltd.

Bhalla, M. et al.; "Microdermabrasion: Reappraisal and Brief Review of Literature"; American Society for Dermatologic Surgery, Inc.; bearing a date of Jun. 2006; pp. 809-814; vol. 32; Blackwell Publishing.

Davari, P. et al.; "A randomized investigator-blind trial of different passes of microdermabrasion therapy and their effects on skin biophysical characteristics"; International Journal of Dermatology; bearing a date of 2008; pp. 508-513; vol. 47; The International Society of Dermatology.

Fang, J-Y. et al.; "Enhancement of topical 5-aminolaevulinic acid delivery by erbium:YAG laser and microdermabrasion: a comparison with iontophoresis and electroporation"; The British Journal of Dermatology; bearing a date of 2004; pp. 132-140; vol. 151; British Association of Dermatologists.

Gelderblom, H. et al.; "Disposition of [G-$^3$H]Paclitaxel and Cremophor EL in a Patient With Severely Impaired Renal Function"; Drug Metabolism and Disposition; bearing a date of 1999; pp. 1300-1305; vol. 27, No. 11; The American Society for Pharmacology and Experimental Therapeutics.

Grimes, P. E.; "Microdermabrasion"; The American Society for Dermatologic Surgery, Inc.; bearing a date of Sep. 2005; pp. 1160-1165; vol. 31, No. 9, Part 2; BC Decker, Inc.

Lee, Woan-Ruoh et al.; "Microdermabrasion as a Novel Tool to Enhance Drug Delivery via the Skin: An Animal Study"; The American Society for Dermatologic Surgery, Inc.; bearing a date of Aug. 2006; pp. 1013-1022; vol. 32, No. 8; Blackwell Publishing.

Rajan, P. et al.; "Skin Barrier Changes Induced by Aluminum Oxide and Sodium Chloride Microdermabrasion"; The American Society for Dermatologic Surgery, Inc.; bearing a date of May 2002; pp. 390-393; vol. 28, No. 5; Blackwell Publishing.

Spencer, J. M. et al.; "Approaches to Document the Efficacy and Safety of Microdermabrasion Procedure"; The Americcan Society for Dermatologic Surgery, Inc.; bearing a date of Nov. 2006; pp. 1353-1357; vol. 32, No. 11; Blackwell Publishing.

\* cited by examiner

As published by Yasui et al.

FIG. 7

700 A method comprising:

710 comparing information regarding at least one aspect of administering at least one frozen particle therapeutic composition to at least one subject and information regarding at least one clinical outcome following receipt by the at least one subject of at least one frozen particle therapeutic composition; and providing output information optionally based on the comparison 720 determining at least one statistical correlation 730 counting the occurrence of at least one clinical outcome 735 determining at least one correlation before the administration of the at least one frozen particle therapeutic composition 740 information regarding the amount of at least one frozen particle therapeutic composition or therapeutic agent administered to at least one biological tissue of a subject 750 information regarding at least one dimension of biological tissue penetration 760 information regarding at least one depth, width, or breadth of administration of at least one frozen particle therapeutic composition to at least one biological tissue of at least one subject 770 information regarding two or more subjects with one or more common attributes 780 genetic attributes, mental attributes, or psychological attributes 790 genotype attributes or phenotype attributes 797 at least one of height; weight; medical diagnosis; familial background; results on one or more medical tests; ethnic background; body mass index; age; presence or absence of at least one disease or condition; species; ethnicity; race; allergies; gender; thickness of epidermis; thickness of dermis; thickness of stratum corneum; keratin deposition; collagen deposition; blood vessel condition; skin condition; hair or fur condition; muscle condition; tissue condition; organ condition; nerve condition; brain condition; presence or absence of at least one biological, chemical, or therapeutic agent in the subject; pregnancy status; lactation status; genetic profile; proteomic profile; partial or whole genetic sequence; partial or whole proteomic sequence; medical history; or blood condition

FIG. 9

900 receipt by the at least one subject of at least one frozen particle therapeutic composition is pursuant to at least one clinical trial 910 creating at least one inclusion criterion and at least one exclusion criterion for a clinical trial involving the at least one frozen particle therapeutic composition 920 suggesting the inclusion of one or more of the at least one subject in at least one clinical trial 930 suggesting the exclusion of one or more of the at least one subject in at least one clinical trial 940 using one or more comparisons to predict at least one clinical outcome regarding at least one second subject 950 the at least one second subject has not received the at least one frozen particle therapeutic composition 960 predicting at least one clinical outcome involving the at least one second subject, wherein the at least one second subject is a plurality of people; and segregating subject identifiers associated with the plurality of people in reference to the predicted at least one clinical outcome 970 determining the eligibility of the at least one second subject for the at least one clinical trial

FIG. 10

1000 A method of predicting a clinical outcome of administering at least one frozen particle therapeutic composition to at least one biological tissue of at least one first subject, comprising:

1010 determining a similarity or a dissimilarity in information regarding at least one aspect of administering at least one therapeutic composition to the at least one biological tissue of the at least one first subject to information regarding at least one aspect of administering at least one therapeutic composition to the at least one biological tissue of the at least one second subject, wherein the at least one second subject attained a clinical outcome following receipt of the at least one frozen particle therapeutic composition; and providing output information optionally based on the determination 1020 information regarding the amount of at least one frozen particle therapeutic composition or therapeutic agent administered to at least one biological tissue of at least one subject 1030 information regarding at least one dimension of biological tissue penetration 1040 information regarding at least one depth, width, or breadth of administration of at least one frozen particle therapeutic composition to at least one biological tissue of at least one subject 1050 information regarding two or more subjects with one or more common attributes 1060 genetic attributes, mental attributes, or psychological attributes 1070 genotype attributes or phenotype attributes 1080 at least one of height; weight; medical diagnosis; familial background; results on one or more medical tests; ethnic background; body mass index; age; presence or absence of at least one disease or condition; species; ethnicity; race; allergies; gender; thickness of epidermis; thickness of dermis; thickness of stratum corneum; keratin deposition; collagen deposition; blood vessel condition; skin condition; hair or fur condition; muscle condition; tissue condition; organ condition; nerve condition; brain condition; presence or absence of at least one biological, chemical, or therapeutic agent in the subject; pregnancy status; lactation status; genetic profile; proteomic profile; partial or whole genetic sequence; partial or whole proteomic sequence; medical history; or blood condition

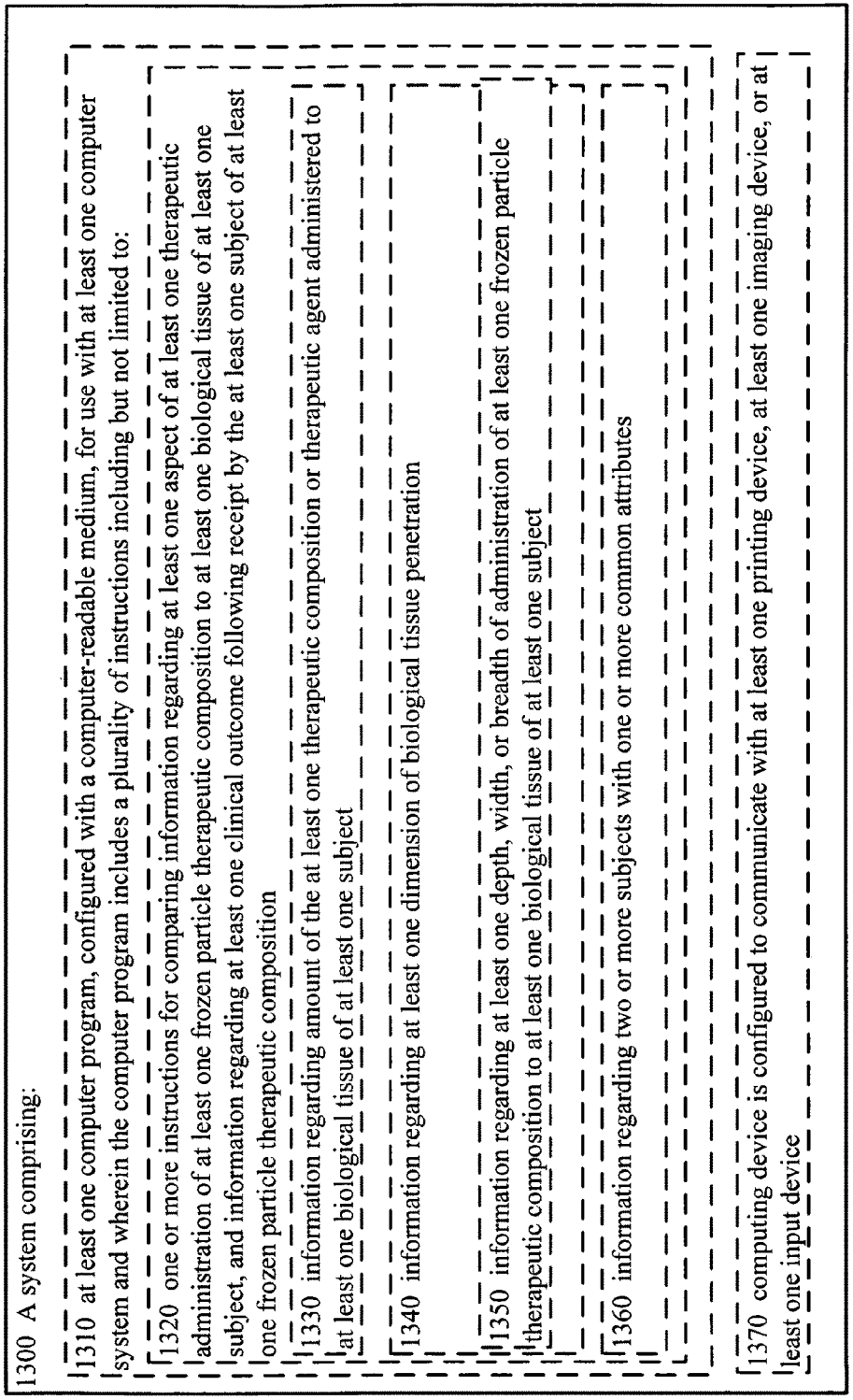

FIG. 13

1300 A system comprising:

1310 at least one computer program, configured with a computer-readable medium, for use with at least one computer system and wherein the computer program includes a plurality of instructions including but not limited to:

1320 one or more instructions for comparing information regarding at least one aspect of at least one therapeutic administration of at least one frozen particle therapeutic composition to at least one biological tissue of at least one subject, and information regarding at least one clinical outcome following receipt by the at least one subject of at least one frozen particle therapeutic composition 1330 information regarding amount of the at least one therapeutic composition or therapeutic agent administered to at least one biological tissue of at least one subject 1340 information regarding at least one dimension of biological tissue penetration 1350 information regarding at least one depth, width, or breadth of administration of at least one frozen particle therapeutic composition to at least one biological tissue of at least one subject 1360 information regarding two or more subjects with one or more common attributes 1370 computing device is configured to communicate with at least one printing device, at least one imaging device, or at least one input device

FIG. 15

1500 receipt by the at least one subject of at least one frozen particle therapeutic composition is pursuant to at least one clinical trial 1510 determining at least one correlation before the administration of the at least one frozen particle therapeutic composition 1520 creating at least one inclusion criterion and at least one exclusion criterion for a clinical trial involving the at least one frozen particle therapeutic composition 1530 suggesting the inclusion of one or more of the at least one subject in at least one clinical trial 1540 suggesting the exclusion of one or more of the at least one subject in at least one clinical trial 1550 using one or more of the at least one comparison to predict at least one clinical outcome regarding at least one second subject 1560 the at least one second subject has not received the at least one frozen particle therapeutic composition 1570 predicting at least one clinical outcome involving the at least one second subject, wherein the at least one second subject is a plurality of people; and segregating subject identifiers associated with the plurality of people in reference to the predicted at least one clinical outcome 1580 determining the eligibility of the at least one second subject for the at least one clinical trial

FIG. 16

1600 A system comprising:

1610 at least one computer program, configured with a computer-readable medium, for use with at least one computer system and wherein the computer program includes a plurality of instructions including but not limited to:

1620 one or more instructions for comparing information regarding at least one aspect of at least one therapeutic administration of at least one frozen particle therapeutic composition to at least one subject, and information regarding at least one frozen particle therapeutic composition involving at least one biological tissue of at least one subject; and one or more instructions for applying one or more comparisons to the information regarding the at least one aspect of therapeutic administration of at least one frozen particle therapeutic composition to a plurality of people 1630 one or more instructions for segregating subject identifiers associated with the plurality of people in reference to at least one of the one or more applied comparisons 1640 information regarding the amount of therapeutic composition or therapeutic agent administered to at least one biological tissue of at least one subject 1650 information regarding at least one dimension of biological tissue penetration 1660 information regarding at least one depth, width, or breadth of administration of at least one frozen particle therapeutic composition to at least one biological tissue of at least one subject 1670 one or more instructions for segregating individual identifiers associated with the plurality of people in reference to at least one characteristic shared by two or more subjects in the plurality of people

FIG. 17

1700 A computer program product comprising:

1710 a signal-bearing medium bearing at least one of 1720 one or more instructions for receiving a first input associated with a first possible dataset, the first possible dataset including data representative of one or more measurements relating to one or more physical attributes of a first subject;

1730 one or more instructions for comparing a value associated with the first possible dataset with a second dataset including values representative of predictive regimen parameters from a second subject with one or more similar or dissimilar physical attributes;

1740 one or more instructions for determining from the comparison at least one frozen particle therapeutic composition regimen for the first subject; and output information optionally based on the comparison 1750 one or more instructions for accessing the first possible dataset in response to the first input 1760 one or more instructions for generating the first possible dataset in response to the first input 1770 one or more instructions for determining a graphical illustration of the first possible dataset 1780 one or more instructions for determining a graphical illustration of the second possible dataset 1790 computer-readable medium | 1792 recordable medium | 1794 communications medium

FIG. 19

1900 A computer program product comprising:

1910 a signal-bearing medium bearing at least one of 1920 one or more instructions responsive to a first possible dataset, the first possible dataset including data representative of one or more measurements relating to one or more physical attributes of a first subject;

1930 one or more instructions for comparing a value associated with the first possible dataset with a second dataset including values representative of predictive regimen parameters for a second subject with one or more similar or dissimilar physical attributes;

1940 one or more instructions for determining from the comparison at least one frozen particle composition or therapeutic composition treatment regimen for the first subject; and output information

FIG. 20

2000 A computer program product comprising:

2010 a signal-bearing medium bearing at least one of 2020 one or more instructions for receiving a first input associated with a first possible dataset, the first possible dataset including data representative of one or more measurements relating to one or more physical attributes of a subject;

2030 one or more instructions for comparing a value associated with the first possible dataset with a second dataset including values representative of parameters relating to one or more expected biological changes following administration of one or more frozen particle therapeutic compositions;

2040 one or more instructions for determining from the comparison at least one biological change following administration of one or more frozen particle therapeutic compositions to the subject; and output information optionally based on the comparison 2050 one or more instructions for accessing the first possible dataset in response to the first input 2060 one or more instructions for generating the first possible dataset in response to the first input 2070 one or more instructions for determining a graphical illustration of the first possible dataset 2080 one or more instructions for determining a graphical illustration of the second possible dataset 2090 computer-readable medium | 2092 recordable medium | 2094 communications medium

FIG. 23

2300 A method comprising:

2310 comparing information regarding at least one aspect of cellular or tissue abrasion or ablation of at least one biological tissue of at least one subject and information regarding at least one clinical outcome following receipt by the at least one subject of at least one frozen particle composition; and providing output information optionally based on the comparison 2320 determining at least one statistical correlation 2330 counting the occurrence of at least one clinical outcome 2340 information regarding quantity of cells or tissue removed or destroyed 2350 information regarding at least one dimension of cellular, tissue, or other material removal or destruction 2360 information regarding at least one depth, width, or breadth of cellular, tissue, or other material removal or destruction 2370 information regarding two or more subjects with one or more common attributes 2380 genetic attributes, mental attributes, or psychological attributes 2390 genotype attributes or phenotype attributes 2397 at least one of height; weight; medical diagnosis; familial background; results on one or more medical tests; ethnic background; body mass index; age; presence or absence of at least one disease or condition; species; ethnicity; race; allergies; gender; thickness of epidermis; thickness of dermis; thickness of stratum corneum; keratin deposition; collagen deposition; blood vessel condition; skin condition; hair or fur condition; muscle condition; tissue condition; organ condition; nerve condition; brain condition; presence or absence of at least one biological, chemical, or therapeutic agent in the subject; pregnancy status; lactation status; genetic profile; proteomic profile; partial or whole genetic sequence; partial or whole proteomic sequence; medical condition; medical history, or blood condition

FIG. 26

2600 A method of predicting a clinical outcome of at least one frozen particle composition treatment for at least one first subject, comprising:

2610 determining a similarity or a dissimilarity in information regarding at least one aspect of cellular or tissue abrasion or ablation of at least one biological tissue of at least one first subject to information regarding at least one aspect of cellular or tissue abrasion or ablation of at least one biological tissue of at least one second subject, wherein the at least one second subject attained a clinical outcome following receipt of the at least one frozen particle composition; and providing output information optionally based on the determination 2620 information regarding quantity of cells or tissue removed or destroyed 2630 information regarding at least one dimension of cellular, tissue or other material removal or destruction 2640 information regarding at least one depth, width, or breadth of cellular, tissue, or other material removal or destruction 2650 information regarding two or more subjects with one or more common attributes 2660 genetic attributes, mental attributes, or psychological attributes 2670 genotype attributes or phenotype attributes 2680 at least one of height; weight; medical diagnosis; familial background; results on one or more medical tests; ethnic background; body mass index; age; presence or absence of at least one disease or condition; species; ethnicity; race; allergies; gender; thickness of epidermis; thickness of dermis; thickness of stratum corneum; keratin deposition; collagen deposition; blood vessel condition; skin condition; hair or fur condition; muscle condition; tissue condition; organ condition; nerve condition; brain condition; presence or absence of at least one biological, chemical, or therapeutic agent in the subject; pregnancy status; lactation status; genetic profile; proteomic profile; partial or whole genetic sequence; partial or whole proteomic sequence; medical condition; or blood condition

FIG. 28

2800 receipt by the at least one subject of at least one frozen particle composition is pursuant to at least one clinical trial 2810 creating at least one inclusion criterion and at least one exclusion criterion for a clinical trial involving the at least one frozen particle composition 2820 suggesting the inclusion of one or more of the at least one subject in at least one clinical trial 2830 suggesting the exclusion of one or more of the at least one subject in at least one clinical trial 2840 using one or more of the at least one determination to predict at least one clinical outcome regarding at least one second subject 2850 the at least one second subject has not received the at least one frozen particle composition 2860 wherein the at least one second subject is a plurality of people; and segregating subject identifiers associated with the plurality of people in reference to the predicted at least one clinical outcome 2870 determining the eligibility of the at least one second subject for the at least one clinical trial

FIG. 29

2900 A system comprising:

2910 at least one computing device;

2920 one or more instructions that when executed on the at least one computing device cause the at least one computing device to receive a first input associated with a first possible dataset, the first possible dataset including data representative of one or more measurements relating to one or more physical attributes of a first subject;

2930 one or more instructions that when executed on the at least one computing device cause the at least one computing device to compare a value associated with the first possible dataset with a second dataset including values representative of predictive regimen parameters related to a second subject with one or more similar or dissimilar physical attributes;

2940 one or more instructions that when executed on the at least one computing device cause the at least one computing device to determine from the comparison at least one frozen particle composition treatment regimen for the first subject; and at least one output optionally based on the determination 2950 one or more instructions that when executed on the at least one computing device cause the at least one computing device to access the first possible dataset in response to the first input 2960 one or more instructions that when executed on the at least one computing device cause the at least one computing device to generate the first possible dataset in response to the first input 2970 one or more instructions that when executed on the at least one computing device cause the at least one computing device to determine a graphical illustration of the possible dataset

FIG. 30

3000 one or more instructions that when executed on the at least one computing device cause the at least one computing device to determine a graphical illustration of the second possible dataset 3005 the treatment regimen includes at least one of cellular or tissue removal, cellular or tissue ablation, debridement, delivery of at least one therapeutic agent, cleaning one or more wounds, removing material from at least one biological tissue, or removing material from at least one blood vessel 3008 at least one frozen particle composition includes at least one of nitrogen, carbon dioxide, hydrogen oxide, helium, neon, xenon, krypton, air, oxygen, chlorine, bromine, argon, polyethylene glycol, acetone, ethyl acetate, dimethyl sulfoxide, dimethyl formamide, dioxane, hexamethylphosphorotriamide, perfluorohydrocarbon, methanol, ethanol, tert-butyl alcohol, formic acid, hydrogen fluoride, ammonia, acetic acid, benzene, carbon tetrachloride, acetonitrile, hexane, methylene chloride, carboxylic acid, saline, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, methane, or diethyl ether 3010 one or more desktop computer, workstation computer, computing system including a cluster of processors, a networked computer, a tablet personal computer, a laptop computer, a mobile device, a mobile telephone, or a personal digital assistant computer 3020 wherein the at least one computing device is configured to communicate with a database to access the first possible dataset 3030 wherein the at least one computing device is configured to communicate with a frozen particle composition selecting apparatus or a frozen particle composition generating apparatus, or both

FIG. 33

3300 A system comprising:

3310 at least one computer program, configured with a computer-readable medium, for use with at least one computer system and wherein the computer program includes a plurality of instructions including but not limited to:

3320 one or more instructions for comparing information regarding at least one aspect of cellular or tissue abrasion or ablation of at least one biological tissue of at least one subject and information regarding at least one clinical outcome following receipt by the at least one subject of at least one frozen particle composition 3330 one or more instructions for determining at least one statistical correlation 3340 one or more instructions for counting the occurrence of at least one clinical outcome 3350 information regarding quantity of cells or tissue removed or destroyed 3360 information regarding at least one dimension of cellular, tissue, or other material removal or destruction 3370 information regarding at least one depth, width, or breadth of cellular, tissue, or other material removal or destruction 3380 information regarding two or more subjects with one or more common attributes

FIG. 35

3500 receipt by the at least one subject of at least one frozen particle composition is pursuant to at least one clinical trial 3510 one or more instructions for determining at least one comparison before the administration of the at least one frozen particle composition to at least one subject 3520 one or more instructions for creating at least one inclusion criterion and at least one exclusion criterion for a clinical trial involving the at least one frozen particle composition 3530 one or more instructions for suggesting the inclusion of one or more of the at least one subject in at least one clinical trial 3540 one or more instructions for suggesting the exclusion of one or more of the at least one subject in at least one clinical trial 3550 one or more instructions for using one or more of the at least one comparison to predict at least one clinical outcome regarding at least one second subject 3560 the at least one second subject has not received the at least one frozen particle composition 3570 one or more instructions for predicting at least one clinical outcome involving the at least one second subject, wherein the at least one second subject is a plurality of people; and segregating subject identifiers associated with the plurality of people in reference to the predicted at least one clinical outcome 3580 wherein the at least one second subject is a plurality of people; and determining the eligibility of the at least one second subject for the at least one clinical trial

FIG. 36

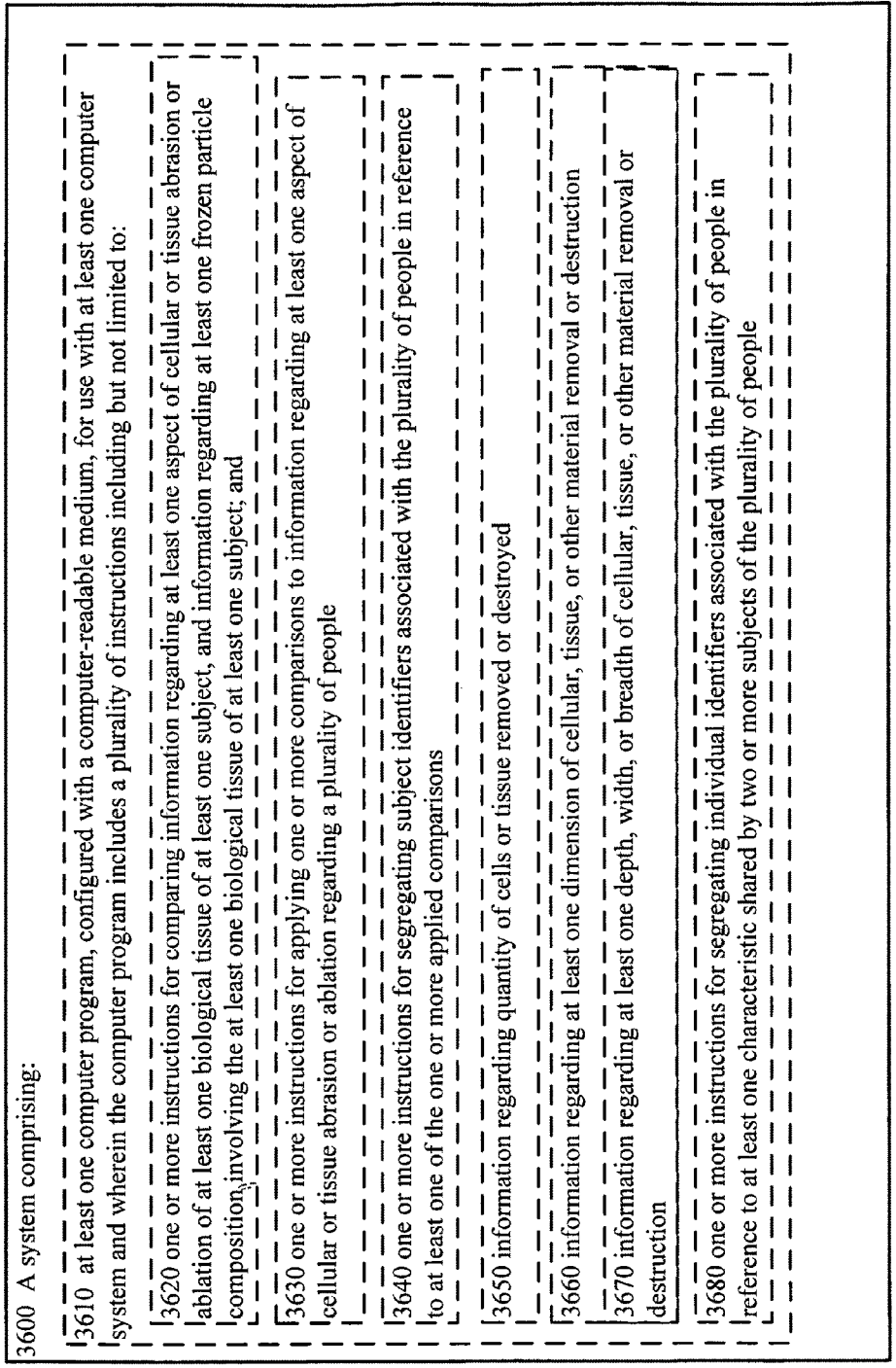

3600 A system comprising:

3610 at least one computer program, configured with a computer-readable medium, for use with at least one computer system and wherein the computer program includes a plurality of instructions including but not limited to:

3620 one or more instructions for comparing information regarding at least one aspect of cellular or tissue abrasion or ablation of at least one biological tissue of at least one subject, and information regarding at least one frozen particle composition, involving the at least one biological tissue of at least one subject; and 3630 one or more instructions for applying one or more comparisons to information regarding at least one aspect of cellular or tissue abrasion or ablation regarding a plurality of people 3640 one or more instructions for segregating subject identifiers associated with the plurality of people in reference to at least one of the one or more applied comparisons 3650 information regarding quantity of cells or tissue removed or destroyed 3660 information regarding at least one dimension of cellular, tissue, or other material removal or destruction 3670 information regarding at least one depth, width, or breadth of cellular, tissue, or other material removal or destruction 3680 one or more instructions for segregating individual identifiers associated with the plurality of people in reference to at least one characteristic shared by two or more subjects of the plurality of people

FIG. 37

3700 A method comprising:

3710 accepting a first input associated with at least one characteristic of at least one biological tissue to be at least partially constructed or at least partially reconstructed;

3720 accepting a second input associated with at least one parameter of at least partially constructing or at least partially reconstructing the at least one biological tissue by administering one or more frozen particle compositions including at least one agent;

3730 wherein the at least one agent includes one or more of a therapeutic agent, adhesive agent, abrasive, reinforcement agent, explosive material, or biological remodeling agent 3740 wherein the administering one or more frozen particle compositions includes administering the one or more frozen particle compositions to at least one substrate 3750 wherein the at least one substrate includes one or more of a cell, tissue, organ, structure, or device 3760 processing results of the first input and the second input 3770 processing results of the first input and the second input includes electronically processing results of the first input and the second input 3780 electronically processing results of the first input and the second input by utilizing one or more of Gaussian smoothing, scaling, homomorphic filtering, parametric estimation techniques, Boolean operations, Monte Carlo simulations, wavelet based techniques, mirroring, smoothing, gradient weighted partial differential equation smoothing, NURBS, polygonal modeling, splines and patches modeling, algorithmic execution, logical decision-making, result prediction, or modification of a CAD design

FIG. 38

3810 wherein the first input includes one or more values related to the at least one characteristic of at least one biological tissue 3820 wherein the first input includes one or more spatial addresses associated with the at least one characteristic of at least one biological tissue 3830 wherein the first input includes one or more of x, y, or z coordinates associated with the at least one characteristic of at least one biological tissue 3840 wherein the at least one characteristic of at least one biological tissue to be at least partially constructed or at least partially reconstructed includes one or more of: morphological feature, anatomical feature, histological feature, tissue hierarchical level, scaffold feature, vascular structure feature, heterogenous tissue feature, mechanical feature, volumetric feature, geometric feature, volumetric representation, mechanical feature, deformation, kinematic feature, surface contour feature, cytometric feature, cell aggregation, cell growth, cell-cell interaction, cell-tissue interaction, biomimetic design, cell pattern, cell deposition, organ hierarchical level, tissue microstructure, cellular microstructure, cell junction feature, tissue junction feature, cell-tissue classification, hard tissue classification, soft tissue classification, tumor diagnosis, or other feature 3850 wherein the at least one characteristic of at least one biological tissue includes one or more of cellular type, cellular function, cellular size, cellular constitution, cellular architecture, cellular durability, cellular source, tissue type, tissue constitution, tissue size, tissue shape, tissue function, tissue architecture, tissue source, tissue durability, organ type, organ constitution, organ size, organ shape, organ function, organ architecture, organ source, or organ durability 3860 wherein the first input includes one or more temporal addresses associated with the at least one characteristic of at least one biological tissue

FIG. 39

3910 wherein the first input includes one or more values derived from at least one image of the at least one biological tissue 3920 wherein the at least one image includes one or more images acquired by one or more of optical coherence tomography, computer-assisted tomography scan, computed tomography, magnetic resonance imaging, positron-emission tomography scan, ultrasound, x-ray, electrical-impedance monitoring, microscopy, spectrometry, flow cytommetry, radioisotope imaging, thermal imaging, multiphoton calcium-imaging, photography, or *in silico* generation 3930 wherein the at least one biological tissue is located in at least one of *in situ, in vitro, in vivo, in utero, in planta, in silico,* or *ex vivo*

3940 wherein the at least one biological tissue is at least partially located in at least one subject 3950 further comprising accepting a third input associated with at least one feature of the at least one subject 3960 wherein the at least one feature of the at least one subject includes one or more of age, gender, genotype, phenotype, proteomic profile, or health condition

FIG. 40

4010 wherein the processing results of the first input and the second input includes determining at least one parameter of at least partially constructing or at least partially reconstructing the at least one biological tissue with one or more frozen particle compositions from one 4020 wherein the second input includes one or more values related to the at least one parameter of at least partially constructing or at least partially reconstructing the at least one biological tissue by administering one or more frozen particle compositions to the at least one substrate 4030 wherein the at least one parameter of at least partially constructing or at least partially reconstructing the at least one biological tissue includes one or more of: porosity of the at least one substrate, pore size of the at least one substrate, interconnectivity of the pores of the at least one substrate, transport properties of the at least one substrate, cell-tissue formation of the at least one substrate, mechanical strength of the at least one substrate, ability for attachment or distribution of the at least one agent included in the one or more frozen particle compositions to the at least one substrate, ability for attachment or distribution of one or more cells or tissues to the at least one substrate, facilitation of at least one nutrient, or tissue formation or tissue growth associated with the at least one substrate 4040 wherein the at least one parameter of at least partially constructing or at least partially reconstructing the at least one biological tissue by administering one or more frozen particle compositions includes one or more of: design of plot or model for administration of one or more frozen particle compositions, constitution of the one or more frozen particle compositions, formulation of the one or more frozen particle compositions, size of the one or more frozen particle compositions, shape of the one or more frozen particle compositions, angle of administration of the one or more frozen particle compositions, velocity of administration of the one or more frozen particle compositions, quantity of frozen particle compositions administered, rate of administration of more than one frozen particle composition, spatial location for administration of one or more frozen particle compositions, temporal location for administration of one or more frozen particle compositions, method of administration of one or more frozen particle compositions, timing of administration of one or more frozen particle compositions, modulation of administration of one or more frozen particle compositions, deposition of one or more frozen particle compositions, or rate of deposition of at least one agent

FIG. 41

4110 wherein the at least one parameter of at least partially constructing or at least partially reconstructing the at least one biological tissue by administering one or more frozen particle compositions includes at least one parameter relating to at least partially ablating or at least partially abrading one or more surfaces of the at least one biological tissue with the one or more frozen particle compositions 4120 wherein the at least one parameter of at least partially constructing or at least partially reconstructing the at least one biological tissue by administering one or more frozen particle compositions includes at least one parameter relating to administering at least one of a therapeutic agent, adhesive agent, biological remodeling agent, reinforcement agent, abrasive, or explosive material with the one or more frozen particle compositions 4130 wherein the one or more values related to the at least one parameter of constructing or reconstructing the at least one biological tissue includes one or more predictive values 4140 wherein the spatial location for administration of one or more frozen particle compositions includes one or more of x, y, or z coordinates 4150 wherein the processing results includes comparing at least one value related to the first input associated with the at least one characteristic of at least one biological tissue to be at least partially constructed or at least partially reconstructed with at least one value related to at least one image of a target biological tissue 4160 wherein the image of a target biological tissue includes an image of a similar biological tissue, or an image of a dissimilar biological tissue

FIG. 43

4310 wherein the processing results includes: comparing one or more values related to the one or more characteristics of the at least one biological tissue that are determined at two or more different times to obtain one or more characteristic comparisons; comparing one or more values related to the at least one parameter of at least partially constructing or at least partially reconstructing the at least one biological tissue at two or more different times to obtain one or more parameter comparisons; comparing the one or more characteristic comparisons with the one or more parameter comparisons to obtain one or more characteristic-characteristic/246parameter-parameter comparisons; and comparing the one or more characteristic-characteristic/246parameter-parameter comparisons to one or more substantially similar results obtained for one or more other at least partially constructed or at least partially reconstructed biological tissues 4320 wherein the administering one or more frozen particle compositions includes depositing the at least one agent on the at least one substrate

FIG. 44

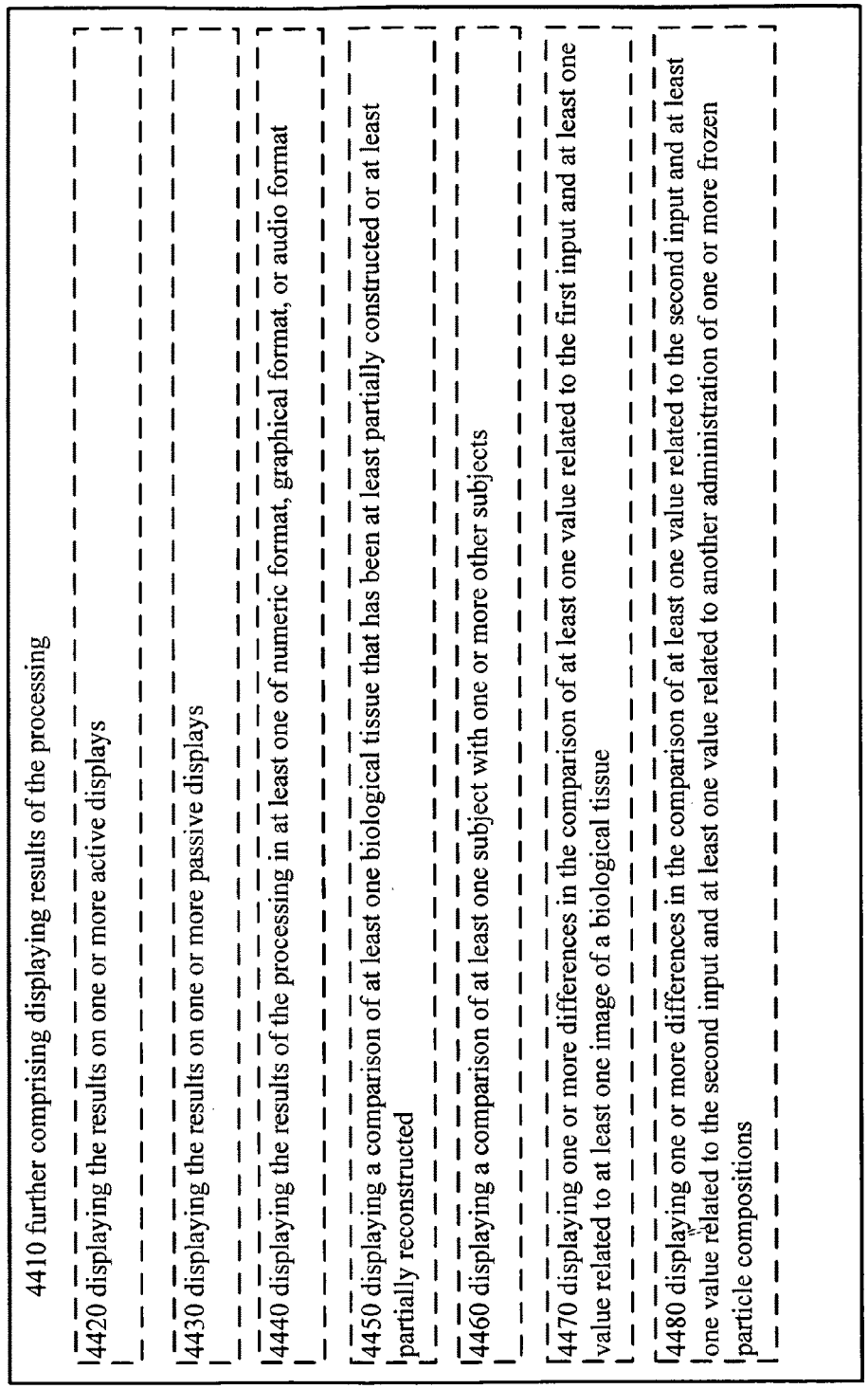

4410 further comprising displaying results of the processing 4420 displaying the results on one or more active displays 4430 displaying the results on one or more passive displays 4440 displaying the results of the processing in at least one of numeric format, graphical format, or audio format 4450 displaying a comparison of at least one biological tissue that has been at least partially constructed or at least partially reconstructed 4460 displaying a comparison of at least one subject with one or more other subjects 4470 displaying one or more differences in the comparison of at least one value related to the first input and at least one value related to at least one image of a biological tissue 4480 displaying one or more differences in the comparison of at least one value related to the second input and at least one value related to another administration of one or more frozen particle compositions

FIG. 46

4610 wherein the one or more frozen particle compositions includes one or more frozen particles of at least one of: hydrogen oxide, nitrogen, oxygen, air, helium, neon, argon, xenon, chlorine, bromine, carbon dioxide, acetone, ethyl acetate, dimethyl sulfoxide, dimethyl formamide, dioxane, tetrahydrofuran, acetonitrile, acetic acid, n-butanol, isopropanol, n-propanol, hexamethylphosphorotriamide, perfluorohydrocarbon, methanol, ethanol, tert-butyl alcohol, formic acid, hydrogen fluoride, ammonia, benzene, carbon tetrachloride, acetonitrile, hexane, dichloromethane, methylene chloride, carboxylic acid, saline, standard saline citrate, methane, toluene, chloroform, polyethylene glycol, acetic acid, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, methane, or diethyl ether.

4620 wherein the at least one agent includes one or more of an adhesive agent, therapeutic agent, reinforcement agent, abrasive, explosive material, or biological remodeling agent 4630 wherein at least one of the adhesive agent, therapeutic agent, reinforcement agent, abrasive, explosive material, or biological remodeling agent includes at least one of an organic or inorganic small molecule, clathrate or caged compound, protocell, coacervate, microsphere, Janus particle, proteinoid, laminate, helical rod, liposome, macroscopic tube, niosome, sphingosome, toroid, vesicular tube, vesicle, small unilamellar vesicle, large unilamellar vesicle, large multilamellar vesicle, multivesicular vesicle, lipid layer, lipid bilayer, micelle, organelle, cell, membrane, nucleic acid, peptide, polypeptide, protein, oligosaccharide, polysaccharide, glycopeptide, glycolipid, sphingolipid, glycosphingolipid, glycoprotein, peptidoglycan, lipid, carbohydrate, metalloprotein, proteoglycan, chromosome, cell nucleus, acid, base, buffer, protic solvent, aprotic solvent, nitric oxide, nitric oxide synthase, nitrous oxide, amino acid, micelle, polymer, bone cement, copolymer, cell receptor, adhesion molecule, cytokine, chemokine, immunoglobulin, antibody, antigen, platelet, extracellular matrix, blood, plasma, cell ligand, zwitterionic material, cationic material, oligonucleotide, nanotube, or piloxymer

FIG. 47

4710 wherein the one or more explosive materials include at least one of a carbonate, carbon dioxide, nitroglycerine, acid, base, epoxy, acrylic polymer or copolymer, acrylamide polymer or copolymer, urethane, hypoxyapatite, or reactive metal 4720 wherein the at least one adhesive agent includes one or more of an acrylic polymer or copolymer, acrylamide polymer or copolymer polymer or copolymer, acrylamide polymer or copolymer, polyacrylic acid, epoxy, urethane, gum arabic, polyester, polyhydroxyalkanoate, poly(L-lactic acid), polyglycolide, polylactic acid, polyether, polyol, polyvinylpyrrolidone, pyroxylin, polymethylacrylate-isobutene-monoisopropylmaleate, siloxane polymer, polylactic-co-glycolic-acid, poly-3-hydroxybutyrate, poly-4-hydroxybutyrate, polyhydroxyvalerate, polyhydroxyhexanoate, polyhydroxyoctanoate, polycaprolactone, poly (e-caprolactone), sialyl Lewis$^x$, heme group, hemoglobin, healon, carboxymethylcellulose, hydroxyapatite, silicone, cadherin, integrin, hydroxyapatite, polyelectrolyte, maleic polyelectrolyte, cellulose, resilin, cyanoacrylate, isocyanate, 2-octyl cyanoacrylate, 2-butyl-n-cyanoacrylate, n-butyl-2-cyanoacrylate, butyl-2-cyanoacrylate, methyl 2-cyanoacrylate, polyisohexylcyanoacrylate, fibrin, thrombin, fibrinogen, hyaluronate, chitin, Factor XIII, Factor XII, silk, nylon, collagen, glycosaminoglycan, selectin, polyurethane, methacrylate, or polysulfide, polyanhydride, polydioxanone, poly-p-dioxanone, silicone, albumin, glutaraldehyde, polyethylene glycol, or gelatin 4730 wherein the one or more reinforcement agents include one or more of polyaramid, vinylester matrix, metal, ceramic, fiberglass, cellulose, broad carbide, aromatic polyamide, nylon, silk, rayon, acetate, modacrylic, olefin, acrylic, polyester, aromatic polyester, poly-lactic acid, vinyon, saran, spandex, vinalon, aromatic nylon, vinylidene chloride, modal, polybenzimidazole, sulfur, lyocell, orlon, zylon, high-performance polyethylene, polypyridobenzimidazole, vectran, acrylonitrile rubber, glass, copper, iron, steel, sodium, potassium, calcium, zinc, manganese, carbon, magnesium, silicon, silica, frozen hydrogen oxide ice, plant matter, animal matter, or mineral matter

FIG. 48

4810 wherein the therapeutic agent includes at least one of an anti-tumor agent, antimicrobial agent, anti-viral agent, analgesic, antiseptic, anesthetic, diagnostic agent, anti-inflammatory agent, vaccine, cell growth inhibitor, cell growth promoter, immunogen, antigen, radioactive agent, apoptotic promoting factor, enzymatic agent, angiogenic factor, anti-angiogenic factor, hormone, vitamin, mineral, nutraceutical, cytokine, chemokine, probiotic, coagulant, anti-coagulant, phage, prodrug, prebiotic, blood sugar stabilizer, smooth muscle cell activator, epinephrine, adrenaline, neurotoxin, neuro-muscular toxin, Botulinum toxin type A, microbial cell or component thereof, or virus or component thereof 4820 wherein the at least one biological remodeling agent includes one or more of a blood cell, chondrocyte, endothelial cell, hepatocyte, keratinocyte, myocyte, osteoblast, osteoclast, osteocyte, mesenchymal cell, stem cell, progenitor cell, or fibroblast 4830 wherein the at least one biological remodeling agent includes one or more of calcium phosphate, albumin, cytokine, pegylated cytokine, bone, cartilage, globulin, fibrin, thrombin, glutaraldehyde-crosslinked pericardium, hide powder, hyaluronic acid, hydroxylapatite, keratin, ligament, nitinol, nucleic acid polymers, polyethylene, polyethylene glycol, polyethylene glycol diacrylate, polyethylene terephthalate fiber, polyglycol, polylactate, polytetrafluoroethylene, polylactic acid, polyglycolic acid, polycaprolactone, PURAMATRIX™ self-assembly peptide hydrogel fibers, linear aliphatic polyester, tendon, fibrinogen, hyaluronate, chitin, chitosan, methylcellulose, alginate, hyaluronic acid, agarose, cellulose, polyaldehyde gluronate, Factor XIII, Factor XII, silk, nylon, collagen, silicone, polyurethane, ceramic powder, elastin, pectin, wax, glycosaminoglycan, poly(α-hydroxyacid), selectin, glutaraldehyde, hydrophobic non-glycosylated protein, hydrogel, peptide hydrogel, or gelatin 4840 wherein the at least one biological remodeling agent includes one or more of Type I collagen, Type II collagen, Type III collagen, Type VII collagen, Type X collagen, elastin fibers, or soluble elastin 4850 wherein the at least one biological remodeling agent is included as part of a carrier that assists in synthesis or activation of the at least one biological remodeling agent

FIG. 49

4900 A method comprising:

4910 accepting input associated with at least one parameter of at least partially constructing or at least partially reconstructing at least one biological tissue by administering one or more frozen particle compositions;

4920 administering one or more frozen particle compositions including at least one agent;

4930 wherein the at least one agent includes one or more of a therapeutic agent, adhesive agent, abrasive, reinforcement agent, explosive material, or biological remodeling agent 4940 evaluating the at least one biological tissue for one or more indicators related to deposition of at least one agent, tissue formation, or tissue growth;

4950 wherein the evaluating at least one biological tissue for one or more indicators includes evaluating at least one of an assay, image, or gross assessment of the at least one biological tissue prior to, during, or subsequent to at least one administration of the one or more frozen particle compositions 4960 wherein the assay includes at least one technique that includes spectroscopy, microscopy, electrochemical detection, polynucleotide detection, histological examination, biopsy analysis, fluorescence resonance energy transfer, electron transfer, enzyme assay, electrical conductivity, isoelectric focusing, chromatography, immunoprecipitation, immunoseparation, aptamer binding, filtration, electrophoresis, immunoassay, or radioactive assay

FIG. 50

5020 wherein the image includes at least one image acquired by one or more of optical coherence tomography, computer-assisted tomography scan, computed tomography, magnetic resonance imaging, positron-emission tomography scan, ultrasound, x-ray, electrical-impedance monitoring, microscopy, spectrometry, flow cytometry, radioisotope imaging, thermal imaging, multiphoton calcium-imaging, photography, or *in silico* generation 5030 wherein the one or more indicators of tissue formation or growth include at least one of cell migration, cell attachment, cell retention, cell differentiation, cell proliferation, apoptosis, diffusion of materials, angiogenesis, nucleic acid expression, protein translation, protein modification, carbohydrate production, carbohydrate secretion, fat production, fat secretion, or protein secretion 5040 wherein the input associated with at least one parameter of at least partially constructing or at least partially reconstructing the at least one biological tissue by administering one or more frozen particle compositions includes one or more of: constitution of the one or more frozen particle compositions, formulation of the one or more frozen particle compositions, size of the one or more frozen particle compositions, shape of the one or more frozen particle compositions, angle of administration of the one or more frozen particle compositions, velocity of administration of the one or more frozen particle compositions, quantity of frozen particle compositions administered, rate of administration of more than one frozen particle composition, spatial location for administration of one or more frozen particle compositions, temporal location for administration of one or more frozen particle compositions, method of administration of one or more frozen particle compositions, timing of administration of one or more frozen particle compositions, modulation of administration of one or more frozen particle compositions, deposition of one or more frozen particle compositions, or rate of deposition of at least one agent

FIG. 51

5110 transmitting one or more signals that include information related to the accepting input and information related to the evaluating the at least one biological tissue 5120 wherein the transmitting one or more signals includes transmitting one or more signals associated with selection of one or more frozen particle compositions for administration 5130 wherein the transmitting one or more signals includes transmitting one or more signals associated with selection of one or more of a biological remodeling agent, adhesive agent, abrasive, therapeutic agent, reinforcement agent, or explosive material associated with the one or more frozen particle compositions 5140 wherein the administering one or more frozen particle compositions includes administering the one or more frozen particle compositions to at least one substrate 5150 wherein the at least one substrate includes one or more of a cell, tissue, organ, structure, or device 5160 wherein the one or more frozen particle compositions include one or more frozen particles of at least one of: hydrogen oxide, nitrogen, oxygen, air, helium, neon, argon, xenon, chlorine, bromine, carbon dioxide, acetone, ethyl acetate, dimethyl sulfoxide, dimethyl formamide, dioxane, tetrahydrofuran, acetonitrile, acetic acid, n-butanol, isopropanol, n-propanol, hexamethylphosphorotriamide, perfluorohydrocarbon, methanol, ethanol, tert-butyl alcohol, formic acid, hydrogen fluoride, ammonia, benzene, carbon tetrachloride, acetonitrile, hexane, dichloromethane, methylene chloride, carboxylic acid, saline, standard saline citrate, methane, toluene, chloroform, polyethylene glycol, acetic acid, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, methane, or diethyl ether.

FIG. 52

5210 wherein the at least one agent includes one or more of an adhesive agent, therapeutic agent, reinforcement agent, abrasive, explosive material, or biological remodeling agent 5220 wherein the adhesive agent, therapeutic agent, reinforcement agent, abrasive, explosive material, or biological remodeling agent includes at least one of an organic or inorganic small molecule, clathrate or caged compound, protocell, coacervate, microsphere, Janus particle, proteinoid, laminate, helical rod, liposome, macroscopic tube, niosome, sphingosome, toroid, vesicular tube, vesicle, small unilamellar vesicle, large unilamellar vesicle, large multilamellar vesicle, multivesicular vesicle, lipid layer, lipid bilayer, micelle, organelle, cell, membrane, nucleic acid, peptide, polypeptide, protein, oligosaccharide, polysaccharide, glycopeptide, glycolipid, sphingolipid, glycosphingolipid, glycoprotein, peptidoglycan, lipid, carbohydrate, metalloprotein, proteoglycan, chromosome, cell nucleus, acid, base, buffer, protic solvent, aprotic solvent, nitric oxide, nitric oxide synthase, nitrous oxide, amino acid, micelle, polymer, bone cement, copolymer, cell receptor, adhesion molecule, cytokine, chemokine, immunoglobulin, antibody, antigen, platelet, extracellular matrix, blood, plasma, cell ligand, zwitterionic material, cationic material, oligonucleotide, nanotube, or piloxymer 5230 wherein the one or more explosive materials include at least one of a carbonate, carbon dioxide, nitroglycerine, acid, base, epoxy, acrylic polymer or copolymer, acrylamide polymer or copolymer, urethane, hypoxyapatite, or reactive metal 5240 wherein the at least one adhesive agent includes one or more of an acrylic polymer or copolymer, acrylamide polymer or copolymer polymer or copolymer, acrylamide polymer or copolymer, polyacrylic acid, epoxy, urethane, gum arabic, polyester, polyhydroxyalkanoate, poly(L-lactic acid), polyglycolide, polylactic acid, polyether, polyol, polyvinylpyrrolidone, pyroxylin, polymethylacrylate-isobutene-monoisopropylmaleate, siloxane polymer, polylactic-co-glycolic-acid, poly-3-hydroxybutyrate, poly-4-hydroxybutyrate, polyhydroxyvalerate, polyhydroxyhexanoate, polydyroxyoctanoate, polycaprolactone, poly (e-caprolactone), sialyl Lewis$^x$, heme group, hemoglobin, healon, carboxymethylcellulose, hydroxyapatite, silicone, cadherin, integrin, hydroxyapatite, polyelectrolyte, maleic polyelectrolyte, cellulose, resilin, cyanoacrylate, isocyanate, 2-octyl cyanoacrylate, 2-butyl-n-cyanoacrylate, n-butyl-2-cyanoacrylate, butyl-2-cyanoacrylate, methyl 2-cyanoacrylate, polyisohexylcyanoacrylate, fibrin, thrombin, fibrinogen, hyaluronate, chitin, Factor XIII, Factor XII, silk, nylon, collagen, glycosaminoglycan, selectin, polyurethane, methacrylate, or polysulfide, polyanhydride, polydioxanone, poly-p-dioxanone, silicone, albumin, glutaraldehyde, polyethylene glycol, or gelatin

FIG. 53

5310 wherein the one or more reinforcement agents include one or more of polyaramid, vinylester matrix, metal, ceramic, fiberglass, cellulose, broad carbide, aromatic polyamide, nylon, silk, rayon, acetate, modacrylic, olefin, acrylic, polyester, aromatic polyester, poly-lactic acid, vinyon, saran, spandex, vinalon, aromatic nylon, vinylidene chloride, modal, polybenzimidazole, sulfur, lyocell, orlon, zylon, high-performance polyethylene, polypyridobenzimidazole, vectran, acrylonitrile rubber, glass, copper, iron, steel, sodium, potassium, calcium, zinc, manganese, carbon, magnesium, silicon, silica, frozen hydrogen oxide ice, plant matter, animal matter, or mineral matter 5320 wherein the therapeutic agent includes at least one of an anti-tumor agent, antimicrobial agent, anti-viral agent, analgesic, antiseptic, anesthetic, diagnostic agent, anti-inflammatory agent, vaccine, cell growth inhibitor, cell growth promoter, immunogen, antigen, radioactive agent, apoptotic promoting factor, enzymatic agent, angiogenic factor, anti-angiogenic factor, hormone, vitamin, mineral, nutraceutical, cytokine, chemokine, probiotic, coagulant, anti-coagulant, phage, prodrug, prebiotic, blood sugar stabilizer, smooth muscle cell activator, epinephrine, adrenaline, neurotoxin, neuro-muscular toxin, Botulinum toxin type A, microbial cell or component thereof, or virus or component thereof 5330 wherein the at least one biological remodeling agent includes one or more of a blood cell, chondrocyte, endothelial cell, hepatocyte, keratinocyte, myocyte, osteoblast, osteoclast, osteocyte, mesenchymal cell, stem cell, progenitor cell, or fibroblast 5340 wherein the at least one biological remodeling agent includes one or more of calcium phosphate, albumin, cytokine, pegylated cytokine, bone, cartilage, globulin, fibrin, thrombin, glutaraldehyde-crosslinked pericardium, hide powder, hyaluronic acid, hydroxylapatite, keratin, ligament, nitinol, nucleic acid polymers, polyethylene, polyethylene glycol, polyethylene glycol diacrylate, polyethylene terephthalate fiber, polyglycol, polylactate, polytetrafluoroethylene, polylactic acid, polyglycolic acid, polycaprolactone, PURAMATRIX™ self-assembly peptide hydrogel fibers, linear aliphatic polyester, tendon, fibrinogen, hyaluronate, chitin, chitosan, methylcellulose, alginate, hyaluronic acid, agarose, cellulose, polyaldehyde gluronate, Factor XIII, Factor XII, silk, nylon, collagen, silicone, polyurethane, ceramic powder, elastin, pectin, wax, glycosaminoglycan, poly(α-hydroxyacid), selectin, glutaraldehyde, hydrophobic non-glycosylated protein, hydrogel, peptide hydrogel, or gelatin 5350 wherein the at least one biological remodeling agent includes one or more of Type I collagen, Type II collagen, Type III collagen, Type VII collagen, Type X collagen, elastin fibers, or soluble elastin

FIG. 54

5400 A method comprising:

5410 receiving one or more signals that include information related to accepting input associated with at least one parameter of at least partially constructing or at least partially reconstructing the at least one biological tissue by administering one or more frozen particle compositions 5420 receiving one or more signals that include information related to evaluating the at least one biological tissue for one or more indicators of tissue formation or growth;

5430 processing the information related to the input associated with at least one parameter of at least partially constructing or at least partially reconstructing the at least one biological tissue and the information related to the evaluating the at least one biological tissue 5440 wherein the evaluating at least one biological tissue for one or more indicators includes evaluating at least one of an assay, image, or gross assessment of the at least one biological tissue prior to, during, or subsequent to at least one administration of the one or more frozen particle compositions 5450 wherein the assay includes at least one technique that includes spectroscopy, microscopy, electrochemical detection, polynucleotide detection, histological examination, biopsy analysis, fluorescence resonance energy transfer, electron transfer, enzyme assay, electrical conductivity, isoelectric focusing, chromatography, immunoprecipitation, immunoseparation, aptamer binding, filtration, electrophoresis, immunoassay, or radioactive assay 5460 wherein the image includes at least one image acquired by one or more of optical coherence tomography, computer-assisted tomography scan, computed tomography, magnetic resonance imaging, positron-emission tomography scan, ultrasound, x-ray, electrical-impedance monitoring, microscopy, spectrometry, flow cytometry, radioisotope imaging, thermal imaging, multiphoton calcium-imaging, photography, or *in silico* generation

FIG. 55

5510 wherein the one or more indicators of tissue formation or growth include at least one of cell migration, cell attachment, cell retention, cell differentiation, cell proliferation, apoptosis, diffusion of materials, angiogenesis, nucleic acid expression, protein translation, protein modification, carbohydrate production, carbohydrate secretion, fat production, fat secretion, or protein secretion 5520 wherein the input associated with at least one parameter of at least partially constructing or at least partially reconstructing the at least one biological tissue by administering one or more frozen particle compositions includes one or more of: constitution of the one or more frozen particle compositions, formulation of the one or more frozen particle compositions, size of the one or more frozen particle compositions, shape of the one or more frozen particle compositions, angle of administration of the one or more frozen particle compositions, velocity of administration of the one or more frozen particle compositions, quantity of frozen particle compositions administered, rate of administration of more than one frozen particle composition, spatial location for administration of one or more frozen particle compositions, temporal location for administration of one or more frozen particle compositions, method of administration of one or more frozen particle compositions, timing of administration of one or more frozen particle compositions, modulation of administration of one or more frozen particle compositions, deposition of one or more frozen particle compositions, or rate of deposition of at least one agent 5530 wherein the receiving one or more signals includes receiving one or more signals associated with selection of one or more frozen particle compositions for administration 5540 wherein the receiving one or more signals includes receiving one or more signals associated with the selection of at least one of a biological remodeling agent, adhesive agent, abrasive, therapeutic agent, reinforcement agent, or explosive material associated with the one or more frozen particle compositions

FIG. 56

5610 wherein the administering one or more frozen particle compositions includes administering the one or more frozen particle compositions to at least one substrate 5620 wherein the at least one substrate includes one or more of a cell, tissue, organ, structure, or device 5630 wherein the one or more frozen particle compositions includes one or more frozen particles of at least one of: hydrogen oxide, nitrogen, oxygen, air, helium, neon, argon, xenon, chlorine, bromine, carbon dioxide, acetone, ethyl acetate, dimethyl sulfoxide, dimethyl formamide, dioxane, tetrahydrofuran, acetonitrile, acetic acid, n-butanol, isopropanol, n-propanol, hexamethylphosphorotriamide, perfluorohydrocarbon, methanol, ethanol, tert-butyl alcohol, formic acid, hydrogen fluoride, ammonia, benzene, carbon tetrachloride, acetonitrile, hexane, dichloromethane, methylene chloride, carboxylic acid, saline, standard saline citrate, methane, toluene, chloroform, polyethylene glycol, acetic acid, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, methane, or diethyl ether.

5640 wherein the at least one agent includes one or more of an adhesive agent, therapeutic agent, reinforcement agent, abrasive, explosive material, or biological remodeling agent 5650 wherein the adhesive agent, therapeutic agent, reinforcement agent, abrasive, explosive material, or biological remodeling agent includes at least one of an organic or inorganic small molecule, clathrate or caged compound, protocell, coacervate, microsphere, Janus particle, proteinoid, laminate, helical rod, liposome, macroscopic tube, niosome, sphingosome, toroid, vesicular tube, vesicle, small unilamellar vesicle, large unilamellar vesicle, large multilamellar vesicle, multivesicular vesicle, lipid layer, lipid bilayer, micelle, organelle, cell, membrane, nucleic acid, peptide, polypeptide, protein, oligosaccharide, polysaccharide, glycopeptide, glycolipid, sphingolipid, glycosphingolipid, glycoprotein, peptidoglycan, lipid, carbohydrate, metalloprotein, proteoglycan, chromosome, cell nucleus, acid, base, buffer, protic solvent, aprotic solvent, nitric oxide, nitric oxide synthase, nitrous oxide, amino acid, micelle, polymer, bone cement, copolymer, cell receptor, adhesion molecule, cytokine, chemokine, immunoglobulin, antibody, antigen, platelet, extracellular matrix, blood, plasma, cell ligand, zwitterionic material, cationic material, oligonucleotide, nanotube, or piloxymer

FIG. 57

5710 wherein the one or more explosive materials include at least one of a carbonate, carbon dioxide, nitroglycerine, acid, base, epoxy, acrylic polymer or copolymer, acrylamide polymer or copolymer, urethane, hypoxyapatite, or reactive metal 5720 wherein the at least one adhesive agent includes one or more of an acrylic polymer or copolymer, acrylamide polymer or copolymer polymer or copolymer, acrylamide polymer or copolymer, polyacrylic acid, epoxy, urethane, gum arabic, polyester, polyhydroxyalkanoate, poly(L-lactic acid), polyglycolide, polylactic acid, polyether, polyol, polyvinylpyrrolidone, pyroxylin, polymethylacrylate-isobutene-monoisopropylmaleate, siloxane polymer, polylactic-co-glycolic-acid, poly-3-hydroxybutyrate, poly-4-hydroxybutyrate, polyhydroxyvalerate, polydydroxyhexanoate, polydyroxyoctanoate, polycaprolactone, poly (e-caprolactone), sialyl Lewis$^x$, heme group, hemoglobin, healon, carboxymethylcellulose, hydroxyapatite, silicone, cadherin, integrin, hydroxyapatite, polyelectrolyte, maleic polyelectrolyte, cellulose, resilin, cyanoacrylate, isocyanate, 2-octyl cyanoacrylate, 2-butyl-n-cyanoacrylate, n-butyl-2-cyanoacrylate, butyl-2-cyanoacrylate, methyl 2-cyanoacrylate, polyisohexylcyanoacrylate, fibrin, thrombin, fibrinogen, hyaluronate, chitin, Factor XIII, Factor XII, silk, nylon, collagen, glycosaminoglycan, selectin, polyurethane, methacrylate, or polysulfide, polyanhydride, polydioxanone, poly-p-dioxanone, silicone, albumin, glutaraldehyde, polyethylene glycol, or gelatin 5730 wherein the one or more reinforcement agents include one or more of polyaramid, vinylester matrix, metal, ceramic, fiberglass, cellulose, broad carbide, aromatic polyamide, nylon, silk, rayon, acetate, modacrylic, olefin, acrylic, polyester, aromatic polyester, poly-lactic acid, vinyon, saran, spandex, vinalon, aromatic nylon, vinylidene chloride, modal, polybenzimidazole, sulfur, lyocell, orlon, zylon, high-performance polyethylene, polypyridobenzimidazole, vectran, acrylonitrile rubber, glass, copper, iron, steel, sodium, potassium, calcium, zinc, manganese, carbon, magnesium, silicon, silica, frozen hydrogen oxide ice, plant matter, animal matter, or mineral matter 5740 wherein the therapeutic agent includes at least one of an anti-tumor agent, antimicrobial agent, anti-viral agent, analgesic, antiseptic, anesthetic, diagnostic agent, anti-inflammatory agent, vaccine, cell growth inhibitor, cell growth promoter, immunogen, antigen, radioactive agent, apoptotic promoting factor, enzymatic agent, angiogenic factor, anti-angiogenic factor, hormone, vitamin, mineral, nutraceutical, cytokine, chemokine, probiotic, coagulant, anti-coagulant, phage, prodrug, prebiotic, blood sugar stabilizer, smooth muscle cell activator, epinephrine, adrenaline, neurotoxin, neuro-muscular toxin, Botulinum toxin type A, microbial cell or component thereof, or virus or component thereof

FIG. 58

[5810 wherein the at least one biological remodeling agent includes one or more of a blood cell, chondrocyte, endothelial cell, hepatocyte, keratinocyte, myocyte, osteoblast, osteoclast, osteocyte, mesenchymal cell, stem cell, progenitor cell, or fibroblast

[5820 wherein the at least one biological remodeling agent includes one or more of calcium phosphate, albumin, cytokine, pegylated cytokine, bone, cartilage, globulin, fibrin, thrombin, glutaraldehyde-crosslinked pericardium, hide powder, hyaluronic acid, hydroxylapatite, keratin, ligament, nitinol, nucleic acid polymers, polyethylene, polyethylene glycol, polyethylene glycol diacrylate, polyethylene terephthalate fiber, polyglycol, polylactate, polytetrafluoroethylene, polylactic acid, polyglycolic acid, polycaprolactone, PURAMATRIX™ self-assembly peptide hydrogel fibers, linear aliphatic polyester, tendon, fibrinogen, hyaluronate, chitin, chitosan, methylcellulose, alginate, hyaluronic acid, agarose, cellulose, polyaldehyde gluronate, Factor XIII, Factor XII, silk, nylon, collagen, silicone, polyurethane, ceramic powder, elastin, pectin, wax, glycosaminoglycan, poly(α-hydroxyacid), selectin, glutaraldehyde, hydrophobic non-glycosylated protein, hydrogel, peptide hydrogel, or gelatin

[5830 wherein the at least one biological remodeling agent includes one or more of Type I collagen, Type II collagen, Type III collagen, Type VII collagen, Type X collagen, elastin fibers, or soluble elastin

[5840 wherein the at least one biological remodeling agent is included as part of a carrier that assists in synthesis or activation of the at least one biological remodeling agent

FIG. 59

5900 A method comprising:

5910 comparing information regarding at least one parameter for at least partially constructing or at least partially reconstructing at least one biological tissue of a subject by administering one or more frozen particle compositions to the at least one subject and information regarding at least one clinical outcome following receipt by the at least one subject of one or more frozen particle compositions;

5920 providing output information 5930 wherein the output information is based on the comparison 5940 further comprising determining at least one statistical correlation 5950 further comprising counting the occurrence of at least one clinical outcome 5960 wherein the information regarding at least one parameter of at least partially constructing or at least partially reconstructing at least one biological tissue of a subject includes information regarding quantity of cells or tissue at least partially constructed or at least partially reconstructed 5970 wherein the information regarding at least one parameter of at least partially constructing or at least partially reconstructing at least one biological tissue of a subject includes information regarding at least one cellular or tissue source 5980 wherein the information regarding at least one parameter of at least partially constructing or at least partially reconstructing at least one biological tissue of a subject includes information regarding at least one abnormal cellular or tissue source 5990 wherein the information regarding at least one parameter of at least partially constructing or at least partially reconstructing at least one biological tissue of a subject includes information regarding at least one type of cell or tissue

FIG. 60

6010 wherein the at least one agent includes one or more of an adhesive agent, therapeutic agent, reinforcement agent, abrasive, explosive material, or biological remodeling agent 6020 wherein the information regarding at least one parameter of at least partially constructing or at least partially reconstructing at least one biological tissue of a subject includes information regarding at least one dimension of at least one agent deposited 6030 wherein the information regarding at least one parameter of at least partially constructing or at least partially reconstructing at least one biological tissue of at least one subject includes information regarding at least one dimension of at least one depth, width, or breadth of cellular, tissue, or other material removal or destruction 6040 wherein the information regarding at least one clinical outcome following receipt by the at least one subject of one or more frozen particle compositions includes information regarding two or more subjects with one or more common attributes 6050 wherein the one or more common attributes include one or more of genetic attributes, mental attributes, proteomic attributes, phenotypic attributes, or psychological attributes 6060 wherein the one or more common attributes include one or more of height, weight, medical diagnosis, familial background, results on one or more medical tests, ethnic background, body mass index, age, presence or absence of at least one disease or condition, species, ethnicity, race, allergies, gender, thickness of tissue, blood vessel condition, hair or fur condition, skin condition, tissue condition, muscle condition, organ condition, nerve condition, brain condition, presence or absence of at least one biological, chemical, or therapeutic agent in the subject, pregnancy status, lactation status, genetic profile, proteomic profile, partial or whole genetic sequence, partial or whole proteomic sequence, medical condition, medical history, or blood condition

FIG. 61

6110 wherein the output information includes at least one of a response signal, comparison code, comparison plot, diagnostic code, treatment code, test code, code indicative of at least one treatment received, code indicative of at least one prescribed treatment step, code indicative of at least one vaccination administered, code indicative of at least one therapeutic agent administered, code indicative of at least one diagnostic agent administered, code indicative of at least one interaction of an administered agent and at least one biological or chemical agent in the subject; a code indicative of at least one dispertion or location of at least one administered agent; code indicative of at least one detection material administered; code indicative of the depth of penetration of an administered agent, code indicative of the depth of deposition of an administered agent, or a code indicative of the condition of at least one location of an administered frozen particle composition 6120 wherein receipt by the at least one subject of one or more frozen particle compositions is pursuant to at least one clinical trial 6130 further comprising determining at least one correlation before the administration of the one or more frozen particle compositions to the at least one subject 6140 further comprising creating at least one inclusion criterion and at least one exclusion criterion for a clinical trial involving the one or more frozen particle compositions 6150 further comprising suggesting the inclusion of one or more of the at least one subject in at least one clinical trial 6160 further comprising suggesting the exclusion of one or more of the at least one subject in at least one clinical trial

FIG. 62

6210 further comprising using one or more of the at least one correlation to predict at least one clinical outcome regarding at least one second subject 6220 wherein the at least one second subject has not received the one or more frozen particle compositions 6230 further comprising predicting at least one clinical outcome involving the at least one second subject, wherein the at least one second subject is a plurality of people; and segregating subject identifiers associated with the plurality of people in reference to the predicted at least one clinical outcome 6240 further comprising determining the eligibility of the at least one second subject for the at least one clinical trial 6250 wherein the one or more frozen particle compositions includes one or more frozen particles of at least one of: hydrogen oxide, nitrogen, oxygen, air, helium, neon, argon, xenon, chlorine, bromine, carbon dioxide, polyethylene glycol, hydrogen oxide, nitrogen, oxygen, air, helium, neon, argon, xenon, chlorine, bromine, carbon dioxide, acetone, ethyl acetate, dimethyl sulfoxide, dimethyl formamide, dioxane, tetrahydrofuran, acetonitrile, acetic acid, n-butanol, isopropanol, n-propanol, hexamethylphosphorotriamide, perfluorohydrocarbon, methanol, ethanol, tert-butyl alcohol, formic acid, hydrogen fluoride, ammonia, benzene, carbon tetrachloride, acetonitrile, hexane, dichloromethane, methylene chloride, carboxylic acid, saline, standard saline citrate, methane, toluene, chloroform, polyethylene glycol, acetic acid, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, methane, or diethyl ether.

FIG. 63

6310 wherein the at least one agent includes one or more of an adhesive agent, therapeutic agent, reinforcement agent, abrasive, explosive material, or biological remodeling agent 6320 wherein the adhesive agent, therapeutic agent, reinforcement agent, abrasive, explosive material, or biological remodeling agent includes at least one of an organic or inorganic small molecule, clathrate or caged compound, protocell, coacervate, microsphere, Janus particle, proteinoid, laminate, helical rod, liposome, macroscopic tube, niosome, sphingosome, toroid, vesicular tube, vesicle, small unilamellar vesicle, large unilamellar vesicle, large multilamellar vesicle, multivesicular vesicle, lipid layer, lipid bilayer, micelle, organelle, cell, membrane, nucleic acid, peptide, polypeptide, protein, oligosaccharide, polysaccharide, glycopeptide, glycolipid, sphingolipid, glycosphingolipid, glycoprotein, peptidoglycan, lipid, carbohydrate, metalloprotein, proteoglycan, chromosome, cell nucleus, acid, base, buffer, protic solvent, aprotic solvent, nitric oxide, nitric oxide synthase, nitrous oxide, amino acid, micelle, polymer, bone cement, copolymer, cell receptor, adhesion molecule, cytokine, chemokine, immunoglobulin, antibody, antigen, platelet, extracellular matrix, blood, plasma, cell ligand, zwitterionic material, cationic material, oligonucleotide, nanotube, or piloxymer 6330 wherein the one or more explosive materials include at least one of a carbonate, carbon dioxide, nitroglycerine, acid, base, epoxy, acrylic polymer or copolymer, acrylamide polymer or copolymer, urethane, hypoxyapatite, or reactive metal 6340 wherein the at least one adhesive agent includes one or more of an acrylic polymer or copolymer, acrylamide polymer or copolymer polymer or copolymer, acrylamide polymer or copolymer, polyacrylic acid, epoxy, urethane, gum arabic, polyester, polyhydroxyalkanoate, poly(L-lactic acid), polyglycolide, polylactic acid, polyether, polyol, polyvinylpyrrolidone, pyroxylin, polymethylacrylate-isobutene-monoisopropylmaleate, siloxane polymer, polylactic-co-glycolic-acid, poly-3-hydroxybutyrate, poly-4-hydroxybutyrate, polyhydroxyvalerate, polyhydroxyhexanoate, polydroxyoctanoate, polycaprolactone, poly (e-caprolactone), sialyl Lewis$^x$, heme group, hemoglobin, healon, carboxymethylcellulose, hydroxyapatite, silicone, cadherin, integrin, hydroxyapatite, polyelectrolyte, maleic polyelectrolyte, resilin, cyanoacrylate, isocyanate, 2-octyl cyanoacrylate, 2-butyl-n-cyanoacrylate, n-butyl-2-cyanoacrylate, butyl-2-cyanoacrylate, methyl 2-cyanoacrylate, polyisohexylcyanoacrylate, fibrin, thrombin, fibrinogen, hyaluronate, chitin, Factor XIII, Factor XII, silk, nylon, collagen, glycosaminoglycan, selectin, polyurethane, methacrylate, or polysulfide, polyanhydride, polydioxanone, poly-p-dioxanone, silicone, albumin, glutaraldehyde, polyethylene glycol, or gelatin

FIG. 64

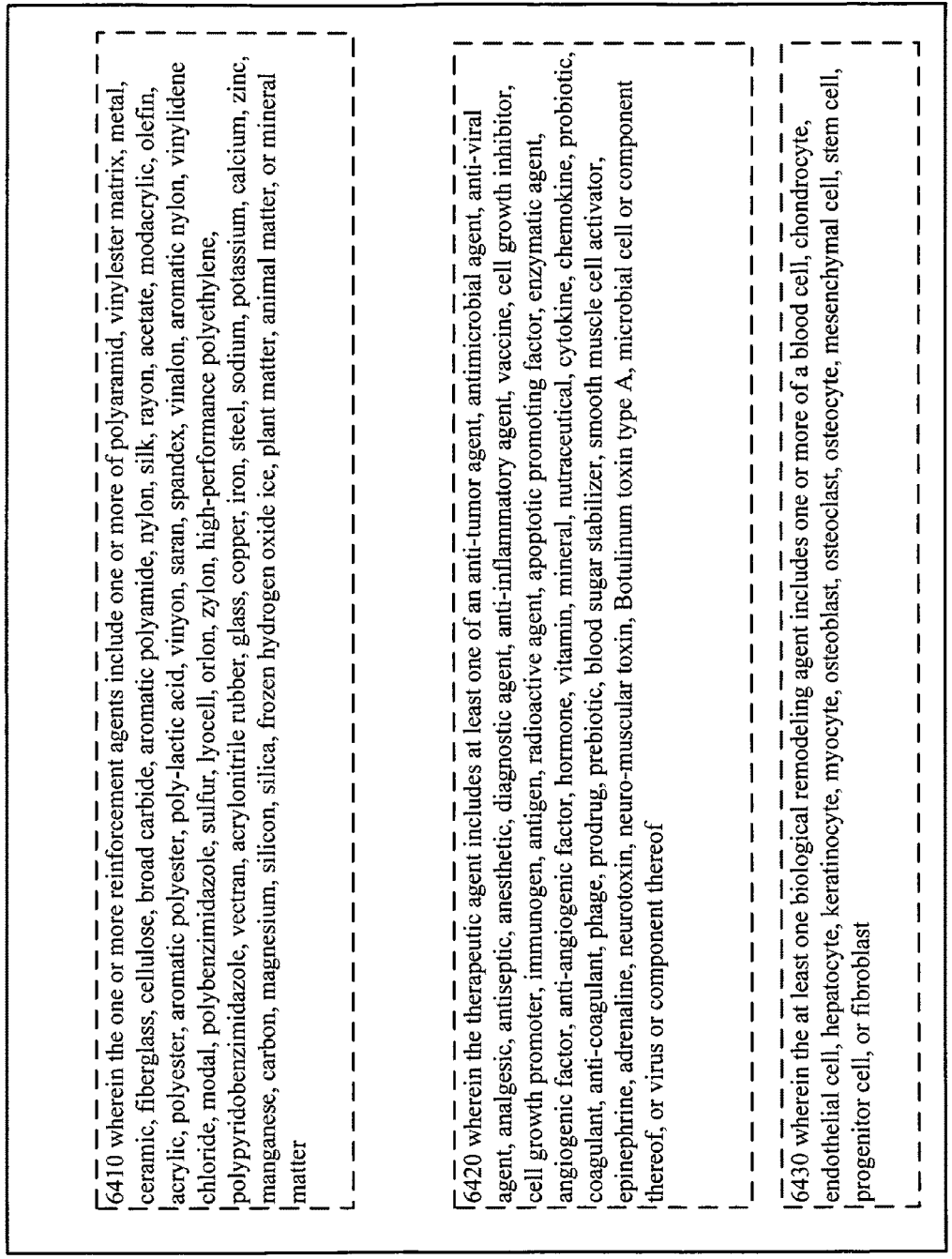

6410 wherein the one or more reinforcement agents include one or more of polyaramid, vinylester matrix, metal, ceramic, fiberglass, cellulose, broad carbide, aromatic polyester, poly-lactic acid, vinyon, saran, spandex, vinalon, aromatic nylon, vinylidene chloride, modal, polybenzimidazole, sulfur, lyocell, orlon, zylon, high-performance polyethylene, polypyridobenzimidazole, vectran, acrylonitrile rubber, glass, copper, iron, steel, sodium, potassium, calcium, zinc, manganese, carbon, magnesium, silicon, silica, frozen hydrogen oxide ice, plant matter, animal matter, or mineral matter 6420 wherein the therapeutic agent includes at least one of an anti-tumor agent, antimicrobial agent, anti-viral agent, analgesic, antiseptic, anesthetic, diagnostic agent, anti-inflammatory agent, vaccine, cell growth inhibitor, cell growth promoter, immunogen, antigen, radioactive agent, apoptotic promoting factor, enzymatic agent, angiogenic factor, anti-angiogenic factor, hormone, vitamin, mineral, nutraceutical, cytokine, chemokine, probiotic, coagulant, anti-coagulant, phage, prodrug, prebiotic, blood sugar stabilizer, smooth muscle cell activator, epinephrine, adrenaline, neurotoxin, neuro-muscular toxin, Botulinum toxin type A, microbial cell or component thereof, or virus or component thereof 6430 wherein the at least one biological remodeling agent includes one or more of a blood cell, chondrocyte, endothelial cell, hepatocyte, keratinocyte, myocyte, osteoblast, osteoclast, osteocyte, mesenchymal cell, stem cell, progenitor cell, or fibroblast

FIG. 65

6510 wherein the at least one biological remodeling agent includes one or more of calcium phosphate, albumin, cytokine, pegylated cytokine, bone, cartilage, globulin, fibrin, thrombin, glutaraldehyde-crosslinked pericardium, hide powder, hyaluronic acid, hydroxylapatite, keratin, ligament, nitinol, nucleic acid polymers, polyethylene, polyethylene glycol, polyethylene glycol diacrylate, polyethylene terephthalate fiber, polyglycol, polylactate, polytetrafluoroethylene, polylactic acid, polyglycolic acid, polycaprolactone, PURAMATRIX™ self-assembly peptide hydrogel fibers, linear aliphatic polyester, tendon, fibrinogen, hyaluronate, chitin, chitosan, methylcellulose, alginate, hyaluronic acid, agarose, cellulose, polyaldehyde gluronate, Factor XIII, Factor XII, silk, nylon, collagen, silicone, polyurethane, ceramic powder, elastin, pectin, wax, glycosaminoglycan, poly(α-hydroxyacid), selectin, glutaraldehyde, hydrophobic non-glycosylated protein, hydrogel, peptide hydrogel, or gelatin 6520 wherein the at least one biological remodeling agent includes one or more of Type I collagen, Type II collagen, Type III collagen, Type VII collagen, Type X collagen, elastin fibers, or soluble elastin 6530 wherein the at least one biological remodeling agent is included as part of a carrier that assists in synthesis or activation of the at least one biological remodeling agent

FIG. 66

6600 A method of predicting a clinical outcome of one or more frozen particle composition treatments for at least one first subject, comprising:

6610 determining a similarity or a dissimilarity in information regarding at least one parameter for at least partially constructing or at least partially reconstructing at least one biological tissue of at least one first subject by administering one or more frozen particle compositions to the at least one first subject with information regarding at least one parameter of at least partially constructing or at least partially reconstructing at least one biological tissue of at least one second subject 6620 wherein the at least one second subject attained a clinical outcome following receipt of one or more frozen particle compositions;

6630 providing output information 6640 wherein providing output information is based on the determination 6650 wherein the information regarding at least one parameter of at least partially constructing or at least partially reconstructing at least one biological tissue of at least second subject includes information regarding quantity of cells or tissue at least partially constructed or at least partially reconstructed 6660 wherein the information regarding at least one parameter of at least partially constructing or at least partially reconstructing at least one biological tissue of at least one first subject includes information regarding at least one cellular or tissue source 6670 wherein the information regarding at least one parameter of at least partially constructing or at least partially reconstructing at least one biological tissue of at least one first subject includes information regarding at least one abnormal cellular or tissue source

FIG. 67

6710 wherein the information regarding at least one parameter of at least one partially constructing or at least partially reconstructing at least one biological tissue of at least one first subject includes information regarding at least one type of cell or tissue 6720 wherein the information regarding at least one parameter of at least one partially constructing or at least partially reconstructing at least one biological tissue of at least one second subject includes information regarding at least one type of cell or tissue 6730 wherein the at least one agent includes one or more of an adhesive agent, abrasive, reinforcement agent, therapeutic agent, biological remodeling agent, or explosive material 6740 wherein the information regarding at least one parameter of at least one partially constructing or at least partially reconstructing at least one biological tissue of at least one first subject includes information regarding at least one dimension of at least one agent deposited 6750 wherein the information regarding at least one parameter of at least one partially constructing or at least partially reconstructing at least one biological tissue of at least one second subject includes information regarding at least one dimension of at least one agent deposited 6760 wherein the information regarding at least one parameter of at least one partially constructing or at least partially reconstructing at least one biological tissue of at least one second subject includes information regarding at least one dimension of at least one depth, width, or breadth of cellular, tissue, or other material removal or destruction 6770 wherein the information regarding at least one parameter of at least one partially constructing or at least partially reconstructing at least one biological tissue of at least one first subject includes information regarding at least one dimension of at least one depth, width, or breadth of cellular, tissue, or other material removal or destruction

FIG. 68

6810 wherein the information regarding at least one clinical outcome following receipt by the at least one second subject of one or more frozen particle compositions includes information regarding two or more subjects with one or more common attributes 6820 wherein the one or more common attributes include one or more of genetic attributes, mental attributes, proteomic attributes, phenotypic attributes, or psychological attributes 6830 wherein the one or more common attributes include one or more of height, weight, medical diagnosis, familial background, results on one or more medical tests, ethnic background, body mass index, age, presence or absence of at least one disease or condition, species, ethnicity, race, allergies, gender, thickness of tissue, blood vessel condition, hair or fur condition, skin condition, tissue condition, muscle condition, organ condition, nerve condition, brain condition, presence or absence of at least one biological, chemical, or therapeutic agent in the subject, pregnancy status, lactation status, genetic profile, proteomic profile, partial or whole genetic sequence, partial or whole proteomic sequence, medical condition, medical history, or blood condition 6840 wherein the output information includes at least one of a response signal, comparison code, comparison plot, diagnostic code, treatment code, test code, code indicative of at least one treatment received, code indicative of at least one prescribed treatment step, code indicative of at least one vaccination administered, code indicative of at least one therapeutic agent administered, code indicative of at least one diagnostic agent administered, code indicative of at least one interaction of an administered agent and at least one biological or chemical agent in the subject; a code indicative of at least one dispersion or location of at least one administered agent; code indicative of at least one detection material administered; code indicative of the depth of penetration of an administered agent, code indicative of the depth of deposition of an administered agent, or a code indicative of the condition of at least one location of an administered frozen particle composition

FIG. 69

6910 wherein receipt by the at least one second subject of one or more frozen particle compositions is pursuant to at least one clinical trial 6920 further comprising determining at least one correlation before the administration of the one or more frozen particle compositions to the at least one first subject 6930 further comprising creating at least one inclusion criterion and at least one exclusion criterion for a clinical trial involving the one or more frozen particle compositions 6940 further comprising suggesting the inclusion of one or more of the at least one first subject in at least one clinical trial 6950 further comprising suggesting the exclusion of one or more of the at least one first subject in at least one clinical trial 6960 further comprising using one or more of the at least one correlation to predict at least one clinical outcome regarding at least one second subject 6970 wherein the at least one second subject has not received the one or more frozen particle compositions 6980 further comprising predicting at least one clinical outcome involving the at least one second subject, wherein the at least one second subject is a plurality of people; and segregating subject identifiers associated with the plurality of people in reference to the predicted at least one clinical outcome

FIG. 70

7010 wherein the one or more frozen particle compositions include one or more frozen particles including at least one of: hydrogen oxide, nitrogen, oxygen, air, helium, neon, argon, xenon, chlorine, bromine, carbon dioxide, acetone, ethyl acetate, dimethyl sulfoxide, dimethyl formamide, dioxane, tetrahydrofuran, acetonitrile, acetic acid, n-butanol, isopropanol, n-propanol, hexamethylphosphorotriamide, perfluorohydrocarbon, methanol, ethanol, tert-butyl alcohol, formic acid, hydrogen fluoride, ammonia, benzene, carbon tetrachloride, acetonitrile, hexane, dichloromethane, methylene chloride, carboxylic acid, saline, standard saline citrate, methane, toluene, chloroform, polyethylene glycol, acetic acid, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, methane, or diethyl ether.

7020 wherein the one or more frozen particle compositions includes one or more of an adhesive agent, therapeutic agent, reinforcement agent, abrasive, explosive material, or biological remodeling agent 7030 wherein the adhesive agent, therapeutic agent, reinforcement agent, abrasive, explosive material, or biological remodeling agent includes at least one of an organic or inorganic small molecule, clathrate or caged compound, protocell, coacervate, microsphere, Janus particle, proteinoid, laminate, helical rod, liposome, macroscopic tube, niosome, sphingosome, toroid, vesicular tube, vesicle, small unilamellar vesicle, large unilamellar vesicle, large multilamellar vesicle, multivesicular vesicle, lipid layer, lipid bilayer, micelle, organelle, cell, membrane, nucleic acid, peptide, polypeptide, protein, oligosaccharide, polysaccharide, glycopeptide, glycolipid, sphingolipid, glycosphingolipid, glycoprotein, peptidoglycan, lipid, carbohydrate, metalloprotein, proteoglycan, chromosome, cell nucleus, acid, base, buffer, protic solvent, aprotic solvent, nitric oxide, nitric oxide synthase, nitrous oxide, amino acid, micelle, polymer, bone cement, copolymer, cell receptor, adhesion molecule, cytokine, chemokine, immunoglobulin, antibody, antigen, platelet, extracellular matrix, blood, plasma, cell ligand, zwitterionic material, cationic material, oligonucleotide, nanotube, or piloxymer 7040 wherein the one or more explosive materials include at least one of a carbonate, carbon dioxide, nitroglycerine, acid, base, epoxy, acrylic polymer or copolymer, acrylamide polymer or copolymer, urethane, hypoxyapatite, or reactive metal

FIG. 71

7110 wherein the at least one adhesive agent includes one or more of an acrylic polymer or copolymer, acrylamide polymer or copolymer polymer or copolymer, acrylamide polymer or copolymer, polyacrylic acid, epoxy, urethane, gum arabic, polyester, polyhydroxyalkanoate, poly(L-lactic acid), polyglycolide, polylactic acid, polyether, polyol, polyvinylpyrrolidone, pyroxylin, polymethylacrylate-isobutene-monoisopropylmaleate, siloxane polymer, polylactic-co-glycolic-acid, poly-3-hydroxybutyrate, poly-4-hydroxybutyrate, polyhydroxyvalerate, polydydroxyhexanoate, polydyhroxyoctanoate, polycaprolactone, poly (e-caprolactone), sialyl Lewis$^x$, heme group, hemoglobin, healon, carboxymethylcellulose, hydroxyapatite, silicone, cadherin, integrin, hydroxyapatite, polyelectrolyte, polyelectrolyte, maleic polyelectrolyte, cellulose, resilin, cyanoacrylate, isocyanate, 2-octyl cyanoacrylate, 2-butyl-n-cyanoacrylate, n-butyl-2-cyanoacrylate, butyl-2-cyanoacrylate, methyl 2-cyanoacrylate, polyisohexylcyanoacrylate, fibrin, thrombin, fibrinogen, hyaluronate, chitin, Factor XIII, Factor XII, silk, nylon, collagen, glycosaminoglycan, selectin, polyurethane, methacrylate, or polysulfide, polyanhydride, polydioxanone, poly-p-dioxanone, silicone, albumin, glutaraldehyde, polyethylene glycol, or gelatin 7120 wherein the one or more reinforcement agents include one or more of polyaramid, vinylester matrix, metal, ceramic, fiberglass, cellulose, broad carbide, aromatic polyamide, nylon, silk, rayon, acetate, modacrylic, olefin, acrylic, polyester, aromatic polyester, poly-lactic acid, vinyon, saran, spandex, vinalon, aromatic nylon, vinylidene chloride, modal, polybenzimidazole, sulfur, lyocell, orlon, zylon, high-performance polyethylene, polypyridobenzimidazole, vectran, acrylonitrile rubber, glass, copper, iron, steel, sodium, potassium, calcium, zinc, manganese, carbon, magnesium, silicon, silica, frozen hydrogen oxide ice, plant matter, animal matter, or mineral matter 7130 wherein the therapeutic agent includes at least one of an anti-tumor agent, antimicrobial agent, anti-viral agent, analgesic, antiseptic, anesthetic, diagnostic agent, anti-inflammatory agent, vaccine, cell growth inhibitor, cell growth promoter, immunogen, antigen, radioactive agent, apoptotic promoting factor, enzymatic agent, angiogenic factor, anti-angiogenic factor, hormone, vitamin, mineral, nutraceutical, cytokine, chemokine, probiotic, coagulant, anti-coagulant, phage, prodrug, prebiotic, blood sugar stabilizer, smooth muscle cell activator, epinephrine, adrenaline, neurotoxin, neuro-muscular toxin, Botulinum toxin type A, microbial cell or component thereof, or virus or component thereof

FIG. 72

7210 wherein the at least one biological remodeling agent includes one or more of a blood cell, chondrocyte, endothelial cell, hepatocyte, keratinocyte, myocyte, osteoblast, osteoclast, osteocyte, mesenchymal cell, stem cell, progenitor cell, or fibroblast 7220 wherein the at least one biological remodeling agent includes one or more of calcium phosphate, albumin, cytokine, pegylated cytokine, bone, cartilage, globulin, fibrin, thrombin, glutaraldehyde-crosslinked pericardium, hide powder, hyaluronic acid, hydroxylapatite, keratin, ligament, nitinol, nucleic acid polymers, polyethylene, polyethylene glycol, polyethylene glycol diacrylate, polyethylene terephthalate fiber, polyglycol, polylactate, polytetrafluoroethylene, polylactic acid, polyglycolic acid, polycaprolactone, PURAMATRIX™ self-assembly peptide hydrogel fibers, linear aliphatic polyester, tendon, fibrinogen, hyaluronate, chitin, chitosan, methylcellulose, alginate, hyaluronic acid, agarose, cellulose, polyaldehyde gluronate, Factor XIII, Factor XII, silk, nylon, collagen, silicone, polyurethane, ceramic powder, elastin, pectin, wax, glycosaminoglycan, poly(α-hydroxyacid), selectin, glutaraldehyde, hydrophobic non-glycosylated protein, hydrogel, peptide hydrogel, or gelatin 7230 wherein the at least one biological remodeling agent includes one or more of Type I collagen, Type II collagen, Type III collagen, Type VII collagen, Type X collagen, elastin fibers, or soluble elastin 7240 wherein the at least one biological remodeling agent is included as part of a carrier that assists in synthesis or activation of the at least one biological remodeling agent

FIG. 74

7410 — one or more instructions that when executed on the at least one computing device cause the at least one computing device to determine from the comparison at least one parameter for administering one or more frozen particle compositions 7420 — one or more instructions that when executed on the at least one computing device cause the at least one computing device to generate at least one response based on the determination 7430 — one or more instructions that when executed on the at least one computing device cause the at least one computing device to access the first possible dataset in response to the first input 7440 — one or more instructions that when executed on the at least one computing device cause the at least one computing device to generate the first possible dataset in response to the first input 7450 — one or more instructions that when executed on the at least one computing device cause the at least one computing device to determine a graphical illustration of the first possible dataset 7460 — one or more instructions that when executed on the at least one computing device cause the at least one computing device to determine a graphical illustration of the second dataset

FIG. 76

7610 — one or more instructions that when executed on the at least one computing device cause the at least one computing device to determine from the comparison at least one characteristic of the at least one biological tissue or organ to be at least partially constructed or at least partially reconstructed by administering one or more frozen particle compositions 7620 — one or more instructions that when executed on the at least one computing device cause the at least one computing device to generate at least one response based on the determination 7630 — one or more instructions that when executed on the at least one computing device cause the at least one computing device to access the first possible dataset in response to the first input 7640 — one or more instructions that when executed on the at least one computing device cause the at least one computing device to generate the first possible dataset in response to the first input 7650 — one or more instructions that when executed on the at least one computing device cause the at least one computing device to determine a graphical illustration of the first possible dataset 7660 — one or more instructions that when executed on the at least one computing device cause the at least one computing device to determine a graphical illustration of the second dataset

FIG. 80

8000 A system comprising:

8010 at least one computer program, configured with a computer-readable medium, for use with at least one computer system and wherein the computer program includes a plurality of instructions including but not limited to:

8020 one or more instructions for accepting a first input associated with at least one characteristic of at least one biological tissue to be at least partially constructed or at least partially reconstructed by administering one or more frozen particle compositions, 8030 one or more instructions for accepting a second input associated with at least one characteristic of at least one parameter of at least partially constructing or at least partially reconstructing the at least one biological tissue by administering one or more frozen particle compositions that include at least one agent;

8040 one or more instructions for processing results of the first input and the second input 8050 one or more instructions for displaying results of the processing 8060 one or more instructions for transmitting one or more signals that include information related to the processing results of the first input and the second input 8070 one or more instructions for administering one or more frozen particle compositions that include at least one agent including a biological remodeling agent, therapeutic agent, adhesive agent, abrasive, reinforcement agent, or explosive material 8080 one or more instructions for evaluating the at last one biological tissue for one or more indicators relating to one or more of deposition of at least one agent, tissue form

FIG. 82

8200 A system comprising:

8210 means for accepting a first input associated with at least one characteristic of at least one biological tissue to be at least partially constructed or at least partially reconstructed;

8220 means for accepting a second input associated with at least one parameter of at least partially constructing or at least partially reconstructing the at least one biological tissue by administering one or more frozen particle compositions including at least one agent;

8230 wherein the at least one agent includes one or more of a therapeutic agent, adhesive agent, abrasive, reinforcement agent, explosive material, or biological remodeling agent 8240 wherein the administering one or more frozen particle compositions includes administering the one or more frozen particle compositions to at least one substrate 8250 wherein the at least one substrate includes one or more of a cell, tissue, organ, structure, or device 8260 means for processing results of the first input and the second input 8270 means for processing results of the first input and the second input include means for electronically processing results of the first input and the second input 8280 means for electronically processing results of the first input and the second input by utilizing one or more of Gaussian smoothing, scaling, homomorphic filtering, parametric estimation techniques, Boolean operations, Monte Carlo simulations, wavelet based techniques, mirroring, smoothing, gradient weighted partial differential equation smoothing, NURBS, polygonal modeling, splines and patches modeling, algorithmic execution, logical decision-making, result prediction, or modification of a CAD design

FIG. 83

8310 wherein the first input includes one or more values related to the at least one characteristic of at least one biological tissue 8320 wherein the first input includes one or more spatial addresses associated with the at least one characteristic of at least one biological tissue 8330 wherein the first input includes one or more of x, y, or z coordinates associated with the at least one characteristic of at least one biological tissue 8340 wherein the at least one characteristic of at least one biological tissue to be at least partially constructed or at least partially reconstructed includes one or more of: morphological feature, anatomical feature, histological feature, tissue hierarchical level, scaffold feature, vascular structure feature, heterogenous tissue feature, mechanical feature, volumetric feature, geometric feature, volumetric representation, mechanical feature, deformation, kinematic feature, surface contour feature, cytometric feature, cell aggregation, cell growth, cell-cell interaction, cell-tissue interaction, biomimetic design, cell pattern, cell deposition, organ hierarchical level, tissue microstructure, cellular microstructure, cell junction feature, tissue junction feature, cell-tissue classification, hard tissue classification, soft tissue classification, tumor diagnosis, or other feature 8350 wherein the at least one characteristic of at least one biological tissue includes one or more of cellular type, cellular function, cellular size, cellular constitution, cellular architecture, cellular durability, cellular source, tissue type, tissue constitution, tissue size, tissue shape, tissue function, tissue architecture, tissue source, tissue durability, organ type, organ constitution, organ size, organ shape, organ function, organ architecture, organ source, or organ durability 8360 wherein the first input includes one or more temporal addresses associated with the at least one characteristic of at least one biological tissue

FIG. 84

8410 wherein the first input includes one or more values derived from at least one image of the at least one biological tissue 8420 wherein the at least one image includes one or more images acquired by one or more of optical coherence tomography, computer-assisted tomography scan, computed tomography, magnetic resonance imaging, positron-emission tomography scan, ultrasound, x-ray, electrical-impedance monitoring, microscopy, spectrometry, flow cytometry, radioisotope imaging, thermal imaging, multiphoton calcium-imaging, photography, or *in silico* generation 8430 wherein the at least one biological tissue is located in at least one of *in situ, in vitro, in vivo, in utero, in planta, in silico,* or *ex vivo*

8440 wherein the at least one biological tissue is at least partially located in at least one subject 8450 further comprising means for accepting a third input associated with at least one feature of the at least one subject 8460 wherein the at least one feature of the at least one subject includes one or more of age, gender, genotype, phenotype, proteomic profile, or health condition

FIG. 85

8510 wherein the means for processing results of the first input and the second input include means for determining at least one parameter of at least partially constructing or at least partially reconstructing the at least one biological tissue with one or more frozen particle compositions from one 8520 wherein the second input includes one or more values related to the at least one parameter of at least partially constructing or at least partially reconstructing the at least one biological tissue by administering one or more frozen particle compositions to the at least one substrate 8530 wherein the at least one parameter of at least partially constructing or at least partially reconstructing the at least one biological tissue includes one or more of: porosity of the at least one substrate, pore size of the at least one substrate, interconnectivity of the pores of the at least one substrate, transport properties of the at least one substrate, cell-tissue formation of the at least one substrate, mechanical strength of the at least one substrate, ability for attachment or distribution of the at least one agent included in the one or more frozen particle compositions to the at least one substrate, ability for attachment or distribution of one or more cells or tissues to the at least one substrate, facilitation of at least one nutrient, or tissue formation or tissue growth associated with the at least one substrate 8540 wherein the at least one parameter of at least partially constructing or at least partially reconstructing the at least one biological tissue by administering one or more frozen particle compositions includes one or more of: design of plot or model for administration of one or more frozen particle compositions, constitution of the one or more frozen particle compositions, formulation of the one or more frozen particle compositions, size of the one or more frozen particle compositions, shape of the one or more frozen particle compositions, angle of administration of the one or more frozen particle compositions, velocity of administration of the one or more frozen particle compositions, quantity of frozen particle compositions administered, rate of administration of more than one frozen particle composition, spatial location for administration of one or more frozen particle compositions, temporal location for administration of one or more frozen particle compositions, method of administration of one or more frozen particle compositions, timing of administration of one or more frozen particle compositions, modulation of administration of one or more frozen particle compositions, deposition of one or more frozen particle compositions, or rate of deposition of at least one agent

FIG. 86

8610 wherein the at least one parameter of at least partially constructing or at least partially reconstructing the at least one biological tissue by administering one or more frozen particle compositions includes at least one parameter relating to at least partially ablating or at least partially abrading one or more surfaces of the at least one biological tissue with the one or more frozen particle compositions 8620 wherein the at least one parameter of at least partially constructing or at least partially reconstructing the at least one biological tissue by administering one or more frozen particle compositions includes at least one parameter relating to administering at least one of a therapeutic agent, adhesive agent, biological remodeling agent, reinforcement agent, abrasive, or explosive material with the one or more frozen particle compositions 8630 wherein the one or more values related to the at least one parameter of constructing or reconstructing the at least one biological tissue includes one or more predictive values 8640 wherein the spatial location for administration of one or more frozen particle compositions includes one or more of x, y, or z coordinates 8650 wherein the means for processing results include means for comparing at least one value related to the first input associated with the at least one characteristic of at least one biological tissue to be at least partially constructed or at least partially reconstructed with at least one value related to at least one image of a target biological tissue 8660 wherein the image of a target biological tissue includes an image of a similar biological tissue, or an image of a dissimilar biological tissue

FIG. 87

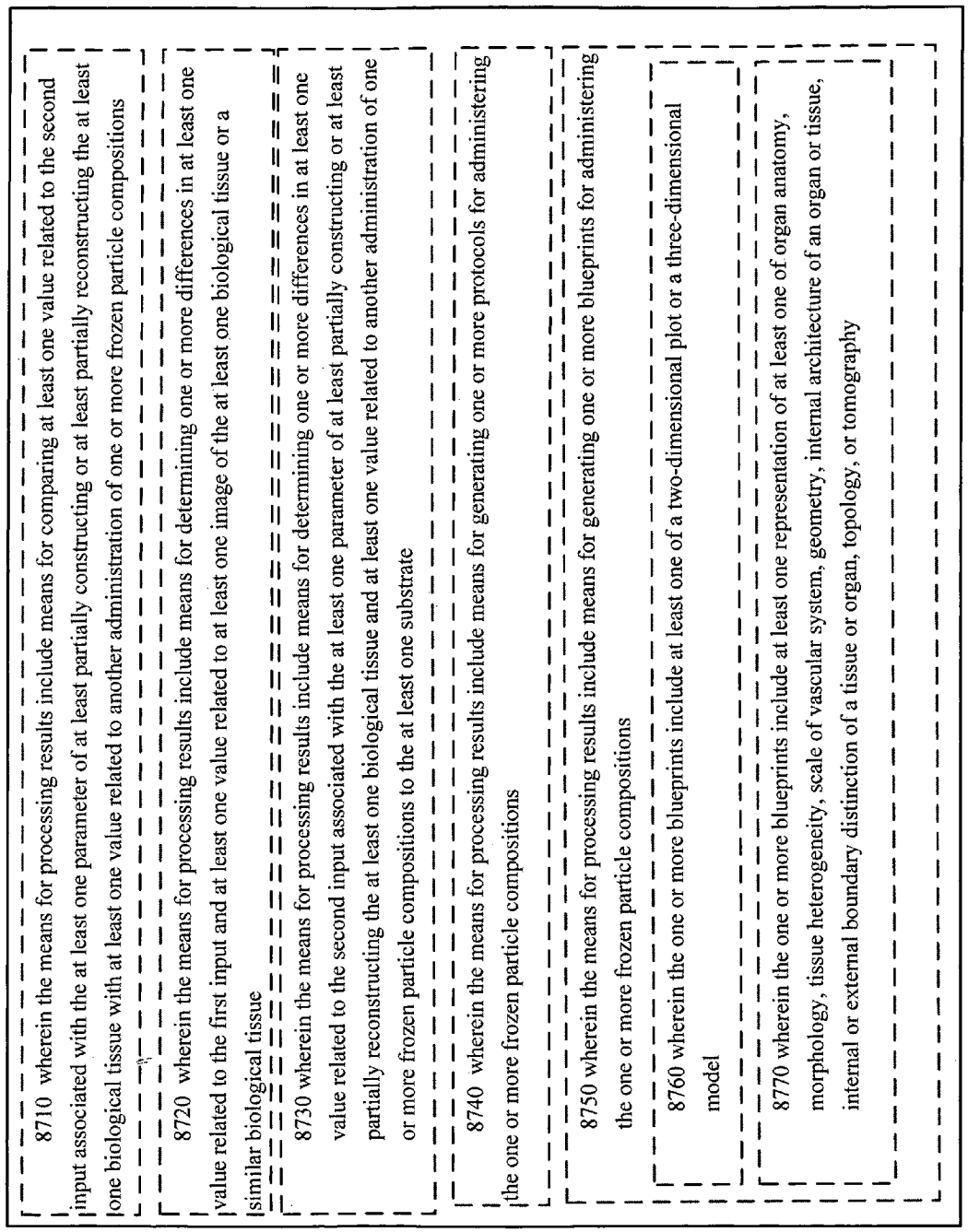

8710 wherein the means for processing results include means for comparing at least one value related to the second input associated with the at least one parameter of at least partially constructing or at least partially reconstructing the at least one biological tissue with at least one value related to another administration of one or more frozen particle compositions 8720 wherein the means for processing results include means for determining one or more differences in at least one value related to the first input and at least one value related to at least one image of the at least one biological tissue or a similar biological tissue 8730 wherein the means for processing results include means for determining one or more differences in at least one value related to the second input associated with the at least one parameter of at least partially constructing or at least partially reconstructing the at least one biological tissue and at least one value related to another administration of one or more frozen particle compositions to the at least one substrate 8740 wherein the means for processing results include means for generating one or more protocols for administering the one or more frozen particle compositions 8750 wherein the means for processing results include means for generating one or more blueprints for administering the one or more frozen particle compositions 8760 wherein the one or more blueprints include at least one of a two-dimensional plot or a three-dimensional model 8770 wherein the one or more blueprints include at least one representation of at least one of organ anatomy, morphology, tissue heterogeneity, scale of vascular system, geometry, internal architecture of an organ or tissue, internal or external boundary distinction of a tissue or organ, topology, or tomography

FIG. 88

8810 wherein the means for processing results include: means for comparing one or more values related to the one or more characteristics of the at least one biological tissue that are determined at two or more different times to obtain one or more characteristic comparisons; means for comparing one or more values related to the at least one parameter of at least one biological tissue at two or more different times to obtain one or more parameter comparisons; means for comparing the one or more characteristic comparisons with the one or more parameter comparisons to obtain one or more characteristic-characteristic/246parameter-parameter comparisons; and means for comparing the one or more characteristic-characteristic/246parameter-parameter comparisons to one or more substantially similar results obtained for one or more other at least partially constructed or at least partially reconstructed biological tissues 8820 wherein the administering one or more frozen particle compositions includes depositing the at least one agent on the at least one substrate

FIG. 91

9110 wherein the one or more frozen particle compositions includes one or more frozen particles of at least one of: hydrogen oxide, nitrogen, oxygen, air, helium, neon, argon, xenon, chlorine, bromine, carbon dioxide, acetone, ethyl acetate, dimethyl sulfoxide, dimethyl formamide, dioxane, tetrahydrofuran, acetonitrile, acetic acid, n-butanol, isopropanol, n-propanol, hexamethylphosphorotriamide, perfluorohydrocarbon, methanol, ethanol, tert-butyl alcohol, formic acid, hydrogen fluoride, ammonia, benzene, carbon tetrachloride, acetonitrile, hexane, dichloromethane, methylene chloride, carboxylic acid, saline, standard saline citrate, methane, toluene, chloroform, polyethylene glycol, acetic acid, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, methane, or diethyl ether.

9120 wherein the at least one agent includes one or more of an adhesive agent, therapeutic agent, reinforcement agent, abrasive, explosive material, or biological remodeling agent 9130 wherein at least one of the adhesive agent, therapeutic agent, reinforcement agent, abrasive, explosive material, or biological remodeling agent includes at least one of an organic or inorganic small molecule, clathrate or caged compound, protocell, coacervate, microsphere, Janus particle, proteinoid, laminate, helical rod, liposome, macroscopic tube, niosome, sphingosome, toroid, vesicular tube, vesicle, small unilamellar vesicle, large unilamellar vesicle, large multilamellar vesicle, multivesicular vesicle, lipid layer, lipid bilayer, micelle, organelle, cell, membrane, nucleic acid, peptide, polypeptide, protein, oligosaccharide, polysaccharide, glycopeptide, glycolipid, sphingolipid, glycosphingolipid, glycoprotein, peptidoglycan, lipid, carbohydrate, metalloprotein, proteoglycan, chromosome, cell nucleus, acid, base, buffer, protic solvent, aprotic solvent, nitric oxide, nitric oxide synthase, nitrous oxide, amino acid, micelle, polymer, bone cement, copolymer, cell receptor, adhesion molecule, cytokine, chemokine, immunoglobulin, antibody, antigen, platelet, extracellular matrix, blood, plasma, cell ligand, zwitterionic material, cationic material, oligonucleotide, nanotube, or piloxymer

FIG. 92

9210 wherein the one or more explosive materials include at least one of a carbonate, carbon dioxide, nitroglycerine, acid, base, epoxy, acrylic polymer or copolymer, acrylamide polymer or copolymer, urethane, hypoxyapatite, or reactive metal 9220 wherein the at least one adhesive agent includes one or more of an acrylic polymer or copolymer, acrylamide polymer or copolymer polymer or copolymer, acrylamide polymer or copolymer, polyacrylic acid, epoxy, urethane, gum arabic, polyester, polyhydroxyalkanoate, poly(L-lactic acid), polyglycolide, polylactic acid, polyether, polyol, polyvinylpyrrolidone, pyroxylin, polymethylacrylate-isobutene-monoisopropylmaleate, siloxane polymer, polylactic-co-glycolic-acid, poly-3-hydroxybutyrate, poly-4-hydroxybutyrate, polyhydroxyvalerate, polydyhydroxyhexanoate, polydyhydroxyoctanoate, polycaprolactone, poly (e-caprolactone), sialyl Lewis$^x$, heme group, hemoglobin, healon, carboxymethylcellulose, hydroxyapatite, silicone, cadherin, integrin, hydroxyapatite, polyelectrolyte, maleic polyelectrolyte, cellulose, resilin, cyanoacrylate, isocyanate, 2-octyl cyanoacrylate, 2-butyl-n-cyanoacrylate, n-butyl-2-cyanoacrylate, butyl-2-cyanoacrylate, methyl 2-cyanoacrylate, polyisohexylcyanoacrylate, fibrin, thrombin, fibrinogen, hyaluronate, chitin, Factor XIII, Factor XII, silk, nylon, collagen, glycosaminoglycan, selectin, polyurethane, methacrylate, or polysulfide, polyanhydride, polydioxanone, poly-p-dioxanone, silicone, albumin, glutaraldehyde, polyethylene glycol, or gelatin 9230 wherein the one or more reinforcement agents include one or more of polyaramid, vinylester matrix, metal, ceramic, fiberglass, cellulose, broad carbide, aromatic polyamide, nylon, silk, rayon, acetate, modacrylic, olefin, acrylic, polyester, aromatic polyester, poly-lactic acid, vinyon, saran, spandex, vinalon, aromatic nylon, vinylidene chloride, modal, polybenzimidazole, sulfur, lyocell, lyocell, orlon, zylon, high-performance polyethylene, polypyridobenzimidazole, vectran, acrylonitrile rubber, glass, copper, iron, steel, sodium, potassium, calcium, zinc, manganese, carbon, magnesium, silicon, silica, frozen hydrogen oxide ice, plant matter, animal matter, or mineral matter

FIG. 93

9310 wherein the therapeutic agent includes at least one of an anti-tumor agent, antimicrobial agent, anti-viral agent, analgesic, antiseptic, anesthetic, diagnostic agent, anti-inflammatory agent, vaccine, cell growth inhibitor, cell growth promoter, immunogen, antigen, radioactive agent, apoptotic promoting factor, enzymatic agent, angiogenic factor, anti-angiogenic factor, hormone, vitamin, mineral, nutraceutical, cytokine, chemokine, probiotic, coagulant, anti-coagulant, phage, prodrug, prebiotic, blood sugar stabilizer, smooth muscle cell activator, epinephrine, adrenaline, neurotoxin, neuro-muscular toxin, Botulinum toxin type A, microbial cell or component thereof, or virus or component thereof 9320 wherein the at least one biological remodeling agent includes one or more of a blood cell, chondrocyte, endothelial cell, hepatocyte, keratinocyte, myocyte, osteoblast, osteoclast, osteocyte, mesenchymal cell, stem cell, progenitor cell, or fibroblast 9330 wherein the at least one biological remodeling agent includes one or more of calcium phosphate, albumin, cytokine, pegylated cytokine, bone, cartilage, globulin, fibrin, thrombin, glutaraldehyde-crosslinked pericardium, hide powder, hyaluronic acid, hydroxylapatite, keratin, ligament, nitinol, nucleic acid polymers, polyethylene, polyethylene glycol, polyethylene glycol diacrylate, polyethylene terephthalate fiber, polyglycol, polylactate, polytetrafluoroethylene, polylactic acid, polyglycolic acid, polycaprolactone, PURAMATRIX™ self-assembly peptide hydrogel fibers, linear aliphatic polyester, tendon, fibrinogen, hyaluronate, chitin, chitosan, methylcellulose, alginate, hyaluronic acid, agarose, cellulose, polyaldehyde gluronate, Factor XIII, Factor XII, silk, nylon, collagen, silicone, polyurethane, ceramic powder, elastin, pectin, wax, glycosaminoglycan, poly(α-hydroxyacid), selectin, glutaraldehyde, hydrophobic non-glycosylated protein, hydrogel, peptide hydrogel, or gelatin 9340 wherein the at least one biological remodeling agent includes one or more of Type I collagen, Type II collagen, Type III collagen, Type VII collagen, Type X collagen, elastin fibers, or soluble elastin 9350 wherein the at least one biological remodeling agent is included as part of a carrier that assists in synthesis or activation of the at least one biological remodeling agent

FIG. 94

9400 A system comprising:

9410 means for accepting input associated with at least one parameter of at least partially constructing or at least partially reconstructing at least one biological tissue by administering one or more frozen particle compositions;

9420 means for administering one or more frozen particle compositions including at least one agent;

9430 wherein the at least one agent includes one or more of a therapeutic agent, adhesive agent, abrasive, reinforcement agent, explosive material, or biological remodeling agent 9440 means for evaluating the at least one biological tissue for one or more indicators related to deposition of at least one agent, tissue formation, or tissue growth;

9450 wherein the means for evaluating at least one biological tissue for one or more indicators include means for evaluating at least one of an assay, image, or gross assessment of the at least one biological tissue prior to, during, or subsequent to at least one administration of the one or more frozen particle compositions 9460 wherein the assay includes at least one technique that includes spectroscopy, microscopy, electrochemical detection, polynucleotide detection, histological examination, biopsy analysis, fluorescence resonance energy transfer, electron transfer, enzyme assay, electrical conductivity, isoelectric focusing, chromatography, immunoprecipitation, immunoseparation, aptamer binding, filtration, electrophoresis, immunoassay, or radioactive assay

FIG. 95

9520 wherein the image includes at least one image acquired by one or more of optical coherence tomography, computer-assisted tomography scan, computed tomography, magnetic resonance imaging, positron-emission tomography scan, ultrasound, x-ray, electrical-impedance monitoring, microscopy, spectrometry, flow cytometry, radioisotope imaging, thermal imaging, multiphoton calcium-imaging, photography, or *in silico* generation 9530 wherein the one or more indicators of tissue formation or growth include at least one of cell migration, cell attachment, cell retention, cell differentiation, cell proliferation, apoptosis, diffusion of materials, angiogenesis, nucleic acid expression, protein translation, protein modification, carbohydrate production, carbohydrate secretion, fat production, fat secretion, or protein secretion 9540 wherein the input associated with at least one parameter of at least partially constructing or at least partially reconstructing the at least one biological tissue by administering one or more frozen particle compositions includes one or more of: constitution of the one or more frozen particle compositions, formulation of the one or more frozen particle compositions, size of the one or more frozen particle compositions, shape of the one or more frozen particle compositions, angle of administration of the one or more frozen particle compositions, velocity of administration of the one or more frozen particle compositions, quantity of frozen particle compositions administered, rate of administration of more than one frozen particle composition, spatial location for administration of one or more frozen particle compositions, temporal location for administration of one or more frozen particle compositions, timing of administration of one or more frozen particle compositions, method of administration of one or more frozen particle compositions, modulation of administration of one or more frozen particle compositions, deposition of one or more frozen particle compositions, or rate of deposition of at least one agent

FIG. 97

9710 wherein the at least one agent includes one or more of an adhesive agent, therapeutic agent, reinforcement agent, abrasive, explosive material, or biological remodeling agent 9720 wherein the adhesive agent, therapeutic agent, reinforcement agent, abrasive, explosive material, or biological remodeling agent includes at least one of an organic or inorganic small molecule, clathrate or caged compound, protocell, coacervate, microsphere, Janus particle, proteinoid, laminate, helical rod, liposome, macroscopic tube, niosome, sphingosome, toroid, vesicular tube, vesicle, small unilamellar vesicle, large unilamellar vesicle, large multilamellar vesicle, multivesicular vesicle, lipid layer, lipid bilayer, micelle, organelle, cell, membrane, nucleic acid, peptide, polypeptide, protein, oligosaccharide, polysaccharide, glycopeptide, glycolipid, sphingolipid, glycosphingolipid, glycoprotein, peptidoglycan, lipid, carbohydrate, metalloprotein, proteoglycan, chromosome, cell nucleus, acid, base, buffer, protic solvent, aprotic solvent, nitric oxide, nitric oxide synthase, nitrous oxide, amino acid, micelle, polymer, bone cement, copolymer, cell receptor, adhesion molecule, cytokine, chemokine, immunoglobulin, antibody, antigen, platelet, extracellular matrix, blood, plasma, cell ligand, zwitterionic material, cationic material, oligonucleotide, nanotube, or piloxymer 9730 wherein the one or more explosive materials include at least one of a carbonate, carbon dioxide, nitroglycerine, acid, base, epoxy, acrylic polymer or copolymer, acrylamide polymer or copolymer, urethane, hypoxyapatite, or reactive metal 9740 wherein the at least one adhesive agent includes one or more of an acrylic polymer or copolymer, acrylamide polymer or copolymer polymer or copolymer, acrylamide polymer or copolymer, polyacrylic acid, epoxy, urethane, gum arabic, polyester, polyhydroxyalkanoate, poly(L-lactic acid), polyglycolide, polylactic acid, polyether, polyol, polyvinylpyrrolidone, pyroxylin, polymethylacrylate-isobutene-monoisopropylmaleate, siloxane polymer, polylactic-co-glycolic-acid, poly-3-hydroxybutyrate, poly-4-hydroxybutyrate, polyhydroxyvalerate, polyhydroxyhexanoate, polyhydroxyoctanoate, polycaprolactone, poly (e-caprolactone), sialyl Lewis$^x$, heme group, hemoglobin, healon, carboxymethylcellulose, hydroxyapatite, silicone, cadherin, integrin, hydroxyapatite, polyelectrolyte, maleic polyelectrolyte, cellulose, resilin, cyanoacrylate, isocyanate, 2-octyl cyanoacrylate, 2-butyl-n-cyanoacrylate, n-butyl-2-cyanoacrylate, butyl-2-cyanoacrylate, methyl 2-cyanoacrylate, polyisohexylcyanoacrylate, fibrin, thrombin, fibrinogen, hyaluronate, chitin, Factor XIII, Factor XII, silk, nylon, collagen, glycosaminoglycan, selectin, polyurethane, methacrylate, or polysulfide, polyanhydride, polydioxanone, poly-p-dioxanone, silicone, albumin, glutaraldehyde, polyethylene glycol, or gelatin

FIG. 98

9810 wherein the one or more reinforcement agents include one or more of polyaramid, vinylester matrix, metal, ceramic, fiberglass, cellulose, broad carbide, aromatic polyamide, nylon, silk, rayon, acetate, modacrylic, olefin, acrylic, polyester, aromatic polyester, poly-lactic acid, vinyon, saran, spandex, vinalon, aromatic nylon, vinylidene chloride, modal, polybenzimidazole, sulfur, lyocell, orlon, zylon, high-performance polyethylene, polypyridobenzimidazole, vectran, acrylonitrile rubber, glass, copper, iron, steel, sodium, potassium, calcium, zinc, manganese, carbon, magnesium, silicon, silica, frozen hydrogen oxide ice, plant matter, animal matter, or mineral matter 9820 wherein the therapeutic agent includes at least one of an anti-tumor agent, antimicrobial agent, anti-viral agent, analgesic, antiseptic, anesthetic, diagnostic agent, anti-inflammatory agent, vaccine, cell growth inhibitor, cell growth promoter, immunogen, antigen, radioactive agent, apoptotic promoting factor, enzymatic agent, angiogenic factor, anti-angiogenic factor, hormone, vitamin, mineral, nutraceutical, cytokine, chemokine, probiotic, coagulant, anti-coagulant, phage, prodrug, prebiotic, blood sugar stabilizer, smooth muscle cell activator, epinephrine, adrenaline, neurotoxin, neuro-muscular toxin, Botulinum toxin type A, microbial cell or component thereof, or virus or component thereof 9830 wherein the at least one biological remodeling agent includes one or more of a blood cell, chondrocyte, endothelial cell, hepatocyte, keratinocyte, myocyte, osteoblast, osteoclast, osteocyte, mesenchymal cell, stem cell, progenitor cell, or fibroblast 9840 wherein the at least one biological remodeling agent includes one or more of calcium phosphate, albumin, cytokine, pegylated cytokine, bone, cartilage, globulin, fibrin, thrombin, glutaraldehyde-crosslinked pericardium, hide powder, hyaluronic acid, hydroxylapatite, keratin, ligament, nitinol, nucleic acid polymers, polyethylene, polyethylene glycol, polyethylene glycol diacrylate, polyethylene terephthalate fiber, polyglycol, polylactate, polytetrafluoroethylene, polylactic acid, polyglycolic acid, polycaprolactone, PURAMATRIX™ self-assembly peptide hydrogel fibers, linear aliphatic polyester, tendon, fibrinogen, hyaluronate, chitin, chitosan, methylcellulose, alginate, hyaluronic acid, agarose, cellulose, polyaldehyde gluronate, Factor XIII, Factor XII, silk, nylon, collagen, silicone, polyurethane, ceramic powder, elastin, pectin, wax, glycosaminoglycan, poly(α-hydroxyacid), selectin, glutaraldehyde, hydrophobic non-glycosylated protein, hydrogel, peptide hydrogel, or gelatin 9850 wherein the at least one biological remodeling agent includes one or more of Type I collagen, Type II collagen, Type III collagen, Type VII collagen, Type X collagen, elastin fibers, or soluble elastin

FIG. 99

9900 A system comprising:

9910 means for receiving one or more signals that include information related to accepting input associated with at least one parameter of at least partially constructing or at least partially reconstructing the at least one biological tissue by administering one or more frozen particle compositions 9920 means for receiving one or more signals that include information related to evaluating the at least one biological tissue for one or more indicators of tissue formation or growth;

9930 means for processing the information related to the input associated with at least one parameter of at least partially constructing or at least partially reconstructing the at least one biological tissue and the information related to the evaluating the at least one biological tissue 9940 wherein the evaluating at least one biological tissue for one or more indicators includes evaluating at least one of an assay, image, or gross assessment of the at least one biological tissue prior to, during, or subsequent to at least one administration of the one or more frozen particle compositions 9950 wherein the assay includes at least one technique that includes spectroscopy, microscopy, electrochemical detection, polynucleotide detection, histological examination, biopsy analysis, fluorescence resonance energy transfer, electron transfer, enzyme assay, electrical conductivity, isoelectric focusing, chromatography, immunoprecipitation, immunoseparation, aptamer binding, filtration, electrophoresis, immunoassay, or radioactive assay 9960 wherein the image includes at least one image acquired by one or more of optical coherence tomography, computer-assisted tomography scan, computed tomography, magnetic resonance imaging, positron-emission tomography scan, ultrasound, x-ray, electrical-impedance monitoring, microscopy, spectrometry, flow cytometry, radioisotope imaging, thermal imaging, multiphoton calcium-imaging, photography, or *in silico* generation

FIG. 100

10010 wherein the one or more indicators of tissue formation or growth include at least one of cell migration, cell attachment, cell retention, cell differentiation, cell proliferation, apoptosis, diffusion of materials, angiogenesis, nucleic acid expression, protein translation, protein modification, carbohydrate production, carbohydrate secretion, fat production, fat secretion, or protein secretion 10020 wherein the input associated with at least one parameter of at least partially constructing or at least partially reconstructing the at least one biological tissue by administering one or more frozen particle compositions includes one or more of: constitution of the one or more frozen particle compositions, formulation of the one or more frozen particle compositions, size of the one or more frozen particle compositions, shape of the one or more frozen particle compositions, angle of administration of the one or more frozen particle compositions, velocity of administration of the one or more frozen particle compositions, quantity of frozen particle compositions administered, rate of administration of more than one frozen particle composition, spatial location for administration of one or more frozen particle compositions, temporal location for administration of one or more frozen particle compositions, method of administration of one or more frozen particle compositions, timing of administration of one or more frozen particle compositions, modulation of administration of one or more frozen particle compositions, deposition of one or more frozen particle compositions, or rate of deposition of at least one agent 10030 wherein the means for receiving one or more signals includes receiving one or more signals associated with selection of one or more frozen particle compositions for administration 10040 wherein the means for receiving one or more signals include means for receiving one or more signals associated with the selection of at least one of a biological remodeling agent, adhesive agent, abrasive, therapeutic agent, reinforcement agent, or explosive material associated with the one or more frozen particle compositions

FIG. 101

10110 wherein the means for administering one or more frozen particle compositions include means for administering the one or more frozen particle compositions to at least one substrate 10120 wherein the at least one substrate includes one or more of a cell, tissue, organ, structure, or device 10130 wherein the one or more frozen particle compositions includes one or more frozen particles of at least one of: hydrogen oxide, nitrogen, oxygen, air, helium, neon, argon, xenon, chlorine, bromine, carbon dioxide, acetone, ethyl acetate, dimethyl sulfoxide, dimethyl formamide, dioxane, tetrahydrofuran, acetonitrile, acetic acid, n-butanol, isopropanol, n-propanol, hexamethylphosphorotriamide, perfluorohydrocarbon, methanol, ethanol, tert-butyl alcohol, formic acid, hydrogen fluoride, ammonia, benzene, carbon tetrachloride, acetonitrile, hexane, dichloromethane, methylene chloride, carboxylic acid, saline, standard saline citrate, methane, toluene, chloroform, polyethylene glycol, acetic acid, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, methane, or diethyl ether.

10140 wherein the at least one agent includes one or more of an adhesive agent, therapeutic agent, reinforcement agent, abrasive, explosive material, or biological remodeling agent 10150 wherein the adhesive agent, therapeutic agent, reinforcement agent, abrasive, explosive material, or biological remodeling agent includes at least one of an organic or inorganic small molecule, clathrate or caged compound, protocell, coacervate, microsphere, Janus particle, proteinoid, laminate, helical rod, liposome, macroscopic tube, niosome, sphingosome, toroid, vesicular tube, vesicle, small unilamellar vesicle, large unilamellar vesicle, large multilamellar vesicle, multivesicular vesicle, lipid layer, lipid bilayer, micelle, organelle, cell, membrane, nucleic acid, peptide, polypeptide, protein, oligosaccharide, polysaccharide, glycopeptide, glycolipid, sphingolipid, glycosphingolipid, glycoprotein, peptidoglycan, lipid, carbohydrate, metalloprotein, proteoglycan, chromosome, cell nucleus, acid, base, buffer, protic solvent, aprotic solvent, nitric oxide, nitric oxide synthase, nitrous oxide, amino acid, micelle, polymer, bone cement, copolymer, cell receptor, adhesion molecule, cytokine, chemokine, immunoglobulin, antibody, antigen, platelet, extracellular matrix, blood, plasma, cell ligand, zwitterionic material, cationic material, oligonucleotide, nanotube, or piloxymer

FIG. 102

10210 wherein the one or more explosive materials include at least one of a carbonate, carbon dioxide, nitroglycerine, acid, base, epoxy, acrylic polymer or copolymer, acrylamide polymer or copolymer, urethane, hypoxyapatite, or reactive metal 10220 wherein the at least one adhesive agent includes one or more of an acrylic polymer or copolymer, acrylamide polymer or copolymer polymer or copolymer, acrylamide polymer or copolymer, polyacrylic acid, epoxy, urethane, gum arabic, polyester, polyhydroxyalkanoate, poly(L-lactic acid), polyglycolide, polylactic acid, polyether, polyol, polyvinylpyrrolidone, pyroxylin, polymethylacrylate-isobutene-monoisopropylmaleate, siloxane polymer, polylactic-co-glycolic-acid, poly-3-hydroxybutyrate, poly-4-hydroxybutyrate, polyhydroxyvalerate, polyhydroxyhexanoate, polyhydroxyoctanoate, polycaprolactone, poly (e-caprolactone), sialyl Lewis$^x$, heme group, hemoglobin, healon, carboxymethylcellulose, hydroxyapatite, silicone, cadherin, integrin, hydroxyapatite, polyelectrolyte, maleic polyelectrolyte, cellulose, resilin, cyanoacrylate, isocyanate, 2-octyl cyanoacrylate, 2-butyl-n-cyanoacrylate, n-butyl-2-cyanoacrylate, butyl-2-cyanoacrylate, methyl 2-cyanoacrylate, polyisohexylcyanoacrylate, fibrin, thrombin, fibrinogen, hyaluronate, chitin, Factor XIII, Factor XII, silk, nylon, collagen, glycosaminoglycan, selectin, polyurethane, methacrylate, or polysulfide, polyanhydride, polydioxanone, poly-p-dioxanone, silicone, albumin, glutaraldehyde, polyethylene glycol, or gelatin 10230 wherein the one or more reinforcement agents include one or more of polyaramid, vinylester matrix, metal, ceramic, fiberglass, cellulose, broad carbide, aromatic polyamide, nylon, silk, rayon, acetate, modacrylic, olefin, acrylic, polyester, aromatic polyester, poly-lactic acid, vinyon, saran, spandex, vinalon, aromatic nylon, vinylidene chloride, modal, polybenzimidazole, sulfur, lyocell, orlon, zylon, high-performance polyethylene, polypyridobenzimidazole, vectran, acrylonitrile rubber, glass, copper, iron, steel, sodium, potassium, calcium, zinc, manganese, carbon, magnesium, silicon, silica, frozen hydrogen oxide ice, plant matter, animal matter, or mineral matter 10240 wherein the therapeutic agent includes at least one of an anti-tumor agent, antimicrobial agent, anti-viral agent, analgesic, antiseptic, anesthetic, diagnostic agent, anti-inflammatory agent, vaccine, cell growth inhibitor, cell growth promoter, immunogen, antigen, radioactive agent, apoptotic promoting factor, enzymatic agent, angiogenic factor, anti-angiogenic factor, hormone, vitamin, mineral, nutraceutical, cytokine, chemokine, probiotic, coagulant, anti-coagulant, phage, prodrug, prebiotic, blood sugar stabilizer, smooth muscle cell activator, epinephrine, adrenaline, neurotoxin, neuro-muscular toxin, Botulinum toxin type A, microbial cell or component thereof, or virus or component thereof

FIG. 103

10310 wherein the at least one biological remodeling agent includes one or more of a blood cell, chondrocyte, endothelial cell, hepatocyte, keratinocyte, myocyte, osteoblast, osteoclast, osteocyte, mesenchymal cell, stem cell, progenitor cell, or fibroblast 10320 wherein the at least one biological remodeling agent includes one or more of calcium phosphate, albumin, cytokine, pegylated cytokine, bone, cartilage, globulin, fibrin, thrombin, glutaraldehyde-crosslinked pericardium, hide powder, hyaluronic acid, hydroxylapatite, keratin, ligament, nitinol, nucleic acid polymers, polyethylene, polyethylene glycol, polyethylene glycol diacrylate, polyethylene terephthalate fiber, polyglycol, polylactate, polytetrafluoroethylene, polylactic acid, polyglycolic acid, polycaprolactone, PURAMATRIX™ self-assembly peptide hydrogel fibers, linear aliphatic polyester, tendon, fibrinogen, hyaluronate, chitin, chitosan, methylcellulose, alginate, hyaluronic acid, agarose, cellulose, polyaldehyde gluronate, Factor XIII, Factor XII, silk, nylon, collagen, silicone, polyurethane, ceramic powder, elastin, pectin, wax, glycosaminoglycan, poly(α-hydroxyacid), selectin, glutaraldehyde, hydrophobic non-glycosylated protein, hydrogel, peptide hydrogel, or gelatin 10330 wherein the at least one biological remodeling agent includes one or more of Type I collagen, Type II collagen, Type III collagen, Type VII collagen, Type X collagen, elastin fibers, or soluble elastin 10340 wherein the at least one biological remodeling agent is included as part of a carrier that assists in synthesis or activation of the at least one biological remodeling agent

FIG. 104

10400 A system comprising:

10410 means for comparing information regarding at least one parameter for at least partially constructing or at least partially reconstructing at least one biological tissue of a subject by administering one or more frozen particle compositions to the at least one subject and information regarding at least one clinical outcome following receipt by the at least one subject of one or more frozen particle compositions;

10420 means for providing output information 10430 wherein the output information is based on the comparison 10440 further comprising means for determining at least one statistical correlation 10450 further comprising means for counting the occurrence of at least one clinical outcome 10460 wherein the information regarding at least one parameter of at least partially constructing or at least partially reconstructing at least one biological tissue of a subject includes information regarding quantity of cells or tissue at least partially constructed or at least partially reconstructed 10470 wherein the information regarding at least one parameter of at least partially constructing or at least partially reconstructing at least one biological tissue of a subject includes information regarding at least one cellular or tissue source 10480 wherein the information regarding at least one parameter of at least partially constructing or at least partially reconstructing at least one biological tissue of a subject includes information regarding at least one abnormal cellular or tissue source 10490 wherein the information regarding at least one parameter of at least partially constructing or at least partially reconstructing at least one biological tissue of a subject includes information regarding at least one type of cell or tissue

FIG. 105

10510 wherein the at least one agent includes one or more of an adhesive agent, therapeutic agent, reinforcement agent, abrasive, explosive material, or biological remodeling agent 10520 wherein the information regarding at least one parameter of at least one partially constructing or at least partially reconstructing at least one biological tissue of a subject includes information regarding at least one dimension of at least one agent deposited 10530 wherein the information regarding at least one parameter of at least one partially constructing or at least partially reconstructing at least one biological tissue of at least one subject includes information regarding at least one dimension of at least one depth, width, or breadth of cellular, tissue, or other material removal or destruction 10540 wherein the information regarding at least one clinical outcome following receipt by the at least one subject of one or more frozen particle compositions includes information regarding two or more subjects with one or more common attributes 10450 wherein the one or more common attributes include one or more of genetic attributes, mental attributes, proteomic attributes, phenotypic attributes, or psychological attributes 10560 wherein the one or more common attributes include one or more of height, weight, medical diagnosis, familial background, results on one or more medical tests, ethnic background, body mass index, age, presence or absence of at least one disease or condition, species, ethnicity, race, allergies, gender, thickness of tissue, blood vessel condition, hair or fur condition, skin condition, tissue condition, muscle condition, organ condition, nerve condition, brain condition, presence or absence of at least one biological, chemical, or therapeutic agent in the subject, pregnancy status, lactation status, genetic profile, proteomic profile, partial or whole genetic sequence, partial or whole proteomic sequence, medical condition, medical history, or blood condition

FIG. 106

10610 wherein the output information includes at least one of a response signal, comparison code, comparison plot, diagnostic code, treatment code, test code, code indicative of at least one treatment received, code indicative of at least one prescribed treatment step, code indicative of at least one vaccination administered, code indicative of at least one therapeutic agent administered, code indicative of at least one diagnostic agent administered, code indicative of at least one interaction of an administered agent and at least one biological or chemical agent in the subject; a code indicative of at least one dispertion or location of at least one administered agent; code indicative of at least one detection material administered; code indicative of the depth of penetration of an administered agent, code indicative of the depth of deposition of an administered agent, or a code indicative of the condition of at least one location of an administered frozen particle composition 10620 wherein receipt by the at least one subject of one or more frozen particle compositions is pursuant to at least one clinical trial 10630 further comprising means for determining at least one correlation before the administration of the one or more frozen particle compositions to the at least one subject 10640 further comprising means for creating at least one inclusion criterion and at least one exclusion criterion for a clinical trial involving the one or more frozen particle compositions 10650 further comprising means for suggesting the inclusion of one or more of the at least one subject in at least one clinical trial 10660 further comprising means for suggesting the exclusion of one or more of the at least one subject in at least one clinical trial

FIG. 107

10710 further comprising means for using one or more of the at least one correlation to predict at least one clinical outcome regarding at least one second subject 10720 wherein the at least one second subject has not received the one or more frozen particle compositions 10730 further comprising means for predicting at least one clinical outcome involving the at least one second subject, wherein the at least one second subject is a plurality of people; and means for segregating subject identifiers associated with the plurality of people in reference to the predicted at least one clinical outcome 10740 further comprising means for determining the eligibility of the at least one second subject for the at least one clinical trial 10750 wherein the one or more frozen particle compositions includes one or more frozen particles of at least one of: hydrogen oxide, nitrogen, oxygen, air, helium, neon, argon, xenon, chlorine, bromine, carbon dioxide, polyethylene glycol, hydrogen oxide, nitrogen, oxygen, air, helium, neon, argon, xenon, chlorine, bromine, carbon dioxide, acetone, ethyl acetate, dimethyl sulfoxide, dimethyl formamide, dioxane, tetrahydrofuran, acetonitrile, acetic acid, n-butanol, isopropanol, n-propanol, hexamethylphosphorotriamide, perfluorohydrocarbon, methanol, ethanol, tert-butyl alcohol, formic acid, hydrogen fluoride, ammonia, benzene, carbon tetrachloride, acetonitrile, hexane, dichloromethane, methylene chloride, carboxylic acid, saline, standard saline citrate, methane, toluene, chloroform, polyethylene glycol, acetic acid, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, methane, or diethyl ether

FIG. 108

10810 wherein the at least one agent includes one or more of an adhesive agent, therapeutic agent, reinforcement agent, abrasive, explosive material, or biological remodeling agent 10820 wherein the adhesive agent, therapeutic agent, reinforcement agent, abrasive, explosive material, or biological remodeling agent includes at least one of an organic or inorganic small molecule, clathrate or caged compound, protocell, coacervate, microsphere, Janus particle, proteinoid, laminate, helical rod, liposome, macroscopic tube, niosome, sphingosome, toroid, vesicular tube, vesicle, small unilamellar vesicle, large unilamellar vesicle, large multilamellar vesicle, multivesicular vesicle, lipid layer, lipid bilayer, micelle, organelle, cell, membrane, nucleic acid, peptide, polypeptide, protein, oligosaccharide, polysaccharide, glycopeptide, glycolipid, sphingolipid, glycosphingolipid, glycoprotein, peptidoglycan, lipid, carbohydrate, metalloprotein, proteoglycan, chromosome, cell nucleus, acid, base, buffer, protic solvent, aprotic solvent, nitric oxide, nitric oxide synthase, nitrous oxide, amino acid, micelle, polymer, bone cement, copolymer, cell receptor, adhesion molecule, cytokine, chemokine, immunoglobulin, antibody, antigen, platelet, extracellular matrix, blood, plasma, cell ligand, zwitterionic material, cationic material, oligonucleotide, nanotube, or piloxymer 10830 wherein the one or more explosive materials include at least one of a carbonate, carbon dioxide, nitroglycerine, acid, base, epoxy, acrylic polymer or copolymer, acrylamide polymer or copolymer, urethane, hypoxyapatite, or reactive metal 10840 wherein the at least one adhesive agent includes one or more of an acrylic polymer or copolymer, acrylamide polymer or copolymer polymer or copolymer, acrylamide polymer or copolymer, polyacrylic acid, epoxy, urethane, gum arabic, polyester, polyhydroxyalkanoate, poly(L-lactic acid), polyglycolide, polylactic acid, polyether, polyol, polyvinylpyrrolidone, pyroxylin, polymethylacrylate-isobutene-monoisopropylmaleate, siloxane polymer, polylactic-co-glycolic-acid, poly-3-hydroxybutyrate, poly-4-hydroxybutyrate, polyhydroxyvalerate, polydydroxyhexanoate, polyhydroxyoctanoate, polycaprolactone, poly (e-caprolactone), sialyl Lewis$^x$, heme group, hemoglobin, healon, carboxymethylcellulose, hydroxyapatite, silicone, cadherin, integrin, hydroxyapatite, polyelectrolyte, maleic polyelectrolyte, cellulose, resilin, cyanoacrylate, isocyanate, 2-octyl cyanoacrylate, 2-butyl-n-cyanoacrylate, n-butyl-2-cyanoacrylate, butyl-2-cyanoacrylate, methyl 2-cyanoacrylate, polyisohexylcyanoacrylate, fibrin, thrombin, fibrinogen, hyaluronate, chitin, Factor XIII, Factor XII, silk, nylon, collagen, glycosaminoglycan, selectin, polyurethane, methacrylate, or polysulfide, polyanhydride, polydioxanone, poly-p-dioxanone, silicone, albumin, glutaraldehyde, polyethylene glycol, or gelatin

FIG. 110

11010 wherein the at least one biological remodeling agent includes one or more of calcium phosphate, albumin, cytokine, pegylated cytokine, bone, cartilage, globulin, fibrin, thrombin, glutaraldehyde-crosslinked pericardium, hide powder, hyaluronic acid, hydroxylapatite, keratin, ligament, nitinol, nucleic acid polymers, polyethylene, polyethylene glycol, polyethylene glycol diacrylate, polyethylene terephthalate fiber, polyglycol, polylactate, polytetrafluoroethylene, polylactic acid, polyglycolic acid, polycaprolactone, PURAMATRIX™ self-assembly peptide hydrogel fibers, linear aliphatic polyester, tendon, fibrinogen, hyaluronate, chitin, chitosan, methylcellulose, alginate, hyaluronic acid, agarose, cellulose, polyaldehyde gluronate, Factor XIII, silk, nylon, collagen, silicone, polyurethane, ceramic powder, elastin, pectin, wax, glycosaminoglycan, poly(α-hydroxyacid), selectin, glutaraldehyde, hydrophobic non-glycosylated protein, hydrogel, peptide hydrogel, or gelatin 11020 wherein the at least one biological remodeling agent includes one or more of Type I collagen, Type II collagen, Type III collagen, Type VII collagen, Type X collagen, elastin fibers, or soluble elastin 11030 wherein the at least one biological remodeling agent is included as part of a carrier that assists in synthesis or activation of the at least one biological remodeling agent

FIG. 111

11100 A system comprising:

11110 means for predicting a clinical outcome of one or more frozen particle composition treatments for at least one first subject 11120 means for determining a similarity or a dissimilarity in information regarding at least one parameter for at least partially constructing or at least partially reconstructing at least one biological tissue of at least one first subject by administering one or more frozen particle compositions to the at least one first subject with information regarding at least one parameter of at least partially constructing or at least partially reconstructing at least one biological tissue of at least one second subject 11130 wherein the at least one second subject attained a clinical outcome following receipt of one or more frozen particle compositions;

11140 means for providing output information 11150 wherein output information is based on the determination 11160 wherein the information regarding at least one parameter of at least partially constructing or at least partially reconstructing at least one biological tissue of at least second subject includes information regarding quantity of cells or tissue at least partially constructed or at least partially reconstructed 11170 wherein the information regarding at least one parameter of at least partially constructing or at least partially reconstructing at least one biological tissue of at least one first subject includes information regarding at least one cellular or tissue source 11180 wherein the information regarding at least one parameter of at least partially constructing or at least partially reconstructing at least one biological tissue of at least one first subject includes information regarding at least one abnormal cellular or tissue source

FIG. 112

11210 wherein the information regarding at least one parameter of at least one first subject includes information regarding at least one type of cell or tissue 11220 wherein the information regarding at least one parameter of at least one second subject includes information regarding at least one type of cell or tissue 11230 wherein the at least one agent includes one or more of an adhesive agent, abrasive, reinforcement agent, therapeutic agent, biological remodeling agent, or explosive material 11240 wherein the information regarding at least one parameter of at least one first subject includes information regarding at least one dimension of at least one agent deposited 11250 wherein the information regarding at least one parameter of at least one second subject includes information regarding at least one dimension of at least one agent deposited 11260 wherein the information regarding at least one parameter of at least one second subject includes information regarding at least one dimension of at least one depth, width, or breadth of cellular, tissue, or other material removal or destruction 11270 wherein the information regarding at least one parameter of at least one first subject includes information regarding at least one dimension of at least one depth, width, or breadth of cellular, tissue, or other material removal or destruction

FIG. 113

11310 wherein the information regarding at least one clinical outcome following receipt by the at least one second subject of one or more frozen particle compositions includes information regarding two or more subjects with one or more common attributes 11320 wherein the one or more common attributes include one or more of genetic attributes, mental attributes, proteomic attributes, phenotypic attributes, or psychological attributes 11330 wherein the one or more common attributes include one or more of height, weight, medical diagnosis, familial background, results on one or more medical tests, ethnic background, body mass index, age, presence or absence of at least one disease or condition, species, ethnicity, race, allergies, gender, thickness of tissue, blood vessel condition, hair or fur condition, skin condition, tissue condition, muscle condition, organ condition, nerve condition, brain condition, presence or absence of at least one biological, chemical, or therapeutic agent in the subject, pregnancy status, lactation status, genetic profile, proteomic profile, partial or whole genetic sequence, partial or whole proteomic sequence, medical condition, medical history, or blood condition 11340 wherein the output information includes at least one of a response signal, comparison code, comparison plot, diagnostic code, treatment code, test code, code indicative of at least one treatment received, code indicative of at least one prescribed treatment step, code indicative of at least one vaccination administered, code indicative of at least one therapeutic agent administered, code indicative of at least one diagnostic agent administered, code indicative of at least one interaction of an administered agent and at least one biological or chemical agent in the subject; a code indicative of at least one dispersion or location of at least one administered agent; code indicative of at least one detection material administered; code indicative of the depth of penetration of an administered agent, code indicative of the depth of deposition of an administered agent, or a code indicative of the condition of at least one location of an administered frozen particle composition

FIG. 114

11410 wherein receipt by the at least one second subject of one or more frozen particle compositions is pursuant to at least one clinical trial 11420 further comprising means for determining at least one correlation before the administration of the one or more frozen particle compositions to the at least one first subject 11430 further comprising means for creating at least one inclusion criterion and at least one exclusion criterion for a clinical trial involving the one or more frozen particle compositions 11440 further comprising means for suggesting the inclusion of one or more of the at least one first subject in at least one clinical trial 11450 further comprising means for suggesting the exclusion of one or more of the at least one first subject in at least one clinical trial 11460 further comprising means for using one or more of the at least one correlation to predict at least one clinical outcome regarding at least one second subject 11470 wherein the at least one second subject has not received the one or more frozen particle compositions 11480 further comprising means for predicting at least one clinical outcome involving the at least one second subject, wherein the at least one second subject is a plurality of people; and means for segregating subject identifiers associated with the plurality of people in reference to the predicted at least one clinical outcome

FIG. 115

11510 wherein the one or more frozen particle compositions include one or more frozen particles including at least one of: hydrogen oxide, nitrogen, oxygen, air, helium, neon, argon, xenon, chlorine, bromine, carbon dioxide, acetone, ethyl acetate, dimethyl sulfoxide, dimethyl formamide, dioxane, tetrahydrofuran, acetonitrile, acetic acid, n-butanol, isopropanol, n-propanol, hexamethylphosphorotriamide, perfluorohydrocarbon, methanol, ethanol, tert-butyl alcohol, formic acid, hydrogen fluoride, ammonia, benzene, carbon tetrachloride, acetonitrile, hexane, dichloromethane, methylene chloride, carboxylic acid, saline, standard saline citrate, methane, toluene, chloroform, polyethylene glycol, acetic acid, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, methane, or diethyl ether.

11520 wherein the one or more frozen particle compositions includes one or more of an adhesive agent, therapeutic agent, reinforcement agent, abrasive, explosive material, or biological remodeling agent 11530 wherein the adhesive agent, therapeutic agent, reinforcement agent, abrasive, explosive material, or biological remodeling agent includes at least one of an organic or inorganic small molecule, clathrate or caged compound, protocell, coacervate, microsphere, Janus particle, proteinoid, laminate, helical rod, liposome, macroscopic tube, niosome, sphingosome, toroid, vesicular tube, vesicle, small unilamellar vesicle, large unilamellar vesicle, large multilamellar vesicle, multivesicular vesicle, lipid layer, lipid bilayer, micelle, organelle, cell, membrane, nucleic acid, peptide, polypeptide, protein, oligosaccharide, polysaccharide, glycopeptide, glycolipid, sphingolipid, glycosphingolipid, glycoprotein, peptidoglycan, lipid, carbohydrate, metalloprotein, proteoglycan, chromosome, cell nucleus, acid, base, buffer, protic solvent, aprotic solvent, nitric oxide, nitric oxide synthase, nitrous oxide, amino acid, micelle, polymer, bone cement, copolymer, cell receptor, adhesion molecule, cytokine, chemokine, immunoglobulin, antibody, antigen, platelet, extracellular matrix, blood, plasma, cell ligand, zwitterionic material, cationic material, oligonucleotide, nanotube, or piloxymer 11540 wherein the one or more explosive materials include at least one of a carbonate, carbon dioxide, nitroglycerine, acid, base, epoxy, acrylic polymer or copolymer, acrylamide polymer or copolymer, urethane, hypoxyapatite, or reactive metal

FIG. 116

11610 wherein the at least one adhesive agent includes one or more of an acrylic polymer or copolymer, acrylamide polymer or copolymer polymer or copolymer, acrylamide polymer or copolymer, polyacrylic acid, epoxy, urethane, gum arabic, polyester, polyhydroxyalkanoate, poly(L-lactic acid), polyglycolide, polylactic acid, polyether, polyol, polyvinylpyrrolidone, pyroxylin, polymethylacrylate-isobutene-monoisopropylmaleate, siloxane polymer, polylactic-co-glycolic-acid, poly-3-hydroxybutyrate, poly-4-hydroxybutyrate, polyhydroxyvalerate, polyhydroxyhexanoate, polydyroxyoctanoate, polycaprolactone, poly (e-caprolactone), sialyl Lewis[x], heme group, hemoglobin, healon, carboxymethylcellulose, hydroxyapatite, silicone, cadherin, integrin, hydroxyapatite, polyelectrolyte, maleic polyelectrolyte, cellulose, resilin, cyanoacrylate, isocyanate, 2-octyl cyanoacrylate, 2-butyl-n-cyanoacrylate, n-butyl-2-cyanoacrylate, butyl-2-cyanoacrylate, methyl 2-cyanoacrylate, polyisohexylcyanoacrylate, fibrin, thrombin, fibrinogen, hyaluronate, chitin, Factor XIII, silk, nylon, collagen, glycosaminoglycan, selectin, polyurethane, methacrylate, or polysulfide, polyanhydride, polydioxanone, poly-p-dioxanone, silicone, albumin, glutaraldehyde, polyethylene glycol, or gelatin 11620 wherein the one or more reinforcement agents include one or more of polyaramid, vinylester matrix, metal, ceramic, fiberglass, cellulose, broad carbide, aromatic polyamide, nylon, silk, rayon, acetate, modacrylic, olefin, acrylic, polyester, aromatic polyester, poly-lactic acid, vinyon, saran, spandex, vinalon, aromatic nylon, vinylidene chloride, modal, polybenzimidazole, sulfur, lyocell, orlon, zylon, high-performance polyethylene, polypyridobenzimidazole, vectran, acrylonitrile rubber, glass, copper, iron, steel, sodium, potassium, calcium, zinc, manganese, carbon, magnesium, silicon, silica, frozen hydrogen oxide ice, plant matter, animal matter, or mineral matter 11630 wherein the therapeutic agent includes at least one of an anti-tumor agent, antimicrobial agent, anti-viral agent, analgesic, antiseptic, anesthetic, diagnostic agent, anti-inflammatory agent, vaccine, cell growth inhibitor, cell growth promoter, immunogen, antigen, radioactive agent, apoptotic promoting factor, enzymatic agent, angiogenic factor, anti-angiogenic factor, hormone, vitamin, mineral, nutraceutical, cytokine, chemokine, probiotic, coagulant, anti-coagulant, phage, prodrug, prebiotic, blood sugar stabilizer, smooth muscle cell activator, epinephrine, adrenaline, neurotoxin, neuro-muscular toxin, Botulinum toxin type A, microbial cell or component thereof, or virus or component thereof

FIG. 117

11710 wherein the at least one biological remodeling agent includes one or more of a blood cell, chondrocyte, endothelial cell, hepatocyte, keratinocyte, myocyte, osteoblast, osteoclast, osteocyte, mesenchymal cell, stem cell, progenitor cell, or fibroblast 11720 wherein the at least one biological remodeling agent includes one or more of calcium phosphate, albumin, cytokine, pegylated cytokine, bone, cartilage, globulin, fibrin, thrombin, glutaraldehyde-crosslinked pericardium, hide powder, hyaluronic acid, hydroxylapatite, keratin, ligament, nitinol, nucleic acid polymers, polyethylene, polyethylene glycol, polyethylene glycol diacrylate, polyethylene terephthalate fiber, polyglycol, polylactate, polytetrafluoroethylene, polylactic acid, polyglycolic acid, polycaprolactone, PURAMATRIX™ self-assembly peptide hydrogel fibers, linear aliphatic polyester, tendon, fibrinogen, hyaluronate, chitin, chitosan, methylcellulose, alginate, hyaluronic acid, agarose, cellulose, polyaldehyde gluronate, Factor XIII, Factor XII, silk, nylon, collagen, silicone, polyurethane, ceramic powder, elastin, pectin, wax, glycosaminoglycan, poly(α-hydroxyacid), selectin, glutaraldehyde, hydrophobic non-glycosylated protein, hydrogel, peptide hydrogel, or gelatin 11730 wherein the at least one biological remodeling agent includes one or more of Type I collagen, Type II collagen, Type III collagen, Type VII collagen, Type X collagen, elastin fibers, or soluble elastin 11740 wherein the at least one biological remodeling agent is included as part of a carrier that assists in synthesis or activation of the at least one biological remodeling agent FIG. 121
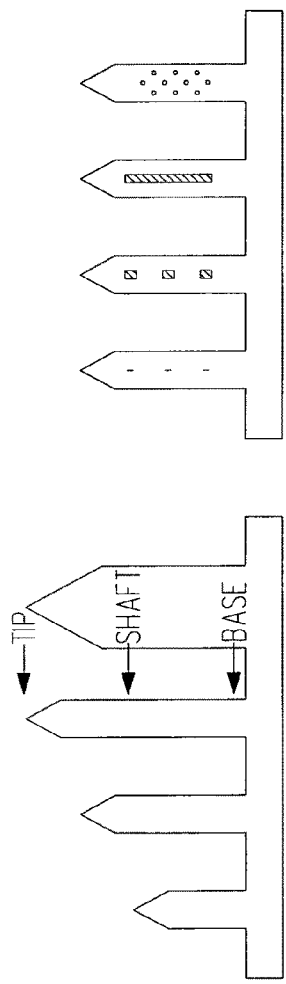
FIG. 121A
FIG. 121B
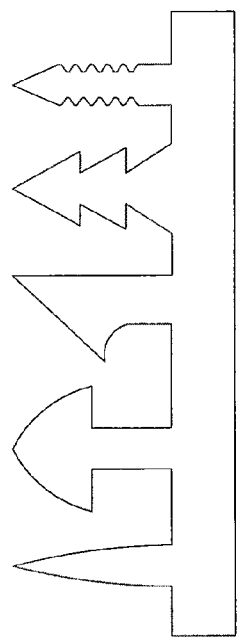
FIG. 121C

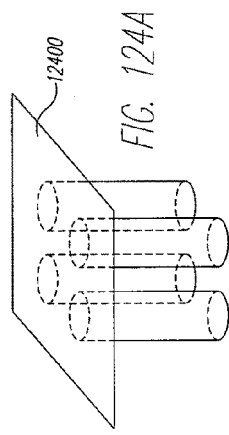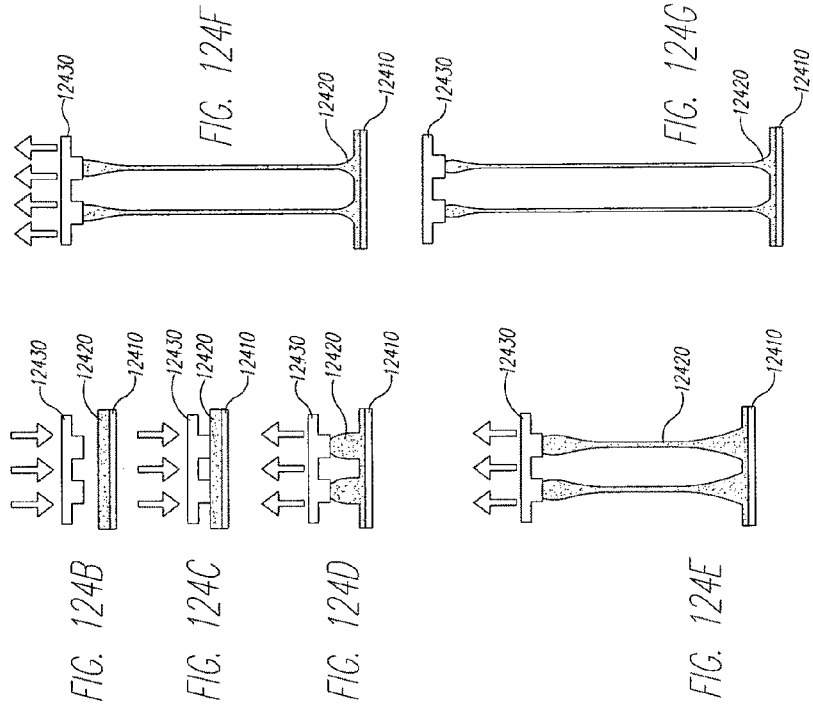
FIG. 124

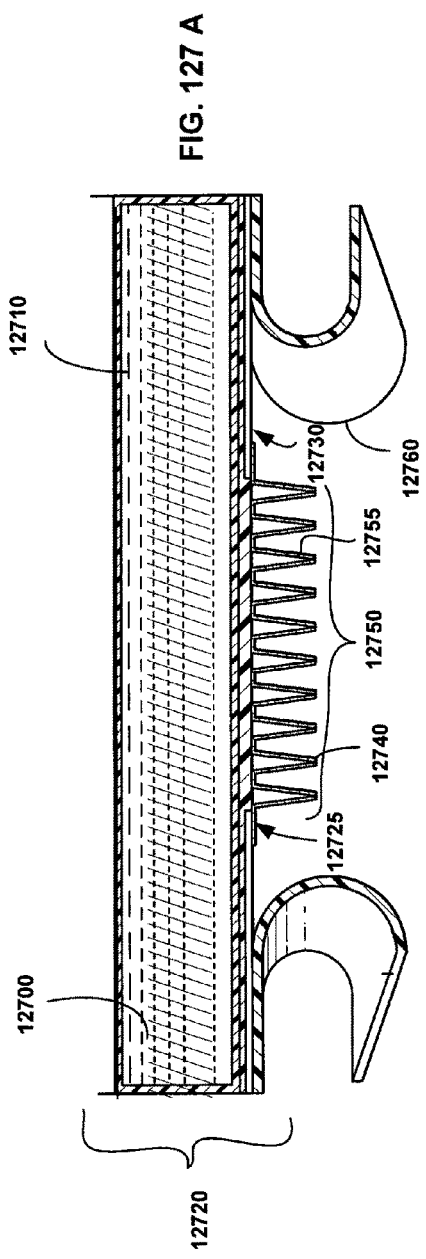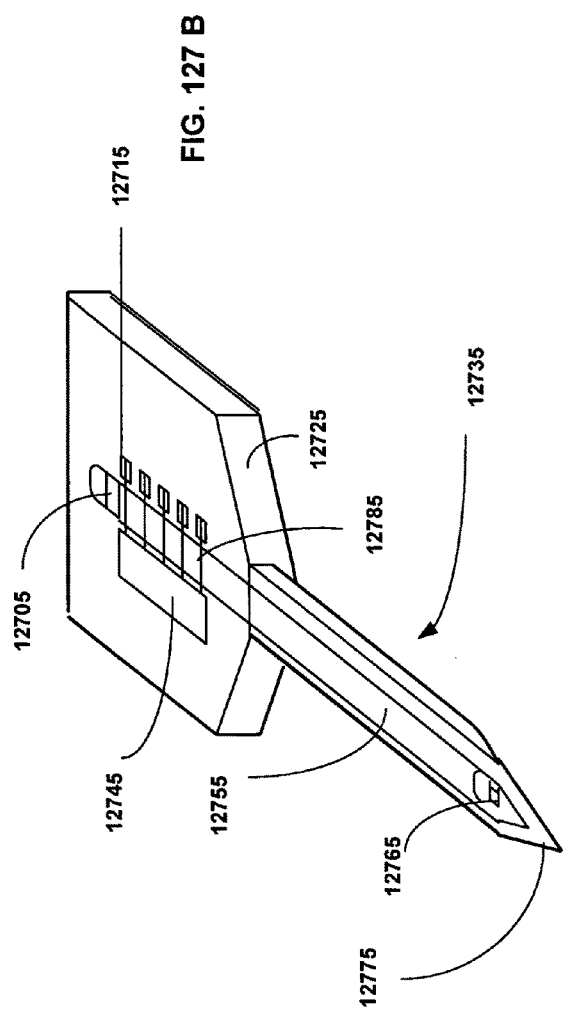
FIG. 127

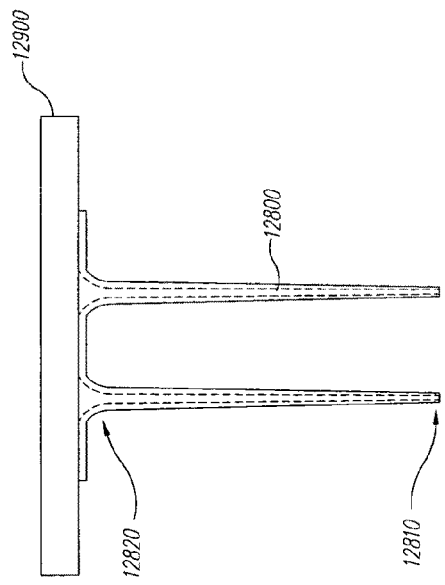
FIG. 129
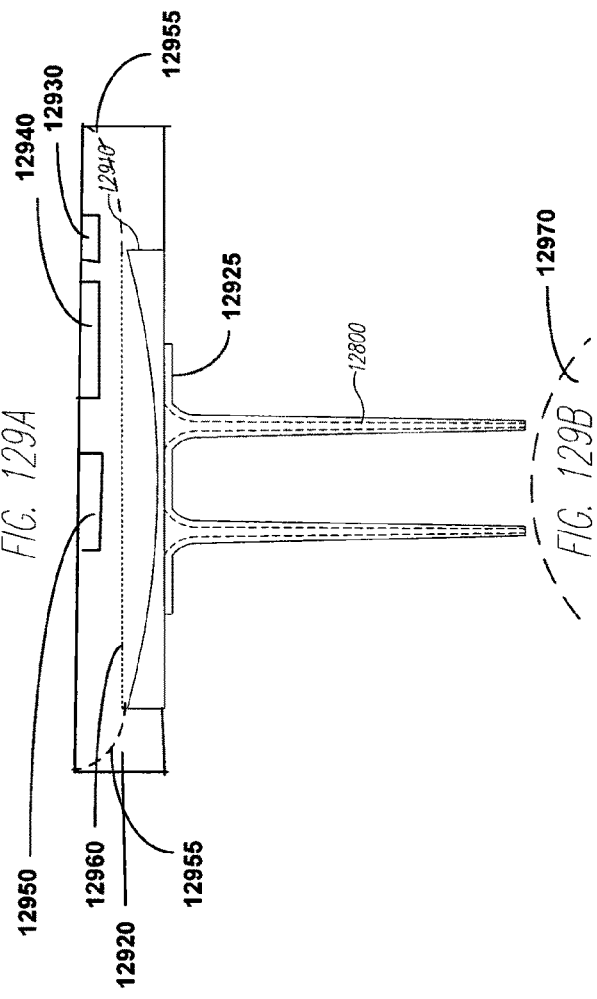

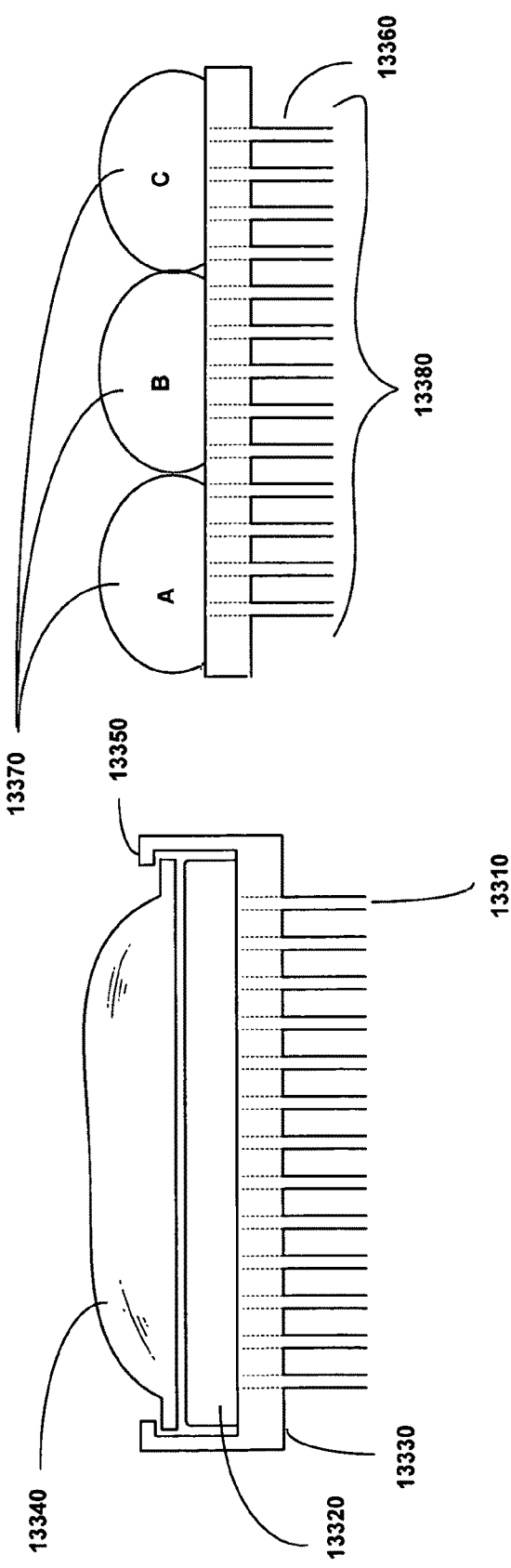

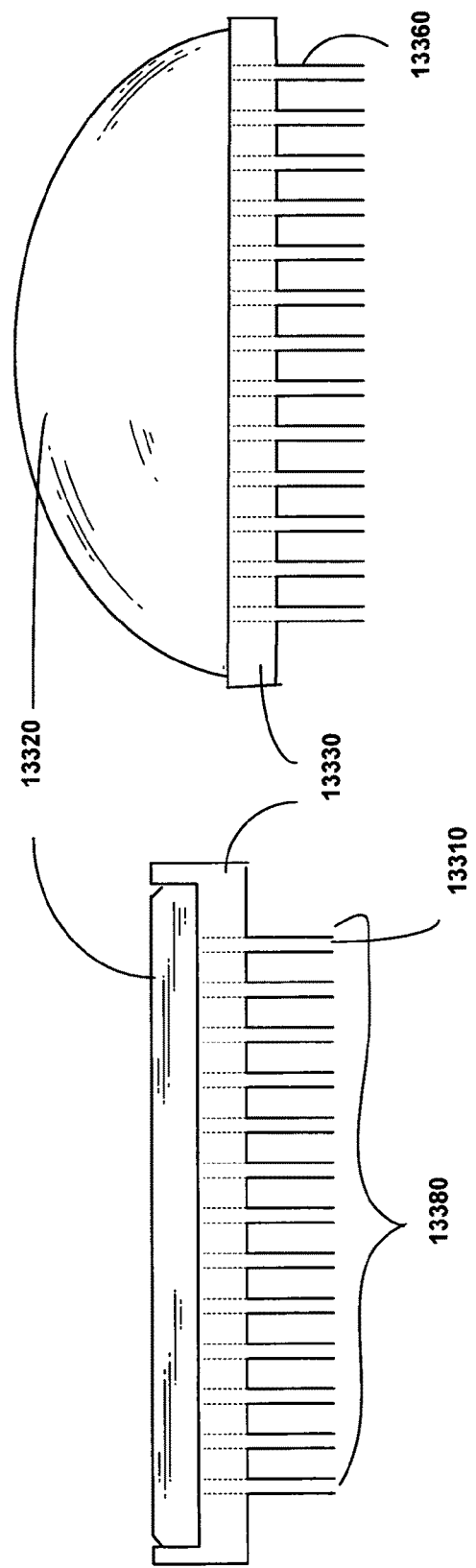

FIG. 135

13500 A computer-implemented method comprising:

13510 receiving one or more signals that include information related to accepting input associated with at least one parameter for making or administering at least one frozen particle composition, frozen piercing implement, or frozen piercing implement device to at least one substrate 13520 wherein the at least one frozen particle composition, frozen piercing implement, or frozen piercing implement device includes at least one agent 13530 receiving one or more signals that include information related to evaluating the at least one substrate for one or more indicators of administration of the at least one frozen particle composition, frozen piercing implement, frozen piercing implement device or agent 13540 processing the information related to the input associated with at least one parameter for making or administering the at least one frozen particle composition, frozen piercing implement, or frozen piercing implement device to at least one substrate and the information related to the evaluating the at least one substrate 13550 generating an output to a user readable display 13560 wherein the evaluating at least one substrate for one or more indicators includes evaluating at least one of an assay, image, or gross assessment of the at least one biological tissue prior to, during, or subsequent to at least one administration of at least one frozen particle composition, frozen piercing implement, or frozen piercing implement device 13570 wherein the assay includes at least one technique that includes spectroscopy, microscopy, electrochemical detection, polynucleotide detection, histological examination, biopsy analysis, fluorescence resonance energy transfer, electron transfer, enzyme assay, electrical conductivity, isoelectric focusing, chromatography, immunoprecipitation, immunoseparation, aptamer binding, filtration, electrophoresis, immunoassay, or radioactive assay

FIG. 136

13610 wherein the image includes at least one image acquired by one or more of x-ray crystallography, laser, holography, optical coherence tomography, computer-assisted tomography scan, computed tomography, magnetic resonance imaging, positron-emission tomography scan, ultrasound, x-ray, laser, holography, electrical-impedance monitoring, microscopy, spectrometry, flow cytommetry, radioisotope imaging, thermal imaging, infrared visualization, multiphoton calcium-imaging, photography, or *in silico* generation 13620 wherein the receiving one or more signals includes receiving one or more signals associated with selection of at least one parameter for making or administering the at least one frozen particle composition, frozen piercing implement, or frozen piercing implement device 13630 wherein the at least one parameter for making the at least one frozen piercing implement device includes one or more of: constitution of the at least one frozen piercing implement of the frozen piercing implement device, constitution of the at least one frozen piercing implement device, formulation of the at least one frozen piercing implement of the frozen piercing implement device, formulation of the at least one frozen piercing implement device, configuration of the at least one frozen piercing implement of the device or frozen piercing implement device, size of the at least one frozen piercing implement of the frozen piercing implement device, size of the at least one frozen piercing implement device, shape of the at least one frozen piercing implement of the frozen piercing implement device, shape of the at least one frozen piercing implement device, physical structure of the at least one frozen piercing implement of the frozen piercing implement device, physical structure of the at least one frozen piercing implement device, physical or chemical integrity of the at least one frozen piercing implement of the frozen piercing implement device, or physical or chemical integrity of the at least one frozen piercing implement device

FIG. 137

13710 wherein the at least one parameter for administering at least one frozen piercing implement device to at least one substrate includes one or more of: substrate type; substrate function; substrate size; substrate constitution; substrate architecture; substrate durability; substrate temperature; temperature of administration conditions; depth of administration of the at least one frozen particle composition or frozen piercing implement; substrate source; one or more temporal coordinates; one or more spatial coordinates; presence or absence of at least one agent; presence or absence of at least one microparticle, nanoparticle, lens, tunable lens, sensor, transducer, actuator, detector, heater, valve, gate, channel, detection material, pump, power source, injector, controller, receiver, transmitter, or circuit; angle of administration of the at least one frozen piercing implement device; force of administration of the at least one frozen piercing implement device; quantity of frozen piercing implement devices administered; rate of administration of more than one frozen piercing implement devices; method of administration of at least one frozen piercing implement device; timing of administration of at least one frozen piercing implement; or rate of delivery of at least one agent of the device 13720 wherein the at least one parameter for making the at least one frozen particle composition or frozen piercing implement includes one or more of: constitution of the at least one frozen particle composition or frozen piercing implement, formulation of the at least one frozen particle composition or frozen piercing implement, configuration of the at least one frozen particle composition or frozen piercing implement, size of the at least one frozen particle composition or frozen piercing implement, density of the at least one frozen particle composition or frozen piercing implement, shape of the at least one frozen particle composition or frozen piercing implement, physical structure of the at least one frozen particle composition or frozen piercing implement, or physical or chemical integrity of the at least one frozen particle composition or frozen piercing implement 13730 wherein the at least one agent includes one or more of an adhesive agent, therapeutic agent, reinforcement agent, abrasive, explosive material, or biological remodeling agent

FIG. 138

13810 wherein the at least one parameter for administering the at least one frozen particle composition or frozen piercing implement includes one or more of: substrate type; substrate function; substrate size; substrate constitution; substrate architecture; substrate durability; substrate temperature; temperature of administration conditions; depth of administration of the at least one frozen particle composition or frozen piercing implement; substrate source; one or more temporal coordinates; one or more spatial coordinates; presence or absence of at least one agent; presence or absence of at least one microparticle, nanoparticle, lens, tunablelens, sensor, transducer, actuator, detector, heater, valve, gate, channel, detection material, pump, power source, injector, controller, receiver, transmitter, or circuit; angle of administration of the at least one frozen piercing implement device; force of administration of the at least one frozen piercing implement device; velocity of administration of the at least one frozen piercing implement device; quantity of frozen piercing implements of the device; quantity of frozen piercing implement devices administered; rate of administration of more than one frozen piercing implement devices; method of administration of at least one frozen piercing implement device; timing of administration of at least one frozen piercing implement; or rate of delivery of at least one agent of the device 13820 wherein the at least one substrate includes one or more of a cell, tissue, organ, structure, device, or food product 13830 wherein the at least one frozen particle composition, frozen piercing implement, or frozen piercing implement device includes one or more frozen piercing implements including at least one of hydrogen oxide, nitrogen, oxygen, air, helium, neon, argon, xenon, chlorine, bromine, carbon dioxide, acetone, ethyl acetate, dimethyl sulfoxide, dimethyl formamide, dioxane, tetrahydrofuran, acetonitrile, acetic acid, n-butanol, isopropanol, n-propanol, hexamethylphosphorotriamide, perfluorohydrocarbon, methanol, ethanol, tert-butyl alcohol, formic acid, hydrogen fluoride, ammonia, benzene, carbon tetrachloride, hexane, dichloromethane, methylene chloride, carboxylic acid, saline, methane, toluene, chloroform, polyethylene glycol, acetic acid, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, or diethyl ether

FIG. 139

13910 wherein the output includes one or more instructions for making the at least one frozen particle composition, frozen piercing implement, or frozen piercing implement device 13920 wherein the output includes at least one graphical description of the at least one frozen particle composition, frozen piercing implement, or frozen piercing implement device 13930 wherein the user includes at least one entity 13940 wherein the entity includes at least one person, or computer 13950 wherein the user readable display includes a human readable display 13960 wherein the user readable display includes one or more active displays 13970 wherein the user readable display includes one or more passive displays 13980 wherein the user readable display includes one or more of a numeric format, graphical format, or audio format 13990 wherein the user readable display includes one or more of a display of one or more differences in the comparison of at least one value related to the first input and at least one value related to at least one property of the at least one frozen particle composition, frozen piercing implement, or frozen piercing implement device 13995 wherein the user readable display includes one or more of a display of one or more differences in the comparison of at least one value related to the second input and at least one value related to at least one parameter for administration of the at least one frozen particle composition, frozen piercing implement, or frozen piercing implement device

FIG. 140
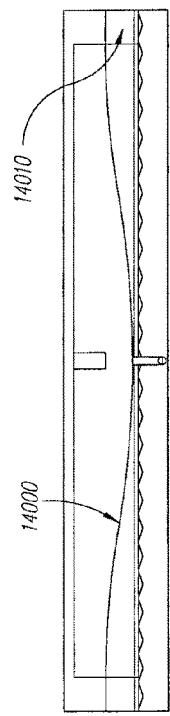
FIG. 140A
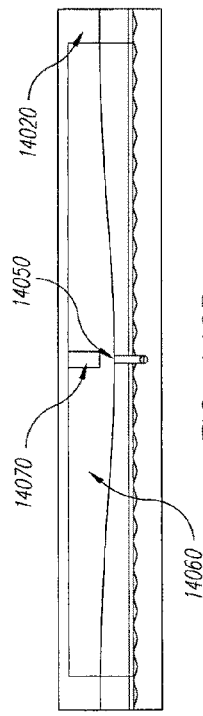
FIG. 140B
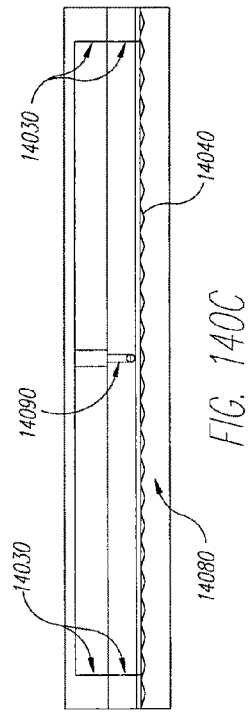
FIG. 140C

FIG. 141

14100 A computer-implemented method comprising:

14110 accepting a first input associated with at least one parameter for making at least one frozen particle composition or frozen piercing implement;

14120 accepting a second input associated with at least one parameter for administering the at least one frozen particle composition or frozen piercing implement to at least one substrate;

14130 wherein the at least one frozen particle composition or frozen piercing implement includes at least one agent 14140 wherein the at least one agent includes one or more of a therapeutic agent, adhesive agent, abrasive, reinforcement agent, explosive material, or biological remodeling agent 14150 wherein the at least one substrate includes one or more of a cell, tissue, organ, structure, device or food product 14160 processing the first input and the second input 14170 wherein processing the first input and the second input includes electronically processing the first input and the second input 14180 wherein electronically processing the first input and the second input by utilizing one or more of Gaussian smoothing, scaling, homomorphic filtering, parametric estimation techniques, Boolean operations, Monte Carlo simulations, wavelet based techniques, mirroring, smoothing, gradient weighted partial differential equation smoothing, NURBS, polygonal modeling, splines and patches modeling, algorithmic execution, logical decision-making, result prediction, Finite Element Analysis, or modification of a CAD design 14190 generating an output to a user readable display

FIG. 142

14210 wherein the first input includes one or more values related to the at least one parameter for making the at least one frozen particle composition or frozen piercing implement 14220 wherein the first input includes one or more values derived from at least one image of at least one frozen particle composition or frozen piercing implement 14230 wherein the at least one image includes one or more images acquired by at least one of laser, holography, x-ray, crystallography, optical coherence tomography, computer-assisted tomography scan, computed tomography, magnetic resonance imaging, positron-emission tomography scan, ultrasound, x-ray, electrical-impedance monitoring, microscopy, spectrometry, flow cytometry, radioisotope imaging, thermal imaging, infrared visualization, multiphoton calcium-imaging, photography, or in silico generation 14250 wherein the at least one parameter for making the at least one frozen particle composition or frozen piercing implement includes one or more property including: constitution of the at least one frozen particle composition or frozen piercing implement, configuration of the at least one frozen particle composition or frozen piercing implement, configuration of the at least one frozen particle composition or frozen piercing implement, formulation of the at least one frozen particle composition or frozen piercing implement, size of the at least one frozen particle composition or frozen piercing implement, density of the at least one frozen particle composition or frozen piercing implement, shape of the at least one frozen particle composition or frozen piercing implement, physical structure of the at least one frozen particle composition or frozen piercing implement, or physical or chemical integrity of the at least one frozen particle composition or frozen piercing implement

FIG. 143

14310 wherein the at least one parameter for administering at least one frozen particle composition or frozen piercing implement to at least one substrate includes one or more of: substrate type; substrate function; substrate size; substrate constitution; substrate architecture; substrate durability; substrate temperature; temperature of administration conditions; depth of administration of the at least one frozen particle composition or frozen piercing implement; substrate source; one or more temporal coordinates; one or more spatial coordinates; presence or absence of at least one agent; presence or absence of one or more sensors, valves, gates, channels, transducers, circuits, nanoparticles, microactuators, microdetectors, microheaters, or detection materials; angle of administration of the at least one frozen particle composition or frozen piercing implement; velocity of administration of the at least one frozen particle composition or frozen piercing implement; quantity of frozen particle compositions or frozen piercing implements administered; rate of administration of more than one frozen particle compositions or frozen piercing implements; method of administration of at least one frozen particle composition or frozen piercing implement; timing of administration of at least one frozen particle composition or frozen piercing implement; or rate of delivery of at least one agent 14330 wherein the at least one substrate is located in at least one of *in situ, in vitro, in vivo, in utero, in planta, in silico*, or *ex vivo*

14340 wherein the at least one substrate is at least partially located in at least one subject 14350 further comprising accepting a third input associated with at least one feature of the at least one subject 14360 wherein the at least one feature of the at least one subject includes one or more of: age, gender, genotype, phenotype, proteomic profile, lipidomic profile, glycomic profile, system biology profile, circulatory condition, respiratory condition, blood condition, lymph condition, anatomic landscape, body contour, or health condition

FIG. 144

14410 wherein the at least one parameter for administering at least one frozen particle composition or frozen piercing implement includes at least one parameter relating to administering at least one of a therapeutic agent, adhesive agent, biological remodeling agent, reinforcement agent, abrasive, or explosive material by way of the at least one frozen particle composition or frozen piercing implement 14420 wherein the at least one parameter for administering at least one frozen particle composition or frozen piercing implement includes at least one parameter relating to at least partially ablating or at least partially abrading one or more surfaces of the at least one substrate with the at least one frozen particle composition or frozen piercing implement 14430 wherein the processing the first input and the second input includes determining at least one parameter for administering at least one frozen particle composition or frozen piercing implement from one or more values derived from at least one image of the at least one frozen particle composition or frozen piercing implement 14440 wherein the second input includes one or more values related to the at least one parameter for administering at least one frozen particle composition or frozen piercing implement 14450 wherein the one or more values related to the at least one parameter for administering at least one frozen particle composition or frozen piercing implement includes one or more predictive values 14460 wherein the processing the first input and the second input includes comparing at least one value related to the first input associated with the at least one parameter for making the at least one frozen particle composition or frozen piercing implement with at least one value related to at least one property of the frozen particle composition or frozen piercing implement 14470 wherein the processing the first input and the second input includes determining one or more differences in at least one value related to the first input and at least one value related to at least one image of the at least one frozen particle composition or frozen piercing implement

FIG. 145

14510 wherein the processing the first input and the second input includes determining one or more differences in at least one value related to the second input associated with the at least one parameter for administering at least one frozen particle composition or frozen piercing implement 14520 wherein the processing the first input and the second input includes generating one or more protocols for administering the at least one frozen particle composition or frozen piercing implement 14530 wherein the administering at least one frozen particle composition or frozen piercing implement to at least one substrate includes delivering at least one agent to at least one substrate 14550 wherein the output includes one or more instructions for making the at least one frozen particle composition or frozen piercing implement 14560 wherein the output includes at least one graphical description of the at least one frozen particle composition or frozen piercing implement 14570 wherein the user includes at least one entity 14575 wherein the entity includes at least one person, or computer 14580 wherein the user readable display includes a human readable display 14590 wherein the user readable display includes one or more active displays 14595 wherein the user readable display includes one or more passive displays 14598 wherein the user readable display includes one or more of a numeric format, graphical format, or audio format

FIG. 146

14610 wherein the user readable display includes one or more of a display of one or more differences in the comparison of at least one value related to the first input and at least one value related to at least one property of the at least one frozen particle composition or frozen piercing implement 14615 wherein the user readable display includes one or more of a display of one or more differences in the comparison of at least one value related to the second input and at least one value related to at least one parameter for administration of the at least one frozen particle composition or frozen piercing implement 14618 further comprising transmitting one or more signals that include information related to the processing results of the first input and the second input 14620 wherein the transmitting one or more signals includes transmitting one or more signals associated with selection of at least one parameter for making at least one frozen particle composition or frozen piercing implement 14630 wherein the transmitting one or more signals includes transmitting one or more signals associated with selection of at least one parameter for administering the at least one frozen particle composition or frozen piercing implement 14640 wherein the transmitting one or more signals includes transmitting one or more signals associated with comparing the information related to the processing the first input and the second input 14650 wherein the at least one frozen particle composition or frozen piercing implement includes one or more of hydrogen oxide, nitrogen, oxygen, air, helium, neon, argon, xenon, chlorine, bromine, carbon dioxide, acetone, ethyl acetate, dimethyl sulfoxide, dimethyl formamide, dioxane, tetrahydrofuran, acetonitrile, acetic acid, n-butanol, isopropanol, n-propanol, hexamethylphosphorotriamide, perfluorohydrocarbon, methanol, ethanol, tert-butyl alcohol, formic acid, hydrogen fluoride, ammonia, benzene, carbon tetrachloride, hexane, dichloromethane, methylene chloride, carboxylic acid, saline, standard saline citrate, methane, toluene, chloroform, polyethylene glycol, acetic acid, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, or diethyl ether

FIG. 147

14710 further comprising making at least one frozen particle composition or frozen piercing implement 14720 further comprising administering at least one frozen particle composition or frozen piercing implement to at least one substrate 14730 further comprising evaluating the at least one substrate for one or more indicators related to at least one parameter for administering the at least one frozen particle composition or frozen piercing implement 14740 wherein the evaluating at least one substrate for one or more indicators includes evaluating at least one of an assay, image, or gross assessment of the at least one substrate prior to, during, or subsequent to at least one administration of the at least one frozen particle composition or frozen piercing implement 14750 wherein the assay includes at least one technique including spectroscopy, microscopy, electrochemical detection, polynucleotide detection, histological examination, biopsy analysis, fluorescence resonance energy transfer, electron transfer, enzyme assay, electrical conductivity, isoelectric focusing, chromatography, immunoprecipitation, immunoseparation, aptamer binding, filtration, electrophoresis, immunoassay, or radioactive assay 14755 wherein the at least one image includes one or more images acquired by at least one of laser, holography, x-ray crystallography, optical coherence tomography, computer-assisted tomography scan, computed tomography, magnetic resonance imaging, positron-emission tomography scan, ultrasound, x-ray, electrical-impedance monitoring, microscopy, spectrometry, flow cytommetry, radioisotope imaging, thermal imaging, infrared visualization, multiphoton calcium-imaging, photography, or *in silico* generation 14760 further comprising transmitting one or more signals that include information relating to the accepting a first input or a second input and information related to the evaluating the at least one substrate 14770 wherein the transmitting one or more signals includes transmitting one or more signals associated with selection of at least one parameter for making the at least one frozen particle composition or frozen piercing implement 14780 wherein the transmitting one or more signals includes transmitting one or more signals associated with selection of at least one parameter for administering the at least one frozen particle composition or frozen piercing implement

FIG. 148

14800 A computer-implemented method, comprising:

14810 receiving one or more signals that include information related to accepting input associated with at least one parameter for making or administering at least one frozen particle composition or frozen piercing implement to at least one substrate;

14820 receiving one or more signals that include information related to evaluating the at least one substrate for one or more indicators of administration of the at least one frozen particle composition, or frozen piercing implement;

14830 processing the information related to the input associated with at least one parameter for making or administering the at least one frozen particle composition or frozen piercing implement to at least one substrate and the information related to the evaluating the at least one substrate 14840 wherein the at least one frozen particle composition or frozen piercing implement includes at least one agent 14850 wherein the evaluating at least one substrate for one or more indicators includes evaluating at least one of an assay, image, or gross assessment of the at least one substrate prior to, during, or subsequent to at least one administration of at least one frozen particle composition or frozen piercing implement 14860 wherein the assay includes at least one technique that includes spectroscopy, microscopy, electrochemical detection, polynucleotide detection, histological examination, biopsy analysis, fluorescence resonance energy transfer, electron transfer, enzyme assay, electrical conductivity, isoelectric focusing, chromatography, immunoprecipitation, immunoseparation, aptamer binding, filtration, electrophoresis, immunoassay, or radioactive assay 14870 wherein the image includes at least one image acquired by one or more of x-ray crystallography, laser, holography, optical coherence tomography, computer-assisted tomography scan, computed tomography, magnetic resonance imaging, positron-emission tomography scan, ultrasound, x-ray, electrical-impedance monitoring, microscopy, spectrometry, flow cytommetry, radioisotope imaging, thermal imaging, infrared visualization, multiphoton calcium-imaging, photography, or *in silico* generation 14880 generating an output to a user readable display

FIG. 149

14910 wherein the input associated with at least one parameter for administering at least one frozen particle composition or frozen piercing implement to at least one substrate includes one or more of: substrate type; substrate function; substrate size; substrate constitution; substrate architecture; substrate durability; substrate temperature; temperature of administration conditions; depth of administration of the at least one frozen particle composition or frozen piercing implement; substrate source; one or more temporal coordinates; one or more spatial coordinates; presence or absence of at least one agent; presence or absence of at least one microparticle, nanoparticle, lens, tunable lens, sensor, regulator, transducer, actuator, detector, heater, valve, gate, channel, detection material, pump, energy source, injector, controller, receiver, transmitter, or circuit; angle of administration of the at least one frozen particle composition or frozen piercing implement; velocity of administration of the at least one frozen particle composition or frozen piercing implement; quantity of frozen particle compositions or frozen piercing implements administered; rate of administration of more than one frozen particle compositions or frozen piercing implements; method of administration of at least one frozen particle composition or frozen piercing implement; timing of administration of at least one frozen particle composition or frozen piercing implement; or rate of delivery of at least one agent 14920 wherein the input associated with at least one parameter for making the at least one frozen particle composition or frozen piercing implement includes one or more property including: constitution of the at least one frozen particle composition or frozen piercing implement, formulation of the at least one frozen particle composition or frozen piercing implement, size of the at least one frozen particle composition or frozen piercing implement, density of the at least one frozen particle composition or frozen piercing implement, shape of the at least one frozen particle composition or frozen piercing implement, physical structure of the at least one frozen particle composition or frozen piercing implement, or physical or chemical integrity of the at least one frozen particle composition or frozen piercing implement

FIG. 150

15010 wherein the at least one agent includes one or more of an adhesive agent, therapeutic agent, reinforcement agent, abrasive, explosive material, or biological remodeling agent 15020 wherein the receiving one or more signals includes receiving one or more signals associated with selection of at least one parameter for making or administering the at least one frozen particle composition or frozen piercing implement 15030 wherein the at least one substrate includes one or more of a cell, tissue, organ, structure, device, or food product 15040 wherein the at least one frozen particle composition or frozen piercing implement includes one or more of hydrogen oxide, nitrogen, oxygen, air, helium, neon, argon, xenon, chlorine, bromine, carbon dioxide, acetone, ethyl acetate, dimethyl sulfoxide, dimethyl formamide, dioxane, tetrahydrofuran, acetic acid, n-butanol, isopropanol, n-propanol, hexamethylphosphortriamide, perfluorohydrocarbon, methanol, ethanol, tert-butyl alcohol, formic acid, hydrogen fluoride, ammonia, benzene, carbon tetrachloride, acetonitrile, hexane, dichloromethane, methylene chloride, carboxylic acid, saline, standard saline citrate, toluene, chloroform, polyethylene glycol, acetic acid, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, methane, or diethyl ether 15050 wherein the output includes one or more instructions for making the at least one frozen particle composition or frozen piercing implement 15055 wherein the output includes at least one graphical description of the at least one frozen particle composition or frozen piercing implement 15060 wherein the user includes at least one entity 15065 wherein the entity includes at least one person, or computer 15070 wherein the user readable display includes a human readable display 15080 wherein the user readable display includes one or more active displays 15090 wherein the user readable display includes one or more passive displays 15095 wherein the user readable display includes one or more of a numeric format, graphical format, or audio format 15096 wherein the user readable display includes one or more of a display of one or more differences in the comparison of at least one value related to the first input and at least one value related to at least one property of the at least one frozen particle composition or frozen piercing implement 15097 wherein the user readable display includes one or more of a display of one or more differences in the comparison of at least one value related to the second input and at least one value related to at least one parameter for administration of the at least one frozen particle composition or frozen piercing implement.

FIG. 151

15100 A computer-implemented method comprising:

15110 accepting a first input associated with at least one parameter for making at least one frozen piercing implement device;

15120 accepting a second input associated with at least one parameter for administering the at least one frozen piercing implement device to at least one substrate;

15125 wherein the at least one substrate includes one or more of a cell, tissue, organ, structure, device, or food product 15130 wherein the at least one frozen piercing implement device includes at least one of a frozen piercing implement array device, frozen piercing implement fluidic device, or frozen piercing implement injection device 15140 wherein the frozen piercing implement injection device includes a frozen piercing implement auto-injection device 15150 wherein the at least one frozen piercing implement device includes at least one agent 15160 wherein the at least one agent includes one or more of a therapeutic agent, adhesive agent, abrasive, reinforcement agent, explosive material, or biological remodeling agent 15170 wherein the at least one agent is located in at least one frozen piercing implement of the device 15180 processing the first input and the second input 15190 wherein processing the first input and the second input includes electronically processing results of the first input and the second input 15195 wherein electronically processing the first input and the second input by utilizing one or more of Gaussian smoothing, scaling, homomorphic filtering, parametric estimation techniques, Boolean operations, Monte Carlo simulations, wavelet based techniques, mirroring, smoothing, gradient weighted partial differential equation smoothing, NURBS, polygonal modeling, splines and patches modeling, algorithmic execution, logical decision-making, result prediction, Finite Element Analysis, or modification of a CAD design 15198 generating an output to a user readable display

FIG. 152

15210 wherein the first input includes one or more values related to the at least one parameter for making the at least one frozen piercing implement device 15220 wherein the at least one parameter for making the at least one frozen piercing implement device includes one or more of: constitution of the at least one frozen piercing implement device, constitution of the frozen piercing implement of the at least one frozen piercing implement device, formulation of the at least one frozen piercing implement device, formulation of the frozen piercing implement of the at least one frozen piercing implement device, size of the at least one frozen piercing implement device, size of the frozen piercing implement of the at least one frozen piercing implement device, shape of the at least one frozen piercing implement device, shape of the frozen piercing implement of the at least one frozen piercing implement device, physical structure of the at least one frozen piercing implement device, physical structure of the frozen piercing implement of the at least one frozen piercing implement device, physical or chemical integrity of the at least one frozen piercing implement device or physical or chemical integrity of the frozen piercing implement of the at least one frozen piercing implement device 15230 wherein the at least one parameter for administering at least one frozen piercing implement device to at least one substrate includes one or more of: substrate type; substrate function; substrate size; substrate constitution; substrate architecture; substrate durability; substrate temperature; temperature of administration conditions; depth of administration of the at least one frozen particle composition or frozen piercing implement; substrate source; one or more temporal coordinates; one or more spatial coordinates; presence or absence of at least one agent; presence or absence of at least one microparticle, nanoparticle, lens, tunable lens, sensor, regulator, transducer, actuator, detector, heater, valve, gate, channel, detection material, pump, energy source, injector, controller, receiver, transmitter, or circuit; angle of administration of the at least one frozen piercing implement device; velocity of administration of the at least one frozen piercing implement device; quantity of frozen piercing implements of the device; quantity of frozen piercing implement devices administered; rate of administration of more than one frozen piercing implement devices; method of administration of at least one frozen piercing implement device; timing of administration of at least one frozen piercing implement; or rate of delivery of at least one agent of the device

FIG. 153

15310 wherein the one or more values related to the at least one parameter for administering at least one frozen piercing implement device includes one or more predictive values 15320 wherein the at least one parameter for administering at least one frozen piercing implement device includes at least one parameter relating to at least partially ablating or at least partially abrading one or more surfaces of the at least one substrate with the at least one frozen piercing implement device 15330 wherein the first input includes one or more values derived from at least one property of at least one frozen piercing implement device 15340 wherein the at least one substrate is located in at least one of *in situ, in vitro, in vivo, in utero, in planta, in silico,* or *ex vivo*

15350 wherein the at least one substrate is at least partially located in at least one subject 15360 further comprising accepting a third input associated with at least one feature of the at least one subject 15370 wherein the at least one feature of the at least one subject includes one or more of age, gender, genotype, phenotype, proteomic profile, lipidomic profile, glycomic profile, system biology profile, lymph condition, circulatory condition, respiratory condition, blood condition, anatomic landscape, body contour, or health condition 15380 wherein the output includes one or more instructions for making the at least one frozen piercing implement device 15390 wherein the output includes at least one graphical description of the at least one frozen piercing implement device

FIG. 154

15407 wherein the user readable display includes one or more of a display of one or more differences in the comparison of at least one value related to the first input and at least one value related to at least one property of the at least one frozen particle composition or frozen piercing implement 15408 wherein the user readable display includes one or more of a display of one or more differences in the comparison of at least one value related to the second input and at least one value related to at least one parameter for administration of the at least one frozen particle composition or frozen piercing implement 15410 wherein the processing the first input and the second input includes determining at least one parameter for making at least one frozen piercing implement device from one or more values derived from at least one characteristic of at least one frozen piercing implement of the frozen piercing implement device 15420 wherein the second input includes one or more values related to the at least one parameter for administering at least one frozen piercing implement device to the at least one substrate 15430 wherein the processing the first input and the second input includes comparing at least one value related to the first input associated with the at least one parameter for making the frozen piercing implement device with at least one value related to at least one property of the at least one frozen piercing implement 15440 wherein the processing the first input and the second input includes determining one or more differences in at least one value related to the first input and at least one value related to at least one property of the at least one frozen piercing implement device 15450 wherein the processing the first input and the second input includes determining one or more differences in at least one value related to the second input associated with the one or more parameters of administering at least one frozen piercing implement device to the at least one substrate 15460 wherein the processing the first input and the second input includes generating one or more protocols for administering the at least one frozen piercing implement device

FIG. 155

15510 wherein the administering at least one frozen piercing implement device includes delivering at least one agent to the at least one substrate by way of the at least one frozen piercing implement device 15518 wherein the user includes at least one entity 15520 wherein the entity includes at least one person, or computer 15530 wherein the user readable display includes a human readable display 15540 wherein the user readable display includes one or more active displays 15550 wherein the user readable display includes one or more passive displays 15560 wherein the user readable display includes one or more of a numeric format, graphical format, or audio format 15570 wherein the user readable display includes one or more of a display of one or more differences in the comparison of at least one value related to the first input and at least one value related to at least one property of the at least one frozen piercing implement device 15580 wherein the user readable display includes one or more of a display of one or more differences in the comparison of at least one value related to the second input and at least one value related to at least one parameter for administration of the at least one frozen piercing implement device

FIG. 156

15610 further comprising transmitting one or more signals that include information related to the processing the first input and the second input 15620 wherein the transmitting one or more signals includes transmitting one or more signals associated with selection of at least one parameter for making the at least one frozen piercing implement device 15630 wherein the transmitting one or more signals includes transmitting one or more signals associated with selection of one or more agents to be delivered by the at least one frozen piercing implement device 15640 wherein the transmitting one or more signals includes transmitting one or more signals associated with comparing the information related to the processing the first input and the second input 15650 wherein the at least one frozen piercing implement device includes one or more frozen piercing implements that include at least one of hydrogen oxide, nitrogen, oxygen, air, helium, neon, argon, xenon, chlorine, bromine, carbon dioxide, acetone, ethyl acetate, dimethyl sulfoxide, dimethyl formamide, dioxane, tetrahydrofuran, acetic acid, n-butanol, isopropanol, n-propanol, hexamethylphosphorotriamide, perfluorohydrocarbon, methanol, ethanol, tert-butyl alcohol, formic acid, hydrogen fluoride, ammonia, benzene, carbon tetrachloride, acetonitrile, hexane, dichloromethane, methylene chloride, carboxylic acid, saline, standard saline citrate, toluene, chloroform, polyethylene glycol, acetic acid, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, methane, or diethyl ether

FIG. 158

15800 A computer-implemented method comprising:

15810 receiving one or more signals that include information related to accepting input associated with at least one parameter for making or administering at least one frozen particle composition, frozen piercing implement, or frozen piercing implement device to at least one substrate; wherein the at least one frozen particle composition, frozen piercing implement, or frozen piercing implement device includes at least one agent 15815 generating an output to a user readable display 15820 receiving one or more signals that include information related to evaluating the at least one substrate for one or more indicators of administration of the at least one frozen particle composition, frozen piercing implement, frozen piercing implement device or agent;

15830 processing the information related to the input associated with at least one parameter for making or administering the at least one frozen particle composition, frozen piercing implement, or frozen piercing implement device to at least one substrate and the information related to the evaluating the at least one substrate 15840 wherein the evaluating at least one substrate for one or more indicators includes evaluating at least one of an assay, image, or gross assessment of the at least one substrate prior to, during, or subsequent to at least one administration of at least one frozen particle composition, frozen piercing implement, or frozen piercing implement device 15850 wherein the assay includes at least one technique that includes spectroscopy, microscopy, electrochemical detection, polynucleotide detection, histological examination, biopsy analysis, fluorescence resonance energy transfer, electron transfer, enzyme assay, electrical conductivity, isoelectric focusing, chromatography, immunoprecipitation, immunoseparation, aptamer binding, filtration, electrophoresis, immunoassay, or radioactive assay 15860 wherein the image includes at least one image acquired by one or more of x-ray crystallography, laser, holography, optical coherence tomography, computer-assisted tomography scan, computed tomography, magnetic resonance imaging, positron-emission tomography scan, ultrasound, x-ray, electrical-impedance monitoring, microscopy, spectrometry, flow cytometry, radioisotope imaging, thermal imaging, infrared visualization, multiphoton calcium-imaging, photography, or *in silico* generation 15870 wherein the receiving one or more signals includes receiving one or more signals associated with selection of at least one parameter for making or administering the at least one frozen particle composition, frozen piercing implement, or frozen piercing implement device

FIG. 159

15910 wherein the at least one parameter for making the at least one frozen piercing implement device includes one or more of: constitution of the at least one frozen piercing implement of the frozen piercing implement device, constitution of the at least one frozen piercing implement device, formulation of the at least one frozen piercing implement of the frozen piercing implement device, formulation of the at least one frozen piercing implement device, size of the at least one frozen piercing implement of the frozen piercing implement device, size of the at least one frozen piercing implement device, shape of the at least one frozen piercing implement of the frozen piercing implement device, shape of the at least one frozen piercing implement device, physical structure of the at least one frozen piercing implement of the frozen piercing implement device, physical structure of the at least one frozen piercing implement device, physical or chemical integrity of the at least one frozen piercing implement of the frozen piercing implement device, physical or chemical integrity of the at least one frozen piercing implement device, or presence or absence of at least one microparticle, nanoparticle, lens, tunable lens, sensor, transducer, actuator, detector, heater, valve, gate, channel, detection material, pump, energy source, injector, controller, receiver, transmitter, or circuit, in the at least one frozen piercing implement or frozen piercing implement device 15920 wherein the at least one parameter for administering at least one frozen piercing implement device to at least one substrate includes one or more of: substrate type; substrate function; substrate size; substrate constitution; substrate architecture; substrate durability; substrate temperature; temperature of administration conditions; depth of administration of the at least one frozen particle composition or frozen piercing implement; substrate source; one or more temporal coordinates; one or more spatial coordinates; presence or absence of at least one agent; presence or absence of at least one microparticle, nanoparticle, lens, tunable lens, sensor, regulator, transducer, actuator, detector, heater, valve, gate, channel, detection material, pump, energy source, injector, controller, receiver, transmitter, or circuit; angle of administration of the at least one frozen piercing implement device; velocity of administration of the at least one frozen piercing implement device; quantity of frozen piercing implements of the device; quantity of frozen piercing implement devices administered; rate of administration of more than one frozen piercing implement devices; method of administration of at least one frozen piercing implement device; timing of administration of at least one frozen piercing implement; or rate of delivery of at least one agent of the device

FIG. 160

16010 wherein the at least one agent includes one or more of an adhesive agent, therapeutic agent, reinforcement agent, abrasive, explosive material, or biological remodeling agent 16020 wherein the at least one substrate includes one or more of a cell, tissue, organ, structure, device, or food product 16030 wherein the at least one frozen particle composition, frozen piercing implement, or frozen piercing implement device includes one or more of hydrogen oxide, nitrogen, oxygen, air, helium, neon, argon, xenon, chlorine, bromine, carbon dioxide, acetone, ethyl acetate, dimethyl sulfoxide, dimethyl formamide, dioxane, tetrahydrofuran, acetonitrile, n-butanol, isopropanol, n-propanol, hexamethylphosphorotriamide, perfluorohydrocarbon, methanol, ethanol, tert-butyl alcohol, formic acid, hydrogen fluoride, ammonia, benzene, carbon tetrachloride, acetonitrile, hexane, dichloromethane, methylene chloride, carboxylic acid, saline, standard saline citrate, toluene, chloroform, polyethylene glycol, acetic acid, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, methane, or diethyl ether 16035 wherein the output includes one or more instructions for making the at least one frozen particle composition, frozen piercing implement, or frozen piercing implement device 16040 wherein the output includes at least one graphical description of the at least one frozen particle composition, frozen piercing implement, or frozen piercing implement device 16050 wherein the user includes at least one entity 16055 wherein the entity includes at least one person, or computer 16060 wherein the user readable display includes a human readable display 16065 wherein the user readable display includes one or more active displays 16070 wherein the user readable display includes one or more passive displays 16075 wherein the user readable display includes one or more of a numeric format, graphical format, or audio format 16076 wherein the user readable display includes one or more of a display of one or more differences in the comparison of at least one value related to the first input and at least one value related to at least one property of the at least one frozen particle composition, frozen piercing implement, or frozen piercing implement device 16077 wherein the user readable display includes one or more of a display of one or more differences in the comparison of at least one value related to the second input and at least one value related to at least one parameter for administration of the at least one frozen particle composition, frozen piercing implement, or frozen piercing implement device

FIG. 161

16110 wherein the at least one parameter for making the at least one frozen particle composition or frozen piercing implement includes one or more of: constitution of the at least one frozen particle composition or frozen piercing implement, configuration of the at least one frozen particle composition or frozen piercing implement, formulation of the at least one frozen particle composition or frozen piercing implement, size of the at least one frozen particle composition or frozen piercing implement, density of the at least one frozen particle composition or frozen piercing implement, shape of the at least one frozen particle composition or frozen piercing implement, physical structure of the at least one frozen particle composition or frozen piercing implement, or physical or chemical integrity of the at least one frozen particle composition or frozen piercing implement 16120 wherein the at least one parameter for administering the at least one frozen particle composition or frozen piercing implement includes one or more of: substrate type; substrate function; substrate size; substrate constitution; substrate architecture; substrate durability; substrate temperature; temperature of administration conditions; depth of administration of the at least one frozen particle composition or frozen piercing implement; substrate source; one or more temporal coordinates; one or more spatial coordinates; presence or absence of at least one agent; presence or absence of at least one microparticle, nanoparticle, lens, tunable lens, sensor, transducer, actuator, detector, heater, valve, gate, channel, detection material, pump, power source, injector, controller, receiver, transmitter, or circuit; angle of administration of the at least one frozen piercing implement device; velocity of administration of the at least one frozen particle composition or frozen piercing implement device; quantity of frozen piercing implement devices administered; rate of piercing implements of the device; quantity of frozen piercing implement devices administered; rate of administration of more than one frozen piercing implement devices; method of administration of at least one frozen piercing implement device; timing of administration of at least one frozen piercing implement; or rate of delivery of at least one agent of the device

FIG. 162

16200 A method comprising:

16210 making at least one frozen particle composition, frozen piercing implement, or frozen piercing implement device

→

16220 administering at least one frozen particle composition, frozen piercing implement, or frozen piercing implement device to at least one substrate

FIG. 163

16300 A system comprising:

16310 means for receiving one or more signals that include information related to accepting input associated with at least one parameter for making or administering at least one frozen particle composition or frozen piercing implement to at least one substrate, the frozen particle composition or frozen piercing implement including at least one agent;

16320 means for receiving one or more signals that include information related to evaluating the at least one substrate for one or more indicators of administration of the at least one frozen particle composition, frozen piercing implement, or agent;

16330 means for processing the information related to the input associated with at least one parameter for making or administering the at least one frozen particle composition or frozen piercing implement to at least one substrate and the information related to the evaluating the at least one substrate;

16340 means for generating an output to a user readable display 16350 wherein evaluating at least one substrate for one or more indicators includes evaluating at least one of an assay, image, or gross assessment of the at least one biological tissue prior to, during, or subsequent to at least one administration of the at least one frozen particle composition or frozen piercing implement 16360 wherein the assay includes at least one technique that includes spectroscopy, microscopy, electrochemical detection, polynucleotide detection, histological examination, biopsy analysis, fluorescence resonance energy transfer, electron transfer, enzyme assay, electrical conductivity, isoelectric focusing, chromatography, immunoprecipitation, immunoseparation, aptamer binding, filtration, electrophoresis, immunoassay, or radioactive assay 16370 wherein the image includes at least one image acquired by one or more of x-ray crystallography, laser, holography, optical coherence tomography, computer-assisted tomography scan, computed tomography, magnetic resonance imaging, positron-emission tomography scan, ultrasound, x-ray, electrical-impedance monitoring, microscopy, spectrometry, flow cytometry, radioisotope imaging, thermal imaging, infrared visualization, multiphoton calcium-imaging, photography, or *in silico* generation

FIG. 164

16410 wherein the input associated with at least one parameter for administering at least one frozen particle composition or frozen piercing implement to at least one substrate includes one or more of: substrate type; substrate function; substrate size; substrate constitution; substrate architecture; substrate durability; substrate temperature; temperature of administration conditions; depth of administration of the at least one frozen particle composition or frozen piercing implement; substrate source; one or more temporal coordinates; one or more spatial coordinates; presence or absence of at least one agent; presence or absence of at least one microparticle, nanoparticle, lens, tunable lens, sensor, transducer, actuator, detector, heater, valve, gate, channel, detection material, pump, power source, injector, controller, receiver, transmitter, or circuit; angle of administration of the at least one frozen particle composition or frozen piercing implement; velocity of administration of the at least one frozen particle composition or frozen piercing implement; quantity of frozen particle compositions or frozen piercing implements administered; rate of administration of more than one frozen particle compositions or frozen piercing implements; method of administration of at least one frozen particle composition or frozen piercing implement; timing of administration of at least one frozen particle composition or frozen piercing implement; or rate of delivery of at least one agent 16420 wherein the at least one agent includes one or more of an adhesive agent, therapeutic agent, reinforcement agent, abrasive, explosive material, or biological remodeling agent 16430 wherein the means for receiving one or more signals includes means for receiving one or more signals associated with selection of at least one parameter for making the at least one frozen particle composition or frozen piercing implement 16440 wherein the at least one parameter for making the at least one frozen particle composition or frozen piercing implement includes one or more property including: constitution of the at least one frozen particle composition or frozen piercing implement, configuration of the at least one frozen particle composition or frozen piercing implement, formulation of the at least one frozen particle composition or frozen piercing implement, size of the at least one frozen particle composition or frozen piercing implement, density of the at least one frozen particle composition or frozen piercing implement, shape of the at least one frozen particle composition or frozen piercing implement, physical structure of the at least one frozen particle composition or frozen piercing implement, physical or chemical integrity of the at least one frozen particle composition or frozen piercing implement

FIG. 165

16510 wherein the at least one substrate includes one or more of a cell, tissue, organ, structure, device, or food product 16520 wherein the at least one frozen particle composition or frozen piercing implement includes one or more of hydrogen oxide, nitrogen, oxygen, air, helium, neon, argon, xenon, chlorine, bromine, carbon dioxide, acetone, ethyl acetate, dimethyl sulfoxide, dimethyl formamide, dioxane, tetrahydrofuran, acetonitrile, acetic acid, n-butanol, isopropanol, n-propanol, hexamethylphosphorotriamide, perfluorohydrocarbon, methanol, ethanol, tert-butyl alcohol, formic acid, hydrogen fluoride, ammonia, benzene, carbon tetrachloride, hexane, dichloromethane, methylene chloride, carboxylic acid, saline, methane, toluene, chloroform, polyethylene glycol, acetic acid, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, or diethyl ether 16530 wherein the output includes one or more instructions for making the at least one frozen particle composition or frozen piercing implement 16540 wherein the output includes at least one graphical description of the at least one frozen particle composition or frozen piercing implement 16550 wherein the user includes at least one entity 16560 wherein the entity includes at least one person, or computer 16570 wherein the user readable display includes a human readable display 16580 wherein the user readable display includes one or more active displays 16590 wherein the user readable display includes one or more passive displays 16595 wherein the user readable display includes one or more of a numeric format, graphical format, or audio format

FIG. 166

16610 wherein the user readable display includes one or more of a display of one or more differences in the comparison of at least one value related to the first input and at least one value related to at least one property of the at least one frozen particle composition or frozen piercing implement 16620 wherein the user readable display includes one or more of a display of one or more differences in the comparison of at least one value related to the second input and at least one value related to at least one parameter for administration of the at least one frozen particle composition or frozen piercing implement

FIG. 167

16700 A system comprising:

16710 means for accepting a first input associated with at least one parameter for making at least one frozen piercing implement device 16720 means for accepting a second input associated with at least one parameter for administering the at least one frozen piercing implement device 16730 means for processing the first input and the second input 16740 means for generating an output to a user readable display 16750 wherein the at least one frozen piercing implement device includes at least one of a frozen piercing implement array device, frozen piercing implement fluidic device, or frozen piercing implement injection device 16760 wherein the frozen piercing implement injection device includes a frozen piercing implement auto-injection device 16770 wherein the means for processing the first input and the second input includes means for electronically processing the first input and the second input 16780 wherein the means for processing the first input and the second input includes means for electronically processing the first input and the second input by utilizing one or more of Gaussian smoothing, scaling, homomorphic filtering, parametric estimation techniques, Boolean operations, Monte Carlo simulations, wavelet based techniques, mirroring, smoothing, gradient weighted partial differential equation smoothing, NURBS, polygonal modeling, splines and patches modeling, algorithmic execution, logical decision-making, result prediction, Finite Element Analysis, or modification of a CAD design

FIG. 168

16810 wherein the frozen piercing implement device includes at least one agent 16820 wherein the at least one agent is located in at least one frozen piercing implement of the device 16830 wherein the at least one agent includes one or more of a therapeutic agent, adhesive agent, abrasive, reinforcement agent, explosive material, or biological remodeling agent 16840 wherein the at least one substrate includes one or more of a cell, tissue, organ, structure, device, or food product 16850 wherein the first input includes one or more values related to the at least one parameter for making the at least one frozen piercing implement device 16860 wherein the at least one parameter for making the at least one frozen piercing implement device includes one or more of: constitution of the at least one frozen piercing implement of the frozen piercing implement device, constitution of the at least one frozen piercing implement device, configuration of the at least one frozen piercing implement, configuration of the at least one frozen piercing implement or frozen piercing implement device, formulation of the at least one frozen piercing implement of the frozen piercing implement device, formulation of the at least one frozen piercing implement device, size of the at least one frozen piercing implement of the frozen piercing implement device, size of the at least one frozen piercing implement device, shape of the at least one frozen piercing implement of the frozen piercing implement device, shape of the at least one frozen piercing implement device, physical structure of the at least one frozen piercing implement of the frozen piercing implement device, physical structure of the at least one frozen piercing implement device, physical or chemical integrity of the at least one frozen piercing implement of the frozen piercing implement device, or physical or chemical integrity of the at least one frozen piercing implement device

FIG. 169

16910 wherein the at least one parameter for administering at least one frozen piercing implement device to at least one substrate includes one or more of: substrate type; substrate function; substrate size; substrate constitution; substrate architecture; substrate durability; substrate temperature; temperature of administration conditions; depth of administration of the at least one frozen particle composition or frozen piercing implement; substrate source; one or more temporal coordinates; one or more spatial coordinates; presence or absence of at least one agent; presence or absence of at least one microparticle, nanoparticle, lens, tunable lens, sensor, transducer, actuator, detector, heater, valve, gate, channel, detection material, pump, power source, injector, controller, receiver, transmitter, or circuit; angle of administration of the at least one frozen piercing implement device; velocity of administration of the at least one frozen piercing implement device; quantity of frozen piercing implements of the device; quantity of frozen piercing implement devices administered; rate of administration of more than one frozen piercing implement devices; method of administration of at least one frozen piercing implement device; timing of administration of at least one frozen piercing implement; or rate of delivery of at least one agent of the device 16920 wherein the at least one parameter for administering at least one frozen piercing implement device includes at least one parameter relating to at least partially ablating or at least partially abrading one or more surfaces of the at least one substrate with the at least one frozen piercing implement device 16930 wherein the first input includes one or more values derived from at least one property of at least one frozen piercing implement device 16940 wherein the at least one substrate is located in at least one of *in situ, in vitro, in vivo, in utero, in planta, in silico,* or *ex vivo*

16950 wherein the at least one substrate is at least partially located in at least one subject 16960 further comprising means for accepting a third input associated with at least one feature of the at least one subject

FIG. 170

17010 wherein the at least one feature of the at least one subject includes one or more of age, gender, genotype, phenotype, proteomic profile, lipidomic profile, glycomic profile, system biology profile, lymph condition, circulatory condition, respiratory condition, blood condition, anatomic landscape, body contour, or health condition 17020 wherein the means for processing the first input and the second input includes means for determining at least one parameter for administering at least one frozen piercing implement device from one or more values derived from at least one image of at least one frozen piercing implement device, or at least one image of at least one frozen piercing implement 17030 wherein the second input includes one or more values related to the at least one parameter for administering at least one frozen piercing implement device to the at least one substrate 17040 wherein the one or more values related to the at least one parameter for administering at least one frozen piercing implement device includes one or more predictive values 17050 wherein the means for processing the first input and the second input includes means for comparing at least one value related to the first input associated with the at least one parameter for making the frozen piercing implement device with at least one value related to at least one property of at least one frozen piercing implement of the device, or at least one frozen piercing implement device 17060 wherein the means for processing the first input and the second input includes means for determining one or more differences in at least one value related to the first input and at least one value related to at least one property of at least one frozen piercing implement device or at least one frozen piercing implement of the device 17070 wherein the means for processing the first input and the second input includes means for determining one or more differences in at least one value related to the second input associated with the one or more parameters of administering at least one frozen piercing implement device to the at least one substrate

FIG. 171

17110 wherein the means for processing the first input and the second input includes means for generating one or more protocols for administering the at least one frozen piercing implement device 17120 wherein the output includes one or more instructions for making the at least one frozen piercing implement device 17130 wherein the output includes at least one graphical description of the at least one frozen piercing implement device 17140 wherein the user includes at least one entity 17150 wherein the entity includes at least one person, or computer 17160 wherein the user readable display includes a human readable display 17170 wherein the user readable display includes one or more active displays 17180 wherein the user readable display includes one or more passive displays 17185 wherein the user readable display includes one or more of a numeric format, graphical format, or audio format 17190 wherein the user readable display includes one or more of a display of one or more differences in the comparison of at least one value related to the first input and at least one value related to at least one property of the at least one frozen piercing implement device

FIG. 172

17210 wherein the user readable display includes one or more of a display of one or more differences in the comparison of at least one value related to the second input and at least one value related to at least one parameter for administering the at least one frozen piercing implement device 17220 further comprising means for transmitting one or more signals that include information related to the means for processing the first input and the second input 17230 wherein the means for transmitting one or more signals includes means for transmitting one or more signals associated with selection of at least one parameter for making the at least one frozen piercing implement device 17240 wherein the means for transmitting one or more signals includes means for transmitting one or more signals associated with selection of one or more agents to be delivered by the at least one frozen piercing implement device 17250 wherein the at least one agent includes one or more of an adhesive agent, therapeutic agent, reinforcement agent, abrasive, explosive material, or biological remodeling agent

FIG. 173

17310 wherein the means for transmitting one or more signals includes means for transmitting one or more signals associated with at least one parameter for making or administering at least one frozen piercing implement device 17320 wherein the means for transmitting one or more signals includes means for transmitting one or more signals associated with means for comparing the information related to the means for processing the first input and the second input 17330 wherein the at least one frozen piercing implement device includes one or more frozen piercing implements that include at least one of hydrogen oxide, nitrogen, oxygen, air, helium, neon, argon, xenon, chlorine, bromine, carbon dioxide, acetone, ethyl acetate, dimethyl sulfoxide, dimethyl formamide, dioxane, tetrahydrofuran, acetonitrile, acetic acid, n-butanol, isopropanol, n-propanol, hexamethylphosphorotriamide, perfluorohydrocarbon, methanol, ethanol, tert-butyl alcohol, formic acid, hydrogen fluoride, ammonia, benzene, carbon tetrachloride, hexane, dichloromethane, methylene chloride, carboxylic acid, saline, standard saline citrate, methane, toluene, chloroform, polyethylene glycol, acetic acid, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, or diethyl ether 17340 further comprising means for making at least one frozen piercing implement device 17350 further comprising means for administering at least one frozen piercing implement device to at least one substrate 17360 further comprising means for evaluating the at least one substrate for one or more indicators related to at least one parameter for administering the at least one frozen piercing implement device 17370 wherein the means for evaluating at least one substrate for one or more indicators includes means for evaluating at least one of an assay, image, or gross assessment of the at least one substrate prior to, during, or subsequent to at least one administration of the at least one frozen piercing implement device

FIG. 174

17410 wherein the assay includes at least one technique including spectroscopy, microscopy, electrochemical detection, polynucleotide detection, histological examination, biopsy analysis, fluorescence resonance energy transfer, electron transfer, enzyme assay, electrical conductivity, isoelectric focusing, chromatography, immunoprecipitation, immunoseparation, aptamer binding, filtration, electrophoresis, immunoassay, or radioactive assay 17420 wherein the at least one image includes one or more images acquired by at least one of laser, holography, x-ray crystallography, optical coherence tomography, computer-assisted tomography scan, computed tomography, magnetic resonance imaging, positron-emission tomography scan, ultrasound, x-ray, electrical-impedance monitoring, microscopy, spectrometry, flow cytommetry, radioisotope imaging, thermal imaging, infrared visualization, multiphoton calcium-imaging, photography, or *in silico* generation 17430 further comprising means for transmitting one or more signals that include information relating to the accepting a first input or a second input and information related to the evaluating the at least one substrate 17440 wherein the means for transmitting one or more signals includes means for transmitting one or more signals associated with selection of at least one parameter for making the at least one frozen piercing implement device 17460 wherein the means for transmitting one or more signals includes means for transmitting one or more signals associated with selection of at least one parameter for administering the at least one frozen piercing implement device

FIG. 175

17500 A system comprising:

17510 means for accepting a first input associated with at least one parameter for making at least one frozen particle composition or frozen piercing implement 17520 means for accepting a second input associated with at least one parameter for administering the at least one frozen particle composition or frozen piercing implement to at least one substrate 17530 means for processing the first input and the second input 17540 means for generating an output to a user readable display 17550 wherein the at least one parameter for administering at least one frozen particle composition or frozen piercing implement includes at least one parameter relating to at least partially ablating or at least partially abrading one or more surfaces of the at least one substrate with the at least one frozen particle composition or frozen piercing implement 17560 wherein the means for processing the first input and the second input includes means for electronically processing the first input and the second input 17570 wherein the means for processing the first input and the second input includes means for electronically processing the first input and the second input by utilizing one or more of Gaussian smoothing, scaling, homomorphic filtering, parametric estimation techniques, Boolean operations, Monte Carlo simulations, wavelet based techniques, mirroring, smoothing, gradient weighted partial differential equation smoothing, NURBS, polygonal modeling, splines and patches modeling, algorithmic execution, logical decision-making, result prediction, Finite Element Analysis, or modification of a CAD design 17580 wherein the first input includes one or more values related to the at least one parameter for making the at least one frozen particle composition or frozen piercing implement

FIG. 176

17610 wherein the at least one parameter for making the at least one frozen particle composition or frozen piercing implement includes one or more property including: constitution of the at least one frozen particle composition or frozen piercing implement, configuration of the at least one frozen particle composition or frozen piercing implement, formulation of the at least one frozen particle composition or frozen piercing implement, size of the at least one frozen particle composition or frozen piercing implement, density of the at least one frozen particle composition or frozen piercing implement, shape of the at least one frozen particle composition or frozen piercing implement, physical structure of the at least one frozen particle composition or frozen piercing implement, physical or chemical integrity of the at least one frozen particle composition or frozen piercing implement, or presence or absence of a microparticle, nanoparticle, lens, tunable lens, sensor, transducer, actuator, detector, heater, valve, gate, channel, detection material, pump, power source, injector, controller, receiver, transmitter, or circuit 17620 wherein the at least one parameter for administering at least one frozen particle composition or frozen piercing implement to at least one substrate includes one or more of: substrate type; substrate function; substrate size; substrate constitution; substrate architecture; substrate durability; substrate temperature; temperature of administration conditions; depth of administration of the at least one frozen particle composition or frozen piercing implement; substrate source; one or more temporal coordinates; one or more spatial coordinates; presence or absence of at least one agent; presence or absence of one or more sensors, valves, gates, channels, transducers, circuits, nanoparticles, microactuators, microdetectors, microheaters, or detection materials; angle of administration of the at least one frozen particle composition or frozen piercing implement; velocity of administration of the at least one frozen particle composition or frozen piercing implement; quantity of frozen particle compositions or frozen piercing implements administered; rate of administration of more than one frozen particle compositions or frozen piercing implements; method of administration of at least one frozen particle composition or frozen piercing implement; timing of administration of at least one frozen particle composition or frozen piercing implement; or rate of delivery of at least one agent 17630 wherein the at least one agent includes one or more of an adhesive agent, therapeutic agent, reinforcement agent, abrasive, explosive material, or biological remodeling agent

FIG. 177

17710 wherein the at least one substrate includes one or more of a cell, tissue, organ, structure, device, or food product 17720 wherein the first input includes one or more values derived from at least one property of the at least one frozen particle composition or frozen piercing implement 17730 wherein the at least one substrate is located in at least one of *in situ, in vitro, in vivo, in utero, in planta, in silico,* or *ex vivo*

17740 wherein the at least one substrate is at least partially located in at least one subject 17750 further comprising means for accepting a third input associated with at least one feature of the at least one subject 17760 wherein the at least one feature of the at least one subject includes one or more of age, gender, genotype, phenotype, proteomic profile, lipidomic profile, glycomic profile, system biology profile, lymph condition, circulatory condition, respiratory condition, blood condition, anatomic landscape, body contour, or health condition 17770 wherein the means for processing the first input and the second input includes means for determining at least one parameter for administering at least one frozen particle composition or frozen piercing implement from one or more values derived from at least one parameter for administering the at least one frozen particle composition or frozen piercing implement 17780 wherein the means for processing the first input and the second input includes means for determining one or more differences in at least one value related to the second input and at least one value related to at least one parameter for administering of at least one frozen particle composition or frozen piercing implement to at least one substrate

FIG. 178

17810 wherein the second input includes one or more values related to the at least one parameter for administering at least one frozen particle composition or frozen piercing implement to the at least one substrate 17820 wherein the one or more values related to the at least one parameter for administering at least one frozen particle composition or frozen piercing implement includes one or more predictive values 17830 wherein the means for processing the first input and the second input includes means for comparing at least one value related to the first input associated with the at least one parameter for making the at least one frozen particle composition or frozen piercing implement with at least one value related to at least one value related to at least one property of the frozen particle composition or frozen piercing implement 17840 wherein the means for processing the first input and the second input includes means for determining one or more differences in at least one value related to the first input and at least one value related to at least one property of the at least one frozen particle composition or frozen piercing implement 17850 wherein the means for processing the first input and the second input includes means for generating one or more protocols for administering the at least one frozen particle composition or frozen piercing implement 17860 wherein the output includes one or more instructions for making the at least one frozen particle composition or frozen piercing implement 17870 wherein the output includes at least one graphical description of the at least one frozen particle composition or frozen piercing implement 17880 wherein the user includes at least one entity

FIG. 179

17910 wherein the entity includes at least one person, or computer 17920 wherein the user readable display includes a human readable display 17930 wherein the user readable display includes one or more active displays 17940 wherein the user readable display includes one or more passive displays 17950 wherein the user readable display includes one or more of a numeric format, graphical format, or audio format 17960 wherein the user readable display includes one or more of a display of one or more differences in the comparison of at least one value related to the first input and at least one value related to at least one property of the at least one frozen particle composition or frozen piercing implement 17970 wherein the user readable display includes one or more of a display of one or more differences in the comparison of at least one value related to the second input and at least one value related to at least one parameter for administration of the at least one frozen particle composition or frozen piercing implement 17980 further comprising means for transmitting one or more signals that include information related to the processing of the first input and the second input 17990 wherein the means for transmitting one or more signals includes means for transmitting one or more signals associated with selection of at least one parameter for making the at least one frozen particle composition or frozen piercing implement

FIG. 180

18010 wherein the means for transmitting one or more signals includes means for transmitting one or more signals associated with comparing the information related to the processing of the first input and the second input 18020 wherein the means for transmitting one or more signals includes means for transmitting one or more signals associated with comparing the information related to the processing of the first input and the second input 18030 wherein the at least one frozen particle composition or frozen piercing implement includes one or more of hydrogen oxide, nitrogen, oxygen, air, helium, neon, argon, xenon, chlorine, bromine, carbon dioxide, acetone, ethyl acetate, dimethyl sulfoxide, dimethyl formamide, dioxane, tetrahydrofuran, acetonitrile, acetic acid, n-butanol, isopropanol, n-propanol, hexamethylphosphorotriamide, perfluorohydrocarbon, methanol, ethanol, tert-butyl alcohol, formic acid, hydrogen fluoride, ammonia, benzene, carbon tetrachloride, hexane, dichloromethane, methylene chloride, carboxylic acid, saline, standard saline citrate, methane, toluene, chloroform, polyethylene glycol, acetic acid, Ringer's solution, lactated Ringer's solution, Hartmann's solution, acetated Ringer's solution, phosphate buffered solution, TRIS-buffered saline solution, Hank's balanced salt solution, Earle's balanced salt solution, HEPES-buffered saline, dextrose, glucose, or diethyl ether 18040 further comprising means for making at least one frozen particle composition or frozen piercing implement 18050 further comprising means for administering at least one frozen particle composition or frozen piercing implement to at least one substrate 18060 further comprising means for evaluating the at least one substrate for one or more indicators related to at least one parameter for administering the at least one frozen particle composition or frozen piercing implement 18070 wherein the evaluating at least one substrate for one or more indicators includes evaluating at least one of an assay, image, or gross assessment of the at least one substrate prior to, during, or subsequent to at least one administration of the at least one frozen particle composition or frozen piercing implement

FIG. 181

18110 wherein the assay includes at least one technique including spectroscopy, microscopy, electrochemical detection, polynucleotide detection, histological examination, biopsy analysis, fluorescence resonance energy transfer, electron transfer, enzyme assay, electrical conductivity, isoelectric focusing, chromatography, immunoprecipitation, immunoseparation, aptamer binding, filtration, electrophoresis, immunoassay, or radioactive assay 18120 wherein the at least one image includes one or more images acquired by at least one of laser, holography, x-ray crystallography, optical coherence tomography, computer-assisted tomography scan, computed tomography, magnetic resonance imaging, positron-emission tomography scan, ultrasound, x-ray, electrical-impedance monitoring, microscopy, spectrometry, flow cytommetry, radioisotope imaging, thermal imaging, infrared visualization, multiphoton calcium-imaging, photography, or *in silico* generation 18130 further comprising means for transmitting one or more signals that include information relating to the accepting a first input or a second input and information related to the evaluating the at least one substrate 18140 wherein the means for transmitting one or more signals includes means for transmitting one or more signals associated with selection of at least one parameter for making the at least one frozen particle composition or frozen piercing implement 18150 wherein the means for transmitting one or more signals includes means for transmitting one or more signals associated with selection of at least one parameter for administering the at least one frozen particle composition or frozen piercing implement

FIG. 182

18200 A system comprising:

18210 means for receiving one or more signals that include information related to accepting input associated with at least one parameter for making or administering at least one frozen particle composition, frozen piercing implement, or frozen piercing implement device to at least one substrate; wherein the at least one frozen particle composition, frozen piercing implement, or frozen piercing implement of the device includes at least one agent 18220 means for receiving one or more signals that include information related to evaluating the at least one substrate for one or more indicators of administration of at least one frozen particle composition, frozen piercing implement, frozen piercing implement device, or agent 18230 means for processing the information related to the input associated with at least one parameter for making or administering the at least one frozen particle composition, frozen piercing implement, or frozen piercing implement device to at least one substrate and the information related to the evaluating the at least one substrate 18240 means for generating an output to a user readable display 18250 wherein the at least one frozen piercing implement device includes at least one of a frozen piercing implement device, frozen piercing implement fluidic device, or frozen piercing implement injection device 18260 wherein the frozen piercing implement injection device includes a frozen piercing implement auto-injection device 18270 wherein the evaluating at least one substrate for one or more indicators includes means for evaluating at least one of an assay, image, or gross assessment of the at least one biological tissue prior to, during, or subsequent to at least one administration of at least one frozen particle composition, frozen piercing implement, or frozen piercing implement device 18280 wherein the assay includes at least one technique that includes spectroscopy, microscopy, electrochemical detection, polynucleotide detection, histological examination, biopsy analysis, fluorescence resonance energy transfer, electron transfer, enzyme assay, electrical conductivity, isoelectric focusing, chromatography, immunoprecipitation, immunoseparation, aptamer binding, filtration, electrophoresis, immunoassay, or radioactive assay

FIG. 183

18310 wherein the image includes at least one image acquired by one or more of x-ray crystallography, laser, holography, optical coherence tomography, computer-assisted tomography scan, computed tomography, magnetic resonance imaging, positron-emission tomography scan, ultrasound, x-ray, electrical-impedance monitoring, microscopy, spectrometry, flow cytommetry, radioisotope imaging, thermal imaging, infrared visualization, multiphoton calcium-imaging, photography, or *in silico* generation 18320 wherein the means for receiving one or more signals includes means for receiving one or more signals associated with selection of at least one parameter for making or administering the at least one frozen particle composition, frozen piercing implement, or frozen piercing implement device 18330 wherein the at least one parameter for making the at least one frozen piercing implement device includes one or more of: constitution of the at least one frozen piercing implement device, formulation of the at least one frozen piercing implement device, constitution of the at least one frozen piercing implement device, formulation of the at least one frozen piercing implement device, configuration of the at least one frozen piercing implement of the device, configuration of the at least one frozen piercing implement device, size of the at least one frozen piercing implement of the frozen piercing implement device, size of the at least one frozen piercing implement device, shape of the at least one frozen piercing implement of the frozen piercing implement device, shape of the at least one frozen piercing implement device, physical structure of the at least one frozen piercing implement device, physical structure of the at least one frozen piercing piercing implement device, physical or chemical integrity of the at least one frozen piercing implement of the frozen piercing implement device, or physical or chemical integrity of the at least one frozen piercing implement device 18340 wherein the at least one parameter for administering at least one frozen piercing implement device to at least one substrate includes one or more of: substrate type; substrate function; substrate size; substrate constitution; substrate architecture; substrate durability; substrate temperature; temperature of administration conditions; depth of administration of the at least one frozen particle composition or frozen piercing implement; substrate source; one or more temporal coordinates; one or more spatial coordinates; presence or absence of at least one agent; presence or absence of at least one microparticle, nanoparticle, lens, tunable lens, sensor, transducer, actuator, detector, heater, valve, gate, channel, detection material, pump, power source, injector, controller, receiver, transmitter, or circuit; angle of administration of the at least one frozen piercing implement device; velocity of administration of the at least one frozen piercing implement device; quantity of frozen piercing implements of the device; quantity of frozen piercing implement devices administered; rate of administration of more than one frozen piercing implement devices; method of administration of at least one frozen piercing implement device; timing of administration of at least one frozen piercing implement; or rate of delivery of at least one agent of the device

FIG. 184

18410 wherein the at least one agent includes one or more of an adhesive agent, therapeutic agent, reinforcement agent, abrasive, explosive material, or biological remodeling agent 18420 wherein the at least one substrate includes one or more of a cell, tissue, organ, structure, device, or food product 18430 wherein the at least one frozen piercing implement device includes one or more frozen piercing implements that include at least one of hydrogen oxide, nitrogen, oxygen, air, helium, neon, argon, xenon, chlorine, bromine, carbon dioxide, acetone, ethyl acetate, dimethyl sulfoxide, dimethyl formamide, dioxane, tetrahydrofuran, acetonitrile, acetic acid, n-butanol, isopropanol, n-propanol, hexamethylphosphorotriamide, perfluorohydrocarbon, methanol, ethanol, tert-butyl alcohol, formic acid, hydrogen fluoride, ammonia, benzene, carbon tetrachloride, hexane, dichloromethane, methylene chloride, carboxylic acid, saline, methane, toluene, chloroform, polyethylene glycol, acetic acid, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, or diethyl ether 18440 wherein the output includes one or more instructions for making the at least one frozen particle composition, frozen piercing implement, or frozen piercing implement device 18450 wherein the output includes at least one graphical description of the at least one frozen particle composition, frozen piercing implement, or frozen piercing implement device 18460 wherein the user includes at least one entity 18470 wherein the entity includes at least one person, or computer 18480 wherein the user readable display includes a human readable display 18490 wherein the user readable display includes one or more active displays 18495 wherein the user readable display includes one or more passive displays

FIG. 185

18510 wherein the user readable display includes one or more of a numeric format, graphical format, or audio format 18520 wherein the user readable display includes one or more of a display of one or more differences in the comparison of at least one value related to the first input and at least one value related to at least one property of the at least one frozen particle composition, frozen piercing implement, or frozen piercing implement device 18530 wherein the user readable display includes one or more of a display of one or more differences in the comparison of at least one value related to the second input and at least one value related to at least one parameter for administration of the at least one frozen particle composition, frozen piercing implement, or frozen piercing implement device 18540 wherein the at least one parameter for making the at least one frozen particle composition or frozen piercing implement includes one or more of: constitution of the at least one frozen particle composition or frozen piercing implement, formulation of the at least one frozen particle composition or frozen piercing implement, configuration of the at least one frozen particle composition or frozen piercing implement, size of the at least one frozen particle composition or frozen piercing implement, density of the at least one frozen particle composition or frozen piercing implement, shape of the at least one frozen particle composition or frozen piercing implement, physical structure of the at least one frozen particle composition or frozen piercing implement, or physical or chemical integrity of the at least one frozen particle composition or frozen piercing implement 18550 wherein the at least one parameter for administering the at least one frozen particle composition or frozen piercing implement includes one or more of: substrate type; substrate function; substrate size; substrate constitution; substrate architecture; substrate durability; substrate temperature; temperature of administration conditions; depth of administration of the at least one frozen particle composition or frozen piercing implement; substrate source; one or more temporal coordinates; one or more spatial coordinates; presence or absence of at least one agent; presence or absence of at least one microparticle, nanoparticle, lens, tunablelens, sensor, transducer, actuator, detector, heater, valve, gate, channel, detection material, pump, power source, injector, controller, receiver, transmitter, or circuit; angle of administration of the at least one frozen particle composition or frozen piercing implement device; force of administration of the at least one frozen piercing implement device; velocity of administration of the at least one frozen piercing implement device; quantity of frozen piercing implements of the device; quantity of frozen piercing implement devices administered; rate of administration of more than one frozen piercing implement devices; method of administration of at least one frozen piercing implement device; timing of administration of at least one frozen piercing implement; or rate of delivery of at least one agent of the device

FIG. 186

18600 A system comprising:

18610 at least one computing device 18620 one or more instructions that when executed on the at least one computing device cause the at least one computing device to receive a first input associated with a first possible dataset 18630 the first possible dataset including data representative of at least one parameter for making or administering at least one frozen particle composition or frozen piercing implement 18640 one or more instructions that when executed generate an output to a user readable display 18650 further comprising one or more instructions that when executed on the at least one computing device cause the at least one computing device to compare a value associated with the first possible dataset with a second dataset including values of at least one predictive parameter for making the at least one frozen particle composition or frozen piercing implement 18660 further comprising one or more instructions that when executed on the at least one computing device cause the at least one computing device to determine a graphical illustration of the second possible dataset 18670 wherein the at least one parameter for making the at least one frozen particle composition or frozen piercing implement includes one or more of: constitution of the at least one frozen particle composition or frozen piercing implement, formulation of the at least one frozen particle composition or frozen piercing implement, size of the at least one frozen particle composition or frozen piercing implement, density of the at least one frozen particle composition or frozen piercing implement, shape of the at least one frozen particle composition or frozen piercing implement, physical structure of the at least one frozen particle composition or frozen piercing implement, or physical or chemical integrity of the at least one frozen particle composition or frozen piercing implement

FIG. 187

18710 wherein the at least one parameter for administering the at least one frozen particle composition or frozen piercing implement includes one or more of: substrate type; substrate function; substrate size; substrate constitution; substrate architecture; substrate durability; substrate temperature; temperature of administration conditions; depth of administration of the at least one frozen particle composition or frozen piercing implement; substrate source; one or more temporal coordinates; one or more spatial coordinates; presence or absence of at least one agent; presence or absence of at least one microparticle, nanoparticle, lens, tunable lens, sensor, transducer, actuator, detector, heater, valve, gate, channel, detection material, pump, power source, injector, controller, receiver, transmitter, or circuit; angle of administration of the at least one frozen piercing implement device; velocity of administration of the at least one frozen piercing implement device; quantity of frozen piercing implements of the device; quantity of frozen piercing implement devices administered; rate of administration of more than one frozen piercing implement devices; method of administration of at least one frozen piercing implement device; timing of administration of at least one frozen piercing implement; or rate of delivery of at least one agent of the device 18720 further comprising one or more instructions that when executed on the at least one computing device cause the at least one computing device to determine from the comparison at least one parameter for making or administering at least one frozen particle composition or frozen piercing implement to at least one substrate 18730 further comprising one or more instructions that when executed on the at least one computing device cause the at least one computing device to generate at least one response support structured on the determination 18740 further comprising one or more instructions that when executed on the at least one computing device cause the at least one computing device to access the first possible dataset in response to the first input 18750 further comprising one or more instructions that when executed on the at least one computing device cause the at least one computing device to generate the first possible dataset in response to the first input 18760 further comprising one or more instructions that when executed on the at least one computing device cause the at least one computing device to determine a graphical illustration of the first possible dataset

FIG. 189

18910 wherein the user readable display includes one or more of a display of one or more differences in the comparison of at least one value related to the second input and at least one value related to at least one parameter for administration of the at least one frozen particle composition or frozen piercing implement

FIG. 190

19000 A system comprising:

19010 circuitry for accepting a first input associated with one or more parameters for making at least one frozen particle composition or frozen piercing implement 19020 circuitry for accepting a second input associated with one or more parameters for administering at least one frozen particle composition or frozen piercing implement to at least one substrate 19030 circuitry for processing the first input and the second input 19040 circuitry for generating an output to a user readable display 19050 wherein the one or more parameters for making at least one frozen particle composition or frozen piercing implement include at least one value derived from an image 19060 wherein the image includes a 2-dimensional or 3-dimensional image 19070 wherein the image includes at least one image acquired by one or more of x-ray crystallography, laser, holography, optical coherence tomography, computer-assisted tomography scan, computed tomography, magnetic resonance imaging, positron-emission tomography scan, ultrasound, x-ray, electrical-impedance monitoring, microscopy, spectrometry, flow cytometry, radioisotope imaging, thermal imaging, infrared visualization, multiphoton calcium-imaging, photography, or *in silico* generation 19080 wherein the image includes at least one CAD drawing 19090 wherein the image includes at least one characteristic of the at least one frozen particle composition or frozen piercing implement 19095 wherein the at least one characteristic includes one or more of inner diameter, outer diameter, shape, at least one major dimension, or constitution

FIG. 191

19110 further comprising circuitry for displaying results of the processing 19120 further comprising circuitry for transmitting one or more signals that include information related to the processing the first input and the second input 19130 further comprising circuitry for evaluating the at least one substrate for one or more indicators relating to one or more of: quantitative delivery of at least one agent; depth of piercing the at least one substrate; spatial coordinates for administration of at least one frozen particle composition; at least one frozen piercing implement or at least one agent; temporal coordinates for administration of at least one frozen particle composition, at least one frozen piercing implement, or at least one agent; substrate type; substrate function; substrate size; substrate constitution; substrate architecture; substrate durability; substrate temperature; temperature of administration conditions; depth of administration of the at least one frozen particle composition or frozen piercing implement; substrate source; any substrate response to administration of at least one frozen piercing implement, at least one frozen particle composition, or at least one agent 19140 wherein the at least one agent includes at least one therapeutic agent, reinforcement agent, abrasive, explosive material, adhesive agent, or biological remodeling agent 19150 wherein the output includes one or more instructions for making the at least one frozen particle composition or frozen piercing implement 19160 wherein the output includes at least one graphical description of the at least one frozen particle composition or frozen piercing implement 19170 wherein the user includes at least one entity 19180 wherein the entity includes at least one person, or computer

FIG. 192

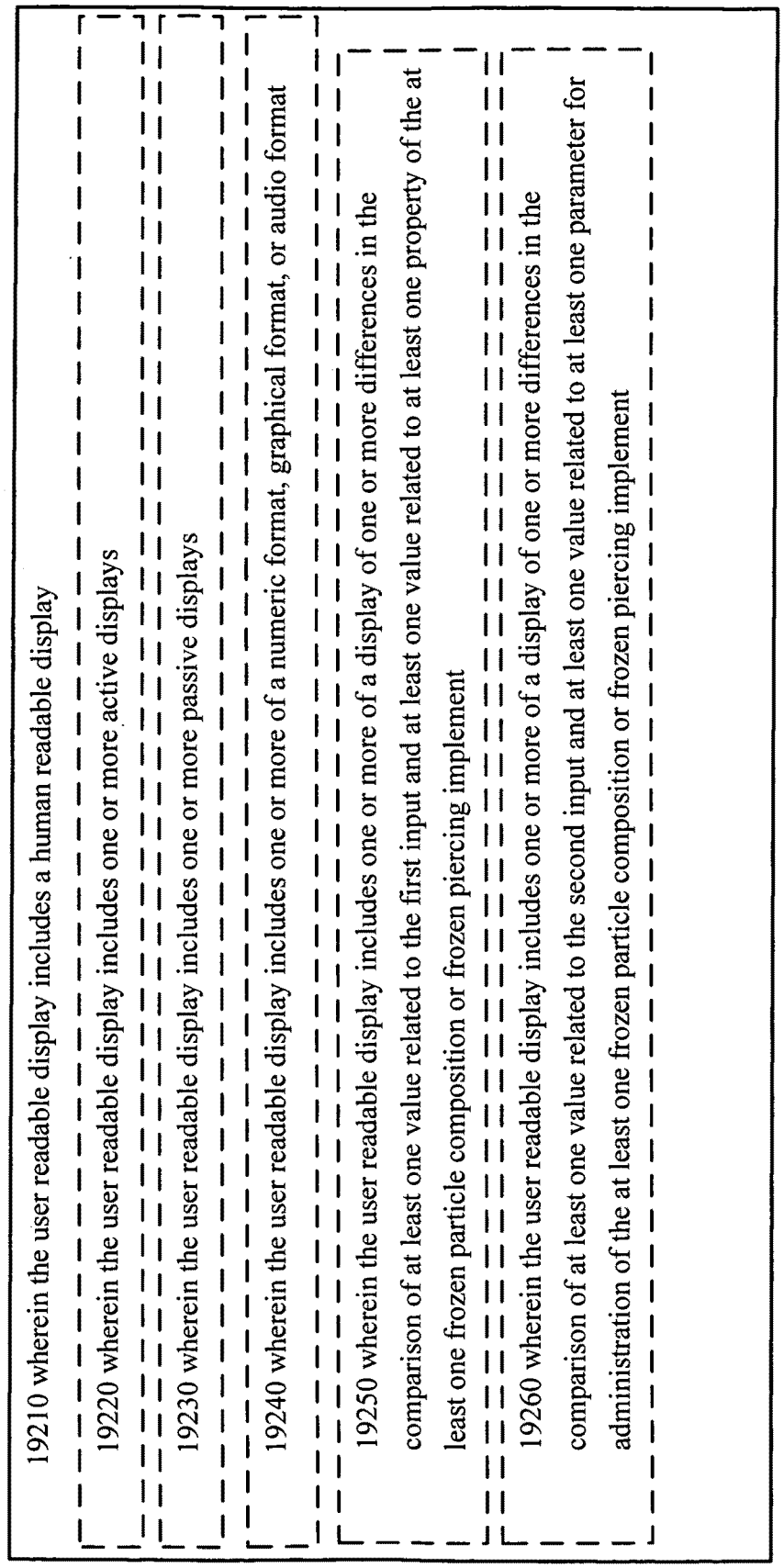

19210 wherein the user readable display includes a human readable display 19220 wherein the user readable display includes one or more active displays 19230 wherein the user readable display includes one or more passive displays 19240 wherein the user readable display includes one or more of a numeric format, graphical format, or audio format 19250 wherein the user readable display includes one or more of a display of one or more differences in the comparison of at least one value related to the first input and at least one value related to at least one property of the at least one frozen particle composition or frozen piercing implement 19260 wherein the user readable display includes one or more of a display of one or more differences in the comparison of at least one value related to the second input and at least one value related to at least one parameter for administration of the at least one frozen particle composition or frozen piercing implement

FIG. 193

19300 A computer program product comprising:

19310 a recordable medium bearing one or more instructions for accepting a first input associated with at least one parameter for making at least one frozen particle composition or frozen piercing implement 19320 one or more instructions for accepting a second input associated with at least one parameter for administering the at least one frozen particle composition or frozen piercing implement to at least one substrate 19330 one or more instructions for processing the first input and the second input 19340 one or more instructions for generating an output to a user readable display 19350 wherein the recordable medium includes a computer-readable medium 19360 wherein the recordable medium includes a communications medium 19370 further comprising one or more instructions for displaying results of the processing 19380 further comprising one or more instructions for transmitting one or more signals that include information related to the processing the first input and the second input 19390 further comprising one or more instructions for evaluating the at least one substrate for one or more indicators relating to one or more of: quantitative delivery of at least one agent, depth of piercing the at least one substrate, spatial location of delivery of at least one agent, or temporal location of delivery of at least one agent 19395 wherein the at least one agent includes at least one therapeutic agent, reinforcement agent, abrasive, explosive material, adhesive agent, or biological remodeling agent

FIG. 194

19410 wherein the first input includes at least one parameter for making the at least one frozen particle composition or frozen piercing implement includes one or more of: constitution of the at least one frozen particle composition or frozen piercing implement, formulation of the at least one frozen particle composition or frozen piercing implement, configuration of the at least one frozen particle composition or frozen piercing implement, size of the at least one frozen particle composition or frozen piercing implement, density of the at least one frozen particle composition or frozen piercing implement, shape of the at least one frozen particle composition or frozen piercing implement, physical structure of the at least one frozen particle composition or frozen piercing implement, or physical or chemical integrity of the at least one frozen particle composition or frozen piercing implement 19420 wherein the second input includes at least one parameter for administering the at least one frozen particle composition or frozen piercing implement includes one or more of: substrate type; substrate function; substrate size; substrate constitution; substrate architecture; substrate durability; substrate temperature; temperature of administration conditions; depth of administration of the at least one frozen particle composition or frozen piercing implement; substrate source; one or more temporal coordinates; one or more spatial coordinates; presence or absence of at least one agent; presence or absence of at least one microparticle, nanoparticle, lens, tunable lens, sensor, transducer, actuator, detector, heater, valve, gate, channel, detection material, pump, power source, injector, controller, receiver, transmitter, or circuit; angle of administration of the at least one frozen particle composition or frozen piercing implement device; velocity of administration of the at least one frozen particle composition or frozen piercing implement device; quantity of frozen piercing implements of the device; quantity of frozen piercing implement devices administered; rate of administration of more than one frozen piercing implement devices; method of administration of at least one frozen piercing implement device; timing of administration of at least one frozen piercing implement; or rate of delivery of at least one agent of the device 19430 wherein the output includes one or more instructions for making the at least one frozen particle composition or frozen piercing implement 19440 wherein the output includes at least one graphical description of the at least one frozen particle composition or frozen piercing implement

FIG. 195

19510 wherein the user includes at least one entity 19520 wherein the entity includes at least one person, or computer 19530 wherein the user readable display includes a human readable display 19540 wherein the user readable display includes one or more active displays 19550 wherein the user readable display includes one or more passive displays 19560 wherein the user readable display includes one or more of a numeric format, graphical format, or audio format 19570 wherein the user readable display includes one or more of a display of one or more differences in the comparison of at least one value related to the first input and at least one value related to at least one property of the at least one frozen particle composition or frozen piercing implement 19580 wherein the user readable display includes one or more of a display of one or more differences in the comparison of at least one value related to the second input and at least one value related to at least one parameter for administration of the at least one frozen particle composition or frozen piercing implement

FIG. 196

19600 A system comprising:

19610 a recordable medium bearing one or more instructions for accepting a first input associated with at least one parameter for making at least one frozen particle composition or frozen piercing implement 19620 one or more instructions for accepting a second input associated with at least one parameter for administering at least one frozen particle composition or frozen piercing implement 19630 one or more instructions for processing the first input and the second input 19640 one or more instructions for generating an output to a user readable display 19650 wherein the recordable medium includes a computer-readable medium 19660 wherein the recordable medium includes a communications medium 19670 further comprising one or more instructions for transmitting one or more signals that include information related to the processing the first input and the second input 19680 further comprising one or more instructions for evaluating the at least one substrate for one or more indicators relating to one or more of: quantitative delivery of at least one agent, depth of piercing the at least one substrate, spatial location of delivery of at least one agent, or temporal location of delivery of at least one agent 19690 wherein the at least one agent includes at least one therapeutic agent, reinforcement agent, abrasive, explosive material, adhesive agent, or biological remodeling agent

FIG. 197

19710 wherein the first input includes at least one parameter for making the at least one frozen particle composition or frozen piercing implement includes one or more of: constitution of the at least one frozen particle composition or frozen piercing implement, configuration of the at least one frozen particle composition or frozen piercing implement, formulation of the at least one frozen particle composition or frozen piercing implement, size of the at least one frozen particle composition or frozen piercing implement, density of the at least one frozen particle composition or frozen piercing implement, shape of the at least one frozen particle composition or frozen piercing implement, physical structure of the at least one frozen particle composition or frozen piercing implement, or physical or chemical integrity of the at least one frozen particle composition or frozen piercing implement 19720 wherein the second input includes at least one parameter for administering the at least one frozen particle composition or frozen piercing implement includes one or more of: substrate type; substrate function; substrate size; substrate constitution; substrate architecture; substrate durability; substrate temperature; temperature of administration conditions; depth of administration of the at least one frozen particle composition or frozen piercing implement; substrate source; one or more temporal coordinates; one or more spatial coordinates; presence or absence of at least one agent; presence or absence of at least one microparticle, nanoparticle, lens, tunable lens, sensor, transducer, actuator, detector, heater, valve, gate, channel, detection material, pump, power source, injector, controller, receiver, transmitter, or circuit; angle of administration of the at least one frozen piercing implement device; velocity of administration of the at least one frozen piercing implement device; quantity of frozen piercing implements of the device; quantity of frozen piercing implement devices administered; rate of administration of more than one frozen piercing implement devices; method of administration of at least one frozen piercing implement device; timing of administration of at least one frozen piercing implement; or rate of delivery of at least one agent of the device 19730 wherein the output includes one or more instructions for making the at least one frozen particle composition or frozen piercing implement

FIG. 198

19810 wherein the output includes at least one graphical description of the at least one frozen particle composition or frozen piercing implement 19820 wherein the user includes at least one entity 19830 wherein the entity includes at least one person, or computer 19840 wherein the user readable display includes a human readable display 19850 wherein the user readable display includes one or more active displays 19860 wherein the user readable display includes one or more passive displays 19870 wherein the user readable display includes one or more of a numeric format, graphical format, or audio format 19880 wherein the user readable display includes one or more of a display of one or more differences in the comparison of at least one value related to the first input and at least one value related to at least one property of the at least one frozen particle composition or frozen piercing implement 19890 wherein the user readable display includes one or more of a display of one or more differences in the comparison of at least one value related to the second input and at least one value related to at least one parameter for administration of the at least one frozen particle composition or frozen piercing implement

FIG. 199

19900 A system comprising:

19910 at least one computer program, configured with a computer-readable medium, for use with at least one computer system and wherein the computer program includes a plurality of instructions including but not limited to: one or more instructions for accepting a first input associated with one or more parameters for making one or more frozen particle compositions or frozen piercing implements to at least one substrate; one or more instructions for accepting a second input associated with one or more parameters for administering one or more frozen particle compositions or frozen piercing implements; one or more instructions for processing the first input and the second input; and one or more instructions for generating an output to a user readable display 19920 further comprising one or more instructions for transmitting one or more signals that include information related to the processing the first input and the second input 19930 further comprising one or more instructions for evaluating the at least one biological tissue for one or more indicators relating to one or more of: quantitative delivery of at least one agent, depth of piercing the at least one substrate, spatial location of delivery of at least one agent, or temporal location of delivery of at least one agent 19940 wherein the at least one agent includes at least one therapeutic agent, reinforcement agent, abrasive, explosive material, adhesive agent, or biological remodeling agent 19950 further comprising at least one computing device 19960 wherein the at least one computing device is configured to communicate with at least one printing device, at least one imaging device, or at least one input device 19970 wherein the first input includes at least one parameter for making the at least one frozen piercing implement device includes one or more of: constitution of the at least one frozen piercing implement device, constitution of the at least one frozen piercing implement device, configuration of the at least one frozen piercing implement or frozen piercing implement device, formulation of the at least one frozen piercing implement device, formulation of the at least one frozen piercing implement device, size of the at least one frozen piercing implement device, size of the at least one frozen piercing implement device, shape of the at least one frozen piercing implement device, shape of the at least one frozen piercing implement device, physical structure of the at least one frozen piercing implement device, physical structure of the at least one frozen piercing implement device, physical or chemical integrity of the at least one frozen piercing implement device, or physical or chemical integrity of the at least one frozen piercing implement device

FIG. 200

20010 wherein the first input includes at least one parameter for making the at least one frozen particle composition or frozen piercing implement includes one or more of: constitution of the at least one frozen particle composition or frozen piercing implement, configuration of the at least one frozen particle composition or frozen piercing implement, formulation of the at least one frozen particle composition or frozen piercing implement, size of the at least one frozen particle composition or frozen piercing implement, density of the at least one frozen particle composition or frozen piercing implement, shape of the at least one frozen particle composition or frozen piercing implement, physical structure of the at least one frozen particle composition or frozen piercing implement, or physical or chemical integrity of the at least one frozen particle composition or frozen piercing implement 20020 wherein the second input includes at least one parameter for administering the at least one frozen particle composition or frozen piercing implement includes one or more of: substrate type; substrate function; substrate size; substrate constitution; substrate architecture; substrate durability; substrate temperature; temperature of administration conditions; depth of administration of the at least one frozen particle composition or frozen piercing implement; substrate source; one or more temporal coordinates; one or more spatial coordinates; presence or absence of at least one agent; presence or absence of at least one microparticle, nanoparticle, lens, tunable lens, sensor, transducer, actuator, detector, heater, valve, gate, channel, detection material, pump, power source, injector, controller, receiver, transmitter, or circuit; angle of administration of the at least one frozen piercing implement device; velocity of administration of the at least one frozen piercing implement device; quantity of frozen piercing implements of the device; quantity of frozen piercing implement devices administered; rate of administration of more than one frozen piercing implement devices; method of administration of at least one frozen piercing implement device; timing of administration of at least one frozen piercing implement; or rate of delivery of at least one agent of the device 20030 wherein the second input includes at least one parameter for administering at least one frozen piercing implement device to at least one substrate includes one or more of: substrate type; substrate function; substrate size; substrate constitution; substrate architecture; substrate durability; substrate temperature; temperature of administration conditions; depth of administration of the at least one frozen particle composition or frozen piercing implement; substrate source; one or more temporal coordinates; one or more spatial coordinates; presence or absence of at least one agent; presence or absence of at least one microparticle, nanoparticle, lens, tunablelens, sensor, transducer, actuator, detector, heater, valve, gate, channel, detection material, pump, power source, injector, controller, receiver, transmitter, or circuit; angle of administration of the at least one frozen piercing implement device; force of administration of the at least one frozen piercing implement device; velocity of administration of the at least one frozen piercing implement device; quantity of frozen piercing implements of the device; quantity of frozen piercing implement devices administered; rate of administration of more than one frozen piercing implement devices; method of administration of at least one frozen piercing implement device; timing of administration of at least one frozen piercing implement; or rate of delivery of at least one agent of the device

FIG. 201

20100 A system comprising:

20110 at least one computing device 20120 one or more instructions that when executed on the at least one computing device cause the at least one computing device to receive a first input associated with a first possible dataset 20130 the first possible dataset including data representative of at least one parameter for making or administering at least one frozen particle composition, frozen piercing implement, or frozen piercing implement device to at least one substrate 20140 one or more instructions for generating an output to a user readable display 20150 wherein the at least one frozen piercing implement device includes at least one frozen piercing implement array device, frozen piercing implement fluidic device, or frozen piercing implement injection device 20160 wherein the frozen piercing implement injection device includes a frozen piercing implement auto-injection device 20170 further comprising one or more instructions that when executed on the at least one computing device cause the at least one computing device to compare a value associated with the first possible dataset with a second dataset including values of at least one predictive parameter for making or administering at least one frozen particle composition, frozen piercing implement, or frozen piercing implement device to at least one substrate 20180 wherein the first input includes at least one parameter for making the at least one frozen piercing implement device includes one or more of: constitution of the at least one frozen piercing implement device, constitution of the at least one frozen piercing implement device, configuration of the at least one frozen piercing implement or frozen piercing implement device, formulation of the at least one frozen piercing implement of the at least one frozen piercing implement device, formulation of the at least one frozen piercing implement device, size of the at least one frozen piercing implement of the frozen piercing implement device, size of the at least one frozen piercing implement device, shape of the at least one frozen piercing implement of the frozen piercing implement device, shape of the at least one frozen piercing implement device, physical structure of the at least one frozen piercing implement of the frozen piercing implement device, physical structure of the at least one frozen piercing implement device, physical or chemical integrity of the at least one frozen piercing implement device, or physical or chemical integrity of the at least one frozen piercing implement device

FIG. 202

20210 wherein the second input includes at least one parameter for administering at least one frozen piercing implement device to at least one substrate includes one or more of: substrate type; substrate function; substrate size; substrate constitution; substrate architecture; substrate durability; substrate temperature; temperature of administration conditions; depth of administration of the at least one frozen particle composition or frozen piercing implement; substrate source; one or more temporal coordinates; one or more spatial coordinates; presence or absence of at least one agent; presence or absence of at least one microparticle, nanoparticle, lens, tunable lens, sensor, transducer, actuator, detector, heater, valve, gate, channel, detection material, pump, power source, injector, controller, receiver, transmitter, or circuit; angle of administration of the at least one frozen piercing implement device; velocity of administration of the at least one frozen piercing implement device; quantity of frozen piercing implements of the device; quantity of frozen piercing implement devices administered; rate of administration of more than one frozen piercing implement devices; method of administration of at least one frozen piercing implement device to at least one substrate one frozen piercing implement; or rate of delivery of at least one agent of the device 20220 further comprising one or more instructions that when executed on the at least one computing device cause the at least one computing device to determine a graphical illustration of the second possible dataset 20230 further comprising one or more instructions that when executed on the at least one computing device cause the at least one computing device to determine from the comparison at least one parameter for administering at least one frozen particle composition, frozen piercing implement, or frozen piercing implement device to at least one substrate 20240 further comprising one or more instructions that when executed on the at least one computing device cause the at least one computing device to generate at least one response support structured on the determination 20250 further comprising one or more instructions that when executed on the at least one computing device cause the at least one computing device to access the first possible dataset in response to the first input

FIG. 203

20310 further comprising one or more instructions that when executed on the at least one computing device cause the at least one computing device to generate the first possible dataset in response to the first input 20320 further comprising one or more instructions that when executed on the at least one computing device cause the at least one computing device to determine a graphical illustration of the first possible dataset 20330 wherein the at least one computing device includes one or more of a desktop computer, workstation computer, or computing system 20340 wherein the at least one computing system includes one or more of a cluster of processors, a networked computer, a tablet personal computer, a laptop computer, a mobile device, a mobile telephone, or a personal digital assistant computer 20350 wherein the output includes one or more instructions for making the at least one frozen particle composition, frozen piercing implement, or frozen piercing implement device 20360 wherein the output includes at least one graphical description of the at least one frozen particle composition, frozen piercing implement, or frozen piercing implement device 20370 wherein the user includes at least one entity 20380 wherein the entity includes at least one person, or computer 20390 wherein the user readable display includes a human readable display

FIG. 204

20410 wherein the user readable display includes one or more active displays 20420 wherein the user readable display includes one or more passive displays 20430 wherein the user readable display includes one or more of a numeric format, graphical format, or audio format 20440 wherein the user readable display includes one or more of a display of one or more differences in the comparison of at least one value related to the first input and at least one value related to at least one property of the at least one frozen particle composition, frozen piercing implement or frozen piercing implement device 20450 wherein the user readable display includes one or more of a display of one or more differences in the comparison of at least one value related to the second input and at least one value related to at least one parameter for administration of the at least one frozen particle composition, frozen piercing implement, or frozen piercing implement device

FIG. 205

20500 A system comprising:

20510 circuitry for accepting a first input associated with at least one parameter for making at least one frozen piercing implement device 20520 circuitry for accepting a second input associated with at least one parameter for administering at least one frozen piercing implement device to at least one substrate 20530 circuitry for processing the first input and the second input 20540 circuitry for generating an output to a user readable display 20550 wherein the at least one frozen piercing implement device includes at least one frozen piercing implement array device, frozen piercing implement fluidic device, or frozen piercing implement injection device 20560 wherein the frozen piercing implement injection device includes a frozen piercing implement auto-injection device 20570 wherein the first input includes at least one value derived from at least one image 20580 wherein the at least one image includes at least one 2-dimensional or 3-dimensional image 20590 wherein the image includes at least one image acquired by one or more of x-ray crystallography, laser, holography, optical coherence tomography, computer-assisted tomography, computed tomography, magnetic resonance imaging, positron-emission tomography scan, ultrasound, x-ray, electrical-impedance monitoring, microscopy, spectrometry, flow cytometry, radioisotope imaging, thermal imaging, infrared visualization, multiphoton calcium-imaging, photography, or *in silico* generation

FIG. 206

20610 wherein the at least one image includes at least one CAD drawing 20620 wherein the at least one image includes at least one characteristic of the at least one frozen piercing implement of the device or the frozen piercing implement device 20630 wherein the at least one characteristic of the one or more frozen piercing implement device includes one or more of number of frozen piercing implements, number of total piercing implements, size of at least one frozen piercing implement, constitution of at least one frozen piercing implement, shape of at least one frozen piercing implement, shape of the device, configuration of the device, spacing of at least two components of the device, spacing of at least two frozen piercing implements of the device, or presence or absence of at least one microparticle, nanoparticle, lens, tunable lens, sensor, transducer, actuator, detector, heater, valve, gate, channel, detection material, pump, power source, injector, controller, receiver, transmitter, or circuit 20640 wherein the first input includes at least one parameter for making the at least one frozen piercing implement device includes one or more of: constitution of the at least one frozen piercing implement of the frozen piercing implement device, constitution of the at least one frozen piercing implement device, configuration of the at least one frozen piercing implement or frozen piercing implement device, formulation of the at least one frozen piercing implement of the frozen piercing implement device, formulation of the at least one frozen piercing implement device, size of the at least one frozen piercing implement of the frozen piercing implement device, size of the at least one frozen piercing implement device, shape of the at least one frozen piercing implement device, physical structure of the at least one frozen piercing implement of the frozen piercing implement device, physical structure of the at least one frozen piercing implement device, physical or chemical integrity of the at least one frozen piercing implement of the frozen piercing implement device, physical or chemical integrity of the at least one frozen piercing implement device, or presence or absence of at least one microparticle, nanoparticle, lens, tunable lens, sensor, transducer, actuator, detector, heater, valve, gate, channel, detection material, pump, power source, injector, controller, receiver, transmitter, or circuit, in the at least one frozen piercing implement or frozen piercing implement device

FIG. 207

20710 wherein the second input includes at least one parameter for administering the at least one frozen piercing implement device includes one or more of: substrate type; substrate function; substrate size; substrate constitution; substrate architecture; substrate durability; substrate temperature; temperature of administration conditions; depth of administration of the at least one frozen particle composition or frozen piercing implement; substrate source; one or more temporal coordinates; one or more spatial coordinates; presence or absence of at least one agent; presence or absence of at least one microparticle, nanoparticle, lens, tunable lens, sensor, transducer, actuator, detector, heater, valve, gate, channel, detection material, pump, power source, injector, controller, receiver, transmitter, or circuit; angle of administration of the at least one frozen piercing implement device; velocity of administration of the at least one frozen piercing implement device; quantity of frozen piercing implements of the device; quantity of frozen piercing implement devices; rate of administration of more than one frozen piercing implement devices; method of administration of at least one frozen piercing implement device; timing of administration of at least one frozen piercing implement; or rate of delivery of at least one agent of the device 20720 further comprising circuitry for transmitting one or more signals that include information related to the processing the first input and the second input 20730 further comprising circuitry for evaluating the at least one substrate for one or more indicators relating to one or more of: quantitative delivery of at least one agent, depth of piercing the at least one substrate, spatial location of delivery of at least one agent, or temporal location of delivery of at least one agent 20740 wherein the at least one agent includes at least one therapeutic agent, reinforcement agent, abrasive, explosive material, adhesive agent, or biological remodeling agent 20750 wherein the output includes one or more instructions for making the at least one frozen particle composition or frozen piercing implement 20760 wherein the output includes at least one graphical description of the at least one frozen particle composition or frozen piercing implement

FIG. 209

20900 A computer program product comprising:

20910 a recordable medium bearing one or more instructions for accepting a first input associated with at least one parameter for making at least one frozen piercing implement device 20920 one or more instructions for accepting a second input associated with at least one parameter for administering the at least one frozen piercing implement device to at least one substrate 20930 one or more instructions for processing the first input and the second input 20940 one or more instructions for generating an output to a user readable display 20950 wherein the recordable medium includes a computer-readable medium 20960 wherein the recordable medium includes a communications medium 20970 further comprising one or more instructions for displaying results of the processing 20980 further comprising one or more instructions for transmitting one or more signals that include information related to the processing the first input and the second input 20990 wherein the first input includes at least one parameter for making the at least one frozen piercing implement device includes one or more of: constitution of the at least one frozen piercing implement device, configuration of the at least one frozen piercing implement device, formulation of the at least one frozen piercing implement device, size of the at least one frozen piercing implement device, shape of the at least one frozen piercing implement device, physical structure of the at least one frozen piercing implement device, physical or chemical integrity of the at least one frozen piercing implement device, or presence or absence of at least one microparticle, nanoparticle, lens, tunable lens, sensor, transducer, actuator, detector, heater, valve, gate, channel, detection material, pump, power source, injector, controller, receiver, transmitter, or circuit, in the at least one frozen piercing implement or frozen piercing implement device

FIG. 210

21010 wherein the at least one parameter for administering at least one frozen piercing implement device to at least one substrate includes one or more of: substrate type; substrate function; substrate size; substrate constitution; substrate architecture; substrate durability; substrate temperature; temperature of administration conditions; depth of administration of the at least one frozen particle composition or frozen piercing implement; substrate source; one or more temporal coordinates; one or more spatial coordinates; presence or absence of at least one agent; presence or absence of at least one microparticle, nanoparticle, lens, tunable lens, sensor, transducer, actuator, detector, heater, valve, gate, channel, detection material, pump, power source, injector, controller, receiver, transmitter, or circuit; angle of administration of the at least one frozen piercing implement device; velocity of administration of the at least one frozen piercing implement device; quantity of frozen piercing implements of the device; quantity of frozen piercing implement devices administered; rate of administration of more than one frozen piercing implement devices; method of administration of at least one frozen piercing implement device; timing of administration of at least one frozen piercing implement; or rate of delivery of at least one agent of the device 21020 further comprising one or more instructions for evaluating the at least one substrate for one or more indicators relating to one or more of: quantitative delivery of at least one agent, depth of piercing the at least one substrate, spatial location of delivery of at least one agent, or temporal location of delivery of at least one agent 21030 wherein the at least one agent includes at least one therapeutic agent, reinforcement agent, abrasive, explosive material, adhesive agent, or biological remodeling agent 21040 wherein the at least one frozen piercing implement device includes at least one frozen piercing implement array device, frozen piercing implement fluidic device, or frozen piercing implement injection device 21050 wherein the frozen piercing implement injection device includes a frozen piercing implement auto-injection device 21060 wherein the output includes one or more instructions for making the at least one frozen piercing implement device

FIG. 211

21110 wherein the output includes at least one graphical description of the at least one frozen piercing implement device 21120 wherein the user includes at least one entity 21130 wherein the entity includes at least one person, or computer 21140 wherein the user readable display includes a human readable display 21150 wherein the user readable display includes one or more active displays 21160 wherein the user readable display includes one or more passive displays 21170 wherein the user readable display includes one or more of a numeric format, graphical format, or audio format 21180 wherein the user readable display includes one or more of a display of one or more differences in the comparison of at least one value related to the first input and at least one value related to at least one property of the at least one frozen piercing implement device 21190 wherein the user readable display includes one or more of a display of one or more differences in the comparison of at least one value related to the second input and at least one value related to at least one parameter for administration of the at least one frozen piercing implement device

FIG. 212

21200 A system comprising:

21210 a recordable medium bearing one or more instructions for accepting a first input associated with at least one parameter for making at least one frozen piercing implement device 21220 one or more instructions for accepting a second input associated with at least one parameter for administering at least one frozen piercing implement device 21230 one or more instructions for processing the first input and the second input 21240 one or more instructions for generating an output to a user readable display 21250 wherein the at least one frozen piercing implement device includes at least one frozen piercing implement array device, frozen piercing implement fluidic device, or frozen piercing implement injection device 21260 wherein the frozen piercing implement injection device includes a frozen piercing implement auto-injection device 21270 wherein the recordable medium includes a computer-readable medium 21280 wherein the recordable medium includes a communications medium 21290 further comprising one or more instructions for transmitting one or more signals that include information related to the processing the first input and the second input

FIG. 213

21310 wherein the first input includes at least one parameter for making the at least one frozen piercing implement device includes one or more of: constitution of the at least one frozen piercing implement of the frozen piercing implement device, constitution of the at least one frozen piercing implement device, configuration of the at least one frozen piercing implement device or frozen piercing implement device, formulation of the at least one frozen piercing implement of the frozen piercing implement device, formulation of the at least one frozen piercing implement device, size of the at least one frozen piercing implement of the frozen piercing implement device, size of the at least one frozen piercing implement device, shape of the at least one frozen piercing implement of the frozen piercing implement device, shape of the at least one frozen piercing implement device, physical structure of the at least one frozen piercing implement device, physical structure of the frozen piercing implement of the at least one frozen piercing implement device, physical or chemical integrity of the at least one frozen piercing implement of the frozen piercing implement device, physical or chemical integrity of the at least one frozen piercing implement device, or presence or absence of at least one microparticle, nanoparticle, lens, tunable lens, sensor, transducer, actuator, detector, heater, valve, gate, channel, detection material, pump, power source, injector, controller, receiver, transmitter, or circuit, in the at least one frozen piercing implement or frozen piercing implement device 21320 wherein the second input includes at least one parameter for administering the at least one frozen piercing implement device includes one or more of: substrate type; substrate function; substrate size; substrate constitution; substrate architecture; substrate durability; substrate temperature; temperature of administration conditions; depth of administration of the at least one frozen particle composition or frozen piercing implement; substrate source; one or more temporal coordinates; one or more spatial coordinates; presence or absence of at least one agent; presence or absence of at least one microparticle, nanoparticle, lens, tunable lens, sensor, transducer, actuator, detector, heater, valve, gate, channel, detection material, pump, power source, injector, controller, receiver, transmitter, or circuit; angle of administration of the at least one frozen piercing implement device; velocity of administration of the at least one frozen piercing implement device; quantity of frozen piercing implements of the device; quantity of frozen piercing implement devices administered; rate of administration of more than one frozen piercing implement devices; method of administration of at least one frozen piercing implement device; timing of administration of at least one frozen piercing implement; or rate of delivery of at least one agent of the device

FIG. 214

21410 further comprising one or more instructions for evaluating the at least one substrate for one or more indicators relating to one or more of: quantitative delivery of at least one agent, depth of piercing the at least one substrate, spatial location of delivery of at least one agent, or temporal location of delivery of at least one agent 21420 wherein the at least one agent includes at least one therapeutic agent, reinforcement agent, abrasive, explosive material, adhesive agent, or biological remodeling agent 21430 wherein the output includes one or more instructions for making the at least one frozen piercing implement device 21440 wherein the output includes at least one graphical description of the at least one frozen piercing implement device 21450 wherein the user includes at least one entity 21460 wherein the entity includes at least one person, or computer 21470 wherein the user readable display includes a human readable display 21480 wherein the user readable display includes one or more active displays 21485 wherein the user readable display includes one or more passive displays 21490 wherein the user readable display includes one or more of a numeric format, graphical format, or audio format 21495 wherein the user readable display includes one or more of a display of one or more differences in the comparison of at least one value related to the first input and at least one value related to at least one property of the at least one frozen piercing implement device 21498 wherein the user readable display includes one or more of a display of one or more differences in the comparison of at least one value related to the second input and at least one value related to at least one parameter for administration of the at least one frozen piercing implement device

FIG. 215

21500 A system comprising:

21510 at least one computer program, configured with a computer-readable medium, for use with at least one computer system and wherein the computer program includes a plurality of instructions including but not limited to: one or more instructions for accepting a first input associated with at least one parameter for making at least one frozen particle composition, frozen piercing implement, or frozen piercing implement device; one or more instructions for accepting a second input associated with at least one parameter for administering at least one frozen piercing implement device; one or more instructions for processing the first input and the second input; and one or more instructions for generating an output to a user readable display 21520 further comprising one or more instructions for transmitting one or more signals that include information related to the processing the first input and the second input 21530 further comprising one or more instructions for evaluating the at least one substrate for one or more indicators relating to one or more of: quantitative delivery of at least one agent, depth of piercing the at least one substrate, spatial location of delivery of at least one agent, or temporal location of delivery of at least one agent 21540 wherein the at least one agent includes at least one therapeutic agent, reinforcement agent, abrasive, explosive material, adhesive agent, or biological remodeling agent

FIG. 217

21710 wherein the output includes one or more instructions for making the at least one frozen piercing implement device 21720 wherein the output includes at least one graphical description of the at least one frozen piercing implement device 21730 wherein the user includes at least one entity 21740 wherein the entity includes at least one person, or computer 21750 wherein the user readable display includes a human readable display 21760 wherein the user readable display includes one or more active displays 21770 wherein the user readable display includes one or more passive displays 21780 wherein the user readable display includes one or more of a numeric format, graphical format, or audio format 21790 wherein the user readable display includes one or more of a display of one or more differences in the comparison of at least one value related to the first input and at least one value related to at least one property of the at least one frozen piercing implement device 21795 wherein the user readable display includes one or more of a display of one or more differences in the comparison of at least one value related to the second input and at least one value related to at least one parameter for administration of the at least one frozen piercing implement device

FIG. 218

21810 wherein the first input includes at least one parameter for making the at least one frozen piercing implement device includes one or more of: constitution of the at least one frozen piercing implement device, constitution of the at least one frozen piercing implement device, configuration of the at least one frozen piercing implement or frozen piercing implement device, formulation of the at least one frozen piercing implement of the frozen piercing implement device, formulation of the at least one frozen piercing implement device, size of the at least one frozen piercing implement of the frozen piercing implement device, size of the at least one frozen piercing implement device, shape of the at least one frozen piercing implement of the frozen piercing implement device, shape of the at least one frozen piercing implement device, physical structure of the at least one frozen piercing implement of the frozen piercing implement device, physical structure of the at least one frozen piercing implement device, physical or chemical integrity of the at least one frozen piercing implement of the frozen piercing implement device, or physical or chemical integrity of the at least one frozen piercing implement device 21820 wherein the second input includes at least one parameter for administering at least one frozen piercing implement device to at least one substrate includes one or more of: substrate type; substrate function; substrate size; substrate constitution; substrate architecture; substrate durability; substrate temperature; temperature of administration conditions; depth of administration of the at least one frozen particle composition or frozen piercing implement; substrate source; one or more temporal coordinates; one or more spatial coordinates; presence or absence of at least one agent; presence or absence of at least one microparticle, nanoparticle, lens, tunablelens, sensor, transducer, actuator, detector, heater, valve, gate, channel, detection material, pump, power source, injector, controller, receiver, transmitter, or circuit; angle of administration of the at least one frozen piercing implement device; force of administration of the at least one frozen piercing implement device; velocity of administration of the at least one frozen piercing implement device; quantity of frozen piercing implements of the device; quantity of frozen piercing implement devices administered; rate of administration of more than one frozen piercing implement devices; method of administration of at least one frozen piercing implement device; timing of administration of at least one frozen piercing implement; or rate of delivery of at least one agent of the device

FROZEN COMPOSITIONS AND METHODS FOR PIERCING A SUBSTRATE

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC§119(e) for provisional patent applications, for any and all parent, grandparent, great-grandparent, etc. applications of the Related Application(s)). All subject matter of the Related Applications and of any and all parent, grandparent, great-grandparent, etc. applications of the Related Applications is incorporated herein by reference to the extent such subject matter is not inconsistent herewith.

Related Applications

For purposes of the USPTO extra-statutory requirements, the present application constitutes a continuation-in-part of U.S. patent application Ser. No. 12/290,671, entitled COMPOSITIONS AND METHODS FOR THERAPEUTIC DELIVERY WITH FROZEN PARTICLES, naming Edward S. Boyden, Roderick A. Hyde, Eric C. Leuthardt, Nathan P. Myhrvold, Elizabeth A. Sweeney and Lowell L. Wood, Jr. as inventors, filed 31 Oct. 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/290,683, entitled COMPOSITIONS AND METHODS FOR THERAPEUTIC DELIVERY WITH FROZEN PARTICLES, naming Edward S. Boyden, Roderick A. Hyde, Eric C. Leuthardt, Nathan P. Myhrvold, Elizabeth A. Sweeney and Lowell L. Wood, Jr. as inventors, filed 31 Oct. 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/290,685, entitled COMPOSITIONS AND METHODS FOR THERAPEUTIC DELIVERY WITH FROZEN PARTICLES, naming Edward S. Boyden, Roderick A. Hyde, Eric C. Leuthardt, Nathan P. Myhrvold, Elizabeth A. Sweeney and Lowell L. Wood, Jr. as inventors, filed 31 Oct. 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/290,686, entitled COMPOSITIONS AND METHODS FOR THERAPEUTIC DELIVERY WITH FROZEN PARTICLES, naming Edward S. Boyden, Roderick A. Hyde, Eric C. Leuthardt, Nathan P. Myhrvold, Elizabeth A. Sweeney and Lowell L. Wood, Jr. as inventors, filed 31 Oct. 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/290,690, entitled COMPOSITIONS AND METHODS FOR THERAPEUTIC DELIVERY WITH FROZEN PARTICLES, naming Edward S. Boyden, Roderick A. Hyde, Eric C. Leuthardt, Nathan P. Myhrvold, Elizabeth A. Sweeney and Lowell L. Wood, Jr. as inventors, filed 31 Oct. 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/290,691, entitled COMPOSITIONS AND METHODS FOR THERAPEUTIC DELIVERY WITH FROZEN PARTICLES, naming Edward S. Boyden, Roderick A. Hyde, Eric C. Leuthardt, Nathan P. Myhrvold, Elizabeth A. Sweeney and Lowell L. Wood, Jr. as inventors, filed 31 Oct. 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/290,684, entitled COMPOSITIONS AND METHODS FOR THERAPEUTIC DELIVERY WITH FROZEN PARTICLES, naming Edward S. Boyden, Roderick A. Hyde, Eric C. Leuthardt, Nathan P. Myhrvold, Elizabeth A. Sweeney and Lowell L. Wood, Jr. as inventors, filed 31 Oct. 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/290,670, entitled COMPOSITIONS AND METHODS FOR SURFACE ABRASION WITH FROZEN PARTICLES, naming Edward S. Boyden, Daniel B. Cook, Roderick A. Hyde, Eric C. Leuthardt, Nathan P. Myhrvold, Elizabeth A. Sweeney and Lowell L. Wood, Jr. as inventors, filed 31 Oct. 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/290,664, entitled COMPOSITIONS AND METHODS FOR SURFACE ABRASION WITH FROZEN PARTICLES, naming Edward S. Boyden, Daniel B. Cook, Roderick A. Hyde, Eric C. Leuthardt, Nathan P. Myhrvold, Elizabeth A. Sweeney and Lowell L. Wood, Jr. as inventors, filed 31 Oct. 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/290,659, entitled COMPOSITIONS AND METHODS FOR SURFACE ABRASION WITH FROZEN PARTICLES, naming Edward S. Boyden, Daniel B. Cook, Roderick A. Hyde, Eric C. Leuthardt, Nathan P. Myhrvold, Elizabeth A. Sweeney and Lowell L. Wood, Jr. as inventors, filed 31 Oct. 2008, now U.S. Pat. No. 8,409,376 which is currently, or is an application of which a currently application is entitled to the benefit of the filing date.

For purposes of the USPTO extra-statutory requirements, the present application constitutes a continuation-in-part of U.S. patent application Ser. No. 12/290,658, entitled COMPOSITIONS AND METHODS FOR SURFACE ABRASION WITH FROZEN PARTICLES, naming Edward S. Boyden, Daniel B. Cook, Roderick A. Hyde, Eric C. Leuthardt, Nathan P. Myhrvold, Elizabeth A. Sweeney and Lowell L. Wood, Jr. as inventors, filed 31 Oct. 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/290,665, entitled COMPOSITIONS AND METHODS FOR SURFACE ABRASION WITH FROZEN PARTICLES, naming Edward S. Boyden, Daniel B. Cook, Roderick A. Hyde, Eric C. Leuthardt, Nathan P. Myhrvold, Elizabeth A. Sweeney and Lowell L. Wood, Jr. as inventors, filed 31 Oct. 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/290,677, entitled COMPOSITIONS AND METHODS FOR SURFACE ABRASION WITH FROZEN PARTICLES, naming Edward S. Boyden, Daniel B. Cook, Roderick A. Hyde, Eric C. Leuthardt, Nathan P. Myhrvold, Elizabeth A. Sweeney and Lowell L. Wood, Jr. as inventors, filed 31 Oct. 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/290,687, entitled COMPOSITIONS AND METHODS FOR SURFACE ABRASION WITH FROZEN PARTICLES, naming Edward S. Boyden, Daniel B. Cook, Roderick A. Hyde, Eric C. Leuthardt, Nathan P. Myhrvold, Elizabeth A. Sweeney and Lowell L. Wood, Jr. as inventors, filed 31 Oct. 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/290,676, entitled COMPOSITIONS AND METHODS FOR SURFACE ABRASION WITH FROZEN PARTICLES, naming Edward S. Boyden, Daniel B. Cook, Roderick A. Hyde, Eric C. Leuthardt, Nathan P. Myhrvold, Elizabeth A. Sweeney and Lowell L. Wood, Jr. as inventors, filed 31 Oct. 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/383,264, entitled COMPOSITIONS AND METHODS FOR DELIVERY OF FROZEN PARTICLE ADHESIVES, naming Edward S. Boyden, Daniel B. Cook, Roderick A. Hyde, Eric C. Leuthardt, Nathan P. Myhrvold, Elizabeth A. Sweeney and Lowell L. Wood, Jr. as inventors, filed 20 Mar. 2009, U.S. Pat. No. 8,545,856 which is currently, or is an application of which a currently application is entitled to the benefit of the filing date.

For purposes of the USPTO extra-statutory requirements, the present application constitutes a continuation-in-part of U.S. patent application Ser. No. 12/383,263, entitled COMPOSITIONS AND METHODS FOR DELIVERY OF FROZEN PARTICLE ADHESIVES, naming Edward S. Boyden, Daniel B. Cook, Roderick A. Hyde, Eric C. Leuthardt, Nathan P. Myhrvold, Elizabeth A. Sweeney and Lowell L. Wood, Jr. as inventors, filed 20 Mar. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/383,260, entitled COMPOSITIONS AND METHODS FOR DELIVERY OF FROZEN PARTICLE ADHESIVES, naming Edward S. Boyden, Daniel B. Cook, Roderick A. Hyde, Eric C. Leuthardt, Nathan P. Myhrvold, Elizabeth A. Sweeney and Lowell L. Wood, Jr. as inventors, filed 20 Mar. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/383,265, entitled COMPOSITIONS AND METHODS FOR DELIVERY OF FROZEN PARTICLE ADHESIVES, naming Edward S. Boyden, Daniel B. Cook, Roderick A. Hyde, Eric C. Leuthardt, Nathan P. Myhrvold, Elizabeth A. Sweeney and Lowell L. Wood, Jr. as inventors, filed 20 Mar. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/383,851, entitled COMPOSITIONS AND METHODS FOR ADMINISTERING COMPARTMENTALIZED FROZEN PARTICLES, naming Edward S. Boyden, Daniel B. Cook, Roderick A. Hyde, Eric C. Leuthardt, Nathan P. Myhrvold, Elizabeth A. Sweeney and Lowell L. Wood, Jr. as inventors, filed 27 Mar. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/383,863, entitled COMPOSITIONS AND METHODS FOR ADMINISTERING COMPARTMENTALIZED FROZEN PARTICLES, naming Edward S. Boyden, Daniel B. Cook, Roderick A. Hyde, Eric C. Leuthardt, Nathan P. Myhrvold, Elizabeth A. Sweeney and Lowell L. Wood, Jr. as inventors, filed 27 Mar. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/383,821, entitled COMPOSITIONS AND METHODS FOR ADMINISTERING COMPARTMENTALIZED FROZEN PARTICLES, naming Edward S. Boyden, Daniel B. Cook, Roderick A. Hyde, Eric C. Leuthardt, Nathan P. Myhrvold, Elizabeth A. Sweeney and Lowell L. Wood, Jr. as inventors, filed 27 Mar. 2009, U.S. Pat. No. 8,545,857 which is currently, or is an application of which a currently application is entitled to the benefit of the filing date.

For purposes of the USPTO extra-statutory requirements, the present application constitutes a continuation-inpart of U.S. patent application Ser. No. 12/383,829, entitled COMPOSITIONS AND METHODS FOR ADMINISTERING COMPARTMENTALIZED FROZEN PARTICLES, naming Edward S. Boyden, Daniel B. Cook, Roderick A. Hyde, Eric C. Leuthardt, Nathan P. Myhrvold, Elizabeth A. Sweeney and Lowell L. Wood, Jr. as inventors, filed 27 Mar. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/384,202, entitled COMPOSITIONS AND METHODS FOR BIOLOGICAL REMODELING WITH FROZEN PARTICLE COMPOSITIONS, naming Edward S. Boyden, Daniel B. Cook, Roderick A. Hyde, Eric C. Leuthardt, Nathan P. Myhrvold, Elizabeth A. Sweeney and Lowell L. Wood, Jr. as inventors, filed 31 Mar. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/384,201, entitled COMPOSITIONS AND METHODS FOR BIOLOGICAL REMODELING WITH FROZEN PARTICLE COMPOSITIONS, naming Edward S. Boyden, Daniel B. Cook, Roderick A. Hyde, Eric C. Leuthardt, Nathan P. Myhrvold, Elizabeth A. Sweeney and Lowell L. Wood, Jr. as inventors, filed 31 Mar. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/384,212, entitled COMPOSITIONS AND METHODS FOR BIOLOGICAL REMODELING WITH FROZEN PARTICLE COMPOSITIONS, naming Edward S. Boyden, Daniel B. Cook, Roderick A. Hyde, Eric C. Leuthardt, Nathan P. Myhrvold, Elizabeth A. Sweeney and Lowell L. Wood, Jr. as inventors, filed 31 Mar. 2009, U.S. Pat. No. 8,545,806 which is currently or is an application of which a currently application is entitled to the benefit of the filing date.

For purposes of the USPTO extra-statutory requirements, the present application constitutes a continuation-in-part of U.S. patent application Ser. No. 12/384,215, entitled COMPOSITIONS AND METHODS FOR BIOLOGICAL REMODELING WITH FROZEN PARTICLE COMPOSITIONS, naming Edward S. Boyden, Daniel B. Cook, Roderick A. Hyde, Eric C. Leuthardt, Nathan P. Myhrvold, Elizabeth A. Sweeney and Lowell L. Wood, Jr. as inventors, filed 31 Mar. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/384,216, entitled COMPOSITIONS AND METHODS FOR BIOLOGICAL REMODELING WITH FROZEN PARTICLE COMPOSITIONS, naming Edward S. Boyden, Daniel B. Cook, Roderick A. Hyde, Eric C. Leuthardt, Nathan P. Myhrvold, Elizabeth A. Sweeney and Lowell L. Wood, Jr. as inventors, filed 31 Mar. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/384,218, entitled COMPOSITIONS AND METHODS FOR BIOLOGICAL REMODELING WITH FROZEN PARTICLE COMPOSITIONS, naming Edward S. Boyden, Daniel B. Cook, Roderick A. Hyde, Eric C. Leuthardt, Nathan P. Myhrvold, Elizabeth A. Sweeney and Lowell L. Wood, Jr. as inventors, filed 31 Mar. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/384,214, entitled COMPOSITIONS AND METHODS FOR BIOLOGICAL REMODELING WITH FROZEN PARTICLE COMPOSITIONS, naming Edward S. Boyden, Daniel B. Cook, Roderick A. Hyde, Eric C. Leuthardt, Nathan P. Myhrvold, Elizabeth A. Sweeney and Lowell L. Wood, Jr. as inventors, filed 31 Mar. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/586,076, entitled FROZEN COMPOSITIONS AND METHODS FOR PIERCING A SUBSTRATE, naming Edward S. Boyden, Daniel B. Cook, Roderick A. Hyde, Eric C. Leuthardt, Nathan P. Myhrvold, Elizabeth A. Sweeney and Lowell L. Wood, Jr. as inventors, filed 15 Sep. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/586,074, entitled FROZEN COMPOSITIONS AND METHODS FOR PIERCING A SUBSTRATE, naming Edward S. Boyden, Daniel B. Cook, Roderick A. Hyde, Eric C. Leuthardt, Nathan P. Myhrvold, Elizabeth A. Sweeney and Lowell L. Wood, Jr. as inventors, filed 15 Sep. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/586,070, entitled FROZEN COMPOSITIONS AND METHODS FOR PIERCING A SUBSTRATE, naming Edward S. Boyden, Daniel B. Cook, Roderick A. Hyde, Eric C. Leuthardt, Nathan P. Myhrvold, Elizabeth A. Sweeney and Lowell L. Wood, Jr. as inventors, filed 15 Sep. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/586,073, entitled FROZEN COMPOSITIONS AND METHODS FOR PIERCING A SUBSTRATE, naming Edward S. Boyden, Daniel B. Cook, Roderick A. Hyde, Eric C. Leuthardt, Nathan P. Myhrvold, Elizabeth A. Sweeney and Lowell L. Wood, Jr. as inventors, filed 15 Sep. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/586,077, entitled FROZEN COMPOSITIONS AND METHODS FOR PIERCING A SUBSTRATE, naming Edward S. Boyden, Daniel B. Cook, Roderick A. Hyde, Eric C. Leuthardt, Nathan P. Myhrvold, Elizabeth A. Sweeney and Lowell L. Wood, Jr. as inventors, filed 15 Sep. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/586,075, entitled FROZEN COMPOSITIONS AND METHODS FOR PIERCING A SUBSTRATE, naming Edward S. Boyden, Daniel B. Cook, Roderick A. Hyde, Eric C. Leuthardt, Nathan P. Myhrvold, Elizabeth A. Sweeney and Lowell L. Wood, Jr. as inventors, filed 15 Sep. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/586,071, entitled FROZEN COMPOSITIONS AND METHODS FOR PIERCING A SUBSTRATE, naming Edward S. Boyden, Daniel B. Cook, Roderick A. Hyde, Eric C. Leuthardt, Nathan P. Myhrvold, Elizabeth A. Sweeney and Lowell L. Wood, Jr. as inventors, filed 15 Sep. 2009, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, *Benefit of Prior-Filed Application*, USPTO Official Gazette Mar. 18, 2003The present Applicant Entity (hereinafter "Applicant") has provided above a specific reference to the application(s)from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

SUMMARY

Compositions, methods, systems, and other embodiments related to one or more frozen particle compositions are described herein. In one embodiment, frozen particle compositions, frozen piercing implements, or frozen piercing implement devices are described.

In one embodiment, a frozen piercing implement comprising a sterile frozen implement configured for piercing at least one substrate is described. In one embodiment, a frozen piercing implement, comprises: a sterile frozen hydrogen oxide implement configured for piercing at least part of at least one substrate. In one embodiment, the sterile frozen hydrogen oxide implement includes at least one agent.

In one embodiment, a method of administering at least one frozen piercing implement to at least one substrate comprises: contacting at least one substrate with at least one frozen piercing implement. In one embodiment, the at least one frozen piercing implement includes sterile frozen hydrogen oxide. In one embodiment, a method of vaccinating a subject comprises: administering to a subject at least one frozen piercing implement. In one embodiment, the at least one frozen piercing implement includes sterile frozen hydrogen oxide and at least one vaccine. In one embodiment, a method comprises: delivering at least one agent to at least one substrate; wherein the at least one agent is included in at least one sterile frozen hydrogen oxide piercing implement. In one embodiment, a method for piercing at least one substrate comprises: piercing at least one substrate with a frozen piercing implement including sterile frozen hydrogen oxide and at least one agent.

In one embodiment, a frozen piercing implement, comprises: at least one sterile frozen solution, the solution including at least one agent; wherein the frozen piercing implement is configured for piercing at least part of at least one substrate. In one embodiment, a method of administering at least one frozen piercing implement to at least one substrate, comprises: contacting at least one substrate with at least one frozen piercing implement, wherein the at least one frozen piercing implement includes at least one sterile frozen solution, the solution including at least one agent. In one embodiment, a method of vaccinating a subject, comprises: administering to a subject at least one frozen piercing implement; wherein the at least one frozen piercing implement includes at least one sterile frozen solution, the solution including at least one vaccine.

In one embodiment, a frozen piercing implement comprises: at least one non-hydrogen oxide frozen solvent; wherein the frozen piercing implement is configured for piercing at least one substrate; and wherein the frozen piercing implement is substantially solid at approximately 65° C., approximately 60° C., approximately 55° C., approximately 50° C., approximately 45° C., approximately 40° C., approximately 37° C., approximately 35° C., approximately 30° C., approximately 25° C., approximately 20° C., approximately 15° C., approximately 10° C., approximately 5° C., approximately 0° C., approximately −5° C., approximately −10° C., approximately −15° C., approximately −20° C., approximately −25° C., approximately −30° C., approximately −40° C., approximately −50° C., approximately −60° C., approximately −70° C., approximately −80° C., approximately −90° C., approximately −100° C., approximately −120° C., approximately −150° C., approximately −170° C., approximately −200° C., approximately −250° C., or any temperature therebetween. In one embodiment, the at least one non-hydrogen oxide frozen solvent is sterile. In one embodiment, the at least one non-hydrogen oxide frozen solvent includes at least one agent In one embodiment, a frozen piercing implement, comprises: at least one frozen agent; and wherein the frozen piercing implement is configured for piercing at least one substrate wherein the frozen piercing implement is substantially solid at approximately 65° C., approximately 60° C., approximately 55° C., approximately 50° C., approximately 45° C., approximately 40° C., approximately 37° C., approximately 35° C., approximately 30° C., approximately 25° C., approximately 20° C., approximately 15° C., approximately 10° C., approximately 5° C., approximately 0° C., approximately −5° C., approximately −10° C., approximately −15° C., approximately −20° C., approximately −25° C., approximately −30° C., approximately −40° C., approximately −50° C., approximately −60° C., approximately −70° C., approximately −80° C., approximately −90° C., approximately −100° C., approximately −120° C., approximately −150° C., approximately −170° C., approximately −200° C., approximately −250° C., or any temperature therebetween.

In one embodiment, a method of administering at least one frozen piercing implement to at least one substrate, comprises: contacting at least one substrate with at least one frozen piercing implement, wherein the at least one frozen piercing implement includes at least one non-hydrogen oxide frozen solvent; and wherein the at least one frozen piercing implement is substantially solid at approximately 65° C., approximately 60° C., approximately 55° C., approximately 50° C., approximately 45° C., approximately 40° C., approximately 37° C., approximately 35° C., approximately 30° C., approximately 25° C., approximately 20° C., approximately 15° C., approximately 10° C., approximately 5° C., approximately 0° C., approximately −5° C., approximately −10° C., approximately −15° C., approximately −20° C., approximately −25° C., approximately −30° C., approximately −40° C., approximately −50° C., approximately −60° C., approximately −70° C., approximately −80° C., approximately −90° C., approximately −100° C., approximately −120° C., approximately −150° C., approximately −170° C., approximately −200° C., approximately −250° C., or any temperature therebetween. In one embodiment, the at least one non-hydrogen oxide frozen solvent is sterile. In one embodiment, the at least one non-hydrogen oxide frozen solvent includes at least one agent.

In one embodiment, a method of administering at least one frozen piercing implement to at least one substrate, comprises:contacting at least one substrate with at least one frozen piercing implement, wherein the at least one frozen piercing implement includes at least one agent; and wherein the at least one frozen piercing implement is substantially solid at approximately 65° C., approximately 60° C., approximately 55° C., approximately 50° C., approximately 45° C., approximately 40° C., approximately 37° C., approximately 35° C., approximately 30° C., approximately 25° C., approximately 20° C., approximately 15° C., approximately 10° C., approximately 5° C., approximately 0° C., approximately −5° C., approximately −10° C., approximately −15° C., approximately −20° C., approximately −25° C., approximately −30° C., approximately −40° C., approximately −50° C., approximately −60° C., approximately −70° C., approximately −80° C., approximately −90° C., approximately −100° C., approximately −120° C., approximately −150° C., approximately −170° C., approximately −200° C., approximately −250° C., or any temperature therebetween.

In one embodiment, a method of vaccinating a subject, comprises: administering to a subject at least one frozen piercing implement; wherein the at least one frozen piercing implement includes at least one non-hydrogen oxide frozen solvent and at least one vaccine; and wherein the at least one frozen piercing implement is substantially solid at approximately 65° C., approximately 60° C., approximately 55° C., approximately 50° C., approximately 45° C., approximately 40° C., approximately 37° C., approximately 35° C., approximately 30° C., approximately 25° C., approximately 20° C., approximately 15° C., approximately 10° C., approximately 5° C., approximately 0° C., approximately −5° C., approximately −10° C., approximately −15° C., approximately −20° C., approximately −25° C., approximately −30° C., approximately −40° C., approximately −50° C., approximately −60° C., approximately −70° C., approximately −80° C., approximately −90° C., approximately −100° C., approximately −120° C., approximately −150° C., approximately −170° C., approximately −200° C., approximately −250° C., or any temperature therebetween. In one embodiment, a method of vaccinating a subject, comprises: administering to a subject at least one frozen vaccine piercing implement; wherein the at least one frozen piercing implement is substantially solid at approximately 65° C., approximately 60° C., approximately 55° C., approximately 50° C., approximately 45° C., approximately 40° C., approximately 37° C., approximately 35° C., approximately 30° C., approximately 25° C., approximately 20° C., approximately 15° C., approximately 10° C., approximately 5° C., approximately 0° C., approximately −5° C., approximately −10° C., approximately −15° C., approximately −20° C., approximately −25° C., approximately −30° C., approximately −40° C., approximately −50° C., approximately −60° C., approximately −70° C., approximately −80° C., approximately −90° C., approximately −100° C., approximately −120° C., approximately −150° C., approximately −170° C., approximately −200° C., approximately −250° C., or any temperature therebetween. In one embodiment, the at least one frozen piercing implement is sterile. In one embodiment, the at least one frozen piercing implement includes at least one agent.

In one embodiment, a frozen piercing implement, comprises: at least one sterile frozen component and at least one agent; wherein the at least one component is substantially in a gaseous state at or above approximately 0.25 bar, approximately 0.5 bar, approximately 1.0 bar, approximately 5.0 bar, approximately 10.0 bar, approximately 25 bar, approximately 50 bar, approximately 100 bar, approximately 200 bar, or approximately 500 bar pressure; and at or above approximately 10° C., approximately 15° C., approximately 20° C., approximately 25° C., approximately 30° C., approximately 37° C., approximately 40° C., approximately 45° C., or approximately 50° C.; and wherein the at least one frozen piercing implement is configured for piercing at least one substrate.

In one embodiment, a method of administering at least one frozen piercing implement to at least one substrate, comprises: contacting at least one substrate with at least one frozen piercing implement, wherein the at least one frozen piercing implement includes at least one sterile frozen component and at least one agent; wherein the at least one sterile frozen component is in a gaseous state at approximately 0.25 bar, approximately 0.5 bar, approximately 1.0 bar, approximately 5.0 bar, approximately 10.0 bar, approximately 25 bar, approximately 50 bar, approximately 100 bar, approximately 200 bar, or approximately 500 bar pressure; and at or above approximately 10° C., approximately 15° C., approximately 20° C., approximately 25° C., approximately 30° C., approximately 37° C., approximately 40° C., approximately 45° C., or approximately 50° C.; and wherein the at least one frozen piercing implement is configured for piercing the at least one substrate.

In one embodiment, a method of vaccinating a subject, comprises: administering to a subject at least one frozen piercing implement; wherein the at least one frozen piercing implement includes at least one sterile frozen component and at least one agent; and wherein the at least one sterile frozen component is in a gaseous state at approximately 0.25 bar, approximately 0.5 bar, approximately 1.0 bar, approximately 5.0 bar, approximately 10.0 bar, approximately 25 bar, approximately 50 bar, approximately 100 bar, approximately 200 bar, or approximately 500 bar pressure; and at or above approximately 10° C., approximately 15° C., approximately 20° C., approximately 25° C., approximately 30° C., approximately 37° C., approximately 40° C., approximately 45° C., or approximately 50° C.; and wherein the at least one frozen piercing implement is configured for piercing at least one substrate.

In one embodiment, an array device comprises: a support structure having a surface; and a plurality of sterile frozen piercing implements extending substantially outward from the support structure. In one embodiment, an array device, comprises: a support structure having a surface; a plurality of piercing implements extending substantially outward from the surface of the support structure; wherein at least one piercing implement of the plurality of piercing implements includes a frozen piercing implement. In one embodiment, a composition, comprises: a plurality of piercing implement array devices joined together, the piercing implement array devices including at least one frozen piercing implement. In one embodiment, a composition, comprises: a support means for an array device; wherein the array device includes one or more frozen piercing implements. In one embodiment, a method of administering at least one array device to at least one substrate, comprises: contacting at least one array device to at least one substrate, wherein the array device includes at least one frozen piercing implement.

In one embodiment, a method of vaccinating a subject, comprises: administering to a subject at least one frozen piercing implement array device; wherein the at least one frozen piercing implement array device includes at least one frozen piercing implement including at least one vaccine.

In one embodiment, a fluidic device, comprises: a support structure at least partially defining at least one compartment; and at least one frozen piercing implement in fluid communication with the at least one compartment. As described herein, in one embodiment, the at least one frozen piercing implement has at least one major dimension of approximately one centimeter or less, approximately one millimeter or less, approximately one micrometer or less, approximately one nanometer, or any value therebetween.

In one embodiment, a fluidic device, comprises: at least one frozen piercing implement, and at least one actuator configured to actuate the at least one frozen piercing implement. As described herein, in one embodiment, at least one frozen piercing implement has at least one major dimension of approximately one centimeter or less, approximately one millimeter or less, approximately one micrometer or less, approximately one nanometer, or any value therebetween.

In one embodiment, the fluidic device further comprises a plurality of frozen piercing implements, and at least one actuator configured to actuate the plurality of frozen piercing implements; wherein each piercing implement has at least one major dimension of approximately one centimeter or less, approximately one millimeter or less, approximately one micrometer or less, approximately one nanometer, or any value therebetween.

Various computer-implemented methods, automated devices, systems, computer program products, and circuitry for any thereof are provided herein. In one embodiment, instructions for making at least one frozen particle composition, frozen piercing implement, or frozen piercing implement device are provided for various non-limiting examples. In one embodiment, instructions for administering at least one frozen particle composition, frozen piercing implement, or frozen piercing implement device are provided for various non-limiting examples.

The various embodiments disclosed are described in greater detail herein.

BRIEF DESCRIPTION OF THE FIGURES

FIG. 7 illustrates a partial view of a method 700 that includes generating at least one response.

FIG. 9 illustrates a partial view of FIG. 7 in which embodiments may be implemented.

FIG. 10 illustrates a partial view of a method 1000 that includes generating at least one response.

FIG. 13 illustrates a partial view of a system 1300 that includes a computer program for executing a computing process on a computing device.

FIG. 15 illustrates a partial view of FIG. 13 in which embodiments may be implemented.

FIG. 16 illustrates a partial view of a system 1600 that includes a computer program for executing a computing process on a computing device.

FIG. 17 illustrates a partial view of a computer program product 1700 for executing a computing process on a computing device.

FIG. 19 illustrates a partial view of a computer program product 1900 for executing a computing process on a computing device.

FIG. 20 illustrates a partial view of a computer program product 2000 for executing a computing process on a computing device.

FIG. 23 illustrates a partial view of a method 2300 that includes generating at least one response.

FIG. 26 illustrates a partial view of a method 2600 that includes generating at least one response.

FIG. 28 illustrates a partial view of FIG. 26 in which embodiments may be implemented.

FIG. 29 illustrates a partial view of a system 2900 that includes a computer program for executing a computing process on a computing device.

FIG. 30 illustrates a partial view of FIG. 29 in which embodiments may be implemented.

FIG. 33 illustrates a partial view of a system 3300 that includes a computer program for executing a computing process on a computing device.

FIG. 35 illustrates a partial view of FIG. 33 in which embodiments may be implemented.

FIG. 36 illustrates a partial view of a system 3600 that includes a computer program for executing a computing process on a computing device.

FIG. 37 illustrates a partial view of a method 3700 in which embodiments may be implemented.

FIG. 38 illustrates a partial view of FIG. 37 in which embodiments may be implemented.

FIG. 39 illustrates a partial view of FIG. 37 in which embodiments may be implemented.

FIG. 40 illustrates a partial view of FIG. 37 in which embodiments may be implemented.

FIG. 41 illustrates a partial view of FIG. 37 in which embodiments may be implemented.

FIG. 43 illustrates a partial view of FIG. 37 in which embodiments may be implemented.

FIG. 44 illustrates a partial view of FIG. 37 in which embodiments may be implemented.

FIG. 46 illustrates a partial view of FIG. 37 in which embodiments may be implemented.

FIG. 47 illustrates a partial view of FIG. 37 in which embodiments may be implemented.

FIG. 48 illustrates a partial view of FIG. 37 in which embodiments may be implemented.

FIG. 49 illustrates a partial view of a method 4900 in which embodiments may be implemented.

FIG. 50 illustrates a partial view of FIG. 49 in which embodiments may be implemented.

FIG. 51 illustrates a partial view of FIG. 49 in which embodiments may be implemented.

FIG. 52 illustrates a partial view of FIG. 49 in which embodiments may be implemented.

FIG. 53 illustrates a partial view of FIG. 49 in which embodiments may be implemented.

FIG. 54 illustrates a partial view of a method 5400 in which embodiments may be implemented.

FIG. 55 illustrates a partial view of FIG. 54 in which embodiments may be implemented.

FIG. 56 illustrates a partial view of FIG. 54 in which embodiments may be implemented.

FIG. 57 illustrates a partial view of FIG. 54 in which embodiments may be implemented.

FIG. 58 illustrates a partial view of FIG. 54 in which embodiments may be implemented.

FIG. 59 illustrates a partial view of a method 5900 in which embodiments may be implemented.

FIG. 60 illustrates a partial view of a method 6000 in which embodiments may be implemented.

FIG. 61 illustrates a partial view of FIG. 60 in which embodiments may be implemented.

FIG. 62 illustrates a partial view of FIG. 60 in which embodiments may be implemented.

FIG. 63 illustrates a partial view of FIG. 60 in which embodiments may be implemented.

FIG. 64 illustrates a partial view of FIG. 60 in which embodiments may be implemented.

FIG. 65 illustrates a partial view of FIG. 60 in which embodiments may be implemented.

FIG. 66 illustrates a partial view of a method 6600 in which embodiments may be implemented.

FIG. 67 illustrates a partial view of FIG. 66 in which embodiments may be implemented.

FIG. 68 illustrates a partial view of FIG. 66 in which embodiments may be implemented.

FIG. 69 illustrates a partial view of FIG. 66 in which embodiments may be implemented.

FIG. 70 illustrates a partial view of FIG. 66 in which embodiments may be implemented.

FIG. 71 illustrates a partial view of FIG. 66 in which embodiments may be implemented.

FIG. 72 illustrates a partial view of FIG. 66 in which embodiments may be implemented.

FIG. 74 illustrates a partial view of FIG. 73 in which embodiments may be implemented.

FIG. 76 illustrates a partial view of FIG. 75 in which embodiments may be implemented.

FIG. 80 illustrates a partial view of a system 8000 in which embodiments may be implemented.

FIG. 82 illustrates a partial view of a system 8200 in which embodiments may be implemented.

FIG. 83 illustrates a partial view of FIG. 82 in which embodiments may be implemented.

FIG. 84 illustrates a partial view of FIG. 82 in which embodiments may be implemented.

FIG. 85 illustrates a partial view of FIG. 82 in which embodiments may be implemented.

FIG. 86 illustrates a partial view of FIG. 82 in which embodiments may be implemented.

FIG. 87 illustrates a partial view of FIG. 82 in which embodiments may be implemented.

FIG. 88 illustrates a partial view of FIG. 82 in which embodiments may be implemented.

FIG. 91 illustrates a partial view of FIG. 82 in which embodiments may be implemented.

FIG. 92 illustrates a partial view of FIG. 82 in which embodiments may be implemented.

FIG. 93 illustrates a partial view of FIG. 82 in which embodiments may be implemented.

FIG. 94 illustrates a partial view of a system 9400 in which embodiments may be implemented.

FIG. 95 illustrates a partial view of FIG. 94 in which embodiments may be implemented.

FIG. 97 illustrates a partial view of FIG. 94 in which embodiments may be implemented.

FIG. 98 illustrates a partial view of FIG. 94 in which embodiments may be implemented.

FIG. 99 illustrates a partial view of a system 9900 in which embodiments may be implemented.

FIG. 100 illustrates a partial view of FIG. 99 in which embodiments may be implemented.

FIG. 101 illustrates a partial view of FIG. 99 in which embodiments may be implemented.

FIG. 102 illustrates a partial view of FIG. 99 in which embodiments may be implemented.

FIG. 103 illustrates a partial view of FIG. 99 in which embodiments may be implemented.

FIG. 104 illustrates a partial view of a system 10400 in which embodiments may be implemented.

FIG. 105 illustrates a partial view of FIG. 104 in which embodiments may be implemented.

FIG. 106 illustrates a partial view of FIG. 104 in which embodiments may be implemented.

FIG. 107 illustrates a partial view of FIG. 104 in which embodiments may be implemented.

FIG. 108 illustrates a partial view of FIG. 104 in which embodiments may be implemented.

FIG. 110 illustrates a partial view of FIG. 104 in which embodiments may be implemented.

FIG. 111 illustrates a partial view of a system 11100 in which embodiments may be implemented.

FIG. 112 illustrates a partial view of FIG. 111 in which embodiments may be implemented.

FIG. 113 illustrates a partial view of FIG. 111 in which embodiments may be implemented.

FIG. 114 illustrates a partial view of FIG. 111 in which embodiments may be implemented.

FIG. 115 illustrates a partial view of FIG. 111 in which embodiments may be implemented.

FIG. 116 illustrates a partial view of FIG. 111 in which embodiments may be implemented.

FIG. 117 illustrates a partial view of FIG. 111 in which embodiments may be implemented.

FIG. 120 illustrates the boiling liquid expansion vapor explosion diagram for carbon dioxide, calculated using the critical point and sinodal curve.

FIG. 121A illustrates particular examples of optional configurations of embodiments including at least one frozen particle composition or frozen piercing implement.

FIG. 121B illustrates particular examples for configurations of embodiments including at least one frozen particle composition or frozen piercing implement with optional at least one cavity.

FIG. 121C illustrates particular examples of optional configurations of embodiments including at least one frozen particle composition or frozen piercing implement.

FIG. 122 illustrates a diagram for a particular force per implement for amount of displacement.

FIG. 123 illustrates perspective views of particular examples of optional configurations of embodiments including at least one frozen particle composition, frozen piercing implement, or frozen piercing implement device.

FIG. 124A illustrates an example of an embodiment including at least one frozen piercing implement or frozen piercing implement device.

FIG. 124B illustrates an example of one embodiment for making at least one frozen particle composition, frozen piercing implement or frozen piercing implement device.

FIG. 124C illustrates an example of one embodiment for making at least one frozen particle composition, frozen piercing implement or frozen piercing implement device.

FIG. 124D illustrates an example of one embodiment for making at least one frozen particle composition, frozen piercing implement or frozen piercing implement device.

FIG. 124E illustrates an example of one embodiment for making at least one frozen particle composition, frozen piercing implement or frozen piercing implement device.

FIG. 124F illustrates an example of one embodiment for making at least one frozen particle composition, frozen piercing implement or frozen piercing implement device.

Figure 1:
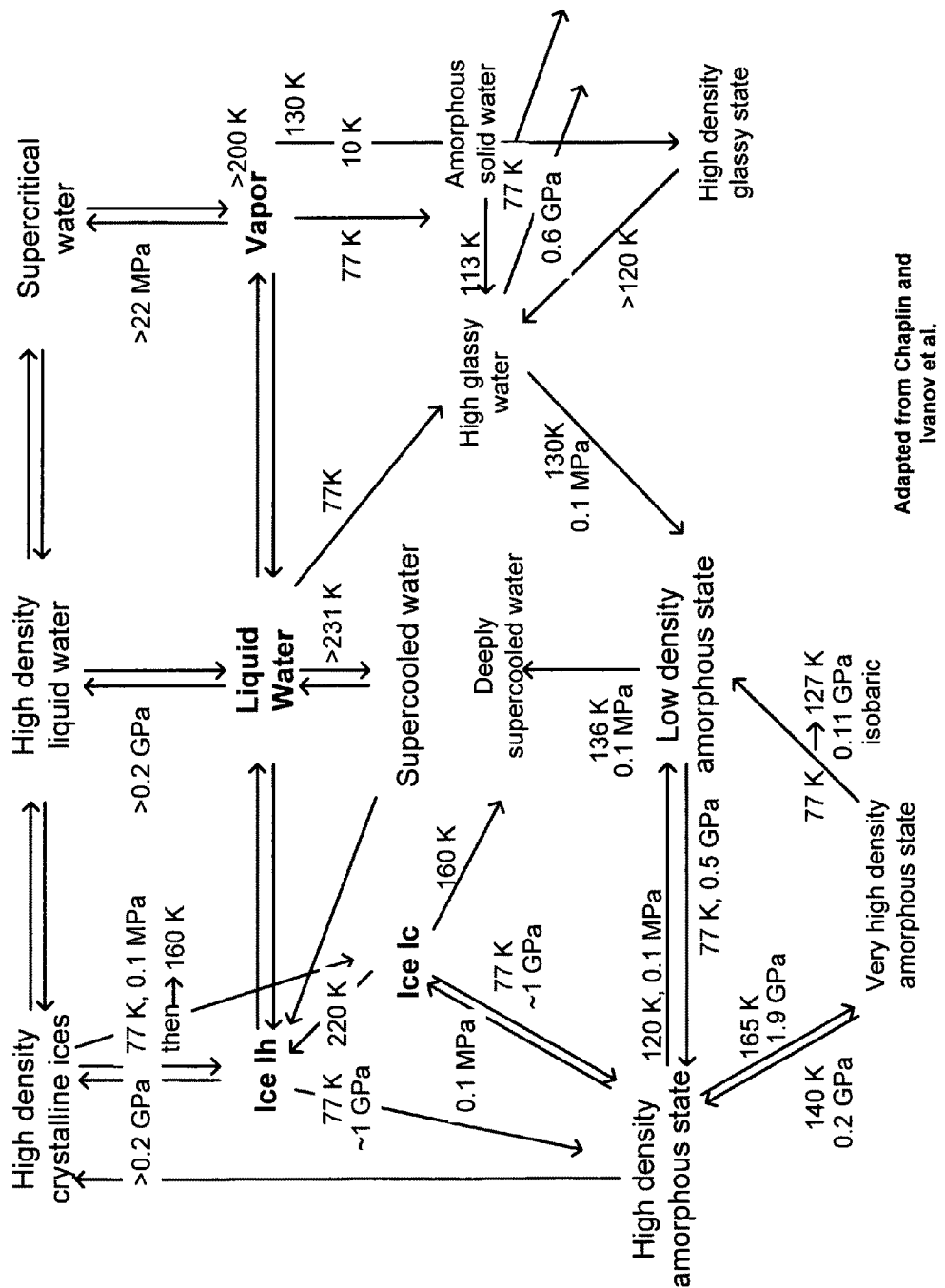
FIG. 1 illustrates particular phases of hydrogen oxide.

FIG. 124G illustrates an example of one embodiment for making at least one frozen particle composition, frozen piercing implement or frozen piercing implement device.

FIG. 125A illustrates cross-sectional view of a piercing implement including one or more functionalized surfaces, and optional channel, according to some illustrated embodiments.

FIG. 125B illustrates cross-sectional view of a piercing implement including one or more functionalized surfaces, and optional channel, according to some illustrated embodiments.

FIG. 125C illustrates cross-sectional view of a piercing implement including one or more functionalized surfaces, and optional channel, according to some illustrated embodiments.

FIG. 125D illustrates an exploded view of the implement illustrated in FIG. 125C, including one or more functional groups in the form of bonded amino groups, according to some illustrated embodiments.

FIG. 125E illustrates an exploded view of an implement, including one or more functional groups in the form of polisilane groups, according to some illustrated embodiments.

FIG. 126A illustrates a cross-sectional view of a plurality of implements, according to some illustrated embodiments.

FIG. 126B illustrates a cross-sectional view of a plurality of implements, according to some illustrated embodiments.

FIG. 126C illustrates a cross-sectional view of a plurality of implements, according to some illustrated embodiments.

FIG. 126D illustrates a cross-sectional view of a plurality of implements, according to some illustrated embodiments.

FIG. 126E illustrates a cross-sectional view of a plurality of implements, according to some illustrated embodiments.

FIG. 126F illustrates a cross-sectional view of a plurality of implements, according to some illustrated embodiments.

FIG. 126G illustrates a cross-sectional view of a plurality of implements, according to some illustrated embodiments.

FIG. 127A illustrates a cross-sectional view of an embodiment including at least one frozen piercing implement device.

FIG. 127B illustrates a perspective view of an embodiment including at least one frozen piercing implement device.

FIG. 128A illustrates a cross-sectional view of an embodiment including at least one frozen piercing implement.

FIG. 128B illustrates a perspective view of a plurality of frozen piercing implements, according to an illustrated embodiment.

FIG. 128C illustrates a perspective view of an embodiment of at least one frozen piercing implement device.

FIG. 128D illustrates a perspective view of an embodiment of at least one frozen piercing implement device.

FIG. 129A illustrates a cross-sectional view of an embodiment of at least one frozen piercing implement.

FIG. 129B illustrates a cross-sectional view of an embodiment of at least one frozen piercing implement.

FIG. 130A illustrates a cross-sectional view of an embodiment of at least one frozen piercing implement device.

FIG. 130B illustrates a cross-sectional view of an embodiment of at least one frozen piercing implement device.

FIG. 131A illustrates a perspective view of an embodiment including a plurality of frozen piercing implements, including at least one frozen piercing implement device.

FIG. 131B illustrates a perspective view of an embodiment including a plurality of frozen piercing implements, including at least one frozen piercing implement device.

FIG. 131C illustrates a perspective view of an embodiment including a plurality of frozen piercing implements, including at least one frozen piercing implement device.

FIG. 131D illustrates a perspective view of an embodiment including a plurality of frozen piercing implements, including at least one frozen piercing implement device.

FIG. 131E illustrates a perspective view of an embodiment including a plurality of frozen piercing implements, including at least one frozen piercing implement device.

FIG. 131F illustrates a perspective view of an embodiment including a plurality of frozen piercing implements, including at least one frozen piercing implement device.

FIG. 131G illustrates a perspective view of an embodiment including a plurality of frozen piercing implements, including at least one frozen piercing implement device.

FIG. 131H illustrates a perspective view of an embodiment including at least one frozen piercing implement device, optionally including a plurality of frozen piercing implements.

Figure 132:
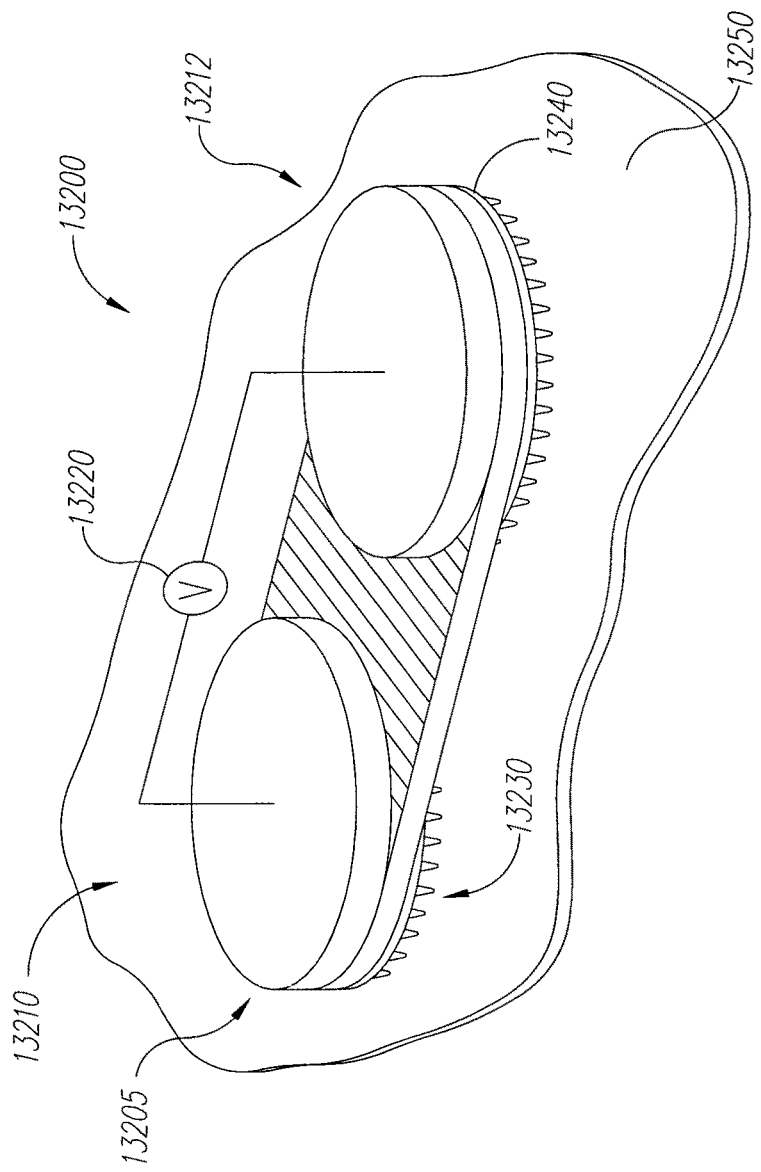

FIG. 132 illustrates a perspective view of an embodiment including at least one frozen piercing implement device, optionally including a plurality of frozen piercing implements.

FIG. 133A illustrates a cross-sectional view of an embodiment including at least one frozen piercing implement device, optionally including a plurality of frozen piercing implements.

FIG. 133B illustrates a cross-sectional view of an embodiment including at least one frozen piercing implement device, optionally including a plurality of frozen piercing implements.

FIG. 134A illustrates a cross-sectional view of an embodiment including at least one frozen piercing implement device, optionally including a plurality of frozen piercing implements.

FIG. 134B illustrates a cross-sectional view of an embodiment including at least one frozen piercing implement device, optionally including a plurality of frozen piercing implements.

FIG. 135 illustrates a partial view of a method 13500, in which embodiments may be implemented.

FIG. 136 illustrates a parital view of the method of FIG. 135, in which embodiments may be implemented.

FIG. 137 illustrates a partial view of the method of FIG. 135, in which embodiments may be implemented.

FIG. 138 illustrates a partial view of the method of FIG. 135, in which embodiments may be implemented.

FIG. 139 illustrates a partial view of the method of FIG. 135, in which embodiments may be implemented.

FIG. 140A-C illustrates a cross-sectional view of an example of an embodiment of a frozen piercing implement device.

FIG. 141 illustrates a partial view of a method 14100, in which embodiments may be implemented.

FIG. 142 illustrates a partial view of the method of FIG. 141, in which embodiments may be implemented.

FIG. 143 illustrates a partial view of the method of FIG. 141, in which embodiments may be implemented.

FIG. 144 illustrates a partial view of the method of FIG. 141, in which embodiments may be implemented.

FIG. 145 illustrates a partial view of the method of FIG. 141, in which embodiments may be implemented.

FIG. 146 illustrates a partial view of the method of FIG. 141, in which embodiments may be implemented.

FIG. 147 illustrates a partial view of the method of FIG. 141, in which embodiments may be implemented.

FIG. 148 illustrates a partial view of a method 14800, in which embodiments may be implemented.

FIG. 149 illustrates a partial view of the method of FIG. 148, in which embodiments may be implemented.

FIG. 150 illustrates a partial view of the method of FIG. 148, in which embodiments may be implemented.

FIG. 151 illustrates a partial view of a method 15100, in which embodiments may be implemented.

FIG. 152 illustrates a partial view of the method of FIG. 151, in which embodiments may be implemented.

FIG. 153 illustrates a partial view of the method of FIG. 151, in which embodiments may be implemented.

FIG. 154 illustrates a partial view of the method of FIG. 151, in which embodiments may be implemented.

FIG. 155 illustrates a partial view of the method of FIG. 151, in which embodiments may be implemented.

FIG. 156 illustrates a partial view of the method of FIG. 151, in which embodiments may be implemented.

Figure 157:
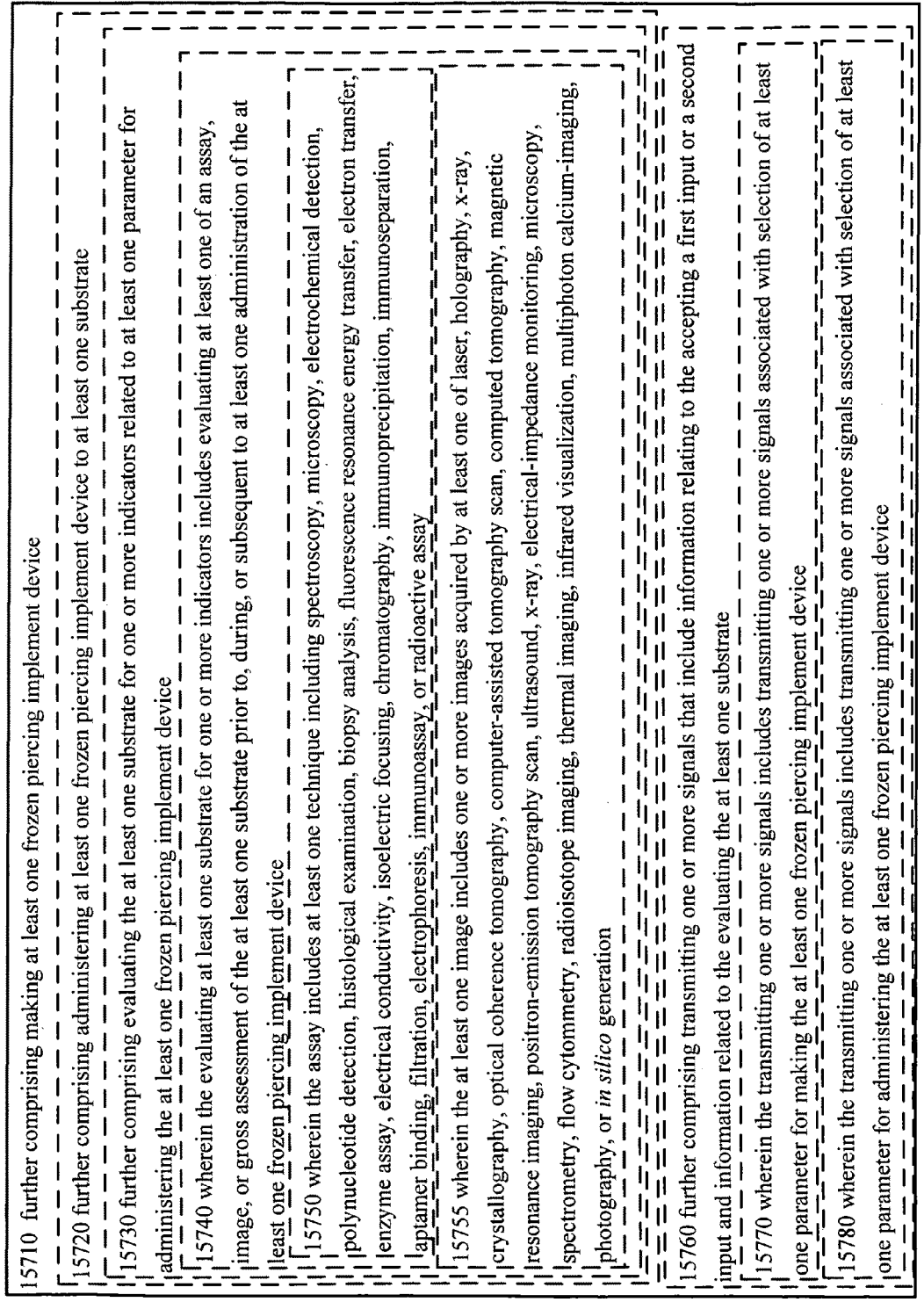

FIG. 157 illustrates a partial view of the method of FIG. 151, in which embodiments may be implemented.

FIG. 158 illustrates a partial view of a method 15800, in which embodiments may be implemented.

FIG. 159 illustrates a partial view of the method of FIG. 158, in which embodiments may be implemented.

FIG. 160 illustrates a partial view of the method of FIG. 158, in which embodiments may be implemented.

FIG. 161 illustrates a partial view of the method of FIG. 158, in which embodiments may be implemented.

FIG. 162 illustrates a partial view of a method 16200, in which embodiments may be implemented.

FIG. 163 illustrates a partial view of a system 16300, in which embodiments may be implemented.

FIG. 164 illustrates partial view of the system of FIG. 163, in which embodiments may be implemented.

FIG. 165 illustrates a partial view of the system of FIG. 163, in which embodiments may be implemented.

FIG. 166 illustrates a partial view of the system of FIG. 163, in which embodiments may be implemented.

FIG. 167 illustrates a partial view of a system 16700, in which embodiments may be implemented.

FIG. 168 illustrates a partial view of the system of FIG. 167, in which embodiments may be implemented.

FIG. 169 illustrates a partial view of the system of FIG. 167, in which embodiments may be implemented.

FIG. 170 illustrates a partial view of the system of FIG. 167, in which embodiments may be implemented.

FIG. 171 illustrates a partial view of the system of FIG. 167, in which embodiments may be implemented.

FIG. 172 illustrates a partial view of the system of FIG. 167, in which embodiments may be implemented.

FIG. 173 illustrates a partial view of the system of FIG. 167, in which embodiments may be implemented.

FIG. 174 illustrates a partial view of the system of FIG. 167, in which embodiments may be implemented.

FIG. 175 illustrates a partial view of a system 17500, in which embodiments may be implemented.

FIG. 176 illustrates a partial view of the system of FIG. 175, in which embodiments may be implemented.

FIG. 177 illustrates a partial view of the system of FIG. 175, in which embodiments may be implemented.

FIG. 178 illustrates a partial view of the system of FIG. 175, in which embodiments may be implemented.

FIG. 179 illustrates a partial view of the system of FIG. 175, in which embodiments may be implemented.

FIG. 180 illustrates a partial view of the system of FIG. 175, in which embodiments may be implemented.

FIG. 181 illustrates a partial view of the system FIG. 175, in which embodiments may be implemented.

FIG. 182 illustrates a partial view of a system 18200, in which embodiments may be implemented.

FIG. 183 illustrates a partial view of the system of FIG. 182, in which embodiments may be implemented.

FIG. 184 illustrates a partial view of the system of FIG. 182, in which embodiments may be implemented.

FIG. 185 illustrates a partial view of the system of FIG. 182, in which embodiments may be implemented.

FIG. 186 illustrates a partial view of a system 18600, in which embodiments may be implemented.

FIG. 187 illustrates a partial view of the system of FIG. 186, in which embodiments may be implemented.

Figure 188:
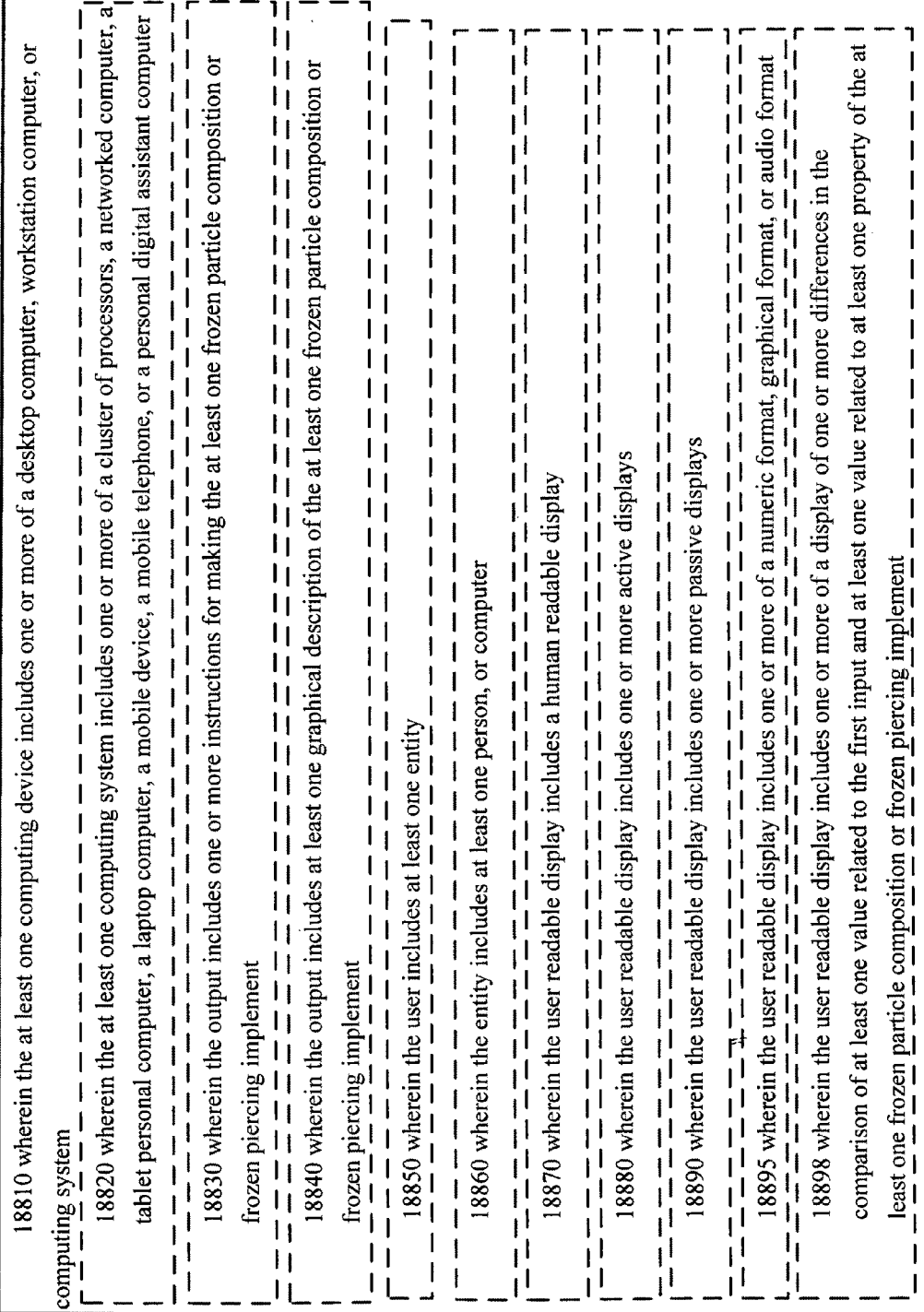

FIG. 188 illustrates a partial view of the system of FIG. 186, in which embodiments may be implemented.

FIG. 189 illustrates a partial view of the system of FIG. 186, in which embodiments may be implemented.

FIG. 190 illustrates a partial view of a system 19000, in which embodiments may be implemented.

FIG. 191 illustrates a partial view of the system of FIG. 190, in which embodiments may be implemented.

FIG. 192 illustrates a partial view of the system of FIG. 190, in which embodiments may be implemented.

FIG. 193 illustrates a partial view of a computer program product 19300, in which embodiments may be implemented.

FIG. 194 illustrates a partial view of the computer program product of FIG. 193, in which embodiments may be implemented.

FIG. 195 illustrates a partial view of the computer program product of FIG. 193, in which embodiments may be implemented.

FIG. 196 illustrates a partial view of a system 19600, in which embodiments may be implemented.

FIG. 197 illustrates a partial view of the system of FIG. 196, in which embodiments may be implemented.

FIG. 198 illustrates a partial view of the system of FIG. 196, in which embodiments may be implemented.

FIG. 199 illustrates a partial view of a system 19900, in which embodiments may be implemented.

FIG. 200 illustrates a partial view of the system of FIG. 199, in which embodiments may be implemented.

FIG. 201 illustrates a partial view of a system 20100, in which embodiments may be implemented.

FIG. 202 illustrates a partial view of the system of FIG. 201, in which embodiments may be implemented.

FIG. 203 illustrates a partial view of the system of FIG. 201, in which embodiments may be implemented.

FIG. 204 illustrates a partial view of the system of FIG. 201, in which embodiments may be implemented.

FIG. 205 illustrates a partial view of a system 20500, in which embodiments may be implemented.

FIG. 206 illustrates a partial view of the system of FIG. 205, in which embodiments may be implemented.

FIG. 207 illustrates a partial view of the system of FIG. 205, in which embodiments may be implemented.

Figure 208:
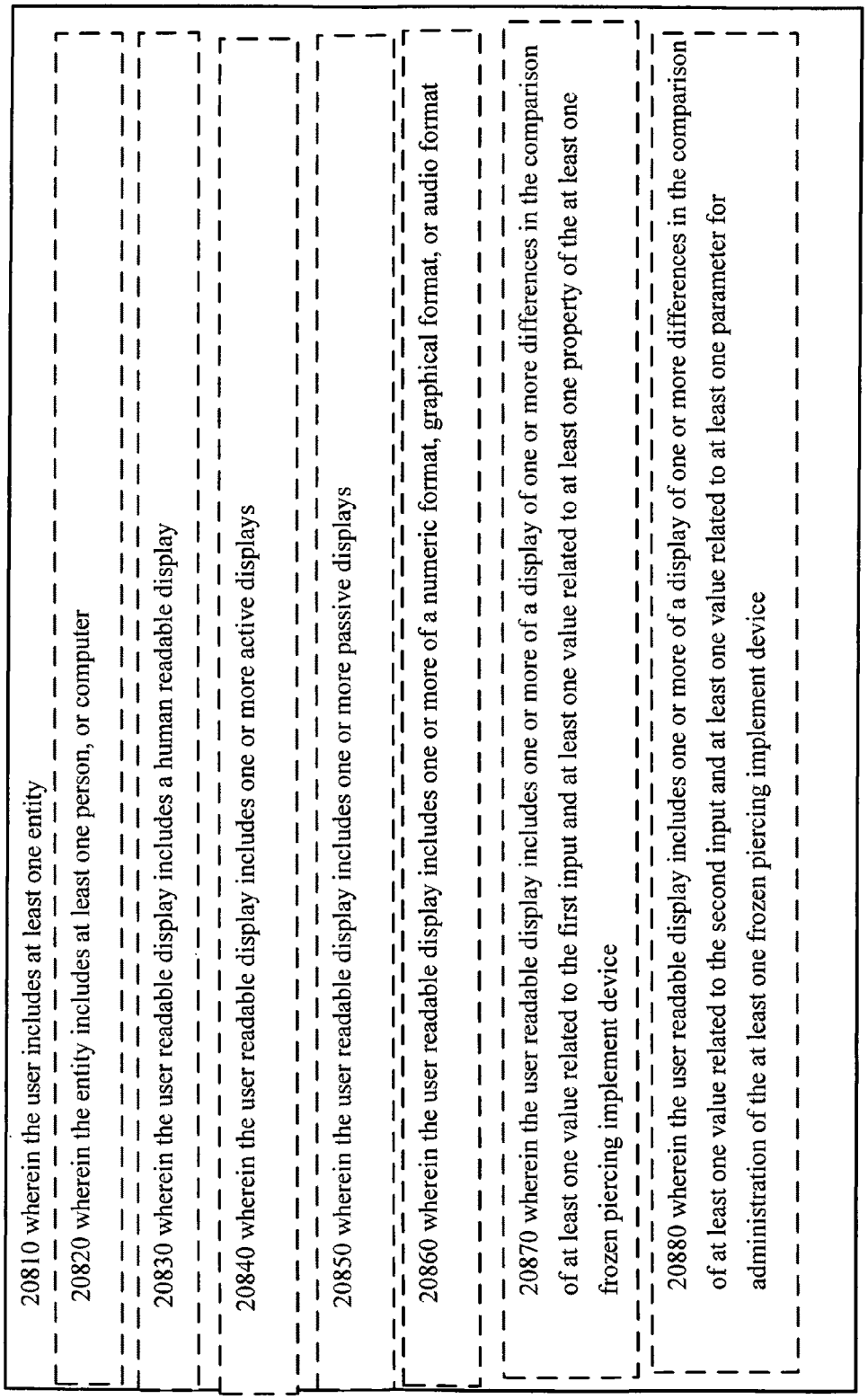

FIG. 208 illustrates a partial view of the system of FIG. 205, in which embodiments may be implemented.

FIG. 209 illustrates a partial view of a computer program product 20900, in which embodiments may be implemented.

FIG. 210 illustrates a partial view of the computer program product of FIG. 209, in which embodiments may be implemented.

FIG. 211 illustrates a partial view of the computer program product of FIG. 209, in which embodiments may be implemented.

FIG. 212 illustrates a partial view of a system 21200, in which embodiments may be implemented.

FIG. 213 illustrates a partial view of the system of FIG. 212, in which embodiments may be implemented.

FIG. 214 illustrates a partial view of the system of FIG. 212, in which embodiments may be implemented.

FIG. 215 illustrates a partial view of a system 21500, in which embodiments may be implemented.

Figure 216:
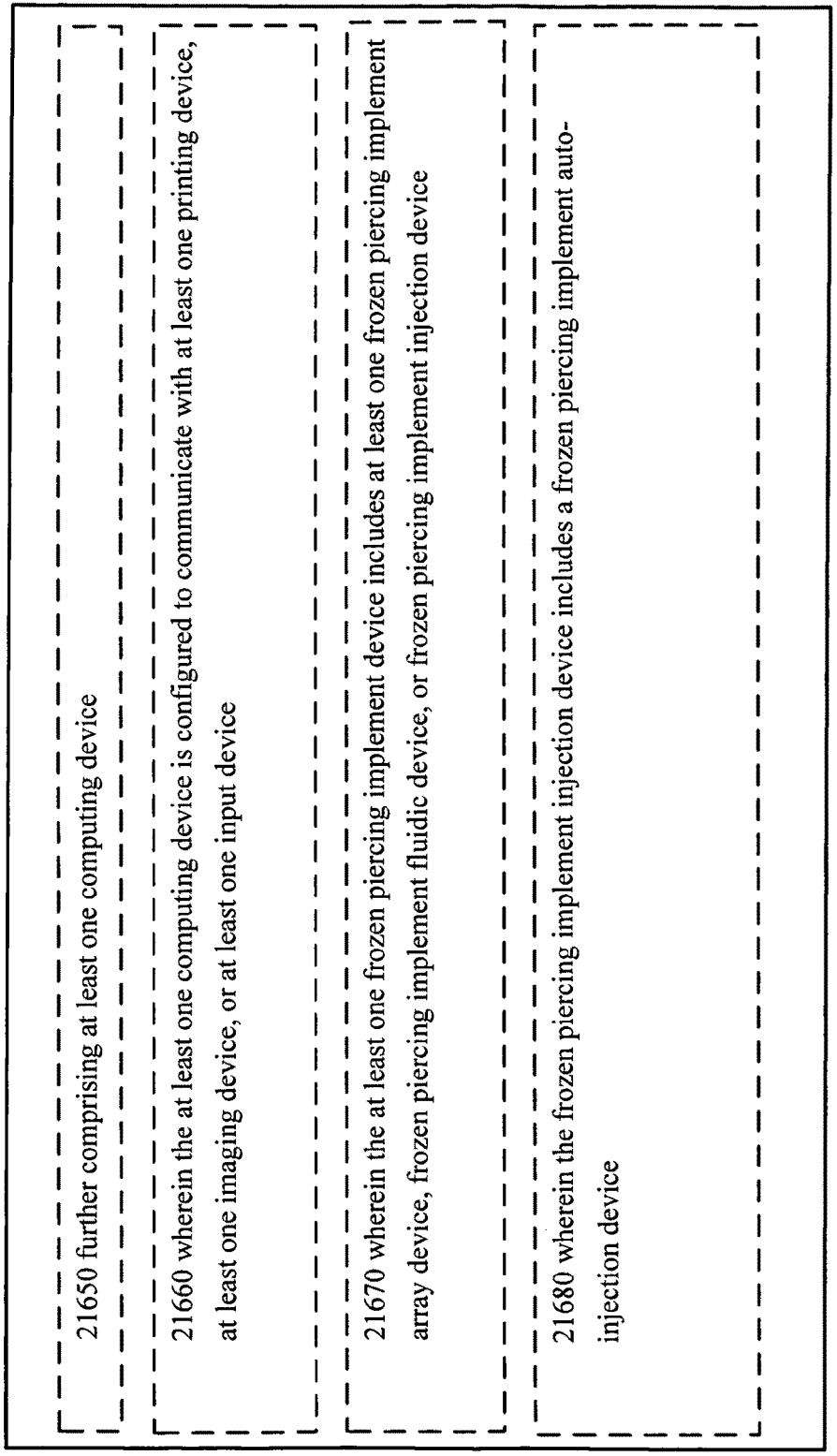

FIG. 216 illustrates a partial view of the system of FIG. 215, in which embodiments may be implemented.

FIG. 217 illustrates a partial view of the system of FIG. 215, in which embodiments may be implemented.

FIG. 218 illustrates a partial view of the system of FIG. 215, in which embodiments may be implemented.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments can be utilized, and other changes can be made, without departing from the spirit or scope of the subject matter presented here.

In one embodiment, at least one frozen particle composition (including therapeutic compositions), device, system, product, machine, or method disclosed herein relates to making, administering, or utilizing one or more frozen particle compositions for various purposes.

Frozen Particles

In one embodiment, the one or more frozen particle compositions, frozen piercing implements, or frozen piercing implement devices include one or more frozen particles and optionally, at least one other agent. In one embodiment, the at least one agent includes at least one of a therapeutic agent, reinforcement agent, abrasive, biological remodeling agent, explosive material, or adhesive agent. In one embodiment, the frozen particle composition or frozen piercing implement (or device) includes at least one material that modulates the rate of diffusion or degradation of the at least one agent. In one embodiment, the at least one material reduces the rate of diffusion or degradation of the at least one agent.

In one embodiment, the at least one agent includes or is substantially in the form of at least one of an organic or inorganic small molecule, clathrate or caged compound, protocell, coacervate, microsphere, Janus particle, proteinoid, laminate, helical rod, liposome, macroscopic tube, niosome, sphingosome, toroid, vesicular tube, vesicle, small unilamellar vesicle, large unilamellar vesicle, large multilamellar vesicle, multivesicular vesicle, lipid layer, lipid bilayer, micelle, organelle, cell, membrane, nucleic acid, peptide, polypeptide, protein, glycopeptide, glycolipid, lipoprotein, sphingolipid, glycosphingolipid, glycoprotein, peptidoglycan, lipid, carbohydrate, metalloprotein, proteoglycan, chromosome, nucleus, acid, support structure, buffer, protic solvent, aprotic solvent, nitric oxide, nitrous oxide, nitric oxide synthase, amino acid, micelle, polymer, copolymer, monomer, prepolymer, cell receptor, adhesion molecule, cytokine, chemokine, immunoglobulin, antibody, antigen, platelet, extracellular matrix, blood, plasma, cell ligand, zwitterionic material, cationic material, oligonucleotide, nanotube, piloxymer, transfersome, gas, element, contaminant, radioactive particle, hormone, microorganism, bacteria, virus, quantum dot, contrast agent, or any part thereof. In one embodiment, the one or more frozen particle compositions, or frozen piercing implements (or devices) include one or more frozen particles made up of at least one frozen constituent. In one embodiment, the one or more frozen particle compositions, or frozen piercing implements (or devices) include one or more frozen particles including a single frozen constituent. In one embodiment, the one or more frozen particles include multiple frozen constituents. In one embodiment, the one or more frozen particle compositions, or frozen piercing implements (or devices) include frozen solute particles, and optionally, at least one agent. In one embodiment, the one or more frozen particle compositions, or frozen piercing implements (or devices) include non-hydrogen oxide frozen solute particles, and optionally, at least one agent. In one embodiment, the one or more frozen particle compostions, or frozen piercing implements (or devices) include frozen solvent particles, and optionally, at least one agent. In one embodiment, the one or more frozen particle compositions, or frozen piercing implements (or devices) include non-hydrogen oxide frozen solvent particles and optionally, at least one agent. In one embodiment, the one or more frozen particle compositions, or frozen piercing implements (or devices) include frozen solution particles, and optionally, at least one agent. In one embodiment, a frozen particle composition, or frozen piercing implement (or device) includes one or more frozen solution particles and at least one agent; wherein the frozen particle composition is in at least one crystalline or amorphous phase.

In one embodiment, the one or more frozen particle compositions, or frozen piercing implements (or devices) include frozen particles of at least one component that is in a gaseous state at or above physiological conditions, which include but are not limited to approximately 0.25 bar, approximately 0.5 bar, approximately 1.0 bar, approximately 5.0 bar, approximately 10.0 bar, approximately 25 bar, approximately 50 bar, approximately 100 bar, approximately 200 bar, or approximately 500 bar pressure; and at or above approximately 10° C., approximately 15° C., approximately 20° C., approximately 25° C., approximately 30° C., approximately 35° C., approximately 37° C., approximately 40° C., approximately 45° C., approximately 50° C.

In one embodiment, the frozen particle composition, or frozen piercing implement (or device) includes one or more frozen particles including at least one of hydrogen oxide, helium, neon, krypton, argon, xenon, nitrogen, chlorine, bromine, methane, oxygen, air, carbon dioxide, polyethylene glycol, acetone, ethyl acetate, dimethyl sulfoxide, dimethyl formamide, dioxane, tetrahydrofuran, acetonitrile, acetic acid, n-butanol, isopropanol, n-propanol, hexamethylphosphorotriamide, perfluorohydrocarbon, methanol, ethanol, tert-butyl alcohol, formic acid, hydrogen fluoride, ammonia, benzene, carbon tetrachloride, hexane, dichloromethane, methylene chloride, carboxylic acid, saline, standard saline citrate, methane, toluene, chloroform, polyethylene glycol, acetic acid, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, methane, diethyl ether, or any solution, suspension, mixture, or colloid including one or more thereof.

In one embodiment, the frozen particle composition, or frozen piercing implement (or device) includes one or more frozen solution particles, optionally including at least one agent; wherein the one or more frozen solution particles have at least one major dimension of approximately one centimeter or less, approximately one millimeter or less, approximately one micrometer or less, approximately one nanometer or less, or any value therebetween.

In one embodiment, at least one of the constituents of the one or more frozen particle compositions or frozen piercing implements (or devices) is frozen. In one embodiment, all of the constituents of the one or more frozen particle compositions or frozen piercing implements (or devices) are frozen. In one embodiment, the one or more frozen particle compositions, or frozen piercing implements (or devices) have at least one major dimension of approximately one decimeter or less, approximately one centimeter or less, approximately one millimeter or less, approximately one micrometer or less, approximately one nanometer or less, approximately one picometer or less, or any value therebetween.

In one embodiment, a plurality of frozen particle compositions or frozen piercing implements (or devices) is delivered or administered, and the plurality includes at least two subsets of frozen particle compositions or frozen piercing implements which can be differentiated based on size. In one embodiment, a plurality of frozen particle compositions or frozen piercing implements includes at least one subset of frozen particle compositions or frozen piercing implements that have at least one major dimension of approximately ten micrometers or less. In one embodiment, the at least one major dimension of the one or more frozen particle compositions or frozen piercing implements (or devices) includes at least one of radius, diameter, length, width, height, or perimeter.

As described herein, in one embodiment, the one or more frozen particle compositions or frozen piercing implements approximate the shape of at least one of a sphere, bullet, flechette, cone, needle, arrow, spear, diamond, pyramid, cylinder, mini ball, shuttlecock, spiral, helical, bell, pear, crystal, cube, spheroid, tetrahedron, crescent, or high aspect ratio shape. The size, shape, weight, or density, as well as other physical parameters of the one or more frozen particle compositions or frozen piercing implements can be adjusted according to a particular parameter for making or administering the frozen particle composition, or frozen piercing implement, or desired goal in utilizing the frozen particle composition(s) or frozen piercing implement(s). In one embodiment, the one or more frozen particle compositions or frozen piercing implements include a plurality of frozen particles that are approximately uniform with regard to size, shape, weight, or density. In one embodiment, the one or more frozen particle compositions or frozen piercing implements include an array of different sizes, shapes, weights, or densities.

In one embodiment, the frozen particle composition, or frozen piercing implements is substantially in the form of a hatchet, saw, rotary device, fork, sciber, graver, spade, screw, pin, needle, blade, knife, razor, scissors, tweezers, scalpel, or other tool. In one embodiment, the frozen particle composition, or frozen piercing implement includes at least one microneedle, micropin, nanoneedle, or nanopin. In one embodiment, the frozen particle composition, or frozen piercing implements includes means for piercing, stitching, extracting material, or administering at least one agent to at least one substrate.

In one embodiment, the one or more frozen particle compositions or frozen piercing implements are substantially solid at about 30° C., about 20° C., about 10° C., about 5° C., about 0° C., about −10° C. about −20° C., about −30° C., about −40° C., about −50° C., about −60° C., about −70° C., about −75° C., about −80° C., about −85° C., about −90° C., about −95° C., about −100° C., about −120° C., about −150° C., about −180° C., about −200° C., about −220° C., about −250° C., or any temperature less than or therebetween. In one embodiment, a frozen piercing implement is substantially solid if it is approximately 1%, approximately 5%, approximately 10% approximately 20%, approximately 30%, approximately 40%, approximately 50%, approximately 60%, approximately 70%, approximately 80%, approximately 90%, approximately 99%, approximately 100% solid, or any value therebetween.

In one embodiment, the frozen particle composition or frozen piercing implement (or device) includes at least one of a solid, liquid, or gas. In one embodiment, the frozen particle composition, or frozen piercing implement (or device) includes at least one of a frozen liquid, or frozen gas. In one embodiment, the frozen particle composition or frozen piercing implement (or device) includes at least one pharmaceutically acceptable carrier or excipient. In one embodiment, the frozen particle composition, or frozen piercing implement (or device) is formulated to be administered by one or more of topical administration, oral administration, enteral administration, mucosal administration, percutaneous administration, or parenteral administration. In one embodiment, parenteral administration includes at least one of intravenous administration, intra-arterial administration, intracardiac administration, subcutaneous administration, intraperitioneal administration, or intramuscular administration. In one embodiment, the frozen particle composition, or frozen piercing implement (or device) is formulated to be administered by high velocity impact. In one embodiment, the frozen particle composition, or frozen piercing implement (or device) is formulated to be administered by one or more devices.

In one embodiment, the at least one frozen particle composition or frozen piercing impelement at least partially melts during administration, or upon contact with the substrate (e.g., biological cell, tissue, or organ). For example, the frozen components of the at least one frozen particle composition or frozen piercing implement will melt or vaporize as a thermal transfer occurs from the environment or substrate (e.g., biological cell, tissue, organ, structure, or device) to the composition or implement. In one example, the heat of a subject's body to which the frozen particle composition or implement is administered at least partially melts or vaporizes at least one component of the composition or implement. In one embodiment, at least part of the composition or implement does not melt or vaporize (e.g., magnetic particles, therapeutic agent, sensor, etc.). In one embodiment, the frozen particle composition or frozen piercing implement acts as a vehicle for delivering at least one agent (therapeutic agent, adhesive agent, biological remodeling agent, etc.) or article (e.g., sensor, detection material, etc.) wherein the vehicle dissipates upon administration.

As described herein, in one embodiment, the substrate is cooled prior to, during, or subsequent to administration of the at least one frozen particle composition or frozen piercing impelement, which reduces the thermal transfer and allows for a slower melting or evaporation process to occur. In one embodiment, all of the constituents of the frozen particle composition or frozen piercing implement are frozen. In one embodiment, at least one constituent of the frozen particle composition or frozen piercing implement is not frozen (e.g., magnetic particle, adhesive agent, sensor, etc.).

In one embodiment, the frozen particle composition, or frozen piercing implement (or device) includes one or more of a suspension, mixture, solution, sol, clathrate, colloid, emulsion, microemulsion, aerosol, ointment, capsule, powder, tablet, suppository, cream, device, paste, resin, liniment, lotion, ampule, elixir, spray, syrup, tincture, detection material, polymer, biopolymer, buffer, adjuvant, diluent, lubricant, disintegration agent, suspending agent, solvent, light-emitting agent, colorimetric agent, glidant, anti-adherent, anti-static agent, surfactant, plasticizer, emulsifying agent, flavor, gum, sweetener, coating, binder, filler, compression aid, encapsulation aid, preservative, granulation agent, spheronization agent, stabilizer, adhesive, pigment, sorbent, nanoparticle, or gel.

In one embodiment, the one or more frozen particles include one or more frozen hydrogen oxide particles. In one embodiment, the frozen particle composition, or frozen piercing implement (or device) includes one or more frozen particles, wherein the frozen hydrogen oxide particle is in one or more phases including at least one of amorphous solid water, low density amorphous ice, high density amorphous ice, very high density amorphous ice, clathrate ice, hyperquenched glassy water, ice Ic, ice Ih, ice II, ice III, ice IV, ice V, ice VI, ice VII, ice VIII, ice IX, ice X, ice XI, ice XII, ice XIII, ice XIV, or ice XV.

In one embodiment, the one or more frozen particle compositions, frozen piercing implements (or devices) include frozen hydrogen oxide particles. Frozen hydrogen oxide, or typical water ice, exists in several non-crystalline forms. Each of these forms has specific physical characteristics such as density and vibrational spectra. Some examples of frozen hydrogen oxide phase transformations are shown in FIG. 1. (See e.g., Chaplin, the worldwide web at lsbu.ac.uldwater; Ivanov et al., Russian J. Gen. Chem. vol. 75, pp. 1851-1856 (2005), each of which is incorporated herein by reference).

Hydrogen oxide (water) has many frozen phases (ices), including crystalline and non-crystalline phases. The crystalline phases generally have the common structure of having hydrogen bonds to four neighboring water molecules, such as two hydrogen atoms near each oxygen atom. Structural data on the known frozen hydrogen oxide polymorphs are shown in Table I, with two known phases of ice XI. (See, e.g., Chaplin, Ibid; and Zheligovskaya, et al., Russian Chem. Rev. 75, pp. 57-76, 2006, each of which is incorporated herein by reference).

TABLE I

Structural Data on the Ice Polymorphs

| Ice polymorph | Density, g/cm$^3$ | Protons | Crystal | Symmetry | Dielectric constant, $\epsilon_S$ | Notes |
|---|---|---|---|---|---|---|
| Hexagonal ice, Ih | 0.92 | disordered | Hexagonal | One C$_6$ | 97.5 | |
| Cubic ice, Ic | 0.92 | disordered | Cubic | four C$_3$ | | |
| LDA, Ia | 0.94 | disordered | Non-crystalline | | | As prepared, can be mixtures of several types |
| HAD | 1.17 | disordered | Non-crystalline | | | As prepared, can be mixtures of several types |
| VHDA | 1.25 | disordered | Non-crystalline | | | |
| II | 1.17 | ordered | Rhombohedral | One C$_3$ | 3.66 | |
| III | 1.14 | disordered | Tetragonal | One C$_4$ | 117 | protons can be partially ordered |
| IV | 1.27 | disordered | Rhombohedral | One C$_3$ | | metastable in ice V phase space |
| V | 1.23 | disordered | Monoclinic | One C$_2$ | 144 | protons can be partially ordered |
| VI | 1.31 | disordered | Tetragonal | One C$_4$ | 193 | protons can be partly ordered |
| VII | 1.50 | disordered | Cubic | four C$_3$ | 150 | two interpenetrating ice Ic frameworks |
| VIII | 1.46 | ordered | Tetragonal | One C$_4$ | 4 | low temperature form of ice VII |
| IX | 1.16 | ordered | Tetragonal | One C$_4$ | 3.74 | low temperature form of ice III, metastable in ice II space |
| X | 2.51 | symmetric | Cubic | four C$_3$ | | symmetric proton form of ice VII |
| XI | 0.92 | ordered | Orthorhombic | three C$_2$ | | low temperature form of ice Ih |
| XI | >2.51 | symmetric | Hexagonal close packed | distorted | | Found in simulations only |
| XII | 1.29 | disordered | Tetragonal | One C$_4$ | | metastable in ice V phase space |
| XIII | 1.23 | ordered | Monoclinic | One C$_2$ | | ordered form of ice V phase |
| XIV | 1.29 | mostly ordered | Orthorhombic | One C$_4$ | | ordered form of ice XII phase |
| XV | 1.31 (?) | ordered | ? | ? | | ordered form of ice VI phase |

Cooling liquid hydrogen oxide below its standard freezing point typically results in the formation of frozen hexagonal ice. However, if the hydrogen oxide is pure and cooled slowly, the liquid hydrogen oxide can be supercooled to approximately −42° C. Amorphous solids harden without crystallizing, such that if hydrogen oxide is cooled rapidly it results in formation of a glass-like state, for example, hyperquenched glassy water. (See e.g., Debenedetti, J. Phys. Condens. Matter, vol. 15, pp. R1669-R1726 (2003), and as cited by Chaplin, worldwideweb at lsbu.ac.uk/water; each of which is incorporated herein by reference.) Generally, hyperquenched glassy water is formed by rapidly spraying a fine mist of micrometer-sized hydrogen oxide droplets into very cold liquefied gas, such as propane. Alternatively, a fine mist of hydrogen oxide can be sprayed onto a very cold frozen cell or tissue, for example, at or below approximately −193° C. Hyperquenched glassy water may also be formed by cooling capillary tubes containing bulk liquid water (~100 μm diameter) with liquid helium, for example, at approximately −269° C. In one embodiment, the frozen particle composition includes a constitutent in a superglass state, or supersolid. For example, solid helium includes a supersolid, or a superglass amorphous solid. See, for example, Hunt, et al., Science, vol. 324, pp. 632-635 (2009), which is incorporated herein by reference.

Figure 2:
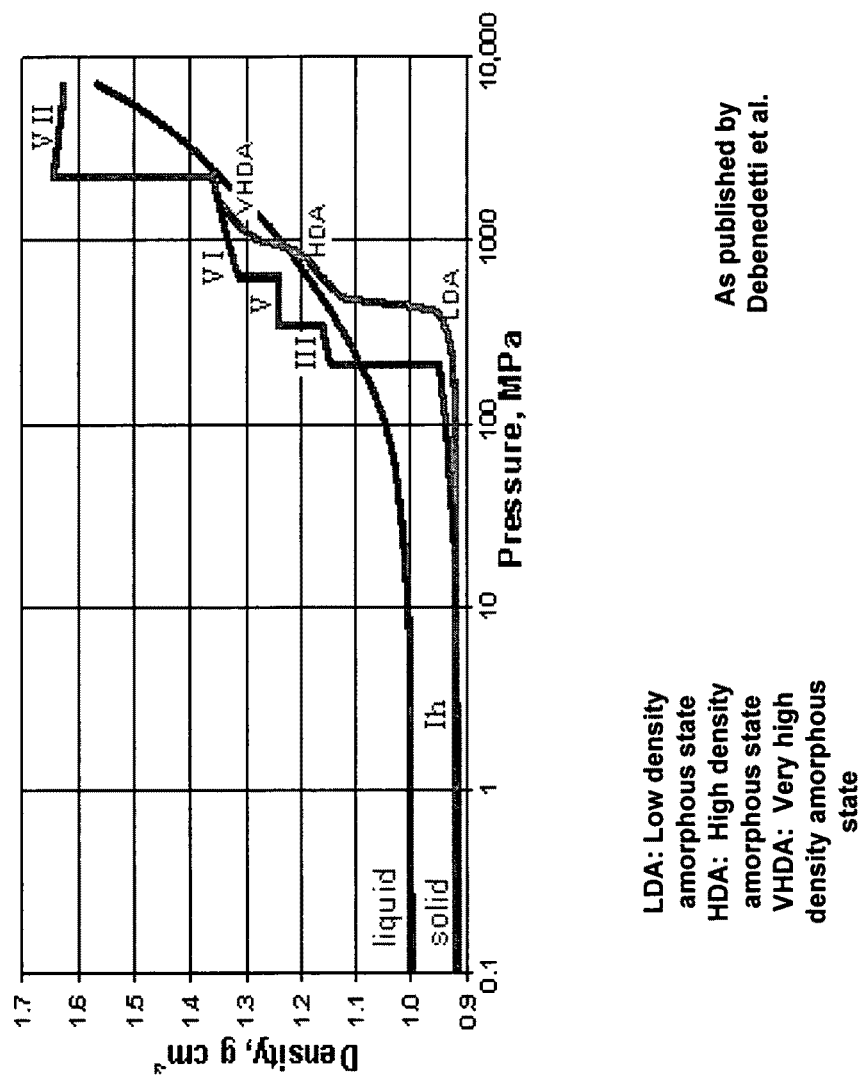
FIG. 2 illustrates the density of hydrogen oxide at various pressure points.
Figure 3:
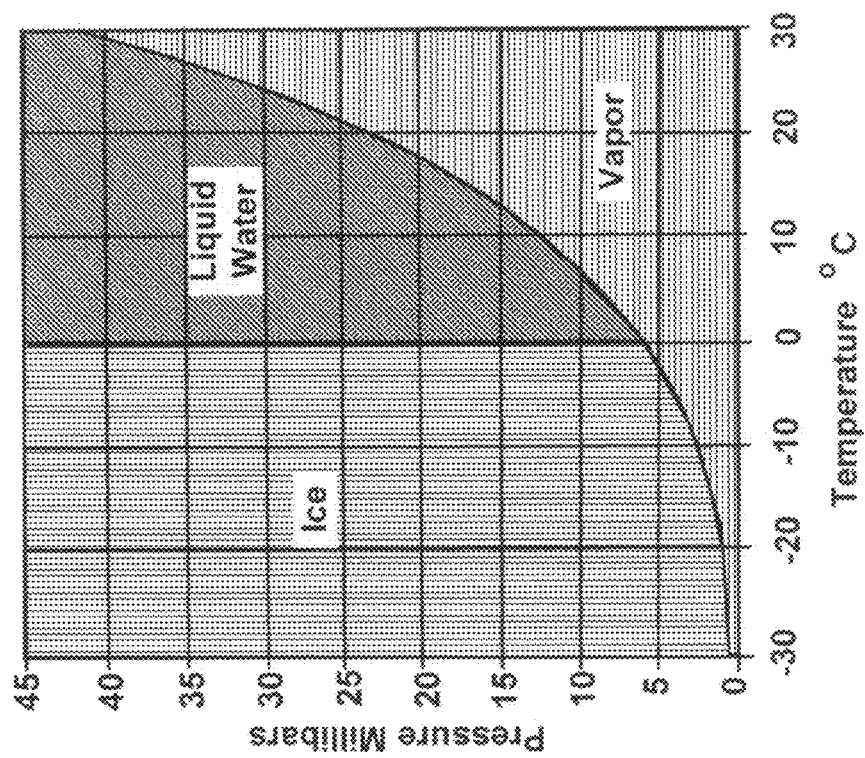
FIG. 3 illustrates particular phases of hydrogen oxide at various pressure and temperature points.
Figure 4:
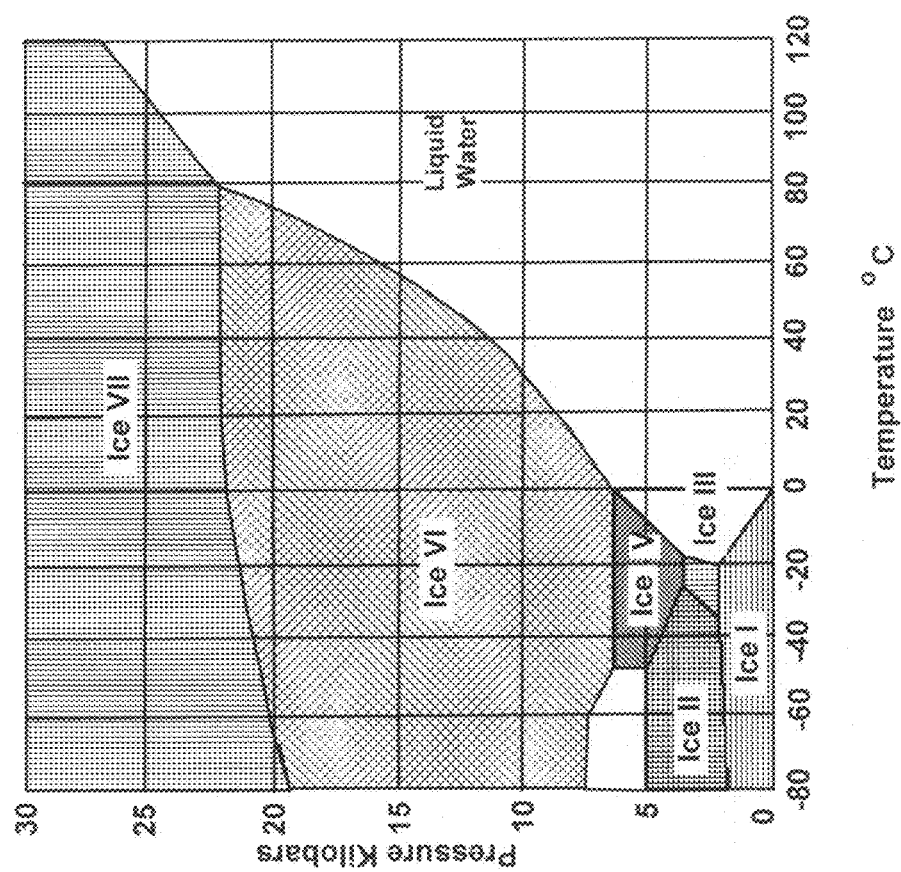
FIG. 4 illustrates particular phases of hydrogen oxide at various pressure and temperature points.

As shown in FIGS. 1-4, hydrogen oxide attains various structures and phases depending upon the temperature or pressure of the environment. As indicated in FIG. 1, for example, hydrogen oxide ice Ic is derived from high density amorphous water or deeply supercooled liquid water, when put under low temperature or higher pressure. Likewise, as indicated in FIG. 2, the hydrogen oxide has a greater density as a liquid than as a solid under ambient conditions (ice Ih). However, at increasing pressure, at least ice stages III, V, VI, and VII exhibit a greater density than liquid hydrogen oxide. FIG. 3 indicates the phase diagram for hydrogen oxide based on pressure and temperature variance, while FIG. 4 shows the specific sub-categories of hydrogen oxide based on physical properties, such as structure and density, among others, as the temperature and pressure vary.

Similarly, amorphous solid water is formed from the slow deposition of hydrogen oxide vapor on a cold metal crystal surface (for example, at less than approximately 2 nm/s), below the temperature of approximately −153° C. Amorphous solid water is a viscous semi-solid material that has a density of approximately 0.94 g/cm$^3$ and harbors gaps and spaces in its structure, as well as reactive hydrogen bonds. These structures are removed by annealing under vacuum pressure, which allows the material to convert to a high density glassy water or low density amorphous ice, depending on the temperature. Typically, high density glassy water, which has a density of approximately 1.1 g/cm$^3$, is formed by vapor deposition at approximately −263° C.

Low-density amorphous (LDA) ice also occurs from heating high-density amorphous (HDA) ice to just above approximately −153° C. at atmospheric pressure, and transforms to cubic ice at approximately −113° C. to −123° C. Low-density amorphous ice is also prepared by submitting low-pressure phases (Ih, Ic, XI, etc.) to high pressure (e.g., approximately 1.0 GPa) at low temperatures (e.g., below approximately −148° C.).

Very-high density amorphous (VHDA) ice is a viscous water state with a density of approximately 1.25 g/cm$^3$, and is prepared by heating high-density amorphous ice to just above approximately −113° C. and approximate pressure of 1.15 GPa. When very-high density amorphous ice is heated at different pressures between, e.g., 0.3 and 2 GPa, it re-crystallizes into only the proton disordered ices III, IV, V, XII, VI and VII in order of increasing pressure, but does not typically re-crystallize into the proton ordered phases (e.g., ice II).

Typically, the density of liquid water increases with increased pressure. When liquid water approaches the critical point in the liquid-vapor phase, water enters a supercritical phase where it exists as small but liquid-like hydrogen-bonded clusters dispersed within a gas-like phase and its physical properties vary according to changing density. Supercritical water is an excellent solvent for non-polar molecules, due to its low dielectric constant and poor hydrogen bonding. Due to these same properties, supercritical water is typically not a good solvent for electrolytes, which tend to form ionic bonds.

As indicated in FIG. 2, hexagonal ice is less dense than liquid water, whereas the other ice phases are all denser and phase changes occur near the liquid and solid densities (See e.g., Loerting et al., J. Phys.: Condens. Matter vol. 18, R919-R977 (2006), which is incorporated herein by reference). Liquid water density varies with change in temperature or pressure, whereas the density of amorphous ice varies only with change in pressure, but not temperature.

Hydrogen oxide has a high heat of vaporization (approximately 40.7 kJ/mol), and a high heat of sublimation (approximately 51.059 kJ/mol at 0° C.), which allows for the frozen particle compositions to remain intact for a short time period during which the particles are delivered to one or more cells or tissues. These properties further enable the frozen particle compositions, or frozen piercing implements to serve as particles for delivery of at least one therapeutic composition to one or more cells or tissues.

Frozen particle compositions, or frozen piercing implements may include a "solid," such as true solids, semi-solids, and viscous fluid, such as gels, polymers, hydrogels, or sols. Frozen particle compositions, or frozen piercing implements including one or more frozen particles may include particles that are at least partially frozen, or are entirely frozen. Frozen particle compositions, or frozen piercing implements including one or more frozen particles may include one or more subset groups of one or more particles, some of which are entirely frozen and some of which are at least partially frozen. For example, a frozen particle composition may be at least about 1% frozen, about 5% frozen, about 10% frozen, about 20% frozen, about 30% frozen, about 40% frozen, about 50% frozen, about 60% frozen, about 70% frozen, about 80% frozen, about 90% frozen, about 95% frozen, about 98% frozen, about 99% frozen, about 100% frozen, or any value there between.

In one embodiment, frozen particle compositions, or frozen piercing implements may include multiple different constitutions, wherein a group of frozen particle compositions, or frozen piercing implements includes at least one subset of multiple frozen particles, wherein each frozen particle has an individual therapeutic agent, adhesive agent, biological remodeling agent, abrasive, explosive material, reinforcement agent, other agent, a common constitution, or unique constitution. The group of frozen particle compositions, or frozen piercing implements may also include at least one subset of multiple frozen particles, wherein each frozen particle includes multiple agents.

A particular plurality of frozen particle compositions, or frozen piercing implements may include multiple frozen particles where various multiple agents are associated with a single particle. Likewise, a particular plurality of frozen particle compositions, or frozen piercing implements may include various multiple agents, where each individual agent is associated with a single frozen particle. In one embodiment, a plurality of frozen particle compositions, or frozen piercing implements includes any number of subsets of frozen particles associated with a particular agent, or other constituent. During the course of any particular method described herein, one or more plurality of frozen particle compositions, or frozen piercing implements, or any particular subset thereof, can be administered in a single treatment or in multiple treatments. A frozen particle composition or frozen piercing implement including at least one therapeutic agent may be referred to as a "therapeutic composition" or "frozen particle therapeutic composition" herein.

In certain instances, the one or more frozen particle compositions, or frozen piercing implements are utilized at a very low temperature, which may increase the degree of penetration of the one or more particles or the one or more compositions or implements for a biological tissue. In certain instances, the one or more frozen particle compositions, or frozen piercing implements are utilized at higher temperatures, depending on the freezing temperature of the constituents of the one or more particles, the goals of administration or treatment, or other factors. For example, the freezing point of nitrogen is approximately −210° C., whereas the freezing point of dimethyl sulfoxide (DMSO) is approximately 18.45° C. In one embodiment, the one or more frozen particle compositions, or frozen piercing implements are utilized at room temperature, or physiological temperature.

Hydrogen oxide becomes more viscous as the temperature is decreased to below approximately 33° C., or the pressure is increased. Ice Ic is generally formed by condensation of water vapor, at ambient pressure and low temperatures (less than approximately −80° C.), or below approximately −38° C. as a mist. (See e.g., Murray et al., Phys. Chem. Chem. Phys. Vol. 8, pp. 186-192 (2006), which is incorporated herein by reference). Ice Ic is also prepared by reducing the pressure on high-pressure hydrogen oxide ice at approximately −196° C. It can be the preferred phase for ice formed from hydrogen oxide droplets smaller than about 15 nm in radius, particularly at low temperatures (e.g., −113° C. to −53° C.). (See e.g., Johari, J. Chem. Phys. vol. 122 pp. 194504 (2005); Zhang, et al., Chem. Phys. Lett. vol. 421, pp. 251-255 (2006), each of which is incorporated herein by reference).

Ice Ih constitutes a large portion of naturally-occurring snow and ice. Since hexagonal ice exhibits changes in the hydrogen bonding, ice Ih shows anomalous reduction in thermal conductivity with increasing pressure (as does cubic ice and low-density amorphous ice). (See e.g., Andersson et al., Phys. Rev. B vol. 65 pp. 140201.1-14201.4 (2002), which is incorporated herein by reference).

Ice II maintains a general rhombohedral unit shape, similar to ice I. The density of ice II is approximately 1.17 g/cm$^3$. Ice III maintains a general tetragonal unit shape, with a density of approximately 1.14 g/cm$^3$. Ice VI also maintains a general tetragonal unit shape, with a density of approximately 1.31 g/cm$^3$. Ice VII is primarily composed of multiple intercalating ice Ic lattices, and has a density of approximately 1.66 g/cm$^3$.

Some non-limiting examples of materials that are included in one or more compositions, or implements described herein include, but are not limited to, liquid nitrogen, which is nontoxic and inert, with a freezing point at 1 atm pressure of approximately −210° C. Liquid helium is nontoxic and inert, with a freezing point at 367 psi of approximately −272.2° C. Liquid argon is nontoxic and inert with a freezing point at 1 atm pressure of approximately −189.4° C. Liquid neon has a freezing point of approximately −245.95° C., while liquid xenon has a freezing point of approximately −111.9° C. The freezing point of liquid dimethyl sulfoxide (DMSO) is approximately 18.45° C., and water or other co-solvents can decrease the freezing point. The freezing point of lactated Ringer's solution is approximately −45° C. These and other materials can be utilized as described herein either alone, or in combination with other materials.

In one embodiment, at least one frozen particle composition, or frozen piercing implement, is made or maintained by utilizing a magnetic time-averaged orbiting potential trap. See, for example, Han et al., Phys. Rev. vol. 57, pp. R4114-4117 (1998), which is incorporated herein by reference. In one embodiment, the at least one frozen particle composition includes one or more Bose-Einstein condensation of a dilute atomic gas. Id.

In one embodiment, the frozen particle composition, or frozen piercing implements includes a clathrate. Clathrate ice forms from water or other liquids, and contains small amounts of non-polar molecules (generally gases) under moderate pressure of a few MPa, and temperatures close to 0° C. Clathrate structures can vary, but generally allow a minimum amount of small molecules to fit into and stabilize gaps without forming covalent or hydrogen bonds with the hydrogen oxide molecules. Certain clathrates are formed at the interface of the liquid phase, under atmospheric pressure. Clathrates include but are not limited to the structural forms of sI, sII, and sh. In certain instances, noble gases can be used to form clathrate compounds with hydrogen oxide or other molecules. Noble gases generally have low polarizability, and tend to be spherically symmetrical, which allows for solubility with the hydrogen oxide cage. In addition, the solubility of the noble gases increases considerably as the temperature is lowered.

The solubility properties of particular noble gases as clathrates with hydrogen oxide are shown in Table IV. (See e.g., Dec et al., J. Solution Chem. vol. 14, pp. 417-429 (1985); Ivanov, et al., J. Struct. Chem. vol. 46, pp. 253-263 (2005); Fernandez-Prini, et al., Elsvier, pp. 73-98 (2004); Ivanov, et al., Russian J. Gen. Chem. vol. 75, pp. 1851-1856 (2005), each of which is incorporated herein by reference.)

TABLE IV

Solubility Properties of the Noble Gases

| Property | | He | Ne | Ar | Kr | Xe | Rn |
|---|---|---|---|---|---|---|---|
| Atomic number | | 2 | 10 | 18 | 36 | 54 | 86 |
| Atomic radius, Å | | 1.08 | 1.21 | 1.64 | 1.78 | 1.96 | 2.11 |
| ΔG° of solution in H$_2$O at 25° C., kJ/mol | | 29.41 | 29.03 | 26.25 | 24.80 | 23.42 | |
| ΔH° of solution in H$_2$O at 25° C., kJ/mol | | −0.59 | −3.80 | −11.98 | −15.29 | −18.99 | |
| ΔS° of solution in H$_2$O at 25° C., J/molK | | −100.6 | −110.1 | −128.2 | −134.5 | −142.2 | |
| Solubility, mM, 5° C., 101,325 Pa | H$_2$O | 0.41 | 0.53 | 2.11 | 4.20 | 8.21 | 18.83 |
| | D$_2$O | 0.49 | 0.61 | 2.38 | 4.61 | 8.91 | 20.41 |
| Solubility minima, ° C. | H$_2$O | 30 | 50 | 90 | 108 | 110 | |
| | D$_2$O | 53 | 53 | 98 | 108 | 116 | |

In one embodiment, the frozen particle composition, or frozen piercing implements includes at least two frozen particles that are joined. In one embodiment, the at least two frozen particles are joined by at least one agent. In one embodiment, the at least two frozen particles are joined by at least one cavity or compartment. In one embodiment, the frozen particle composition, or frozen piercing implement includes a cluster of three or more frozen particles that are joined. In one embodiment, the cluster of three or more frozen particles is joined by at least one agent. In one embodiment, the cluster of three or more frozen particle is joined by at least one cavity or compartment.

Cavitized or Compartmentalized Frozen Particle Compositions or Frozen Piercing Implements In one embodiment, the frozen particle composition, or frozen piercing implement includes at least one frozen particle as described herein, defining at least one cavity or compartment configured for holding at least one agent, article or other material. In one embodiment, the at least one cavity contains at least one agent. In one embodiment, the frozen particle composition, or frozen piercing implement includes at least one frozen particle defining at least one cavity or compartment containing at least one agent, and further including one or more agents located outside of the at least one cavity.

In one embodiment, the frozen particle composition, or frozen piercing implement includes at least one inlet port in fluid communication with the at least one cavity. In one embodiment, the frozen particle composition, or frozen piercing implement includes at least one status indicator. In one embodiment, the at least one status indicator indicates one or more of content of the at least one cavity, amount of cavity space occupied, or amount of cavity space available. In one embodiment, the at least one status indicator includes at least one of a sensor, a magnet, a colorimetric substance, or a physical measuring device. In one embodiment, the at least one status indicator measures one or more of a change in cavity volume, a change in cavity shape, a change in cavity temperature, a change in cavity pressure, a change in cavity pH, a change in frozen particle density, a change in frozen particle volume, a change in frozen particle weight, a change in frozen particle temperature, a change in frozen particle shape, a change in electrical field, a change in vehicle magnetic field, a change in frozen particle pH, a change in the state of an activatable agent of the composition, or a change in the state of an activating factor or inactivating factor of the composition.

In one embodiment, the at least one cavity includes at least one of a permeable, semi-permeable or impermeable partition. In one embodiment, the at least one cavity includes at least one of at least one means for at least partially sealing the cavity. In one embodiment, the at least one cavity includes at least one cap, seal, screw, door, or hinge. In one embodiment, the at least one cavity is substantially in the form of at least one of a space-filling curve, a depression, a helix, a cylinder, a spheroid, a cuboid, a high aspect ratio shape, a tetrahedron, a pyramid, a channel, or a cone.

In one embodiment, the at least one cavity differs in physical or chemical composition from at least one other cavity of the frozen particle. In one embodiment, the cavity or compartment is configured to physically or chemically separate the at least one agent from at least one other cavity of the frozen particle composition, or frozen piercing implement. In one embodiment, the at least one cavity or compartment is configured to physically or chemically separate from at least one other cavity or compartment of the frozen particle composition, or frozen piercing implement during administration. In one embodiment the frozen particle composition, or frozen piercing implement includes at least one agent, and the at least one agent includes at least one agent in a different phase state than the frozen particle composition. In one embodiment, the at least one cavity or compartment includes at least one of a solid, liquid, or gas. In one embodiment, the at least one cavity or compartment includes at least one of a liquid or gas, and at least one other cavity or compartment includes a solid.

In one embodiment, the at least one cavity or compartment includes at least one clathrate. In one embodiment, the at least one cavity or compartment includes at least one matrix. In one embodiment, the at least one cavity or compartment is an inner core cavity of at least one frozen particle composition, or frozen piercing implement. In one embodiment, the at least one cavity or compartment includes an inner core region and wherein the at least one agent is at least one of a liquid or gas. In one embodiment, the at least one cavity or compartment is intercalated with at least one other cavity or compartment. In one embodiment, the at least one cavity is located at a substantially superficial or exterior region of the one or more frozen particle compositions, or frozen piercing implements. In one embodiment, the at least one agent is distributed substantially uniformly within the at least one substantially superficial or exterior region.

In one embodiment, the at least one cavity or compartment has a higher concentration of the at least one agent than any other cavity or compartment. In one embodiment, the at least one cavity or compartment includes a graduated concentration of the at least one agent. In one embodiment, the at least one cavity or compartment includes varying levels of the at least one agent. In one embodiment, the at least one agent is fractionated. In one embodiment, the cavity or compartment includes one or more layers of at least one agent. In one embodiment, the cavity or compartment includes one or more layers of multiple agents. In one embodiment, the at least one agent includes one or more of a pro-drug or precursor compound. In one embodiment, the at least one agent includes one or more time-release or extended-release formulations. In one embodiment, the at least one agent includes an activatable agent. In one embodiment, the at least one agent is configured to activate upon administration of the frozen particle composition, or frozen piercing implement. In one embodiment, the at least one activatable agent is configured to activate by one or more of an enzymatic reaction, a reduction reaction, an oxidation reaction, a reduction-oxidation reaction, a hydrolysis reaction, a dehydration synthesis reaction, a glycosylation reaction, a phosphorylation reaction, a dehydration reaction, a hydration reaction, a decarboxylation reaction, a condensation reaction, a polymerization reaction, a glycolysis reaction, a gluconeogenesis reaction, a fermentation reaction, a photo chemical reaction, a thermal reaction, a magnetic reaction, an electrical reaction, an electrochemical reaction, a photolysis reaction, a photosynthetic reaction, an esterification reaction, altering the pressure on at least one frozen particle composition, or frozen piercing implement, altering the content of at least one frozen particle composition, or frozen piercing implement, altering at least one chemical property of at least one frozen particle composition, or frozen piercing implement, altering at least one physical property of at least one frozen particle composition, or frozen piercing implement, or applying at least one external stimulus to at least one frozen particle composition, or frozen piercing implements.

In one embodiment, the at least one external stimulus includes one or more of light, heat, electrical field, magnetic field, or electromagnetic energy. In one embodiment, the frozen particle composition, or frozen piercing implement further comprises at least one activating factor or at least one inactivating factor capable of modulating the activity of the at least one agent. In one embodiment, the at least one activating factor or the at least one inactivating factor forms at least part of one or more of a lipid conjugate, carbohydrate conjugate, peptide conjugate, polymer-lipid conjugate, fusion protein, antibody or antibody fragment, receptor or receptor fragment, reversible inhibitor, irreversible inhibitor, enzyme, gene repressor, gene suppressor, microRNA, siRNA, kinase, gene activator, DNA-binding protein, polymerase, gene promoter, gene enhancer, diamagnetic chemical, explosive material, reactive metal, adhesive agent, abrasive, reinforcement agent, biological remodeling agent, or therapeutic agent.

In one embodiment, the at least one activating or inactivating agent is configured to activate by one or more of altering the temperature of at least one frozen particle composition, or frozen piercing implement, altering the pressure on at least one frozen particle composition, or frozen piercing implement, altering the content of at least one frozen particle composition, or frozen piercing implement, altering at least one electrical property of at least one frozen particle composition, or frozen piercing implement, altering at least one magnetic property of at least one frozen particle composition, or frozen piercing implement, altering at least one chemical property of at least one frozen particle composition, or frozen piercing implement, altering at least one physical property of at least one frozen particle composition, or frozen piercing implement, or applying at least one external stimulus to at least one frozen particle composition, or frozen piercing implement.

In one embodiment, the at least one cavity or compartment is in substantially in a form that is different than the remainder of the frozen particle composition, or frozen piercing implement. In one embodiment, the at least one cavity or compartment is substantially in the form of at least one of an organic or inorganic small molecule, clathrate or caged compound, protocell, coacervate, microsphere, Janus particle, proteinoid, laminate, helical rod, liposome, macroscopic tube, niosome, sphingosome, toroid, vesicular tube, vesicle, small unilamellar vesicle, large unilamellar vesicle, large multilamellar vesicle, multivesicular vesicle, lipid layer, lipid bilayer, micelle, organelle, cell, membrane, nucleic acid, peptide, polypeptide, protein, glycopeptide, glycolipid, lipoprotein, sphingolipid, glycosphingolipid, glycoprotein, peptidoglycan, lipid, carbohydrate, metalloprotein, proteoglycan, chromosome, nucleus, acid, support structure, buffer, protic solvent, aprotic solvent, nitric oxide, nitrous oxide, nitric oxide synthase, amino acid, micelle, polymer, copolymer, monomer, prepolymer, cell receptor, adhesion molecule, cytokine, chemokine, immunoglobulin, antibody, antigen, platelet, extracellular matrix, blood, plasma, cell ligand, zwitterionic material, cationic material, oligonucleotide, nanotube, piloxymer, transfersome, gas, element, contaminant, radioactive particle, hormone, microorganism, bacteria, virus, quantum dot, contrast agent, or any part thereof. In one embodiment, the agent includes at least one negatively charged substance. In one embodiment, the agent includes at least one positively charged substance.

In one embodiment, a frozen particle composition, or frozen piercing implement comprises a frozen hydrogen oxide particle defining two or more cavities, wherein the two or more cavities each contain at least one agent. In one embodiment, the two or more cavities each contain at least one different agent. In one embodiment, the different agents are configured to combine upon administration of the frozen particle composition, or frozen piercing implement. In one embodiment, the different agents are configured to react upon administration of the frozen particle composition, or frozen piercing implement. In one embodiment, the different agents are configured to act cooperatively or synergistically upon administration of the frozen particle composition, or frozen piercing implement.

In one embodiment, a frozen particle composition comprises a frozen particle composition, or frozen piercing implement defining three or more cavities, wherein the three or more cavities each contain at least one agent. In one embodiment, a frozen particle composition, or frozen piercing implement comprises a frozen particle defining four or more cavities, five or more cavities, six or more cavities, seven or more cavities, eight or more cavities, or any value greater than.

Agents

In one embodiment, the frozen particle composition, or frozen piercing implement includes at least one agent. In one embodiment, the frozen particle provides a vehicle for the at least one agent. In one embodiment, the frozen particle is constituted solely by the at least one agent. In one embodiment, the agent includes at least one nontoxic, biocompatible, bioresorbable, or biodegradable agent. In certain instances, the one or more reinforcement agents, one or more explosive materials, one or more abrasives, one or more adhesive agents, or one or more therapeutic agents, or one or more biological remodeling agents are utilized in the form of a plate, spheroid, resin, powder, solution, flake, sheet, film, ribbon, gel, ball, pellet, or bead. (See e.g., U.S. Pat. No. 5,534,584; U.S. Pat. No. 5,331,046; each of which is incorporated herein by reference). The one or more materials or agents of the frozen particle compositions, or frozen piercing implements can be in the form of a solid, liquid, or gas. In one embodiment, one or more of the agents are the same agent. For example, in one embodiment, the frozen particle composition, or frozen piercing implement includes at least one therapeutic agent that is the same as a reinforcement agent, an adhesive agent, an abrasive, an explosive material, or a biological remodeling agent. In one embodiment, any one single agent is the same as any single other agent (i.e. the constitution of an agent may be the same as another agent, or the function of an agent may be the same as another agent).

In certain instances, at least one agent may be configured to provide more than one function. For example, in one embodiment, the at least one therapeutic agent and the at least one adhesive agent, biological remodeling agent, abrasive, reinforcement agent, or explosive material are the same agent. In one embodiment, the at least one adhesive agent and the at least one biological remodeling agent, therapeutic agent, abrasive, reinforcement agent, or explosive material are the same. In one embodiment, the at least one biological remodeling agent and the at least one adhesive agent, therapeutic agent, abrasive, reinforcement agent, or explosive material are the same agent. In one embodiment, the at least one reinforcement agent and the at least one adhesive agent, therapeutic agent, biological remodeling agent, abrasive, or explosive material are the same. In one embodiment, the at least one abrasive and the at least one adhesive agent, therapeutic agent, biological remodeling agent, explosive material, or reinforcement agent are the same. In one embodiment, the at least one explosive material and abrasive, adhesive agent, therapeutic agent, biological remodeling agent, or explosive material are the same.

In one embodiment, the at least one is included as part of at least one carrier that assists in synthesis or activation of the at least one agent. In one embodiment, the at least one carrier encompasses the at least one agent. In one embodiment, the carrier includes a microbe, other cell (such as a cell from a subject or related to a particular subject, including but not limited to a transgenic cell). In one embodiment, the cellular carrier is included in the one or more frozen particle compositions, or frozen piercing implements described. In one embodiment, the carrier includes or is substantially in the form of at least one of at least one of an organic or inorganic small molecule, clathrate or caged compound, protocell, coacervate, microsphere, Janus particle, proteinoid, laminate, helical rod, liposome, macroscopic tube, niosome, sphingosome, toroid, vesicular tube, vesicle, small unilamellar vesicle, large unilamellar vesicle, large multilamellar vesicle, multivesicular vesicle, lipid layer, lipid bilayer, micelle, organelle, cell, membrane, nucleic acid, peptide, polypeptide, protein, glycopeptide, glycolipid, lipoprotein, sphingolipid, glycosphingolipid, glycoprotein, peptidoglycan, lipid, carbohydrate, metalloprotein, proteoglycan, chromosome, nucleus, acid, support structure, buffer, protic solvent, aprotic solvent, nitric oxide, nitrous oxide, nitric oxide synthase, amino acid, micelle, polymer, copolymer, monomer, prepolymer, cell receptor, adhesion molecule, cytokine, chemokine, immunoglobulin, antibody, antigen, platelet, extracellular matrix, blood, plasma, cell ligand, zwitterionic material, cationic material, oligonucleotide, nanotube, piloxymer, transfersome, gas, element, contaminant, radioactive particle, hormone, microorganism, bacteria, virus, quantum dot, contrast agent, or any part thereof.

In one embodiment, the at least one agent is frozen. In one embodiment, the at least one agent is at least partially frozen. In at least one embodiment, the frozen particle composition, or frozen piercing implement includes one or more frozen particles and at least one agent that is not frozen. In one embodiment, the at least one agent includes two or more components configured to combine upon administration of the at least one agent.

In one embodiment, the at least one agent includes one or more inactive components. In one embodiment, the at least one agent includes two or more components that are configured to activate when combined. In one embodiment, the at least one agent includes one or more components that are configured to activate when administered. In one embodiment, at least two of the one or more components are included in the same or different frozen particle composition, or frozen piercing implement. In one embodiment, at least two of the one or more components each reside in a separate cavity of the same or a different frozen particle composition, or frozen piercing implement. In one embodiment, at least one agent is included as a precursor molecule.

In one embodiment, at least one agent is configured to be activated prior to or subsequent to administration. In one embodiment, at least one agent is configured to be activated after a prolonged time subsequent to administration. For example, in instances where the agent is encased or associated with a polymer or other agent that may insulate one or more reactant or retard the explosive or decomposition process, the release of the agent can be delayed. In one embodiment, the frozen particle composition, or frozen piercing implement includes at least one activatable agent. In one embodiment, the frozen particle composition, or frozen piercing implement includes at least one activating agent or at least one inactivating agent, or both. In one embodiment, the at least one agent includes two or more components configured to combine upon deposition. In one embodiment, the at least one agent includes two or more components configured to react upon deposition.

In one embodiment, the one or more frozen particle compositions, or frozen piercing implements including at least one agent are part of a kit for administration, optionally to at least one substrate (including at least one biological cell or tissue). In one embodiment, one or more subsets of frozen particle compositions, or frozen piercing implements include different agents or different components of an agent and are administered in a kit or device wherein one subset is kept separate from another subset until administration of the frozen particle compositions, or frozen piercing implements.

Reinforcement Agents

In one embodiment disclosed herein, one or more reinforcement agents are included in the frozen particle composition, or frozen piercing implement. Examples of some reinforcement agents include, but are not limited to, polyaramid, vinylester matrix, metal (including but not limited to gold, silver, copper, zinc, brass, tin, bronze, gallium, sodium, potassium, tungsten, steel, iron, carbon, aluminum, copper, platinum, tantalum, rhodium, or alloys thereof), ceramic, fiberglass, cellulose, broad carbide, aromatic polyamide, nylon, silk, rayon, acetate, modacrylic, olefin, acrylic polymer or copolymer, acrylamide polymer or copolymer, polyester, aromatic polyester, poly-lactic acid, vinyon, saran, spandex, vinalon, aromatic nylon, vinylidene chloride, modal, polybenzimidazole, sulfur, lyocell, orlon, zylon, high-performance polyethylene, polypyridobenzimidazole, vectran, acrylonitrile rubber, glass, copper, iron, steel, sodium, potassium, calcium, zinc, manganese, carbon, magnesium, alluvium, sand, sugar, calcite, emery, diamond, novaculite, pumice, rouge, borazon, corundum, zirconia alumina, silicon, silica, frozen hydrogen oxide ice, plant matter, animal matter, or mineral matter. In one embodiment, plant matter may include vegetable matter, nuts or nut products or pieces (e.g., almonds), grains (e.g., oatmeal), wood (e.g., wood fibers) or other stalk material, leaf matter, fruit matter (including pits or seeds or parts thereof), and other plant material.

In one embodiment, one or more reinforcement agents are made by spinning into a fiber, wire, or filament. Some non-limiting examples of reinforcement fibers can be found at, for example, U.S. Pat. No. 5,855,663; U.S. Pat. No. 5,652,058; KEVLAR® technical guide, Polymer Bulletin, vol. 16, pp. 167-174 (1986), and WO/2003/060002, each of which is incorporated herein by reference.

The one or more agents are positioned on or in the one or more frozen particle compositions depending on a given context. For example, the positioning of one or more agents may consider the particular goal of administering the one or more frozen particle compositions, or frozen piercing implements, the components of the at least one frozen particle composition, or frozen piercing implement, or the needs or desires of a particular outcome of treatment or administration of the one or more frozen particle compositions, or frozen piercing implements. In one embodiment, the one or more agents are located at least on the surface or beneath the surface of the one or more frozen particle compositions, or frozen piercing implements. In one embodiment, the one or more agents are located within the one or more frozen particle compositions, or frozen piercing implements.

Figure 5:
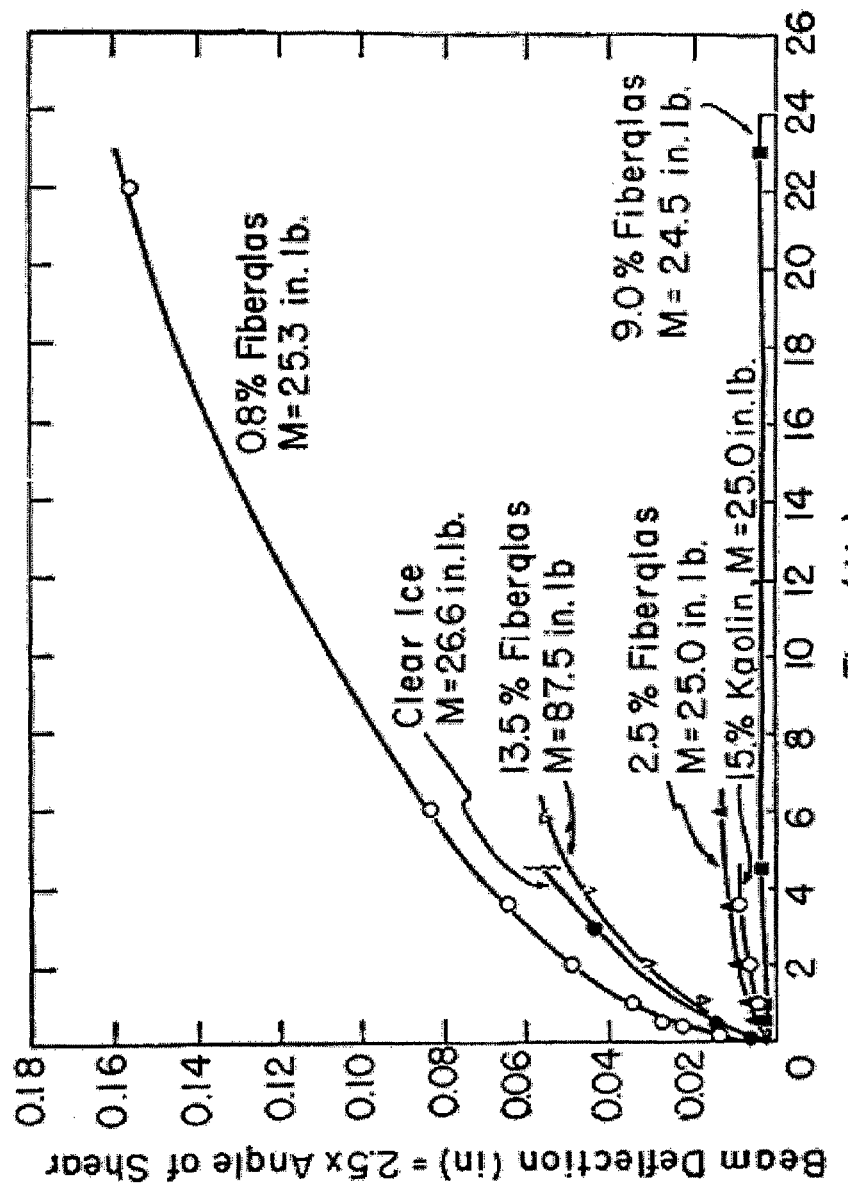
FIG. 5 illustrates the strength of hydrogen oxide samples reinforced with fiberglass or kaolin.
Figure 6:
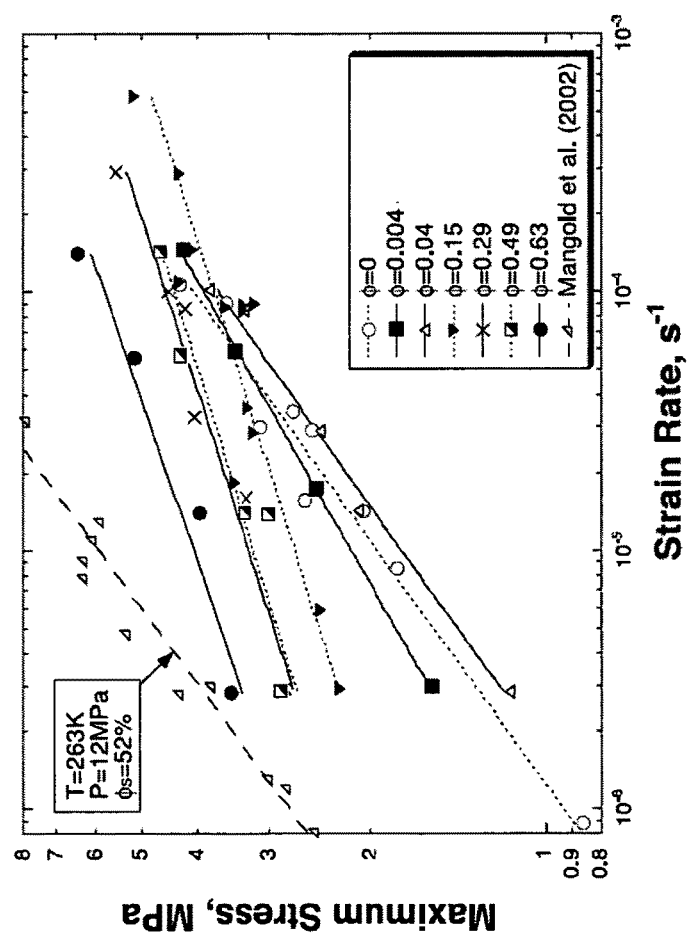
FIG. 6 illustrates the strength of hydrogen oxide samples reinforced with a reinforcement agent.

As shown in published FIGS. 5 and 6, the strength of hydrogen oxide ice samples increases when particular reinforcement agents are added, according to the published studies. As indicated in published FIG. 5, ice samples exhibit increased strength, as measured by beam deflection as an angle of shear when reinforced with fiberglass or kaolin. (See e.g., Kingery, Science, vol. 134, pp. 164-168 (1960), which is incorporated herein by reference). As indicated in FIG. 6, the maximum stress (in MPa) and strain rate increases when particular reinforcement agents are added to the hydrogen oxide ice samples, according to the published studies. (See e.g., Yasui et al, Geophys. Res. Lett., vol. 35, L12206, (2008), which is incorporated herein by reference).

Abrasives

In certain instances, the frozen particle composition or frozen piercing implement described herein includes one or more abrasives. The one or more abrasives may include treated or untreated abrasives, coated abrasives, bonded abrasives, powders, aggregates, composites, or other forms. In one embodiment, the one or more abrasives include, but are not limited to, polyaramid, vinylester matrix, metal, ceramic, fiberglass, cellulose, broad carbide, aromatic polyamide, nylon, silk, rayon, acetate, modacrylic, olefin, acrylic polymer or copolymer, acrylamide polymer or copolymer, polyester, aromatic polyester, poly-lactic acid, vinyon, saran, spandex, vinalon, aromatic nylon, vinylidene chloride, modal, polybenzimidazole, sulfur, lyocell, orlon, zylon, high-performance polyethylene, polypyridobenzimidazole, vectran, acrylonitrile rubber, glass, copper, iron, steel, sodium, potassium, calcium, zinc, manganese, carbon, magnesium, alluvium, sand, sugar, calcite, emery, diamond, novaculite, pumice, rouge, borazon, corundum, zirconia alumina, silicon, silica, frozen hydrogen oxide ice, plant matter, animal matter, or mineral matter. In one embodiment, plant matter may include vegetable matter, nuts or nut products or pieces (e.g., almonds), grains (e.g., oatmeal), wood (e.g., wood fibers) or other stalk material, leaf matter, fruit matter (including pits or seeds or parts thereof), or other plant material. In one embodiment, the abrasive includes at least one depilatory.

Explosive Materials

In one embodiment, one or more frozen particle compositions, or frozen piercing implements include one or more explosive materials. Explosive materials are typically chemically or energetically unstable or produce a sudden expansion of the material with a change in pressure. Such a sudden expansion of the material under pressure changes is generally accompanied by the production of heat. Explosive materials are generally differentiated according to their decomposition rates. Generally, a chemical decomposition rate of an explosive material lakes about one or more years, about one or more days, about one or more hours, about one or more minutes, about one or more seconds, or about a fraction of a second. Certain explosive materials are relatively stable, and may maintain their explosive ability for some amount of time. Other explosive materials have relatively high rates of decomposition and detonate rapidly.

In one embodiment, frozen particle compositions, or frozen piercing implements include one or more explosive materials that may include, for example, at least one of a high explosive or a low explosive. In one embodiment, the one or more explosive materials include at least one of carbonate, carbon dioxide, nitroglycerine, acid, base, epoxy, acrylic polymer or copolymer, acrlyamide polymer or copolymer, urethane, hypoxyapatite, or a reactive metal. In certain instances, the one or more explosive properties are the result of activation of one or more explosive materials.

In certain instances, the one or more explosive properties are the result of inherent tendencies of the frozen particle compositions, or frozen piercing implements themselves. In certain instances, the one or more explosive properties relate to an external event or stimulus, such as a change in temperature or pressure. In certain instances, the one or more explosive properties relate to a change in light intensity. In certain instances, the one or more explosive properties relate to a change in the composition upon administration or contact with at least one composition, cell, tissue, or subject. In certain instances, the one or more explosive properties result from a temperature or pressure increase relating to penetration of at least one cell, tissue, or subject. In certain instances, the one or more explosive properties result from contact with water or other moisture in a cell or tissue. In certain instances, the one or more explosive properties result from contact with at least one substrate. In addition to the intensity of the one or more explosives, the one or more explosive materials may differ with regard to the volatility, density, toxicity, hygroscopicity, or brisance of a particular explosive material.

Explosive materials may contain at least one oxidizer that provides fuel for certain explosive materials. In certain instances, the oxidizer can be an oxidizing element, such as oxygen. In certain instances, the oxidizer reacts with a reactive metal; an example of such a compound includes reacting fine metal powder (e.g., aluminum or magnesium) with an oxidizer (e.g., potassium chlorate or perchlorate). Chemically pure compounds may have high decomposition rates and lead to an explosion, including but not limited to nitroglycerin, acetone peroxide, trinitrotoluene, nitrocellulose, carbon, carbon monoxide, chlorine, potassium nitrate, sulfur, nitrogen compounds (such as nitrite, nitrate, and azide), potassium chlorate and potassium nitrate, hydrogen, ammonium nitrate, phosphorous, dinitrogen tetroxide, or others. In one embodiment, one or more mixtures of organic materials and oxidizers are included. In one embodiment, one or more mixtures of reactive metals and oxidizers or oils are included.

In one embodiment, the one or more explosive materials include carbon dioxide gas. In one embodiment, carbon dioxide gas is entrapped in the frozen particle composition. One method of incorporating carbon dioxide gas into at least one frozen particle composition, or frozen piercing implement includes liquefying the frozen particle composition, or frozen piercing implement and introducing carbon dioxide gas while maintaining the mixture under pressure. (See e.g., U.S. Pat. Nos. 4,289,794; 4,289,790; 4,262,029; 5,439,698, each of which is incorporated herein by reference). The carbon dioxide may also be present as a clathrate compound.

In one embodiment, at least one gasified frozen particle composition, or frozen piercing implement is formed, for example, by contacting fluid with gas under high pressure for a sufficient time period to form a gas hydrate. This gas hydrate is then cooled to a lower temperature in order to freeze the remaining unreacted fluid and entrap the gas hydrate. As one non-limiting example, aqueous liquid and carbon dioxide are kept in contact at approximately 0° C. for a time sufficient under a pressure range including at least approximately 200 psig to approximately 600 psig, while permitting absorption in the liquid of the gas in bound form and formation of the gasified ice. This process yields approximately 25-27.5 milliliters of gas per gram of ice. (See e.g., U.S. Pat. Nos. 4,487,023; 2,975,603; 3,086,370; 3,217,503, and 4,404,807, each of which is incorporated herein by reference).

Similarly, as described in U.S. Pat. No. 2,975,603, which is incorporated herein by reference, water contacted with carbon dioxide at a pressure of approximately 400 psig, in a temperature bath of approximately 0° C., is subsequently placed at −10° C. for 24 hours to effect degasification. As described in U.S. Pat. No. 2,975,603, the resulting product yields approximately 75 volumes of carbon dioxide per gram of ice. Additionally, as described in U.S. Pat. No. 3,086,370, which is incorporated herein by reference, gasified ice products are produced in a similar manner that contain other gases, such as nitrous oxide, sulfur-containing gases, chlorine-containing gases, inert gases, or carbon monoxide.

In one embodiment, the one or more explosive materials include at least one of sodium bicarbonate, citric acid, or both. In one embodiment, the one or more explosive materials include hydrogen peroxide.

In certain instances, the at least one frozen particle composition, or frozen piercing implement is configured to explode during or upon administration. In certain instances, the at least one frozen particle composition, or frozen piercing implement is configured to explode prior to or subsequent to administration. In certain instances, the at least one frozen particle composition, or frozen piercing implement explodes after a prolonged time subsequent to administration or delivery to at least one biological tissue, or other substrate. For example, in one embodiment, the one or more explosive materials are encased or associated with a polymer or other agent that may insulate one or more reactant or retard the explosive or decomposition process.

Therapeutic Agents

In one embodiment, the at least one frozen particle composition, or frozen piercing implement includes at least one therapeutic agent. (See, e.g., The Merck Index, 14th Ed. Merck & Co., Inc., Whitehouse Station, N.J. (2006), which is incorporated herein by reference). Other therapeutic agents that are approved for use in humans can be utilized as at least one therapeutic agent described herein, and can be found at the U.S. Food and Drug Administration website on the worldwide web at fda.gov, the information at which is incorporated herein by reference.

In certain instances, the one or more frozen particles themselves provide at least one therapeutic benefit. In certain instances, the one or more frozen particles act as vehicles for one or more therapeutic agents that provide at least one therapeutic benefit. In one embodiment, the one or more frozen particles including at least one therapeutic agent is inert.

In one embodiment, the at least one therapeutic agent includes at least one of an anti-tumor agent, antimicrobial agent, anti-coagulant, anti-viral agent, analgesic, antiseptic, anesthetic, diagnostic agent, anti-inflammatory agent, vaccine, cell growth inhibitor, cell growth promoter, chemical debridement agent, immunogen, antigen, radioactive agent, apoptosis promoting factor, angiogenic factor, anti-angiogenic factor, hormone, enzymatic factor, enzyme, papain, collagenase, protease, peptidase, elastase, urea, vitamin, mineral, nitrite, nitrate, nutraceutical, histatin, honey, alcium alginate, angiogenic factor, hormone, vitamin, mineral, nutraceutical, cytokine, chemokine, probiotic, sterol, contraceptive, coagulant, anti-coagulant, phage, prodrug, prebiotic, blood sugar stabilizer, smooth muscle cell activator, epinephrine, adrenaline, neurotoxin, neuro-muscular toxin, Botulinum toxin type A, microbial cell or component thereof, or virus or component thereof. In one embodiment, the nutraceutical includes one or more of a flavonoid, antioxidant, beta-carotene, anthocyanin, alpha-linolenic acid, omega-3 fatty acids, yeast, bacteria, algae, other microorganisms, plant products, or animal products. In one embodiment, the analgesic or anesthetic includes one or more of any aminoamid or aminoester local anesthetic, ibuprofen, morphine, codeine, aspirin, acetaminophen, lidocaine/lignocaine, ropivacaine, mepivacaine, benzocaine, chloroprocaine, cocaine, cyclomethycaine, dimethocaine/larocaine, propoxycaine, procaine/novocaine, proparacaine, tetracaine/amethocaine, articaine, bupivacaine, carticaine, cinchocaine/dibucaine, etidocaine, levobupivacaine, piperocaine, prilocaine, trimecaine, saxitoxin, or tetrodotoxin.

In one embodiment, the therapeutic agent includes at least one anti-inflammatory agent, including but not limited to steroids (e.g., betamethasone, hydrocortisone, and derivatives thereof), non-steroidal anti-inflammatory drugs, topical anti-inflammatory agents, or subcutaneously administered non-steroidal anti-inflammatory drugs (e.g. diclofenac). In one embodiment, the therapeutic agent includes one or more of: anti-freeze substances (e.g., polyethylene glycol), anti-sporiasis agents (e.g., dovonex, tazarotene, tars, etc.), pigments (e.g., dihyroxyacetone, melanin, hemoglobin, hemosiderin, iron copper, etc.), depigmenters (e.g., hydroquinone, phenolic compounds, etc.), tattoo colorants (e.g., skin dyes), preservatives (e.g., benzoate, paraben, or salicylate compounds), antioxidants (e.g., conezyme Q, vitamins, etc.), anesthetics (e.g., xylocaine, bupivicane, carbocane, amid or ester-based anesthetics, etc.), vasoconstrictors (e.g., epinephrine, ephedrine, or congeners thereof, etc.), acids (e.g., alpha-hydroxy acid, beta-hydroxy acid, halogenated acetic acid, etc.), irritants (e.g., acids, bases, croton oil, soap, salts of fatty acids, etc.), antibiotics (e.g., penicillin, amoxicillin, erythromyc in, tetracycline, monocycline, minocycline, mupirocin, flagyl, ciprofloxacin, polymixin, gentamycin, etc.), antivirals (e.g., acyclovir, famciclovir, valtrex, etc.), antifungals (e.g., imidazole, nystatin, griseofulvin, sporonox, etc.), depilatories (e.g., eflornithine hydrochloride), proanthrocyanins (e.g., maritime pine extract, tocopheryl acetate, etc.), or other substances utilized for diagnostic, prophylactic, or treatment of afflicting conditions.

In one embodiment, the analgesic includes but is not limited to one or more of paracetamol (acetaminophen), non-steroidal anti-inflammatory drugs (NSAIDs), salicylates, narcotics, or tramadol. In one embodiment, the analgesic includes but is not limited to aspirin, rofecoxib, celecoxib, morphine, codeine, oxycodone, hydrocodone, diamorphine, pethidine, buprenorphine, amitriptyline, carbamazepine, bagapentin, pregabalin, ibuprofen, naproxen, lidocaine, a psychotropic agent, orphenadrine, cyclobenzaprine, scopolamine, atropine, gabapentin, methadone, ketobemidone, or piritramide.

In one embodiment, the at least one therapeutic agent includes one or more antiseptic, including but not limited to one or more of an alcohol, a quaternary ammonium compound, boric acid, hydrogen peroxide, chlorhexidine gluconate, iodine, mercurochrome, octenidine dihydrochloride, phenol (carbolic acid) compounds, sodium chloride, super-oxidized water, superoxidized solution, oxidative reductive potential solution, or sodium hypochlorite.

In one embodiment, the antiseptic includes but is not limited to one or more of povidone-iodine, iodine, ethanol, 1-propanol, 2-propanol/isopropanol, benzalkonium chloride, cetyl trimethylammonium bromide, cetylpyridinium chloride, benzethonium chloride, chlorhexidine, octenidine dihydrochloride, or carbolic acid.

In one embodiment, the at least one therapeutic agent is an antimicrobial agent, and includes at least one of an antifungal agent, antibiotic agent, anti-bacterial, anti-parasitic agent, or anti-worm agent. In certain instances, the antimicrobial agent may occur in nature, or it can be synthetic.

In one embodiment, the at least one therapeutic agent includes one or more of a penicillin, cephalosporin, polymixin, sulfonamide, beta-lactam antibiotic, beta-lactamase inhibitor, enediynes, lincosamide antibiotic, nitroimidazole antibiotic, pleuromutilin antibiotic, polyketide antibiotic, polymyxin antibiotic, polypeptide antibiotic, antimicrobial peptides, quinolone antibiotic, rifamycin antibiotic, sulfonamide antibiotic, tetracycline antibiotic, aminoglycoside antibiotic, macrolide, tetracycline, cyclic lipopeptide, glycylcycline, or oxazolidinone. In one embodiment, the at least one therapeutic agent includes one or more of amoxicillin, tobramycin, levofloxacin, gatifloxacin, moxifloxacin, streptomycin, oxytetracycline, chloramphenicol, or ampicillin.

In one embodiment, the at least one therapeutic agent includes one or more anti-tumor agent, at least one of which may also be identified as a cytotoxic agent, or chemotherapy agent. Non-limiting examples of an anti-tumor agent for use as described herein include at least one of an alkylating agent, antimetabolite, anthracycline, plant alkaloid (such as paclitaxel), topoisomerase inhibitor, monoclonal antibody, or tyrosine kinase inhibitor. In one embodiment, the therapeutic agent includes one or more of imatinib, mechlorethamine, cyclophosphamide, chlorambucil, azathioprine, mercaptopurine, vinca alkaloid, taxane, vincristine, vinblastine, vinorelbine, vindesine, podophyllotoxin, etoposide, teniposide, amsacrine, dactinomycin, trastuzumab, cetuximab, rituximab, bevacizumab, dexamethasone, finasteride, tamoxifen, goserelin, telomerase inhibitor, dichloroacetate, aminopterin, methotrexate, pemetrexed, raltitrexed, cladribine, clofarabine, fludarabine, pentostatin, thioguanine, cytarabine, decitabine, fluorouracil/capecitabine, floxuridine, gemcitabine, enocitabine, sapacitabine, chloromethine, cyclophosphamide, ifosfamide, melphalan, bendamustine, trofosfamide, uramustine, carmustine, fotemustine, lomustine, nimustine, prednimustine, ranimustine, semustine, spretpozocin, carboplatin, cisplatin, nedaplatin, oxaliplatin, triplatin tetranitrate, satraplatin, busulfan, mannosulfan, treosulfan, procarbazine, decarbazine, temozolomide, carboquone, ThioTEPA, triaziquone, triethylenemelamine, docetaxel, larotaxel, ortataxel, tesetaxel, vinflunine, ixabepilone, aclarubicin, daunorubicin, doxorubicin, epirubicin, idarubicin, amrubicin, pirarubicin, valrubicin, zorubicin, metoxantrone, pixantrone, actinomycin, bleomycin, mitomycin, plicamycin, hydroxyurea, camptothecin, topotecan, irinotecan, rubitecan, belotecan, altretamine, amsacrine, bexarotene, estramustine, irofulven, trabectedin, cetuximab, panitumumab, trastuzumab, rituximab, tositumomab, alemtuzumab, bevacizumab, edrecolomab, gemtuzumab, axitinib, bosutinib, cediranib, dasatinib, erlotinib, gefitinib, imatinib, lapatinib, lestaurtinib, nilotinib, semaxanib, sorafenib, sunitinib, vandetanib, alvocidib, seliciclib, aflibercept, denileukin diftitox, aminolevulnic acid, efaproxiral, porfimer sodium, talaporfin, temoporfin, verteporfin, alitretinoin, tretinoin, anagrelide, arsenic trioxide, asparaginase/pegaspergase, atrasentan, bortezomib, carmofur, celecoxib, demecolcine, elesclomol, elasamitrucin, etoglucid, lonidamine, lucanthone, masoprocol, mitobronitol, mitoguanzone, mitotane, oblimersen, omacetaxine, sitimagene ceradenovec, tegafur, testolactone, tiazofurine, tipifarnib, or vorinostat.

In one embodiment, at least one nutraceutical is included. At least one nutraceutical includes but is not limited to, one or more of an extract of plant or animal matter (e.g., an oil, aqueous, or solid extract), a vitamin, a mineral, a mixture or solution, a food supplement, a food additive, a food fortification element, or other nutraceutical. In one embodiment, at least one nutraceutical includes but is not limited to resveratrol, an antioxidant, psyllium, sulforaphane, isoflavonoid, alpha-linolenic acid, beta-carotene, anthocyanins, phytoestrogens, polyphenols, polyphenons, catechins, benzenediols, tannins, phenylpropanoids, caffeine, alcohol, or others.

In one embodiment, at least one therapeutic agent includes one or more vaccine or other prophylactic therapy. In one embodiment, the therapeutic agent includes a diagnostic agent. In one embodiment, the frozen particle composition, or frozen piercing implement including at least one vaccine includes at least one prophylactic vaccine or therapeutic vaccine. In one embodiment, the at least one therapeutic vaccine includes at least one anti-cancer vaccine. In one embodiment, the at least one vaccine includes at least one of a tumor antigen, microbial antigen, viral antigen, immunogen, antigen, live microbe, dead microbe, attenuated microbe, microbe or component thereof, live virus, recombinant virus, killed virus, attenuated virus, virus component, plasmid DNA, nucleic acid, amino acid, peptide, protein, glycopeptide, proteoglycan, glycoprotein, glycolipid, sphingolipid, glycosphingolipid, cancer cell or component thereof, organic or inorganic small molecule, or toxoid.

One or more vaccine may include but not be limited to, vaccines containing killed microorganisms (such as vaccines for flu, cholera, bubonic plague, and hepatitis A), vaccines containing live, attenuated virus or other microorganisms (such as vaccines for yellow fever, measles, rubella, and mumps), live vaccine (such as vaccines for tuberculosis), toxoid (such as vaccines for tetanus, diphtheria, and crotalis atrox), subunit of inactivated or attenuated microorganisms (such as vaccines for HBV, VLP, and HPV), conjugate vaccines (such as vaccines for *H. influenzae* type B), recombinant vector, DNA vaccination. In one embodiment, the at least one vaccine includes but is not limited to rubella, polio, measles, mumps, chickenpox, typhoid, shingles, hepatitis A, hepatitis B, diphtheria, pertussis, rotavirus, influenza, meningococcal disease, pneumonia, tetanus, rattlesnake venom, virus-like particle, or human papillomavirus, or anti-cancer vaccine.

In one embodiment, the at least one therapeutic agent includes at least one adjuvant. The at least one adjuvant may include but not be limited to one or more organic or inorganic compounds. The at least one adjuvant may include but not be limited to at least one of a liposome, virosome, lipid, phospholipid, mineral salt, single-stranded DNA, double-stranded RNA, aluminum salts, microbial components carrying pathogen-associated molecular patterns (e.g., Toll-like receptor ligands or agonists), lipopolysaccharide, molecular antigen cage, CpG motif (e.g., CPG oligodeoxynucleotides), microbial cell wall or component thereof, squalene, oil emulsion, surfactant, saponin, isolated microbial toxin, modified microbial toxin, endogenous immunomodulator, or cytokine. In one embodiment, the at least one adjuvant and the at least one vaccine are located in at least one of the same cavities of the same frozen particle composition. In one embodiment, the at least one adjuvant and the at least one vaccine are located in different cavities of the same frozen particle composition, or frozen piercing implement. In one embodiment, two or more frozen particle compositions, or frozen piercing implements of a plurality of frozen particle compositions, or frozen piercing implements include one or more similar vaccines. In one embodiment, two or more frozen particle compositions, or frozen piercing implements of a plurality of frozen particle compositions, or frozen piercing implements include one or more dissimilar vaccines.

In one non-limiting example, a composition includes one or more frozen particle compositions, or frozen piercing implements including paclitaxel and at least one other constituent including at least one frozen component including air, oxygen, nitrogen, carbon dioxide, hydrogen oxide, helium, neon, xenon, krypton, chlorine, bromine, methane, or argon.

In one non-limiting embodiment, a composition or implement includes one or more frozen particles including one or more pegylated cytokines or one or more anti-tumor compounds; wherein the one or more frozen particles include nitrogen, air, oxygen, carbon dioxide, hydrogen oxide, helium, xenon, krypton, chlorine, bromine, methane, or argon.

Adhesive Agents

In one embodiment, at least one adhesive agent is included in one or more frozen particle compositions, or frozen piercing implements. In one embodiment, the at least one adhesive agent includes at least one monomer, prepolymer, polymer, or copolymer. In one embodiment, the at least one adhesive agent includes at least one monomer of self-polymerizing agent. In one embodiment, the at least one adhesive agent is configured to polymerize upon administration to at least one substrate. In one embodiment, the at least one adhesive agent is configured to polymerize at or above the temperature of the at least one substrate. In one embodiment, the at least one adhesive agent is configured to polymerize at or above the temperature of at least one biological tissue. In one embodiment, the at least one adhesive agent is configured to polymerize at or above the temperature of at least one subject.

In one embodiment, the at least one adhesive agent includes one or more of a cement, glue, paste, fixative, or bonding agent. In one embodiment, the at least one adhesive agent includes one or more of a solid, liquid, or gas.

In one embodiment, the at least one adhesive agent is at least one of non-toxic, biocompatible, biodegradable or bioresorbable. In one embodiment, the at least one adhesive agent resists biodegradation or bioresorption. In one embodiment, the at least one adhesive agent is not biocompatible, or may induce a response from the at least one biological tissue, or subject's body. In one non-limiting example, one or more frozen particle compositions, or frozen piercing implements are administered with or contain at least one therapeutic agent, such as a vaccine, and optionally, at least one adhesive agent (which may act as an adjuvant).

In one embodiment, the at least one adhesive agent is degradable or resorbable (e.g., dissolvable sutures constructed from or secured with an adhesive). See e.g., Sierra, and Saltz, "Surgical Adhesives and Sealants," Technomic Pub. Co., 1996, which is incorporated herein by reference. In one embodiment, the at least one adhesive agent stimulates cell or tissue growth, allowing for healing of a wound (e.g., burn, surgery incision, etc.) while the adhesive agent itself subsequently degrades, dissolves, or is resorbed by the at least one substrate, including at least one biological tissue or the subject's body. In one embodiment, the at least one adhesive agent stimulates or increases tissue regeneration. In one embodiment, the at least one adhesive agent suppresses or decreases scarring or keloid formation or recurrence.

In one embodiment, one or more frozen particle compositions, or frozen piercing implements include at least one liquid adhesive agent. For example, the freezing point of acrylic or epoxy resins is generally approximately −10° C. to −15° C., while the freezing point of hydrogen oxide water is approximately 0° C. Thus, in one embodiment, one or more frozen hydrogen oxide particle compositions, or frozen hydrogen oxide piercing implements include at least one liquid adhesive agent.

In one embodiment, the at least one adhesive agent includes one or more of a hemostat, such as a mechanical hemostat (including but not limited to, porcine gelatin, bovine gelatin, oxidized regenerated cellulose, or polysaccharide spheres), an active hemostat (including but not limited to, bovine thrombin, human pooled thrombin, or recombinant thrombin), a flowable hemostat (including but not limited to, bovine gelatin and human thrombin, or porcine gelatin with or without thrombin), or a hemostat and sealant (such as fibrin sealants of human pooled fibrin; human fibrin; plasma, collagen, and bovine thrombin; animal fibrin or thrombin, or others). In one embodiment, the adhesive agent includes one or more of a sealant (such as polyethylene glycol (PEG) polymers, including dual PEG or single PEG). In one embodiment, the adhesive agent includes but is not limited to albumin (such as bovine serum albumin) and glutaraldehyde. (See, for example, Spotnitz and Burks, Transfusion, pp. 1502-1516, Vol. 48, 2008; which is incorporated herein by reference.) In one embodiment, the adhesive agent is part of one or more adhesive laminates which include at least one adhesive agent and at least one non-adherent substance (which may optionally be biocompatible, bioresorbable, biodegradable, or nontoxic). See, for example, U.S. Patent Application Publication No. 20050153090, which is incorporated herein by reference.

In one embodiment, the at least one adhesive agent includes at least one naturally-occurring substance, such as gelatin, blood plasma, albumin, collagen, fibrin, fibrinogen (including lytic fragments, for example FPA, FPB, fragments D and E), hyaluronate, hyaluronan, glycosaminoglycans, chitin, thrombin, Factor XIII, or other substances. In one embodiment, the at least one adhesive agent includes at least one artificial or synthetic substance, such as an acrylic polymer or copolymer, acrylamide polymer or copolymer, polyacrylic acid (including but not limited to zinc polycarboxylate, resin bonding, or glass ionomer cement), epoxy, urethane, gum arabic, polyester, polyhydroxyalkanoate, poly (L-lactic acid), polyglycolide, polylactic acid, polyether, polyol, polyvinylpyrrolidone, pyroxylin, polymethyacrylate-isobutene-monoisopropylmaleate, siloxane polymer, poly-lactic-co-glycolic-acid, poly-3-hydroxybutyrate, poly-4-hydroxybutyrate, polyhydroxyvalerate, polydydroxyhexanoate, polydyroxyoctanoate, polycaprolactone, poly(e-caprolactone), sialyl Lewis$^x$, heme group, hemoglobin, healon, carboxymethylcellulose, hydroxyapatite, silicone, cadherin, integrin, polyelectrolyte, maleic polyelectrolyte, cellulose, resilin, cyanoacrylate, isocyanate, (including but not limited to 2-octyl cyanoacrylate, 2-butyl-n-cyanoacrylate, monomeric n-butyl-2-cyanoacrylate, butyl-2-cyanoacrylate, methyl 2-cyanoacrylate, or its higher homologs (ethyl, butyl, octyl, etc.), or polyisohexylcyanoacrylate), fibrin, thrombin, firbrinogen, hyaluronate, chitin, Factor XIII, Factor XII, silk, nylon, collagen, glycosaminoglycan, selectin, polyurethane, methacrylate, polysulfide, polyanhydride, polydioxanone, poly-p-dioxanone, albumin, glutaraldehyde, polyethylene glycol, hydrogel, soy or other plant based adhesives, or gelatin. In at least one embodiment, the adhesive agent includes gecko glue. In at least one embodiment, the adhesive agent includes microscopic seta configured to adhere by van der Waals forces.

In one embodiment, the at least one adhesive agent includes one or more of a globin, hemoglobin, heme group, carbohydrate, cell or cell component, silicone, hydroxyapatite, acrylic polymer or copolymer, acrylamide polymer or copolymer, hyaluronate or hyaluronic acid, carboxymethylcellulose, healon, polymer or biopolymer, gelatin-resorcinol-formaldehyde (GRF) combination, a fibrin-collagen combination, or a fibrinogen-thrombin combination. In one embodiment, the at least one adhesive agent includes one or more naturally-occurring, artificial, or synthetic polymers, including but not limited to urethane prepolymers or polymers, cyano-based polymers, polyether, polyol, polyvinylpyrrolidone, pyroxylin/nitrocellulose, polymethylacrylate-isobutene-monoisopropylmaleate, acrylate polymers or siloxane polymers (such as acrylate terpolymer, polyphenylmethylsiloxane, hexamethyldisiloxane or isooctane solvent based polymers). (For other specific examples of adhesive agents see, e.g., U.S. Pat. Nos.: 4,740,534 and 7,264,823; and U.S. Patent Application Nos. 20040097990, 20070161109, and 20070031474, each of which is incorporated herein by reference). In one embodiment, the at least one adhesive agent includes a combination of more than one adhesive agents.

In one embodiment, the at least one adhesive agent includes at least one crosslinking or derivatized agent. In one embodiment, the at least one adhesive agent is configured to form a crosslink bond with at least one component of at least one substrate. In one embodiment the crosslink bond of the at least one adhesive agent is configured for modulation by one or more of a chemical agent, change in pH, change in exposure to air, vacuum, change in moisture content, change in pressure, or change in temperature. In one embodiment, the formation of a crosslink bond of the at least one adhesive agent is configured for modulation by exposure of the at least one adhesive agent to one or more of electromagnetic energy, optical energy, thermal energy, laser energy, ionizing radiation, non-ionizing radiation, or sonic energy.

In one embodiment, one or more constituent of the at least one adhesive agent includes a crosslinked constituent (such as gelatin or albumin that is cross-linked with, for example, glutaraldehyde), or a derivatized constituent (such as derivatized collagen). In one embodiment, the at least one adhesive agent includes one or more constituents that are configured to crosslink with one or more substances in the at least one biological tissue. The crosslinking bond can form upon administration of the at least one adhesive agent to the at least one biological tissue, or upon administration of at least one of a chemical agent (such as an acid, base, enzyme, epoxide, diepoxide, 1,4-butanediol diglycidyl ether, glutaraldehyde, polysaccharide, or other chemical agent), air, moisture (such as from a biological fluid), electromagnetic energy (including ultraviolet light), optical energy, thermal energy, laser energy, ionizing radiation, non-ionizing radiation, or sonic energy to the at least one adhesive agent.

In one embodiment, the at least one adhesive agent includes one or more protein glue, including but not limited to protein, peptide, or amino acid-based substances. In one embodiment, the at least one adhesive agent includes one or more naturally-occurring or synthetic component. In one embodiment, the at least one adhesive agent includes one or more naturally-occurring or synthetic polyphenolic protein from mussels, wherein the polyphenolic protein is optionally cross-linked by a catechol oxidase. In one embodiment, the at least one adhesive agent includes mussel adhesive protein. In one embodiment, the mussel adhesive protein includes lysine, hydroxylated amino acids, and dopa. In certain instances, the mussel adhesive protein includes dihydroxyphenylalanine. In one embodiment, the at least one adhesive agent includes prolamine. In one embodiment, the at least one adhesive agent includes one or more chemotactic agent, such as transforming growth factor beta (TGF-β).

In one embodiment, fibrin sealant or fibrin glue can be formed as indicated in the table herein, or from two components: one containing fibrinogen and calcium chloride solution and the other containing thrombin solution and epsilon amino caproic acid (EACA).

In one embodiment, the at least one adhesive agent includes one or more hydrogel. See, for example, U.S. Pat. No. 6,103,528, which is incorporated herein by reference. One non-limiting example of a hydrogel included in a composition as described herein includes polyethylene glycol, polylactic acid, polytrimethylene carbonate, polycarophil, carbopol, polyox, chitosan, polyvinylpyrrolidone, block polymers or block copolymers, polymethylvinyl ether-maleic anhydride, or other constituents. In certain embodiments, the hydrogel may include a constituent with a polymerizable end cap, such as an acrylate ester. In one embodiment, the at least one adhesive agent at least partially generates a wound dressing, such as a sheet, bandage, film, or other permeable, semi-permeable, or impermeable covering. In one embodiment, the at least one wound dressing at least partially includes natural, synthetic, or artificial skin or skin deposit. (See, for example, Boateng et al., J. Pharm. Sciences. vol. 97, pp. 2892-2923 (2008)).

Some specific non-limiting examples of particular adhesive agents that are included in at least one composition described herein are listed in Table II herein. (Adapted from Smith, Ch. 7, p. 574, Table 1; Ratner, et al, Biomaterials Science, Second Edition, 2004; Elsevier Acad. Press., which is incorporated herein by reference).

TABLE II

| Type of tissue | Components | Possible setting or bonding reaction |
|---|---|---|
| Cyanoacrylate | Butyl or isobutyl cyanoacrylate | Addition polymerization |
| Fibrin sealant | Fibrinogen (with or without Factor XIII) Thrombin, CaCl$_2$ | Clot formation |
| Factor XIII | | Clot formation |
| GRF glue | Gelatin, resorcinol, formaldehyde (glutaraldehyde or glyoxal can be used in addition to or instead of formaldehyde) | Condensation |
| Hydrogel | Block copolymers of PEG, polylactic acid and acrylate esters | Photoinitiated addition polymerization |
| Acrylic bone cement | Methyl methacrylate and polymethyl methacrylate | Pertoxide-amine initiated addition polymerization |
| Dental cements | Zinc oxide powder, phosphoric acid | Acid-base reaction, zinc complexation |
| Zinc phosphate | | Zinc complexation |
| Zinc polycarboxylate | Zinc oxide powder, aqueous polyacrylic acid | Acid-base reaction, zinc complexation |
| Glass ionomer (polyalkenoate) | Ca, Sr, Al silicate glass powder aqueous polyacrylic-itatomic acid or polyacrylic-maleic acid | Acid-base reaction, metal ion complexation |
| Resin-based | Aromatic or urethane dimethacrylate monomers, silicate or other glass fillers aqueous polyacrylic acid-itaconic acid-methacrylate comonomers | Peroxide-amine or photoinitiated polymerization and photoinitiated addition polymerization |
| Resin-modified glass ionomer | Hydroxyethyl methacrylate aromatic or urethane diamethacrylates, Ca, Sr, Al glass powder | |
| Dentin adhesive | Etchant: phosphoric acid primer: carboxylate or phosphate Monomers hydroxyethyl methacrylate/water/solvent Bonding agent: urethane or aromatic dimethacrylate monomers | Photoinitiated addition polymerization |

In one embodiment, the at least one adhesive agent is configured to convert to at least one therapeutic agent upon administration of the at least one adhesive agent. In one embodiment, the at least one adhesive agent is configured to undergo one or more of hydration, hydrolysis, hydrogenolysis, condensation, dehydration, or polymerization upon administration of the at least one adhesive agent. In one embodiment, the at least one adhesive agent includes a methacrylate. In one embodiment, the at least one adhesive agent includes at least one of poly(N,N-dimethyl-N-(ethoxycarbonylmethyl)-N-[2'-(methacryloyloxy)ethyl]-ammonium bromide) or poly(sulfobetaine methacrylate).

In one embodiment, the at least one adhesive agent is configured to form one or more of a hydrogen bond, ionic bond, covalent bond, or noncovalent bond with at least one substrate.

In certain instances, at least one adhesive agent is provided to at least one substrate, including but not limited to at least one biological tissue, in an inactive form. In certain instances, the at least one adhesive agent is configured to polymerize or activate during administration of the at least one adhesive agent to at least one substrate, or shortly thereafter.

In one embodiment, the at least one adhesive agent is compatible with moist or wet tissues. In one embodiment, the at least one adhesive agent distributes evenly over the tissue surface. In one embodiment, the at least one adhesive agent quickly forms a durable bond. In one embodiment, the bonding time of the at least one adhesive agent is controllable. In one embodiment, the bonding time of the at least one adhesive agent is controlled or regulated. In one embodiment, the at least one adhesive degrades in a relatively short period of time. In one embodiment, the at least one adhesive agent is configured to be resorbed by the tissue to which it is applied, or by the subject's body. In one embodiment, the at least one adhesive agent maintains an appropriate viscosity for the application, provides adequate working time prior to bonding or setting, develops good adhesion, modulates hemostasis, modulates wound healing, reduces fibrosis, or provides at least one antimicrobial effect. In one embodiment, the at least one composition including at least one adhesive provides a local depot for at least one therapeutic agent.

In one embodiment, the at least one adhesive agent includes an active surface (i.e. having a bioglass, calcium phosphate, or biochemically active surface that can stimulate an in vivo response). In one embodiment, the at least one adhesive agent assists in delivering one or more therapeutic agents, including but not limited to antibiotics, vaccines, growth factors (e.g., members of the Fibroblast Growth Factor, members of the Bone Morphogenic Protein family, members of the Transforming Growth Factor-beta family, or others), transcription factors, anti-inflammatory agents, pain relievers, hemostatic agents, chemotherapeutic agents (e.g., 5-fluorouracil, paclitaxel, or others), chemokines, cytokines, angiogenic or anti-angiogenic factors, enzymes, stem cells, cellular organelles, or other therapeutic agents described herein.

In one embodiment, the at least one adhesive agent is delivered as a precursor molecule that is configured to activate by an additional activation step or event. In one embodiment, two or more components are configured to combine upon administration of the at least one adhesive agent. In one embodiment, the combination of the two or more components modifies at least one property of the adhesive agent. In one embodiment, the at least one property includes one or more of initiation of adhesive bond formation, strength of adhesive bond, adhesive bonding time, bond flexibility, bond biodegradability, bond bioresorbability, bond biocompatibility, or durability of adhesive bond. In one embodiment, the at least one property includes one or more of polymerization of the adhesive agent, or crosslinking of the adhesive agent. In one embodiment, two or more frozen particle compositions, or frozen piercing implements are administered; wherein at least one administration parameter is different for the two or more frozen particle compositions, or frozen piercing implements. In one embodiment, the at least one administration parameter includes at least one of: constitution of the frozen particle composition, or frozen piercing implement, formulation of the frozen particle composition, or frozen piercing implement, size of the frozen particle compositions, or frozen piercing implements, shape of the frozen particle composition, or frozen piercing implement, angle of administration of the frozen particle composition, or frozen piercing implement, velocity of administration of the frozen particle composition, or frozen piercing implement, quantity of frozen particle compositions, or frozen piercing implements administered, rate of administration of more than one frozen particle composition, or frozen piercing implement, spatial location for administration of the frozen particle compositions, or frozen piercing implements, temporal location for administration of the frozen particle compositions, or frozen piercing implements, method of administration of the frozen particle compositions, or frozen piercing implements, timing of administration of the frozen particle compositions, or frozen piercing implements, modulation of administration of the frozen particle compositions, or frozen piercing implements, deposition of the frozen particle compositions, or frozen piercing implements, or rate of deposition of at least one agent included in the frozen particle compositions, or frozen piercing implements.

In one embodiment, the at least one adhesive agent maintains the approximation of tissue of at least one wound of a subject. In one embodiment, the at least one adhesive agent forms a bond that resists separation between at least two aspects of a substrate. In one embodiment, the at least one adhesive agent is administered to the at least one substrate, such as a biological tissue or structure, prior to, during, or subsequent to a surgical procedure. Specific, non-limiting examples of surgical procedures include thoracic surgery, cardiovascular surgery, vascular surgery, neurological surgery, plastic surgery or aesthetic surgery, ophthalmic surgery, skin or connective tissue surgery, or abdominal surgery.

In one embodiment, at least one frozen particle composition, or frozen piercing implement includes an adhesive agent which provides a means for the repair, closure, maintenance of approximately the same tissue of a wound, treatment of a wound, or joining at least one substrate to another or joining at least one aspect of a substrate to another aspect of the same or different substrate.

In one embodiment, and as described herein, compositions and methods relate to the same or different frozen particle compositions, or frozen piercing implements, and are administered simultaneously, sequentially, randomly, or in another order. In certain instances, the at least one composition is administered that contains at least one adhesive agent as well as one or more other agents, such as bonding agents, that include functional groups or reactive side chains.

In one non-limiting example, polymerizable dimethacrylate monomers mixed with composite formulations are administered to calcified tissue, such as bone or tooth.

In another non-limiting example, acid etching or priming of the cell or tissue surface (such as a calcified surface), is achieved by administration of phosphoric acid or another acidic substance. In certain instances, the acidic substance includes functional groups, such as polycarboxylate or polyphosphate. Next, one or more agents can be administered that react with the functional groups, such as hydrophilic monomers (including but not limited to hydroxyethyl methacrylate).

In one embodiment, the at least one adhesive agent forms one or more of a hydrogen bond, ionic bond, covalent bond, or non-covalent bond upon administration to at least one substrate. In one embodiment the at least one adhesive agent includes at least one crosslinking or derivatized agent. In one embodiment, the at least one adhesive agent forms a crosslink bond with at least one component of at least one substrate to which the adhesive agent is administered. In one embodiment, the crosslink bond of the at least one adhesive agent is modulated by one or more of a chemical agent, change in pH, change in exposure to air, vacuum, change in moisture content, change in pressure, or change in temperature. In one embodiment, formation of a crosslink bond of the at least one adhesive agent is modulated by exposure of the at least one adhesive agent to one or more of electromagnetic energy, optical energy, thermal energy, laser energy, ionizing radiation, non-ionizing radiation, or sonic energy.

In one embodiment, adhesive agents can be selected for a particular use as described herein, based on factors including, but not limited to, viscosity, adhesive tenacity, kinetic rates of monomer formation, polymerization (with or without covalent cross-linking), ability to be cryoprecipitated, tensile strength, ability to restore biomechanical tissue integrity, in vivo effectiveness, or other factors. In certain instances, these or other factors can be measured and selection of the one or more particular adhesive agents can be based on those measurements. In certain instances, these or other factors can be measured by standard methods, including but not limited to, in vitro analysis, in vivo experiments (e.g., animal studies), ex vivo experiments, in planta experiments, or other methods.

In one embodiment, a method for providing at least one agent to at least one substrate comprises administering at least one frozen particle composition, or frozen piercing implement to at least one substrate, wherein the at least one frozen particle composition, or frozen piercing implement includes one or more frozen particles as described herein, and at least one agent.

In one embodiment, a method for providing at least one adhesive agent to at least one substrate comprises administering at least one frozen particle composition, or frozen piercing implement to at least one substrate, wherein the at least one frozen particle composition, or frozen piercing implement includes one or more frozen particles as described herein, and at least one adhesive agent.

In one embodiment, a method of maintaining the approximation of tissue of at least one wound of a subject comprises administering at least one frozen particle composition, or frozen piercing implement to at least one wound of a subject for a time sufficient to maintain the approximation of tissue of the at least one wound; wherein the at least one frozen particle composition, or frozen piercing implement includes one or more frozen particle compositions, or frozen piercing implements including at least one agent (such as an adhesive agent, biological remodeling agent, reinforcement agent, therapeutic agent, abrasive, or explosive material) as described herein.

In one embodiment, the at least one frozen particle composition, or frozen piercing implement includes a detection state that varies with its adhesive state. In one embodiment, the adhesive agent includes one or more epoxy adhesive, acrylic adhesive, urethane adhesive, polyurethane adhesive, silicone adhesive, cationic adhesive, anerobic adhesive, urethane acrylate, polyester acrylate, methacrylate, methyacrylate, or cyanoacrylate.

In one embodiment, the at least one adhesive agent includes at least one α-cyanoacrylate and a fluorescent compound including at least one of a bis-benzoxazolyl compound, pyrylium salt, quantum dot, or coumarin compound. In one embodiment, the at least one adhesive agent includes an a-cyanoacrylate and 2,5-bis-(5-tert-butyl-2-benzoxasolyl)-thiophene. In one embodiment, the at least one adhesive agent includes one or more of a base component, initiator component, or activator component. In one embodiment, the at least one adhesive agent further includes at least one curing component. In one embodiment, the at least one adhesive agent includes at least one photopolymerizable adhesive, photocurable adhesive, thermal curable adhesive, free radical curable adhesive, or aerobic curable adhesive. In one embodiment, the at least one adhesive agent includes one or more adhesive agent configured to polymerize upon exposure to infrared light, ultraviolet light, x-ray, visible light, or other electromagnetic radiation.

In one embodiment, the adhesive agent includes at least one dye coinitiator. In one embodiment, the at least one dye coinitiator includes at least one of a bis-benzoxazolyl compound, pyrylium salt, QTX, safranin O, fluorescein, eosin yellow, eosin Y, eosin B, ethyl eosin, eosin bluish, erythrosine B, erythrosine yellowish blend, toluidine blue, 4',5'-dibromofluorescein, Rose Bengal B, cyanine, pyronin GY, cresyl violet, brilliant green, lissamine green BN, rhodamine B, methylene blue, crystal violet, phosphine oxide, or coumarin compound.

Biological Remodeling Agents

In one embodiment, one or more frozen particle compositions, or frozen piercing implements include at least one biological remodeling agent. In one embodiment, the at least one biological remodeling agent includes one or more extracellular matrix components. In one embodiment, the at least one biological remodeling agent is configured to provide at least one chemical or biochemical function to the at least one biological tissue. In one embodiment, the biological remodeling agent is configured to modulate the growth of at least one biological tissue. In one embodiment, the biological remodeling agent is configured to promote growth of at least one biological tissue. In one embodiment, the at least one biological remodeling agent is configured to promote at least one of cell migration, cell attachment, cell retention, cell differentiation, cell proliferation, apoptosis, angiogenesis, diffusion of materials, nucleic acid expression, protein translation, protein modification, protein secretion, carbohydrate production, carbohydrate secretion, fat production, or fat secretion.

In one embodiment, the biological remodeling agent is configured to inhibit growth of at least one biological tissue. In one embodiment, the at least one biological remodeling agent is configured to inhibit at least one of cell migration, cell attachment, cell retention, cell differentiation, cell proliferation, apoptosis, angiogenesis, diffusion of materials, nucleic acid expression, protein translation, protein modification, protein secretion, carbohydrate production, carbohydrate secretion, fat production, or fat secretion.

In one embodiment, the at least one biological remodeling agent is configured to promote at least partial construction or at least partial reconstruction of at least one biological tissue. In one embodiment, the at least one biological remodeling agent includes at least one cellular or tissue scaffolding component (e.g., collagen, elastin, protein, carbohydrate, nucleic acid, organic or inorganic agent, or other component). In one embodiment, the at least one biological remodeling agent includes at least one cell (e.g., endogenous cell, exogenous cell, transgenic cell, progenitor cell, allogeneic cell, neonatal cell, embryonic cell, stem cell, differentiated cell, blood cell, chondrocyte, endothelial cell, hepatocyte, keratinocyte, myocyte, osteoblast, osteoclast, osteocyte, mesenchymal cell, fibroblast, etc.), other cells are described herein. (See, for example, Nolte et al., Cells Tissues Organs vol. 187, pp. 165-176 (2008), which is incorporated herein by reference.)

In one embodiment, the at least one biological remodeling agent provides a scaffold or matrix for growth, regrowth, restructuring, remodeling, or physically, chemically, or biologically structuring one or more cells or biological tissues. In one embodiment, the at least one biological remodeling agent is configured to provide at least one mechanical structure to the at least one biological tissue. In one embodiment, the at least one biological remodeling agent provides a load-bearing structure to at least one biological tissue.

In one embodiment, the at least one biological remodeling agent is configured to provide oxygenation, nutrition, or other nourishment to at least one biological tissue.

In one embodiment, the at least one biological remodeling agent includes one or more self-organizing structures, including at least one hydrogel, nanofiber, nanoparticle, or helical structure. (See, for example, Pokroy et al, Science vol. 323, pp. 237-240 (2009); U.S. Patent Application Publication No. 20080070304, each of which is incorporated herein by reference.) In one embodiment, the at least one biological remodeling agent includes one or more self-assembling nanofibers or nanoparticles.

In one embodiment, the at least one biological remodeling agent at least partially generates a wound dressing, such as a sheet, bandage, film, or other permeable, semi-permeable, or impermeable covering. In one embodiment, the at least one wound dressing at least partially includes natural, synthetic, or artificial skin, skin substitute, or skin deposit. In one embodiment, the at least one biological remodeling agent includes at least one nanotube (such as a carbon nanotube, DNA nanotube, or other nanotube).

In one embodiment, the at least one biological remodeling agent includes at least one of a tumor antigen, microbial antigen, viral antigen, analgesic, antiseptic, anesthetic, diagnostic agent, anti-inflammatory agent, vaccine, cell growth inhibitor, cell growth promoter, chemical debridement agent, immunogen, antigen, radioactive agent, apoptosis promoting factor, angiogenic factor, anti-angiogenic factor, hormone, enzymatic factor, enzyme, papain, collagenase, protease, peptidase, elastase, urea, vitamin, mineral, nutraceutical, cytokine, chemokine, probiotic, coagulant, anti-coagulant, phage, prodrug, prebiotic, blood sugar stabilizer, smooth muscle cell activator, epinephrine, adrenaline, neurotoxin, neuro-muscular toxin, Botulinum toxin type A, microbial cell or component thereof, or virus or component thereof. In one embodiment, the nutraceutical includes one or more of a flavonoid, antioxidant, beta-carotene, anthocyanin, alpha-linolenic acid, omega-3 fatty acids, yeast, bacteria, algae, other microorganisms, plant products, or animal products.

In one embodiment, a frozen particle composition, or frozen piercing implement, comprises: one or more frozen hydrogen oxide particles that include at least one non-nucleic acid biological remodeling agent.

In one embodiment, the at least one biological remodeling agent is utilized in at least partially constructing or reconstructing at least a portion of one or more biological tissues or organs. In on embodiment, the at least one biological remodeling agent assists in the repair, enhancement, or replacement of at least a portion of at least one biological tissue structure or function. In one embodiment, the at least one biological remodeling agent assists in restoring, maintaining, or improving at least one tissue or organ function.

In one embodiment, at least one frozen particle composition, or frozen piercing implement including at least one biological remodeling agent or adhesive agent is utilized in at least partially generating at least one biological tissue de novo. In one embodiment, at least one frozen particle composition, or frozen piercing implement including at least one biological remodeling agent or adhesive agent is utilized in at least partially repairing at least one damaged or diseased biological tissue. In one embodiment, the at least one damaged or diseased biological tissue is located in vivo. In one embodiment, the at least one damaged or diseased biological tissue includes one or more wounds.

In one embodiment, a method includes at least partially constructing or reconstructing at least one biological tissue or organ by administering one or more frozen particle compositions, or frozen piercing implements in such a manner that at least one agent is deposited, wherein the one or more frozen particle compositions, or frozen piercing implements include at least one biological remodeling agent, at least one adhesive agent, at least one therapeutic agent, at least one reinforcement agent, at least one abrasive, at least one microneedle, or at least one explosive material. In one embodiment, one or more frozen particle compositions, or frozen piercing implements are deposited, resulting in at least partially constructing or reconstructing at least one biological tissue or organ.

In one embodiment, the at least one biological remodeling agent is administered to at least one substrate, as described herein. In one embodiment, the at least one biological remodeling agent includes at least one nontoxic agent. In one embodiment, the at least one biological remodeling agent includes a biocompatible, bioresorbable, or biodegradable agent. In one embodiment, the at least one substrate to which the one or more frozen particle compositions, or frozen piercing implements are deposited or administered is at least one of biocompatible, bioresorbable, or biodegradable.

In one embodiment, at least one scaffold is utilized for construction, reconstruction, or remodeling of at least one biological tissue. In one embodiment, the at least one scaffold is at least partially generated by deposition or administration of one or more frozen particle compositions, or frozen piercing implements including at least one biological remodeling agent. In one embodiment, the at least one scaffold is at least one of biocompatible, bioresorbable, or biodegradable.

In one embodiment, a template or molding is utilized for deposition of one or more frozen particle compositions, or frozen piercing implements including at least one biological remodeling agent. In one embodiment, the frozen particle composition, or frozen piercing implement includes one or more of a biological remodeling agent, a therapeutic agent, abrasive, explosive material, adhesive agent, or other agent. In one embodiment, the template or molding is at least one of nontoxic, biocompatible, bioresorbable, or biodegradable. In one embodiment, the one or more biological remodeling agents, are deposited or administered directly onto at least one substrate that is utilized in constructing, reconstructing, or remodeling at least one biological tissue.

In one embodiment, one or more frozen particle compositions, or frozen piercing implements, including at least one biological remodeling agent, are delivered to at least one scaffold, including a three dimensional porous scaffold. In one embodiment, the scaffold includes means for cell attachment, means for cell proliferation, means for cell differentiation, means for cell migration, means for cell contracting, means for cell expression, means for cell matrix production, or means for cell spreading. In one embodiment, the at least one scaffold includes seeding at least one cell (e.g., a live cell) within at least one scaffold. In one embodiment, seeding at least one cell within the at least one scaffold occurs prior to, simultaneously with, or subsequent to, at least partially generating, implanting, or transplanting the at least one scaffold. In one embodiment, the at least one scaffold includes injecting at least one biological remodeling agent and at least one cell (e.g., a live cell) mixture to the at least one substrate for at least partially constructing, reconstructing, or remodeling at least one biological tissue. In one embodiment, the scaffold is at least partially generated, implanted, or transplanted and is eventually seeded with a subject's own cells, either naturally or artificially.

In one embodiment, the at least one biological remodeling agent includes one or more of calcium phosphate, albumin, cytokine, pegylated cytokine, bone, cartilage, globulin, fibrin, thrombin, glutaraldehyde-crosslinked pericardium, hide powder, hyaluronic acid, hydroxyapatite, keratin, ligament, nitinol, nucleic acid polymers, polyethylene, polyethylene glycol, polyethylene glycol diacrylate, polyethylene terephthalate fiber, polyglycol, polylactate, polytetrafluoroethylene, polylactic acid, polyglycolic acid, polycaprolactone, PURAMATRIX™ self-assembly peptide hydrogel fibers, linear aliphatic polyester, tendon, fibrinogen, hyaluronate, chitin, chitosan, methylcellulose, alginate, hyaluronic acid, agarose, cellulose, polyaldehyde gluronate, Factor XIII, Factor XII, silk, nylon, collagen, elastin, silicone, polyurethane, ceramic powder, pectin, wax, glycosaminoglycan, poly($\alpha$-hydroxyacid), selectin, glutaraldehyde, hydrophobic non-glycosylated protein, hydrogel, peptide hydrogel, or gelatin.

In one embodiment, the at least one biological remodeling agent includes one or more of Type I collagen, Type II collagen, Type III collagen, Type VII collagen, or Type X collagen. In one embodiment, the at least one biological remodeling agent includes one or more of elastin fibers or soluble elastin.

In one embodiment, the biological remodeling agent includes at least one member of the Transforming Growth Factor $\beta$ superfamily, including but not limited to bone morphogenetic/osteogenic proteins (BMPs/OPs), growth differentiation factors, activin A and B, inhibin A and B, Antimullerian hormone, Nodal, TGF-$\beta$ type receptors such as Activin Type I receptors, Activin Type II receptors, transducers/SMAD molecules, ligand inhibitors (e.g., Cerberus, chordin, Dan, Decorin, Follistatin, Gremlin, Lefty, LTBP1, Noggin, THBS1), co-receptors (e.g., BAMBI-Cripto), SARA, or other molecules. (See, for example, Aarabi et al., PLOS Med., vol. 4, Issue 9, pp. 1464-1470 (2007). In one embodiment, the at least one biological remodeling agent includes one or more of epidermal growth factor (EGF), platelet derived growth factor (PDGF), fibroblast growth factor (FGF), insulin-like growth factor (IGF-1), human growth hormone, granulocyte-colony stimulating factor (G-CSF), or granulocyte-macrophage colony-stimulating factor (GM-CSF). In one embodiment, one or more biological remodeling agents include at least one nucleic acid. In one embodiment, one or more biological remodeling agents include at least one RNA or DNA molecule. In one embodiment, the one or more biological remodeling agents include at least one of a protein, carbohydrate, or fat.

Some other non-limiting examples of biological remodeling agents, as well as the general but non-limiting solidification mechanism of each, are set forth in Table III below. Abbreviations include: OPF: oligo(poly(ethylene glycol)fumarate); P(CL/TMC): poly(-caprolactone-co-trimethylene carbonate); PDLLA: poly(D,L-lactide); PEG: poly(ethylene glycol); PEO: poly(ethylene oxide); PEO-PPO-PEO: polyethylene oxide-polypropylene oxide-polyethylene oxide; PhosPEG-dMA: poly(ethylene glycol) di[ethylphosphatidyl (ethylene glycol)methacrylate]; PLA(Glc-Ser): Poly(L-lactic acid-co-glycolic acid-co-L-serine); PLA-PEG: poly(lactic acid)-poly(ethylene glycol; PLAL-ASP: Poly(lactic acid-co-lysine)-poly(aspartic acid); PLGA: Poly (DL-lactic-co-glycolic acid); PLLA: poly(L-lactic acid); PLLA-PEG: poly(L-lactide-ethylene glycol); PNIPAAm: poly(N-isopropylacrylamide); P(NIPAAm-AAc): Poly(N-isopropylacrylamide-acrylic acid); PPF: poly(propylene fumarate); P(PF-co-EG): poly(propylene fumarate-co-ethylene glycol; PVA: poly(vinyl alcohol). (See, for example, Hou et al., M. Mater. Chem., vol. 14, pp. 1915-1923 (2004), which is incorporated herein by reference.)

TABLE III

| Biological Remodeling Agent | Solidification mechanism |
| --- | --- |
| Calcium phosphate | Ceramics setting |
| Chitosan | Thermal gelation |
| Methylcellulose | Thermal gelation |
| Alginate | Photo cross-linking or ionic gelation |
| Hyaluronic acid | Photo cross-linking |
| Agarose | Thermal gelation |
| Fibrin | Thermal gelation |
| Gelatin | Thermal gelation |
| Poly(aldehyde gluronate) | Chemical cross-linking |
| PEG or PEO | Photo cross-linking |
| PEO-PPO-PEO | Thermal gelation |
| PEO-PLLA-PEO | Photo cross-linking |
| PLA-g-PVA | Photo cross-linking |
| PEO-PLLA | Thermal gelation |
| PLGA-PEG | Thermal gelation |
| PEG-co-Poly($\alpha$-hydroxy acid) | Photo cross-linking |
| PVA, PLAL-ASP, P(CL/TMC), PLA(Glc-Ser) or Polyanhydrides | Photo cross-linking |
| PPF, OPF, or P(PF-co-EG) | Photo cross-linking or radical polymerization |
| PhosPEG-dMA | Photo polymerization |
| PNIPAAm-PEG, PNIPAAm-gelatin, P(NIPAAm-AAc) | Thermal gelation |
| PEG based hydrogels | Enzymatic cross-linking or Michael-type addition reaction |
| PLA-PEG-biotin | Self-assembly |

In one embodiment, at least one frozen particle composition, or frozen piercing implement is administered to at least one substrate by pushing, pulling, drilling, utilizing a screw-type action, propelling, ejecting, or accelerating a plurality of frozen particle compositions, or frozen piercing implements toward the at least one substrate. In one embodiment, propelling, ejecting, or accelerating the plurality of frozen particle compositions, or frozen piercing implements toward the at least one substrate includes at a predetermined angle, a predetermined velocity, a predetermined rate of administration, a predetermined spatial pattern, a predetermined location, a predetermined time sequence, or a predetermined depth. In one embodiment, two or more of the plurality of frozen particle compositions, or frozen piercing implements include two or more biological remodeling agents configured to physically or chemically bind upon administration. In one embodiment, administering the one or more frozen particle compositions, or frozen piercing implements to at least one substrate includes contacting the at least one substrate with the one or more frozen particle compositions, or frozen piercing implements. In one embodiment, administering the one or more frozen particle compositions, or frozen piercing implements to at least one substrate includes contacting the at least one substrate with the at least one biological remodeling agent.

Substrates

In one embodiment, the one or more frozen particle compositions, frozen piercing implements, or frozen piercing implement devices are administered to at least one substrate. Specific non-limiting examples of various different substrates are provided throughout the application.

In one embodiment, the at least one substrate includes at least one nontoxic, biodegradable, bioresorbable, or biocompatible substrate. In one embodiment, the at least one substrate includes one or more of a cell, tissue, organ, structure, device, or food product. In one embodiment, the substrate includes at least a portion of which is naturally, artificially, or synthetically derived. In one embodiment, the substrate includes at least a portion of which is genetically altered. In one embodiment, at least one frozen particle composition, or frozen piercing implement is administered to at least one cell or cell component for gene delivery.

In one embodiment, the structure or device may include a prosthesis, cell matrix or scaffold, tissue matrix or scaffold, supplement, implement, bandage, tourniquet, wound dressing, splint, stent, patch, gauze, covering, shunt, needle, scalpel, matrix, sponge, mesh, woven fabric, knitted fabric, film, instrument, or other tool or item. (See, for example, U.S. Patent Application Publication No. 20070021816, which is incorporated herein by reference.) In one embodiment, the device includes at least one mechanical or electrical device. In one embodiment, the device includes, but is not limited to, at least one mechanical or electrical device. Examples of particular devices are described herein.

In one embodiment, the substrate is located in at least one of in situ, in vitro, in vivo, in utero, in planta, in silico, or ex vivo. In one embodiment, the at least one substrate is transplanted or implanted into at least one subject. In one embodiment, the at least one substrate is ingested by at least one subject. In one embodiment, the at least one substrate includes at least one biological cell or tissue. In one embodiment, the at least one biological cell or tissue is from at least one donor or recipient. In one embodiment, the at least one donor includes at least one cadaver. In one embodiment, the at least one substrate includes at least one implantable or transplantable substrate. In one embodiment, the at least one substrate is transplanted or implanted into at least one subject. In one embodiment, the at least one substrate includes at least one biological tissue from at least one donor or recipient.

In one embodiment, the temperature of the substrate is adjusted for administration of one or more frozen particle compositions, or frozen piercing implements. In one embodiment, the temperature of the substrate is increased or decreased in order to adjust the rate of melting, sublimation, evaporation, transformation, activation, etc. of the one or more frozen particle compositions, or frozen piercing implements or a component thereof.

In one embodiment, the pressure exerted on a substrate is adjusted for administration of one or more frozen particle compositions, or frozen piercing implements. In one embodiment, the pressure exerted on a substrate is increased or decreased in order to adjust the rate of melting, sublimation, evaporation, transformation, activation, etc. of the one or more frozen particle compositions, or frozen piercing implements or a component thereof. In one embodiment, the at least one substrate includes at least one polymer or hydrogel.

In one embodiment, the at least one agent is delivered to a single biological cell or tissue. In one embodiment, the at least one substrate is ingested by at least one subject. In one embodiment, the at least one substrate includes at least one implantable or transplantable substrate. In one embodiment, the at least one substrate is transplanted or implanted into at least one subject. In one embodiment, the substrate includes at least one biological tissue from at least one donor or recipient. In one embodiment, the at least one substrate includes at least a portion of at least one subject. In certain embodiments, administering at least one frozen particle composition or frozen piercing implement includes self-administering the at least one frozen piercing implement by the at least one subject.

In one embodiment, the at least one biological tissue includes one or more of a plant part, or whole plant. In one embodiment, the at least one biological tissue includes one or more of a stalk, stem, leaf, root, or tendril. In one embodiment, the at least one biological tissue includes at least one of meristem tissue, plant embryo tissue, cotyledon tissue, shoot apex tissue, scutellum tissue, epicotyl tissue, hypocotyl tissue, stamen tissue, receptacle tissue, anther tissue, stigma tissue, ovary tissue, carpel tissue, endosperm tissue, or seed germ tissue. In one embodiment, the at least one biological tissue includes transgenic tissue. In one embodiment, the transgenic tissue includes meristem tissue cells for later generations. Non-limiting examples of plants that are included are cereal crops, fruits, nuts, vegetables, woody species, ornamental flower, cash crops (e.g., tobacco), and other plants.

In one embodiment, one or more frozen particle compositions, or frozen piercing implements are delivered to a substrate including at least one food or beverage product, or other product for consumption. In one embodiment, the at least one food product includes one or more of an animal, plant, fungal, or other biological food product. In one embodiment, the at least one food product includes at least one non-biological based food product. In one embodiment, the at least one food product includes, but not limited to at least one of a grain product; vegetable, fruit, leaf, stem, or other plant product; meat, milk, eggs, or other animal product; including processed products thereof. In one embodiment, one or more frozen particle compositions, or frozen piercing implements are delivered to at least one of a juice, cut food product, canned food product, pulped food product, frozen food product, homogenized food product, sterilized food product, dehydrated food product, or otherwise processed food product. In one embodiment, one or more frozen particle compositions, or frozen piercing implements include at least one component of a food product.

In one embodiment, one or more frozen particle compositions, or frozen piercing implements are delivered to at least one product for consumption. In one embodiment, the product for consumption includes, but is not limited to at least one of a hygienic product (e.g., toothpaste, deodorant, perfume, shampoo, soap, etc.), a cosmetic product (e.g., lotion, lipstick, nail polish, or other facial cosmetics, etc.).

In one embodiment, one or more frozen particle compositions, or frozen piercing implements are delivered to at least one outdoor or indoor area (e.g., road surface, carpet, ice rink, garden, jungle, etc.).

In one embodiment, the substrate includes, but is not limited to, biological tissue as described herein. For example, biological tissue includes soft tissues (such as connective tissue, or other soft tissue), or hard tissues (including calcified tissue, such as bone or teeth). In one embodiment, a cell includes, but is not limited to, at least one of an autologous cell, allogenic, xenogenic, stem cell, or syngenic cell. The one or more cells may include endogenous or exogenous cells relative to a particular subject. In one embodiment, the at least one substrate includes one or more stem cells (e.g., hematopoietic stem cells, adipocyte stem cells, neuronal stem cells, embryonic stem cells, hepatic stem cells, dermal stem cells, pancreatic stem cells, stem cells related to bone, stem cells related to muscle, or others). In one embodiment, the substrate includes at least one wound, or cell mass. Other examples of cells and biological tissues are described herein at other sections.

In one embodiment, the at least one biological tissue includes but is not limited to, one or more of cartilage, skin, scalp, hair, nail, nail bed, teeth, eye, ear, ovary, oviduct, tongue, tonsil, adenoid, liver, bone, pancreas, stomach, appendix, duct, valve, smooth muscle, blood vessel, bone marrow, blood, lymph, heart, lung, brain, breast, kidney, bladder, urethra, ureter, gall bladder, uterus, prostate, testes, vas deferens, fallopian tubes, large intestine, small intestine, esophagus, oral cavity, nasal cavity, otic cavity, connective tissue, muscle tissue, or adipose tissue. In one embodiment, the at least one tissue includes one or more of a tendon, vein (e.g., femoral or saphenous vein), artery, or capillary. In one embodiment, the at least one biological tissue includes embryonic or fetal tissue. In one embodiment, the at least one biological tissue includes a mucosal surface. In one embodiment, the at least one biological tissue includes a plant, animal, fungal or other food product (e.g., biological food product). In one embodiment, the at least one biological tissue includes meat.

In one embodiment, the treatment of at least one biological tissue includes one or more of ossicular chain reconstruction in otlogic surgery, nerve anastomosis (e.g. peripheral nerve anastomosis); cerebralspinal fluid sealing in neurological repair, vascular repair or anastomosis, ocular repair, gastrological repair, urological repair, skin closure, bronchial repair (e.g. bronchial stump leakage), alveolar repair, or dental fillings. In one embodiment, the at least one biological tissue includes fetal tissues or organs (e.g. in utero) and can include any of the tissues or organs described herein.

In one embodiment, the at least one biological tissue is located in at least one tissue or organ related to transplantation. In one embodiment, transplantation includes extraction or implantation of the at least one tissue or organ. In one embodiment, the at least one tissue or organ related to transplantation is extracted from at least one first biological source or subject and implanted into at least one second biological source or subject. In one embodiment, the at least one tissue or organ related to transplantation is cultured prior to implantation in a subject. In one embodiment, the tissue or organ related to transplantation is an artificial or synthetically derived tissue or organ (e.g. a bladder, heart, kidney, liver, pancreas, skin, eye, lung, nerve, blood vessel, and others). In one embodiment, the tissue or organ related to transplantation involves at least two sources (i.e. multiple species, partially artificial or synthetic, multiple biological cells or tissues including stem cells). In one embodiment, the at least one tissue or organ related to transplantation includes at least one donor or recipient tissue or organ. In one embodiment, the at least one tissue or organ is at least partly autologous.

In one embodiment, one or more blood vessels, including at least one of a vein, artery, or capillary is at least partially made by utilizing one or more frozen particle compositions, or frozen piercing implements. In one embodiment, the one or more blood vessels include at least one vascular graft at least partially made by utilizing one or more frozen particle compositions, or frozen piercing implements. In one embodiment, the at least one vascular graft includes at least one autologous component. See, for example, McAllister et al., Abstract, Lancet, vol. 373, No. 9673, pp. 1440-1446 (2009), which is incorporated herein by reference.

In one embodiment, the at least one substrate includes at least one cell mass. In one embodiment, the at least one cell mass includes at least one of a scar, pore, pit, eschar, granuloma, keloid, artheromatous plaque, abscess, pustule, scaling (e.g., psoriasis or eczema), infected tissue, hair follicle, necrotic tissue, stratum corneum, wrinkle, wound, tumor, skin structure, nevus, cyst, lesion, callus, neoplastic tissue, gangrenous tissue, or cellular deposit. In one embodiment, the at least one cell mass includes at least one benign or malignant tumor. In one embodiment, the at least one benign or malignant tumor relates to one or more of a melanoma, lymphoma, leukemia, sarcoma, blastoma, or carcinoma.

In one embodiment, the at least one cell mass is related to at least one blood clot, embolus, microorganism accumulation, blood vessel obstruction, duct obstruction, bowel obstruction, infection, gangrene, connective tissue destruction, tissue or organ damage, injury, white blood cell accumulation, or cancer.

In one embodiment, the at least one substrate includes one or more wounds. In one embodiment, the one or more wounds are located in at least one biological tissue or organ. In one embodiment, the one or more wounds are located in one or more of skin tissue, muscle tissue, eye tissue, nervous tissue, peritoneal tissue, an organ, connective tissue, neoplastic tissue, or bone tissue.

In one embodiment, the one or more wounds are located in at least one subject. The one or more wounds include but are not limited to at least one of an incision (including surgical incision such as for facial or other aesthetic construction or reconstruction, or other cranio-facial surgeries, laproscopic procedures, birthing assistance, or other surgical procedures), fracture, irritation, episiotomy, laceration, endovascular occlusion (e.g., aneurism), blood vessel anastomosis, nerve repair, abrasion, cerebral spinal fluid leak, puncture wound, penetration wound, gunshot wound, iatrogenic wound, severing, infection, ulcer, pressure sore, lesion, chemical burn (including but not limited to exposure to an irritant, plant, or synthetic chemical), dental caries, first-degree burn, second-degree burn, third-degree burn, fourth-degree burn, fifth-degree burn, or sixth-degree burn. In certain instances, the wound can be a result of a bite, such as a bite from an animal, insect, or arachnid.

In one embodiment, the at least one subject includes one or more of a vertebrate or invertebrate animal. In one embodiment, the at least one subject includes a fungus, or plant (including crop plants, as described herein). In one embodiment, the at least one subject includes insect cells, insects, bacteria, algae, plankton, or protozoa. In one embodiment, the at least one subject includes one or more of a reptile, mammal, amphibian, bird, or fish. In one embodiment, the at least one subject includes at least one human. In one embodiment, the at least one subject includes at least one of livestock, pet, zoo animal, undomesticated herd animal, wild animal, or product animal.

In one embodiment, the at least one subject includes at least one of a sheep, goat, frog, dog, cat, rat, mouse, vermin, monkey, duck, horse, cow, pig, chicken, shellfish, fish, turkey, llama, alpaca, bison, buffalo, ape, primate, ferret, wolf, fox, coyote, deer, rabbit, guinea pig, yak, chinchilla, mink, reindeer, elk, camel, fox, elk, deer, raccoon, donkey, or mule.

Detection Materials

In one embodiment, the one or more frozen particle compositions, or frozen piercing implements include at least one of a polymer, biopolymer, nanoparticle, sensor, micro-syringe, actuator, circuit, or other detection material. Such detection materials may allow for visualization of the one or more frozen particle compositions, or frozen piercing implements, the administration process, or provide other benefits (including but not limited to reinforcement, adhesive, biological remodeling, abrasive, explosive, or therapeutic benefits). In one embodiment, the nanoparticle includes one or more of a nanorod, nanobone, nanocapsule, or other particle. In one embodiment, the nanoparticle releases its payload when exposed to an energy source, including heat or light. In one embodiment, the nanoparticles have a time-release payload of, for example, one or more therapeutic agents, adhesive agents, biological remodeling agents, reinforcement agents, abrasives, explosive materials, or other agents.

In certain instances, the detection material can be located on or in the one or more frozen particle compositions, or frozen piercing implements, or it can be intermixed with the one or more frozen particle compositions, or frozen piercing implements. In certain instances, the detection material provides a "tracer" agent that allows for visualization of one or more locations of administration of the at least one frozen particle composition, or frozen piercing implement. For example, in one embodiment, the detection material includes a particle with altered isotopes (e.g., for altering the mass of particles as a tracer). In one embodiment, only certain frozen particle compositions, or frozen piercing implements of a plurality of frozen particle compositions, or frozen piercing implements include one or more detection materials. In one embodiment, one or more detection materials are included in one or more frozen particle compositions, or frozen piercing implements in a predictable or predictive manner, for example, about every $2^{nd}$, about every $3^{rd}$, about every $4^{th}$, about every $5^{th}$, about every $6^{th}$, about every $7^{th}$, about every $8^{th}$, about every $9^{th}$, about every $10^{th}$, about every $20^{th}$, about every $50^{th}$, about every $100^{th}$, about every $1000^{th}$, about every $2000^{th}$, or about every $5000^{th}$, etc. frozen particle composition, or frozen piercing implement includes one or more detection materials.

In certain instances the detection material is located on the at least one frozen particle composition, or frozen piercing implement or the at least one frozen particle. In other instances, the detection material is separate from the at least one frozen particle composition, or frozen piercing implement. In certain instances, the detection material forms a mixture with the frozen particle composition, or frozen piercing implement. In certain instances, the detection material is separate from the one or more frozen particle compositions, or frozen piercing implements and is administered at approximately the same time, in approximately the same place, or in approximately the same manner as the one or more frozen particle compositions, or frozen piercing implements. In one embodiment, the detection material is located in at least one cavity or compartment of the one or more frozen particle compositions, or frozen piercing implements.

In one embodiment, detection material includes a detection label including but not limited to, a colorimetric label, a radioactive label, a light-emitting label (such as a luminescent compound, a fluorescent compound, a phosphorescent compound, or a quantum dot), a nucleic acid label, a protein label, an antibody label, a ligand label, a receptor label, a magnetic label, or other detection label. In one embodiment, the at least one detection material includes but is not limited to, at least one electronic identification device. In one embodiment, the at least one electronic identification device includes at least one radio frequency identification device.

In one embodiment, the at least one detection material includes but is not limited to, at least one radioactive element. In one embodiment, the radioactive element includes but is not limited to, $^{32}P$, $^{35}S$, $^{13}C$, $^{131}I$, $^{191}Ir$, $^{192}Ir$, $^{193}Ir$, $^{201}Tl$, or $^{201}Tl$, $^{3}H$. In one embodiment, the at least one detection material includes at least one radioactive, luminescent, colorimetric or odorous substance. In one embodiment, the at least one colorimetric substance includes one or more of an inorganic, organic, biological, natural, artificial, or synthetic substance. The colorimetric substance may include, but not be limited to a dye or a pigment. The colorimetric substance may include a chromogenic substrate.

In one embodiment, the at least one detection material includes at least one light-emitting substance, such as a luminescent substance, a fluorescent substance, phosphorescent substance, or quantum dot. In one embodiment, the at least one detection material is nontoxic, biocompatible, bioresorbable, or biodegradable.

Some examples of colorimetric substances include, but are not limited to, colored agents that have an affinity for a cell or tissue, such as acid dyes (e.g., water-soluble anionic dyes), basic dyes (e.g., water-soluble cationic dyes), direct or substantive dyes (e.g., stains for nucleic acids, proteins, lipids, carbohydrates, cell populations, tissues, or organelles), mordant dyes, vat dyes, reactive dyes, disperse dyes, azo dyes, sulfur dyes, food dyes, solvent dyes, carbene dyes, or others. Some examples of chromophores that can be utilized include, but are not limited to, dyes that are based on or derivatives of acridine, anthraquinone, arymethane (e.g., diphenyl methane, triphenyl methane), —N═N azo structure, phthalocyanine, diazonium salts, —NO$_2$ nitro functional group, —N═O nitroso functional group, phthalocyanine, quinine, azin, eurhodin, safranin, indamin, indophenol, oxazin, oxazone, thiazin, thiazole, xanthene, fluorine, pyronin, fluorine, rhodamine, or others. In one embodiment, the colorimetric substance includes trypan blue.

In one embodiment, the detection material includes at least one light-emitting substance, including but not limited to luminescent substances (e.g. bioluminescent substances, chemiluminescent substances, luciferin, isoluminol, luminescent minerals, etc.). In one embodiment, the detection material includes one or more one or more fluorescent tags, including but not limited to fluorescein, phycobilin, phycoerythrin, phycourobilin, chlorophyll, phycocyanin, allophycocyanin, green fluorescent protein, or others. In one embodiment, the at least one detection material includes but is not limited to, at least one of a diamagnetic particle, ferromagnetic particle, paramagnetic particle, super paramagnetic contrast agent, particle with altered isotope, or other magnetic particle.

Some non-limiting examples of particular diamagnetic substances include wood, water, organic compounds (such as petroleum), metals (including copper, mercury, gold, bismuth), or benzoic acid.

Methods, Devices, Systems for Administering a Frozen Particle Composition or Frozen Piercing Implement As described herein, a device or machine (including a computer) may be utilized in various aspects relating to compositions, methods, or systems relating to one or more frozen particle compositions, or frozen piercing implements (or the devices thereof). Non-limiting examples of such aspects may include predicting or calculating various properties or characteristics relating to the one or more frozen particle compositions, or frozen piercing implements, any substrate, any subject, any administration device, or any administration protocol. Any method disclosed herein is implicitly intended to also include "means for" carrying out the method. One or more methods disclosed include computer-implemented methods.

In one embodiment, a method or means for making one or more frozen particle compositions, or frozen piercing implements optionally includes at least one agent. In one embodiment, a method or means for administering or delivering one or more frozen particle compositions, or frozen piercing implements is disclosed. In one embodiment, a method or means for administering at least one frozen particle composition, or frozen piercing implement includes administering at least one agent to a substrate.

In one embodiment, the at least one agent may provide promoting wound healing; promoting healing of skin, cartilage, or bone; filling of skin wrinkles or flaws; filling of connective tissue; treating vesico-ureteral reflux; treating urinary incontinence; fixing prostheses or materials to at least one biological tissue; or producing at least one film, gel, or membrane for use in vitro or in vivo to assist in a biological function.

In one embodiment, a method or means for of providing at least one agent, such as a biological remodeling agent, to at least one substrate comprises administering one or more frozen particle compositions to at least one substrate, wherein the one or more frozen particle compositions, or frozen piercing implements include at least one biological remodeling agent as described herein. In one embodiment, the one or more frozen particle compositions, or frozen piercing implements have one or more phases including at least one of amorphous solid water, low density amorphous ice, high density amorphous ice, very high density amorphous ice, clathrate ice, hyperquenched glassy water, ice Ic, ice II, ice III, ice IV, ice V, ice VI, ice VII, ice VIII, ice IX, ice X, ice XI, ice XII, ice XIII, ice XIV, or ice XV. In one embodiment, the one or more frozen particle compositions, or frozen piercing implements including one or more frozen particles and at least one agent have one or more phases including at least one of amorphous solid water, low density amorphous ice, high density amorphous ice, very high density amorphous ice, clathrate ice, hyperquenched glassy water, ice Ic, ice II, ice III, ice IV, ice V, ice VI, ice VII, ice VIII, ice IX, ice X, ice XI, ice XII, ice XIII, ice XIV, or ice XV.

In one embodiment, a method or means for at least partially constructing or at least partially reconstructing at least one biological tissue or organ comprises administering one or more frozen particle compositions, or frozen piercing implements that include at least one agent (such as at least one of a biological remodeling agent, adhesive agent, therapeutic agent, reinforcement agent, abrasive, or explosive material) in such a manner that the at least one agent is deposited. In one embodiment, the at least one agent includes at least one biological remodeling agent.

In one embodiment, the method or means for includes abrading or ablating one or more surfaces of the at least one substrate prior to, during, or subsequent to the administering of the one or more frozen particle compositions, or frozen piercing implements. In one embodiment, the method or means for administering one or more frozen particle compositions, or frozen piercing implements is provided in such a manner as to induce at least one cellular event. In one embodiment, the at least one cellular event includes one or more of: cell migration, cell attachment, cell retention, cell differentiation, cell proliferation, apoptosis, diffusion of materials, angiogenesis, nucleic acid expression, protein translation, protein modification, carbohydrate production, carbohydrate secretion, protein secretion, fat production or fat secretion. In one embodiment, the method further includes administering at least one component including an optical, photonic, or electronic article. In one embodiment, the at least one article is configured to communicate with at least one computer system. In one embodiment, the at least one article is configured to monitor at least one characteristic of the at least one biological tissue.

As described herein, in one embodiment, computer-aided tissue engineering (CATE) is utilized in the design (including tissue scaffold design), image processing, predicting, modeling, simulation, manufacturing, administration or delivery of at least one frozen particle composition, or frozen piercing implement, informatics (including computer-aided tissue classification and application for tissue identification and characterization at different tissue hierarchical levels), or other aspects of tissue reconstruction with one or more frozen particle compositions, or frozen piercing implements described. In one embodiment, computer-aided tissue engineering compares information regarding at least one of design, Image processing, predicting, modeling, simulation, manufacturing, administration or delivery of at least one frozen particle composition, or frozen piercing implement, or informatics for at least one biological tissue with at least one dataset or database. In one embodiment, a dataset or database is generated from information regarding at least one of design, image processing, predicting, modeling, simulation, manufacturing, administration or delivery of at least one frozen particle composition, or frozen piercing implement, informatics, or other aspect of tissue reconstruction with one or more frozen particle compositions, or frozen piercing implements described.

In one embodiment, ink-jet printing is utilized for stereo-model fabrication, or for direct biological tissue construction, reconstruction, or remodeling through deposition or administration of one or more frozen particle compositions. (See, for example, Mironov, et al, Trends in Biotech. Vol. 21, No. 4; pp. 157-161 (2003), which is incorporated herein by reference.) In one embodiment, the one or more frozen particle compositions, or frozen piercing implements include one or more agents that fuse upon administration or deposition. (See, for example, Jakab, et al, Tissue Eng. Part A, Vol. 14, No. 3 pp. 413-421 (2008), which is incorporated herein by reference.)

In one embodiment, at least one of rapid prototyping (including but not limited to stereolithography), fused deposition modeling, three-dimensional printing, selective deposition modeling, solid free-form fabrication (SFF), selective laser sintering, laminated object manufacturing, gas foaming, solvent casting and particulate leaching, emulsification, freeze-drying, phase separation, shape deposition manufacturing, or other method is utilized with administration of one or more frozen particle compositions, or frozen piercing implements for tissue reconstruction. (See, for example, U.S. Patent Application Publication No. 20040075196; Barry, et al., Phil. Trans. R. Soc. A vol. 364, pp. 249-261 (2006); and U.S. Patent Application Publication No. 20080145639, each of which is incorporated herein by reference.) In one embodiment, a model is used for designing or developing the architecture of the at least one biological tissue prior to administering or depositing the one or more frozen particle compositions, or frozen piercing implements for at least partially constructing, at least partially reconstructing, or at least partially remodeling at least one biological tissue. In one embodiment, the one or more frozen particle compositions, or frozen piercing implements are administered or deposited directly onto at least one substrate for at least partially constructing, at least partially reconstructing, or at least partially remodeling at least one biological tissue. In one embodiment, the at least partial reconstruction, at least partial construction, or at least partial remodeling of at least one biological tissue includes depositing at least one agent of at least one frozen particle composition, or frozen piercing implement. In one embodiment, the at least partial reconstruction, at least partial construction, or at least partial remodeling of at least one biological tissue includes at least partially abrading or ablating at least one surface of at least one substrate (e.g., biological tissue) with at least one frozen particle composition, or frozen piercing implement.

In one embodiment, sample cells are grown ex vivo, introduced with scaffold in the appropriate environment for cell or tissue growth utilizing one or more frozen particle compositions, or frozen piercing implements, and the cells implanted or transplanted into at least one subject. (See, for example, Sun et al., Biotechnol. Appl. Biochem. vol. 39, pp. 29-47 (2004), which is incorporated herein by reference.)

Computer-aided tissue modeling utilized in conjunction with certain embodiments for administration of one or more frozen particle compositions, or frozen piercing implements includes imaging data acquisition. For example, a medical imaging modality must be capable of one or more of producing three-dimensional views of anatomy, differentiating heterogenous tissue types and displaying the vascular structure, as well as generating computational tissue models.

In one embodiment, computer-aided tissue modeling utilized in conjunction with certain embodiments for administration of one or more frozen particle compositions, or frozen piercing implements includes generating at least one of a two-dimensional plot or a three-dimensional model. In one embodiment, a two-dimensional plot or three-dimensional view of anatomical modeling includes one or more of geometry, morphology, volumetric representation, mechanical, deformation, kinematic modeling, contour-based modeling, surface extraction, or solid modeling. In one embodiment, anatomical modeling occurs by way of computer-assisted tomography (CAT) or computed tomography (CT) scan, positron emission tomography (PET) scan, magnetic-resonance imaging (MRI), ultrasound, electrical-impedance monitoring, x-ray, microscopy, multiphoton calcium-imaging, or other imaging technique or device. (See, for example, Girod et al, J. Cranio-Max. Surgery vol. 29, pp. 156-158 (2001), which is incorporated herein by reference.) In one embodiment, multiple three-dimensional images are assembled or integrated for modeling of the tissue or organ.

Computer-aided tissue information utilized in conjunction with administration of one or more frozen particle compositions, or frozen piercing implements includes one or more of cell or tissue classification, hard tissue classification, soft tissue classification, tumor diagnosis, morphometric or cytometric information, tumor cell detection, tissue properties, cell aggregation, cell or tissue growth, cell to cell interaction, or cell to tissue interaction.

In one embodiment, at least one computer system is configured to provide one or more instructions to one or more devices for deposition or administration of one or more frozen particle compositions, or frozen piercing implements. In one embodiment, at least one device is configured to deposit or administer one or more frozen particle compositions, or frozen piercing implements on any x, y, or z axis. In one embodiment, the at least one computer system provides one or more instructions for predicting, controlling, or varying the administration of one or more frozen particle compositions, or frozen piercing implements or deposition of at least one agent included in the one or more frozen particle compositions, or frozen piercing implements on any x, y, or z location. In one embodiment, the at least one computer system provides one or more instructions for temporal, spatial, or regional locations for deposition or administration of one or more frozen particle compositions, or frozen piercing implements. Other components of the at least one computer system or device are included in the figures as described.

Computer-aided tissue scaffold design and manufacturing utilized in conjunction with certain embodiments for administration of one or more frozen particle compositions, or frozen piercing implements includes one or more of tissue scaffold modeling, biomimetic design, tissue scaffold fabrication, hybrid scaffold and cells, cell pattern, printing and deposition, or blueprint and organ hierarchical modeling. For example, in one embodiment, at least one parameter for at least partially constructing, at least partially reconstructing, or at least partially remodeling at least one tissue that are considered in design and administration of one or more frozen particle compositions, or frozen piercing implements, includes one or more of porosity, pore size, interconnectivity, transport properties, cell-tissue formation, mechanical strength, facilitation of attachment or distribution, growth of regenerative tissue and facilitate the transport of nutrients or other factors.

In one embodiment, the one or more frozen particle compositions, or frozen piercing implements are administered to at least one substrate by way of biopolymer deposition layering. For example, technology related to a micronozzle-based layered manufacturing, a microsyringe-based deposition, three dimensional plotting (e.g., Bioplotter, Envision Tech., Marl, Germany), or micromolding (e.g., by vacuum-molding) are capable of being utilized with the one or more frozen particle composition, or frozen piercing implement deposition. (See, for example, U.S. Patent Application Publication No. 20060195179.)

In one embodiment, the reconstructed tissue manufactured by use of one or more frozen particle compositions, or frozen piercing implements includes at least one material that mimics natural structures or functions, or enhances natural tissue growth. For example, in one embodiment, one or more frozen particle compositions, or frozen piercing implements are included in "smart" tissue scaffolds including one or more of a sensor, syringe, therapeutic agent, electronic article, nano-scale device, micro-scale device, or feedback mechanism. For example, at least one biosensor, circuit, or other electronic article can be included for monitoring tissue growth, dissolution, deterioration, biochemical function, structural integrity or function, immunological reaction, or other activities or conditions; or for providing a feedback mechanism. In one embodiment, the at least one optical, photonic, or electronic article included in the at least one tissue or organ is capable of communicating with at least one computer system.

In addition, one or more agents are included in one embodiment of the tissue reconstructed with one or more frozen particle compositions, or frozen piercing implements. Such agents include at least one of a therapeutic agent, abrasive, explosive material, adhesive agent, reinforcement agent, biological remodeling agent, one or more cells, or other agent. In one embodiment, the reconstructed or remodeled tissue includes at least one gene-activated matrix that allows for incorporation of one or more specific genes when one or more cells are administered to the matrix, or are allowed to migrate to the matrix. In one embodiment, one or more frozen particle compositions, or frozen piercing implements are utilized in three-dimensional cell or organ printing.

As described herein, in one embodiment the at least one biological remodeling agent includes one or more of: scaffolding materials, cells, nutrients, growth factors, or other components for at least partially constructing at least one tissue or organ de novo. See Sun, et al, Ibid.

In one embodiment, a scaffold is constructed, at least in part by seeding living cells into the scaffold. As described herein, various materials are capable of being utilized as a scaffold by delivering one or more frozen particle compositions, or frozen piercing implements, or deposition of at least one agent included in one or more frozen particle compositions, or frozen piercing implements. In particular, materials including but not limited to, pastes, resins, gels, bone cements, cellulose, silicone, polyurethanes, hydrogels, chitosan, or ceramic powders can be used.

Also as described herein, one or more materials utilized for the scaffold can be used for cell seeding, delivery systems for one or more therapeutic agents, other agents, or for integrating one or more angiogenic factors, growth factors, cytokines, or other agents.

In one embodiment, a composition includes an ex vivo biological tissue or organ that is at least partially constructed or at least partially reconstructed by administering one or more frozen particle compositions, or frozen piercing implements. In one embodiment, the one or more frozen particle compositions, or frozen piercing implements include at least one of a therapeutic agent, adhesive agent, biological remodeling agent, explosive material, abrasive, or reinforcement agent.

In one embodiment, the ex vivo biological tissue or organ is at least partially constructed or at least partially reconstructed de novo by administering one or more frozen particle compositions, or frozen piercing implements. In one embodiment, the one or more frozen particle compositions, or frozen piercing implements are administered to at least one substrate. In one embodiment, the at least one substrate includes one or more of a cell, tissue, organ, structure, or device. In one embodiment, the composition further includes at least one article including an optical, photonic, or electronic article. In one embodiment, the at least one article is configured to communicate with at least one computer system. In one embodiment, the at least one article is configured to monitor at least one characteristic of the at least one biological tissue or organ. In one embodiment, the at least one characteristic of the at least one biological tissue or organ includes one or more of: tissue formation, tissue growth, cell proliferation, cell differentiation, apoptosis, dissolution, deterioration, nuclear division, biochemical function of at least one cell, biochemical function of at least one tissue, biochemical function of at least one organ, structural integrity, structural function, immunological reaction, or durability of the at least one biological tissue or organ. In one embodiment, the at least one characteristic of the at least one biological tissue or organ includes one or more of tissue formation associated with at least one substrate, tissue growth associated with at least one substrate, cell proliferation associated with at least one substrate, cell differentiation associated with at least one substrate, apoptosis associated with at least one substrate, dissolution associated with at least one substrate, deterioration associated with at least one substrate, biochemical function of at least one cell or tissue associated with at least one substrate, structural integrity of at least one substrate, structural function of at least one substrate, immunological reaction to at least one substrate, or durability of at least one substrate.

In one embodiment, a composition comprises a support means for aiding in at least partially constructing or at least partially reconstructing at least one biological tissue or organ; and one or more frozen particle compositions, or frozen piercing implements as described herein. In one embodiment, the one or more frozen particle compositions, or frozen piercing implements include at least one biological remodeling agent, adhesive agent, explosive material, abrasive, reinforcement agent, or therapeutic agent. In one embodiment, the support means includes at least one substrate configured for biological tissue formation or tissue growth. In one embodiment, the support means includes one or more of a cell scaffold, a tissue scaffold, extracellular matrix, methylcellulose, agarose, cellulose, a cell, a polymer, or other substrate. In one embodiment, the support means includes at least one substrate configured for promoting one or more of: cell migration, cell attachment, cell retention, cell differentiation, cell proliferation, apoptosis, diffusion of materials, angiogenesis, nucleic acid expression, protein translation, protein modification, protein secretion, carbohydrate production, carbohydrate secretion, fat production, or fat secretion.

In one embodiment, the one or more frozen particle compositions, or frozen piercing implements are deposited on a pre-existing substrate scaffolding, such as a flat or honeycomb film. See, for example, Nishikawa et al., Mat. Res. Soc. Symp. Proc. Vol. 724 pp, N11.7.1-N 11.7.6 (2002). In one embodiment, at least one agent included in one or more frozen particle compositions, or frozen piercing implements are deposited such that the scaffolding is formed entirely from such deposition.

In one embodiment, the one or more frozen particle compositions, or frozen piercing implements include one or more cells. In one embodiment, the one or more cells are deposited during administration of the one or more frozen particle compositions, or frozen piercing implements. In one embodiment, the one or more frozen particle compositions, or frozen piercing implements are administered to at least one substrate. In one embodiment, the one or more cells serve particular functions. In one embodiment, the one or more cells serve at least one function including: seeding the scaffold, populating the tissue, reducing an immune reaction, facilitating tissue function, promoting cellular or tissue formation, promoting cellular or tissue proliferation, promoting cellular or tissue differentiation, promoting cellular or tissue apoptosis, modulating diffusion of materials, or increasing tissue growth.

In one embodiment, at least one scaffold, or other substrate is at least partially generated in at least one of in vitro, in vivo, ex vivo, in utero, or in planta. In one embodiment, one or more cells are utilized for seeding at least one scaffold in at least one of in vitro, in vivo, ex vivo, in utero, or in planta. In one embodiment, the scaffold or other substrate is at least partially generated in at least one of in vitro, in vivo, ex vivo, in utero, or in planta, and subsequently is transplanted or implanted into at least one subject. In one embodiment, the subject includes the same subject in which the scaffold or other substrate was at least partially generated. In one embodiment, wherein the scaffold or other substrate is transplanted or implanted, the scaffold or other substrate is modified in vitro, in vivo, ex vivo, in utero, or in planta prior to transplantation or implantation into at least one subject. In one embodiment, the at least one scaffold or at least one remodeled or reconstructed tissue is transplanted or implanted one or more times. In at least on embodiment, at least one substrate, including at least one tissue scaffold, is at least partially generated in vivo, and subsequently relocated within the same subject. (See, for example, Ripamonti et al., J. Anat. Vol. 209, pp. 447-468 (2006), which is incorporated herein by reference.)

In one embodiment, construction, reconstruction, or remodeling of at least one biological tissue or organ includes at least one of designing a blueprint or model. In one embodiment, the blueprint or model includes a software representation containing bio-information, graphical representation, physical or material information, or anatomic or geometric information. In one embodiment, the blueprint or model includes a process model, including a software representation that contains the printing operation control commands, process planning, or toolpath generated for the blueprint or model and machine hardware and control system. In one embodiment, the blueprint or model includes a process machine, including at least one of a hardware representation that is capable of printing; and a tissue or organ culture system that is capable of maintaining or growing the printed living biological tissues. In one embodiment, the three dimensional organ or tissue printing with one or more frozen particle compositions, or frozen piercing implements includes at least one of pre-processing or developing plots or blueprints for the tissue or organ; processing or actual organ printing; or post-processing or organ conditioning and accelerated organ maturation.

In one embodiment, the blueprint or model includes a description or representation of details of organ anatomy, morphology, tissue heterogeneity, or vascular systems at different tissue or organ organizational scales. In one embodiment, deposition of at least one tissue remodeling agent includes a process planning program control system. In one embodiment, a toolpath program is included. In certain instances, the blueprint or model provides at least one description of the anatomy, geometry, internal architecture of an organ or tissue of interest (including tissue heterogeneity), individual tissue geometry and boundary distinction within the tissue or organ of interest; at least one definition of vascular networks and three dimensional topology in an organ of interest; or at least one database of information based on organ or tissue geometry, heterogeneity, and vascular network used for toolpath or other program generation of three-dimensional cell or organ printing.

In one embodiment, the blueprint or model is constructed from three dimensional organ anatomy, tomography, or geometry information provided by medical imaging data (for example, as provided for by CT, PET, MRI, ultrasound, x-ray, multiphoton calcium-imaging, or other imaging). Such images can be modified, simulated, transformed, processed (e.g., electronically processed), or modeled by a computer system, including by computer program, such as NURBS, polygonal modeling, or splines and patches modeling. (See, for example, Sun et al, Ibid.) For example, Boolean, scaling, Gaussian smoothing, homomorphic filtering, parametric estimation techniques, Monte Carlo simulations, wavelet based methods, smoothing, mirroring, gradient weighted partial differential equation smoothing (PDE), or other operations can be used to modify a CAD or other design. (See, for example, U.S. Patent Application Publication No. 20060233454, and U.S. Pat. No. 7,353,153, U.S. Pat. No. 7,212,958; each of which is incorporated herein by reference.) In one embodiment, a computer system utilized in at least partial tissue construction, reconstruction, or remodeling includes at least one software program interface to convert the CAD design or device into a heterogeneous material or assembly for formation of the tissue or organ by deposition of at least one agent included in one or more frozen particle compositions, or frozen piercing implements, or administration of one or more frozen particle compositions, or frozen piercing implements. (See, for example, U.S. Patent Application Publication No. 20060105011, which is incorporated herein by reference.) In one embodiment, processing results include utilizing one or more of algorithmic execution, logical decision-making, or result prediction.

In one embodiment, one or more adjacent areas of constructed or reconstructed tissues or organs include similar biological remodeling agents. In one embodiment, one or more adjacent areas of constructed or reconstructed tissues or organs include different biological remodeling agents. In one embodiment, one or more substrate scaffolds are utilized to at least partially construct, at least partially reconstruct, or at least partially remodel at least one tissue or at least one organ. In one embodiment, the one or more substrate scaffolds include low microporosity, for strong structural or mechanical load, while one or more adjacent areas include high microporosity as well as embedded angiogenic factors, cytokines, cells, or other agents for seeding the structural component(s).

In one embodiment, three-dimensional CAD based models of the desired tissue are capable of being modified by Boolean operations, or separated into components or elements that each are independently exportable to freeform-fabrication technologies. In one embodiment, heterogeneous blocks are assembled brick-like into a tissue or organ. In one embodiment, solid structural models are manufactured out of substrate materials including for example, quartz or Teflon®. The models are then infiltrated with vasculature, living tissue, cells, or other agents. (See, for example, Sun et al, Ibid.)

In one embodiment, a method or means for performing the same includes accepting a first input associated with at least one characteristic of at least one biological tissue to be at least partially constructed or at least partially reconstructed; accepting a second input associated with at least one parameter of at least partially constructing or at least partially reconstructing the at least one biological tissue by administering one or more frozen particle compositions, or frozen piercing implements including at least one agent; and processing results of the first input and the second input. In one embodiment, the method or means for performing the method is implemented by a computer, including a computer system.

In one embodiment, the processing results of the first input and the second input includes electronically processing results of the first input and the second input. In one embodiment, the processing results of the first input and the second input includes electronically processing results of the first input and the second input by utilizing one or more of Gaussian smoothing, scaling, homomorphic filtering, parametric estimation techniques, Boolean operations, Monte Carlo simulations, wavelet based techniques, mirroring, smoothing, gradient weighted partial differential equation smoothing, NURBS, polygonal modeling, algorithmic execution, logical decision-making, result prediction, splines and patches modeling, or modification of a CAD design.

In one embodiment, the at least one agent includes one or more of a therapeutic agent, adhesive agent, abrasive, reinforcement agent, explosive material, or biological remodeling agent. In one embodiment, the administering one or more frozen particle compositions, or frozen piercing implements includes administering the one or more frozen particle compositions, or frozen piercing implements to at least one substrate. In one embodiment, the at least one substrate includes one or more of a cell, tissue, organ, structure, or device.

In one embodiment, the first input includes one or more values related to the at least one characteristic of at least one biological tissue. In one embodiment, the first input includes one or more spatial addresses associated with the at least one characteristic of at least one biological tissue. In one embodiment, the first input includes one or more of x, y, or z coordinates associated with the at least one characteristic of at least one biological tissue. In one embodiment, the at least one characteristic of at least one biological tissue to be constructed or reconstructed includes one or more of: morphological feature, anatomical feature, histological feature, tissue hierarchical level, scaffold feature, vascular structure feature, heterogenous tissue feature, mechanical feature, volumetric feature, geometric feature, volumetric representation, mechanical feature, deformation, kinematic feature, surface contour feature, cytometric feature, cell aggregation, cell growth, cell-cell interaction, cell-tissue interaction, biomimetic design, cell pattern, cell deposition, organ hierarchical level, tissue microstructure, cellular microstructure, cell junction feature, tissue junction feature, cell-tissue classification, hard tissue classification, soft tissue classification, tumor diagnosis, or other feature.

In one embodiment, the first input includes one or more temporal addresses associated with the at least one characteristic of at least one biological tissue. In one embodiment, the first input includes one or more values derived from at least one image of the at least one biological tissue. In one embodiment, the at least one image includes one or more images acquired by one or more of laser, holography, x-ray crystallography, optical coherence tomography, computer-assisted tomography scan, computed tomography, magnetic resonance imaging, positron-emission tomography scan, ultrasound, x-ray, electrical-impedance monitoring, microscopy, spectrometry, flow cytommetry, radioisotope imaging, thermal imaging, multiphoton calcium-imaging, photography, or in silico generation.

In one embodiment, the at least one characteristic of at least one biological tissue includes one or more of cellular type, cellular function, cellular size, cellular constitution, cellular architecture, cellular durability, cellular source, tissue type, tissue constitution, tissue size, tissue shape, tissue function, tissue architecture, tissue source, tissue durability, organ type, organ constitution, organ size, organ shape, organ function, organ architecture, organ source, or organ durability. In one embodiment, the at least one biological tissue is located in at least one of in situ, in vitro, in vivo, in utero, in planta, in silico, or ex vivo. In one embodiment, the at least one biological tissue is at least partially located in at least one subject.

In one embodiment, the method or means for performing the method further comprises accepting a third input associated with at least one feature of the at least one subject. In one embodiment, the at least one feature of the at least one subject includes one or more of age, gender, genotype, phenotype, proteomic profile, or health condition.

In one embodiment, the first input includes one or more values derived from at least one image of the at least one biological tissue at least partially located in at least one subject. In one embodiment, the processing results of the first input and the second input includes determining at least one parameter of at least partially constructing or at least partially reconstructing the at least one biological tissue with one or more frozen particle compositions, or frozen piercing implements from one or more values derived from at least one image of the at least one biological tissue.

In one embodiment, the second input includes one or more values related to the at least one parameter of at least partially constructing or at least partially reconstructing the at least one biological tissue by administering one or more frozen particle compositions, or frozen piercing implements to the at least one substrate. In one embodiment, the at least one parameter of at least partially constructing or at least partially reconstructing the at least one biological tissue includes one or more of porosity of the at least one substrate, pore size of the at least one substrate, interconnectivity of the pores of the at least one substrate, transport properties of the at least one substrate, cell-tissue formation of the at least one substrate, mechanical strength of the at least one substrate, ability for attachment or distribution of the at least one agent included in the one or more frozen particle compositions, or frozen piercing implements to the at least one substrate, ability for attachment or distribution of one or more cells or tissues to the at least one substrate, facilitation of at least one nutrient, or tissue formation or tissue growth associated with the at least one substrate.

In one embodiment, the one or more values related to the at least one parameter of constructing or reconstructing the at least one biological tissue includes one or more predictive values. In one embodiment, the at least one parameter of at least partially constructing or at least partially reconstructing the at least one biological tissue by administering one or more frozen particle compositions, or frozen piercing implements includes one or more of: design of plot or model for administration of one or more frozen particle compositions, or frozen piercing implements, constitution of the one or more frozen particle compositions, or frozen piercing implements, formulation of the one or more frozen particle compositions, or frozen piercing implements, size of the one or more frozen particle compositions, or frozen piercing implements, shape of the one or more frozen particle compositions, or frozen piercing implements, angle of administration of the one or more frozen particle compositions, or frozen piercing implements, velocity of administration of the one or more frozen particle compositions, or frozen piercing implements, quantity of frozen particle compositions, or frozen piercing implements administered, rate of administration of more than one frozen particle composition, spatial location for administration of one or more frozen particle compositions, or frozen piercing implements, temporal location for administration of one or more frozen particle compositions, or frozen piercing implements, method or means for administration of one or more frozen particle compositions, or frozen piercing implements, timing of administration of one or more frozen particle compositions, or frozen piercing implements, modulation of administration of one or more frozen particle compositions, or frozen piercing implements, deposition of one or more frozen particle compositions, or frozen piercing implements, or rate of deposition of at least one agent.

In one embodiment, the at least one parameter of at least partially constructing or at least partially reconstructing the at least one biological tissue by administering one or more frozen particle compositions, or frozen piercing implements includes at least one parameter relating to at least partially ablating or at least partially abrading one or more surfaces of the at least one biological tissue with the one or more frozen particle compositions, or frozen piercing implements. In one embodiment, the at least one parameter of at least partially constructing or at least partially reconstructing the at least one biological tissue by administering one or more frozen particle compositions, or frozen piercing implements includes at least one parameter relating to administering at least one of a therapeutic agent, adhesive agent, biological remodeling agent, reinforcement agent, abrasive, or explosive material with the one or more frozen particle compositions, or frozen piercing implements. In one embodiment, the spatial location for administration of one or more frozen particle compositions, or frozen piercing implements includes one or more of x, y, or z coordinates.

In one embodiment, the processing results includes comparing at least one value related to the first input associated with the at least one characteristic of at least one biological tissue to be at least partially constructed or at least partially reconstructed with at least one value related to at least one image of a target biological tissue. In one embodiment, the image of a target biological tissue includes an image of a similar biological tissue, or an image of a dissimilar biological tissue. In one embodiment, administering one or more frozen particle compositions, or frozen piercing implements includes depositing the at least one agent on the at least one substrate. In one embodiment, processing results includes comparing at least one value related to the second input associated with the at least one parameter of at least partially constructing or at least partially reconstructing the at least one biological tissue with at least one value related to another administration of one or more frozen particle compositions, or frozen piercing implements.

In one embodiment, processing results includes determining one or more differences in at least one value related to the first input and at least one value related to at least one image of the at least one biological tissue or a similar biological tissue. In one embodiment, processing results includes determining one or more differences in at least one value related to the second input associated with the at least one parameter of at least partially constructing or at least partially reconstructing the at least one biological tissue and at least one value related to another administration of one or more frozen particle compositions, or frozen piercing implements to the at least one substrate. In one embodiment, processing results includes generating one or more protocols for administering the one or more frozen particle compositions, or frozen piercing implements. Other related embodiments are described in detail herein.

As described herein, at least one frozen particle composition or therapeutic composition described herein is useful in one or more methods or means for performing the method(s), including one or more of a method for abrasion of at least one biological tissue surface of a subject by delivering at least one composition to at least one surface of at least one biological tissue of a subject in a manner sufficient to abrade the at least one surface of the at least one biological tissue; a method of delivering at least one therapeutic agent to at least one biological tissue; a method of vaccinating a subject; a method of treating a tissue related to transplantation; a method for cleaning one or more wounds; a method for oxygenating wounds; a method for debridement of tissue or cells; a method for removing material from one or more blood vessel, and others. These and other methods include utilizing one or more composition or therapeutic composition described hererein.

In one embodiment, a method of providing at least one agent to at least one biological tissue of a subject comprises administering at least one frozen particle composition, frozen piercing implement, or frozen piercing implement device to at least one biological tissue, wherein the at least one frozen particle composition, frozen piercing implement, or frozen piercing implement device includes one or more frozen particles defining at least one cavity and at least one agent; and the at least one cavity containing at least one agent.

In one embodiment, a method of vaccinating a subject comprises administering to at least one biological tissue of a subject at least one frozen particle composition, frozen piercing implement, or frozen piercing implement device, wherein the at least one frozen particle composition, frozen piercing implement, or frozen piercing implement device includes one or more frozen particles defining at least one cavity; the at least one cavity containing at least one vaccine. In one embodiment, a method of vaccinating at least one substrate, such as a biological tissue, includes administering to the substrate at least one frozen particle composition, frozen piercing implement, or frozen piercing implement device, wherein the at least one frozen particle composition, frozen piercing implement, or frozen piercing implement device includes one or more frozen particles defining at least one cavity; the at least one cavity containing at least one vaccine.

In one embodiment, a method of providing at least one frozen particle composition or frozen piercing implement to at least one biological tissue of a subject comprises administering at least one frozen particle composition or frozen piercing implement to at least one biological tissue, wherein the at least one frozen particle composition or frozen piercing implement includes one or more frozen particles including at least one cavity configured for holding at least one agent.

In one embodiment, a method for abrasion of at least one biological tissue surface of a subject includes delivering at least one composition (frozen particle composition, frozen piercing implement, etc.) to at least one surface of at least one biological tissue of a subject in a manner sufficient to abrade the at least one surface of the at least one biological tissue. As discussed herein, particular methods are disclosed for abrading or ablating at least one surface of at least one biological tissue.

In one particular example, skin abrasion for superficial resurfacing (e.g., microdermabrasion) can be used to treat acne, scars, hyperpigmentation, and other skin blemishes, as described herein. Microscissiuning creates microchannels in the skin by eroding the outer layers of skin with sharp microscopic metal granules (Carlisle Scientific, Carlisle, Mass.), and Med Pharm Ltd (Charlbury, UK) has developed a novel dermal abrasion device (D3S) for the delivery of difficult to formulate therapeutics ranging from hydrophilic low molecular weight compounds to other biopharmaceuticals, and can be utilized in conjunction with administration of at least one composition described herein. See e.g., Roberts, et al., Clin. Exp. Pharmacol. Physiol. vol. 24, pp. 874-9 (1997); Murthy, et al., J. Controlled Rel. vol. 93, pp. 49-57 (2003); each of which is incorporated herein by reference.

Abrading at least one surface of at least one biological tissue may entail debridement of at least one biological tissue. In certain instances, debridement may include removal or destruction of dead, damaged, or infected cells or tissues. In certain instances, debridement can be included as part of an additional course of treatment (e.g., surgery). In one embodiment, debridement may include penetrating one or more healthy cells or tissues in order to facilitate healing. In one embodiment, debridement may include penetrating one or more healthy cells or tissues near in proximity to one or more unhealthy cells or tissues of a subject.

In one embodiment, one or more of the debridement methods described herein include penetrating one or more cells or biological tissues of a subject with at least one frozen particle composition, frozen piercing implement (or therapeutic composition), wherein the one or more cells or tissues are chemically or physically partitioned or segregated from at least one other part of the tissue or another tissue. In one embodiment, a method for debridement of at least one biological tissue of a subject includes delivering at least one frozen particle composition, frozen piercing implement, or therapeutic composition to at least one biological tissue of a subject wherein the at least one biological tissue is partitioned from another biological tissue or part of another biological tissue, and at least one frozen particle composition, frozen piercing implement, or therapeutic composition penetrates the at last one biological tissue with or without removing any tissue.

As described herein, in certain instances, a therapeutic agent is included with the at least one frozen particle composition to form a therapeutic composition, as described herein. In certain instances, one or more reinforcement agents or one or more explosive materials can be included in the at least one frozen particle composition or therapeutic composition.

In one embodiment, a method for removing one or more materials from at least one biological tissue includes delivering or administering at least one frozen particle composition, frozen piercing implement, frozen piercing implement device, or therapeutic composition to the at least one biological tissue. In one embodiment, the at least one biological tissue includes one or more tissues described herein. In one embodiment, the one or more materials may include one or more materials described herein.

In one embodiment, a method for removing one or more materials from at least one blood vessel of at least one subject includes delivering at least one composition to at least one blood vessel of a subject in a manner sufficient to remove one or more materials.

In certain instances, a method for abrasion of at least one biological tissue or organ surface related to transplantation is included. In one embodiment, the at least one biological tissue or organ includes one or more of the biological tissues or organs described herein.

In one embodiment, delivering at least one composition to at least one surface of at least one biological tissue of a subject includes contacting the at least one surface of at least one biological tissue of a subject with the composition. In one embodiment, delivering at least one composition to at least one surface of at least one biological tissue of a subject includes contacting the at least one surface of at least one biological tissue of a subject with the one or more frozen particle compositions, or frozen piercing implements. In one embodiment, delivering at least one composition to at least one surface of at least one biological tissue of a subject includes rupturing one or more cells of at least one surface of at least one biological tissue of a subject with the one or more frozen particle compositions, or frozen piercing implements.

In one embodiment, a method described herein includes extracting or collecting material from the at least one abraded surface of at least one biological tissue. Such extraction or collection may include the use of at least one vacuum, aspirator, container, instrument, tool, device, chemical, laser, stylet, cannula, light source, scope (e.g., laparascope), needle, scalpel, shunt, stent, bag, film, filter, suction apparatus, tube, compressed gas, fluid (e.g., fluid stream or mist), magnifying apparatus, imaging device, vapor deposition, film deposition, computing device, or system.

In one embodiment, at least one of the needle, scalpel, or other tools or instruments utilized in extracting or collecting material from the at least one cell, tissue, or subject, includes one or more frozen particle compositions, or frozen piercing implements (e.g., frozen hydrogen oxide, or other agents as described herein). Thus, the one or more frozen particle compositions, or frozen piercing implements are fashioned or molded for use as microneedles or other instruments (e.g., scalpels, blades, tools, etc.). In one embodiment, the one or more frozen particle compositions, or frozen piercing implements are administered prior to, during, or subsequent to surgery. In one embodiment, the one or more frozen particle compositions, or frozen piercing implements are administered during surgery, and just prior to closing the surgical setting.

In one embodiment, the extracted or collected material includes at least one organic or inorganic material. In one embodiment, the material includes one or more cells from the at least one abraded surface of at least one biological tissue. In one embodiment, the at least one material includes at least part of a: cell, granuloma, eschar, callus, atheromatous plaque, abscess, pustule, infected tissue, scaling, microorganism, blood clot, embolus, blood vessel obstruction, duct obstruction, bowel obstruction, necrotic tissue, stratum corneum, hair follicle, nevus, wrinkle, keloid, biofilm, calculus, plaque, tartar, dandruff, keratin, collagen, dust, dirt, metal, glass, hair or fur, cellular secretion, microorganism, blood cell, blood gas, blood component, organelle, cell membrane, cell nucleus, particulate matter, or connective tissue.

In one embodiment, the at least one material includes at least one of: enzyme, acid, amino acid, peptide, polypeptide, protein, oligonucleotide, nucleic acid, ribonucleic acid, oligosaccharide, polysaccharide, glycopeptide, glycolipid, lipoprotein, sphingolipid, glycosphingolipid, glycoprotein, peptidoglycan, lipid, carbohydrate, metalloprotein, proteoglycan, chromosome, adhesion molecule, cytokine, chemokine, immunoglobulin, antibody, antigen, platelet, extracellular matrix, blood plasma, cell wall, hormone, organic compound, inorganic compound, salt, or cell ligand.

In one embodiment, the at least one material includes at least one of: glucose, lactate, urea, uric acid, glycogen, oxygen, carbon dioxide, carbon monoxide, ketone, nitric oxide, nitrous oxide, alcohol, alkaloid, opioid, cannabinol, endorphin, epinephrine, dopamine, serotonin, nicotine, amphetamine, methamphetamine, anabolic steroid, hydrocodone, hemoglobin, heparin, clotting factor, tumor antigen, pH, albumin, ATP, NADH, $FADH_2$, pyruvate, sulfur, mercury, lead, creatinine, cholesterol, alpha-fetoprotein, chorionic gonadotropin, estrogen, progesterone, testosterone, thyroxine, melatonin, calcitonin, antimullerian hormone, adiponectin, angiotensin, cholecystokinin, corticotrophin-releasing hormone, erythropoietin, bilirubin, creatine, follicle-stimulating hormone, gastrin, ghrelin, glucagon, gonadotropin-releasing hormone, inhibin, growth hormone, growth hormone-releasing hormone, insulin, human placental lactogen, oxytocin, orexin, luteinizing hormone, leptin, prolactin, somatostatin, thrombopoietin, cortisol, aldosterone, estradiol, estriol, estrone, leukotriene, brain natriuretic peptide, neuropeptide Y, histamine, vitamin, mineral, endothelin, renin, enkephalin, DHEA, DHT, alloisoleucine, toxic substance, illegal substance, therapeutic agent, or any metabolite thereof.

As indicated herein, in one embodiment, a method for providing at least one therapeutic agent to at least one biological tissue of a subject is included. In one embodiment, the at least one therapeutic agent is delivered to at least one biological tissue prior to, during, or subsequent to surgery. In certain instances, at least one therapeutic agent includes one or more therapeutic agents described herein. In one embodiment, a method of providing at least one therapeutic agent to at least one biological tissue of a subject includes delivering at least one composition to at least one biological tissue, including one or more frozen hydrogen oxide particles including at least one therapeutic agent; wherein the at least one composition has at least one crystalline or amorphous phase.

As disclosed herein for other embodiments, a method of vaccinating a subject includes administering at least one composition that includes at least one vaccine, as well as one or more abrasives, one or more reinforcement agents, or one or more explosive materials. In one embodiment, the vaccine described herein relates to a therapeutic or prophylactic vaccine, and in certain instances the vaccine relates to an anti-cancer vaccine. In one embodiment, the one or more abrasives are the same as the one or more reinforcement agents, or the one or more explosive materials. In one embodiment, the one or more abrasives are different than the one or more reinforcement agents. In one embodiment, the one or more abrasives are different than the one or more explosive materials.

In certain instances, for example with at least one vaccine composition or method relate to vaccinating wildlife animals (e.g. vaccinating raccoons for rabies, or bison for brucellosis). In certain instances, the vaccine compositions, and methods described herein relate to vaccinating domesticated animals (such as cattle, horses, sheep, or goats). In certain instances, vaccine compositions and methods described herein relate to vaccinating a group of subjects, such as a population, a herd, a pride, a gaggle, a pack, flock, band, cluster, school, brood, troop, colony, or other group. In certain instances, vaccinating a group of subjects is included as a route to regulate or control infection within a group of subjects.

In one embodiment, the one or more frozen particle compositions, or frozen piercing implements are delivered or administered to the at least one substrate, such as at least one biological tissue, in a directed manner such that the tissue is etched, tattooed, shaped, carved, or otherwise modified. In one embodiment, the directed manner is predetermined based on information, such as from the at least one biological tissue, the subject, the at least one frozen particle composition, the context of the debridement, the health of the biological tissue, the health of the subject, or other information.

Frozen Piercing Implements

In one embodiment, a frozen piercing implement includes one or more means for piercing at least one substrate, means for delivering at least one agent to at least one substrate, or means for sensing or extracting at least one material from at least one substrate.

In one embodiment, the frozen piercing implement comprises a sterile frozen hydrogen oxide implement configured for piercing at least part of at least one substrate. In one embodiment, the sterile frozen hydrogen oxide is substantially in one or more phases including at least one of amorphous solid water, low density amorphous ice, high density amorphous ice, very high density amorphous ice, clathrate ice, hyperquenched glassy water, ice Ic, ice Ih, ice II, ice III, ice IV, ice V, ice VI, ice VII, ice VIII, ice IX, ice X, ice XI, ice XII, ice XIII, ice XIV, or ice XV.

In one embodiment, the frozen piercing implement includes at least one sterile frozen solution, the solution including at least one agent; wherein the frozen piercing implement is configured for piercing at least part of at least one substrate.

In one embodiment, the frozen piercing implement includes at least one non-hydrogen oxide frozen solvent; wherein the frozen piercing implement is configured for piercing at least one substrate; and wherein the frozen piercing implement is substantially solid at approximately 65° C., approximately 60° C., approximately 55° C., approximately 50° C., approximately 45° C., approximately 40° C., approximately 37° C., approximately 35° C., approximately 30° C., approximately 25° C., approximately 20° C., approximately 15° C., approximately 10° C., approximately 5° C., approximately 0° C., approximately −5° C., approximately −10° C., approximately −15° C., approximately −20° C., approximately −25° C., approximately −30° C., approximately −40° C., approximately −50° C., approximately −60° C., approximately −70° C., approximately −80° C., approximately −90° C., approximately −100° C., approximately −120° C., approximately −150° C., approximately −170° C., approximately −200° C., approximately −250° C., or any temperature therebetween. In one embodiment, the at least one non-hydrogen-oxide frozen solvent includes at least one of acetone, ethyl acetate, dimethyl sulfoxide, dimethyl formamide, dioxane, tetrahydrofuran, acetonitrile, acetic acid, n-butanol, isopropanol, n-propanol, hexamethylphosphorotriamide, perfluorohydrocarbon, methanol, ethanol, tert-butyl alcohol, formic acid, hydrogen fluoride, ammonia, benzene, carbon tetrachloride, acetonitrile, hexane, dichloromethane, methylene chloride, carboxylic acid, saline, standard saline citrate, methane, toluene, chloroform, or diethyl ether. In one embodiment, the frozen piercing implement further comprises at least one of polyethylene glycol, Ringer's solution, lactated Ringer's solution, Hartmann's solution, acetated Ringer's solution, phosphate buffered solution, TRIS-buffered saline solution, Hank's balanced salt solution, Earle's balanced salt solution, HEPES-buffered saline, dextrose, or glucose.

In one embodiment, the frozen piercing implement, comprises: at least one sterile frozen component and at least one agent; wherein the at least one component is substantially in a gaseous state at or above approximately 0.25 bar, approximately 0.5 bar, approximately 1.0 bar, approximately 5.0 bar, approximately 10.0 bar, approximately 25 bar, approximately 50 bar, approximately 100 bar, approximately 200 bar, or approximately 500 bar pressure; and at or above approximately 10° C., approximately 15° C., approximately 20° C., approximately 25° C., approximately 30° C., approximately 37° C., approximately 40° C., approximately 45° C., or approximately 50° C.; and wherein the at least one frozen piercing implement is configured for piercing at least one substrate. In one embodiment, the at least one component includes one or more of nitrogen, helium, neon, xenon, oxygen, air, krypton, chlorine, bromine, or argon.

In one embodiment, the frozen piercing implement has at least one major dimension of approximately one centimeter or less, approximately one millimeter or less, approximately one micrometer or less, approximately one nanometer, or any value therebetween. In one embodiment, the frozen piercing implement is substantially in the form of one or more frozen particles. In one embodiment, the at least one major dimension includes at least one of a radius, diameter, length, width, height, or perimeter.

In one embodiment, the frozen piercing implement is configured for delivering at least one agent to the at least one substrate. As described herein, the at least one agent includes at least one of a therapeutic agent, explosive material, reinforcement agent, adhesive agent, biological remodeling agent, or abrasive. In one embodiment, the at least one agent includes at least one of a nontoxic, biocompatible, bioresorbable, or biodegradable agent. In one embodiment, the at least one agent includes at least one sterile or sterilizing agent. In one embodiment, the at least one sterilizing agent includes at least one antimicrobial compound. In one embodiment, the at least one sterilizing agent includes at least one antiseptic. In one embodiment, the at least one agent is included as an outer coating of the frozen piercing implement. In one embodiment, the at least one agent is encapsulated within the frozen piercing implement. In one embodiment, the at least one agent is included as part of a carrier that assists in synthesis or activation of the at least one agent. In one embodiment, the at least one agent includes one or more components that are inactive. In one embodiment, the one or more components are configured to be activated by administration. In one embodiment, the at least one agent includes one or more of a prodrug or precursor compound.

In one embodiment, the frozen piercing implement is substantially solid at approximately 0° C., approximately −10° C., approximately −20° C., approximately −30° C., approximately −40° C., approximately −50° C., approximately −60° C., approximately −70° C., approximately −75° C., approximately −80° C., approximately −85° C., approximately −90° C., approximately −95° C., approximately −100° C., approximately −120° C., approximately −150° C., approximately −180° C., approximately −200° C., approximately −220° C., approximately −250° C., or any temperature less than or therebetween.

In one embodiment, the frozen piercing implement includes at least one cavity. In one embodiment, at least one agent is located in the at least one cavity. In one embodiment, the frozen piercing implement includes at least two different agents configured to combine upon administration of the frozen piercing implement. In one embodiment, the at least two different agents are configured to react upon administration of the frozen piercing implement. In one embodiment, the at least two different agents are configured to act cooperatively or synergistically upon administration of the frozen piercing implement.

In one embodiment, the frozen piercing implement further comprises at least one detection material. As described herein, in one embodiment, the detection material includes at least one of a contrast agent, sensor, or electronic identification device. In one embodiment, the at least one electronic identification device includes at least one radio frequency identification device. In one embodiment, the detection material includes at least one of a radioactive, luminescent, colorimetric or odorous substance. In one embodiment, the at least one radioactive, luminescent, colorimetric or odorous substance includes at least one temperature-sensitive substance. In one embodiment, the detection material includes at least one of a diamagnetic particle, ferromagnetic particle, paramagnetic particle, super paramagnetic contrast agent, particle with altered isotope, or other magnetic particle.

In one embodiment, the frozen piercing implement includes at least one conduit configured to deliver at least one electrical charge, electromagnetic energy, or other substances. In one embodiment, the frozen piercing implement includes one or more cavities or channels. The cavity can be in the form of a pit, pore, core, coating, or other area of concentration.

In one embodiment, the at least one channel extends across at least one major dimension of the at least one frozen piercing implement. In one embodiment, the at least one channel includes at least one of an organic or inorganic small molecule, clathrate or caged compound, protocell, coacervate, microsphere, Janus particle, proteinoid, laminate, helical rod, liposome, macroscopic tube, niosome, sphingosome, toroid, vesicular tube, vesicle, small unilamellar vesicle, large unilamellar vesicle, large multilamellar vesicle, multivesicular vesicle, lipid layer, lipid bilayer, micelle, organelle, cell, membrane, nucleic acid, peptide, polypeptide, protein, glycopeptide, glycolipid, lipoprotein, sphingolipid, glycosphingolipid, glycoprotein, peptidoglycan, lipid, carbohydrate, metalloprotein, proteoglycan, chromosome, nucleus, acid, support structure, buffer, protic solvent, aprotic solvent, nitric oxide, nitrous oxide, nitric oxide synthase, amino acid, micelle, polymer, copolymer, monomer, prepolymer, cell receptor, adhesion molecule, cytokine, chemokine, immunoglobulin, antibody, antigen, platelet, extracellular matrix, blood, plasma, cell ligand, zwitterionic material, cationic material, oligonucleotide, nanotube, piloxymer, transfersome, gas, element, contaminant, radioactive particle, hormone, microorganism, bacteria, virus, quantum dot, contrast agent, or any part thereof. In one embodiment, a method comprises sensing or extracting at least one material from the at least one substrate. Thus, the at least one frozen piercing implement or frozen particle composition can include methods for chemical testing of a subject (e.g., pharmaceutical drugs, illicit drugs, toxins or poisons, biochemical disorders, or dietary deficiencies, etc.).

In one embodiment, the at least one channel is configured to deliver at least one agent or at least one detection material to the at least one substrate. In one embodiment, the at least one channel is configured to deliver at least one agent, or detection material by at least one of van der Waals forces, gravitational force, electrostatic energy, hydration attraction, hydration repulsion, hydrophobic attraction, hydrophobic repulsion, diffusion, osmosis, mechanical pump, electroosmosis, electrophoresis, convection, sublimation, hydroloysis, magnetic attraction or repulsion, capillary action, pressure gradient, concentration gradient, electricity, ultrasound, receptor binding, heat, chemical, chemical reaction, tunablemicrolens or nanolens, gate or valve, or external applied force. In one embodiment, the external applied force includes one or more of physical propulsion, thermal displacement, laminar flow, turbulent flow, x-rays, gamma rays, electron beams, proton beams, or acoustic droplet ejection. In one embodiment, the at least one channel of the frozen piercing implement contains at least one agent. In one embodiment, the at least one channel of the frozen piercing implement contains at least one of an ion exchange material, ion selective material, permeable material, solid material, or semi-permeable material. In one embodiment, the wall thickness of the at least one channel is approximately 1 nm, approximately 10 nm, approximately 50 nm, approximately 100 nm, approximately 1 µm, approximately 5 µm, approximately 10 µm, approximately 15 µm, approximately 20 µm, approximately 50 µm, approximately 100 µm, approximately 120 µm, approximately 150 µm, approximately 200 µm, approximately 250 µm, approximately 300 µm, approximately 350 µm, approximately 400 µm, approximately 450 µm, approximately 500 µm, approximately 600 µm, approximately 700 µm, approximately 800 µm, approximately 900 µm, approximately 1 mm, approximately 2 mm, approximately 3 mm, approximately 4 mm, approximately 5 mm, or any value therebetween. In one embodiment, at least one surface of the at least one channel is substantially hydrophobic. In one embodiment, at least one surface of the at least one channel is substantially hydrophilic.

In one embodiment, the at least one frozen piercing implement includes one or more layers. In one embodiment, the at least one frozen piercing implement includes at least one layer of a different constitution than at least one other layer. In one embodiment, the frozen piercing implement approximates the shape of at least one of a sphere, bullet, flechette, cone, frustrum, needle, arrow, spear, diamond, pyramid, cylinder, mini ball, shuttlecock, spiral, bell, pear, crystal, cube, spheroid, tetrahedron, crescent, possesses a high aspect ratio shape, or any combination thereof. In one embodiment, the frozen piercing implement possesses a high aspect ratio shape from largest to smallest dimension of greater than or approximately equal to 1.1, greater than or approximately equal to 1.5, greater than or approximately equal to 2.0, greater than or approximately equal to 3.0, greater than or approximately equal to 5.0, greater than or approximately equal to 10.0, greater than or approximately equal to 20.0, greater than or approximately equal to 50.0, greater than or approximately equal to 100.0, greater than or approximately equal to 1000.0, or any value therebetween.

In one embodiment, the at least one implement is configured to melt or evaporate prior to, during, or subsequent to contacting the at least one substrate. In one embodiment, the at least one implement is configured to melt within the at least one substrate. In one embodiment, the at least one implement is configured to be substantially removed from the at least one substrate. In one embodiment, the at least one implement is configured to penetrate at least an outer surface layer of the at least one substrate.

In one embodiment, the frozen piercing implement includes at least a portion of a piercing instrument. In one embodiment, the frozen piercing implement includes at least approximately 5%, approximately 10%, approximately 20%, approximately 30%, approximately 40%, approximately 50%, approximately 60%, approximately 70%, approximately 80%, approximately 90%, approximately 100%, or any value less than or therebetween portion of a piercing instrument. In one embodiment, the piercing instrument includes at least one of metal, wood, plastic, fiberglass, or other material. In one embodiment, the piercing instrument includes at least one solid internal portion. In one embodiment, the at least one solid internal portion is sterile. In one embodiment, the implement includes at least one solid internal portion and at least one sterile frozen hydrogen oxide external coating. In one embodiment, the frozen external coating is configured to melt or evaporate prior to, during, or subsequent to piercing the at least one substrate. In one embodiment, the at least one solid internal portion is configured to be removed from the at least one substrate. In one embodiment, the at least one implement is configured to break off within the at least one substrate. In one embodiment, the at least one implement is configured to break off due to an applied load. In one embodiment, the at least one implement is configured to break off due to thermal input. In one embodiment, the thermal input includes at least one thermal input from at least one internal or external source. In one embodiment, the at least one external source includes the at least one substrate. In one embodiment, the at least one implement is configured to break off due to at least one weak portion of the implement.

In one embodiment, the frozen piercing implement further includes at least one non-frozen implement holding device. In one embodiment, the at least one non-frozen implement holding device includes at least one handle, robotic arm, or surgical device. In one embodiment, the frozen piercing implement is approximately solid. In one embodiment, the frozen piercing implement is approximately semi-permeable. In one embodiment, the frozen piercing implement includes one or more pits or ports. In one embodiment, the frozen piercing implement includes at least one substantially tapered end. In one embodiment, the at least one substantially tapered end includes an angle of approximately 30°, approximately 40°, approximately 50°, approximately 60°, approximately 70°, approximately 80°, approximately 90°, or any value therebetween or greater. In one embodiment, the angle includes a wall angle.

In one embodiment, the frozen piercing implement includes at least one substantially beveled end. In one embodiment, the at least one substantially beveled end includes an angle of approximately 30°, approximately 40°, approximately 50°, approximately 60°, approximately 70°, approximately 80°, approximately 90°, or any value therebetween or greater. In one embodiment, the angle includes a wall angle. In one embodiment, the frozen piercing implement includes at least one substantially jagged or substantially serrated end. In one embodiment, the frozen piercing implement substantially approximates at least one projection. In one embodiment, the at least one projection substantially terminates in at least one tip. In one embodiment, the at least one tip is substantially hollow. In one embodiment, a substantially jagged or serrated end includes multiple protrusions or peaks. In one embodiment, the serrated or substantially jagged end allows for increased substrate penetration, increased substrate ablation or abrasion, increased end surface area, or increased carrying capacity for at least one agent. See, for example, U.S. Pat. No. 5,457,041, which is incorporated herein by reference.

In one embodiment, the radius of the at least one tip is approximately 1 nm, approximately 10 nm, approximately 100 nm, approximately 1 μm, approximately 5 μm, approximately 10 μm, approximately 15 μm, approximately 20 μm, approximately 50 μm, approximately 100 μm, approximately 120 μm, approximately 150 μm, approximately 200 μm, approximately 250 μm, approximately 300 μm, approximately 350 μm, approximately 400 μm, approximately 450 μm, approximately 500 μm, approximately 600 μm, approximately 700 μm, approximately 800 μm, approximately 900 μm, approximately 1 mm, approximately 2 mm, approximately 3 mm, approximately 4 mm, approximately 5 mm, or any value therebetween.

In one embodiment, the radius of curvature of the tip is approximately 1 nm, approximately 10 nm, approximately 100 nm, approximately 1 μm, approximately 5 μm, approximately 10 μm, approximately 50 μm, approximately 100 μm, approximately 500 μm, approximately 1 mm, approximately 5 mm, or any value therebetween. In one embodiment, the frozen piercing implement includes at least one port. In one embodiment, the at least one port includes at least one side port. In one embodiment, the at least one port includes at least one end port. In one embodiment, the at least one port includes at least one inlet port. In one embodiment, the at least one inlet port is in fluid communication with at least one channel. In one embodiment, the at least one port includes at least one outlet port. In one embodiment, the at least one outlet port is in fluid communication with at least one channel. In one embodiment, the at least one port includes at least one inlet port in fluid communication with at least one outlet port.

In one embodiment, the frozen piercing implement is formulated to be administered to the at least one substrate. In one embodiment, the at least one substrate includes one or more of a cell, tissue, organ, structure, device, or food product. In one embodiment, the at least one substrate includes at least one food product.

In one embodiment, the frozen piercing implement is configured to pierce at least one substrate to a depth of approximately 1 μm, approximately 5 μm, approximately 10 μm, approximately 15 μm, approximately 20 μm, approximately 50 μm, approximately 100 μm, approximately 120 μm, approximately 150 μm, approximately 200 μm, approximately 250 μm, approximately 300 μm, approximately 350 μm, approximately 400 μm, approximately 450 μm, approximately 500 μm, approximately 600 μm, approximately 700 μm, approximately 800 μm, approximately 900 μm, approximately 1 mm, approximately 2 mm, approximately 3 mm, approximately 4 mm, approximately 5 mm, or any value therebetween. In one embodiment, the at least one frozen piercing implement is configured to abrade or ablate at least one substrate surface. In one embodiment, the plurality of frozen piercing implements is positioned such that each frozen piercing implement of the array device contacts a single cell of at least one biological tissue.

In one embodiment, the piercing includes abrading or ablating at least a portion of the surface of the at least one substrate. In one embodiment, the piercing includes abrading or ablating one or more cells or tissues.

In one embodiment, the at least one frozen piercing implement includes at least one sensor. In one embodiment, the at least one sensor includes at least one sensor configured for detecting at least one of a biochemical, electrical, optical, functional, physical, chemical, biological, or structural characteristic of the at least one material. In one embodiment, the at least one frozen piercing implement is configured for extracting at least one material from the at least one substrate. In one embodiment, the at least one material includes one or more of a cell, organic or inorganic small molecule, vesicle, micelle, organelle, cell membrane, nucleic acid, peptide, polypeptide, protein, oligosaccharide, polysaccharide, glycopeptide, glycolipid, lipoprotein, sphingolipid, glycosphingolipid, glycoprotein, peptidoglycan, lipid, carbohydrate, metalloprotein, proteoglycan, chromosome, cell nucleus, amino acid, polymer, cell receptor, adhesion molecule, cytokine, chemokine, immunoglobulin, antibody, antigen, platelet, extracellular matrix, blood, plasma, cell ligand, zwitterionic material, cationic material, oligonucleotide, transfersome, gas, element, contaminant, radioactive particle, hormone, or any part thereof.

In one embodiment, the at least one frozen piercing implement is configured for extracting at least one material from the at least one substrate by at least one of: van der Waals forces, gravitational pull, electrostatic energy, hydration attraction, hydration repulsion, hydrophobic attraction, hydrophobic repulsion, magnetic attraction, magnetic repulsion, capillary action, or external applied force. In one embodiment, the frozen piercing implement further comprises at least one of an organic or inorganic small molecule, clathrate or caged compound, protocell, coacervate, microsphere, Janus particle, proteinoid, laminate, helical rod, liposome, macroscopic tube, niosome, sphingosome, toroid, vesicular tube, vesicle, small unilamellar vesicle, large unilamellar vesicle, large multilamellar vesicle, multivesicular vesicle, lipid layer, lipid bilayer, micelle, organelle, cell, membrane, nucleic acid, peptide, polypeptide, protein, glycopeptide, glycolipid, lipoprotein, sphingolipid, glycosphingolipid, glycoprotein, peptidoglycan, lipid, carbohydrate, metalloprotein, proteoglycan, chromosome, nucleus, acid, support structure, buffer, protic solvent, aprotic solvent, nitric oxide, nitrous oxide, nitric oxide synthase, amino acid, micelle, polymer, copolymer, monomer, prepolymer, cell receptor, adhesion molecule, cytokine, chemokine, immunoglobulin, antibody, antigen, platelet, extracellular matrix, blood, plasma, cell ligand, zwitterionic material, cationic material, oligonucleotide, nanotube, piloxymer, transfersome, gas, element, contaminant, radioactive particle, hormone, microorganism, bacteria, virus, quantum dot, contrast agent, or any part thereof.

In one embodiment, the frozen piercing implement includes one or more of nitrogen, oxygen, air, helium, neon, argon, xenon, chlorine, bromine, carbon dioxide, acetone, ethyl acetate, dimethyl sulfoxide, dimethyl formamide, dioxane, tetrahydrofuran, acetonitrile, acetic acid, n-butanol, isopropanol, n-propanol, hexamethylphosphorotriamide, perfluorohydrocarbon, methanol, ethanol, tert-butyl alcohol, formic acid, hydrogen fluoride, ammonia, benzene, carbon tetrachloride, hexane, dichloromethane, methylene chloride, carboxylic acid, saline, standard saline citrate, methane, toluene, chloroform, polyethylene glycol, acetic acid, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, or diethyl ether.

In one embodiment, a plurality of frozen piercing implements is disclosed. In one embodiment, the frozen piercing implement is included in at least one frozen piercing implement device. In one embodiment, the at least one frozen piercing implement device includes at least one of a frozen piercing implement array device, frozen piercing implement fluidic device, or frozen piercing implement injection device. In one embodiment, the frozen piercing implement device includes at least one of a patch, bandage, shunt, wound dressing, splint, computer mouse, telephone, mobile phone, writing instrument, article of clothing, blanket, pen-type device, other article of manufacture, or medical instrument. In one embodiment, the frozen piercing implement device includes at least one cooling element. In one embodiment, the at least one cooling element includes one or more of a refrigeration mechanism, heat exchanger, thermoelectric, cold plate, low temperature thermal ballast, or phase change material.

In one embodiment, the frozen piercing implement includes one or more of a suspension, mixture, solution, sol, clathrate, colloid, emulsion, microemulsion, aerosol, ointment, capsule, powder, tablet, suppository, cream, device, paste, resin, liniment, lotion, ampule, elixir, spray, syrup, tincture, detection material, polymer, biopolymer, buffer, adjuvant, diluent, lubricant, disintegration agent, suspending agent, solvent, light-emitting agent, colorimetric agent, glidant, anti-adherent, anti-static agent, surfactant, plasticizer, emulsifying agent, flavor, gum, sweetener, coating, binder, filler, compression aid, encapsulation aid, preservative, granulation agent, spheronization agent, stabilizer, adhesive, pigment, sorbent, nanoparticle, or gel. In one embodiment, the frozen piercing implement further comprises at least one pharmaceutically-acceptable carrier or excipient.

In one embodiment, the frozen piercing implement is substantially in the form of at least one blade. In one embodiment, the at least one blade is at least part of one or more of a knife, razor, scissors, hatchet, saw, rotary device, or scalpel. In one embodiment, the at least one frozen piercing implement is configured as a tweezers, fork, scriber, graver, spade, screw, needle or pin. In one embodiment, the needle or pin include at least one macroneedle, macropin, microneedle, micropin, nanoneedle, or nanopin. In one embodiment, the frozen piercing implement is formulated to be administered by one or more of topical administration, oral administration, enteral administration, mucosal administration, percutaneous administration, or parenteral administration. In one embodiment, the frozen piercing implement is formulated to be administered by high velocity impact. In one embodiment, the frozen piercing implement is formulated to be administered by one or more devices.

In certain instances, the frozen piecing implement is utilized in compositions or methods for delivery of at least one agent, including but not limited to a therapeutic agent, adhesive agent, reinforcement agent, biological remodeling agent, explosive material, or abrasive.

In one embodiment, the frozen piercing implementation is utilized in compositions or methods for transdermal therapeutic agent delivery, including but not limited to vaccine delivery.

In one embodiment, the frozen piercing implements or tools are utilized in compositions or methods for electrotherapy, nucleic acid sampling, protein sampling, cell sampling, tissue sampling, nucleic acid analysis, protein analysis, cell analysis, tissue analysis, iontophoresis, or other technique. In one embodiment, the at least one frozen piercing implement includes at least one of a channel, pump, sensor, injector, actuator, heater, detector, controller, transducer, receiver, transmitter, circuit, lens, tunable lens, valve, gate, nanoparticle, microparticle, power source, or detection material. In one embodiment, the frozen piercing implement includes at least one waveguide that provides a path to guide energy waves.

In one embodiment, the frozen piercing implement includes a length of approximately 1 µm, approximately 5 µm, approximately 10 µm, approximately 15 µm, approximately 20 µm, approximately 50 µm, approximately 100 µm, approximately 120 µm, approximately 150 µm, approximately 200 µm, approximately 250 µm, approximately 300 µm, approximately 350 µm, approximately 400 µm, approximately 450 µm, approximately 500 µm, approximately 600 µm, approximately 700 µm, approximately 800 µm, approximately 900 µm, approximately 1 mm, approximately 2 mm, approximately 3 mm, approximately 4 mm, approximately 5 mm, approximately 10 mm, approximately 20 mm, approximately 30 mm, approximately 40 mm, approximately 50 mm, approximately 60 mm, approximately 70 mm, approximately 80 mm, approximately 90 mm, approximately 100 mm, approximately 200 mm, approximately 300 mm, approximately 400 mm, approximately 500 mm, approximately 600 mm, approximately 700 mm, approximately 800 mm, approximately 900 mm, approximately 1 cm, approximately 10 cm, approximately 20 cm, or any value therebetween.

In one embodiment, the frozen piercing implement has a substantially solid form. In one embodiment, the frozen piercing implement has a substantially semi-permeable form. In one embodiment, the frozen piercing implement includes at least one channel, providing the frozen piercing implement with at least one inner diameter and at least one outer diameter.

In one embodiment, the frozen piercing implement includes an outer diameter of approximately 1 nm, approximately 10 nm, approximately 100 nm, approximately 1 µm, approximately 5 µm, approximately 10 µm, approximately 15 µm, approximately 20 µm, approximately 50 µm, approximately 100 µm, approximately 120 µm, approximately 150 µm, approximately 200 µm, approximately 250 µm, approximately 300 µm, approximately 350 µm, approximately 400 µm, approximately 450 µm, approximately 500 µm, approximately 600 µm, approximately 700 µm, approximately 800 µm, approximately 900 µm, approximately 1 mm, approximately 2 mm, approximately 3 mm, approximately 4 mm, approximately 5 mm, approximately 10 mm, approximately 20 mm, approximately 30 mm, approximately 40 mm, approximately 50 mm, approximately 60 mm, approximately 70 mm, approximately 80 mm, approximately 90 mm, approximately 100 mm, approximately 200 mm, approximately 300 mm, approximately 400 mm, approximately 500 mm, approximately 600 mm, approximately 700 mm, approximately 800 mm, approximately 900 mm, approximately 1 cm, approximately 10 cm, or any value therebetween.

In one embodiment, the frozen piercing implement has an inner diameter, and includes an inner diameter of approximately 1 nm, approximately 10 nm, approximately 100 nm, approximately 1 µm, approximately 5 µm, approximately 10 µm, approximately 15 µm, approximately 20 µm, approximately 50 µm, approximately 100 µm, approximately 120 µm, approximately 150 µm, approximately 200 µm, approximately 250 µm, approximately 300 µm, approximately 350 µm, approximately 400 µm, approximately 450 µm, approximately 500 µm, approximately 600 µm, approximately 700 µm, approximately 800 µm, approximately 900 µm, approximately 1 mm, approximately 2 mm, approximately 3 mm, approximately 4 mm, approximately 5 mm, approximately 10 mm, approximately 20 mm, approximately 30 mm, approximately 40 mm, approximately 50 mm, approximately 60 mm, approximately 70 mm, approximately 80 mm, approximately 90 mm, approximately 100 mm, approximately 200 mm, approximately 300 mm, approximately 400 mm, approximately 500 mm, approximately 600 mm, approximately 700 mm, approximately 800 mm, approximately 900 mm, approximately 1 cm, approximately 10 cm, or any value therebetween.

In one embodiment, a single frozen piercing implement pierces a single cell. In one embodiment, a single frozen piercing implement pierces multiple cells. In one embodiment, a single frozen piercing implement pierces at least one biological tissue. Most cells in an animal, such as a human, are approximately 10-30 µm in diameter, while most plant and fungal cells are approximately 10-100 µm in diameter. Thus, in one embodiment, at least one of the inner or outer diameter is configured in size according to the targeted cell(s).

In one embodiment, the pressure exerted on a substrate is adjusted for use of one or more frozen piercing implements. In one embodiment, the pressure exerted on a substrate is increased or decreased in order to adjust the rate of melting, sublimation, evaporation, transformation, activation, etc. of the one or more frozen piercing implements or a component thereof.

In one embodiment, the frozen piercing implement is configured to pierce or penetrate at least one substrate. In at least one embodiment, at least a portion of the at least one substrate includes skin or surface of a tissue, organ, or subject's body. In one embodiment, the frozen piercing implement is configured to pierce or penetrate at least a portion of the stratum corneum, epidermis, or dermis layer of the skin. In one embodiment, the frozen piercing implement is administered prior to, during, or subsequent to surgery.

In one embodiment, the at least one frozen piercing implement is configured to substantially form at least one blade. In one embodiment, the at least one blade is at least part of one or more of a knife, razor, scissors, hatchet, saw, rotary device, or scalpel. In one embodiment, the at least one frozen piercing implement is configured as a tweezers, fork, scriber, graver, spade, needle or pin. In one embodiment, the needle or pin include at least one macroneedle, macropin, microneedle, micropin, nanoneedle, or nanopin.

The epidermis layer of the skin is approximately 100-150 µm thick, and includes an outermost layer, the stratum corneum, which is approximately 10-15 µm in thickness. In certain areas, the blood vessels are generally present more superficially than nerves, which allows for delivery of at least one agent, or extraction of at least one material from the skin and underlying tissue, largely without activating the nerves and signaling pain. See, e.g., Kumar and Philip, Trop. J. Pharm Res. 6(1):633-644 (2007), which is incorporated herein by reference. In certain instances, it is desirable to penetrate the epidermis and/or dermis layer of the skin in order to deliver at least one agent (including but not limited to a therapeutic agent) to a subcutaneous, intravenous, or other location beneath the skin. In one embodiment, the frozen piercing implement is configured to deliver at least one agent beneath the surface of the skin or outer covering of the tissue, organ, or subject's body. In one embodiment, the frozen piercing implement is configured to pierce or penetrate the skin largely without activating nerves beneath the skin.

In one embodiment, the frozen piercing implement includes at least one functionalized surface. In one embodiment, the functionalized surface includes one or more functional groups including but not limited to at least one of a binding group (e.g., coupling agents, and the like), a linking group (e.g., spacer groups, organic spacer groups, and the like), or a matrix-forming group. Some examples of binding groups include but are not limited to at least one acrylate, alkoxysilane, alkyl thiol, arene, azido, carboxylate, chlorosilane, alkoxysilane, acetocysilane, silazane, disilazane, disulfide, epoxide, ester, hydrosilyl, isocyanate, phosphoamidite, isonitrile, methacrylate, nitrene, nitrile, quinone, silane, sulfhydryl, thiol, vinyl group, and the like. Some examples of linking groups include but are not limited to at least on dendrimer, polymer, hydrophilic polymer, hyperbranched polymer, poly(amino acid), polyacrylamide, polyacrylate, polyethylene glycol, polyethylenimine, polymethacrylate, polyphosphazene, carbohydrate, monosaccharide, disaccharide, polysaccharide, polysiloxane, polystyrene, polyurethane, propylene, amino acid, nucleic acid, polypeptide, protein, copolymer, block copolymer, and the like. Some examples of matrix-forming groups include but are not limited to at least one dendrimer polyamine polymer, bovine serum albumin, casein, glycolipid, lipid, heparin, glycosaminoglycan, mucin, surfactant, polyoxyethylene-based surfaceactive substance (e.g., polyoxyethlene-polyoxypropylene copolymer, polyoxyethylene 12 tridecyl ether, polyoxyethylene 18 tridecyl ether, polyoxyethylene 6 tridecyl ether, polyoxyethylene sorbitan tetraoleate, polyoxyethylene sorbitol hexaoleate, and the like) polyethylene glycol, saccharide, polysaccharide, serum dilution, and the like.

In one embodiment, the one or more functional groups include charged functional groups capable of maintaining a positive or negative charge over a wide range of pH. Some examples of charged functional groups include but are not limited to at least one cation, anion, amine, acid, halocarbon, sulfonic acid, quaternary amine, metal, $—NH_3^+$, $—COOH$, $—COO—$, $—SO_3$, $CH_2N^+(CH_3)_3$, and the like.

In one embodiment, the one or more frozen piercing implements are tested for constitution, physical structure, physical integrity, or other property. In one embodiment, the one or more frozen piercing implements are designed with assistance from at least one computer program or computing device.

In one embodiment, a method of administering at least one frozen piercing implement to at least one substrate comprises contacting at least one frozen piercing implement with at least one substrate, wherein the at least one frozen piercing implement includes sterile frozen hydrogen oxide and at least one agent; and wherein the frozen piercing implement has at least one major dimension of approximately one centimeter or less, approximately one millimeter or less, approximately one micrometer or less, approximately one nanometer or less, or any value therebetween.

In one embodiment, wherein administering the at least one frozen piercing implement to at least one substrate includes propelling, ejecting, or accelerating the at least one frozen piercing implement toward the at least one substrate at a predetermined angle, a predetermined velocity, a predetermined rate of administration, a predetermined depth, a predetermined location, a predetermined time sequence, or a predetermined spatial pattern. In one embodiment, the method further comprises varying the rate, velocity, or angle at which the at least one frozen piercing implement is administered to the at least one substrate. In one embodiment, the method includes administering the at least one frozen piercing implement to at least one substrate by propelling, ejecting, or accelerating a plurality of frozen piercing implements toward the at least one substrate.

In one embodiment, the frozen piercing implement is configured to pierce or penetrate at least one substrate. Certain examples of substrates are provided herein. In one embodiment, the temperature of the substrate is adjusted prior to, during, or subsequent to administration of one or more frozen piercing implements. In one embodiment, the temperature of the substrate is increased or decreased in order to adjust the rate, for example, of melting, sublimation, evaporation, transformation, activation, etc. of the one or more frozen piercing implements or a component thereof. In one embodiment, the method further comprises adjusting the temperature of the at least one substrate prior to, during, or subsequent to administering the one or more frozen piercing implements to at least approximately 37° C., approximately 36° C., approximately 35° C., approximately 34° C., approximately 33° C., approximately 32° C., approximately 31° C., approximately 30° C., approximately 29° C., approximately 28° C., approximately 27° C., approximately 26° C., approximately 25° C., approximately 24° C., approximately 23° C., approximately 22° C., approximately 21° C., approximately 20° C., approximately 19° C., approximately 18° C., approximately 17° C., approximately 16° C., approximately 15° C., approximately 14° C., approximately 13° C., approximately 12° C., approximately 11° C., approximately 10° C., approximately 9° C., approximately 8° C., approximately 7° C., approximately 6° C., approximately 5° C., approximately 4° C., approximately 3° C., approximately 2° C., approximately 1° C., approximately 0° C., or any temperature therebetween.

In one embodiment, contacting at least one substrate includes at least one of cutting, stitching, cauterizing, freezing, perforating, penetrating, ablating, or abrading at least a part of the surface of the at least one substrate. In one embodiment, administering the at least one substrate occurs in conjunction with cryosurgery, cryotherapy, or mesotherapy.

In one embodiment, contacting at least one substrate affects one or more of electrical resistance of the at least one substrate, or permeability of the at least one substrate. In one embodiment, at least one frozen piercing implement is administered to at least one substrate as party of a method for vaccination. In one embodiment, a method of vaccinating a subject comprises administering at least one frozen piercing implement or frozen particle composition described herein.

Frozen Piercing Implement Devices

In one embodiment, at least one frozen piercing implement or frozen particle composition (including a therapeutic composition) is utilized to fabricate at least one device. In one embodiment, the frozen piercing implement device includes at least one array device, fluidic device, or injection device. In one embodiment, the frozen piercing implement device includes at least one of a patch, bandage, shunt, wound dressing, splint, computer mouse, telephone, mobile phone, writing instrument, article of clothing, blanket, pen-type device, other article of manufacture, or medical instrument.

In one embodiment, a fluidic device, comprises: a support structure at least partially defining at least one compartment; and at least one frozen piercing implement in fluid communication with the at least one compartment; wherein the at least one frozen piercing implement has at least one major dimension of approximately one centimeter or less, approximately one millimeter or less, approximately one micrometer or less, approximately one nanometer or less, or any value therebetween.

In one embodiment, an array device, comprises: a support structure having a surface; and a plurality of sterile frozen piercing implements extending substantially outward from the support structure. In one embodiment, the plurality of sterile frozen piercing implements having at least one major dimension of approximately one centimeter or less, approximately one millimeter or less, approximately one micrometer or less, approximately one nanometer or less, or any value therebetween.

In one embodiment, an array device comprises: a support structure having a surface; a plurality of piercing implements extending substantially outward from the surface of the support structure; wherein at least one piercing implement of the plurality of piercing implements includes a frozen piercing implement. In one embodiment, the at least one frozen piercing implement has at least one major dimension of approximately one centimeter or less, approximately one millimeter or less, approximately one micrometer or less, approximately one nanometer or less, or any value therebetween.

In one embodiment, a composition, comprises: a plurality of piercing implement array devices joined together, the piercing implement array devices including at least one frozen piercing implement.

In one embodiment, a composition, comprises: a support means for an array device; wherein the array device includes one or more frozen piercing implements.

In one embodiment, the plurality of sterile frozen piercing implements have at least one major dimension of approximately one centimeter or less, approximately one millimeter or less, approximately one micrometer or less, approximately one nanometer, or any value therebetween. In one embodiment, the plurality of sterile frozen piercing implements extends substantially perpendicular to the support structure. In certain instances, the frozen piercing implements extend through the support structure, or from the surface of the support structure. In one embodiment, the support structure itself includes at least one frozen composition. In one embodiment, the support structure includes at least one frozen composition also included in at least one frozen piercing implement. In one embodiment, the support structure is at least partially frozen. In one embodiment, the support structure and at least one frozen piercing implement of the plurality of frozen piercing implements include at least one common constituent.

In one embodiment, the plurality of frozen piercing implements are positioned substantially parallel to each other. In one embodiment, the plurality of frozen piercing implements are positioned substantially in a predetermined spatial pattern. In one embodiment, the predetermined spatial pattern is at least partially periodic. In one embodiment, the plurality of frozen piercing implements includes an area density of implements greater than or approximately equal to 1 µm, greater than or approximately equal to 10 µm, greater than or approximately equal to 50 µm, greater than or approximately equal to 100 µm, greater than or approximately equal to 500 µm, greater than or approximately equal to 1 mm, greater than or approximately equal to 10 mm, greater than or approximately equal to 50 mm, greater than or approximately equal to 100 mm, greater than or approximately equal to 500 mm, greater than or approximately equal to 1 cm, or any value there between. In one embodiment, the plurality of frozen piercing implements include approximately the same length.

In one embodiment, the length of a frozen piercing implement is associated with the position or location of the frozen piercing implement in the array device. In one embodiment, the length of a frozen piercing implement is actuatable. In one embodiment, at least one frozen piercing implement is configured to be deactivated. In one embodiment, the at least one frozen piercing implement configured to be deactivated is deactivated by at least one component of the array device or the frozen piercing implement. In one embodiment, the at least one frozen piercing implement configured to be deactivated is deactivated by thermal transfer to the at least one frozen piercing implement.

In one embodiment, the plurality of frozen piercing implements is positioned as at least a portion of a fluidic or injection device. In one embodiment, the plurality of frozen piercing implements is positioned in fluid communication with at least one compartment configured to be mechanically regulated. In one embodiment, at least one frozen piercing implement of the plurality of frozen piercing implements includes one or more of hydrogen oxide, nitrogen, oxygen, air, helium, neon, argon, xenon, chlorine, bromine, carbon dioxide, acetone, ethyl acetate, dimethyl sulfoxide, dimethyl formamide, dioxane, tetrahydrofuran, acetonitrile, acetic acid, n-butanol, isopropanol, n-propanol, hexamethylphosphorotriamide, perfluorohydrocarbon, methanol, ethanol, tert-butyl alcohol, formic acid, hydrogen fluoride, ammonia, benzene, carbon tetrachloride, hexane, dichloromethane, methylene chloride, carboxylic acid, saline, standard saline citrate, methane, toluene, chloroform, polyethylene glycol, acetic acid, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, or diethyl ether.

In one embodiment, at least one frozen piercing implement of the plurality of frozen piercing implements is configured to deliver at least one agent. In one embodiment, the at least one major dimension includes at least one of the radius, diameter, length, width, height, or perimeter. In one embodiment, at least one frozen piercing implement of the plurality further comprises at least one agent. In one embodiment, each frozen piercing implement of the plurality includes at least one agent different than the agent of every other frozen piercing implement of the plurality. In one embodiment, at least one frozen piercing implement of the plurality includes at least two different agents. In one embodiment, the device includes at least two different agents. In one embodiment, the at least one agent includes at least one antigen. In one embodiment, each frozen piercing implement of the plurality includes at least one antigen. In one embodiment, the at least one antigen includes at least one allergen. In one embodiment, the frozen piercing implement is configured for delivering the at least one agent. In one embodiment, the at least one agent includes at least one of a nontoxic, biocompatible, bioresorbable, or biodegradable agent.

In one embodiment, at least two frozen piercing implements of the plurality of frozen piercing implements have at least one agent in common. In one embodiment, each frozen piercing implement of the plurality of frozen piercing implements has at least one agent in common. In one embodiment, each frozen piercing implement of the plurality of frozen piercing implement is different from every other piercing implement by varying one or more of: size of implement, shape of implement, or constitution of implement. In one embodiment, at least two frozen piercing implements of the plurality of frozen piercing implement differ in one or more of: size of implement, shape of implement, or constitution of implement.

As described herein, in one embodiment, at least one of the plurality of frozen piercing implements is substantially solid at approximately 0° C., approximately −10° C., approximately −20° C., approximately −30° C., approximately −40° C., approximately −50° C., approximately −60° C., approximately −70° C., approximately −75° C., approximately −80° C., approximately −85° C., approximately −90° C., approximately −95° C., approximately −100° C., approximately −120° C., approximately −150° C., approximately −180° C., approximately −200° C., approximately −220° C., approximately −250° C., or any value less than or therebetween. Ranges for consideration of substantially solid state are provided herein.

In one embodiment, the array device has at least one major dimension of approximately one centimeter or less, approximately one millimeter or less, approximately one micrometer or less, approximately one nanometer, or any value therebetween. In one embodiment, the plurality of frozen piercing implements includes a two dimensional array. In one embodiment, the plurality of frozen piercing implements includes a three dimensional array. In one embodiment, the plurality of frozen piercing implements are arranged in at least one configuration including a regular or irregular shape. In one embodiment, the plurality of frozen piercing implements are arranged in at least one configuration including at least one of a rectangle, square, circle, triangle, or polygon.

In one embodiment, at least one frozen piercing implement of the plurality of frozen piercing implements includes at least one functionalized surface. In one embodiment, the at least one functionalized surface includes one or more functionalities including one or more of charge functionality, hydrophobic functionality, hydrophilic functionality, chemically reactive functionality, organo functionality, or wetability. In one embodiment, the at least one functionalized surface includes one or more functional groups including at least one of an agent, alcohol, hydroxyl, amine, aldehyde, dye, ketone, carbonyl, thiol, alkoxysilane, phosphate, carboxyl, carboxylic acid, carboxylate, nucleic acid, amino acid, polypeptide, protein, lipid, carbohydrate, metal, —$NH_3^+$, —COOH, —COO—, —$SO_3$, $CH_2N^+(CH_3)_3$, —$(CH_2)_xCH_3$, —$C((CH_2)_xCF_3)_3$, —$CH_2N(C_2H_5)_2$, —$NH_2$, —$(CH_2)_x$COOH, —$(OCH_2CH_2)_xCH_3$, —SiOH, or —OH. In one embodiment, the at least one functionalized surface includes at least part of an outer surface. In one embodiment, the at least one functionalized surface includes at least part of an inner surface.

In one embodiment, the array device further comprises at least one channel. In one embodiment, the at least one channel includes at least one cross-coupling flow channel. In one embodiment, at least one frozen piercing implement of the plurality of frozen piercing implements includes at least one inlet port. In one embodiment, the at least one inlet port is in fluid communication with at least one channel of at least one frozen piercing implement. In one embodiment, the at least one inlet port is in fluid communication with at least one channel of the array device. In one embodiment, at least one frozen piercing implement of the plurality of frozen piercing implements includes a plurality of inlet ports. In one embodiment, at least one frozen piercing implement of the plurality of frozen piercing implements includes at least one outlet port. In one embodiment, the at least one outlet port is in fluid communication with at least one channel of at least one frozen piercing implement. In one embodiment, the at least one outlet port is in fluid communication with at least one channel of the array device. In one embodiment, at least one frozen piercing implement of the plurality of frozen piercing implements includes a plurality of outlet ports. In one embodiment, the array device further comprises at least one of a nanoparticle, microparticle, sensor, valve, gate, channel, transducer, actuator, detector, heater, circuit, or detection material.

In one embodiment, at least one implement of the plurality of frozen piercing implements includes at least one sensor. In one embodiment, at least one implement of the plurality of frozen piercing implements is configured for extracting at least one material from at least one substrate. Various non-limiting examples of materials capable of being sensed, extracted, or collected from a substrate are provided herein.

In one embodiment, at least one implement of the plurality of frozen piercing implements further includes at least one of an organic or inorganic small molecule, clathrate or caged compound, protocell, coacervate, microsphere, Janus particle, proteinoid, laminate, helical rod, liposome, macroscopic tube, niosome, sphingosome, toroid, vesicular tube, vesicle, small unilamellar vesicle, large unilamellar vesicle, large multilamellar vesicle, multivesicular vesicle, lipid layer, lipid bilayer, micelle, organelle, cell, membrane, nucleic acid, peptide, polypeptide, protein, glycopeptide, glycolipid, lipoprotein, sphingolipid, glycosphingolipid, glycoprotein, peptidoglycan, lipid, carbohydrate, metalloprotein, proteoglycan, chromosome, nucleus, acid, support structure, buffer, protic solvent, aprotic solvent, nitric oxide, nitrous oxide, nitric oxide synthase, amino acid, micelle, polymer, copolymer, monomer, prepolymer, cell receptor, adhesion molecule, cytokine, chemokine, immunoglobulin, antibody, antigen, platelet, extracellular matrix, blood, plasma, cell ligand, zwitterionic material, cationic material, oligonucleotide, nanotube, piloxymer, transfersome, gas, element, contaminant, radioactive particle, hormone, microorganism, bacteria, virus, quantum dot, contrast agent, or any part thereof.

In one embodiment, the plurality of frozen piercing implements includes at least approximately 2 implements, approximately 5 implements, approximately 10 implements, approximately 20 implements, approximately 50 implements, approximately 100 implements, approximately 200 implements, approximately 300 implements, approximately 400 implements, approximately 500 implements, approximately 600 implements, approximately 700 implements, approximately 800 implements, approximately 900 implements, approximately 1000 implements, approximately 5000 implements, approximately 10000 implements, or any value therebetween or greater. In one embodiment, the spacing between two or more frozen piercing implements includes at least approximately 1 nm, approximately 5 nm, approximately 10 nm, approximately 20 nm, approximately 50 nm, approximately 80 nm, approximately 100 nm, approximately 200 nm, approximately 300 nm, approximately 400 nm, approximately 500 nm, approximately 600 nm, approximately 700 nm, approximately 800 nm, approximately 900 nm, approximately 1 µm, approximately 5 µm, approximately 10 µm, approximately 15 µm, approximately 20 µm, approximately 50 µm, approximately 100 µm, approximately 120 µm, approximately 150 µm, approximately 200 µm, approximately 500 µm, approximately 1 mm, approximately 5 mm, approximately 10 mm, approximately 100 mm, approximately 500 mm, approximately 1 cm, approximately 5 cm, approximately 10 cm, or any value therebetween or greater. In one embodiment, the array device further comprises at least one attachment component configured to secure the array device to at least one substrate. In one embodiment, the at least one attachment component includes at least one adhesive material. In one embodiment, the device is configured to substantially form a patch.

In one embodiment, the array device further comprises at least one compartment. In one embodiment, at least one compartment includes at least one syringe or at least one valve. In one embodiment, at least one compartment is configured to hold at least one material extracted from at least one substrate. In one embodiment, at least one agent includes at least one of an adhesive agent, therapeutic agent, reinforcement agent, abrasive, biological remodeling agent, or explosive material.

In one embodiment, the array device further comprises at least one compartment in fluid communication with at least one frozen piercing implement of the plurality of frozen piercing implements. In one embodiment, the at least one compartment is configured for holding at least one agent. In one embodiment, the at least one compartment is configured for holding at least one cryogenic substance. In one embodiment, the array device further comprises a plurality of compartments in fluid communication with at least one frozen piercing implement of the plurality of frozen piercing implements. In one embodiment, the plurality of compartments includes at least one first compartment configured to hold at least one different substance from at least one second compartment. In one embodiment, the plurality of compartments includes at least one first compartment configured to hold at least one first agent, wherein the at least one first agent is different from at least one other agent located in at least one second compartment. In one embodiment, the plurality of compartments includes at least one first compartment configured to hold at least one first agent, and at least one second compartment configured to hold a pharmaceutically acceptable carrier or excipient. In one embodiment, two or more compartments are configured to interact with at least one means for intermixing the contents of the two or more compartments prior to or during administration of the array device to at least one substrate. In one embodiment, wherein the at least one means for intermixing includes mechanical disruption of at least one compartment, altering porosity of at least one compartment, electrochemical degradation of at least one compartment, valve opening of at least one compartment, chemical degradation of at least one compartment, or altering magnetic field of at least one compartment. In one embodiment, the array device is in electronic communication with at least one computing device.

In one embodiment, a composition comprises a plurality of frozen piercing implement array devices joined together.

In one embodiment, the at least one support structure for an array device, fluidic device, or injection device includes at least one of a nanoparticle, sensor, circuit, lens, heater, detector, controller, or actuator. In one embodiment, the support structure includes at least one wave guide.

In one embodiment, the heater includes a microheater or nanoheater. In one embodiment, the detector includes a microdetector or nanodetector. In one embodiment, the actuator includes a microactuator or a nanoactuator. In one embodiment, the actuator includes a rotational actuator including carbon nanotubes. See, for example, Fennimore et al., Nature (Abstract) vol. 424, pp. 408-410 (2003), which is incorporated herein by reference. In one embodiment, the actuator includes a biological molecular motor or switch (e.g., kinesin, myosin, ATP synthase, etc.). See, for example, Dessinges et al., PNAS vol. 101, no. 17, pp. 6439-6444 (2004); and the world wide web at: timeshighereducation.co.uk/story.asp?storyCode=202789&sectioncode=26, the content for each of which is incorporated herein by reference.

In one embodiment, the lens includes a liquid micro-lens array activated by selective electrowetting on polar electric crystals, including but not limited to litium niobate. See, for example, Grilli et al., Optics Express, vol. 16, no. 11, (2008), which is incorporated herein by reference.

In one embodiment, the frozen piercing implement, or frozen piercing implement device, is configured to pierce at least one substrate in a substantially painless manner. In one embodiment, the frozen piercing implement, or frozen piercing implement device, is configured to pierce one or more biological cells or tissues of a subject in a substantially painless manner.

In one embodiment, the frozen piercing implement, or frozen piercing implement device, is utilized in conjunction with at least one other substrate-piercing tool, including but not limited to transdermal agent delivery iontophoresis, ultrasound, vacuum, viruses, pH, heat, light, chemical enhancers, electric fields, photomechanical waves, mesotherapy, electroporation, electrofusion, electroosmosis, velocity based enhancement techniques (such as needle-free injections), tape stripping, powderjecting, transfersomes, agent-embedded tattoos or other etchings, abrasion or ablation, controlled heat aided delivery, laser radiation, magnetophoresis, or others. See, for example, Kumar and Philip, Trop. J. Pharm. Res. 6(1):633-644 (2007), which is incorporated herein by reference. In one embodiment, the frozen piercing implement or frozen particle composition includes at least one general anesthetic. In one embodiment, the frozen piercing implement or frozen particle composition including a general anesthetic is configured to be used as at least part of a defense weapon.

In one embodiment, the frozen piercing implement includes at least one projection. In one embodiment, the frozen piercing implement is configured to pierce at least one substrate to a depth of approximately 1 μm, approximately 5 μm, approximately 10 μm, approximately 15 μm, approximately 20 μm, approximately 50 μm, approximately 100 μm, approximately 120 μm, approximately 150 μm, approximately 200 μm, approximately 250 μm, approximately 300 μm, approximately 350 μm, approximately 400 μm, approximately 450 μm, approximately 500 μm, approximately 600 μm, approximately 700 μm, approximately 800 μm, approximately 900 μm, approximately 1 mm, approximately 2 mm, approximately 3 mm, approximately 4 mm, approximately 5 mm, approximately 10 mm, approximately 20 mm, approximately 30 mm, approximately 40 mm, approximately 50 mm, approximately 60 mm, approximately 70 mm, approximately 80 mm, approximately 90 mm, approximately 100 mm, approximately 200 mm, approximately 300 mm, approximately 400 mm, approximately 500 mm, approximately 600 mm, approximately 700 mm, approximately 800 mm, approximately 900 mm, approximately 1 cm, approximately 10 cm, approximately 20 cm, or any value therebetween.

In one embodiment, the frozen particle implement administration depth is controlled by mechanical means. For example, the implement administration depth may be limited by a sheath or casing. In one embodiment, the frozen particle implement depth is controlled by a positioner on the array that can control the depth of administration. In one embodiment, the positioner is configured to mechanically control the depth of administration of at least one frozen piercing implement (or other implement if located in an array device). Other factors that can influence administration depth include the geometry of the implement, constitution of the implement, administration time, manner of administration, or at least one parameter of the substrate (including, but not limited to temperature, constitution, density, location, etc.)

In one embodiment, one or more frozen piercing implement array device includes at least two frozen piercing implements positioned on or through the surface of at least one base or support structure. In one embodiment, a flange or other member is configured on the array device to provide physical support to the device, to provide stabilization when the device is placed on the substrate, or to control penetration of the substrate by the at least one piercing implement.

In one embodiment, the frozen piercing implement array device is an in-plane array device. In one embodiment, the frozen piercing implement array device is an out-of-plane array device.

In one embodiment, the device includes a particular arrangement of the piercing implements on the base or support structure (e.g., square, hexagonal, triangular, diamond, rectangular, or other patterning), varying the distribution of the piercing implements within a specific patterned or designed array device, varying at least one dimension of the piercing implement (e.g., number of piercing implements, piercing implement radius, etc.), number of solid versus channeled piercing implements, among other features, can affect the functionality of the array device. See, for example, Al-Qallaf and Bhusan Das, J Drug Target., vol. 17, no. 2, pp. 108-122 (2009), which is incorporated herein by reference.

Furthermore, optimization of the surface area of the array device, optimization of the piercing implement radius and length, optimization of the number of piercing implements per row, optimization of the aspect ratio of the distance between piercing implements, while considering the substrate thickness or permeability, can be conducted according to well-established principles. Id. For example, the following equation has been used in published studies to calculate skin permeability when using microneedles: $K=f(D/Lh)$, where K is the approximate skin permeability of the agent (or other agent) intended to be administered, f is the approximate fractional skin area after insertion by the microneedles, D is the approximate effective diffusion coefficient of the therapeutic agent in the skin, and $L_h$ is the approximate length of the hole resulting from the piercing of the skin. Id. In one embodiment, the therapeutic agent molecules may traverse through various disruptions in the skin thickness (i.e., epidermis) from the frozen piercing implement of the array device to the blood supply. In one embodiment, the agent may be absorbed as the frozen piercing implement melts or sublimates. In one embodiment, particularly with channeled, or hollowed, microneedles, the therapeutic agent may move through the bore of the implement. In one embodiment, the path of the therapeutic agent represents the approximate length of the microneedle. In one embodiment, the path of the therapeutic agent may be less than or greater than the approximate length of the microneedle due to expansion or contraction of the microneedle upon contact or penetration of the substrate.

In one embodiment, the array device is administered to at least one external surface of a subject. In one embodiment, the array device is administered to at least one internal surface of a subject (for example, by utilizing a catheter, laparascope, or other tool). In one embodiment, the array device is surgically implanted into a subject.

In one embodiment, the one or more frozen piercing implements are combined with at least one syringe. In one embodiment, the syringe includes a micro- or nano-syringe. In one embodiment, the one or more frozen piercing implements are combined with at least one pen-type delivery device. For example, the pen-type delivery device includes a housing assembly, a hub assembly, a plunger for driving the piercing implement out of the housing assembly and into the substrate, an optional compartment containing a desired substance to be administered, and an optional mechanism for piercing the compartment and releasing the substance. See, for example, U.S. Patent App. Pub. No. 20030050602, which is incorporated herein by reference.

In one embodiment, one or more frozen piercing implements are combined with a fluidic system. In one embodiment, the fluidic system includes a microfluidic system. In one embodiment, the fluidic system includes a nanofluidic system. In one embodiment, the fluidic system includes at least one of a channel, pump, sensor, injector, actuator, heater, detector, controller, transducer, receiver, transmitter, circuit, lens, tunable lens, valve, gate, nanoparticle, microparticle, power source, or detection material.

In one embodiment, the valve includes a valve actuated by a motor. In one embodiment, the valve includes a slide-valve, optionally actuated by a motor. As described herein, in one embodiment, the motor includes a biological based motor (e.g. kinesin, myosin, ATP synthase), or a micro- or nano-stepping motor. See, for example, Morishima et al, $7^{th}$ Int.

Conf. Miniaturized Chem. and Biochem. Anal. Sys. pp. 1033-1036 (Oct. 5-9, 2003), which is incorporated herein by reference.

In one embodiment, the fluidic device includes a closed loop system capable of delivering at least one agent, sensing, or extracting at least one material from at least one substrate. In one embodiment, the fluidic system includes at least one compartment. In one embodiment, the fluidic system senses or analyzes at least one material from at least one substrate. In one embodiment, the analysis includes sensing an enzyme or enzymatic reaction including, but not limited to glucose oxidase or glucose dehydrogenase. In one embodiment, the fluidic device includes at least one transducer, such as an electrochemical or optical transducer.

In one embodiment, the fluidic system includes detecting or sensing at least one material from the at least one substrate, extracting the at least one material in order to analyze and determine a medical treatment (including preventative, diagnostic, or responsive), and administering at least one agent. In one embodiment, the closed loop system is configured in the form of a patch, bandage, or other attachment vehicle.

In one embodiment, a sensor, such as an enzyme electrode for glucose, for example, includes a screen-printed electrode on the surface of which is immobilized glucose oxidase, and an electron mediator, such as ferrocene or its derivatives. Electrons generated by the oxidation of glucose are transferred from glucose oxidase to the electrode by way of the mediator, and the concentration of glucose is proportional to the current generated. See, for example, U.S. Pat. No. 7,344,499, which is incorporated herein by reference. In one embodiment, near-infrared spectroscopy is utilized for detecting at least one material in at least one substrate. For example, the concentration of extracted glucose in a gel is detected by the absorption of the near-infrared light that passes through the chamber. Id.

In one embodiment, at least one frozen piercing implement is adapted to include at least one sensor or sensing component. For example, an enzyme (such as glucose oxidase) can be coated on the surface of one or more frozen piercing implements, distributed within the frozen piercing implement, or at least partially filling an otherwise hollow frozen piercing implement.

In one embodiment, the frozen piercing implement device includes at least one sensor in communication with at least one electronic component. In one embodiment, the at least one electronic component includes at least one of a power source (for example, a battery), transducer, storage device, display, receiver, or other electronic component. The at least one electronic component can be included with at least one piercing implement, support structure, compartment, or other aspect of the frozen piercing implement device.

In one embodiment, the at least one sensor can be calibrated by utilizing the concentration of at least one same or different analyte, measured by another means. For example, the analyte can be normalized (by a linear or non-linear relationship), reducing the variability between analysis events.

In one embodiment, the fluidic device includes at least one attachment component configured to secure the array device to at least one substrate. In one embodiment, the at least one attachment component includes at least one adhesive material.

In one embodiment, the fluidic device includes at least one vacuum to induce flow in at least one direction through at least one piercing implement.

In one embodiment, the frozen piercing implement includes at least one surfactant. In one embodiment, the surfactant includes at least one ionic surfactant. In one embodiment, the at least one ionic surfactant includes one or more of an alkyl ammonium salt, bile acid or salt, fatty acid, carnitine, oligopeptide, polypeptide, acyl lactylate, mono-diacetylated tartaric acid ester of a mono-diglyceride, succinylated monoglyceride, citric acid ester of mono-diglyceride, alginate salt, propylene glycol alginate, lecithin, hydrogenated lecithin, lysolecithin, hydrogenated lysolecithin, lysophospholipid, phospholipid, alkylsulfate salt, fatty acid salt, sodium docusate, or mixtures or derivatives of any thereof.

Additional Methods, Devices, and Systems for Making and Administering Frozen Particle Compositions, Frozen Piercing Implements, and Frozen Piercing Implement Devices As described herein, a device or machine (including a computer) may be utilized in various aspects relating to compositions, methods, or systems relating to one or more frozen particle compositions, or frozen piercing implements. Non-limiting examples of such aspects may include predicting or calculating various properties or characteristics relating to the one or more frozen particle compositions, or frozen piercing implements, any substrate, any subject, any administration device, or any administration protocol. Any method disclosed herein is implicitly intended to also include "means for" carrying out the method. One or more methods disclosed include computer-implemented methods.

In one embodiment, a method or means for making one or more frozen particle compositions, or frozen piercing implements optionally includes at least one agent. In one embodiment, a method or means for administering or delivering one or more frozen particle compositions, or frozen piercing implements is disclosed. In one embodiment, a method or means for administering at least one frozen particle composition, or frozen piercing implement includes administering at least one agent to a substrate.

In one embodiment, at least one computer system is configured to provide one or more instructions to one or more devices for deposition or administration of one or more frozen particle compositions, or frozen piercing implements. In one embodiment, at least one device is configured to deposit or administer one or more frozen particle compositions, or frozen piercing implements on any x, y, or z axis. In one embodiment, the at least one computer system provides one or more instructions for predicting, controlling, or varying the administration of one or more frozen particle compositions, or frozen piercing implements or deposition of at least one agent included in the one or more frozen particle compositions, or frozen piercing implements on any x, y, or z location. In one embodiment, the at least one computer system provides one or more instructions for temporal, spatial, or regional locations for deposition or administration of one or more frozen particle compositions, or frozen piercing implements. Other components of the at least one computer system or device are included in the figures as described.

In one embodiment, one or more methods, devices, or systems described herein include making or administering one or more frozen particle compositions or frozen piercing implements. In one embodiment, frozen particle compositions or frozen piercing implements as described herein are made by one or more processes. In one embodiment, at least one process described herein is adaptable for a micro- or nano-scale fabrication of the frozen particle compositions, or frozen piercing implements. See, for example, U.S. Patent Application Publication No. 20020193754, which is incorporated herein by reference.

In one embodiment, a method for making at least one frozen piercing implement includes etching a frozen composition with a chemical. In one embodiment, the chemical includes at least one alcohol. In one embodiment, the alcohol includes at least one of methanol, or ethanol. In one embodiment, the chemical agent includes at least one salt or salt solution. In one embodiment, a method for making at least one frozen piercing implement includes etching a frozen composition with an acid or a base. In one embodiment, a method for making at least one frozen piercing implement includes etching a frozen composition with oxyfuel gas cutting (sometimes referred to as "flame cutting"). In one embodiment, the base includes sodium hydroxide, chromium trioxide, ammonium fluoride, ammonium hydroxide, hydrogen peroxide, or potassium hydroxide. In one embodiment, the acid includes phenol, acetic acid, nitric acid, hydrofluoric acid, sulfuric acid, phosphoric acid, or hydrochloric acid. In one embodiment, a method for making at least one piercing implement includes etching a frozen composition with fluid hydrogen oxide (e.g., gas or liquid). In one embodiment, a method for making at least one piercing implement includes etching a frozen composition with a fluid form of at least one constituent of the frozen composition (including but not limited to a frozen block or film).

In one embodiment, the etching includes a fluid jet stream. For example, in one embodiment, a water jet cutter is utilized in etching at least one frozen composition. In one embodiment, the fluid jet stream includes a gas or liquid jet stream. In one embodiment, the fluid jet stream includes at least one chemical. In one embodiment, the at least one chemical includes at least one agent. In one embodiment, the at least one chemical includes at least one polymer (e.g., a linear macromolecular partially hydrolyzed polyacrylamide, such as found in SUPER WATER™, available from Berkeley Chemical Research, Inc.)

In one embodiment, the fluid jet stream includes air. In one embodiment, the pressure of the fluid jet stream includes at least approximately 0.5 psi, approximately 1 psi, approximately 5 psi, approximately 10 psi, approximately 20 psi, approximately 30 psi, approximately 40 psi, approximately 50 psi, approximately 60 psi, approximately 70 psi, approximately 80 psi, approximately 90 psi, approximately 100 psi, approximately 150 psi, approximately 200 psi, approximately 500 psi, approximately 1,000 psi, approximately 5,000 psi, approximately 10,000 psi, approximately 20,000 psi, approximately 30,000 psi, approximately 40,000 psi, approximately 50,000 psi, approximately 60,000 psi, approximately 70,000 psi, approximately 80,000 psi, approximately 90,000 psi, or any value therebetween or greater. The pressure of the fluid jet stream can also be adjusted according to other factors, including but not limited to the width or diameter of the stream, the abrasive flow rate, or the jet stream traverse rate. See, for example, Srinivasu and Babu, Appl. Soft Comp. vol. 8, pp. 809-819 (2008), which is incorporated herein by reference. For example, a narrow jet stream will generally have greater cutting power than a wider jet stream due to increased pressure at the nozzle. See, for example, the world wide web at jetedge.com, the content of which is incorporated herein by reference.

In one embodiment, the etching includes thermal etching. For example, crystalline substances can be etched in a saturated air atmosphere, with an etching time of a few seconds, to several weeks. See, for example, Krausz and Gold, J of Colloid and Interface Sci., vol. 25, pp. 255-262 (1967).

In one embodiment, the etching includes laser etching. For example, frozen piercing implements can be cut from a film, sheet, strip, block, or other form of frozen composition with an infrared laser. In one embodiment, the laser is guided by a CAD/CAM design.

In one embodiment, bores are etched (for example, with a physical or chemical etchant) in the material (such as a frozen composition) and the remainder of the piercing implement is etched away around the bores. In one embodiment, the piercing implements and their bores (if included) are etched simultaneously, or bores are etched into existing piercing implements.

In one embodiment, bores from the backside of the material (such as a frozen composition) are generated using a front-to-backside infrared alignment, and etching from the backside of the material.

In one embodiment, the etching time includes at least approximately 10 seconds, at least approximately 20 seconds, at least approximately 30 seconds, at least approximately 1 minute, at least approximately 5 minutes, at least approximately 10 minutes, at least approximately 20 minutes, at least approximately 30 minutes, at least approximately 2 hours, at least approximately 5 hours, at least approximately 10 hours, at least approximately 24 hours, at least approximately 2 days, at least approximately 5 days, at least approximately 1 week, at least approximately 2 weeks, at least approximately 3 weeks, at least approximately 1 month, at least approximately 3 months, or any value therebetween. Various factors can influence the etching time required, including but not limited to at least one of: etching temperature, etching chemical, constitution of material being etched, thickness of material being etched, or desired characteristic of the frozen piercing implement(s).

The etched radius for a particular composition can be controlled by varying the etchant (e.g., chemical, thermal, or other), the amount of time exposed to the etchant, the temperature of the etchant or etching environment, the constituency of the composition being etched, desired size, or shape of the etching, thickness of the composition being etched, or other factors.

In one embodiment, the frozen particle compositions, or frozen piercing implements, are designed with the aid of a computer device, computer system, computer program product, or computer-implemented method. In one embodiment, the frozen particle compositions, or frozen piercing implements, are generated with the aid of a computer device, computer system, computer program product, or computer-implemented method. In one embodiment, the frozen particle compositions, or frozen piercing implements, are administered with the aid of a computer device, computer system, computer program product, or computer-implemented method.

In one embodiment, a simulation for a mask is generated, optionally with assistance from a computer device, computer system, computer program product, or computer-implemented method. See, for example, Wilke et al., Euro. Micro & Nano Systems 20-21(2004), which is incorporated herein by reference. As discussed by Wilke et al., a mask can be designed on the basis of a Simode simulation, and optical microscopy as well as scanning electron microscopy can be utilized to examine single microneedles resulting from the etching process. Id. Thus, by varying the etching times, temperatures, and other factors, microneedles can be consistently reproduced with high accuracy. Id. In one embodiment, an array device including a plurality of microneedles can be generated that can be peeled off for use. Id.

In one embodiment, a thermal etchant is utilized for fabricating one or more frozen piercing implements. In one embodiment, a fluid jet (e.g., gas or liquid) is utilized for etching one or more frozen piercing implements. In one embodiment, a laser beam is utilized for etching one or more frozen piercing implements. In one embodiment, an electron beam is utilized for etching one or more frozen piercing implements. In one embodiment, an ion beam is utilized for etching one or more frozen piercing implements.

In one embodiment, at least one frozen fluid (including but not limited to at least one solid condensed gas) is deposited onto a cryogenically cooled support surface (e.g., metal, or silicon surface) in the chamber of a combined scanning electron microscope and focused ion beam apparatus (FEI Co., Hillsboro, Oreg.). See, for example, King et al, Nano Lett. vol. 5, pp. 1157-1160 (2005), which is herein incorporated by reference. Next, the ice surface is exposed to focused energetic electron or gallium ion beams, which stimulates local removal of ice. Id. In one embodiment, the beams are programmed to produce at least one pattern in the ice. Id. Additional ice can be removed by in situ sublimation (e.g., by eliminating liquid surface tension effects) by fluid jet, or by other means. Id.

In one embodiment, the ice is deposited at a rate of approximately 1 μm/second, approximately 1 nm/second, approximately 1 mm/second, approximately 1 cm/second, or any value therebetween. In one embodiment, the ice is deposited using a leak valve controlled vapor flow that is directed onto the cooled support surface or sample. In one embodiment, the cooled sample or cooled support surface is maintained at approximately 128 K (approximately −145° C.). Id. In one embodiment, the fluid includes hydrogen oxide. In one embodiment, the hydrogen oxide is deposited on the cooled support surface by way of a magnesium sulfate-water vapor source, and water vapor pressure is controlled by at least one leak valve. Id.

In one embodiment, the etching system includes at least one cold finger located near the sample surface to ensure a sufficient thermal gradient to keep unwanted species from condensing on the support surface or sample surface. Id. In one embodiment, the cold finger is placed approximately 1 mm from the surface, approximately 2 mm from the surface, approximately 3 mm from the surface, approximately 4 mm from the surface, approximately 5 mm from the surface, approximately 6 mm from the surface, approximately 7 mm from the surface, approximately 8 mm from the surface, approximately 9 mm from the surface, approximately 10 mm from the surface, approximately 1 cm from the surface, approximately 1 dm from the surface, or any value therebetween. In one embodiment, the temperature of the sample surface can be controlled within approximately +/−1 K (approximately +/−1 degree C.). Id. In one embodiment, scanning electron microscopy can be utilized to observe etching of the frozen fluid composition. Id.

In one embodiment, the laser beam includes at least one of a carbon dioxide laser, or a Erbium:YAG laser. See, for example, U.S. Patent Application Publication No. 20080290065, which is herein incorporated by reference. Erbium:YAG lasers are commonly used in the medical sector, since the laser beam pinpoints the maximum absorption spike of water. Id. In one embodiment, the laser beam (e.g., carbon dioxide, erbium:YAG, eximer, argon, KTP, krypton fluoride, xenon chloride, xenon fluoride, helium neon, neodynmium: YAG, erbium glass, erbium:YAG, holmium:YAG, Ruby (chromium sapphire), gallium arsenide, or other) etches a frozen fluid by way of explosive vaporization. Id.

In one embodiment, the laser type is selected based on the absorption wavelength of laser energy by the frozen composition. Such an absorption profile can be generated, if not already known, using standard techniques.

In one embodiment, the laser beam is part of an etching system for forming one or more frozen piercing implements. In one embodiment, the laser system includes at least one first mirror that is optionally connected to at least one first driver under command of at least one controller. In one embodiment, the laser system includes at least one second mirror that is optionally connected to at least one second driver under command of at least one controller. In one embodiment, the at least one first driver and the at least one second driver are the same driver. In one embodiment, the at least one first driver and the at least one second driver are different drivers. In one embodiment, at least one of the at least one first driver or the at least one second driver includes at least one of a servo-galvanometer driver device, or a stepper motor driver device. Id.

In one embodiment, the at least one first mirror controls x-axis positioning of the laser. In one embodiment, the at least one second mirror controls y-axis positioning of the laser. In one embodiment, the etching system includes at least one third mirror. In one embodiment, the at least one third mirror is configured to operate as a shutter for directing the laser beam away from the material to be etched. In one embodiment, the laser system includes one or more instructions for etching the frozen material into one or more frozen piercing implements.

In one embodiment, the frozen particle compositions, or frozen piercing implements, are fabricated by pouring a liquid suspension, solution, or mixture, of the desired constituents into a vessel, mold or frame, and optionally completing the filling under vacuum. See, for example, Park et al., Pharm Res. vol. 23, no. 5 (2006), which is incorporated herein by reference. Following filling the mold, the constituents of the mold are optionally concentrated by way of evaporation or other process. Id. Next, the mold is frozen under conditions and time sufficient to at least partially solidify the constituents of the mold. Finally, the frozen particle compositions, or frozen piercing implements, are released from the vessel, mold or frame. Id.

As discussed herein, the conditions and time sufficient to at least partially solidify at least one fluid includes the particular points of state function or phase transition for the fluid. For example, first-order phase transitions involve a latent heat. During a first-order phase transition, the system either absorbs or releases a fixed amount of energy, and the temperature of the system stays constant as heat is added. In another example, second-order phase transitions have no associated latent heat, such as the glass transition of polymeric materials at the glass transition temperature of the polymer. The glass transition temperature can be measured by the change in the slope of the heating energy versus temperature curve that results from the measurement on a differential scanning calorimetry device. Accordingly, a fluid composition's phase or state varies with certain parameters of the conditions sufficient to at least partially solidify the fluid composition. For example, the state variables of pressure and temperature assist to define specific conditions sufficient to at least partially solidify a particular fluid.

As discussed herein, the mold or frame can be made from any material that allows fabrication of the frozen piercing implements. In one embodiment, the mold or frame itself is frozen. In one embodiment, the mold or frame includes at least one metal, glass, or plastic. In one embodiment, the mold or frame is disposable. In one embodiment, the mold or frame is reusable.

In one embodiment, the frozen particle compositions, or frozen piercing implements are spray or dip coated with at least one agent. Id. In one embodiment, the at least one agent includes at least one adhesive agent, therapeutic agent, reinforcement agent, biological remodeling agent, abrasive, or explosive material.

In one embodiment, the frozen particle compositions, or frozen piercing implements, are fabricated by layer deposition on a support structure (which may or may not be frozen).

In one embodiment, the frozen particle compositions, or frozen piercing implements, are fabricated by drawing lithography. See, for example, WO2008010682, which is incorporated herein by reference. In one embodiment, the frozen particle compositions, or frozen piercing implements, are fabricated as solid or hollow compositions by laying down a frozen composition on the surface of a support structure, and removing the implement.

In one embodiment, one or more frozen particle compositions or frozen piercing implements are made by spraying at least one fluid composition into at least one compartment. In one embodiment, the at least one compartment includes at least one fluid. In one embodiment, the at least one fluid includes at least one gas or liquid. In one embodiment, the at least one fluid includes at least one supercooled liquid. In one embodiment, the at least one liquid includes liquid nitrogen, liquid carbon dioxide, liquid argon, liquid helium, or other inert or reactive liquid. In one embodiment, the at least one fluid includes at least one of liquid nitrogen, liquid carbon dioxide, liquid hydrogen, liquid oxygen, liquid helium, liquid methane, methane/ammonia, a halogenated hydrocarbon, liquid neon, liquid argon, liquid mercury, air, cold saline, cold sodium hydroxide, cold potassium hydroxide, cold potassium chloride, cold sodium chloride solution, or hydrogen sulfide. In one embodiment, the at least one fluid includes at least one of tetrachloromethane; trichlorofluoromethane; dichlorodifluoromethane; bromochlorodifluoromethane; dibromodifluoromethane; chlorotrifluoromethane; bromotrifluoromethane; carbon tetrafluoride; trichloromethane; dichlorofluoromethane; chlorodifluoromethane; bromodifluoromethane; drifluoromethane; dichloromethane; chloromethane; fluoromethane; methane; hexachloroethane; pentachlorofluoroethane; 1,1,2,2,-tetrachloro-1,2-difluoroethane; 1,1,1,2-tetrachloro-2,2-difluoroethane; 1,1,2-trichlorotrifluoroethane; 1,1,1-trichlorotrifluoroethane; 1,2-dichlorotetrafluoroethane; 1,1-dichlorotetrafluoroethane; dibromoetetrafluoroethane; chloropentafluoroethane; hexafluoroethane; pentachloroethane; 1,1,2,2-tetrachloro-1-fluoroethane; 1,1,2-trichloro-2,2-difluoroethane; 1,1,2-trichloro-1,2-difluoroethane; 1,1,1-trichloro-2,2-difluoroethane; 2,2-dichloro-1,1,1-trifluoroethane; 1,2-dichloro-1,1,2-trifluoroethane; 1,1-dichloro-1,2,2-trifluoroethane; 2-chloro-1,1,2,2-tetrafluoroethane; pentafluoroethane; (difluoromethoxy)(trifluoro)methane; 1,1,2,2-tetrachloroethane; 1,1,1,2-tetrachloroethane; 1,1,2-trichloro-2-fluoroethane; 1,1,2-trichloro-1-fluoroethane; 1,1,1-trichloro-2-fluoroethane; dichlorodifluoroethane; 1,1,-dichloro-2,2-difluoroethane; 1,2-dichloro-1,1-difluoroethane; 1,1-dichloro-1,2-difluoroethane; 1,2-dibromo-1,1-difluoroethane; 1-chloro-1,2,2-trifluoroethane; 1-chloro-2,2,2-trifluoroethane; 1-chloro-1,1,2-trifluoroethane; 1,1,2,2-tetrafluoroethane; 1,1,1,2-tetrafluoroethane; bis(difluoromethyl)ether; 1,1,2-trichloroethane; 1,1,1-trichloroethane; 1,2-dichloro-1-fluoroethane; 1,2-dibromo-1-fluoroethane; 1,1-dichloro-1-fluoroethane; chlorodifluoroethane; 1-chloro-1,2-difluoroethane; 1-chloro-1,1-difluoroethane; 1,1,2-trifluoroethane; 1,1,1-trifluoroethane; methyl trifluoromethyl ether; 2,2,2-trifluoroethyl methyl ether; 1,2-dichloroethane; 1,1-dichloroethane; chlorofluoroethane; 1-chloro-1-fluoroethane; 1,2-difluoroethane; 1,1-difluoroethane; chloroethane; fluoroethane; ethane; 1,1,1,2,2,3,3-heptachloro-3-fluoropropane; hexachlorodifluoropropane; 1,1,1,3,3-pentachloro-2,2,3-trifluoropropane; 1,2,2,3-tetrachloro-1,1,3,3-tetrafluoropropane; 1,1,1-trichloro-2,2,3,3,3-pentafluoropropane; 1,2-dichloro-1,1,2,3,3,3-hexafluoropropane; 1,3-dichloro-1,1,2,2,3,3-hexafluoropropane; 1-chloro-1,1,2,2,3,3,3-heptafluoropropane; 2-chloro-1,1,1,2,3,3,3-heptafluoropropane; octafluoropropane; 1,1,1,2,2,3-hexachloro-3-fluoropropane; pentachlorodifluoropropane; 1,1,1,3,3-pentachloro-2,2-difluoropropane; tetrachlorotrifluoropropane; 1,1,3,3-tetrachloro-1,2,2-trifluoropropane; 1,1,1,3-tetrachloro-2,2,3-trifluoropropane; trichlorotetrafluoropropane; 1,3,3-trichloro-1,1,2,2-tetrafluoropropane; 1,1,3-trichloro-1,2,2,3-tetrafluoropropane; 1,1,1-trichloro-2,2,3,3-tetrafluoropropane; dichloropentafluoropropane; 2,2-dichloro-1,1,1,3,3-pentafluoropropane; 2,3-dichloro-1,1,1,2,3-pentafluoropropane; 1,2-dichloro-1,1,2,3,3-pentafluoropropane; 3,3-dichloro-1,1,1,2,2-pentafluoropropane; 1,3-dichloro-1,1,2,2,3-pentafluoropropane; 1,1-dichloro-1,2,2,3,3-pentafluoropropane; 1,2-dichloro-1,1,3,3,3-pentafluoropropane; 1,3-dichloro-1,1,2,3,3-pentafluoropropane; 1,1-dichloro-1,2,3,3,3-pentafluoropropane; chlorohexafluoropropane; 2-chloro-1,1,1,2,3,3-hexafluoropropane; 3-chloro-1,1,1,2,2,3-hexafluoropropane; 1-chloro-1,1,2,2,3,3-hexafluoropropane; 2-chloro-1,1,1,3,3,3-hexafluoropropane; 1-chloro-1,1,2,3,3,3-hexafluoropropane; 1,2,2,3,3,3-heptafluoropropane; trifluoromethyl 1,1,2,2-tetrafluoroethyl ether; 1,1,1,2,3,3,3-heptafluoropropane; trifluoromethyl 1,2,2,2-tetrafluoroethyl ether; pentachlorofluoropropane; tetrachlorodifluoropropane; 1,1,3,3-tetrachloro-2,2-difluoropropane; 1,1,1,3-tetrachloro-2,2-difluoropropane; trichlorotrifluoropropane; 1,1,3-trichloro-2,2,3-trifluoropropane; 1,1,3-trichloro-1,2,2-trifluoropropane; 1,1,1-trichloro-2,2,3-trifluoropropane; dichlorotetrafluoropropane; 2,2-dichloro-1,1,3,3-tetrafluoropropane; 2,2-dichloro-1,1,1,3-tetrafluoropropane; 1,2-dichloro-1,2,3,3-tetrafluoropropane; 2,3-dichloro-1,1,1,2-tetrafluoropropane; 1,2-dichloro-1,1,2,3-tetrafluoropropane; 1,3-dichloro-1,2,2,3-tetrafluoropropane; 1,1-dichloro-2,2,3,3-tetrafluoropropane; 1,3-dichloro-1,1,2,2-tetrafluoropropane; 1,1-dichloro-1,2,2,3-tetrafluoropropane; 2,3-dichloro-1,1,1,3-tetrafluoropropane; 1,3-dichloro-1,1,3,3-tetrafluoropropane; 1,1-dichloro-1,3,3,3-tetrafluoropropane; chloropentafluoropropane; 1-chloro-1,2,2,3,3-pentafluoropropane; 3-chloro-1,1,1,2,3-pentafluoropropane; 1-chloro-1,1,2,2,3-pentafluoropropane; 2-chloro-1,1,1,3,3-pentafluoropropane; 1-chloro-1,1,3,3,3-pentafluoropropane; 1,1,1,2,2,3-hexafluoropropane; 1,1,1,2,3,3-hexafluoropropane; 1,1,1,3,3,3-hexafluoropropane; 1,2,2,2-tetrafluoroethyl difluoromethyl ether; hexafluoropropane; tetrachlorofluoropropane; trichlorodifluoropropane; dichlorotrifluoropropane; 1,3-dichloro-1,2,2-trifluoropropane; 1,1-dichloro-2,2,3-trifluoropropane; 1,1-dichloro-1,2,2-trifluoropropane; 2,3-dichloro-1,1,1-trifluoropropane; 1,3-dichloro-1,2,3-trifluoropropane; 1,3-dichloro-1,1,2-trifluoropropane; chlorotetrafluoropropane; 2-chloro-1,2,3,3-tetrafluoropropane; 2-chloro-1,1,1,2-tetrafluoropropane; 3-chloro-1,1,2,2-tetrafluoropropane; 1-chloro-1,2,2,3-tetrafluoropropane; 1-chloro-1,1,2,2-tetrafluoropropane; 2-chloro-1,1,3,3-tetrafluoropropane; 2-chloro-1,1,1,3-tetrafluoropropane; 3-chloro-1,1,2,3-tetrafluoropropane; 1-chloro-1,1,1,2-tetrafluoropropane; 1-chloro-1,1,2,3-tetrafluoropropane; 3-chloro-1,1,1,3-tetrafluoropropane; 1-chloro-1,1,3,3-tetrafluoropropane; 1,1,2,2,3-pentafluoropropane; pentafluoropropane; 1,1,2,3,3-pentafluoropropane; 1,1,1,2,3-pentafluoropropane; 1,1,1,3,3-pentafluoropropane; methyl pentafluoroethyl ether; difluoromethyl 2,2,2-trifluoroethyl ether; difluoromethyl 1,1,2-trifluoroethyl ether; trichlorofluoropropane; dichlorodifluoropropane; 1,3-dichloro-2,2-difluoropropane; 1,1-dichloro-2,2-difluoropropane; 1,2-dichloro-1,1-difluoropropane; 1,1-dichloro-1,2-difluoropropane; chlorotrifluoropropane 2-chloro-1,2,3-trifluoropropane; 2-chloro-1,1,2-trifluoropropane; 1-chloro-2,2,3-trifluoropropane; 1-chloro-1,2,2-trifluoropropane; 3-chloro-1,1,2-trifluoropropane; 1-chloro-1,2,3-trifluoropropane; 1-chloro-1,1,2-trifluoropropane; 3-chloro-1,3,3-trifluoropropane; 3-chloro-1,1,1-trifluoropropane; 1-chloro-1,1,3-trifluoropropane; 1,1,2,2-tetrafluoropropane; methyl 1,1,2,2-tetrafluoroethyl ether; dichlorofluoropropane; 1,2-dichloro-2-fluoropropane; chlorodifluoropropane; 1-chloro-2,2-difluoropropane; 3-chloro-1,1-difluoropropane; 1-chloro-1,3-difluoropropane; trifluoropropane; chlorofluoropropane; 2-chloro-2-fluoropropane; 2-chloro-1-fluoropropane; 1-chloro-1-fluoropropane; difluoropropane; fluoropropane; propane; dichlorohexafluorocyclobutane; chloroheptafluorocyclobutane; octafluorocyclobutane; decafluorobutane; perfluoropropyl methyl ether; perfluoroisopropyl methyl ether; 1,1,1,3,3-pentafluorobutane; tetradecafluorohexane; butane; isobutane; pentane; isopentane; diethyl ether; methyl formate; methylamine; ethylamine; nitrous oxide; sulfur dioxide; krypton; 1,1-dichloro-2,2-difluoroethylene; chlorotrifluoroethylene; tetrafluoroethylene; trichloroethylene; cis-1,2-dichloroethylene; 1,1-difluoroethylene; chloroethylene; fluoroethylene; ethylene; hexafluoropropylene; hexafluoropropene trimer; propylene; hydrofluorocarbon; chlorofluorocarbon; hydrochlorofluorocarbon; or the like.

In one embodiment, the at least one fluid composition is sprayed beneath the surface of the fluid bath. In one embodiment, the at least one fluid composition is sprayed just above the surface of the fluid bath. In one embodiment, at least one mechanism is utilized to form or break up frozen compositions into frozen particle compositions, or frozen piercing implements. In one embodiment, the at least one mechanism includes at least one of vibration, physical mixing, bubble mixing, or sonication. See, for example, U.S. Pat. No. 4,704,873, which is incorporated herein by reference.

In one embodiment, one or more frozen particle compositions or frozen piercing implements are made by spraying at least one fluid composition into at least one freezing chamber by way of at least one inlet port, whereby as the at least one fluid composition travels through the chamber, the at least one fluid droplets freeze into solid particles. In one embodiment, the at least one freezing chamber includes at least one carrier gas. In one embodiment, the at least one freezing chamber is held under a vacuum. In one embodiment, the at least one fluid composition particles travel through the freezing chamber by at least one force including gravity, magnetism, electrostatic energy, electromagnetic energy, centrifugal force, centripetal force, capillary action, hydrophobic or hydrophilic attraction or repulsion, van der Waals forces, or other force. In one embodiment, the one or more frozen particle compositions, or frozen piercing implements are collected by at least one outlet port. See, for example, U.S. Pat. No. 5,219,746, which is incorporated herein by reference.

In one embodiment, one or more frozen particle compositions or frozen piercing implements are made by utilizing a system for continuously or serially making and administering the one or more frozen particle compositions or frozen piercing implements. In one embodiment, the system includes at least one device for making one or more frozen particle compositions or frozen piercing implements and at least one device for administering one or more frozen particle compositions or frozen piercing implements. In one embodiment, the system includes at least one hose connecting the at least one device for making and the at least one device for administering the one or more frozen particle compositions or frozen piercing implements. In one embodiment, the system includes at least one carrier gas. In one embodiment, the at least one device for administering the one or more frozen particle compositions or frozen piercing implements includes at least one handheld or portable device. In one embodiment, the at least one handheld device includes at least one propulsion gun.

In one embodiment, the device includes at least one component for directing administration of the at least one frozen particle composition or at least one frozen piercing implement. In one embodiment, the at least one component includes at least one nozzle. In one embodiment, the at least one nozzle includes at least one de Laval nozzle. In one embodiment, the one or more frozen particle compositions, or frozen piercing implements move at least partially through the delivery device by way of Venturi effect.

In one embodiment, one or more frozen particle compositions or frozen piercing implements are made by utilizing an extrusion process in a chamber maintained under pressure, and including at least one carrier gas for administration of the frozen particle compositions or frozen piercing implements. See, for example, U.S. Pat. No. 5,666,821, which is incorporated herein by reference.

In one embodiment, one or more frozen particle compositions or frozen piercing implements are made by utilizing at least one cutting mechanism with at least one frozen fluid or frozen composition substantially in the form of a block, ribbon, sheet, or other form. See, for example, U.S. Pat. Nos. 5,913,711; and 5,520,572, each of which is incorporated herein by reference.

In one embodiment, one or more frozen particle compositions or frozen piercing implements are made by grinding or pulverizing at least one frozen composition. In one embodiment, at least one frozen composition is ground with an auger and delivered under pressure with at least one carrier gas. See, for example, U.S. Pat. No. 6,174,225, which is incorporated herein by reference.

In one embodiment, one or more frozen particle compositions or frozen piercing implements are made by utilizing an ink jet style printer. See, for example, U.S. Pat. No. 7,306,316, which is incorporated herein by reference. In one embodiment, the ink jet style printer utilizes at least one supercooled fluid. In one embodiment, the supercooled fluid includes at least one cryogenic fluid. In one embodiment, the ink jet style printer includes a non-direct contact mechanism for administering the one or more frozen particle compositions or frozen piercing implements to at least one substrate. In one embodiment, the ink jet style printer includes at least one chamber under a vacuum.

In one embodiment, one or more frozen particle compositions or frozen piercing implements are made by utilizing a rotary device. See, for example, U.S. Pat. No. 4,703,590, which is incorporated herein by reference. In one embodiment, the rotary device provides at least one mold. In one embodiment, at least one fluid composition is introduced to the at least one mold, and while the rotary device rotates through a freezing chamber, the at least one fluid composition in the at least one mold becomes at least partially frozen. As the rotary device rotates further, the at least one frozen particle composition exits the at least one mold.

In one embodiment, the one or more frozen particle compositions or frozen piercing implements are made by utilizing a "pelletizer." See, for example, U.S. Pat. No. 4,617,064, which is incorporated herein by reference. In one embodiment, the one or more frozen particle compositions or frozen piercing implements are made, for example, by utilizing a holding tank, cooling reservoir, compressor, and delivery device with a carrier gas. See, for example, U.S. Pat. No. 6,306,119, which is incorporated herein by reference.

In one embodiment, the one or more frozen particle compositions or frozen piercing implements are made by depositing at least one fluid composition on at least one support surface. In one embodiment, a screen-like material, for example, a nonperforated sheet, strip, or plane receives atomized droplets (e.g. water droplets), which are then frozen to form ice crystals. See, for example, U.S. Pat. No. 6,764,493, which is incorporated herein by reference. In one embodiment, a wire mesh screen moves through a temperature controlled water bath that coats the mesh with a thin water layer. Id. In one embodiment, as the mesh enters the cold environment, ice crystals form and are brushed or scraped from the mesh with a brush. Id. In one embodiment, temperature and pressure sensors within the vessel can be used by the control device to adjust carrier fluid temperature and input pressure. Id.

In one embodiment, the one or more frozen particle compositions or frozen piercing implements are made by extruding at least one fluid composition through at least one aperture, die or nozzle. See, for example, U.S. Pat. No. 6,986,265, which is incorporated herein by reference. In one embodiment, the nozzle includes at least one de Laval nozzle. In one embodiment, at least one frozen composition in the form of a ribbon, block, or sheet, for example, is passed through the at least one aperture, die or nozzle. In one embodiment, at least one fluid composition is provided to a freezing chamber configured to freeze the at least one fluid composition, and subsequently extruded.

In one embodiment, the one or more frozen particle compositions or frozen piercing implements are administered to at least one substrate. In one embodiment, the one or more frozen particle compositions or frozen piercing implements are administered by way of compressed gas, blast plate, high-speed rotor, or electrostatic acceleration (e.g., subatomic accelerators). See, for example, U.S. Pat. No. 4,945,050, which is incorporated herein by reference.

In one embodiment, one or more frozen particle compositions or one or more frozen piercing implements are made by utilizing electrospray techniques. In one embodiment, electrospray techniques are conducted in a vacuum. See, for example, Castro and Bocanegra, Applied Phys. Lett. vol. 88, pp. 123105-1-123105-3; and U.S. Pat. No. 2,048,651, each of which is incorporated herein by reference. In one embodiment, electrospray techniques provide a narrow drop size distribution, whose mean diameter can be controlled from at least tens of nanometers to at least hundreds of microns. Id. In one embodiment, two concentric needles are fed with the conducting fluid and non-aqueous fluids through inner and outer needles, respectively. Id. In one embodiment, when an electric field is applied, the free charges in the conducting fluid migrate to the interface with the non-aqueous fluid. Id. In one embodiment, the flow-rates fed to the needles is controllable, which allows for varying contributions from the conducting fluid or non-aqueous constituents. Id. In one embodiment, colloidal propulsion efficiency depends on the ratio of mass vs. charge of the droplets. Id. When a conducting fluid surface is charged to a sufficiently high electrical potential, the interface generally forms a cone, usually referred to as a Taylor cone. Id. A Taylor cone of hydrogen oxide held in a vacuum freezes almost immediately. Id. However, when the conducting liquid includes hydrogen oxide, and the non-aqueous fluid includes at least one oil, a Taylor cone exists in a vacuum without freezing. Id. Thus, electrospray conditions can be modified according to the constituents of the frozen particle compositions, or frozen piercing implements.

In one embodiment, electrospraying is conducted by exposing fibers of viscous fluid composition to static electricity having one pole electrically connected with the fluid composition and the opposite pole electrically connected with at least one collection surface. See, for example, U.S. Pat. No. 2,048,651, which is incorporated herein by reference. In one embodiment, the viscous fluid composition includes a cold fluid composition. In one embodiment, the collection surface is approximately at or below the freezing point of the at least one fluid composition.

In one embodiment, one or more methods described herein can be utilized for fabricating one or more of frozen piercing implements, frozen piercing implement devices, including but not limited to frozen piercing implement arrays, fluidic devices, or injection devices, or other associated frozen tools and devices thereof.

As described herein, general fabrication techniques can be utilized, or adapted for making frozen particle compositions, including frozen piercing implements. Examples of such fabrication techniques include form-molding, etching, deposition, micromachining, and freeze-mixing. In one embodiment, the one or more frozen piercing implements are fabricated by utilizing multiple processes.

In one embodiment, one or more frozen piercing implements are fabricated by utilizing electrochemical etching. In one embodiment, a frozen composition (e.g., in block, ribbon, or sheet form) is masked for areas of piercing implements, and etched utilizing at least one electrolytic solution. In one embodiment, the electrolytic solution is cold, to prevent disintegration or dissolution of the frozen composition. In one embodiment, the electroylytic solution includes at least one of sodium, potassium, fluoride, chloride, bromide, calcium, magnesium, hydrogen phosphate, or hydrogen carbonate.

In one embodiment, one or more frozen piercing implements are formed by splintering or abrading a frozen composition. For example, a frozen composition block or ribbon can be splintered or abraded by utilizing a machine that includes at least one abrading wheel, or annular splint carrier. See, for example, U.S. Pat. No. 1,613,623, which is herein incorporated by reference.

In one embodiment, frozen piercing implements are formed by utilizing a frozen composition and a lithography process. In one embodiment, the lithography process includes at least photolithography. In one embodiment, the lithography process includes at least electron beam lithography. In one embodiment, etching includes wet etching or dry etching. For example, wet etching can utilize chemicals alone or in combination with an energy source, to at least partially remove material surrounding a device, or to remove one or more layers from the surface of the material to be etched. In one embodiment, the frozen composition is a film or block.

In one embodiment, etching includes plasma etching or reactive ion etching. For example, reactive ion etching includes introducing at least one etching gas into the chamber with the composition to be etched. In one embodiment, plasma is created by radiofrequency power, and reactive species (radicals and ions) are generated in the plasma. In one embodiment, reactive species diffuse onto the surface of the composition, while byproducts from the chemical reaction are desorbed and exhausted from the chamber. In one embodiment, the reactive ion etching system includes at least one of a parallel plate etching configuration with at least one electrode (e.g. 5 inch quartz electrode), and at least one radio frequency generator (e.g. 1 kW, 15 MHz). See, for example, U.S. Patent Application Publication No. 20020193754, which is herein incorporated by reference. In one embodiment, the system further includes at least one of a mass flow controller, throttle valve, controller, or vacuum pump. Id. In one embodiment, reactive ion etching removes at least one layer of material to be etched.

In one embodiment, etching includes isotropic etching or anisotropic etching. In one embodiment, undercutting is used to remove material from under a mask. In one embodiment, undercutting is conducted with at least one of a chemical, a mechanical force, an electromagnetic force, an electrical force, a thermal change, or a combination thereof. In one embodiment, undercutting is conducted with a laser, or fluid jet beam. In one embodiment, undercutting is conducted by a thermal source (including but not limited to conduction, convection, or radiation).

In one embodiment, a masking material is deposited onto a frozen composition and patterned into dots having a diameter approximately equal to the base of the desired frozen piercing implements. The frozen composition is then subjected to etching by a standard method, some of which are described herein. The regions protected by the mask remain and form the frozen piercing implements. In one embodiment, the mask is insulative. In one embodiment, the mask is heated or chemically treated. In one embodiment, etching continues until the mask falls off due to underetching, thereby generating an array of frozen piercing implements.

In one embodiment, a "donut-shaped" mask is utilized to etch hollow frozen piercing implements with inner and outer walls being etched simultaneously. See, for example, U.S. Pat. No. 6,334,856, which is incorporated herein by reference.

In one embodiment, a robotic array-spotting device (e.g., DNA microarrayer) is utilized to generate droplets. See, for example, Park et al., Biomed Devices, vol. 11, pp. 129-133 (2009), which is incorporated herein by reference. In one embodiment, the droplets are approximately uniform in size or position. In general, microarrayers can generate many identical liquid droplets on a support structure. Id. In addition, the droplets generally have high resolution and droplet volume can be controlled. Id. In one embodiment, a microarrayer can generate greater than approximately one thousand droplets per square centimeter. Id. Subsequently, the droplets are frozen, and fabricated into frozen piercing implements. In one embodiment, a channel network is made by placing a thin wire (e.g., metal wire) on a flat surface, dropping droplets onto the wire, and freezing the droplets, forming wells along the wire channel. Id. In one embodiment, the channel network is utilized in at least one array device, or fluidic device described herein.

In one embodiment, frozen piercing implements are fabricated by utilizing a micromold having tapered walls. For example, a micromold can be made, for example, by molding a pre-existing 3-dimensional array of microneedles or other piercing implements. The micromold is then surface plated or coated by, for example, vapor deposition of one or more constituents. In one embodiment, at least one constituent is spin-cast in the micromold and frozen. In one embodiment, a micromold can be made, for example, by laser ablation techniques.

In one embodiment, the constituents of the composition (i.e., at least one fluid and at least one agent) are combined and blended in at least one polymer (e.g., cellulose, polylactic acid, polyglycolic acid, or copolymers thereof, etc.), binder, or pharmaceutical carrier or excipient. Next, the composition is spun in a mold (e.g., a micromold or nanomold), defining at least one cavity at 3000 rpm for 5 minutes. See, for example, Oh and Kwon, CRS conference presentation (2007), available on the worldwide web at: theraject.com/files/Demonstration_of_Dose-controlled_Delivery_by_Dissolvable_Micro-needle_Arrays.pdf, the content of which is incorporated herein by reference. In one embodiment, at least two cavities of the mold are loaded with at least two different compositions. Next, the compositions are at least partly frozen prior to, during, or subsequent to spin-casting. The composition on the exterior of the cavities is optionally removed following centrifugation. Id. In the spun-cast system, the higher density substances will be forced toward the top (e.g. tip) of the piercing implements. Id.

Devices including at least one frozen piercing implement can also be fashioned, for example, utilizing a mold (e.g., micromold, or nanomold). See, for example, Park et al, Ibid.

In one embodiment, for example, the mold is fabricated from an epoxy (e.g. using high-aspect-ratio SU-8 epoxy photoresist master structures to form polydimethyl siloxane molds). In one embodiment, injection molding is utilized for fabricating the piercing implements from the molds. Id. In one embodiment, an asymmetric masking process during etching of the mold is utilized to form beveled or other shaped tips. Id. In one embodiment, microlenses are utilized for fabricating the molds (which can be altered by changing the focal point of the microlens). Id.

In one embodiment, the frozen piercing implement support structure includes a hydrophobic, super hydrophobic, omniphobic, hydrophilic, or amphiphilic surface. In one embodiment, the support structure includes a polymeric surface. In one embodiment, the support structure includes one or more of glass, plastic, metal, or at least one frozen material. In one embodiment, the support structure includes at least one of silicon, copper, silver, gold, platinum, rubidium, or polytetrafluoroethylene.

In one embodiment, the surface of a support structure is coated with a fluid (including a viscous form) of at least one constituent of the final frozen implement. In one embodiment, a mold or frame is configured with at least one characteristic for fabricating the piercing implement. For example, the at least one characteristic may include but not be limited to the desired size, shape, optional one or more ports, outer diameter, inner diameter (for hollow or partially hollow implements), length, inclination angle of at least one side, array pattern, etc. In one embodiment, the mold or frame is includes a comb-like configuration. In one embodiment, the mold or frame is then drawn into the fluid constituent material. In one embodiment, the mold or frame itself is coated with the fluid constituent material. In one embodiment, the fluid constituent material is frozen while it is drawn with the mold or frame. In one embodiment, the drawing process is carried out by fixing the support structure and moving the mold or frame upward or downward, or by fixing the mold or frame, and drawing the support structure upward or downward. In one embodiment, at least one desired characteristic of the piercing implements can be fabricated by varying the drawing speed, or by shaping or cutting with a mechanical cutter, electrical cutter, magnetic cutter, thermal cutter, or cutter of another source. In one embodiment, the cutter includes a laser beam.

In one embodiment, the frozen piercing implements are evaporated before removing from the mold or frame. In one embodiment, at least one additional layer is applied to the frozen piercing implements by, for example, vapor deposition, spray coating, dip coating, or other process.

In one embodiment, the frozen piercing implements are removed from the mold or frame by varying the humidity, pressure, or temperature of the piercing implements or the mold or frame. In one embodiment, the mold or frame is heated to release the implements. In one embodiment, the mold or frame is fashioned such that it can be adapted to be heated by electrical, mechanical, thermal, electromagnetic, or other source of heat. In one embodiment, the mold or frame includes a hand-in-glove configuration. In one embodiment, at least one heater heats the mold or frame by way of conduction, convection, or radiation. In one embodiment, the mold or frame is coated (for example, with a polymer, oil, wax, film, etc.) for easier removal of the piercing implements. In one embodiment, the mold or frame is coated with polytetrafluoroethylene.

In one embodiment, the frozen piercing implements are removed from the mold or frame by applying at least one solvent to the mold, frame, or frozen piercing implements. In one embodiment, the solvent includes a liquid form of at least one constituent of the frozen piercing implement. In one embodiment, the solvent includes a salt solution. In one embodiment, the solvent includes an aqueous or non-aqueous fluid.

In one embodiment, the frozen piercing implements are removed from the mold or frame by applying at least one of mechanical energy, electrical energy, electromagnetic energy, magnetic energy, or thermal energy. In one embodiment, the frozen piercing implements are removed from the mold or frame by applying one or more of a vibrational force, torsional force, compressive force, rarefaction force, or contact force (including but not limited to a collision force, such as an elastic collision or inelastic collision). In one embodiment, the frame or mold includes a portion with at least one energy producing or energy conducting component. In one embodiment, the frame or mold is stacked together in a sandwich configuration with at least one energy producing or energy conducting component layer in between. In one embodiment, the energy producing or energy conducting component includes a mesh electrical mat. See, for example, U.S. Pat. No. 7,241,979, which is incorporated herein by reference. In one embodiment, the mold or frame includes at least one thermoregulator or other regulator. In one embodiment, the energy producing or energy conducting component includes at least one thermoregulator or other regulator.

In one embodiment, the frozen particle compositions, or frozen piercing implements are fabricated by vapor condensation or deposition onto a support surface, including but not limited to a cryo-surface. See, for example, Hallbrucker et al, J. Phys. Chem. 93, pp. 4986-4990 (1989); and Mayer and Pletzer, J. Chem. Phys. 80 (6) pp. 2939-2952, each of which is incorporated herein by reference. In one embodiment, the cryo-surface includes a cryoplate or cryowire. For example, samples of amorphous solid water are prepared by depositing water vapors from a reservoir of hydrogen oxide held at room temperature through a fine metering valve and a tume into a high vacuum system, where the hydrogen oxide is condensed on a copper structure precooled to approximately 77K (approximately −196° C.). Id. In one embodiment, a baffle is used above the entrance tube to avoid supersonic flow of the hydrogen oxide vapor, which can cause rough surfacing of the particles. Id. In one embodiment, a supersonic flow of the hydrogen oxide vapor is desired, and no baffle is used. For example, in the absence of a baffle, supersonic expansion by adiabatic cooling gives a frozen amorphous solid particle with pores or voids, which allow for other fluids, including but not limited to inert gases (e.g., oxygen, nitrogen, or helium), to be adsorbed or enclosed within the frozen particle composition. Id. For example, the microporous structure allows amorphous ice a large ability to trap gases within the solid frozen particle composition. See, for example, Westley, et al., J. Chem. Phys. vol. 108, pp. 3321-3326 (1998), which is incorporated herein by reference.

In one embodiment, a method of making a frozen particle composition, including a frozen piercing implement, includes a standard refrigeration mechanism for cooling or supercooling at least one fluid constituent. For example, one form of standard refrigeration for freezing fluids includes a helix of stacked pipe coils surrounding and supporting a central support member having a hollow core, covered by a sleeve member. See, for example, U.S. Pat. No. 4,351,157, which is incorporated herein by reference. In one embodiment, the pipe helix includes an evaporator and includes a metal, such as copper. Id. In one embodiment, the hollow central support member includes an insulating material, such as foam or plastic. Id. In one embodiment, the sleeve member includes a highly thermally conductive material, such as aluminum. Id. In one embodiment, the sleeve member is in substantial surface contact with the outer surface of the pipe helix. Id. Other standard refrigeration components are disposed in housing and can include at least one of a compressor, expansion valve, filtering and drying element liquid receiving means, condenser, or condenser fan. Id. In one embodiment, the refrigeration means utilizes standard refrigerating fluids, such as FREON®. Id. In one embodiment, the helix of coils surrounded by a thermally conductive metal in substantial surface contact with the stack of coils results in formation of a frozen layer on the outer surface of the thermally conductive sleeve, even in environments not otherwise conducive to formation of frozen compositions, or frozen piercing implements. Id. This frozen layer on the outer surface of the thermally conductive sleeve can be etched, cut, or otherwise fabricated into frozen particle compositions, or frozen piercing implements.

In one embodiment, the frozen composition utilized for fabricating frozen particle compositions, or frozen piercing implements is exposed to conditions for a time sufficient to at least partially thaw the frozen composition. Subsequently, the at least partially thawed composition is frozen solid again. In one embodiment, the freeze-thaw-freeze alters the surface of the frozen composition. See, for example, U.S. Pat. No. 1,891,230, which is incorporated herein by reference. In one embodiment, the altered surface includes a hardened outer surface, or "crust." Id. In one embodiment, the frozen composition is embossed or stamped in order to fabricate at least one frozen particle composition, or frozen piercing implement. Id. In one embodiment, the frozen composition undergoes at least one thaw or partial thaw while contacting the embossing or stamping mold or equipment. In one embodiment, the frozen composition is exposed to at least one additional freezing temperature while contacting the embossing or stamping mold or equipment. In one embodiment, the embossing or stamping mold or other equipment is heated while contacting the frozen composition. In one embodiment, the frozen composition is positioned on a surface, and the embossing or stamping occurs from one side or one direction. In one embodiment, the frozen composition is positioned so as to "thread" through an embossing or stamping device, wherein the embossing or stamping occurs from more than one side or more than one direction. In one embodiment, the frozen particle compositions, or frozen piercing implements are collected subsequent to the embossing or stamping. Id. In one embodiment, the frozen particle compositions, or frozen piercing implements, are collected into a cryofluid or refrigerant. In one embodiment, the frozen particle compositions, or frozen piercing implements, are collected in at least one compartment. In one embodiment, the at least one compartment includes at least one refrigerant or cryogenic fluid. In one embodiment, the at least one compartment includes at least one of liquid nitrogen, liquid Freon®, liquid oxygen, or supercooled fluid.

Figure 126:
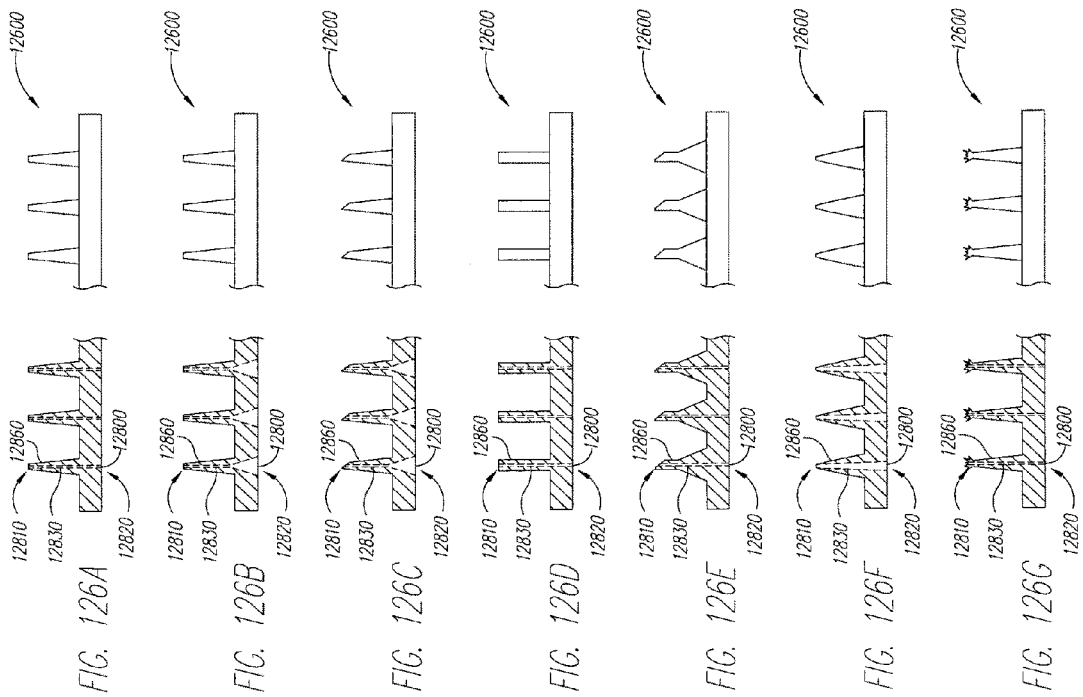

In one embodiment, the frozen piercing implement includes a sidewall, or shaft, as shown in FIGS. 121, 126, and others. In one embodiment, the angle of the sidewall, or angle of the piercing implement tip, includes at least one of at least approximately 0°, approximately 5°, approximately 10°, approximately 20°, approximately 30°, approximately 40°, approximately 45°, approximately 50°, approximately 60°, approximately 70°, approximately 80°, approximately 90°, or any value therebetween or greater.

In one embodiment, an apparatus is used for preparing frozen hydrogen oxide particle compositions. See, for example, Mayer and Pletzer, Ibid. For example, in one embodiment, frozen particle compositions are prepared by admitting hydrogen oxide vapor from a reservoir of liquid hydrogen oxide at room temperature, through a needle valve and a nozzle into a high vacuum system, condensing the vapor on a support structure precooled to approximately 77 K (approximately −196° C.). Id. In the apparatus, vapor is condensed directly in the sealed bottom part of a 10 mm diameter glass tube. Id. In one embodiment, the frozen particles are prepared in situ, and devitrification is conducted in the presence of gas or in vacuo. Id. In one embodiment, the apparatus allows for observation of the devitrification either in vacuo without any prior contact of the hydrogen oxide with inert gas, or in the presence of various inert noncondensible gases (99.99% purity). Id.

In one embodiment, the apparatus includes copper tubes of various lengths (with 13 and 4 mm inner diameter) used as nozzles. Id. Various nozzle shapes can be used. Id. Additionally, the apparatus includes an optional baffle or deflector, such as a copper plate held at room temperature between the nozzle exit and the cryoplate. Id. In one embodiment, an oil diffusion pump with 130 l/s pumping capacity is used, with a base pressure of $10^{-5}$ and $10^{-6}$ mbar during condensation. Id. The hydrogen oxide condensates can be transferred from the copper cryoplate into liquid nitrogen, and subsequently with a liquid nitrogen cooled spoon to an analytical instrument, or other location. Id.

In one embodiment, frozen hydrogen oxide particle compositions were prepared by condensation of gas evaporating from a surface of ice Ih at approximately 210 K (approximately −63° C.), with a chloroform slush bath. Id. In one embodiment, the coolfinger apparatus is inserted into a large tube with a sealed flat bottom for the crystalline ice reservoir, without the need for the nozzle. Id.

In one embodiment, differential thermal analysis of a sample of the resulting frozen hydrogen oxide particle compositions is conducted are conducted using standard techniques. Id. In one embodiment, the samples are heated from between approximately 83 K (approximately −190° C.) and approximately 90 K (approximately −183° C.) with 6 degrees/minute as a heating rate. Id.

In one embodiment, frozen particle compositions including at least, for example, methanol, toluene, butanol, ethanol, pentanol, or isopropylbenzene are prepared in the same manner, utilizing the apparatus as depicted in published studies. Id.

In one embodiment, the size, morphology, or porosity can be modulated by altering the temperature, pressure, or angle of incidence for which the vapor is deposited. See, for example, Hallbrucker et al, Ibid. In one embodiment, including at least one second fluid with the frozen particles during an annealing process, results in incorporation of the at least one second fluid in the frozen particle compositions, or frozen piercing implements. Id. For example, on heating amorphous solid water from approximately 77K (approximately −196° C.) a decrease in surface area occurs and sintering proceeds as pores close and become isolated. Id. In one embodiment, for example, the annealing process is carried out in the presence of nitrogen or other gases, and the adsorbed gases become enclosed in the pores during sintering. Id. The gas cannot be removed by pumping at low temperatures, but is gradually given off during the warming of the sample up to approximately 273 K (approximately 0° C.). Id. Accordingly, the frozen particle compositions, or frozen piercing implements that include at least one second fluid generally retain a larger size than the frozen particle compositions, or frozen piercing implements that do not contain an additional fluid. Id.

In one embodiment, at least one of the vapor deposition process or the annealing process is at least partially conducted in a vacuum, which generates frozen particle compositions, or frozen piercing implements at least substantially without other gases present in the frozen particle compositions, or frozen piercing implements. Id.

In one embodiment, ice Ic is formed by heating amorphous solid water or hyperquenched glassy water to approximately 150 K to approximately 162 K (approximately −123° C. to approximately −111° C.). Id. In one embodiment, a reversible glass to liquid transition occurs with an onset temperature of approximately 136 K+/−1 K (approximately −137° C.+/−1° C.) with a range of transition of approximately 14 K, or 14° C., and the increase in heat capacity is approximately 1.9+/−0.2 J/Kmol. Id. In one embodiment, the heat of crystallization of amorphous solid water to ice Ic is approximately −1.29+/−0.01 kJ/mol. Id.

In one embodiment, for example, published studies have shown that hydrogen oxide prepared at a temperature lower than approximately 140K (approximately −133° C.) include amorphous granules in submicrometer size. See, for example, Boxe et al., Abstract, J Colloid and Interface Sci. Vol. 309 pp. 412-418 (2007), which is incorporated by reference herein. In one embodiment, for example, at near 180-200K (approximately −93° C.—approximately −73° C.), solid hydrogen oxide produces hexagonal or cubic granules or particles in micrometer size or smaller. Id. Ice particle size can be increased, for example, by brief annealing at even warmer temperatures to sizes approaching approximately 10 µM. Id. In one embodiment, the particle size or phase is monitored or controlled. For example, environmental scanning electron microscopy can be used to assess particle size and phase of particles that develop from the vapor deposition process. Id. In one embodiment, the specific surface area of particles can be determined from BET (Brunauer, Emmett, and Teller) analysis of gas adsorption isotherms, as well as other methods. Id. In one embodiment, the BET analysis includes gas adsorption of isotherms in the temperature range from approximately 83.5 to 261 K (approximately −190° C. to −12° C.). Id. As indicated in published studies, the specific surface area of particles generated by vapor deposition were approximately 102 m$^2$/g at approximately 83.5K (approximately −190° C.) to approximately 0.87 m$^2$/g at approximately 150K (approximately −123° C.), indicating that a transition from amorphous to crystalline form of hydrogen oxide occurs at approximately 150K (approximately −123° C.).

In one embodiment, frozen particle compositions, or frozen piercing implements are prepared in a cryopumped ultra-high vacuum chamber capable of reaching a base pressure of approximately 1×10$^{-10}$ Torr, as published by Westley et al Ibid. In one embodiment, ice films are grown on an optically flat gold electrode of a quartz crystal resonator for a microbalance. Id. For example, the crystal holder is attached to a closed-cycle refrigerator and surrounded by two heat shields at approximately 30 K (approximately −243° C.) and 60 K (approximately −213° C.), respectively. Id. The films are formed by flowing degassed high-purity vapor through an array of 0.5 mm long, 50 μm diameter capillaries approximately perpendicular to the gold surface. Id. Films of thickness between approximately 0.01 μm and approximately 3 μm were grown at rates in the range of 0.6 nm/minute to 2 nm/minute at support structure temperatures of approximately 30 K (approximately −243° C.) to 140 K (approximately −133° C.). Id. In one embodiment, morphology, density and porosity of frozen particle compositions can be varied according to one or more of the constitution of the support structure, the direction of the fluid flow, or the vacuum conditions. Id.

In one embodiment, varying the angular distribution of the incident vapor molecules to the support structure controls the morphology or porosity of the frozen particle compositions. See, for example, Stevenson, et al., Science vol. 283, pp. 1505-1507 (1999). For example, in one embodiment, vapor deposited on a support structure by collimated, effusive hydrogen oxide beams have a region of uniform thickness (umbra) surrounded by a region of decreasing thickness (penumbra), whereas vapor deposited on a support structure by ambient vapor are uniform across the entire sample, as verified by Auger electron spectroscopy and temperature-programmed desorption. Id. In one embodiment, the deposition rates of hydrogen oxide vapor on a support structure include 0.02 to 0.12 bilayer per second, where 1 bilayer is approximately equal to $1.1 \times 10^{15}$ molecules per square centimeter). Id. In one embodiment, adsorption of gas (e.g., oxygen, argon, or nitrogen) by amorphous solid water frozen particle compositions, or frozen piercing implements grown with a deposition angle less than or equal to approximately 20° is similar to the adsorption by a crystalline ice film. Id. In one embodiment, adsorption of gas by amorphous solid water frozen particle compositions, or frozen piercing implements grown with a deposition angle greater than approximately 30° C. increases markedly, reaching a maximum when the angle of deposition is approximately equal to 70° C. Id. At the maximum gas adsorption, amorphous solid water adsorbs more than 20 times the amount of gas adsorbed by a crystalline ice film. Id.

In on embodiment, morphology, density, or porosity can be controlled by the angle of incidence of the vapor particles contacting the support structure, as illustrated by ballistic deposition. Id. For example, the formation of porous, columnar films by oblique deposition has been demonstrated to be controllable for a variety for structurally-stable, high-melting point solids, including but not limited to metals, oxides, or semiconductors. Id. Accordingly, for preparation of frozen particle compositions, or frozen piercing implements, morphology, density, or porosity can be controlled by angle of vapor deposition from approximately straight-line trajectories that yield less porous surfaces to an increasing or decreasing angle of deposition, that result in films of varying thicknesses and growth rates, providing a shadow of particular background regions of the support structure. Id.

In one embodiment, frozen particle compositions, or frozen piercing implements are prepared by controlling the pressure and temperature of hydrogen oxide, or other particle composition constituent, introduced as a liquid, gas, or solid. In one embodiment, ice Ic is prepared by hyperquenching pure hydrogen oxide droplets onto a cold substrate (below approximately 190 K, or approximately −83° C.), as described herein. In one embodiment, ice Ic is prepared by freezing hydrogen oxide clusters (approximately 6.6-5.5 nm) at 200 K (approximately −73° C.), or by homogenous freezing at approximately 235 K (approximately −38° C.) of an emulsion of hydrogen oxide droplets in an oil matrix. See, for example, Murray and Bertram, Phys. Chem. Chem. Phys. vol. 8, pp. 186-192 (2006), which is herein incorporated by reference.

In one embodiment, emulsions of pure hydrogen oxide droplets are prepared by mixing distilled, filtered hydrogen oxide with an oil phase in a proportion of approximately 30-40% water in oil (by mass). Id. In one embodiment, the oil phase includes approximately 10% surfactant (such as lanolin) in hydrocarbon oil (such as paraffin oil). Id. In one embodiment, emulsions are cooled to approximately 173 K (or approximately −100° C.) at a rate of approximately 10 K (or degrees Celsius)/minute, while monitoring ice reflection (with the diffraction angle of approximately 24° or approximately) 40°. Id. In one embodiment, the freezing range of pure hydrogen oxide is between approximately 237.5+/−1 K and 230.4+/−1 K (approximately −35.6° C.+/−1° C. and −42.75° C.+/−1° C.), which indicates that neither the oil nor surfactant significantly alters the nucleation process of the freezing droplets. Id.

In one embodiment, the mixture is agitated for 5-10 minutes or until the droplets are of the desired size, which can be determined by standard techniques, such as optical microscopy. Id. Droplet size can be varied by adjusting the agitation time, and droplet size allows for selection of ice structure with nearly all frozen particles existing as ice Ic at a volume median diameter of approximately 5.6 μm. Id. Ice Ic is stable in the emulsions, as in other contexts, below approximately 240 K (approximately −33° C.), when it undergoes a solid state transformation to ice Ih (unless formed in nanoporous material). Id. In one embodiment, selecting for ice Ic during crystallization of hydrogen oxide can be conducted by keeping the rate of heat dissipation greater than the rate of heat production by the crystallization process. Id.

As with other methods of preparing frozen particle compositions, or frozen piercing implements, the structures of the frozen particle compositions, or frozen piercing implements prepared in this manner can be analyzed by standard techniques, including for example, x-ray diffraction. Id.

In one embodiment, the frozen particle compositions, or frozen piercing implements are made by contacting at least one sterile first fluid droplet with at least one surface. In one embodiment, the at least one surface includes at least one hydrophobic, super hydrophobic, or omniphobic surface. In one embodiment, the at least one sterile first fluid droplet changes in density while the fluid solidifies or freezes. In one embodiment, the at least one droplet is exposed to at least one force. In one embodiment, the at least one force includes one or more of gravitational force, centrifugal force, centripetal force, magnetic force, electromagnetic force, capillary action, surface tension, expansion force, pneumatic force, air pressure, fluid pressure, electromotive force, or electrical force. In one embodiment, as the droplet density changes, at least one frozen projection is formed. In one embodiment, the at least one frozen projection includes a hollow tube through which supercooled fluid passes and freezes at the tip, thereby growing the at least one projection. In one embodiment, the at least one frozen projection forms by way of reverse sublimation. In one embodiment, the at least one frozen projection forms in accordance with the Bally-Dorsey model. See, for example, Libbrecht and Lui, on the worldwide web at: its.caltech.edu/~atomic/snowcrystals/icespikes/
icespikes.htm; and Blanchard, J. Meteorology, vol. 8, pp. 268-269 (1951), each of which is incorporated herein by reference. In one embodiment, the at least one frozen projection forms by way of crystallization.

In one embodiment, the frozen particle compositions, or frozen piercing implements, are fabricated by pulling a roll or tube of the composition while increasing the temperature or pressure on the composition in order to increase the viscosity. See, for example, Purves, Biophys. J. vol. 29, pp. 523-530 (1980), which is incorporated herein by reference. For particular compositions that may have low viscosity, or low tensile strength, at least one agent can be added to increase these characteristics. For example, one or more of a polymer, wax, fat, carbohydrate, protein, gelatin, or other agent can be added to the fluid composition, for example, hydrogen oxide or another constituent in order to increase tensile strength.

In one embodiment, the frozen particle compositions, or frozen piercing implements are generated by first combining the constituents, including any additional agents (such as therapeutic agents, reinforcement agents, abrasives, explosive materials, adhesive agents, biological remodeling agents, or other agents) under appropriate conditions. Next, the combined constituents are freeze dried. As indicated herein, in one embodiment, the frozen particle compositions, or frozen piercing implements include but are not limited to mixtures, solutions, suspensions, dispersions, gels, or other combinations.

In one embodiment, the frozen particle compositions, or frozen piercing implements, are fabricated by spinning. In one embodiment, the frozen particle compositions, or frozen piercing implements, are fabricated by melt-spinning, dry spinning, gel spinning, extrusion spinning, electro-spinning, direct spinning, or wet spinning. In one embodiment, gel spinning is conducted with DMSO as a solvent, or as part of the spun composition. See, for example, Fukae et al., Abstract, Polymer Comm., vol. 46, pp. 11193-11194 (2005), which is herein incorporated by reference.

In one embodiment, the frozen particle compositions, or frozen piercing implements, are fabricated by embossing or casting. In one embodiment, molds for embossing or casting are machined, milled, drilled, or pressed according to standard techniques. In addition, as described herein, standard lithographic methods can be used, followed by electroplating or wet/dry etching for preparing molds. In one embodiment, isothermal embossing is utilized, in which the constituents and the mold are heated above the glass transition temperature, and then pressed against the mold. In one embodiment, non-isothermal embossing is utilized, in which the mold alone is heated and pressed. As described herein, in certain cases where the glass transition temperature for a particular frozen particle composition, or frozen piercing implements is low, the articles used to make the frozen particle compositions, or frozen piercing implements are also kept at a low temperature, and heating any particular article occurs relative to the glass transition temperature.

In one embodiment, a frozen piercing implement or frozen piercing implement device is embossed in a frozen composition. A mold fabricated from a pre-existing microneedle array, for example, can be utilized. The micromold is coated with at least one constituent by, for example, vapor deposition, and the frozen piercing implements are etched from the non-embossed side until the embossed cavity is exposed. See, for example, U.S. Pat. No. 7,344,499, which is incorporated herein by reference. Next, at least one constituent is deposited on the embossed side and sidewalls, but not on the non-embossed side. Id. The micromold is then removed to form the frozen piercing implement(s).

In one embodiment, the frozen particle compositions, or frozen piercing implements, are fabricated by injection molding or rapid-injection molding. In one embodiment, for example, the combined constituents are injected into a cavity or die, then cooled under conditions sufficient to solidify the constituents. In one embodiment, the composition solidifies in a short amount of time. In one embodiment, the composition solidifies in a longer period of time. In certain instances, depending on the constitution of a particular composition, the time from injection to solidification can be adjusted for specific desired results. See, for example, U.S. Pat. No. 6,572, 796, which is incorporated herein by reference.

In one embodiment, the frozen particle compositions, or frozen piercing implements are made by calendering. In certain instances, the constituents are combined and placed under conditions sufficient to solidify the combined constituents (including but not limited to high pressure or lower temperature) before or during calendering the combined constituents into a sheet or layer on a base. Various constituents can be layered together in multiple layers, or can be combined in a single layer. The frozen particles can then be further processed to attain the desired size, shape, etc. by cutting, etching, embossing, or similar technique.

In one embodiment, the devices associated with or including at least one frozen piercing implement, including but not limited to frozen piercing implement array devices, fluidic devices, or injection devices, are at least partially fabricated by micromachining techniques. In one embodiment, surface micromachining, bulk micromachining, or a combination thereof is used.

In one embodiment, the frozen piercing implements are made by providing at least one fluid composition, and utilizing at least one force configured to induce at least one projection in the at least one fluid composition. In one embodiment, the at least one force includes at least one of: gravitational force, centrifugal force, centripetal force, magnetic force, electromagnetic force, capillary action, surface tension, expansion force, pneumatic force, air pressure, fluid pressure, electromotive force, or electrical force, or the like.

In general, the volumetric flow rate Q forming icicle-like piercing implements is on the order of tens of milliliters per hour (approximately 0.01 cm$^3$/second), and icicle radii are generally in the range of approximately 1-10cm. See, for example, Short et al., Phys. Fluids, vol. 18, pp. 083101-1-5, (2006), which is incorporated herein by reference. As such, a cylindrical icicle of radius r, has an aqueous film flow of thickness h, and since h is smaller than r over nearly the entire icicle surface, the velocity profile in the layer may be determined as that flowing on a flat surface. Id. If y is a coordinate normal (or approximately so) to the surface and θ is the angle that the tangent vector τ makes with respect to the horizontal, then the Stokes equation for gravity-driven flow is $v_w d^2 u/dy^2 = \sin\theta$, where g is the gravitational acceleration and $v_w = 0.01 cm^2$/second is the kinematic viscosity of hydrogen oxide. Id.

Additionally, piercing implements can be made from a single drop or droplet of at least one fluid composition by applying a scaling factor or the aspect ratio. Id. For example, dimensionless profiles can be constructed for a desired form by applying the formula for the "ideal icicle shape," in accordance with naturally occurring icicle shapes, which is $\rho = 4/3 (\zeta^{1/2}+2)\sqrt{\zeta^{1/2}-1}$. Id. Likewise, for example, evaluating the asymptotic form at some point on the surface $(\rho^*, \zeta^*)$ where the aspect ratio (length/width) is $A = \zeta^*/\rho^*$, and the shape can be written as $\zeta/\zeta^* \approx (\rho/\rho^*)^{4/3}$, a universal, self-similar form, regardless of the droplet size. Id. In this regard, it is possible to predict or compute parameters for a frozen piercing implement based on the natural formation of icicles.

In one embodiment, acoustic force is utilized to induce at least one projection from at least one fluid composition. For example, the shape of a drop or bubble can be distorted, and internal flow manipulated, by shifting the resonant frequencies of natural shape oscillations. See, for example, Trinh, et al., Jet Propulsion Lab white paper, available at the worldwide web at trs-new.jpl.nasa.gov/dspace/bitstream/2014/20280/1/98-1182.pdf, the content of which is incorporated herein by reference.

In one embodiment, the frozen particle compositions are made with at least one compound that has been sterilized (e.g., by filtration, by ultraviolet light, or other method), degassed, or deionized.

In one embodiment, at least one first fluid composition is contacted with at least one second fluid for a time and condition sufficient to form one or more frozen particle compositions, or frozen piercing implements as described herein.

In one embodiment, at least one agent (e.g., a reinforcement agent) is utilized to freeze with one or more components, or substances. In one embodiment, the at least one agent is substantially a solid, and at least one substance or component is substantially a liquid. The combination is then frozen, and frozen particle compositions are generated as described herein.

In one embodiment, one or more frozen particle compositions or frozen piercing implements are extruded by way of a die, or molding. In one embodiment, the constituents are combined during the extrusion process. In one embodiment, a spinneret is utilized for extrusion of frozen particle compositions or frozen piercing implements. In certain instances, the compositions are extruded in a semi-solid state, and then further solidified. In one embodiment, different dies or extrusion plates are used with the spinneret in order to form particular cross-sectional shapes (e.g., round, trilobal, pentagonal, octagonal, etc.). In one embodiment, a configuration can be used that resists bending of the extrudate, particularly when the extrudate is composed of multiple constituents. See, for example, PCT Publication No. WO/2000/070131, which is incorporated herein by reference.

In one embodiment, one or more frozen particle compositions, or frozen piercing implements are generated with assistance of at least one refrigerant or cryogen, including but not limited to liquid nitrogen, liquid carbon dioxide, etc.

In one embodiment, at least one agent (e.g., a reinforcement agent) is utilized to crystallize one or more components or substances. The crystallization is frozen, and frozen particle compositions, or frozen piercing implements are generated as described herein.

In one embodiment, the size of at least one frozen particle composition is measured. In one embodiment, the size of at least one frozen particle composition is measured according to particle size distribution. In one embodiment, the frozen particle composition size may be measured by, for example, sieve analysis, optical counting methods, electron microscopy, disc centrifugation, electrozone sensing, dynamic light scattering, electroresistance counting methods, scanning tunneling microscopy, atomic force microscopy, sedimentation techniques, laser diffraction methods, acoustic spectroscopy, ultrasound attenuation spectroscopy, and the like. In one embodiment, the size distributions are measured, for example, by utilizing an electrical mobility sizing technique in accordance with the National Institute of Standards and Technology Standard Reference Material Particles. See, for example, Application Note SMPS-003, on the worldwide web at tsi.com; the subject matter of which is herein incorporated by reference. In one embodiment, the size distribution of a particular lot of frozen particle compositions, or frozen piercing implements is measured by utilizing, for example, a Scanning Mobility Particle Sizer™ (SMPS) spectrometer. Id. For example, the SMPS spectrometer utilizes a differential mobility analyzer to size classify the particle stream and a condensation particle counter to determine the concentration at each size. Id. The differential mobility analyzer utilizes the fact that a particles' electrical mobility ($Z_p$, or the ability of a charged particle to move in an electric field) is roughly inversely proportional to particle diameter. Id. Additionally, size distribution measurements can be made in real-time with the SMPS spectrometer. Id.

In one embodiment, size distributions of electrospray droplets from a Taylor cone are directly measured by using a freezing method and a transmission electron microscope image processing. See, for example, Ki Ku, et al., Abstract, J. Aerosol Sci., vol. 32, no. 12, pp. 1459-1477 (2001), which is incorporated herein by reference.

In one embodiment, one or more methods, devices, or systems described herein include delivering or administering one or more frozen particle compositions, or frozen piercing implements by high velocity impact. In one embodiment, the one or more devices that utilize high velocity impact delivery provide at least one of localized delivery, targeted delivery, sustained delivery, modulated delivery, feedback controlled delivery. In some instances, an example of a device that can be used for administering one or more of the compositions described herein includes a handheld device, such as a wand, pen, baton, hose, sprayer, spigot, gun (e.g., particle or pellet gun), or other device. In certain instances, the device is at least part of a built-in delivery device, such as can be included in a wall, an overhead device, a corral, a gate, or a device that includes a cavity into which a subject can be placed for administration or delivery of at least one composition described herein. In certain instances, the device has robotic action. In any of these instances, the device can be remotely controlled, for example, by a human, computer system, or computer program. In one embodiment, the device can be built in, for example, in a room (e.g., hospital room, surgical room, greenhouse, food or beverage facility, outdoor or indoor arena or stadium, home, institutions, etc.).

In one embodiment, a method for making one or more frozen particle compositions, or frozen piercing implements includes passing one or more droplets of at least one fluid composition through a compartment that is configured to provide conditions for a time sufficient to freeze the one or more droplets; wherein the compartment includes at least one hydrophobic surface and wherein the at least one fluid composition includes at least one fluid and at least one agent. In one embodiment, the at least one hydrophobic surface is reversible to at least one hydrophilic surface. In one embodiment, the reversible hydrophobic surface includes at least one vanadium oxide nanostructured film. See, for example, Lim et al, J. Am. Chem. Soc., Abstract, vol. 129, pp. 4128-4129 (2007), which is incorporated herein by reference. For example, fabrication of a roselike nanostructured vanadium oxide ($V_2O_5$) film with photoinduced surface wettability switching can be conducted by drop-casting a suspension of vanadium oxide particles. Id. In one embodiment, the suspension of vanadium oxide particles is synthesized with the sol-gel method. Id. In one embodiment, alkylamine is added to the vanadium oxide, in such a manner that alkyl chains are intercalated between the vanadium oxide layers. Id. The surface is tunable, for example, by exposing the surface to ultraviolet light, the surface becomes superhydrophilic, while exposure to darkness renders the surface superhydrophobic. Id.

In one embodiment, a method for administering at least one frozen piercing implement to at least one substrate comprises contacting at least one substrate with at least one frozen piercing implement.

In one embodiment, administering the at least one frozen piercing implement to at least one substrate includes accelerating, propelling, pushing, pulling, or ejecting the at least one frozen piercing implement toward the at least one substrate. In one embodiment, administering the at least one frozen piercing implement to at least one substrate includes drilling or administering with a screw-type action. In one embodiment, administering the at least one frozen piercing implement to at least one substrate includes accelerating, propelling, pushing, pulling, or ejecting the at least one substrate toward the at least one frozen piercing implement. In one embodiment, administering the at least one frozen piercing implement to at least one substrate includes propelling, ejecting, pushing, pulling, drilling, or accelerating the at least one frozen piercing implement toward the at least one substrate with at least one of a predetermined angle, predetermined velocity, predetermined force, predetermined substrate stress, predetermined rate of administration, predetermined depth, predetermined location, predetermined time sequence, or predetermined spatial pattern. In one embodiment, the method further comprises varying the rate, velocity, force, or angle at which the at least one frozen piercing implement is administered to the at least one substrate.

In one embodiment, administering the at least one frozen piercing implement to at least one substrate includes propelling, ejecting, pushing, pulling, drilling, or accelerating a plurality of frozen piercing implements toward the at least one substrate. In one embodiment, propelling, ejecting, pushing, pulling, drilling, or accelerating the plurality of frozen piercing implements toward the at least one substrate includes propelling, ejecting, or accelerating the plurality of frozen piercing implements at one or more of a predetermined angle, predetermined velocity, predetermined rate of administration, predetermined spatial pattern, predetermined location, predetermined time sequence, predetermined force, predetermined substrate stress, or predetermined depth. In one embodiment, two or more of the plurality of frozen piercing implements each includes at least one agent that physically or chemically bind upon administration. In one embodiment, administering the at least one frozen piercing implement occurs prior to, during, or subsequent to surgery.

In one embodiment, the method further comprises varying the rate, velocity, force, or angle at which the at least one frozen particle composition, frozen piercing implement, or frozen piercing implement device is administered to the at least one substrate. In one embodiment, administering the at least one frozen particle composition, frozen piercing implement, or frozen piercing implement device occurs prior to, during, or subsequent to surgery.

In one embodiment, the method further comprises administering to the at least one substrate at least one article including an optical, photonic, or electronic article. In one embodiment, the at least one article is configured to communicate with at least one computer system. In one embodiment, the at least one article is configured to monitor at least one characteristic of the at least one substrate. In one embodiment, the at least one substrate includes at least one biological cell or tissue, and the at least one characteristic of the at least one substrate includes one or more of: tissue formation, tissue growth, cell proliferation, cell differentiation, nuclear division, apoptosis, dissolution, deterioration, biochemical function of at least one cell, biochemical function of at least one tissue, biochemical function of at least one organ, structural integrity, structural function, immunological reaction, or durability of the at least one biological tissue.

In one embodiment, the at least one article includes at least one temperature-sensitive substance. In one embodiment, the at least one article is intermixed with the at least one frozen particle composition, frozen piercing implement, or frozen piercing implement device. In one embodiment, the at least one article is located in the at least one frozen piercing implement. In one embodiment, the at least one article includes at least one electronic identification device. In one embodiment, the at least one electronic identification device includes at least one radio frequency identification device.

In one embodiment, the at least one article includes at least one radioactive, luminescent, colorimetric or odorous substance. In one embodiment, the at least one article is configured to sense at least one change in temperature. In one embodiment, the at least one article includes at least one of a diamagnetic particle, ferromagnetic particle, paramagnetic particle, super paramagnetic contrast agent, particle with altered isotope, or other magnetic particle.

In one embodiment, the method further comprises adjusting the temperature of the at least one substrate prior to, during, or subsequent to administering the at least one frozen piercing implement to at least approximately 37° C., approximately 36° C., approximately 35° C., approximately 34° C., approximately 33° C., approximately 32° C., approximately 31° C., approximately 30° C., approximately 29° C., approximately 28° C., approximately 27° C., approximately 26° C., approximately 25° C., approximately 24° C., approximately 23° C., approximately 22° C., approximately 21° C., approximately 20° C., approximately 19° C., approximately 18° C., approximately 17° C., approximately 16° C., approximately 15° C., approximately 14° C., approximately 13° C., approximately 12° C., approximately 11° C., approximately 10° C., approximately 9° C., approximately 8° C., approximately 7° C., approximately 6° C., approximately 5° C., approximately 4° C., approximately 3° C., approximately 2° C., approximately 1° C., approximately 0° C., or any temperature less than or therebetween.

In one embodiment, contacting at least one substrate includes at least one of cutting, stitching, cauterizing, freezing, perforating, penetrating, ablating, or abrading at least a part of the surface of the at least one substrate. In one embodiment, administering the at least one substrate occurs in conjunction with cryosurgery, cryotherapy, or mesotherapy.

In one embodiment, the method further comprises sensing or extracting at least one material from the at least one substrate. Various non-limiting examples of materials that are capable of being sensed or extracted from at least one substrate are provided herein.

In one embodiment, contacting at least one substrate affects one or more of electrical resistance of the at least one substrate, or permeability of the at least one substrate. In one embodiment, the method further comprises withdrawing the at least one frozen piercing implement from the at least one substrate.

In one embodiment, a method of vaccinating a subject includes administering to a subject at least one frozen particle composition, frozen piercing implement, or frozen piercing implement device that includes at least one vaccine. Specific examples of compositions including frozen piercing implements including vaccines are described herein.

In one embodiment, a method includes delivering at least one agent to at least one substrate, wherein the agent is included as part of a frozen piercing implement. In one embodiment, a method for piercing at least one substrate includes piercing at least one substrate with a frozen piercing implement including at least one agent. Specific examples of compositions including frozen piercing implements are described herein.

In one embodiment, a method for administering a frozen piercing implement device that includes at least one frozen piercing implement includes contacting the frozen piercing implement device (e.g., an array device, fluidic device, or injection device, etc.) with at least one substrate. In one embodiment, a method for delivering at least one agent includes administering at least one frozen piercing implement device to at least one substrate, wherein at least one frozen piercing implement of the device includes at least one agent. In one embodiment, the at least one frozen piercing implement is coated with at least one agent. In one embodiment, the at least one agent is encapsulated in the at least one frozen piercing implement. In one embodiment, at least one frozen piercing implement includes at least one conduit configured to deliver at least one agent. In one embodiment, the at least one frozen piercing implement array is administered to at least one substrate prior to, during, or subsequent to administering a trans-substrate patch or iontophoretic device. In one embodiment, the trans-substrate patch includes a transdermal patch.

In one embodiment, at least one material is extracted from the at least one substrate. Various non-limiting examples of materials that are capable of being extracted from at least one substrate are described herein. In one embodiment, the at least one material extracted from the at least one substrate is held in at least one compartment. In one embodiment, spring means, a cantilever, gate, expandable balloon, rigid balloon, or other regulatory means, are configured to cause a change in volume, and corresponding change in internal pressure, of the compartment. For example, in one embodiment, the compartment includes a movable, rigid top with fixed, rigid side walls, wherein the interface between the walls and top include a gas-tight seal (for example, by placement of a gasket or other seal). See, for example, U.S. Pat. No. 7,344,499, which is herein incorporated by reference.

In one embodiment, at least one material is extracted by way of an osmotic pump. Id. In one embodiment, a volume expansion or pressure reduction in the compartment drives the at least one material into the compartment. In one embodiment, a Luer-Lock syringe or similar device is used for all sizes of macro-, micro-, or nano-implements.

In one embodiment, the at least one first compartment is configured to hold at least one material extracted from the at least one substrate. In one embodiment, the at least one second compartment is configured to hold at least one agent or other substance to be administered to the at least one substrate. In one embodiment, the at least one first compartment and the at least one second compartment are the same compartment, and includes at least one mode of intaking at least one extracted material, and at least one mode of expelling at least one agent or other substance (e.g., at least one detection material).

In one embodiment, the at least one agent is configured to move from the compartment to the substrate by diffusion, sublimation, explosive force, fracturable membrane, mechanical or electrical gate, magnetic force, or other means. In one embodiment, the at least one agent moves from the compartment to the substrate by means including a pump (e.g., osmotic pump), or a plunger. In one embodiment, the compartment includes a syringe or pump connected to the support structure.

In one embodiment, the frozen piercing implement device includes a sealing mechanism to assist in maintaining at least one agent in the compartment until it is ready to be delivered or mixed with the contents of another compartment. In one embodiment, the sealing mechanism is a fracturable barrier interposed between the compartment and the support structure. In one embodiment, the frozen piercing implement device includes a means for indicating that administration of the device has been at least initiated or completed. In one embodiment, the means for indicating includes a color change. In one embodiment, the frozen piercing implement device includes, for example, a rate control means, such a as a semi-permeable membrane, that assists in regulating flow through at least one frozen piercing implement. In one embodiment, the frozen piercing implement device includes multiple compartments.

In one embodiment, the frozen piercing implement device including at least one frozen piercing implement or portion thereof, includes a closed-loop delivery system. For example, at least one agent is delivered at the time of administration of the at least one frozen piercing implement device to at least one substrate. Subsequently, at least one material is extracted or collected from the at least one substrate. In one embodiment, the at least one material is analyzed by at least one sensor in at least one piercing implement. In one embodiment, the at least one material is analyzed by at least one sensor in at least one optional compartment. In one embodiment, a feedback, or closed-loop provides instructions to at least one controller to dispense at least one agent to the at least one substrate. See, for example, U.S. Pat. No. 6,256,533, which is incorporated herein by reference.

In one embodiment, a method includes affecting electrical resistance in the outer surface of a subject. For example, according to published studies, piercing skin with microneedles causes a 50-fold reduction in the skin's electrical resistance, which is comparable to the reduction in electrical resistance by piercing skin with a 30-gauge "macroneedle." See, for example, U.S. Pat. No. 6,334,856, which is incorporated herein by reference.

In one embodiment, a method includes affecting the skin permeability of a subject. For example, solid microneedles inserted into the skin and left in place create pathways for transport across the skin, and increase skin permeability. See, for example, U.S. Pat. No. 7,344,499, which is incorporated herein by reference. In another example, solid microneedles inserted into skin and then removed increase skin permeability. Id. In another example, hollow microneedles inserted into the skin and left in place increase skin permeability and transport across the skin. Id.

In one embodiment, at least one detection material is utilized with the frozen piercing implement device. In one embodiment, the at least one detection material is located in the frozen piercing implement. In one embodiment, the at least one detection material is located in the at least one compartment. In one embodiment, the at least one detection material is configured to indicate a color change as the at least one extracted material contacts the frozen piercing implement. In one embodiment, the at least one detection material is configured to indicate a color change as the at least one extracted material contacts the at least one compartment. In one embodiment, the at least one detection material is configured to indicate the presence of at least one extracted material. In one embodiment, the at least one detection material is configured to indicate the depth of administration of the frozen piercing implement or frozen particle composition. In one embodiment, the at least one detection material is configured to indicate the depth of administration of at least one agent delivered by the frozen piercing implement or frozen particle composition.

In one embodiment, the device includes at least one nozzle, such as a venturi nozzle, de Laval nozzle, or virtual Laval nozzle. See, for example, U.S. Pat. Nos. 4,038,786; 4,707,951; and 5,779,523, each of which is incorporated herein by reference. In one embodiment, the device includes at least one amplifier to increase the flow or passage of the one or more frozen particle compositions, or frozen piercing implements through or out of the device. See, for example, U.S. Pat. No. 4,398,820, which is incorporated herein by reference. In one embodiment, the device includes at least one injector, such as an oblique injector, that allows for introduction of a fluid (e.g., a gas or liquid) to assist in moving the one or more frozen particle compositions, or frozen piercing implements through or out of the device. (See, for example, U.S. Pat. No. 4,555,872, which is incorporated herein by reference.)

In one embodiment, administering or delivering the at least one frozen particle composition, or frozen piercing implement includes at least one of accelerating, ejecting, or propelling the frozen particle composition, or frozen piercing implement. In one embodiment, the at least one frozen particle composition, or frozen piercing implement is accelerated, ejected, or propelled to or at a predetermined pressure or predetermined velocity for delivery of the at least one frozen particle composition or frozen piercing implement to a desired location on or in the at least one substrate (e.g., a biological tissue). In certain instances, the at least one frozen particle composition, or frozen piercing implement is accelerated, ejected, or propelled at a particular pressure, angle, or velocity. In certain instances, the at least one frozen particle composition, or frozen piercing implement is accelerated, ejected, or propelled at a predetermined pressure, angle, or velocity.

The angle, velocity or pressure determined for delivery of the at least one frozen particle composition, or frozen piercing implement can depend on certain factors, for example, including but not limited to, size and density of the frozen particle composition, or frozen piercing implement, content of the frozen particle composition, or frozen piercing implement, desired effect or outcome of administration of the frozen particle composition, or frozen piercing implement, density of the target tissue, density of surrounding tissue, type of tissue, architecture of the tissue, and other factors. In certain instances, the desired angle, velocity or pressure for accelerating, ejecting, or propelling the at least one frozen particle composition, or frozen piercing implement described herein will be the minimum angle, velocity or pressure needed to achieve desired penetration of the substrate (including a biological tissue) with the frozen particle composition, or frozen piercing implements whether for surface abrasion, therapeutic delivery, or other goal.

In addition to the angle and velocity of accelerating, ejecting, or propelling the at least one composition, other factors can affect the depth of penetration of a particular composition, including, for example, one or more characteristics of the particular composition (e.g., size, shape, or constitution of the frozen particle composition, or frozen piercing implement) or one or more characteristics of administration of the particular composition (e.g., the quantity of frozen particle compositions, or frozen piercing implements administered, distance between the delivery device and the target substrate).

The means for accelerating, ejecting, or propelling the one or more frozen particle compositions, or frozen piercing implements described herein are non-limiting, and may include general methods for making, formulating, and delivering the one or more frozen particle compositions, or frozen piercing implements. For example, the one or more frozen particle compositions, or frozen piercing implements may be delivered to at least one substrate (such as a biological tissue) by carrier gas under pressure, mechanical or electrical impulse assistance, centripetal or centrifugal force, or others, some of which are described herein. (See e.g., U.S. Pat. No. 4,945,050 and PCT application WO 92/01802, each of which is incorporated herein by reference). In certain instances, the one or more frozen particle compositions, or frozen piercing implements are made, propelled, accelerated, or ejected simultaneously. Thus, the frozen particle compositions, or frozen piercing implements can be made while propelled, the frozen particle compositions, or frozen piercing implements can be made while accelerated, the frozen particle compositions, or frozen piercing implements can be made while ejected, or any combination thereof.

In one embodiment, the one or more frozen particle compositions, or frozen piercing implements are delivered or administered by utilizing a carrier fluid. In one embodiment, the carrier fluid includes a carrier gas. In one embodiment, the carrier fluid includes a cold fluid, including a super cooled fluid. In one embodiment, the carrier fluid includes dehumidified air. In one embodiment, the carrier fluid includes at least one inert gas. In one embodiment, a method for administering one or more frozen particle compositions, or frozen piercing implements includes controlling the density of the one or more frozen particle compositions, or frozen piercing implements. In one embodiment, the method further includes monitoring the temperature of at least part of the substrate to which the one or more frozen particle compositions, or frozen piercing implements are administered or are intended to be administered. In one embodiment, the method includes slowing or stopping the delivering of the one or more frozen particle compositions, or frozen piercing implements if the temperature of the at least part of the substrate becomes lower than at least one preset limit In one embodiment, the method includes monitoring the velocity, depth of impact or penetration, constitution one the one or more frozen particle compositions, or frozen piercing implements, or other parameter of administration of the one or more frozen particle compositions, or frozen piercing implements.

In one embodiment, the frozen piercing implements include at least one sensor located at the initial point of contact with at least one substrate. In one embodiment, the at least one sensor monitors pressure at the piercing implement tip.

In one embodiment, the one or more frozen particle compositions are delivered or administered by an inkjet printer-type apparatus or device, by a thermal bubble device, by ultrasound-mediated transdermal drug transport, or by other device. When a voltage is applied, an inkjet-type apparatus generates a pressure pulse by change in shape or size of a chamber containing a fluid (or solid), and the pressure pulse drives the contents from the chamber. In one particular instance, a high velocity device (such as a powderject, air guns, or slingshot type devices) is utilized for administration of at least one frozen particle composition or frozen piercing implement as described here.

For example, in one embodiment, at least one frozen particle composition or frozen piercing implement is propelled by way of a powderject system, as described by Kumar and Philip (Trop. J. Pharm. Res., vol. 6, No. 1, pp. 633-644 (2007), which is incorporated herein by reference). The powderject system utilizes high-speed gas flow (such as helium) that is usually painless and causes minimal bleeding or damage to the skin. (See also e.g., Tang et al., Pharm. Res., vol. 19, pp. 1160-69 (2002), which is incorporated herein by reference). As described by Kumar and Philip, particles are contained in a cassette between two polycarbonate membranes located at the end of a chamber (Kumar and Philip, Trop. J. Pharm. Res., vol. 6, No. 1, pp. 633-644 (2007), which is incorporated herein by reference). As described by Kumar and Philip, the polycarbonate membranes are ruptured when a carrier gas enters the chamber under high pressure, and the rapid expansion of the gas forms a shock wave that travels down the nozzle at a speed of approximately 600-900 m/s. Velocities of up to about 800 m/s at the nozzle exit are reported, and the momentum density of the particles within the gas flow can be optimized for desired depth of penetration upon delivery to a biological tissue. (Kumar and Philip, Trop. J. Pharm. Res., vol. 6, No. 1, pp. 633-644 (2007), which is incorporated herein by reference). In the powderject system, particle velocity is controlled by nozzle geometry, membrane burst strength, and gas pressure. (See e.g., U.S. Pat. Nos. 5,630,796; and 5,699,880, which are incorporated herein by reference).

Metered-dose transdermal sprays may also be used for delivery of at least one frozen particle composition or frozen piercing implement, as described herein. As described by Rathbone, et al., in one particular example, a topical solution containing a volatile then nonvolatile vehicle including a therapeutic agent is administered as a single-phase solution. (See Rathbone, et al., Modified Release of Drug Delivery Technology, NY, Marcel Dekker, Inc. vol. 126, pp. 471-619 (2004), which is incorporated herein by reference). A finite metered-dose application of the formulation to intact skin results in evaporation of the volatile component, leaving the remaining nonvolatile penetration enhancer or therapeutic agent to partition into the stratum corneum and creating a reservoir of the therapeutic agent(s). See Rathbone, Ibid; and Kumar, et al., Trop. J. Pharm. Res., vol. 6, pp. 633-644 (2007), each of which is incorporated herein by reference.

In addition to these particular examples of devices that can be utilized for administration of the compositions described herein, the compositions can be administered in conjunction with other delivery devices. Likewise, the compositions described herein for abrasion of at least one biological tissue can be delivered to the at least one tissue by any means described herein. Some such means for delivery of the compositions described herein include, but are not limited to, ultrasound, iontophoresis (which involves applying an electrical potential across skin or other tissue in order to increase penetration of ionizable agents), diffusion, electroporation, photomechanical waves (such as by producing pulses with Q-switched or mode-locked lasers to the skin or other tissue), needle-free injections, electro-osmosis, artificial vesicles, laser radiation, magnetophoresis (utilizing a diamagnetic substance for use with a magnetic field for increased penetration of the composition into the biological tissue), microscissuining, controlled heat aided delivery (which involves heating the skin prior to or during administration), tattoos, three-dimensional holograms, or etchings.

In one embodiment, Rathbone et al. have described artificial vesicles that mimic cell vesicles (such as TRANSFERSOMES®, from IDEA AG, Germany) can be utilized for administration of one or more composition described herein. Artificial vesicles penetrate the skin barrier along the transcutaneous moisture gradient and causes “virtual” pores between the cells in an organ without affecting its biological properties. (See, e.g., Modified Release Drug Delivery Technology, NY, Marcel Dekker, Inc., vol. 126, pp. 471-619 (2004), which is incorporated herein by reference). In addition, liposomes, erythrocyte ghosts, and niosomes also serve as carriers and can be utilized in the administration of at least one frozen particle composition or frozen piercing implement described herein.

In one embodiment, the one or more frozen particle compositions, or frozen piercing implements are generated by spraying a jet or mist of the composition constituents into a low temperature environment (solid, liquid, gas, or any combination thereof) such that the compositions freeze and form frozen particles. In one embodiment, streams of frozen particles are extruded at low temperatures through fine ducts and into a low temperature environment. In one embodiment, the one or more frozen particles are propelled through a nozzle or other delivery apparatus. In one embodiment, the one or more frozen particles are delivered by utilizing flash boiling or BLEVE, or other explosion, of a cold liquid. In one particular example, liquid nitrogen is flash boiled in order to accelerate, eject, or propel one or more frozen particles for delivery or administration to at least one cell, tissue, or subject. In one embodiment, the flash boiling is induced by one or more laser pulses (e.g., an infrared laser pulse). In one embodiment, the one or more frozen particles are prepared, delivered, or administered by another means.

In certain instances, it is desirable to deliver the one or more frozen particle compositions, or frozen piercing implements to at least one cell or tissue, or administer the one or more frozen particle compositions, or frozen piercing implements to at least one subject. In at least one instance, the one or more frozen particle compositions, or frozen piercing implements include a plurality of frozen particle compositions, or frozen piercing implements that include two or more subsets of frozen particle compositions, or frozen piercing implements that are delivered or administered in sequential order. In one embodiment, the sequential order is predetermined, based on factors relating to, for example, the at least one cell or tissue, the at least one subject, or the at least one frozen particle composition, or frozen piercing implement. In one embodiment, the sequential order is determined, for example, during the course of delivery or administration of at least one of the one or more frozen particles or at least one frozen particle composition, or frozen piercing implement. In one embodiment, the sequential order is determined by a software program. In one embodiment, the sequential order of delivery is randomized.

In one embodiment, the sequential order includes one or more subsets of frozen particle compositions, or frozen piercing implements that vary in size, shape, weight, density, location of delivery or administration, time of delivery or administration, angle of delivery or administration, or velocity of delivery or administration. In one embodiment, one or more subsets of frozen particle compositions, or frozen piercing implements are delivered or administered according to a course of treatment (e.g., at least one subset of relatively small frozen particle compositions, or frozen piercing implements are administered first, followed by at least one subset of relatively larger frozen particle compositions, or frozen piercing implements; at least one subset of frozen particle compositions, or frozen piercing implements are administered in a relatively fast velocity, followed by at least one subset of frozen particle compositions, or frozen piercing implements administered by a relatively slow velocity; at least one subset of frozen particle compositions, or frozen piercing implements approximately shaped as spheroids are administered followed by at least one subset of frozen particle compositions, or frozen piercing implements approximately shaped as bullets, etc.).

In one embodiment, the at least one frozen particle composition, or frozen piercing implement is propelled using a pressure set at least about 1 psi, about 5 psi, about 10 psi, about 20 psi, about 30 psi, about 40 psi, about 50 psi, at least about 100 psi, at least about 200 psi, at least about 300 psi, at least about 400 psi, at least about 450 psi, at least about 500 psi, at least about 600 psi, at least about 700 psi, at least about 800 psi, at least about 900 psi, at least about 1000 psi, at least about 1100 psi, at least about 1200 psi, at least about 1300 psi, at least about 1400 psi, at least about 1500 psi, about 2000 psi, about 2500 psi, about 3000 psi, about 3500 psi, about 4000 psi, about 5000 psi, about 6000 psi, about 7000 psi, about 8000 psi, about 9000 psi, about 10000 psi, about 20000 psi, about 30000 psi, about 40000 psi, about 50000 psi, or any value therebetween.

In one embodiment, the at least one frozen particle composition, or frozen piercing implement is propelled at a pressure ranging from approximately 350 psi to approximately 1000 psi. In one embodiment, for example for penetrating the skin (particularly epidermis or dermis), the at least one frozen particle composition, or frozen piercing implement is propelled at a pressure of approximately 800 psi to approximately 1000 psi. See, for example, Menon et al., Skin Pharmacol. Physiol. vol. 20, pp. 141-147 (2007), which is incorporated herein by reference. For example, microwounds caused by gold beads bombarding the skin did not reseal with stratum corneum lipids after 24 hours of organ culture. Id. In one embodiment, these microwounds allow for increased permeability of the substrate for delivery of at least one agent.

In one embodiment, the at least one frozen particle composition, or frozen piercing implement is propelled to or at a predetermined depth, predetermined velocity, predetermined rate of administration, predetermined angle, predetermined spatial location, predetermined depth, predetermined time sequence, or predetermined spatial pattern for delivery of the at least one composition to a desired location of the at least one biological tissue. In one embodiment, the velocity, rate, or angle of administration of the one or more frozen particle compositions, or frozen piercing implements are variable. In one embodiment, a method of administering one or more frozen particle compositions, or frozen piercing implements includes varying the rate, velocity, or angle. In one embodiment, a method includes multiple administrations of the one or more frozen particle compositions, or frozen piercing implements, wherein at least two of the administrations include different velocities, rates, or angles of delivery.

In one embodiment, the at least one frozen particle composition, or frozen piercing implement is propelled to or at a velocity of approximately 1 m/s, approximately 5 m/s, approximately 10 m/s, approximately 20 m/s, approximately 30 m/s, approximately 40 m/s, approximately 50 m/s, approximately 60 m/s, approximately 70 m/s, approximately 80 m/s, approximately 90 m/s, approximately 100 m/s, approximately 200 m/s, approximately 300 m/s, approximately 400 m/s, approximately 500 m/s, approximately 600 m/s, approximately 700 m/s, approximately 800 m/s, approximately 900 m/s, approximately 1000 m/s, approximately 1500 m/s, approximately 2000 m/s, approximately 3000 m/s, approximately 4000 m/s, approximately 5000 m/s, or any value greater or therebetween.

In one embodiment, the at least one frozen particle composition, or frozen piercing implement is accelerated or ejected toward the at least one substrate (such as a biological tissue) to a velocity of approximately 1 m/s, approximately 5 m/s, approximately 10 m/s, approximately 20 m/s, approximately 30 m/s, approximately 40 m/s, approximately 50 m/s, approximately 60 m/s, approximately 70 m/s, approximately 80 m/s, approximately 90 m/s, approximately 100 m/s, approximately 200 m/s, approximately 300 m/s, approximately 400 m/s, approximately 500 m/s, approximately 600 m/s, approximately 700 m/s, approximately 800 m/s, approximately 900 m/s, approximately 1000 m/s, approximately 1500 m/s, approximately 2000 m/s, approximately 3000 m/s, approximately 4000 m/s, approximately 5000 m/s, or any value greater or therebetween.

In one embodiment, delivering at least one frozen particle composition, or frozen piercing implement to at least one substrate (such as a biological tissue) includes accelerating, ejecting, or propelling a plurality of frozen particle compositions, or frozen piercing implements toward the at least one substrate (including a biological tissue). In one embodiment, the plurality of frozen particle compositions, or frozen piercing implements is administered to at least one substrate including at a predetermined angle, a predetermined velocity, a predetermined rate of administration, a predetermined spatial pattern, a predetermined spatial location, a predetermined time sequence, or a predetermined depth. Such a plurality of particles may include one embodiment wherein two or more frozen particle compositions, or frozen piercing implements of the plurality include one or more similar agents. Likewise, a plurality of frozen particle compositions, or frozen piercing implements may include one embodiment wherein two or more frozen particle compositions, or frozen piercing implements include one or more dissimilar agents. In one embodiment, the rate, velocity, or angle at which the one or more frozen particle compositions, or frozen piercing implements are administered is variable.

In one embodiment, a device for making and propelling one or more frozen particle compositions, or frozen piercing implements includes at least one particle accelerator. In one embodiment, the particle accelerator includes a linear, circular or spherical accelerator. In one embodiment, the particle accelerator includes a spiral, conical, helical, or conic-helical accelerator. In one embodiment, the particle accelerator includes a 2-dimensional or 3-dimensional accelerator.

For example, in a 2-dimensional spiral, polar coordinates can be expressed as a function of angle $\theta$, where the radius r is a continuous monotonic function of angle $\theta$, and a and b are arbitrary positive real constants. For example, several embodiments are shown in FIG. 135A-K.

As described herein, a plurality of frozen particle compositions, or frozen piercing implements may include one or more subsets, which can be delivered or administered in an order of operations. In one embodiment, the order of operations includes delivery or administration in a pattern. In one embodiment, the order of operations includes delivery or administration in a predetermined pattern. In one embodiment, the order of operations includes delivery or administration in sequential order. In one embodiment, the order of operations includes delivery or administration at random.

For embodiments described herein, those having skill in the art will recognize that the state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein can be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In some implementations described herein, logic and similar implementations may include software or other control structures. Electronic circuitry, for example, may have one or more paths of electrical current constructed and arranged to implement various functions as described herein. In some implementations, one or more media can be configured to bear a device-detection implementation when such media hold or transmit device detection instructions operable to perform as described herein. In some variants, for example, implementations may include an update or modification of existing software or firmware, or of gate arrays or programmable hardware, such as by performing a reception of or a transmission of one or more instructions in relation to one or more operations described herein. Alternatively or additionally, in some variants, an implementation may include special-purpose hardware, software, firmware components, and/or general-purpose components executing or otherwise invoking special-purpose components. Specifications or other implementations can be transmitted by one or more instances of tangible transmission media as described herein, optionally by packet transmission or otherwise by passing through distributed media at various times.

Alternatively or additionally, implementations may include executing a special-purpose instruction sequence or invoking circuitry for enabling, triggering, coordinating, requesting, or otherwise causing one or more occurrences of virtually any functional operations described herein. In some variants, operational or other logical descriptions herein can be expressed as source code and compiled or otherwise invoked as an executable instruction sequence. In some contexts, for example, C++ or other code sequences can be compiled or implemented in high-level descriptor languages (e.g., a logic-synthesizable language, a hardware description language, a hardware design simulation, and/or other such similar mode(s) of expression). For example, some or all of the logical expression can be manifested as a Verilog-type hardware description or other circuitry model before physical implementation in hardware. Those skilled in the art will recognize how to obtain, configure, and optimize suitable transmission or computational elements, material supplies, actuators, or other structures in light of these teachings.

Figure 8:
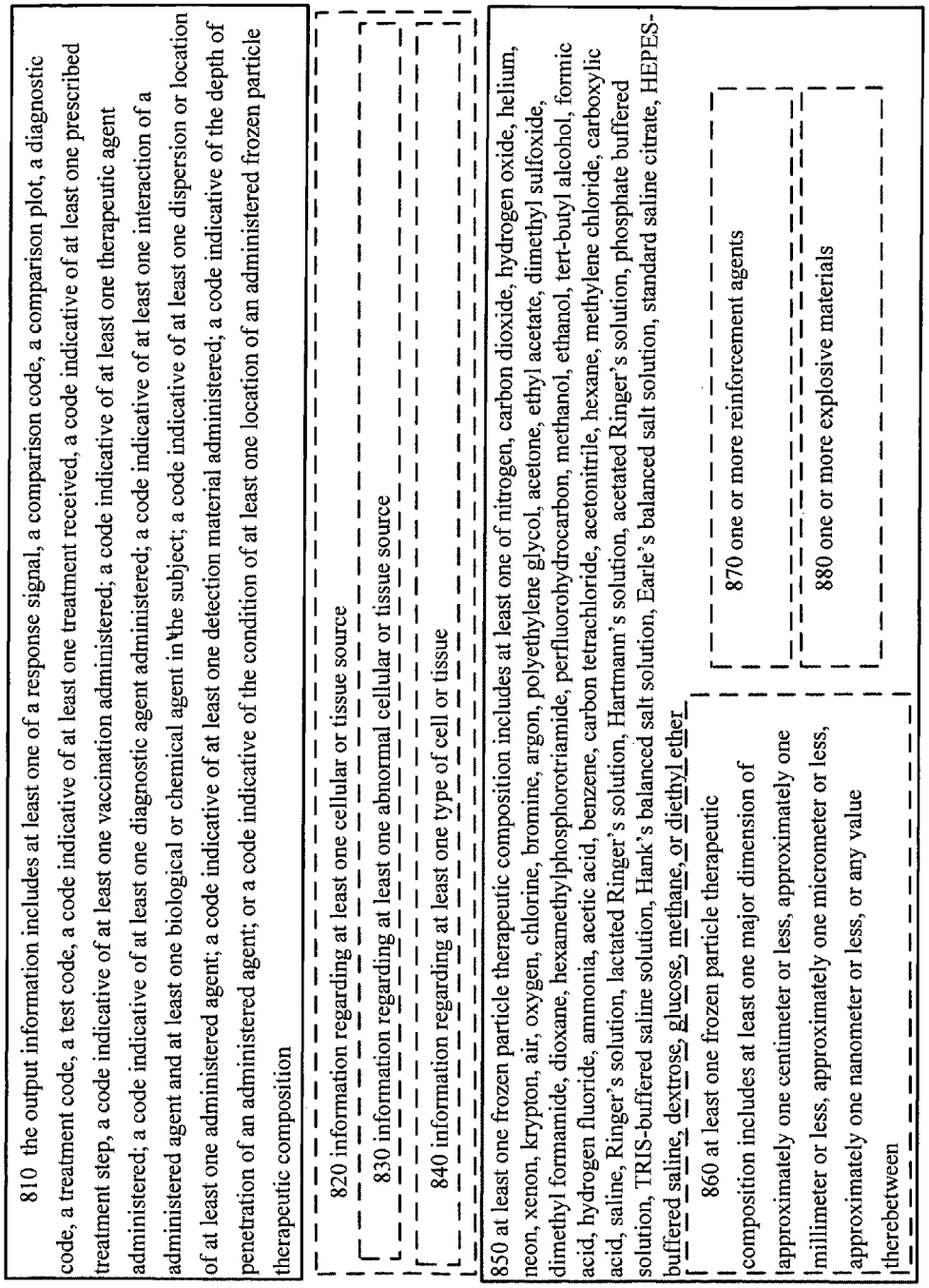
FIG. 8 illustrates a partial view of FIG. 7 in which embodiments may be implemented.

As indicated in FIGS. 7-9, one embodiment, a method 700 includes comparing 710 information regarding at least one aspect of administering at least one frozen particle composition (or frozen piercing implement) to at least one subject and information regarding at least one clinical outcome following receipt by the at least one subject of at least one frozen particle composition (or frozen piercing implement); and providing output information optionally based on the comparison.

In one embodiment, the method includes determining at least one statistical correlation 720. In one embodiment, the method includes counting the occurrence of at least one clinical outcome 730. In one embodiment, the method includes determining at least one correlation before the administration of the at least one frozen particle composition (or frozen piercing implement) 735. In one embodiment, information regarding at least one aspect of administering at least one frozen particle composition (or frozen piercing implement) includes information regarding the amount of at least one frozen particle composition (or frozen piercing implement) or therapeutic agent administered to at least one biological tissue of a subject 740. In one embodiment, the information regarding at least one aspect of administering or delivering at least one frozen particle composition (or frozen piercing implement) includes information regarding at least one dimension of biological tissue penetration 750. In one embodiment, information regarding the at least one dimension of biological tissue penetration includes information regarding at least one of depth, width, or breadth of administration of at least one frozen particle composition (or frozen piercing implement) to at least one biological tissue of at least one subject 760.

In one embodiment, the information regarding at least one aspect of administering at least one frozen particle composition (or frozen piercing implement) includes information regarding two or more subjects with one or more common attributes 770. In one embodiment, the one or more common attributes include genetic attributes, mental attributes, or psychological attributers 780. In at least on embodiment, the one or more common attributes include genotype attributes or phenotype attributers 790.

In one embodiment, the one or more common attributers 797 include at least one of height; weight; medical diagnosis; familial background; results on one or more medical tests; ethnic background; body mass index; age; presence or absence of at least one disease or condition; species; ethnicity; race; allergies; gender; thickness of epidermis; thickness of dermis; thickness of stratum corneum; keratin deposition; collagen deposition; blood vessel condition; skin condition; hair or fur condition; muscle condition; tissue condition; organ condition; nerve condition; brain condition; presence or absence of at least one biological, chemical, or therapeutic agent in the subject; pregnancy status; lactation status; genetic profile; proteomic profile; lipidomic profile, glycomic profile, system biology profile, partial or whole genetic sequence; partial or whole proteomic sequence; medical history; lymph condition, circulatory condition, respiratory condition, or blood condition.

In one embodiment, the output information 810 includes at least one of a response signal, a comparison code, a comparison plot, a diagnostic code, a treatment code, a test code, a code indicative of at least one treatment received, a code indicative of at least one prescribed treatment step, a code indicative of at least one vaccination delivered; a code indicative of at least one therapeutic agent delivered; a code indicative of at least one diagnostic agent delivered; a code indicative of at least one interaction of a delivered agent and at least one biological or chemical agent in the subject; a code indicative of at least one dispersion or location of at least one delivered agent; a code indicative of at least one detection material delivered; a code indicative of the depth of penetration of a delivered agent; or a code indicative of the condition of at least one location of an administered or delivered frozen particle composition (or frozen piercing implement). In one embodiment, the at least one aspect of cellular or tissue abrasion or ablation includes information regarding at least one cellular or tissue source 820. In one embodiment, the information regarding at least one tissue source includes information regarding at least one abnormal cellular or tissue source 830. In one embodiment, the information regarding at least one cellular or tissue source includes information regarding at least one type of cell or tissue 840. In one embodiment, the cellular or tissue source includes at least one cell or biological tissue described herein.

In one embodiment, the at least one frozen particle composition, frozen piercing implement, frozen piercing implement device, or therapeutic composition includes at least one of nitrogen, carbon dioxide, hydrogen oxide, helium, neon, xenon, krypton, chlorine, bromine, methane, oxygen, air, argon, polyethylene glycol, acetone, ethyl acetate, dimethyl sulfoxide, dimethyl formamide, dioxane, hexamethylphosphorotriamide, perfluorohydrocarbon, methanol, ethanol, tert-butyl alcohol, formic acid, hydrogen fluoride, ammonia, acetic acid, benzene, carbon tetrachloride, hexane, methylene chloride, carboxylic acid, saline, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, or diethyl ether 850.

In one embodiment, the at least one frozen particle composition, frozen piercing implement, frozen piercing implement device, or therapeutic composition includes at least one major dimension of approximately one decimeter or less, or approximately one centimeter or less, approximately one millimeter or less, approximately one micrometer or less, approximately one nanometer or less, or any value therebetween 860.

In one embodiment, the at least one frozen particle composition, frozen piercing implement, frozen piercing implement device, or therapeutic composition includes one or more reinforcement agents 870. In one embodiment, the at least one frozen particle composition (or frozen piercing implement) or therapeutic composition includes one or more explosive materials 880. In one embodiment, the receipt by the at least one subject of at least one frozen particle composition (or frozen piercing implement) or therapeutic composition is pursuant to at least one clinical trial 900.

In one embodiment, the method includes creating at least one inclusion criterion and at least one exclusion criterion for a clinical trial involving the at least one frozen particle composition (or frozen piercing implement) or therapeutic composition 910. In one embodiment, the method further comprises suggesting the inclusion of one or more of the at least one subject in at least one clinical trial 920. In one embodiment, the method further comprises suggesting the exclusion of one or more of the at least one subject in at least one clinical trial 930. In certain instances, multiple subjects from multiple clinical trials are included. In one embodiment, the method further includes using one or more of the at least one comparison to predict at least one clinical outcome regarding at least one second subject 940. In one embodiment, the at least one second subject has not received the at least one frozen particle composition (or frozen piercing implement) or therapeutic composition 950. In one embodiment, the at least one second subject is a plurality of people; and the method further comprises segregating subject identifiers associated with the plurality of people in reference to the predicted at least one clinical outcome 960. In one embodiment, the at least one second subject is a plurality of people; and the method further comprises determining the eligibility of the at least one second subject for the at least one clinical trial 970.

Figure 11:
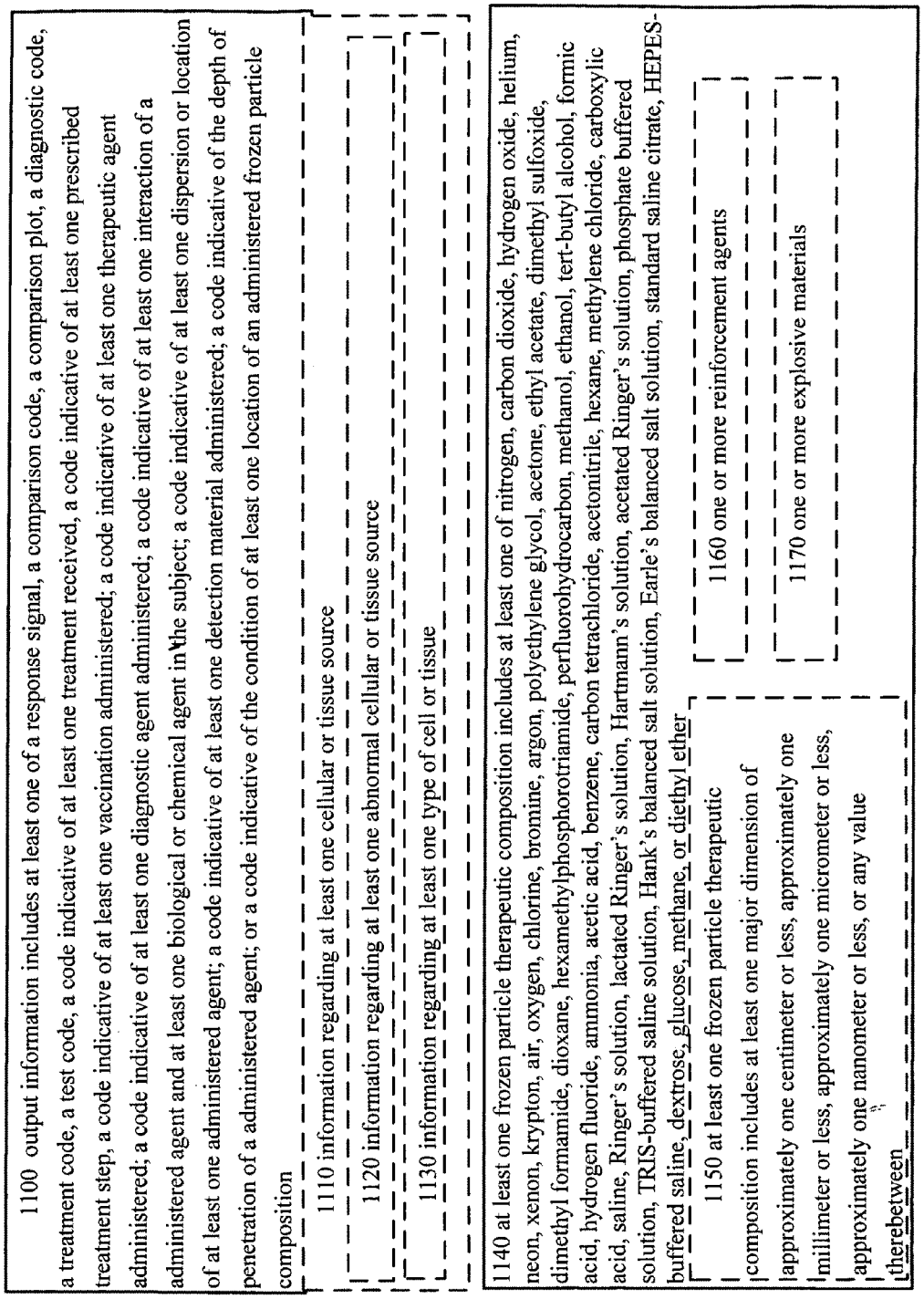
FIG. 11 illustrates a partial view of FIG. 10 in which embodiments may be implemented.
Figure 12:
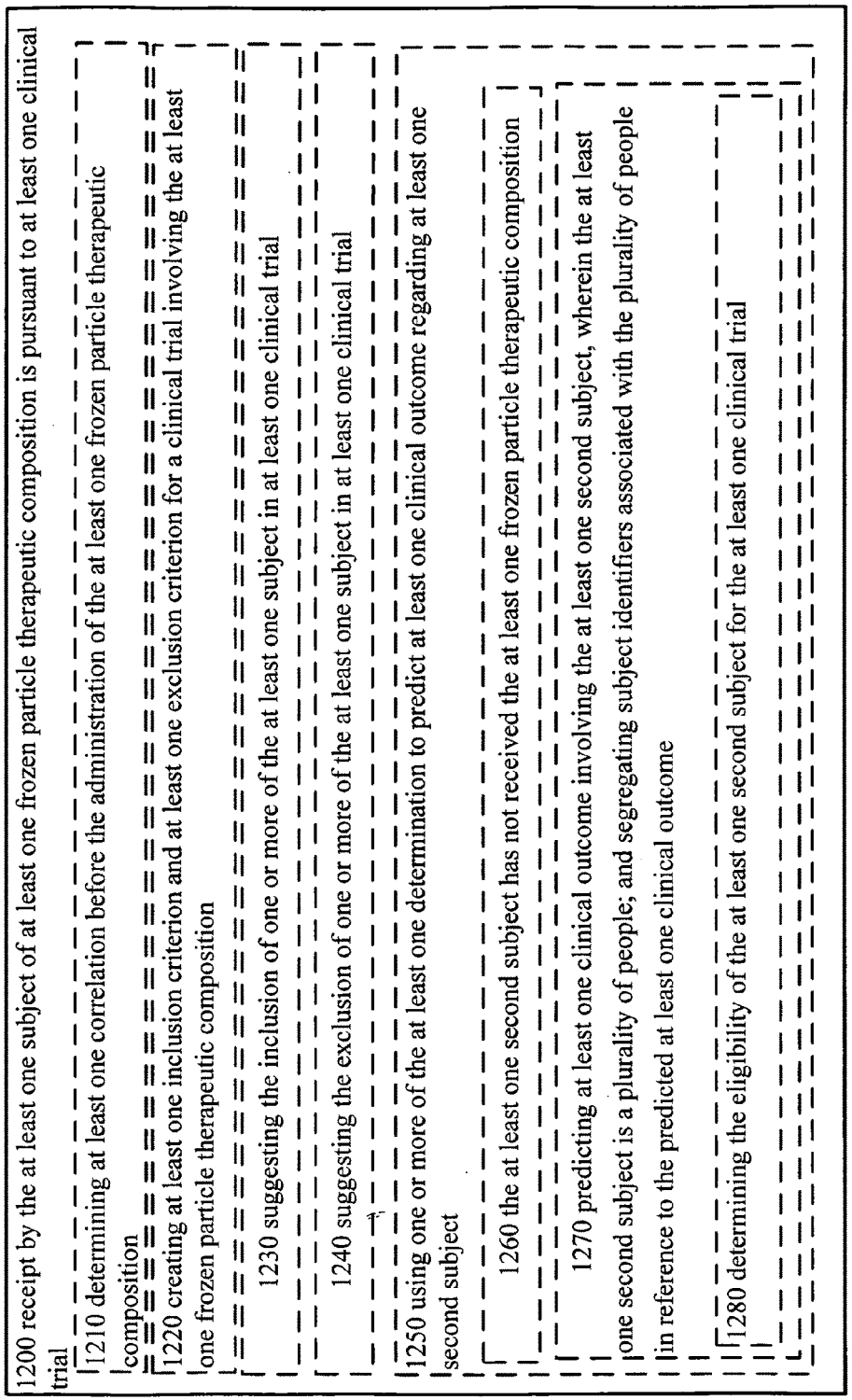
FIG. 12 illustrates a partial view of FIG. 10 in which embodiments may be implemented.

As indicated in FIGS. 10-12, at least one aspect includes a method 1000 relating to predicting a clinical outcome of administering at least one frozen particle therapeutic composition (or frozen piercing implement) to at least one biological tissue of at least one first subject includes determining a similarity or a dissimilarity in information regarding at least one aspect of administering at least one therapeutic composition (or frozen piercing implement) to the at least one biological tissue of the at least one first subject to information regarding at least one aspect of administering at least one therapeutic composition (or frozen piercing implement) to the at least one biological tissue of the at least one second subject, wherein the at least one second subject attained a clinical outcome following receipt of the at least one frozen particle therapeutic composition(or frozen piercing implement); and providing output information optionally based on the determination 1010.

In one embodiment, the information regarding the at least one aspect of administering at least one frozen particle therapeutic composition (or frozen piercing implement) includes information 1020 regarding the amount of at least one frozen particle therapeutic composition (or frozen piercing implement) or therapeutic agent delivered to at least one biological tissue of a subject. In one embodiment, the information regarding the at least one aspect of administering at least one frozen particle therapeutic composition (or frozen piercing implement) includes information 1030 regarding at least one dimension of biological tissue penetration. In one embodiment, the information regarding the at least one dimension of biological tissue penetration includes information 1040 regarding at least one of depth, width, or breadth of delivery of at least one frozen particle therapeutic composition (or frozen piercing implement) to at least one biological tissue of at least one subject; or information 1050 regarding two or more subjects with common attributes.

In one embodiment, the one or more common attributes include genetic attributes, mental attributes, or psychological attributers 1060. In at least on embodiment, the one or more common attributes include genotype attributes or phenotype attributers 1070.

In one embodiment, the one or more common attributers 1080 include at least one of height; weight; medical diagnosis; familial background; results on one or more medical tests; ethnic background; body mass index; age; presence or absence of at least one disease or condition; species; ethnicity; race; allergies; gender; thickness of epidermis; thickness of dermis; thickness of stratum corneum; keratin deposition; collagen deposition; blood vessel condition; skin condition; hair or fur condition; muscle condition; tissue condition; organ condition; nerve condition; brain condition; presence or absence of at least one biological, chemical, or therapeutic agent in the subject; pregnancy status; lactation status; genetic profile; proteomic profile; partial or whole genetic sequence; medical history; partial or whole proteomic sequence; lymph condition, or blood condition.

In one embodiment, the output information 1100 includes at least one of a response signal, a comparison code, a comparison plot, a diagnostic code, a treatment code, a test code, a code indicative of at least one treatment received, a code indicative of at least one prescribed treatment step, a code indicative of at least one vaccination delivered; a code indicative of at least one therapeutic agent delivered; a code indicative of at least one diagnostic agent delivered; a code indicative of at least one interaction of a delivered agent and at least one biological or chemical agent in the subject; a code indicative of at least one dispersion or location of at least one delivered agent; a code indicative of at least one detection material delivered; a code indicative of the depth of penetration of a delivered agent; or a code indicative of the condition of at least one location of an administered or delivered frozen particle composition (or frozen piercing implement) or therapeutic composition. In one embodiment, the at least one aspect of cellular or tissue abrasion or ablation includes information regarding at least one cellular or tissue source 1110. In one embodiment, the information regarding at least one tissue source includes information regarding at least one abnormal cellular or tissue source 1120. In one embodiment, the information regarding at least one cellular or tissue source includes information regarding at least one type of cell or tissue 1130. In one embodiment, the cellular or tissue source includes at least one cell or biological tissue described herein.

In one embodiment, the at least one frozen particle composition (or frozen piercing implement) includes at least one of nitrogen, carbon dioxide, hydrogen oxide, helium, neon, xenon, krypton, chlorine, bromine, methane, oxygen, air, argon, polyethylene glycol, acetone, ethyl acetate, dimethyl sulfoxide, dimethyl formamide, dioxane, hexamethylphosphorotriamide, perfluorohydrocarbon, methanol, ethanol, tert-butyl alcohol, formic acid, hydrogen fluoride, ammonia, acetic acid, benzene, carbon tetrachloride, hexane, methylene chloride, carboxylic acid, saline, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, or diethyl ether 1140.

In one embodiment, the at least one frozen particle composition (or frozen piercing implement) or therapeutic composition includes at least one major dimension of approximately one decimeter or less, or approximately one centimeter or less, approximately one millimeter or less, approximately one micrometer or less, approximately one nanometer or less, or any value therebetween 1150.

In one embodiment, the at least one frozen particle composition (or frozen piercing implement) or therapeutic composition includes one or more reinforcement agents 1160. In one embodiment, the at least one frozen particle composition (or frozen piercing implement) or therapeutic composition includes one or more explosive materials 1170.

In one embodiment, the receipt by the at least one subject of at least one frozen particle composition (or frozen piercing implement) or therapeutic composition is pursuant to at least one clinical trial 1200. In one embodiment, the method further comprises determining at least one correlation before the administration or delivery of the at least one frozen particle composition (or frozen piercing implement) or therapeutic composition to at least one subject 1210. The at least one subject includes, but is not limited to at least one subject described herein.

In one embodiment, the method includes creating at least one inclusion criterion and at least one exclusion criterion for a clinical trial involving the at least one frozen particle composition or therapeutic composition 1220. In one embodiment, the method further comprises suggesting the inclusion of one or more of the at least one subject in at least one clinical trial 1230. In one embodiment, the method further comprises suggesting the exclusion of one or more of the at least one subject in at least one clinical trial 1240. In certain instances, multiple subjects from multiple clinical trials are included. In one embodiment, the method further includes using one or more of the at least one comparison to predict at least one clinical outcome regarding at least one second subject 1250. In one embodiment, the at least one second subject has not received the at least one frozen particle composition (or frozen piercing implement) or therapeutic composition 1260. In one embodiment, the method includes predicting at least one clinical outcome involving the at least one second subject, and the at least one second subject is a plurality of people; and the method further comprises segregating subject identifiers associated with the plurality of people in reference to the predicted at least one clinical outcome 1270.

In one embodiment, the at least one second subject is a plurality of people; and the method further comprises determining the eligibility of the at least one second subject for the at least one clinical trial 1280.

Figure 14:
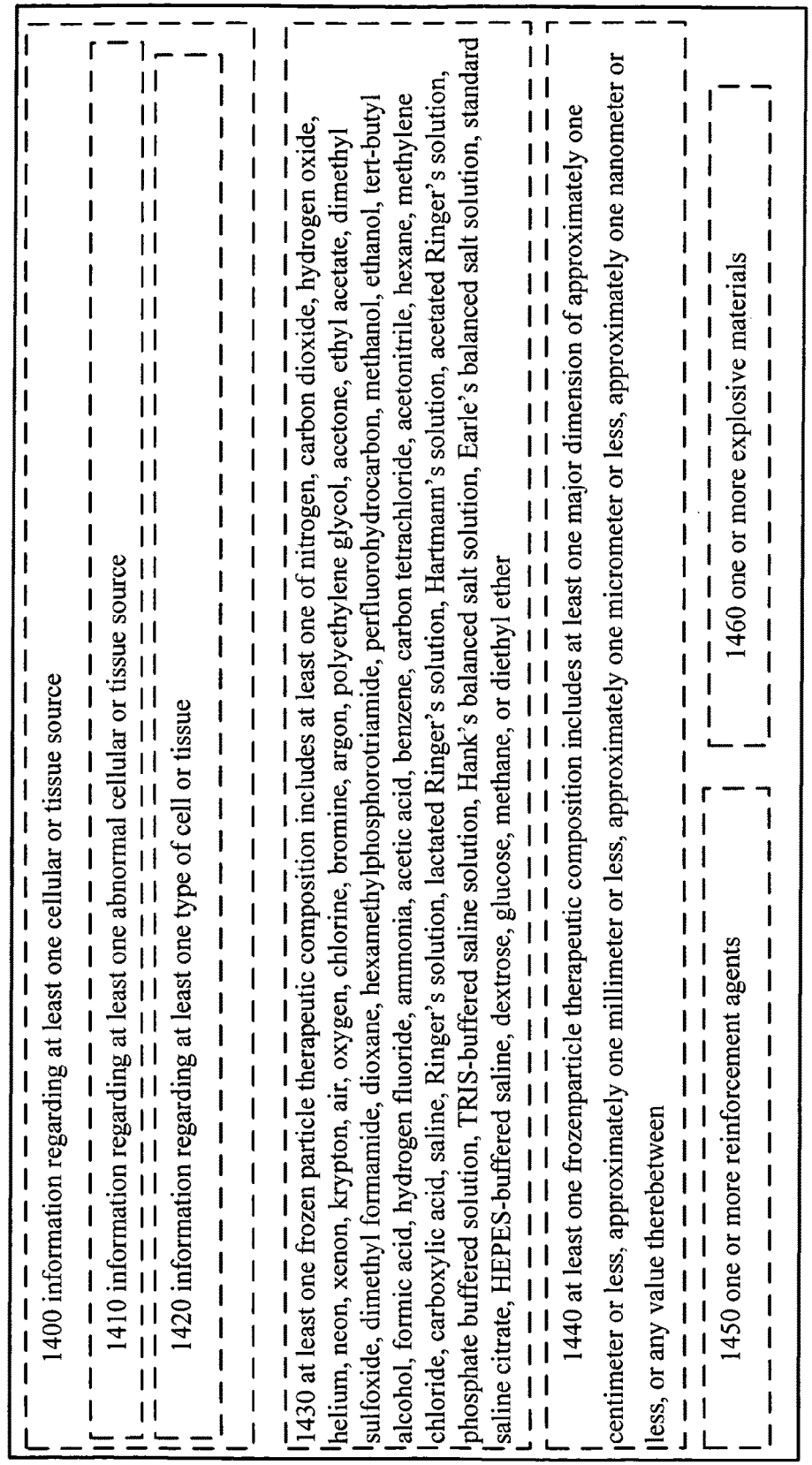
FIG. 14 illustrates a partial view of FIG. 13 in which embodiments may be implemented.

As shown in FIGS. 13-15, one embodiment includes a system 1300 including at least one computer program 1310, configured with a computer-readable medium, for use with at least one computer system and wherein the computer program includes a plurality of instructions including but not limited to one or more instructions 1320 for comparing information regarding at least one aspect of at least one therapeutic administration of at least one frozen particle composition (or frozen piercing implement) or therapeutic composition to at least one subject. In one embodiment, information 1330 regarding amount of the at least one frozen particle composition, (or frozen piercing implement), therapeutic composition, or therapeutic agent administered to at least one biological tissue of at least one subject. In one embodiment, information regarding at least one aspect of at least one therapeutic administration of at least one frozen particle composition (or frozen piercing implement) or therapeutic composition includes information regarding at least one dimension of biological tissue penetration 1340. In one embodiment, information regarding at least one aspect of at least one therapeutic administration of at least one frozen particle composition (or frozen piercing implement) or therapeutic composition includes information regarding at least one of depth, width, or breadth of administration of at least one frozen particle composition (or frozen piercing implement) or therapeutic composition to at least one biological tissue of at least one subject 1350. In one embodiment, information regarding at least one aspect of at least one therapeutic administration includes information regarding two or more subjects with one or more common attributers 1360. In one embodiment, the computing device is configured to communicate with at least one imaging device. In one embodiment, the computing device is configured to communicate with at least one printing device. In one embodiment, the computing device is configured to communicate with at least one input device 1370.

In one embodiment, the information regarding at least one aspect of therapeutic administration of at least one therapeutic composition includes information regarding at least one cellular or tissue source 1400; information regarding at least one abnormal cellular or tissue source 1410; or information regarding at least one type of cell or tissue 1420. In one embodiment, at least one frozen particle composition (or frozen piercing implement) or therapeutic composition includes at least one of nitrogen, carbon dioxide, hydrogen oxide, helium, neon, xenon, krypton, chlorine, bromine, methane, oxygen, air or argon. In one embodiment, the at least one frozen particle composition (or frozen piercing implement) or therapeutic composition includes at least one of polyethylene glycol, acetone, ethyl acetate, dimethyl sulfoxide, dimethyl formamide, dioxane, hexamethylphosphorotriamide, perfluorohydrocarbon, methanol, ethanol, tert-butyl alcohol, formic acid, hydrogen fluoride, ammonia, acetic acid, benzene, carbon tetrachloride, hexane, methylene chloride, carboxylic acid, saline, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, or diethyl ether 1430. In one embodiment, at least one frozen particle composition (or frozen piercing implement) or therapeutic composition includes at least one major dimension of approximately one decimeter or less, approximately one centimeter or less, approximately one millimeter or less, approximately one micrometer or less, approximately one nanometer or less, or any value therebetween 1440. In one embodiment, the at least one frozen particle composition (or frozen piercing implement) or therapeutic composition includes one or more reinforcement agents 1450 or one or more explosive materials 1460.

In one embodiment, the receipt by the at least one subject of at least one frozen particle composition (or frozen piercing implement) or therapeutic composition is pursuant to at least one clinical trial 1500. In one embodiment, the system further comprises determining at least one correlation before the delivery or administration of the at least one frozen particle composition (or frozen piercing implement) or therapeutic composition to at least one subject 1510.

In one embodiment, the method includes creating at least one inclusion criterion and at least one exclusion criterion for a clinical trial involving the at least one frozen particle composition (or frozen piercing implement) or therapeutic composition 1520. In one embodiment, the instructions further comprise suggesting the inclusion of one or more of the at least one subject in at least one clinical trial 1530. In certain instances, multiple subjects from multiple clinical trials are included.

In one embodiment, the instructions include suggesting the exclusion of one or more of the at least one subject in at least one clinical trial 1540.

In one embodiment, a method includes using one or more of the at least one comparison to predict at least one clinical outcome regarding at least one second subject 1550. In one embodiment, the at least one second subject has not received the at least one frozen particle composition (or frozen piercing implement) or therapeutic composition 1560. In one embodiment, the at least one second subject is a plurality of people; and further comprising segregating subject identifiers associated with the plurality of people in reference to the predicted at least one clinical outcome 1570.

In one embodiment, the using one or more of the at least one comparison, wherein the at least one second subject is a plurality of people; and further comprising determining the eligibility of the at least one second subject for the at least one clinical trial 1580.

As indicated in FIG. 16, one embodiment relates to a system 1600 including at least one computer program 1610 configured with a computer-readable medium, for use with at least one computer system and wherein the computer program includes a plurality of instructions including but not limited to one or more instructions 1620 for comparing information regarding at least one aspect of at least one therapeutic administration of at least one frozen particle therapeutic composition (or frozen piercing implement) to at last one subject, and information regarding at least one frozen particle therapeutic composition (or frozen piercing implement) involving at least one biological tissue of at least one subject; and one or more instructions for applying one or more comparisons to the information regarding the at least one aspect of therapeutic administration of at least one frozen particle therapeutic composition (or frozen piercing implement) to a plurality of people. In one embodiment, the computer program includes one or more instructions 1630 for segregating subject identifiers associated with the plurality of people in reference to at least one of the one or more applied comparisons. In one embodiment, information regarding at least one aspect of at least one therapeutic administration includes information 1640 regarding the amount of at least one frozen particle composition (or frozen piercing implement), therapeutic composition or therapeutic agent administered to at least one biological tissue of at least one subject; information 1650 regarding at least one dimension of biological tissue penetration; information 1660 regarding at least one of depth, width, or breadth of administration of at least one frozen particle therapeutic composition to at least one biological tissue of at least one subject. In one embodiment, the computer program includes one or more instructions 1670 for segregating individual identifiers associated with the plurality of people in reference to at least one characteristic shared by two or more subjects in the plurality of people.

As shown in FIG. 17, one embodiment relates to a computer program product 1700 that includes a signal bearing medium 1710 bearing at least one of one or more instructions 1720 for receiving a first input associated with a first possible dataset, the first possible dataset including data representative of one or more measurements relating to one or more physical attributes of a first subject; one or more instructions 1730 for comparing a value associated with the first possible dataset with a second dataset including values representative of predictive regimen parameters from a second subject with one or more similar or dissimilar physical attributes; one or more instructions 1740 for determining from the comparison at least one frozen particle therapeutic composition (or frozen piercing implement) regimen for the first subject and output information; one or more instructions 1750 for accessing the first possible dataset in response to the first input; one or more instructions 1760 for generating the first possible dataset in response to the first input; one or more instructions 1770 for determining a graphical illustration of the first possible dataset; one or more instructions 1780 for determining a graphical illustration of the second possible dataset; and at least one generated output optionally based on the determination.

In one embodiment, the computer program product includes a signal bearing medium that includes a computer-readable medium 1790. In one embodiment, the signal bearing medium of the computer program product includes a recordable medium 1792. In one embodiment, the computer program product includes a signal bearing medium that includes a communications medium 1794.

Figure 18:
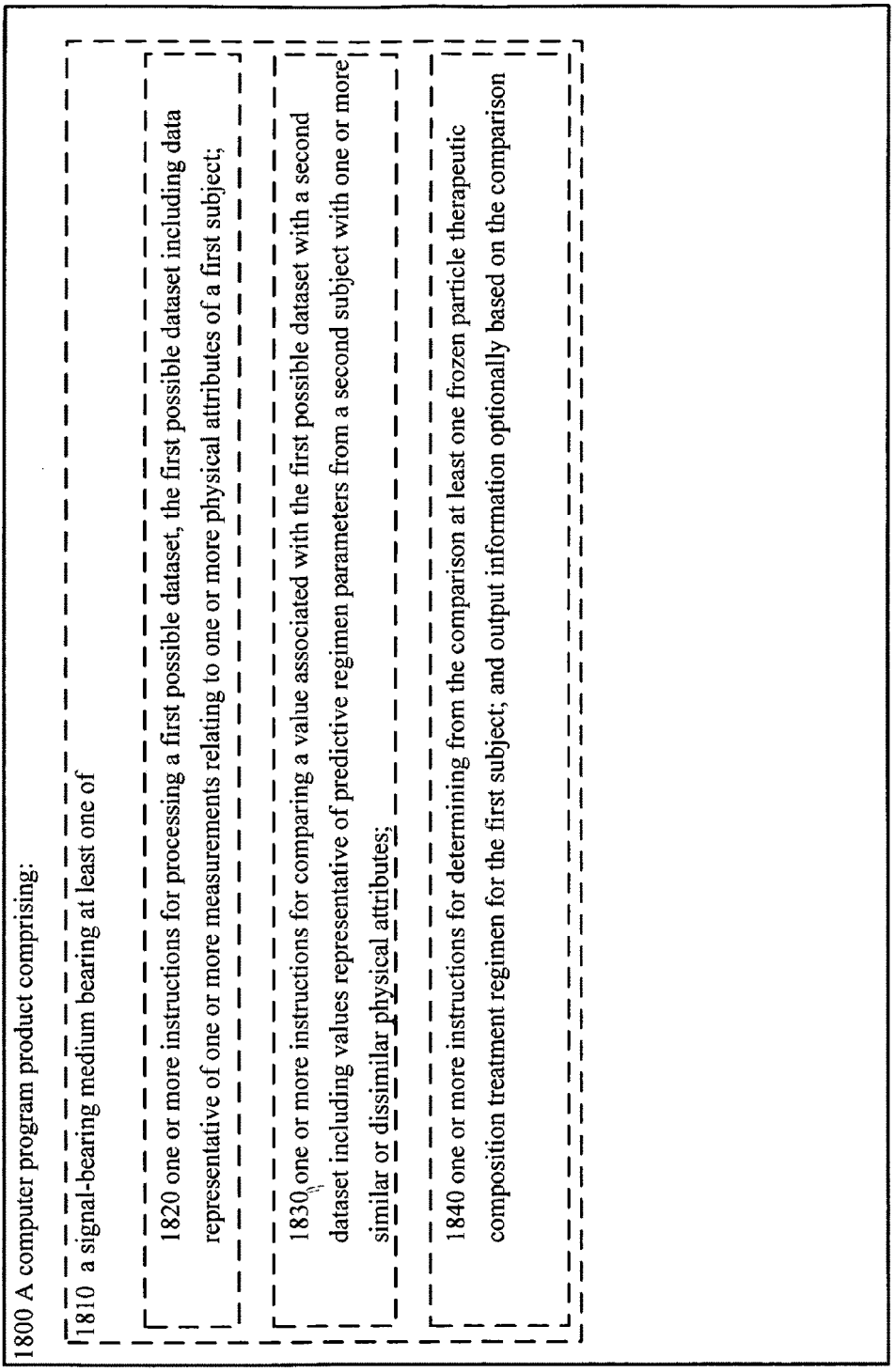
FIG. 18 illustrates a partial view of a computer program product 1800 for executing a computing process on a computing device.

As indicated in FIG. 18, one embodiment relates to a computer program product 1800 that includes a signal bearing medium 1810 bearing at least one of one or more instructions 1820 for processing a first possible dataset, the first possible dataset including data representative of one or more measurements relating to one or more physical attributes of a first subject; one or more instructions 1830 for comparing a value associated with the first possible dataset with a second dataset including values representative of predictive regimen parameters from a second subject with one or more similar or dissimilar physical attributes; one or more instructions 1840 for determining from the comparison at least one frozen particle composition (or frozen piercing implement) or therapeutic composition treatment regimen for the first subject, and output information.

As indicated in FIG. 19, one embodiment relates to a computer program product 1900 that includes a signal bearing medium 1910 bearing at least one of one or more instructions 1920 responsive to a first possible dataset, the first possible dataset including data representative of one or more measurements relating to one or more physical attributes of a first subject; one or more instructions 1930 for comparing a value associated with the first possible dataset with a second dataset including values representative of predictive regimen parameters for a second subject with one or more similar or dissimilar physical attributes; one or more instructions 1940 for determining from the comparison at least one frozen particle composition (or frozen piercing implement) or therapeutic composition treatment regimen for the first subject; and output information optionally based on the determination.

As shown in FIG. 20, one embodiment relates to a computer program product 2000 that includes a signal bearing medium 2010 bearing at least one of one or more instructions 2020 for receiving a first input associated with a first possible dataset, the first possible dataset including data representative of one or more measurements relating to one or more physical attributes of a subject; one or more instructions 2030 for comparing a value associated with the first possible dataset with a second dataset including values representative of parameters relating to one or more expected biological changes following administration of one or more frozen particle compositions (or frozen piercing implements) or therapeutic compositions; one or more instructions 2040 for determining from the comparison at least one biological change following administration of one or more frozen particle compositions (or frozen piercing implements) or therapeutic compositions to the subject; at least one generated output optionally based on the determination.

In one embodiment, the computer program product includes one or more instructions 2050 for accessing the first possible dataset in response to the first input. In one embodiment, the computer program product includes one or more instructions 2060 for generating the first possible dataset in response to the first input.

In one embodiment, the computer program product includes one or more instructions 2070 for determining a graphical illustration of the first possible dataset. In one embodiment, the computer program product includes one or more instructions 2080 for determining a graphical illustration of the second possible dataset. In one embodiment, the signal bearing medium includes a computer-readable medium 2090. In one embodiment, the signal bearing medium includes a recordable medium 2092. In one embodiment, the signal bearing medium includes a communications medium 2094.

Figure 21:
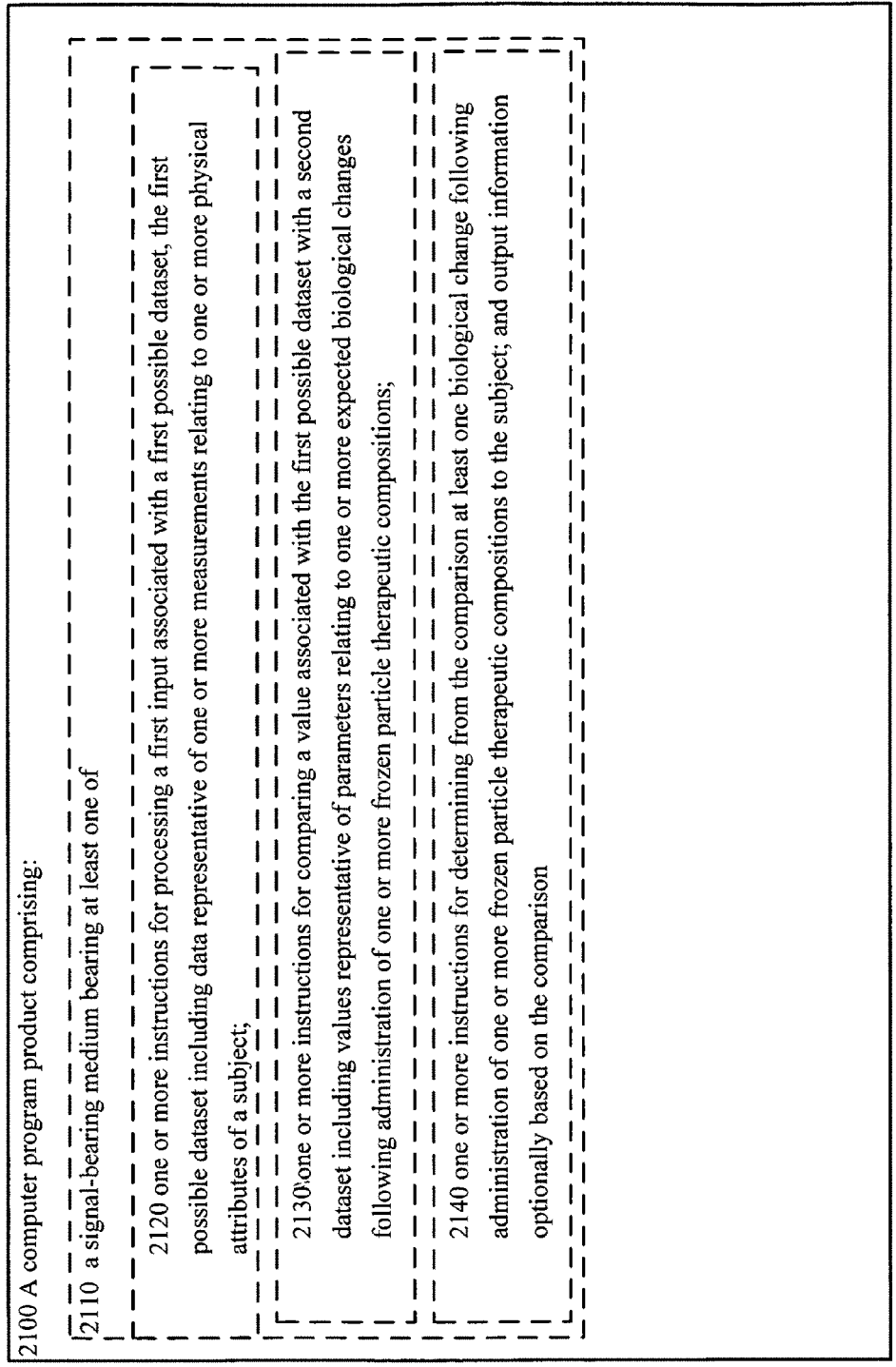
FIG. 21 illustrates a partial view of a computer program product 2100 for executing a computing process on a computing device.

As indicated in FIG. 21, one embodiment a computer program product 2100 includes a signal bearing medium 2110 bearing at least one of one or more instructions 2120 for processing a first input associated with a first possible dataset, the first possible dataset including data representative of one or more measurements relating to one or more physical attributes of a subject; one or more instructions 2130 for comparing a value associated with the first possible dataset with a second dataset including values representative of parameters relating to one or more expected biological changes following administration of one or more frozen particle compositions (or frozen piercing implements) or therapeutic compositions; one or more instructions 2140 for determining from the comparison at least one biological change following administration of one or more frozen particle compositions (or frozen piercing implements) or therapeutic compositions to the subject; at least one generated output optionally based on the determination.

Figure 22:
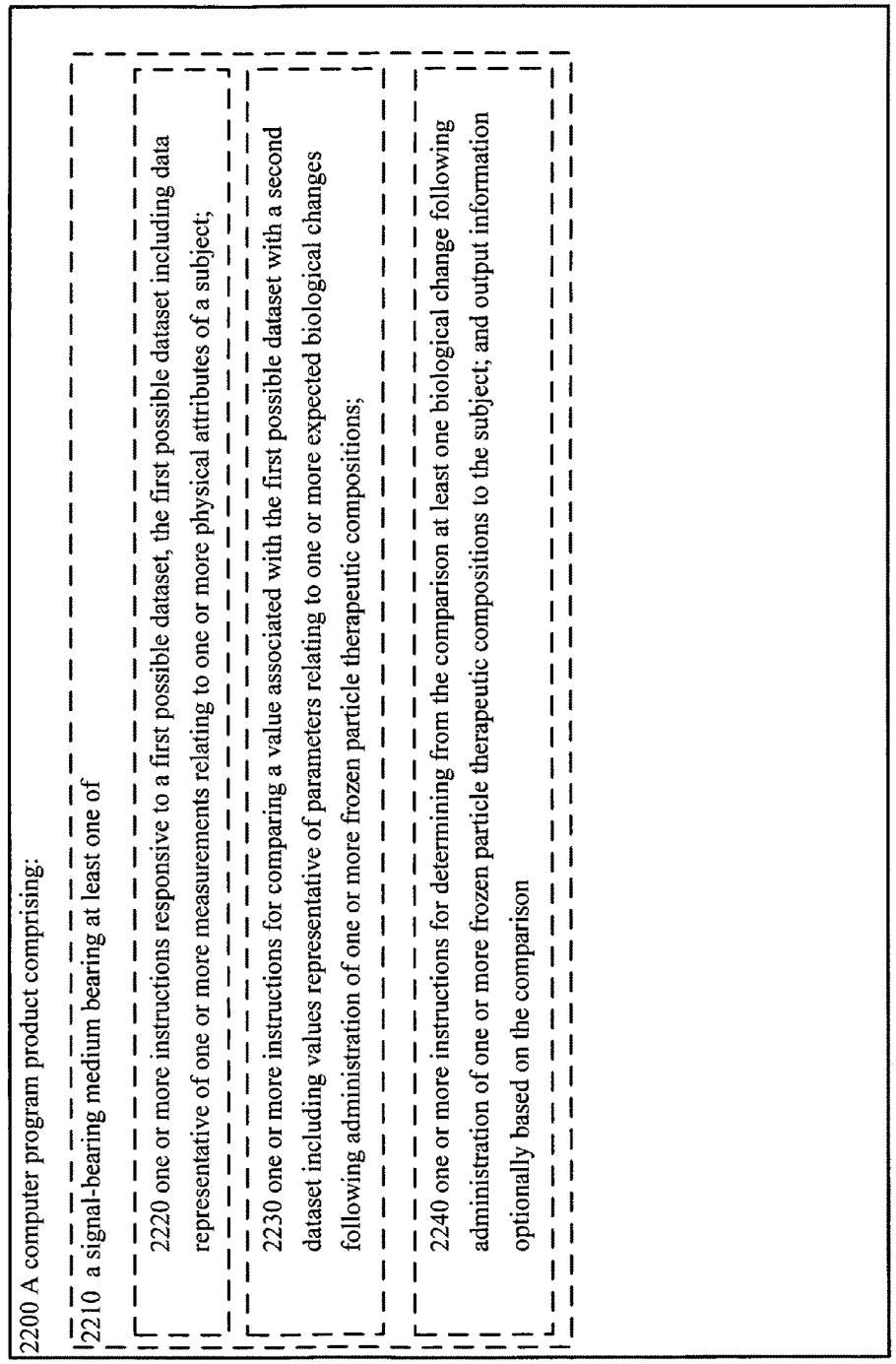
FIG. 22 illustrates a partial view of a computer program product 2200 for executing a computing process on a computing device.

As shown in FIG. 22, one embodiment relates to a computer program product 2200 includes a signal bearing medium 2210 bearing at least one of one or more instructions 2220 responsive to a first possible dataset, the first possible dataset including data representative of one or more measurements relating to one or more physical attributes of a subject; one or more instructions 2230 for comparing a value associated with the first possible dataset with a second dataset including values representative of parameters relating to one or more expected biological changes following administration of one or more frozen particle compositions (or frozen piercing implements) or therapeutic compositions; one or more instructions 2240 for determining from the comparison at least one biological change following administration of one or more frozen particle compositions (or frozen piercing implements) or therapeutic compositions to the subject; and output information optionally based on the determination.

Figure 24:
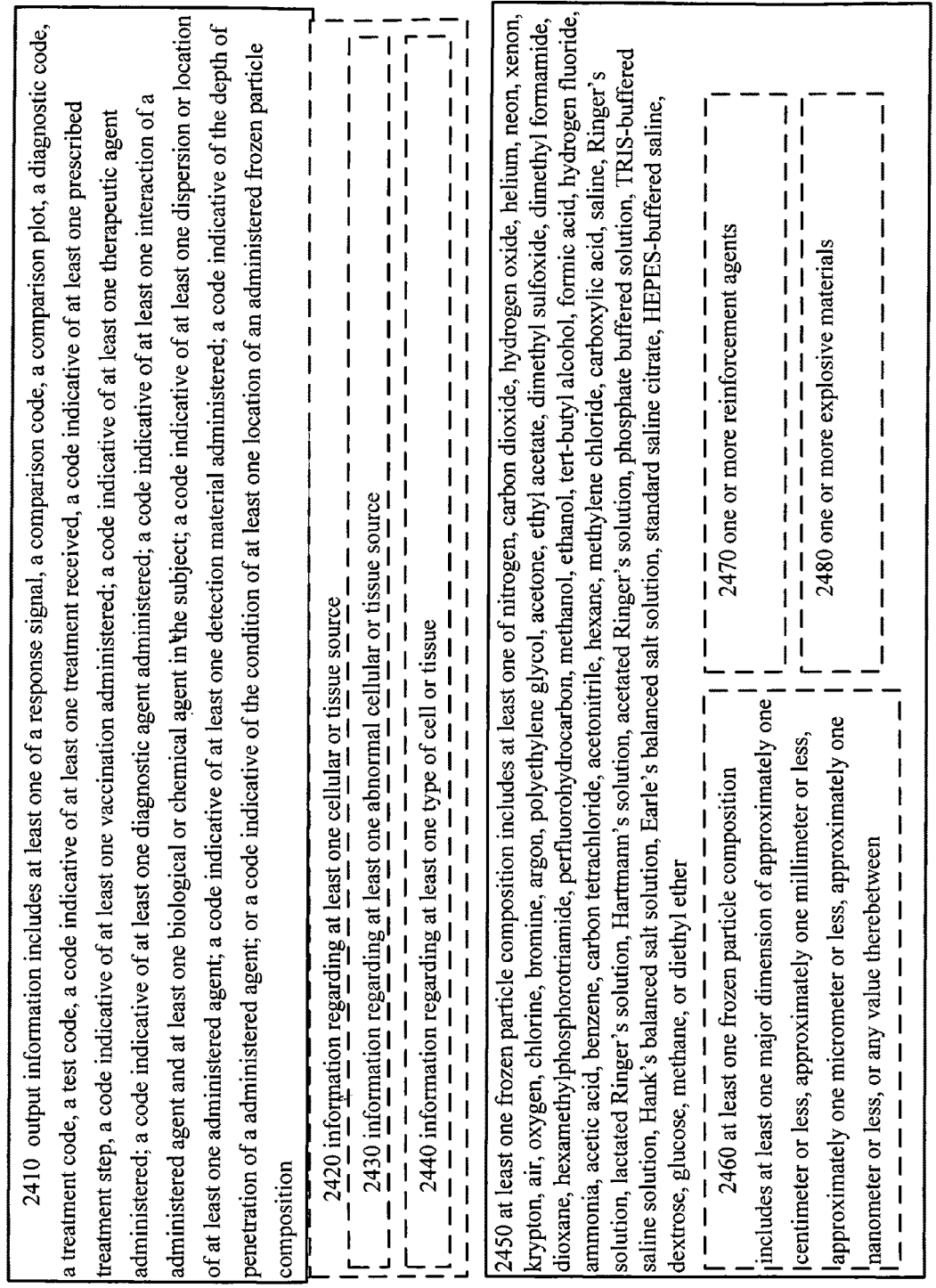
FIG. 24 illustrates a partial view FIG. 23 in which embodiments may be implemented.
Figure 25:
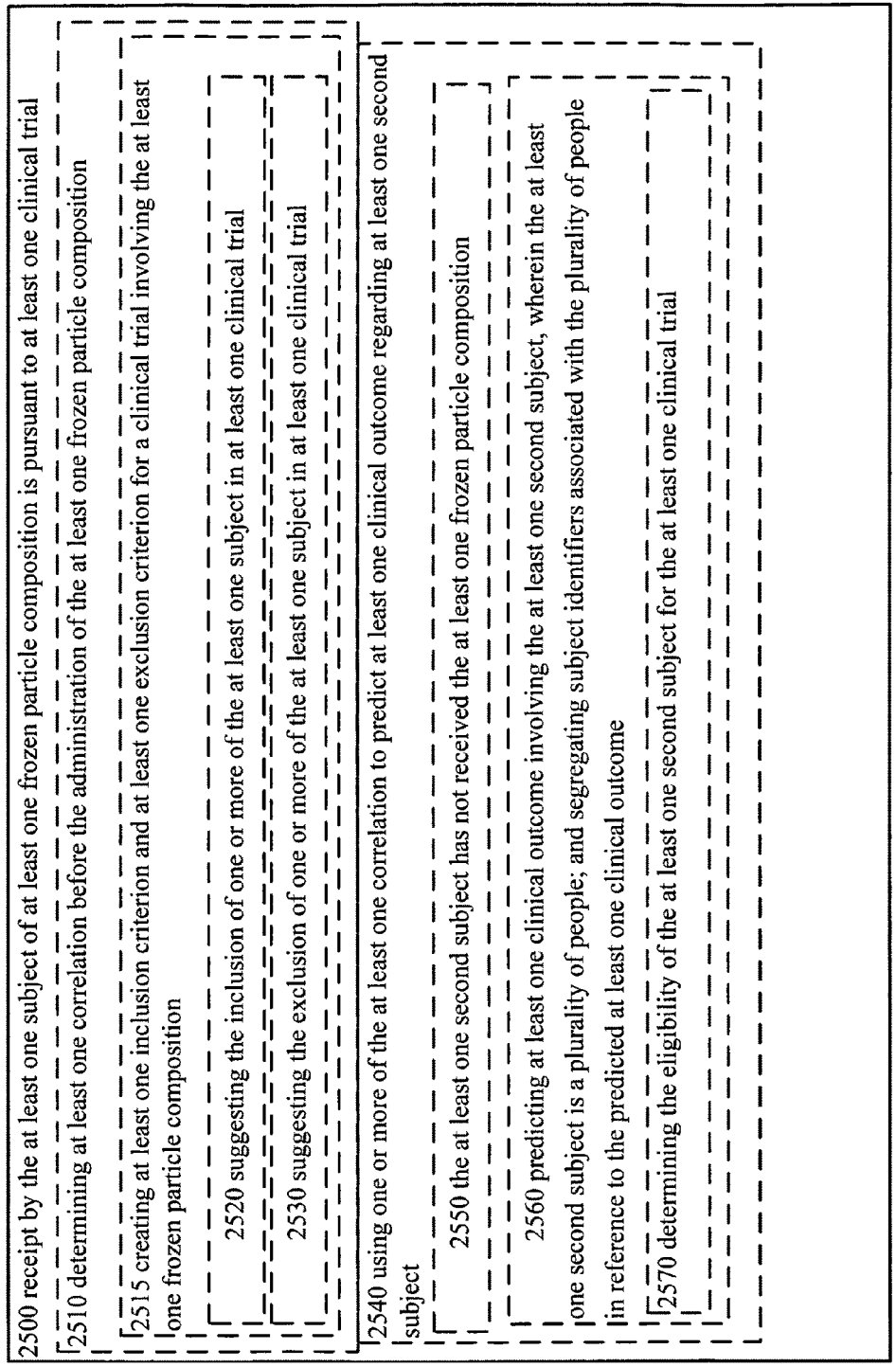
FIG. 25 illustrates a partial view FIG. 23 in which embodiments may be implemented.

As indicated in FIGS. 23-25, one embodiment, a method 2300 includes comparing 2310 information regarding at least one aspect of cellular or tissue abrasion or ablation of at least one biological tissue of at least one subject and information regarding at least one clinical outcome following receipt by the at least one subject of at least one frozen particle composition (or frozen piercing implement) or therapeutic composition; and providing output information optionally based on the determination. In one embodiment, the method includes determining at least one statistical correlation 2320. In one embodiment, the method includes counting the occurrence of at least one clinical outcome 2330. In one embodiment, the information regarding at least one aspect of cellular or tissue abrasion or ablation includes information regarding quantity of cells or tissue removed or destroyed 2340. In one embodiment, the information regarding at least one aspect of cellular or tissue abrasion or ablation includes information regarding at least one dimension of cellular or tissue removal or destruction, or removal or destruction of other materials, such as plaque, extracellular matrix, collagen, elastin, protein, or other materials 2350. In one embodiment, information regarding the at least one dimension of cellular removal or destruction includes information regarding at least one of depth, width, or breadth of cellular removal or destruction 2360.

In one embodiment, the information regarding at least one aspect of cellular or tissue abrasion or ablation includes information regarding two or more subjects with one or more common attributers 2370. In one embodiment, the one or more common attributes include genetic attributes, mental attributes, or psychological attributers 2380. In at least on embodiment, the one or more common attributes include genotype attributes or phenotype attributers 2390.

In one embodiment, the one or more common attributers 2397 include at least one of height; weight; medical diagnosis; familial background; results on one or more medical tests; ethnic background; body mass index; age; presence or absence of at least one disease or condition; species; ethnicity; race; allergies; gender; thickness of epidermis; thickness of dermis; thickness of stratum corneum; keratin deposition; collagen deposition; blood vessel condition; skin condition; hair or fur condition; muscle condition; tissue condition; organ condition; nerve condition; brain condition; presence or absence of at least one biological, chemical, or therapeutic agent in the subject; pregnancy status; lactation status; genetic profile; proteomic profile; partial or whole genetic sequence; medical history; partial or whole proteomic sequence; lymph condition, or blood condition.

In one embodiment, the output information 2410 includes at least one of a response signal, a comparison code, a comparison plot, a diagnostic code, a treatment code, a test code, a code indicative of at least one treatment received, a code indicative of at least one prescribed treatment step, a code indicative of at least one vaccination delivered; a code indicative of at least one therapeutic agent delivered; a code indicative of at least one diagnostic agent delivered; a code indicative of at least one interaction of a delivered agent and at least one biological or chemical agent in the subject; a code indicative of at least one dispersion or location of at least one delivered agent; a code indicative of at least one detection material delivered; a code indicative of the depth of penetration of a delivered agent; or a code indicative of the condition of at least one location of a delivered or administered frozen particle composition (or frozen piercing implement). In one embodiment, the at least one aspect of cellular or tissue abrasion or ablation includes information regarding at least one cellular or tissue source 2420. In one embodiment, the information regarding at least one tissue source includes information regarding at least one abnormal cellular or tissue source 2430. In one embodiment, the information regarding at least one cellular or tissue source includes information regarding at least one type of cell or tissue 2440. In one embodiment, the cellular or tissue source includes at least one cell or biological tissue described herein.

In one embodiment, the at least one frozen particle composition (or frozen piercing implement) or therapeutic composition includes at least one of nitrogen, carbon dioxide, hydrogen oxide, helium, neon, xenon, krypton, chlorine, bromine, methane, oxygen, air, argon, polyethylene glycol, acetone, ethyl acetate, dimethyl sulfoxide, dimethyl formamide, dioxane, hexamethylphosphorotriamide, perfluorohydrocarbon, methanol, ethanol, tert-butyl alcohol, formic acid, hydrogen fluoride, ammonia, acetic acid, benzene, carbon tetrachloride, hexane, methylene chloride, carboxylic acid, saline, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, or diethyl ether 2450.

In one embodiment, the at least one frozen particle composition (or frozen piercing implement) includes at least one major dimension of approximately one decimeter or less, or approximately one centimeter or less, approximately one millimeter or less, approximately one micrometer or less, approximately one nanometer or less, or any value therebetween 2460.

In one embodiment, the at least one frozen particle composition (or frozen piercing implement) includes one or more reinforcement agents 2470. In one embodiment, the at least one frozen particle composition (or frozen piercing implement) includes one or more explosive materials 2480. In one embodiment, the receipt by the at least one subject of at least one frozen particle composition (or frozen piercing implement) is pursuant to at least one clinical trial 2500. In one embodiment, the method further comprises determining at least one correlation 2510 before the delivery or administration of the at least one frozen particle composition (or frozen piercing implement) to at least one subject. The at least one subject includes, but is not limited to at least one subject described herein.

In one embodiment, the method includes creating at least one inclusion criterion and at least one exclusion criterion for a clinical trial involving the at least one frozen particle composition (or frozen piercing implement) or therapeutic composition 2515. In one embodiment, the method further comprises suggesting the inclusion of one or more of the at least one subject in at least one clinical trial 2520. In one embodiment, the method further comprises suggesting the exclusion of one or more of the at least one subject in at least one clinical trial 2530. In certain instances, multiple subjects from multiple clinical trials are included. In one embodiment, the method further includes using one or more of the at least one correlation to predict at least one clinical outcome regarding at least one second subject 2540. In one embodiment, the at least one second subject has not received the at least one frozen particle composition (or frozen piercing implement) or therapeutic composition 2550. In one embodiment, the method further comprises predicting at least one clinical outcome involving the at least one second subject, wherein the at least one second subject is a plurality of people; and segregating subject identifiers associated with the plurality of people in reference to the predicted at least one clinical outcome 2560. In one embodiment, the at least one second subject is a plurality of people; and the method further comprises determining the eligibility of the at least one second subject for the at least one clinical trial 2570.

Figure 27:
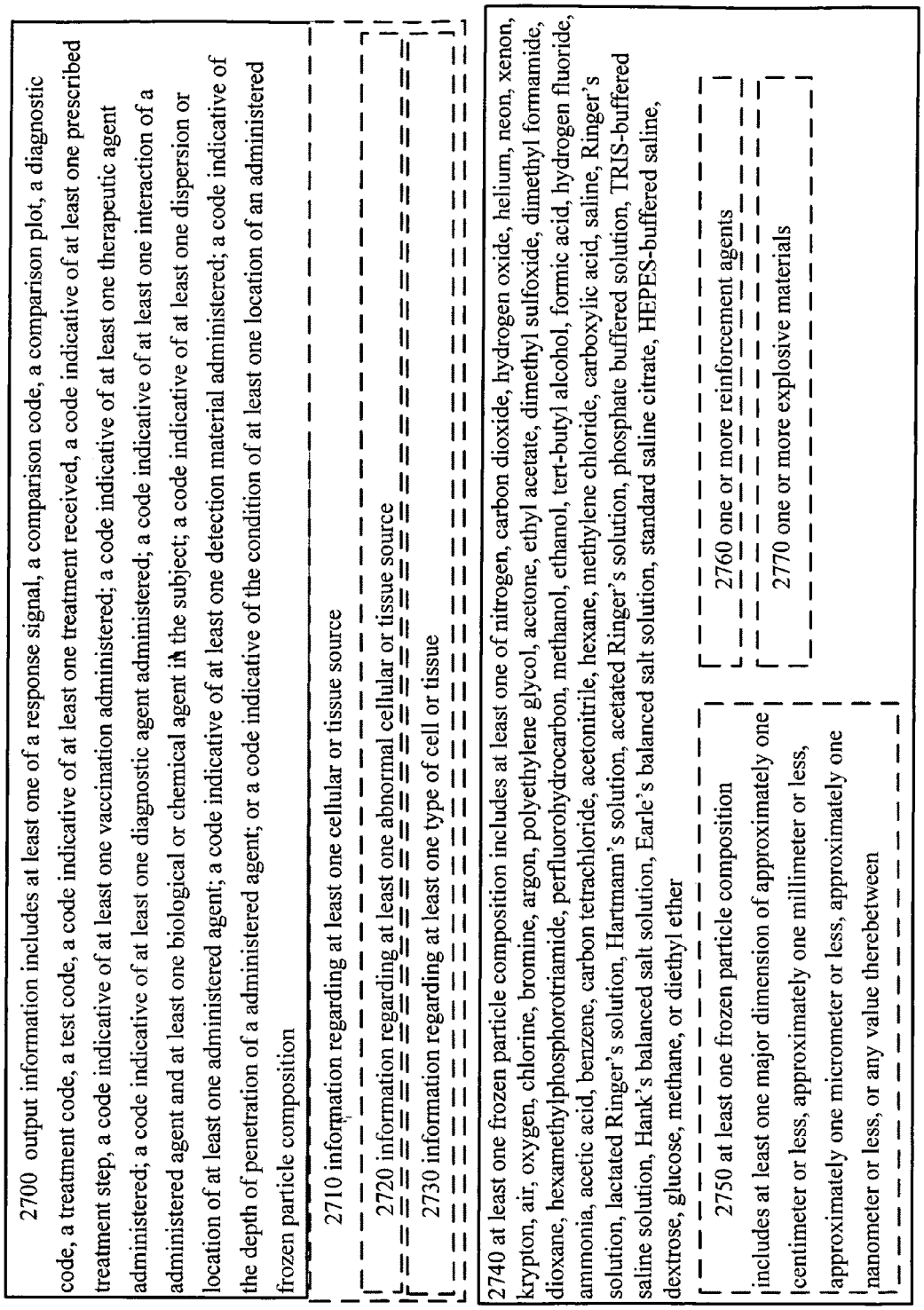
FIG. 27 illustrates a partial view of FIG. 26 in which embodiments may be implemented.

As indicated in FIGS. 26-28, one embodiment relates to a method 2600 of predicting a clinical outcome of at least one frozen particle composition (or frozen piercing implement) treatment for at least one first subject includes determining 2610 a similarity or a dissimilarity in information regarding at least one aspect of cellular or tissue abrasion or ablation of at least one biological tissue of at least one first subject to information regarding at least one aspect of cellular or tissue abrasion or ablation of at least one biological tissue of at least one second subject, wherein the at least one second subject attained a clinical outcome following receipt of the at least one frozen particle composition or therapeutic composition; and providing output information optionally based on the determination.

In one embodiment, the information regarding at least one aspect of cellular or tissue abrasion or ablation includes information regarding the quantity of cells or tissue removed or destroyed 2620. In one embodiment, the information regarding at least one aspect of cellular or tissue abrasion or ablation includes information regarding at least one dimension of cellular, tissue, or other material removal or destruction 2630. In one embodiment, the at least one dimension of cellular removal or destruction includes information regarding at least one of depth, width, or breadth of cellular removal or destruction 2640. In one embodiment, the information regarding at least one aspect of cellular or tissue abrasion or ablation includes information regarding two or more subjects with one or more common attributers 2650.

In one embodiment, the one or more common attributes include but are not limited to genetic attributes, mental attributes, or psychological attributers 2660. In one embodiment, the one or more common attributes include genotype attributes or phenotype attributers 2670.

In one embodiment, the one or more common attributes include at least one of height; weight; medical diagnosis; familial background; results on one or more medical tests; ethnic background; body mass index; age; presence or absence of at least one disease or condition; species; ethnicity; race; allergies; gender; thickness of epidermis; thickness of dermis; thickness of stratum corneum; keratin deposition; collagen deposition; blood vessel condition; skin condition; hair or fur condition; muscle condition; tissue condition; organ condition; nerve condition; brain condition; presence or absence of at least one biological, chemical, or therapeutic agent in the subject; pregnancy status; lactation status; medical history; genetic profile; proteomic profile; partial or whole genetic sequence; partial or whole proteomic sequence; lymph condition, medical history, or blood condition 2680.

In one embodiment, the output information includes at least one of a response signal, a comparison code, a comparison plot, a diagnostic code, a treatment code, a test code, a code indicative of at least one treatment received, a code indicative of at least one prescribed treatment step, a code indicative of at least one vaccination delivered; a code indicative of at least one therapeutic agent delivered; a code indicative of at least one diagnostic agent delivered; a code indicative of at least one interaction of a delivered agent and at least one biological or chemical agent in the subject; a code indicative of at least one dispersion or location of at least one delivered agent; a code indicative of at least one detection material delivered; a code indicative of the depth of penetration of a delivered agent; or a code indicative of the condition of at least one location of a delivered or administered frozen particle composition (or frozen piercing implement) 2700.

In one embodiment, the information regarding at least one aspect of cellular or tissue abrasion or ablation includes information regarding at least one cellular or tissue source 2710. In one embodiment, the cellular or tissue source includes but is not limited to at least one biological tissue or cell described herein. In one embodiment, the information regarding at least one tissue source includes information regarding at least one abnormal cellular or tissue source 2720. In one embodiment, the information regarding at least one cellular or tissue source includes information regarding at least one type of cell or tissue 2730. In one embodiment, the information regarding at least one aspect of cellular or tissue abrasion or ablation includes information regarding at least one type of cell or tissue.

In one embodiment, the at least one frozen particle composition (or frozen piercing implement) or therapeutic composition includes at least one of nitrogen, carbon dioxide, hydrogen oxide, helium, neon, xenon, krypton, chlorine, bromine, methane, oxygen, air or argon. In one embodiment, the at least one frozen particle composition (or frozen piercing implement) or therapeutic composition includes at least one of polyethylene glycol, acetone, ethyl acetate, dimethyl sulfoxide, dimethyl formamide, dioxane, hexamethylphosphorotriamide, perfluorohydrocarbon, methanol, ethanol, tert-butyl alcohol, formic acid, hydrogen fluoride, ammonia, acetic acid, benzene, carbon tetrachloride, hexane, methylene chloride, carboxylic acid, saline, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, or diethyl ether 2740.

In one embodiment, the at least one frozen particle composition (or frozen piercing implement) or therapeutic composition includes at least one major dimension of approximately one decimeter or less, or approximately one centimeter or less, or approximately one millimeter or less, or approximately one micrometer or less, or approximately one nanometer or less, or any value therebetween 2750.

In one embodiment, the at least one frozen particle composition (or frozen piercing implement) or therapeutic composition includes one or more reinforcement agents 2760. In one embodiment, the at least one frozen particle composition (or frozen piercing implement) or therapeutic composition includes one or more explosive materials 2770.

In one embodiment, the receipt by the at least one subject of at least one frozen particle composition (or frozen piercing implement) or therapeutic composition is pursuant to at least one clinical trial 2800. In one embodiment, the method includes creating at least one inclusion criterion and at least one exclusion criterion for a clinical trial involving the at least one frozen particle composition (or frozen piercing implement) or therapeutic composition 2810. In one embodiment, the method further comprises suggesting the inclusion of one or more of the at least one subject in at least one clinical trial 2820. In certain instances, multiple subjects from multiple clinical trials are included. In one embodiment, the method includes suggesting the exclusion of one or more of the at least one subject in at least one clinical trial 2830.

In one embodiment, a method includes using one or more of the at least one determination to predict at least one clinical outcome regarding at least one second subject 2840. In one embodiment, the at least one second subject has not received the at least one frozen particle composition (or frozen piercing implement) or therapeutic composition 2850. In one embodiment, the at least one second subject is a plurality of people; and the method further comprises segregating subject identifiers associated with the plurality of people in reference to the predicted at least one clinical outcome 2860.

In one embodiment, the using one or more of the at least one comparison, wherein the at least one second subject is a plurality of people; and the method further comprises determining the eligibility of the at least one second subject for the at least one clinical trial 2870.

As indicated in FIGS. 29-30, at least one aspect relates to a system 2900 that includes at least one computing device 2910; one or more instructions 2920 that when executed on the at least one computing device cause the at least one computing device to receive a first input associated with a first possible dataset, the first possible dataset including data representative of one or more measurements relating to one or more physical attributes of a first subject; one or more instructions 2930 that when executed on the at least one computing device cause the at least one computing device to compare a value associated with the first possible dataset with a second dataset including values representative of predictive regimen parameters related to a second subject with one or more similar or dissimilar physical attributes; one or more instructions 2940 that when executed on the at least one computing device cause the at least one computing device to determine from the comparison at least one frozen particle composition (or frozen piercing implement) treatment regimen for the first subject; and at least one generated output optionally based on the determination; one or more instructions 2950 that when executed on the at least one computing device cause the at least one computing device to access the first possible dataset in response to the first input; one or more instructions 2960 that when executed on the at least one computing device cause the at least one computing device to generate the first possible dataset in response to the first input; one or more instructions 2970 that when executed on the at least one computing device cause the at least one computing device to determine a graphical illustration of the possible dataset; or one or more instructions 3000 that when executed on the at least one computing device cause the at least one computing device to determine a graphical illustration of the second possible dataset. In one embodiment, the treatment regimen includes at least one of cellular or tissue removal, cellular or tissue ablation, debridement, delivery of at least one therapeutic agent, cleaning one or more wounds, oxygenating wounds, removing material from at least one biological tissue, or removing material from at least one blood vessel 3005. In at least one nitrogen, carbon dioxide, hydrogen oxide, helium, neon, xenon, krypton, chlorine, bromine, methane, oxygen, air, argon, polyethylene glycol, acetone, ethyl acetate, dimethyl sulfoxide, dimethyl formamide, dioxane, hexamethylphosphorotriamide, perfluorohydrocarbon, methanol, ethanol, tert-butyl alcohol, formic acid, hydrogen fluoride, ammonia, acetic acid, benzene, carbon tetrachloride, hexane, methylene chloride, carboxylic acid, saline, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, or diethyl ether 3008.

In one embodiment, the at least one computing device includes one or more desktop computer, workstation computer, computing system including a cluster of processors, a networked computer, a tablet personal computer, a laptop computer, a mobile device, a mobile telephone, or a personal digital assistant computer 3010. In one embodiment, the at least one computing device is configured to communicate with a database to access the first possible dataset 3020. In one embodiment, the at least one computing device is configured to communicate with a frozen particle composition (or frozen piercing implement) selecting apparatus, a frozen particle composition (or frozen piercing implement) generating apparatus, or both 3030.

Figure 31:
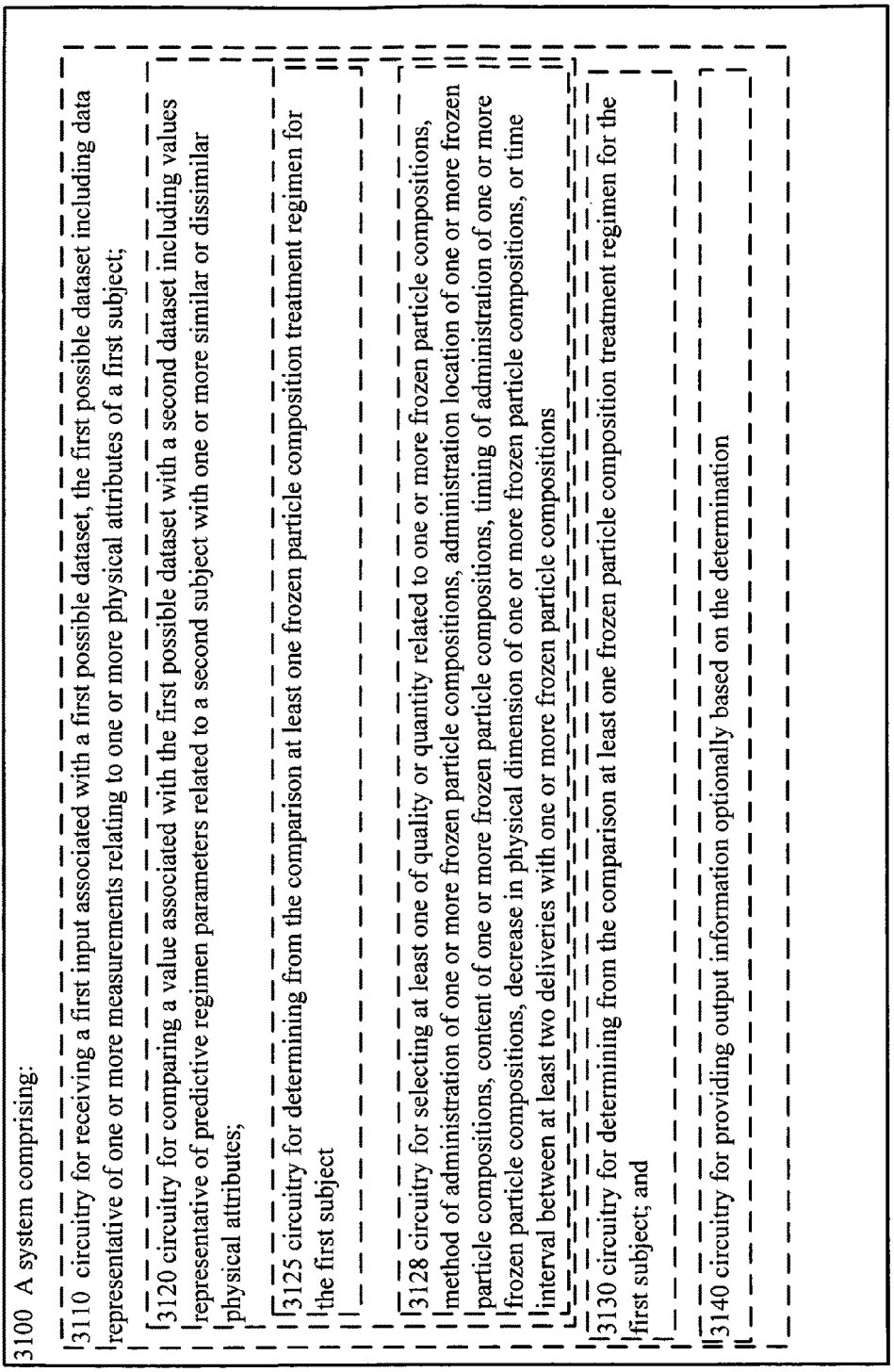
FIG. 31 illustrates a partial view of a system 3100 that includes a computer program for executing a computing process on a computing device.
Figure 32:
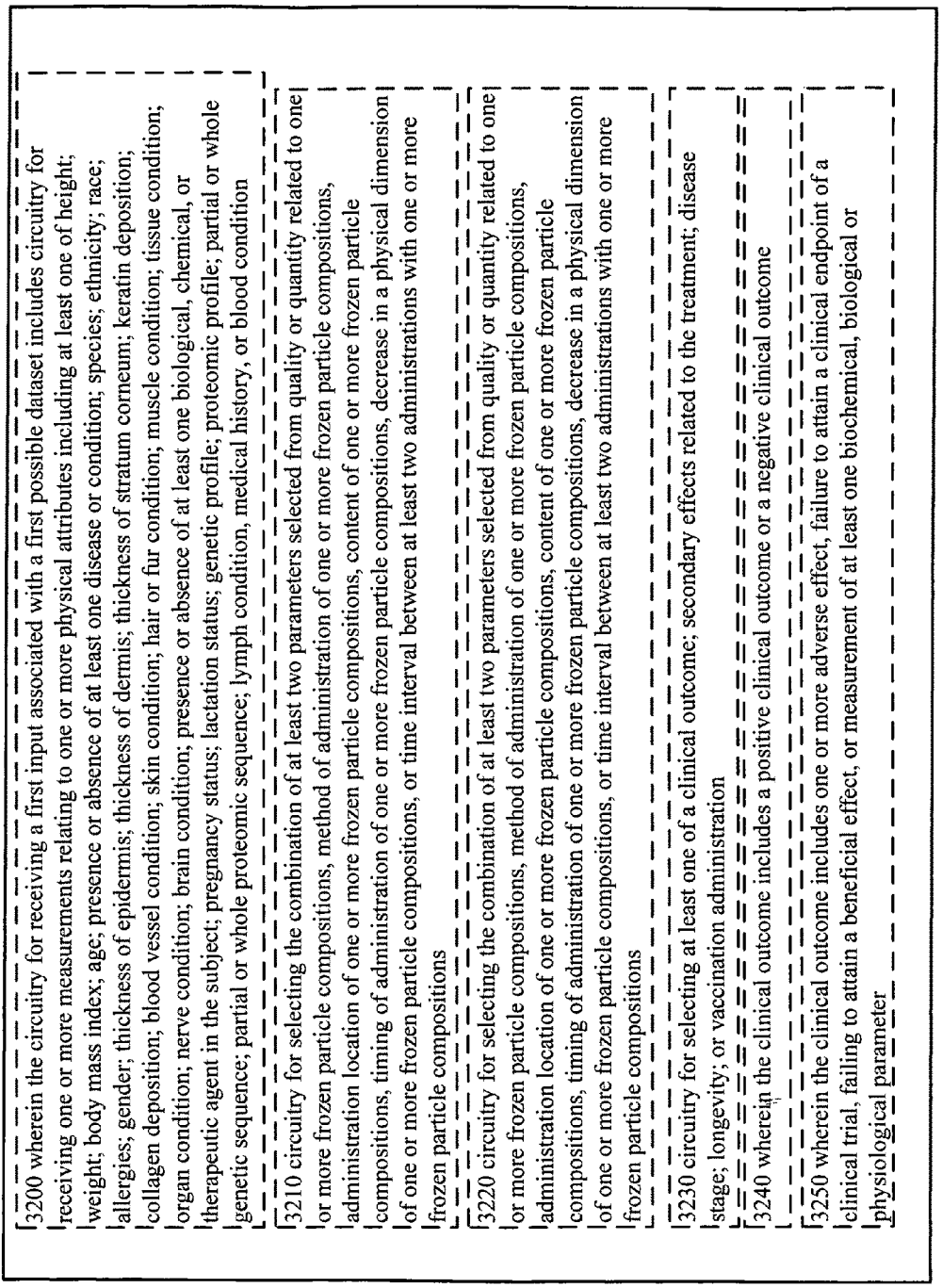
FIG. 32 illustrates a partial view of FIG. 31 in which embodiments may be implemented.

As shown in FIGS. 31-32, at least one aspect relates to a system 3100 including circuitry 3110 for receiving a first input associated with a first possible dataset, the first possible dataset including data representative of one or more measurements relating to one or more physical attributes of a first subject; circuitry 3120 for comparing a value associated with the first possible dataset with a second dataset including values representative of predictive regimen parameters related to a second subject with one or more similar or dissimilar physical attributes; circuitry 3125 for determining from the comparison at least one frozen particle composition (or frozen piercing implement) treatment regimen for the first subject; circuitry 3128 for selecting at least one of quality or quantity related to one or more frozen particle compositions (or frozen piercing implements), method of administration of one or more frozen particle compositions (or frozen piercing implements), administration location of one or more frozen particle compositions (or frozen piercing implements), content of one or more frozen particle compositions (or frozen piercing implements), timing of administration of one or more frozen particle compositions (or frozen piercing implements), decrease in physical dimension of one or more frozen particle compositions (or frozen piercing implements) or time interval between at least two deliveries with one or more frozen particle compositions (or frozen piercing implements).

In one embodiment, the system includes circuitry 3130 for determining from the comparison at least one frozen particle composition (or frozen piercing implement) treatment regimen for the first subject; and circuitry 3140 for providing output information optionally based on the comparison. In one embodiment, the circuitry for receiving a first input associated with a first possible dataset includes circuitry 3200 for receiving one or more measurements relating to one or more physical attributes including at least one of height; weight; body mass index; age; presence or absence of at least one disease or condition; species; ethnicity; race; allergies; gender; thickness of epidermis; thickness of dermis; thickness of stratum corneum; keratin deposition; collagen deposition; blood vessel condition; skin condition; hair or fur condition; muscle condition; tissue condition; organ condition; nerve condition; brain condition; presence or absence of at least one biological, chemical, or therapeutic agent in the subject; pregnancy status; lactation status; genetic profile; medical history; proteomic profile; partial or whole genetic sequence; partial or whole proteomic sequence; medical history; lymph condition, or blood condition.

In one embodiment, the system includes circuitry 3210 for selecting the combination of at least two parameters selected from quality or quantity related to one or more frozen particle compositions (or frozen piercing implements), method of administration of one or more frozen particle compositions (or frozen piercing implements), administration location of one or more frozen particle compositions (or frozen piercing implements), content of one or more frozen particle compositions (or frozen piercing implements), timing of administration of one or more frozen particle compositions (or frozen piercing implements), decrease in a physical dimension of one or more frozen particle compositions (or frozen piercing implements), or time interval between at least two administrations or deliveries with one or more frozen particle compositions (or frozen piercing implements).

In one embodiment, the system includes circuitry 3220 for selecting the combination of at least two parameters selected from quality or quantity related to one or more frozen particle compositions (or frozen piercing implements), method of administration of one or more frozen particle compositions (or frozen piercing implements), administration location of one or more frozen particle compositions (or frozen piercing implements), content of one or more frozen particle compositions (or frozen piercing implements), timing of administration of one or more frozen particle compositions (or frozen piercing implements), decrease in a physical dimension of one or more frozen particle compositions (or frozen piercing implements), or time interval between at least two administrations with one or more frozen particle compositions (or frozen piercing implements).

In one embodiment, the system includes circuitry 3230 for selecting at least one of a clinical outcome; secondary effects related to the treatment; disease stage; longevity; or vaccination administration. In one embodiment, the clinical outcome 3240 includes a positive clinical outcome or a negative clinical outcome. In one embodiment, the clinical outcome includes one or more adverse effect, failure to attain a clinical endpoint of a clinical trial, failing to attain a beneficial effect, or measurement of at least one biochemical, biological or physiological parameter 3250.

Figure 34:
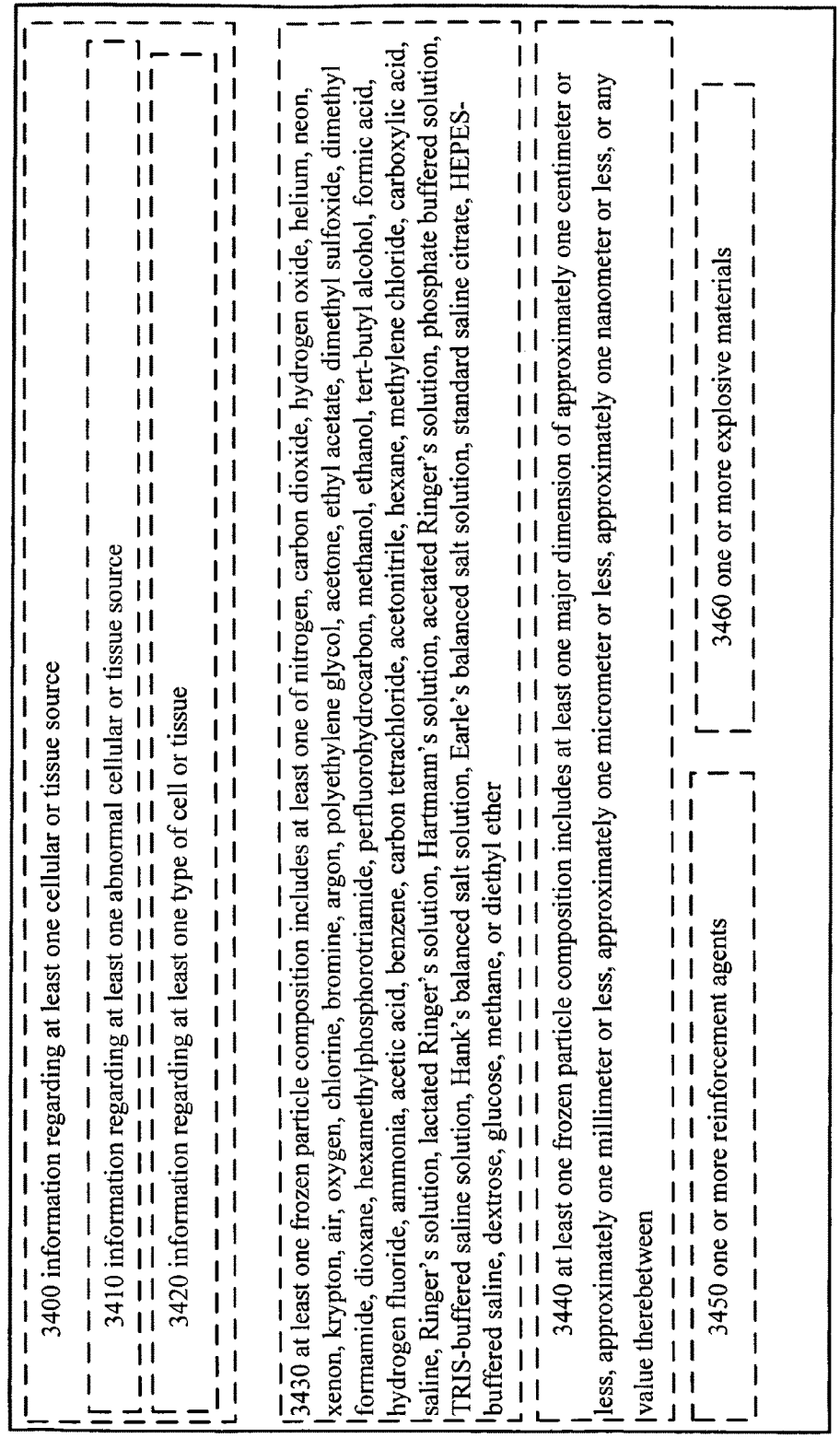
FIG. 34 illustrates a partial view of FIG. 33 in which embodiments may be implemented.

FIGS. 33-35 illustrate a partial view of a system 3300 including at least one computer program 3310 configured with a computer-readable medium, for use with at least one computer system and wherein the computer program includes a plurality of instructions including but not limited to one or more instructions 3320 for determining at least one comparison between information regarding at least one aspect of cellular or tissue abrasion or ablation of at least one biological tissue of at least one subject and information regarding at least one clinical outcome following receipt by the at least one subject of at least one frozen particle composition (or frozen piercing implement). In one embodiment, the system includes one or more instructions 3330 for determining at least one statistical correlation. In one embodiment, the system includes one or more instructions 3340 for counting the occurrence of at least one clinical outcome. In one embodiment, information regarding at least one aspect of cellular or tissue abrasion or ablation includes information 3350 regarding quantity of cells or tissue removed or destroyed; information 3360 regarding at least one dimension of cellular, tissue or other material removal or destruction; information 3370 regarding at least one of depth, width, or breadth of cellular removal or destruction; or information 3380 regarding two or more subjects with one or more common attributes. In one embodiment, the information regarding at least one aspect of cellular or tissue abrasion or ablation includes information 3400 regarding at least one cellular or tissue source, including information 3410 regarding at least one abnormal cellular or tissue source or information 3420 regarding at least one type of cell or tissue.

In one embodiment, the at least one frozen particle composition (or frozen piercing implement) or therapeutic composition includes at least one of polyethylene glycol, acetone, ethyl acetate, dimethyl sulfoxide, dimethyl formamide, dioxane, hexamethylphosphorotriamide, perfluorohydrocarbon, methanol, ethanol, tert-butyl alcohol, formic acid, hydrogen fluoride, ammonia, acetic acid, benzene, carbon tetrachloride, hexane, methylene chloride, carboxylic acid, saline, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, or diethyl ether 3430. In one embodiment, at least one frozen particle composition (or frozen piercing implement) includes at least one major dimension of approximately one decimeter or less, approximately one centimeter or less, approximately one millimeter or less, approximately one micrometer or less, approximately one nanometer or less, or any value therebetween 3440. In one embodiment, the at least one frozen particle composition (or frozen piercing implement) includes one or more reinforcement agents 3450. In one embodiment, the at least one frozen particle composition (or frozen piercing implement) includes one or more explosive materials 3460.

In one embodiment, the receipt by the at least one subject of at least one frozen particle composition (or frozen piercing implement) or therapeutic composition is pursuant to at least one clinical trial 3500. In one embodiment, the system further comprises one or more instructions for determining at least one comparison before the delivery or administration of the at least one frozen particle composition (or frozen piercing implement) or therapeutic composition to at least one subject 3510.

In one embodiment, the system includes one or more instructions for creating at least one inclusion criterion and at least one exclusion criterion for a clinical trial involving the at least one frozen particle composition (or frozen piercing implement) or therapeutic composition 3520. In one embodiment, the system further comprises one or more instructions for suggesting the inclusion of one or more of the at least one subject in at least one clinical trial 3530. In certain instances, multiple subjects from multiple clinical trials are included.

In one embodiment, the system further includes one or more instructions for suggesting the exclusion of one or more of the at least one subject in at least one clinical trial 3540. In one embodiment, the system includes one or more instructions for using one or more of the at least one comparison to predict at least one clinical outcome regarding at least one second subject 3550. In one embodiment, the at least one second subject has not received the at least one frozen particle composition (or frozen piercing implement) or therapeutic composition 3560. In one embodiment, the system includes predicting at least one clinical outcome involving the at least one second subject, wherein the at least one second subject is a plurality of people; and segregating subject identifiers associated with the plurality of people in reference to the predicted at least one clinical outcome 3570. In one embodiment, the at least one second subject is a plurality of people; and the system further comprises determining the eligibility of the at least one second subject for the at least one clinical trial 3580.

As indicated in FIG. 36, at least one aspect relates to a system 3600 that includes at least one computer program 3610, configured with a computer-readable medium, for use with at least one computer system and wherein the computer program includes a plurality of instructions including but not limited to one or more instructions 3620 for comparing information regarding at least one aspect of cellular or tissue abrasion or ablation of at least one biological tissue of at least one subject and information regarding at least one frozen particle composition (or frozen piercing implement) involving the at least one biological tissue of at least one subject; and one or more instructions 3630 for applying one or more comparisons to information regarding at least one aspect of cellular or tissue abrasion or ablation regarding a plurality of people. In one embodiment, one or more instructions 3640 for segregating subject identifiers associated with the plurality of people in reference to at least one of the one or more applied comparisons. In one embodiment, the information regarding at least one aspect of cellular or tissue abrasion or ablation includes information 3650 regarding quantity of cells or tissue removed or destroyed; information 3660 regarding at least one dimension of cellular, tissue or other material removal or destruction; or information 3670 regarding at least one of depth, width, or breadth of cellular removal or destruction. In one embodiment, the system includes one or more instructions 3680 for segregating individual identifiers associated with the plurality of people in reference to at least one characteristic shared by two or more subjects of the plurality of people.

As indicated in FIG. 37, at least one aspect relates to a method 3700 comprising accepting a first input 3710 associated with at least one characteristic of at least one biological tissue to be at least partially constructed or at least partially reconstructed; accepting a second input 3720 associated with at least one parameter of at least partially constructing or at least partially reconstructing the at least one biological tissue by administering one or more frozen particle compositions (or frozen piercing implements) including at least one agent. In one embodiment, the at least one agent 3730 includes one or more of a therapeutic agent, adhesive agent, abrasive, reinforcement agent, explosive material, or biological remodeling agent. In one embodiment, administering 3740 the one or more frozen particle compositions (or frozen piercing implements) includes administering the one or more frozen particle compositions (or frozen piercing implements) to at least one substrate. In one embodiment, the at least one substrate 3750 includes one or more of a cell, tissue, organ, structure, or device.

In one embodiment, the method includes processing results 3760 of the first input and the second input. In one embodiment, processing results of the first input and the second input includes electronically processing 3770 results of the first input and the second input. In one embodiment, processing results of the first input and the second input includes 3780 electronically processing results of the first input and the second input by utilizing one or more of Gaussian smoothing, scaling, homomorphic filtering, parametric estimation techniques, Boolean operations, Monte Carlo simulations, wavelet based techniques, mirroring, smoothing, gradient weighted partial differential equation smoothing, NURBS, polygonal modeling, splines and patches modeling, algorithmic execution, logical decision-making, result prediction, Finite Element Analysis, or modification of a CAD design.

As indicated in FIG. 38, in one embodiment, the first input 3810 includes one or more values related to the at least one characteristic of at least one biological tissue. In one embodiment, the first input includes one or more spatial addresses 3820 associated with the at least one characteristic of at least one biological tissue. In one embodiment, the first input includes one or more of x, y, or z coordinates 3830 associated with the at least one characteristic of at least one biological tissue.

In one embodiment, the at least one characteristic 3840 of at least one biological tissue to be at least partially constructed or at least partially reconstructed includes one or more of: morphological feature, anatomical feature, histological feature, tissue hierarchical level, scaffold feature, vascular structure feature, heterogenous tissue feature, mechanical feature, volumetric feature, geometric feature, volumetric representation, mechanical feature, deformation, kinematic feature, surface contour feature, cytometric feature, cell aggregation, cell growth, cell-cell interaction, cell-tissue interaction, biomimetic design, cell pattern, cell deposition, organ hierarchical level, tissue microstructure, cellular microstructure, cell junction feature, tissue junction feature, cell-tissue classification, hard tissue classification, soft tissue classification, tumor diagnosis, or other feature.

In one embodiment, the at least one characteristic 3850 of at least one biological tissue includes one or more of cellular type, cellular function, cellular size, cellular constitution, cellular architecture, cellular durability, cellular source, tissue type, tissue constitution, tissue size, tissue shape, tissue function, tissue architecture, tissue source, tissue durability, organ type, organ constitution, organ size, organ shape, organ function, organ architecture, organ source, or organ durability. In one embodiment, the first input 3860 includes one or more temporal addresses associated with the at least one characteristic of at least one biological tissue.

As indicated in FIG. 39, in one embodiment, the first input 3910 includes one or more values derived from at least one image of the at least one biological tissue. In one embodiment, the at least one image 3920 includes one or more images acquired by one or more of laser, holography, x-ray crystallography, optical coherence tomography, computer-assisted tomography scan, computed tomography, magnetic resonance imaging, positron-emission tomography scan, ultrasound, x-ray, electrical-impedance monitoring, microscopy, spectrometry, flow cytommetry, radioisotope imaging, thermal imaging, multiphoton calcium-imaging, photography, or in silico generation.

In one embodiment, the at least one biological tissue 3930 is located in at least one of in situ, in vitro, in vivo, in utero, in planta, in silico, or ex vivo. In one embodiment, the at least one biological tissue 3940 is at least partially located in at least one subject. In one embodiment, the method further comprises accepting a third input 3950 associated with at least one feature of the at least one subject. In one embodiment, the at least one feature 3960 of the at least one subject includes one or more of age, gender, genotype, phenotype, proteomic profile, or health condition.

As indicated in FIGS. 40-41, in one embodiment, the processing results 4010 of the first input and the second input includes determining at least one parameter of at least partially constructing or at least partially reconstructing the at least one biological tissue with one or more frozen particle compositions (or frozen piercing implements) from one or more values derived from at least one image of the at least one biological tissue. In one embodiment, the second input 4020 includes one or more values related to the at least one parameter of at least partially constructing or at least partially reconstructing the at least one biological tissue by administering one or more frozen particle compositions (or frozen piercing implements) to the at least one substrate. In one embodiment, 4130 the one or more values related to the at least one parameter of constructing or reconstructing the at least one biological tissue includes one or more predictive values.

In one embodiment, the at least one parameter 4030 of at least partially constructing or at least partially reconstructing the at least one biological tissue includes one or more of porosity of the at least one substrate, pore size of the at least one substrate, interconnectivity of the pores of the at least one substrate, transport properties of the at least one substrate, cell-tissue formation of the at least one substrate, mechanical strength of the at least one substrate, ability for attachment or distribution of the at least one agent included in the one or more frozen particle compositions (or frozen piercing implements) to the at least one substrate, ability for attachment or distribution of one or more cells or tissues to the at least one substrate, facilitation of at least one nutrient, or tissue formation or tissue growth associated with the at least one substrate.

In one embodiment, the at least one parameter 4040 of at least partially constructing or at least partially reconstructing the at least one biological tissue by administering one or more frozen particle compositions (or frozen piercing implements) includes one or more of: design of plot or model for administration of one or more frozen particle compositions(or frozen piercing implements), constitution of the one or more frozen particle compositions (or frozen piercing implements), formulation of the one or more frozen particle compositions (or frozen piercing implements), size of the one or more frozen particle compositions (or frozen piercing implements), shape of the one or more frozen particle compositions (or frozen piercing implements), angle of administration of the one or more frozen particle compositions (or frozen piercing implements), velocity of administration of the one or more frozen particle compositions (or frozen piercing implements), quantity of frozen particle compositions (or frozen piercing implements) administered, rate of administration of more than one frozen particle composition (or frozen piercing implement), spatial location for administration of one or more frozen particle compositions (or frozen piercing implements), temporal location for administration of one or more frozen particle compositions (or frozen piercing implements), method of administration of one or more frozen particle compositions (or frozen piercing implements), timing of administration of one or more frozen particle compositions (or frozen piercing implements), modulation of administration of one or more frozen particle compositions (or frozen piercing implements), deposition of one or more frozen particle compositions (or frozen piercing implements), or rate of deposition of at least one agent.

In one embodiment, the at least one parameter 4110 of at least partially constructing or at least partially reconstructing the at least one biological tissue by administering one or more frozen particle compositions (or frozen piercing implements) includes at least one parameter relating to at least partially ablating or at least partially abrading one or more surfaces of the at least one biological tissue with the one or more frozen particle compositions (or frozen piercing implements).

In one embodiment, the at least one parameter 4120 of at least partially constructing or at least partially reconstructing the at least one biological tissue by administering one or more frozen particle compositions (or frozen piercing implements) includes at least one parameter relating to administering at least one of a therapeutic agent, adhesive agent, biological remodeling agent, reinforcement agent, abrasive, or explosive material with the one or more frozen particle compositions (or frozen piercing implements).

In one embodiment, the spatial location 4140 for administration of one or more frozen particle compositions (or frozen piercing implements)includes one or more of x, y, or z coordinates. In one embodiment, the processing results 4150 includes comparing at least one value related to the first input associated with the at least one characteristic of at least one biological tissue to be at least partially constructed or at least partially reconstructed with at least one value related to at least one image of a target biological tissue. In one embodiment 4160, the image of a target biological tissue includes an image of a similar biological tissue, or an image of a dissimilar biological tissue.

Figure 42:
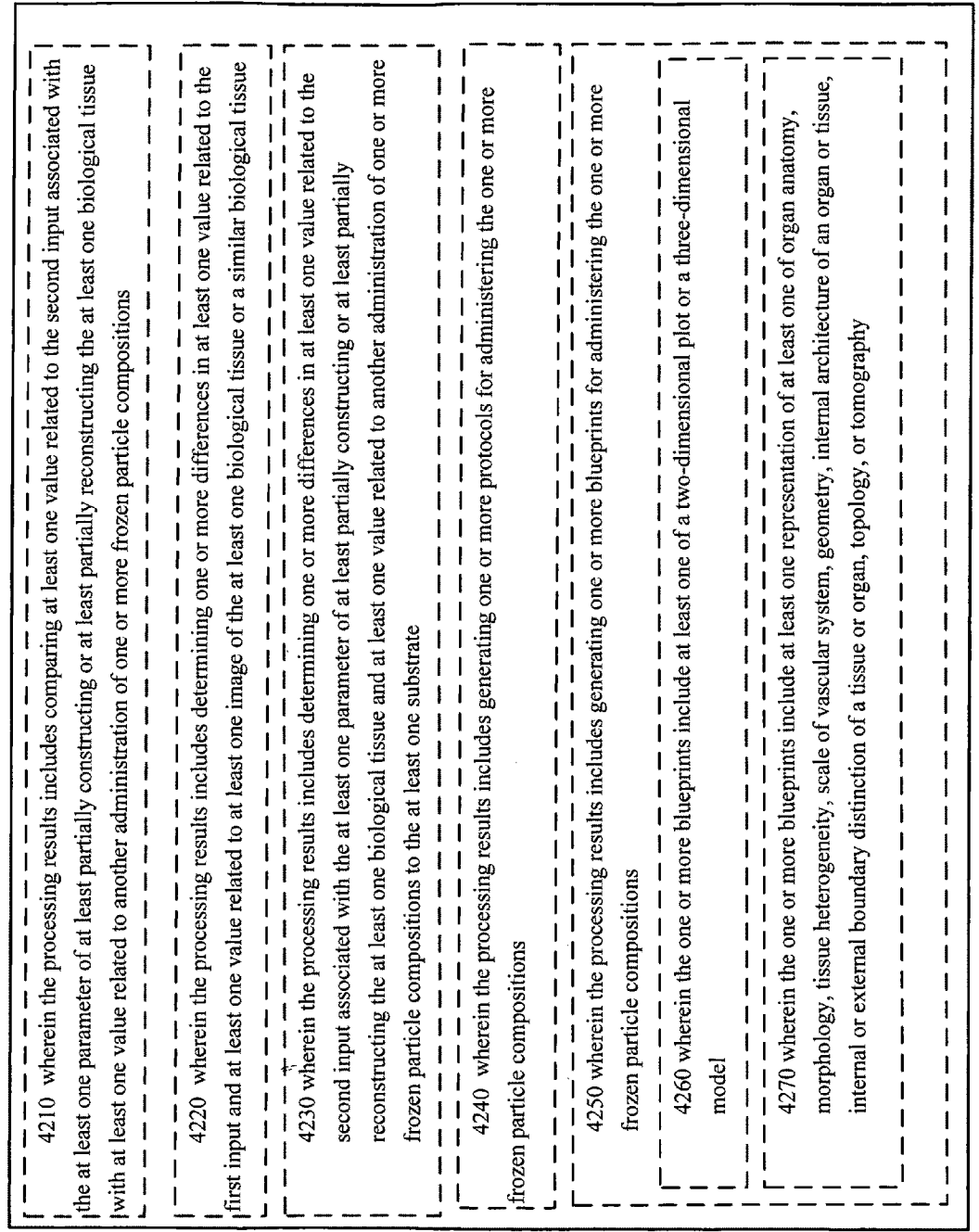
FIG. 42 illustrates a partial view of FIG. 37 in which embodiments may be implemented.

As indicated in FIG. 42, the processing results 4210 includes comparing at least one value related to the second input associated with the at least one parameter of at least partially constructing or at least partially reconstructing the at least one biological tissue with at least one value related to another administration of one or more frozen particle compositions (or frozen piercing implements). In one embodiment 4220, the processing results includes determining one or more differences in at least one value related to the first input and at least one value related to at least one image of the at least one biological tissue or a similar biological tissue. In one embodiment 4230, the processing results includes determining one or more differences in at least one value related to the second input associated with the at least one parameter of at least partially constructing or at least partially reconstructing the at least one biological tissue and at least one value related to another administration of one or more frozen particle compositions (or frozen piercing implements) to the at least one substrate.

In one embodiment 4240, the processing results includes generating one or more protocols for administering the one or more frozen particle compositions (or frozen piercing implements). In one embodiment 4250, the processing results includes generating one or more blueprints for administering the one or more frozen particle compositions (or frozen piercing implements). In one embodiment 4260, the one or more blueprints include at least one of a two-dimensional plot or a three-dimensional model. In one embodiment 4270, the one or more blueprints include at least one representation of at least one of organ anatomy, morphology, tissue heterogeneity, scale of vascular system, geometry, internal architecture of an organ or tissue, internal or external boundary distinction of a tissue or organ, topology, or tomography.

As indicated in FIG. 43, the processing results 4310 includes: comparing one or more values related to the one or more characteristics of the at least one biological tissue that are determined at two or more different times to obtain one or more characteristic comparisons; comparing one or more values related to the at least one parameter of at least partially constructing or at least partially reconstructing the at least one biological tissue at two or more different times to obtain one or more parameter comparisons; comparing the one or more characteristic comparisons with the one or more parameter comparisons to obtain one or more characteristic-characteristic/parameter-parameter comparisons; and comparing the one or more characteristic-characteristic/parameter-parameter comparisons to one or more substantially similar results obtained for one or more other at least partially constructed or at least partially reconstructed biological tissues. In one embodiment 4320, the administering one or more frozen particle compositions (or frozen piercing implements) includes depositing the at least one agent on the at least one substrate.

As indicated in FIG. 44, the method further comprises 4410 displaying results of the processing. In one embodiment 4420, the displaying results of the processing includes displaying the results on one or more active displays. In one embodiment 4430, the displaying results of the processing includes displaying the results on one or more passive displays. In one embodiment 4440, the displaying results of the processing includes displaying the results of the processing in at least one of numeric format, graphical format, or audio format.

In one embodiment 4450, the displaying results of the processing includes displaying a comparison of at least one biological tissue that has been at least partially constructed or at least partially reconstructed. In one embodiment 4460, the displaying results of the processing includes displaying a comparison of at least one subject with one or more other subjects. In one embodiment 4470, the displaying results of the processing includes displaying one or more differences in the comparison of at least one value related to the first input and at least one value related to at least one image of a biological tissue. In one embodiment 4480, the displaying results of the processing includes displaying one or more differences in the comparison of at least one value related to the second input and at least one value related to another administration of one or more frozen particle compositions (or frozen piercing implements).

Figure 45:
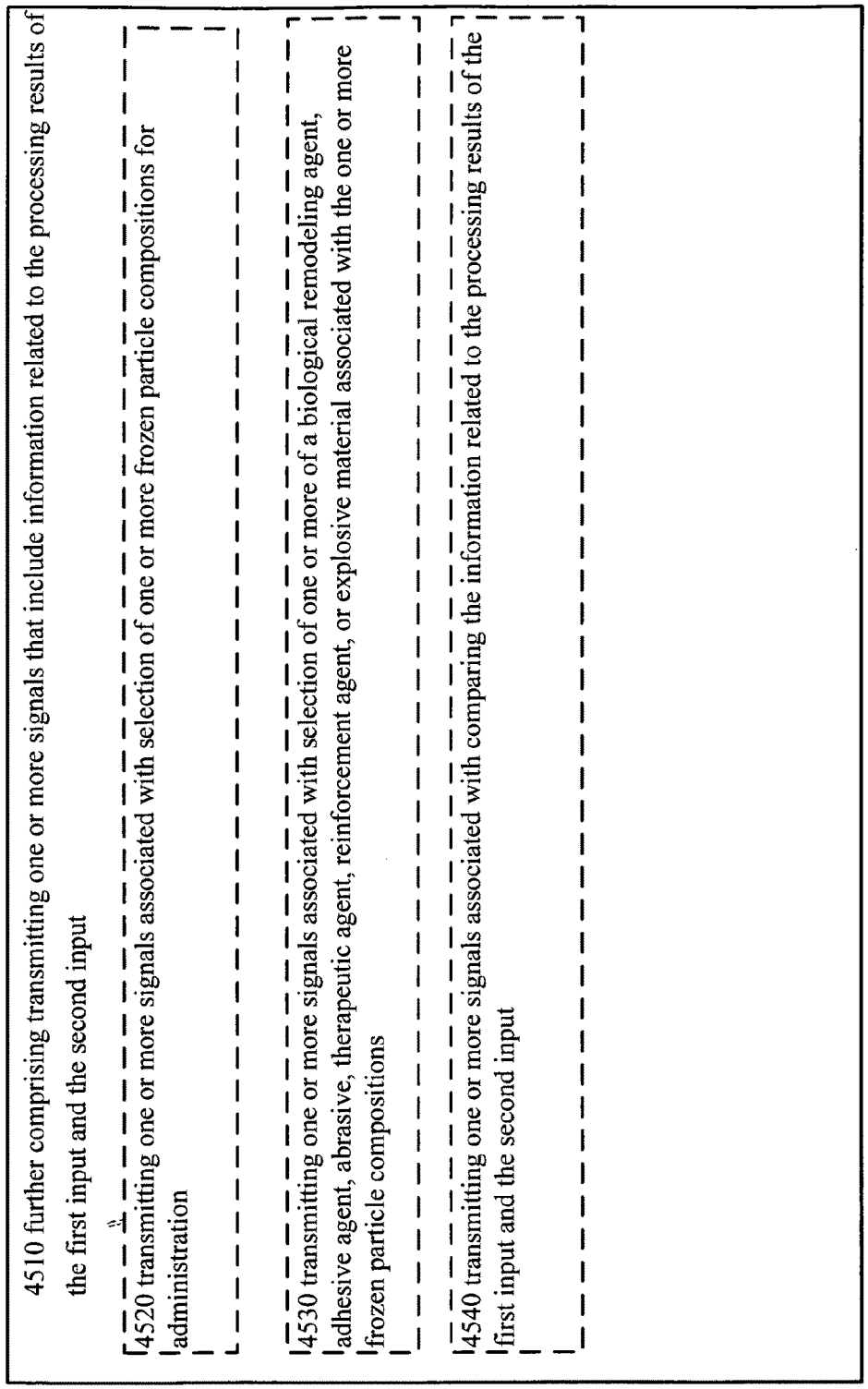
FIG. 45 illustrates a partial view of FIG. 37 in which embodiments may be implemented.

As indicated in FIG. 45, the method further comprises transmitting 4510 one or more signals that include information related to the processing results of the first input and the second input. In one embodiment 4520, the transmitting one or more signals includes transmitting one or more signals associated with selection of one or more frozen particle compositions (or frozen piercing implements) for administration. In one embodiment 4530, the transmitting one or more signals includes transmitting one or more signals associated with selection of one or more of a biological remodeling agent, adhesive agent, abrasive, therapeutic agent, reinforcement agent, or explosive material associated with the one or more frozen particle compositions (or frozen piercing implements). In one embodiment 4540, the transmitting one or more signals includes transmitting one or more signals associated with comparing the information related to the processing results of the first input and the second input.

As indicated in FIG. 46, the one or more frozen particle compositions (or frozen piercing implements) 4610 include one or more frozen particles including at least one of hydrogen oxide, nitrogen, oxygen, air, helium, neon, argon, xenon, chlorine, bromine, carbon dioxide, acetone, ethyl acetate, dimethyl sulfoxide, dimethyl formamide, dioxane, tetrahydrofuran, acetonitrile, acetic acid, n-butanol, isopropanol, n-propanol, hexamethylphosphorotriamide, perfluorohydrocarbon, methanol, ethanol, tert-butyl alcohol, formic acid, hydrogen fluoride, ammonia, benzene, carbon tetrachloride, hexane, dichloromethane, methylene chloride, carboxylic acid, saline, standard saline citrate, methane, toluene, chloroform, polyethylene glycol, acetic acid, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, methane, or diethyl ether.

In one embodiment 4620, the at least one agent includes one or more of an adhesive agent, therapeutic agent, reinforcement agent, abrasive, explosive material, or biological remodeling agent. In one embodiment 4630, at least one of the adhesive agent, therapeutic agent, reinforcement agent, abrasive, explosive material, or biological remodeling agent is substantially in the form of at least one of an organic or inorganic small molecule, clathrate or caged compound, protocell, coacervate, microsphere, Janus particle, proteinoid, laminate, helical rod, liposome, macroscopic tube, niosome, sphingosome, toroid, vesicular tube, vesicle, small unilamellar vesicle, large unilamellar vesicle, large multilamellar vesicle, multivesicular vesicle, lipid layer, lipid bilayer, micelle, organelle, cell, membrane, nucleic acid, peptide, polypeptide, protein, oligosaccharide, polysaccharide, glycopeptide, glycolipid, sphingolipid, glycosphingolipid, glycoprotein, peptidoglycan, lipid, carbohydrate, metalloprotein, proteoglycan, chromosome, cell nucleus, acid, base, buffer, protic solvent, aprotic solvent, nitric oxide, nitric oxide synthase, nitrous oxide, amino acid, micelle, polymer, bone cement, copolymer, cell receptor, adhesion molecule, cytokine, chemokine, immunoglobulin, antibody, antigen, platelet, extracellular matrix, blood, plasma, cell ligand, zwitterionic material, cationic material, oligonucleotide, nanotube, or piloxymer.

As indicated in FIG. 47, the one or more explosive materials 4710 include at least one of a carbonate, carbon dioxide, nitroglycerine, acid, base, epoxy, acrylic polymer or copolymer, acrylamide polymer or copolymer, urethane, hypoxyapatite, or reactive metal. In one embodiment 4720, the at least one adhesive agent includes one or more of an acrylic polymer or copolymer, acrylamide polymer or copolymer polymer or copolymer, acrylamide polymer or copolymer, polyacrylic acid, epoxy, urethane, gum arabic, polyester, polyhydroxyalkanoate, poly(L-lactic acid), polyglycolide, polylactic acid, polyether, polyol, polyvinylpyrrolidone, pyroxylin, polymethylacrylate-isobutene-monoisopropylmaleate, siloxane polymer, polylactic-co-glycolic-acid, poly-3-hydroxybutyrate, poly-4-hydroxybutyrate, polyhydroxyvalerate, polydydroxyhexanoate, polydyroxyoctanoate, polycaprolactone, poly(e-caprolactone), sialyl Lewis$^x$, heme group, hemoglobin, healon, carboxymethylcellulose, hydroxyapatite, silicone, cadherin, integrin, hydroxyapatite, polyelectrolyte, maleic polyelectrolyte, cellulose, resilin, cyanoacrylate, isocyanate, 2-octyl cyanoacrylate, 2-butyl-n-cyanoacrylate, n-butyl-2-cyanoacrylate, butyl-2-cyanoacrylate, methyl 2-cyanoacrylate, polyisohexylcyanoacrylate, fibrin, thrombin, fibrinogen, hyaluronate, chitin, Factor XIII, Factor XII, silk, nylon, collagen, glycosaminoglycan, selectin, polyurethane, methacrylate, or polysulfide, polyanhydride, polydioxanone, poly-p-dioxanone, silicone, albumin, glutaraldehyde, polyethylene glycol, or gelatin.

In at least one embodiment 4730, the one or more reinforcement agents include one or more of polyaramid, vinylester matrix, metal, ceramic, cotton, hemp, fiberglass, cellulose, broad carbide, aromatic polyamide, nylon, silk, rayon, acetate, modacrylic, olefin, acrylic, polyester, aromatic polyester, poly-lactic acid, vinyon, saran, spandex, vinalon, aromatic nylon, vinylidene chloride, modal, polybenzimidazole, sulfur, lyocell, orlon, zylon, high-performance polyethylene, polypyridobenzimidazole, vectran, acrylonitrile rubber, glass, copper, iron, steel, sodium, potassium, calcium, zinc, manganese, carbon, magnesium, silicon, silica, frozen hydrogen oxide ice, plant matter, animal matter, or mineral matter.

As indicated in FIG. 48, the therapeutic agent 4810 includes at least one of an anti-tumor agent, antimicrobial agent, anti-viral agent, analgesic, antiseptic, anesthetic, diagnostic agent, anti-inflammatory agent, vaccine, cell growth inhibitor, cell growth promoter, immunogen, antigen, radioactive agent, apoptosis promoting factor, enzymatic agent, angiogenic factor, anti-angiogenic factor, hormone, vitamin, mineral, nutraceutical, cytokine, chemokine, probiotic, coagulant, anti-coagulant, phage, prodrug, prebiotic, blood sugar stabilizer, smooth muscle cell activator, epinephrine, adrenaline, neurotoxin, neuro-muscular toxin, Botulinum toxin type A, microbial cell or component thereof, or virus or component thereof.

In one embodiment 4820 the at least one biological remodeling agent includes one or more of a blood cell, chondrocyte, endothelial cell, hepatocyte, keratinocyte, myocyte, osteoblast, osteoclast, osteocyte, mesenchymal cell, stem cell, progenitor cell, or fibroblast. In one embodiment, 4830, the at least one biological remodeling agent includes one or more of calcium phosphate, albumin, cytokine, pegylated cytokine, bone, cartilage, globulin, fibrin, thrombin, glutaraldehyde-crosslinked pericardium, hide powder, hyaluronic acid, hydroxylapatite, keratin, ligament, nitinol, nucleic acid polymers, polyethylene, polyethylene glycol, polyethylene glycol diacrylate, polyethylene terephthalate fiber, polyglycol, polylactate, polytetrafluoroethylene, polylactic acid, polyglycolic acid, polycaprolactone, PURAMATRIX™ self-assembly peptide hydrogel fibers, linear aliphatic polyester, tendon, fibrinogen, hyaluronate, chitin, chitosan, methylcellulose, alginate, hyaluronic acid, agarose, cellulose, polyaldehyde gluronate, Factor XIII, Factor XII, silk, nylon, collagen, silicone, polyurethane, ceramic powder, elastin, pectin, wax, glycosaminoglycan, poly($\alpha$-hydroxyacid), selectin, glutaraldehyde, hydrophobic non-glycosylated protein, hydrogel, peptide hydrogel, or gelatin. In one embodiment 4840, the at least one biological remodeling agent includes one or more of Type I collagen, Type II collagen, Type III collagen, Type VII collagen, Type X collagen, elastin fibers, or soluble elastin. In one embodiment 4850, the at least one biological remodeling agent is included as part of a carrier that assists in synthesis or activation of the at least one biological remodeling agent.

As indicated in FIGS. 49-51, a method 4900 comprises accepting input 4910 associated with at least one parameter of at least partially constructing or at least partially reconstructing at least one biological tissue by administering one or more frozen particle compositions (or frozen piercing implements); administering 4920 one or more frozen particle compositions (or frozen piercing implements) including at least one agent; wherein 4930 the at least one agent includes one or more of a biological remodeling agent, therapeutic agent, reinforcement agent, explosive material, abrasive, or adhesive agent; evaluating 4940 the at least one biological tissue for one or more indicators related to deposition of at least one agent, tissue formation, or tissue growth; and transmitting 5110 one or more signals that include information related to the accepting input and information related to the evaluating the at least one biological tissue.

In one embodiment 4950, the evaluating at least one biological tissue for one or more indicators includes evaluating at least one of an assay, image, or gross assessment of the at least one biological tissue prior to, during, or subsequent to at least one administration of the one or more frozen particle compositions (or frozen piercing implements). In one embodiment 4960, the assay includes at least one technique that includes spectroscopy, microscopy, electrochemical detection, polynucleotide detection, histological examination, biopsy analysis, fluorescence resonance energy transfer, electron transfer, enzyme assay, electrical conductivity, isoelectric focusing, chromatography, immunoprecipitation, immunoseparation, aptamer binding, filtration, electrophoresis, immunoassay, or radioactive assay.

In one embodiment 5020, the image includes at least one image acquired by one or more of laser, holography, x-ray crystallography, optical coherence tomography, computer-assisted tomography scan, computed tomography, magnetic resonance imaging, positron-emission tomography scan, ultrasound, x-ray, electrical-impedance monitoring, microscopy, spectrometry, flow cytommetry, radioisotope imaging, thermal imaging, multiphoton calcium-imaging, photography, or in silico generation. In one embodiment 5030, wherein the one or more indicators of tissue formation or growth include at least one of cell migration, cell attachment, cell retention, cell differentiation, cell proliferation, apoptosis, diffusion of materials, angiogenesis, nucleic acid expression, protein translation, protein modification, carbohydrate production, carbohydrate secretion, fat production, fat secretion, or protein secretion.

In one embodiment 5040, the input associated with at least one parameter of at least partially constructing or at least partially reconstructing the at least one biological tissue by administering one or more frozen particle compositions (or frozen piercing implements) includes one or more of: constitution of the one or more frozen particle compositions (or frozen piercing implements), formulation of the one or more frozen particle compositions (or frozen piercing implements), size of the one or more frozen particle compositions (or frozen piercing implements), shape of the one or more frozen particle compositions (or frozen piercing implements), angle of administration of the one or more frozen particle compositions (or frozen piercing implements), velocity of administration of the one or more frozen particle compositions (or frozen piercing implements), quantity of frozen particle compositions (or frozen piercing implements) administered, rate of administration of more than one frozen particle composition (or frozen piercing implement), spatial location for administration of one or more frozen particle compositions (or frozen piercing implements), temporal location for administration of one or more frozen particle compositions (or frozen piercing implements), method of administration of one or more frozen particle compositions (or frozen piercing implements), timing of administration of one or more frozen particle compositions (or frozen piercing implements), modulation of administration of one or more frozen particle compositions (or frozen piercing implements), deposition of one or more frozen particle compositions (or frozen piercing implements), or rate of deposition of at least one agent.

In one embodiment 5120, the transmitting one or more signals includes transmitting one or more signals associated with selection of one or more frozen particle compositions (or frozen piercing implements) for administration. In one embodiment 5130, the transmitting one or more signals includes transmitting one or more signals associated with selection of one or more of a biological remodeling agent, adhesive agent, abrasive, therapeutic agent, reinforcement agent, or explosive material associated with the one or more frozen particle compositions (or frozen piercing implements). In one embodiment 5140, the administering one or more frozen particle compositions (or frozen piercing implements) includes administering the one or more frozen particle compositions (or frozen piercing implements) to at least one substrate. In one embodiment 5150, the at least one substrate includes one or more of a cell, tissue, organ, structure, or device. In one embodiment 5160, the one or more frozen particle compositions (or frozen piercing implements) include one or more frozen particles including at least one of hydrogen oxide, nitrogen, oxygen, air, helium, neon, argon, xenon, chlorine, bromine, carbon dioxide, acetone, ethyl acetate, dimethyl sulfoxide, dimethyl formamide, dioxane, tetrahydrofuran, acetonitrile, acetic acid, n-butanol, isopropanol, n-propanol, hexamethylphosphorotriamide, perfluorohydrocarbon, methanol, ethanol, tert-butyl alcohol, formic acid, hydrogen fluoride, ammonia, benzene, carbon tetrachloride, hexane, dichloromethane, methylene chloride, carboxylic acid, saline, standard saline citrate, methane, toluene, chloroform, polyethylene glycol, acetic acid, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, methane, or diethyl ether.

As indicated in FIG. 52, the at least one agent 5210 includes one or more of an adhesive agent, therapeutic agent, reinforcement agent, abrasive, explosive material, or biological remodeling agent. In one embodiment 5220, the adhesive agent, therapeutic agent, reinforcement agent, abrasive, explosive material, or biological remodeling agent is substantially in the form of at least one of an organic or inorganic small molecule, clathrate or caged compound, protocell, coacervate, microsphere, Janus particle, proteinoid, laminate, helical rod, liposome, macroscopic tube, niosome, sphingosome, toroid, vesicular tube, vesicle, small unilamellar vesicle, large unilamellar vesicle, large multilamellar vesicle, multivesicular vesicle, lipid layer, lipid bilayer, micelle, organelle, cell, membrane, nucleic acid, peptide, polypeptide, protein, oligosaccharide, polysaccharide, glycopeptide, glycolipid, sphingolipid, glycosphingolipid, glycoprotein, peptidoglycan, lipid, carbohydrate, metalloprotein, proteoglycan, chromosome, cell nucleus, acid, base, buffer, protic solvent, aprotic solvent, nitric oxide, nitric oxide synthase, nitrous oxide, amino acid, micelle, polymer, bone cement, copolymer, cell receptor, adhesion molecule, cytokine, chemokine, immunoglobulin, antibody, antigen, platelet, extracellular matrix, blood, plasma, cell ligand, zwitterionic material, cationic material, oligonucleotide, nanotube, or piloxymer.

In one embodiment 5230, the one or more explosive materials include at least one of a carbonate, carbon dioxide, nitroglycerine, acid, base, epoxy, acrylic polymer or copolymer, acrylamide polymer or copolymer, urethane, hypoxyapatite, or reactive metal. In one embodiment 5240, the at least one adhesive agent includes one or more of an acrylic polymer or copolymer, acrylamide polymer or copolymer polymer or copolymer, acrylamide polymer or copolymer, polyacrylic acid, epoxy, urethane, gum arabic, polyester, polyhydroxyalkanoate, poly(L-lactic acid), polyglycolide, polylactic acid, polyether, polyol, polyvinylpyrrolidone, pyroxylin, polymethylacrylate-isobutene-monoisopropylmaleate, siloxane polymer, polylactic-co-glycolic-acid, poly-3-hydroxybutyrate, poly-4-hydroxybutyrate, polyhydroxyvalerate, polydydroxyhexanoate, polydyroxyoctanoate, polycaprolactone, poly(e-caprolactone), sialyl Lewis$^x$, heme group, hemoglobin, healon, carboxymethylcellulose, hydroxyapatite, silicone, cadherin, integrin, hydroxyapatite, polyelectrolyte, maleic polyelectrolyte, cellulose, resilin, cyanoacrylate, isocyanate, 2-octyl cyanoacrylate, 2-butyl-n-cyanoacrylate, n-butyl-2-cyanoacrylate, butyl-2-cyanoacrylate, methyl 2-cyanoacrylate, polyisohexylcyanoacrylate, fibrin, thrombin, fibrinogen, hyaluronate, chitin, Factor XIII, Factor XII, silk, nylon, collagen, glycosaminoglycan, selectin, polyurethane, methacrylate, or polysulfide, polyanhydride, polydioxanone, poly-p-dioxanone, silicone, albumin, glutaraldehyde, polyethylene glycol, or gelatin.

As indicated in FIG. 53, the one or more reinforcement agents 5310 include one or more of polyaramid, vinylester matrix, metal, ceramic, fiberglass, cellulose, broad carbide, aromatic polyamide, nylon, silk, rayon, acetate, modacrylic, olefin, acrylic, polyester, aromatic polyester, poly-lactic acid, vinyon, saran, spandex, vinalon, aromatic nylon, vinylidene chloride, modal, polybenzimidazole, sulfur, lyocell, orlon, zylon, high-performance polyethylene, polypyridobenzimidazole, vectran, acrylonitrile rubber, glass, copper, iron, steel, sodium, potassium, calcium, zinc, manganese, carbon, magnesium, silicon, silica, frozen hydrogen oxide ice, plant matter, animal matter, or mineral matter.

In one embodiment 5320, the therapeutic agent includes at least one of an anti-tumor agent, antimicrobial agent, antiviral agent, analgesic, antiseptic, anesthetic, diagnostic agent, anti-inflammatory agent, vaccine, cell growth inhibitor, cell growth promoter, immunogen, antigen, radioactive agent, apoptosis promoting factor, enzymatic agent, angiogenic factor, anti-angiogenic factor, hormone, vitamin, mineral, nutraceutical, cytokine, chemokine, probiotic, coagulant, anti-coagulant, phage, prodrug, prebiotic, blood sugar stabilizer, smooth muscle cell activator, epinephrine, adrenaline, neurotoxin, neuro-muscular toxin, Botulinum toxin type A, microbial cell or component thereof, or virus or component thereof. In one embodiment 5330, the at least one biological remodeling agent includes one or more of a blood cell, chondrocyte, endothelial cell, hepatocyte, keratinocyte, myocyte, osteoblast, osteoclast, osteocyte, mesenchymal cell, stem cell, progenitor cell, or fibroblast.

In one embodiment 5340, the at least one biological remodeling agent includes one or more of calcium phosphate, albumin, cytokine, pegylated cytokine, bone, cartilage, globulin, fibrin, thrombin, glutaraldehyde-crosslinked pericardium, hide powder, hyaluronic acid, hydroxylapatite, keratin, ligament, nitinol, nucleic acid polymers, polyethylene, polyethylene glycol, polyethylene glycol diacrylate, polyethylene terephthalate fiber, polyglycol, polylactate, polytetrafluoroethylene, polylactic acid, polyglycolic acid, polycaprolactone, PURAMATRIX™ self-assembly peptide hydrogel fibers, linear aliphatic polyester, tendon, fibrinogen, hyaluronate, chitin, chitosan, methylcellulose, alginate, hyaluronic acid, agarose, cellulose, polyaldehyde gluronate, Factor XIII, Factor XII, silk, nylon, collagen, silicone, polyurethane, ceramic powder, elastin, pectin, wax, glycosaminoglycan, poly($\alpha$-hydroxyacid), selectin, glutaraldehyde, hydrophobic non-glycosylated protein, hydrogel, peptide hydrogel, or gelatin.

In one embodiment 5350, the at least one biological remodeling agent includes one or more of Type I collagen, Type II collagen, Type III collagen, Type VII collagen, Type X collagen, elastin fibers, or soluble elastin.

As indicated in FIG. 54, a method 5400 comprises receiving 5410 one or more signals that include information related to accepting input associated with at least one parameter of at least partially constructing or at least partially reconstructing the at least one biological tissue by administering one or more frozen particle compositions (or frozen piercing implements); receiving 5420 one or more signals that include information related to evaluating the at least one biological tissue for one or more indicators of tissue formation or growth; and processing 5430 the information related to the input associated with at least one parameter of at least partially constructing or at least partially reconstructing the at least one biological tissue and the information related to the evaluating the at least one biological tissue. In one embodiment 5440, the evaluating at least one biological tissue for one or more indicators includes evaluating at least one of an assay, image, or gross assessment of the at least one biological tissue prior to, during, or subsequent to at least one administration of one or more frozen particle compositions (or frozen piercing implements).

In one embodiment 5450, the assay includes at least one technique that includes spectroscopy, microscopy, electrochemical detection, polynucleotide detection, histological examination, biopsy analysis, fluorescence resonance energy transfer, electron transfer, enzyme assay, electrical conductivity, isoelectric focusing, chromatography, immunoprecipitation, immunoseparation, aptamer binding, filtration, electrophoresis, immunoassay, or radioactive assay. In one embodiment 5460, the image includes at least one image acquired by one or more of optical coherence tomography, computer-assisted tomography scan, computed tomography, magnetic resonance imaging, positron-emission tomography scan, ultrasound, x-ray, x-ray crystallography, laser, holography, electrical-impedance monitoring, microscopy, spectrometry, flow cytommetry, radioisotope imaging, thermal imaging, multiphoton calcium-imaging, photography, or in silico generation.

As indicated in FIG. 55, the one or more indicators 5510 of tissue formation or growth include at least one of: cell migration, cell attachment, cell retention, cell differentiation, cell proliferation, apoptosis, diffusion of materials, angiogenesis, nucleic acid expression, protein translation, protein modification, carbohydrate production, carbohydrate secretion, fat production, fat secretion, or protein secretion.

In one embodiment 5520, the input associated with at least one parameter of at least partially constructing or at least partially reconstructing the at least one biological tissue includes one or more of: constitution of the one or more frozen particle compositions (or frozen piercing implements), formulation of the one or more frozen particle compositions (or frozen piercing implements), size of the one or more frozen particle compositions (or frozen piercing implements), shape of the one or more frozen particle compositions (or frozen piercing implements), angle of administration of the one or more frozen particle compositions (or frozen piercing implements), velocity of administration of the one or more frozen particle compositions (or frozen piercing implements), quantity of frozen particle compositions (or frozen piercing implements) administered, rate of administration of more than one frozen particle composition(or frozen piercing implement), spatial location for administration of one or more frozen particle compositions (or frozen piercing implements), temporal location for administration of one or more frozen particle compositions (or frozen piercing implements), method of administration of one or more frozen particle compositions (or frozen piercing implements), timing of administration of one or more frozen particle compositions (or frozen piercing implements), modulation of administration of one or more frozen particle compositions (or frozen piercing implements), deposition of one or more frozen particle compositions (or frozen piercing implements), or rate of deposition of at least one agent.

In one embodiment 5530, the receiving one or more signals includes receiving one or more signals associated with selection of one or more frozen particle compositions (or frozen piercing implements) for administration. In one embodiment 5540, the receiving one or more signals includes receiving one or more signals associated with the selection of at least one of a biological remodeling agent, adhesive agent, abrasive, therapeutic agent, reinforcement agent, or explosive material associated with the one or more frozen particle compositions (or frozen piercing implements).

As indicated in FIG. 56, in one embodiment 5610, the administering one or more frozen particle compositions (or frozen piercing implements) includes administering the one or more frozen particle compositions (or frozen piercing implements) to at least one substrate. In one embodiment 5620, the at least one substrate includes one or more of a cell, tissue, organ, structure, or device. In one embodiment 5630, the one or more frozen particle compositions (or frozen piercing implements) include one or more frozen particles including at least one of hydrogen oxide, nitrogen, oxygen, air, helium, neon, argon, xenon, chlorine, bromine, carbon dioxide, acetone, ethyl acetate, dimethyl sulfoxide, dimethyl formamide, dioxane, tetrahydrofuran, acetonitrile, acetic acid, n-butanol, isopropanol, n-propanol, hexamethylphosphorotriamide, perfluorohydrocarbon, methanol, ethanol, tert-butyl alcohol, formic acid, hydrogen fluoride, ammonia, benzene, carbon tetrachloride, hexane, dichloromethane, methylene chloride, carboxylic acid, saline, standard saline citrate, methane, toluene, chloroform, polyethylene glycol, acetic acid, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, methane, or diethyl ether.

In one embodiment 5640, the at least one agent includes one or more of an adhesive agent, therapeutic agent, reinforcement agent, abrasive, explosive material, or biological remodeling agent. In one embodiment 5650, the adhesive agent, therapeutic agent, reinforcement agent, abrasive, explosive material, or biological remodeling agent is substantially in the form of at least one of an organic or inorganic small molecule, clathrate or caged compound, protocell, coacervate, microsphere, Janus particle, proteinoid, laminate, helical rod, liposome, macroscopic tube, niosome, sphingosome, toroid, vesicular tube, vesicle, small unilamellar vesicle, large unilamellar vesicle, large multilamellar vesicle, multivesicular vesicle, lipid layer, lipid bilayer, micelle, organelle, cell, membrane, nucleic acid, peptide, polypeptide, protein, oligosaccharide, polysaccharide, glycopeptide, glycolipid, sphingolipid, glycosphingolipid, glycoprotein, peptidoglycan, lipid, carbohydrate, metalloprotein, proteoglycan, chromosome, cell nucleus, acid, base, buffer, protic solvent, aprotic solvent, nitric oxide, nitric oxide synthase, nitrous oxide, amino acid, micelle, polymer, bone cement, copolymer, cell receptor, adhesion molecule, cytokine, chemokine, immunoglobulin, antibody, antigen, platelet, extracellular matrix, blood, plasma, cell ligand, zwitterionic material, cationic material, oligonucleotide, nanotube, or piloxymer.

As indicated in FIG. 57, the one or more explosive materials 5710 include at least one of a carbonate, carbon dioxide, nitroglycerine, acid, base, epoxy, acrylic polymer or copolymer, acrylamide polymer or copolymer, urethane, hypoxyapatite, or reactive metal. In one embodiment 5720, the at least one adhesive agent includes one or more of an acrylic polymer or copolymer, acrylamide polymer or copolymer polymer or copolymer, acrylamide polymer or copolymer, polyacrylic acid, epoxy, urethane, gum arabic, polyester, polyhydroxyalkanoate, poly(L-lactic acid), polyglycolide, polylactic acid, polyether, polyol, polyvinylpyrrolidone, pyroxylin, polymethylacrylate-isobutene-monoisopropylmaleate, siloxane polymer, polylactic-co-glycolic-acid, poly-3-hydroxybutyrate, poly-4-hydroxybutyrate, polyhydroxyvalerate, polydroxyhexanoate, polydroxyoctanoate, polycaprolactone, poly(e-caprolactone), sialyl Lewis$^x$, heme group, hemoglobin, healon, carboxymethylcellulose, hydroxyapatite, silicone, cadherin, integrin, hydroxyapatite, polyelectrolyte, maleic polyelectrolyte, cellulose, resilin, cyanoacrylate, isocyanate, 2-octyl cyanoacrylate, 2-butyl-n-cyanoacrylate, n-butyl-2-cyanoacrylate, butyl-2-cyanoacrylate, methyl 2-cyanoacrylate, polyisohexylcyanoacrylate, fibrin, thrombin, fibrinogen, hyaluronate, chitin, Factor XIII, Factor XII, silk, nylon, collagen, glycosaminoglycan, selectin, polyurethane, methacrylate, or polysulfide, polyanhydride, polydioxanone, poly-p-dioxanone, silicone, albumin, glutaraldehyde, polyethylene glycol, or gelatin. In one embodiment 5730, the one or more reinforcement agents include one or more of polyaramid, vinylester matrix, metal, ceramic, fiberglass, cellulose, broad carbide, aromatic polyimide, nylon, silk, rayon, acetate, modacrylic, olefin, acrylic, polyester, aromatic polyester, poly-lactic acid, vinyon, saran, spandex, vinalon, aromatic nylon, vinylidene chloride, modal, polybenzimidazole, sulfur, lyocell, orlon, zylon, high-performance polyethylene, polypyridobenzimidazole, vectran, acrylonitrile rubber, glass, copper, iron, steel, sodium, potassium, calcium, zinc, manganese, carbon, magnesium, silicon, silica, frozen hydrogen oxide ice, plant matter, animal matter, or mineral matter.

In one embodiment 5740, the therapeutic agent includes at least one of an anti-tumor agent, antimicrobial agent, antiviral agent, analgesic, antiseptic, anesthetic, diagnostic agent, anti-inflammatory agent, vaccine, cell growth inhibitor, cell growth promoter, immunogen, antigen, radioactive agent, apoptosis promoting factor, enzymatic agent, angiogenic factor, anti-angiogenic factor, hormone, vitamin, mineral, nutraceutical, cytokine, chemokine, probiotic, coagulant, anti-coagulant, phage, prodrug, prebiotic, blood sugar stabilizer, smooth muscle cell activator, epinephrine, adrenaline, neurotoxin, neuro-muscular toxin, Botulinum toxin type A, microbial cell or component thereof, or virus or component thereof.

In one embodiment 5810, the at least one biological remodeling agent includes one or more of a blood cell, chondrocyte, endothelial cell, hepatocyte, keratinocyte, myocyte, osteoblast, osteoclast, osteocyte, mesenchymal cell, stem cell, progenitor cell, or fibroblast. In one embodiment 5820, the at least one biological remodeling agent includes one or more of calcium phosphate, albumin, cytokine, pegylated cytokine, bone, cartilage, globulin, fibrin, thrombin, glutaraldehyde-crosslinked pericardium, hide powder, hyaluronic acid, hydroxylapatite, keratin, ligament, nitinol, nucleic acid polymers, polyethylene, polyethylene glycol, polyethylene glycol diacrylate, polyethylene terephthalate fiber, polyglycol, polylactate, polytetrafluoroethylene, polylactic acid, polyglycolic acid, polycaprolactone, PURAMATRIX™ self-assembly peptide hydrogel fibers, linear aliphatic polyester, tendon, fibrinogen, hyaluronate, chitin, chitosan, methylcellulose, alginate, hyaluronic acid, agarose, cellulose, polyaldehyde gluronate, Factor XIII, Factor XII, silk, nylon, collagen, silicone, polyurethane, ceramic powder, elastin, pectin, wax, glycosaminoglycan, poly($\alpha$-hydroxyacid), selectin, glutaraldehyde, hydrophobic non-glycosylated protein, hydrogel, peptide hydrogel, or gelatin. In one embodiment 5830, the at least one biological remodeling agent includes one or more of Type I collagen, Type II collagen, Type III collagen, Type VII collagen, Type X collagen, elastin fibers, or soluble elastin.

In one embodiment 5840, the at least one biological remodeling agent is included as part of a carrier that assists in synthesis or activation of the at least one biological remodeling agent.

As indicated in FIG. 59, a method 5900 comprises comparing information 5910 regarding at least one parameter for at least partially constructing or at least partially reconstructing at least one biological tissue of a subject by administering one or more frozen particle compositions (or frozen piercing implements) to the at least one subject and information regarding at least one clinical outcome following receipt by the at least one subject of one or more frozen particle compositions (or frozen piercing implements); and providing output information 5920. In one embodiment 5930, the output information is based on the comparison. In one embodiment 5940, the method further comprises determining at least one statistical correlation. In one embodiment 5950, the method further comprises counting the occurrence of at least one clinical outcome. In one embodiment 5960, the information regarding at least one parameter of at least partially constructing or at least partially reconstructing at least one biological tissue of a subject includes information regarding quantity of cells or tissue at least partially constructed or at least partially reconstructed. In one embodiment 5970, the information regarding at least one parameter of at least partially constructing or at least partially reconstructing at least one biological tissue of a subject includes information regarding at least one cellular or tissue source. In one embodiment 5980, the information regarding at least one parameter of at least partially constructing or at least partially reconstructing at least one biological tissue of a subject includes information regarding at least one abnormal cellular or tissue source. In one embodiment 5990, the information regarding at least one parameter of at least partially constructing or at least partially reconstructing at least one biological tissue of a subject includes information regarding at least one type of cell or tissue.

As indicated in FIG. 60, the at least one agent 6010 includes at least one agent including at least one adhesive agent, abrasive, reinforcement agent, therapeutic agent, biological remodeling agent, or explosive material. In one embodiment 6020, the information regarding at least one parameter of at least partially constructing or at least partially reconstructing at least one biological tissue of a subject includes information regarding at least one dimension of at least one agent deposited. In one embodiment 6030, the information regarding at least one parameter of at least partially constructing or at least partially reconstructing at least one biological tissue of at least one subject includes information regarding at least one dimension of at least one depth, width, or breadth of cellular, tissue, or other material removal or destruction. In one embodiment 6040, the information regarding at least one clinical outcome following receipt by the at least one subject of one or more frozen particle compositions (or frozen piercing implements) includes information regarding two or more subjects with one or more common attributes.

In one embodiment 6050, the one or more common attributes include one or more of genetic attributes, mental attributes, proteomic attributes, phenotypic attributes, or psychological attributes. In one embodiment 6060, the one or more common attributes include one or more of height, weight, medical diagnosis, familial background, results on one or more medical tests, ethnic background, body mass index, age, presence or absence of at least one disease or condition, species, ethnicity, race, allergies, gender, thickness of tissue, blood vessel condition, hair or fur condition, skin condition, tissue condition, muscle condition, organ condition, nerve condition, brain condition, presence or absence of at least one biological, chemical, or therapeutic agent in the subject, pregnancy status, lactation status, genetic profile, proteomic profile, partial or whole genetic sequence, partial or whole proteomic sequence, medical condition, medical history, or blood condition.

As indicated in FIG. 61, the output information 6110 includes at least one of a response signal, comparison code, comparison plot, diagnostic code, treatment code, test code, code indicative of at least one treatment received, code indicative of at least one prescribed treatment step, code indicative of at least one vaccination administered, code indicative of at least one therapeutic agent administered, code indicative of at least one diagnostic agent administered, code indicative of at least one interaction of an administered agent and at least one biological or chemical agent in the subject; a code indicative of at least one dispertion or location of at least one administered agent; code indicative of at least one detection material administered; code indicative of the depth of penetration of an administered agent, code indicative of the depth of deposition of an administered agent, or a code indicative of the condition of at least one location of an administered frozen particle composition (or frozen piercing implement).

In one embodiment 6120, receipt by the at least one subject of one or more frozen particle compositions (or frozen piercing implements) is pursuant to at least one clinical trial. In one embodiment 6130, the method further comprises determining at least one correlation before the administration of the one or more frozen particle compositions (or frozen piercing implements) to the at least one subject.

In one embodiment 6140, the method further comprises creating at least one inclusion criterion and at least one exclusion criterion for a clinical trial involving the one or more frozen particle compositions (or frozen piercing implements). In one embodiment 6150, the method further comprises suggesting the inclusion of one or more of the at least one subject in at least one clinical trial. In one embodiment 6160, the method further comprises suggesting the exclusion of one or more of the at least one subject in at least one clinical trial.

As indicated in FIG. 62, the method further comprising using one or more of the at least one correlation 6210 to predict at least one clinical outcome regarding at least one second subject. In one embodiment 6220, the at least one second subject has not received the one or more frozen particle compositions (or frozen piercing implements). In one embodiment 6230, the method further comprises predicting at least one clinical outcome involving the at least one second subject, wherein the at least one second subject is a plurality of people; and segregating subject identifiers associated with the plurality of people in reference to the predicted at least one clinical outcome. In one embodiment 6240, the method further comprises determining the eligibility of the at least one second subject for the at least one clinical trial.

In one embodiment 6250, the one or more frozen particle compositions (or frozen piercing implements) include one or more frozen particles including at least one of hydrogen oxide, nitrogen, oxygen, air, helium, neon, argon, xenon, chlorine, bromine, carbon dioxide, acetone, ethyl acetate, dimethyl sulfoxide, dimethyl formamide, dioxane, tetrahydrofuran, acetonitrile, acetic acid, n-butanol, isopropanol, n-propanol, hexamethylphosphorotriamide, perfluorohydrocarbon, methanol, ethanol, tert-butyl alcohol, formic acid, hydrogen fluoride, ammonia, benzene, carbon tetrachloride, hexane, dichloromethane, methylene chloride, carboxylic acid, saline, standard saline citrate, methane, toluene, chloroform, polyethylene glycol, acetic acid, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, methane, or diethyl ether.

As indicated in FIG. 63, the at least one agent 6310 includes one or more of an adhesive agent, therapeutic agent, reinforcement agent, abrasive, explosive material, or biological remodeling agent. In one embodiment 6320, the adhesive agent, therapeutic agent, reinforcement agent, abrasive, explosive material, or biological remodeling agent is substantially in the form of at least one of an organic or inorganic small molecule, clathrate or caged compound, protocell, coacervate, microsphere, Janus particle, proteinoid, laminate, helical rod, liposome, macroscopic tube, niosome, sphingosome, toroid, vesicular tube, vesicle, small unilamellar vesicle, large unilamellar vesicle, large multilamellar vesicle, multivesicular vesicle, lipid layer, lipid bilayer, micelle, organelle, cell, membrane, nucleic acid, peptide, polypeptide, protein, oligosaccharide, polysaccharide, glycopeptide, glycolipid, sphingolipid, glycosphingolipid, glycoprotein, peptidoglycan, lipid, carbohydrate, metalloprotein, proteoglycan, chromosome, cell nucleus, acid, base, buffer, protic solvent, aprotic solvent, nitric oxide, nitric oxide synthase, nitrous oxide, amino acid, micelle, polymer, bone cement, copolymer, cell receptor, adhesion molecule, cytokine, chemokine, immunoglobulin, antibody, antigen, platelet, extracellular matrix, blood, plasma, cell ligand, zwitterionic material, cationic material, oligonucleotide, nanotube, or piloxymer. In one embodiment 6330, the one or more explosive materials include at least one of a carbonate, carbon dioxide, nitroglycerine, acid, base, epoxy, acrylic polymer or copolymer, acrylamide polymer or copolymer, urethane, hypoxyapatite, or reactive metal. In one embodiment 6340, the at least one adhesive agent includes one or more of an acrylic polymer or copolymer, acrylamide polymer or copolymer polymer or copolymer, acrylamide polymer or copolymer, polyacrylic acid, epoxy, urethane, gum arabic, polyester, polyhydroxyalkanoate, poly(L-lactic acid), polyglycolide, polylactic acid, polyether, polyol, polyvinylpyrrolidone, pyroxylin, polymethylacrylate-isobutene-monoisopropylmaleate, siloxane polymer, polylactic-co-glycolic-acid, poly-3-hydroxybutyrate, poly-4-hydroxybutyrate, polyhydroxyvalerate, polydydroxyhexanoate, polydyroxyoctanoate, polycaprolactone, poly(e-caprolactone), sialyl Lewis$^x$, heme group, hemoglobin, healon, carboxymethylcellulose, hydroxyapatite, silicone, cadherin, integrin, hydroxyapatite, polyelectrolyte, maleic polyelectrolyte, cellulose, resilin, cyanoacrylate, isocyanate, 2-octyl cyanoacrylate, 2-butyl-n-cyanoacrylate, n-butyl-2-cyanoacrylate, butyl-2-cyanoacrylate, methyl 2-cyanoacrylate, polyisohexylcyanoacrylate, fibrin, thrombin, fibrinogen, hyaluronate, chitin, Factor XIII, Factor XII, silk, nylon, collagen, glycosaminoglycan, selectin, polyurethane, methacrylate, or polysulfide, polyanhydride, polydioxanone, poly-p-dioxanone, silicone, albumin, glutaraldehyde, polyethylene glycol, or gelatin.

As indicated in FIG. 64, the one or more reinforcement agents 6410 include one or more of polyaramid, vinylester matrix, metal, ceramic, fiberglass, cellulose, broad carbide, aromatic polyamide, nylon, silk, rayon, acetate, modacrylic, olefin, acrylic, polyester, aromatic polyester, poly-lactic acid, vinyon, saran, spandex, vinalon, aromatic nylon, vinylidene chloride, modal, polybenzimidazole, sulfur, lyocell, orlon, zylon, high-performance polyethylene, polypyridobenzimidazole, vectran, acrylonitrile rubber, glass, copper, iron, steel, sodium, potassium, calcium, zinc, manganese, carbon, magnesium, silicon, silica, frozen hydrogen oxide ice, plant matter; animal matter, or mineral matter.

In one embodiment 6420, the therapeutic agent includes at least one of an anti-tumor agent, antimicrobial agent, antiviral agent, analgesic, antiseptic, anesthetic, diagnostic agent, anti-inflammatory agent, vaccine, cell growth inhibitor, cell growth promoter, immunogen, antigen, radioactive agent, apoptosis promoting factor, enzymatic agent, angiogenic factor, anti-angiogenic factor, hormone, vitamin, mineral, nutraceutical, cytokine, chemokine, probiotic, coagulant, anti-coagulant, phage, prodrug, prebiotic, blood sugar stabilizer, smooth muscle cell activator, epinephrine, adrenaline, neurotoxin, neuro-muscular toxin, Botulinum toxin type A, microbial cell or component thereof, or virus or component thereof. In one embodiment 6430, the at least one biological remodeling agent includes one or more of a blood cell, chondrocyte, endothelial cell, hepatocyte, keratinocyte, myocyte, osteoblast, osteoclast, osteocyte, mesenchymal cell, stem cell, progenitor cell, or fibroblast.

As indicated in FIG. 65, the at least one biological remodeling agent 6510 includes one or more of calcium phosphate, albumin, cytokine, pegylated cytokine, bone, cartilage, globulin, fibrin, thrombin, glutaraldehyde-crosslinked pericardium, hide powder, hyaluronic acid, hydroxylapatite, keratin, ligament, nitinol, nucleic acid polymers, polyethylene, polyethylene glycol, polyethylene glycol diacrylate, polyethylene terephthalate fiber, polyglycol, polylactate, polytetrafluoroethylene, polylactic acid, polyglycolic acid, polycaprolactone, PURAMATRIX™ self-assembly peptide hydrogel fibers, linear aliphatic polyester, tendon, fibrinogen, hyaluronate, chitin, chitosan, methylcellulose, alginate, hyaluronic acid, agarose, cellulose, polyaldehyde gluronate, Factor XIII, Factor XII, silk, nylon, collagen, silicone, polyurethane, ceramic powder, elastin, pectin, wax, glycosaminoglycan, poly($\alpha$-hydroxyacid), selectin, glutaraldehyde, hydrophobic non-glycosylated protein, hydrogel, peptide hydrogel, or gelatin. In one embodiment 6520, the at least one biological remodeling agent includes one or more of Type I collagen, Type II collagen, Type III collagen, Type VII collagen, Type X collagen, elastin fibers, or soluble elastin. In one embodiment 6530, the at least one biological remodeling agent is included as part of a carrier that assists in synthesis or activation of the at least one biological remodeling agent.

As indicated in FIG. 66, a method 6600 of predicting a clinical outcome of one or more frozen particle composition (or frozen piercing implement) treatments for at least one first subject, comprises determining 6610 a similarity or a dissimilarity in information regarding at least one parameter for at least partially constructing or at least partially reconstructing at least one biological tissue of at least one first subject by administering one or more frozen particle compositions (or frozen piercing implements) to the at least one first subject with information regarding at least one parameter of at least partially constructing or at least partially reconstructing at least one biological tissue of at least one second subject, wherein the at least one second subject 6620 attained a clinical outcome following receipt of one or more frozen particle compositions (or frozen piercing implements); and providing output information 6630.

In one embodiment 6640, providing output information is based on the determination. In one embodiment 6650, the information regarding at least one parameter of at least partially constructing or at least partially reconstructing at least one biological tissue of at least second subject includes information regarding quantity of cells or tissue at least partially constructed or at least partially reconstructed. In one embodiment 6660, the information regarding at least one parameter of at least partially constructing or at least partially reconstructing at least one biological tissue of at least one first subject includes information regarding at least one cellular or tissue source. In one embodiment 6670, the information regarding at least one parameter of at least partially constructing or at least partially reconstructing at least one biological tissue of at least one first subject includes information regarding at least one abnormal cellular or tissue source.

As indicated in FIG. 67, the information 6710 regarding at least one parameter of at least partially constructing or at least partially reconstructing at least one biological tissue of at least one first subject includes information regarding at least one type of cell or tissue. In one embodiment 6720, the information regarding at least one parameter of at least partially constructing or at least partially reconstructing at least one biological tissue of at least one second subject includes information regarding at least one type of cell or tissue. In one embodiment 6730, the at least one agent includes one or more of an adhesive agent, abrasive, reinforcement agent, therapeutic agent, biological remodeling agent, or explosive material. In one embodiment 6740, the information regarding at least one parameter of at least partially constructing or at least partially reconstructing at least one biological tissue of at least one first subject includes information regarding at least one dimension of at least one agent deposited.

In one embodiment 6750, the information regarding at least one parameter of at least partially constructing or at least partially reconstructing at least one biological tissue of at least one second subject includes information regarding at least one dimension of at least one agent deposited. In one embodiment 6760, the information regarding at least one parameter of at least partially constructing or at least partially reconstructing at least one biological tissue of at least one second subject includes information regarding at least one dimension of at least one depth, width, or breadt of cellular, tissue, or other material removal or destruction. In one embodiment 6770, the information regarding at least one parameter of at least partially constructing or at least partially reconstructing at least one biological tissue of at least one first subject includes information regarding at least one dimension of at least one depth, width, or breadth of cellular, tissue, or other material removal or destruction.

As indicated in FIG. 68, the information 6810 regarding at least one clinical outcome following receipt by the at least one second subject of one or more frozen particle compositions (or frozen piercing implements) includes information regarding two or more subjects with one or more common attributes. In one embodiment 6820, the one or more common attributes include one or more of genetic attributes, mental attributes, proteomic attributes, phenotypic attributes, or psychological attributes. In one embodiment 6830, the one or more common attributes include one or more of height, weight, medical diagnosis, familial background, results on one or more medical tests, ethnic background, body mass index, age, presence or absence of at least one disease or condition, species, ethnicity, race, allergies, gender, thickness of tissue, blood vessel condition, hair or fur condition, skin condition, tissue condition, muscle condition, organ condition, nerve condition, brain condition, presence or absence of at least one biological, chemical, or therapeutic agent in the subject, pregnancy status, lactation status, genetic profile, proteomic profile, partial or whole genetic sequence, partial or whole proteomic sequence, medical condition, medical history, or blood condition. In one embodiment 6840, the output information includes at least one of a response signal, comparison code, comparison plot, diagnostic code, treatment code, test code, code indicative of at least one treatment received, code indicative of at least one prescribed treatment step, code indicative of at least one vaccination administered, code indicative of at least one therapeutic agent administered, code indicative of at least one diagnostic agent administered, code indicative of at least one interaction of an administered agent and at least one biological or chemical agent in the subject; a code indicative of at least one dispersion or location of at least one administered agent; code indicative of at least one detection material administered; code indicative of the depth of penetration of an administered agent, code indicative of the depth of deposition of an administered agent, or a code indicative of the condition of at least one location of an administered frozen particle composition (or frozen piercing implement).

As indicated in FIG. 69, in one embodiment 6910, receipt by the at least one second subject of one or more frozen particle compositions (or frozen piercing implements) is pursuant to at least one clinical trial. In one embodiment 6920, the method further comprises determining at least one correlation before the administration of the one or more frozen particle compositions (or frozen piercing implements) to the at least one first subject. In one embodiment 6930, the method further comprises creating at least one inclusion criterion and at least one exclusion criterion for a clinical trial involving the one or more frozen particle compositions (or frozen piercing implements). In one embodiment 6940, the method further comprises suggesting the inclusion of one or more of the at least one first subject in at least one clinical trial. In one embodiment 6950, the method further comprises suggesting the exclusion of one or more of the at least one first subject in at least one clinical trial.

In one embodiment 6960, the method further comprises using one or more of the at least one correlation to predict at least one clinical outcome regarding at least one second subject. In one embodiment 6970, the at least one second subject has not received the one or more frozen particle compositions (or frozen piercing implements). In one embodiment 6980, the method further comprises predicting at least one clinical outcome involving the at least one second subject, wherein the at least one second subject is a plurality of people; and segregating subject identifiers associated with the plurality of people in reference to the predicted at least one clinical outcome.

As indicated in FIG. 70, in one embodiment 7010, the one or more frozen particle compositions (or frozen piercing implements) include one or more frozen particles including at least one of hydrogen oxide, nitrogen, oxygen, air, helium, neon, argon, xenon, chlorine, bromine, carbon dioxide, acetone, ethyl acetate, dimethyl sulfoxide, dimethyl formamide, dioxane, tetrahydrofuran, acetronitrile, acetic acid, n-butanol, isopropanol, n-propanol, hexamethylphosphorotriamide, perfluorohydrocarbon, methanol, ethanol, tert-butyl alcohol, formic acid, hydrogen fluoride, ammonia, benzene, carbon tetrachloride, hexane, dichloromethane, methylene chloride, carboxylic acid, saline, standard saline citrate, methane, toluene, chloroform, polyethylene glycol, acetic acid, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, or diethyl ether.

In one embodiment 7020, the one or more frozen particle compositions (or frozen piercing implements) include one or more of an adhesive agent, therapeutic agent, reinforcement agent, abrasive, explosive material, or biological remodeling agent. In one embodiment 7030, the adhesive agent, therapeutic agent, reinforcement agent, abrasive, explosive material, or biological remodeling agent is substantially in the form of at least one of an organic or inorganic small molecule, clathrate or caged compound, protocell, coacervate, microsphere, Janus particle, proteinoid, laminate, helical rod, liposome, macroscopic tube, niosome, sphingosome, toroid, vesicular tube, vesicle, small unilamellar vesicle, large unilamellar vesicle, large multilamellar vesicle, multivesicular vesicle, lipid layer, lipid bilayer, micelle, organelle, cell, membrane, nucleic acid, peptide, polypeptide, protein, oligosaccharide, polysaccharide, glycopeptide, glycolipid, sphingolipid, glycosphingolipid, glycoprotein, peptidoglycan, lipid, carbohydrate, metalloprotein, proteoglycan, chromosome, cell nucleus, acid, base, buffer, protic solvent, aprotic solvent, nitric oxide, nitric oxide synthase, nitrous oxide, amino acid, micelle, polymer, bone cement, copolymer, cell receptor, adhesion molecule, cytokine, chemokine, immunoglobulin, antibody, antigen, platelet, extracellular matrix, blood, plasma, cell ligand, zwitterionic material, cationic material, oligonucleotide, nanotube, or piloxymer.

In one embodiment 7040, the one or more explosive materials include at least one of a carbonate, carbon dioxide, nitroglycerine, acid, base, epoxy, acrylic polymer or copolymer, acrylamide polymer or copolymer, urethane, hypoxyapatite, or reactive metal.

As indicated in FIG. 71, the at least one adhesive agent 7110 includes one or more of an acrylic polymer or copolymer, acrylamide polymer or copolymer polymer or copolymer, acrylamide polymer or copolymer, polyacrylic acid, epoxy, urethane, gum arabic, polyester, polyhydroxyalkanoate, poly(L-lactic acid), polyglycolide, polylactic acid, polyether, polyol, polyvinylpyrrolidone, pyroxylin, polymethylacrylate-isobutene-monoisopropylmaleate, siloxane polymer, polylactic-co-glycolic-acid, poly-3-hydroxybutyrate, poly-4-hydroxybutyrate, polyhydroxyvalerate, polydydroxyhexanoate, polydyroxyoctanoate, polycaprolactone, poly(e-caprolactone), sialyl Lewis$^x$, heme group, hemoglobin, healon, carboxymethylcellulose, hydroxyapatite, silicone, cadherin, integrin, hydroxyapatite, polyelectrolyte, maleic polyelectrolyte, cellulose, resilin, cyanoacrylate, isocyanate, 2-octyl cyanoacrylate, 2-butyl-n-cyanoacrylate, n-butyl-2-cyanoacrylate, butyl-2-cyanoacrylate, methyl 2-cyanoacrylate, polyisohexylcyanoacrylate, fibrin, thrombin, fibrinogen, hyaluronate, chitin, Factor XIII, Factor XII, silk, nylon, collagen, glycosaminoglycan, selectin, polyurethane, methacrylate, or polysulfide, polyanhydride, polydioxanone, poly-p-dioxanone, silicone, albumin, glutaraldehyde, polyethylene glycol, or gelatin.

In one embodiment 7120, the one or more reinforcement agents include one or more of polyaramid, vinylester matrix, metal, ceramic, fiberglass, cellulose, broad carbide, aromatic polyamide, nylon, silk, rayon, acetate, modacrylic, olefin, acrylic, polyester, aromatic polyester, poly-lactic acid, vinyon, saran, spandex, vinalon, aromatic nylon, vinylidene chloride, modal, polybenzimidazole, sulfur, lyocell, orlon, zylon, high-performance polyethylene, polypyridobenzimidazole, vectran, acrylonitrile rubber, glass, copper, iron, steel, sodium, potassium, calcium, zinc, manganese, carbon, magnesium, silicon, silica, frozen hydrogen oxide ice, plant matter, animal matter, or mineral matter.

In one embodiment 7130, the therapeutic agent includes at least one of an anti-tumor agent, antimicrobial agent, antiviral agent, analgesic, antiseptic, anesthetic, diagnostic agent, anti-inflammatory agent, vaccine, cell growth inhibitor, cell growth promoter, immunogen, antigen, radioactive agent, apoptosis promoting factor, enzymatic agent, angiogenic factor, anti-angiogenic factor, hormone, vitamin, mineral, nutraceutical, cytokine, chemokine, probiotic, coagulant, anti-coagulant, phage, prodrug, prebiotic, blood sugar stabilizer, smooth muscle cell activator, epinephrine, adrenaline, neurotoxin, neuro-muscular toxin, Botulinum toxin type A, microbial cell or component thereof, or virus or component thereof.

As indicated in FIG. 72, the at least one biological remodeling agent 7210 includes one or more of a blood cell, chondrocyte, endothelial cell, hepatocyte, keratinocyte, myocyte, osteoblast, osteoclast, osteocyte, mesenchymal cell, stem cell, progenitor cell, or fibroblast. In one embodiment 7220, the at least one biological remodeling agent includes one or more of calcium phosphate, albumin, cytokine, pegylated cytokine, bone, cartilage, globulin, fibrin, thrombin, glutaraldehyde-crosslinked pericardium, hide powder, hyaluronic acid, hydroxylapatite, keratin, ligament, nitinol, nucleic acid polymers, polyethylene, polyethylene glycol, polyethylene glycol diacrylate, polyethylene terephthalate fiber, polyglycol, polylactate, polytetrafluoroethylene, polylactic acid, polyglycolic acid, polycaprolactone, PURAMATRIX™ self-assembly peptide hydrogel fibers, linear aliphatic polyester, tendon, fibrinogen, hyaluronate, chitin, chitosan, methylcellulose, alginate, hyaluronic acid, agarose, cellulose, polyaldehyde gluronate, Factor XIII, Factor XII, silk, nylon, collagen, silicone, polyurethane, ceramic powder, elastin, pectin, wax, glycosaminoglycan, poly($\alpha$-hydroxyacid), selectin, glutaraldehyde, hydrophobic non-glycosylated protein, hydrogel, peptide hydrogel, or gelatin. In one embodiment 7230, the at least one biological remodeling agent includes one or more of Type I collagen, Type II collagen, Type III collagen, Type VII collagen, Type X collagen, elastin fibers, or soluble elastin. In one embodiment 7240, the at least one biological remodeling agent is included as part of a carrier that assists in synthesis or activation of the at least one biological remodeling agent.

Figure 73:
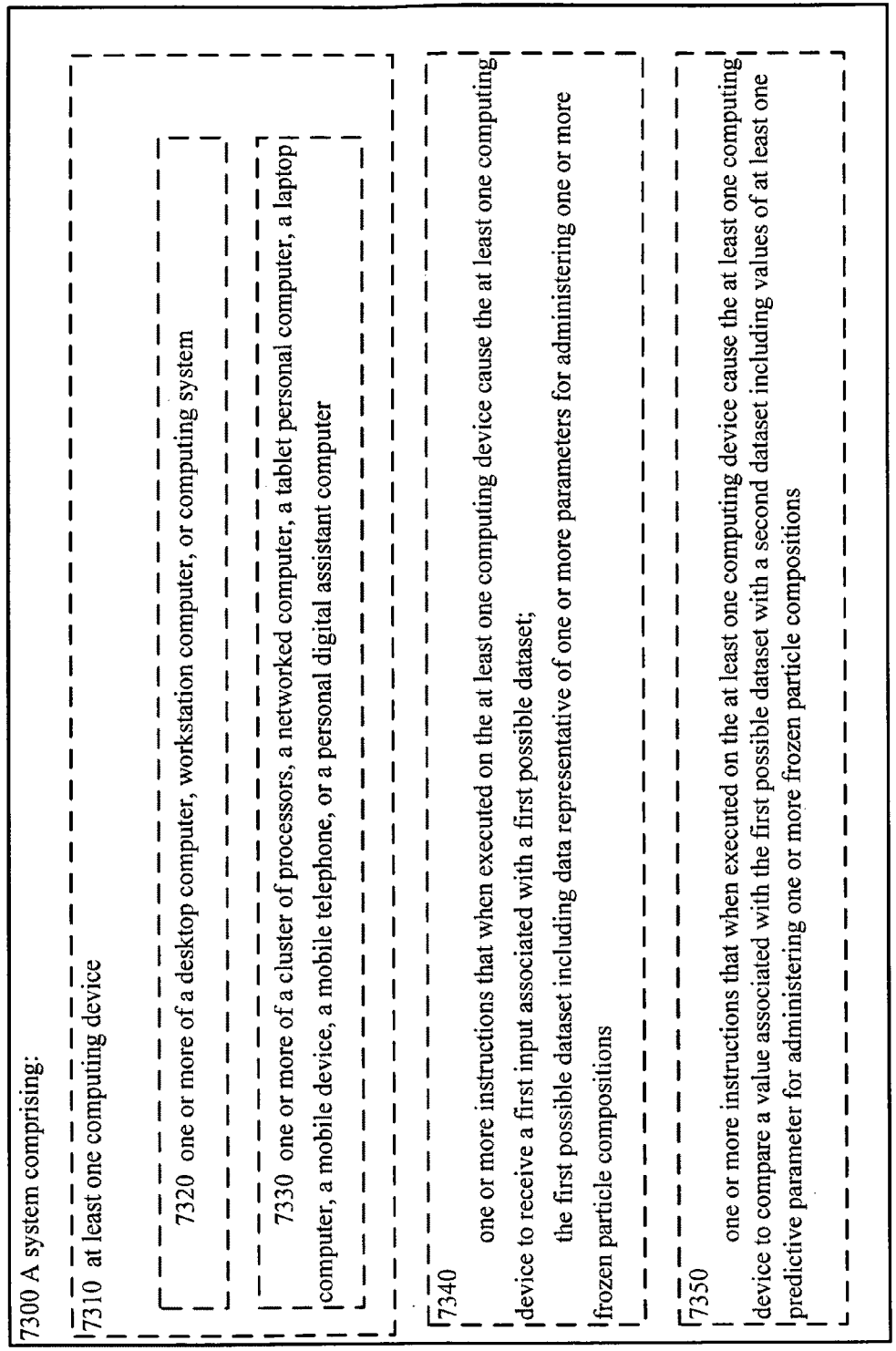
FIG. 73 illustrates a partial view of a system 7300 in which embodiments may be implemented.

As indicated in FIG. 73, a system 7300 comprises at least one computing device 7310; one or more instructions 7340 that when executed on the at least one computing device cause the at least one computing device to receive a first input associated with a first possible dataset, the first possible dataset including data representative of one or more parameters for administering one or more frozen particle compositions (or frozen piercing implements). In one embodiment 7350, the system further comprises one or more instructions that when executed on the at least one computing device cause the at least one computing device to compare a value associated with the first possible dataset with a second dataset including values of at least one predictive parameter for administering one or more frozen particle compositions (or frozen piercing implements). In one embodiment 7320, the at least one computing device includes one or more of a desktop computer, workstation computer, or computing system. In one embodiment 7330, the at least one computing system includes one or more of a cluster of processors, a networked computer, a tablet personal computer, a laptop computer, a mobile device, a mobile telephone, or a personal digital assistant computer.

As indicated in FIG. 74, the system further comprises one or more instructions 7460 that when executed on the at least one computing device cause the at least one computing device to determine a graphical illustration of the second possible dataset.

In one embodiment 7410, the system further comprises one or more instructions that when executed on the at least one computing device cause the at least one computing device to determine from the comparison at least one parameter for administering one or more frozen particle compositions (or frozen piercing implements). In one embodiment 7420, the system further comprises one or more instructions that when executed on the at least one computing device cause the at least one computing device to generate at least one response based on the determination. In one embodiment 7430, the system further comprises one or more instructions that when executed on the at least one computing device cause the at least one computing device to access the first possible dataset in response to the first input.

In one embodiment 7440, the system further comprises one or more instructions that when executed on the at least one computing device cause the at least one computing device to generate the first possible dataset in response to the first input.

In one embodiment 7450, the system further comprises one or more instructions that when executed on the at least one computing device cause the at least one computing device to determine a graphical illustration of the first possible dataset.

Figure 75:
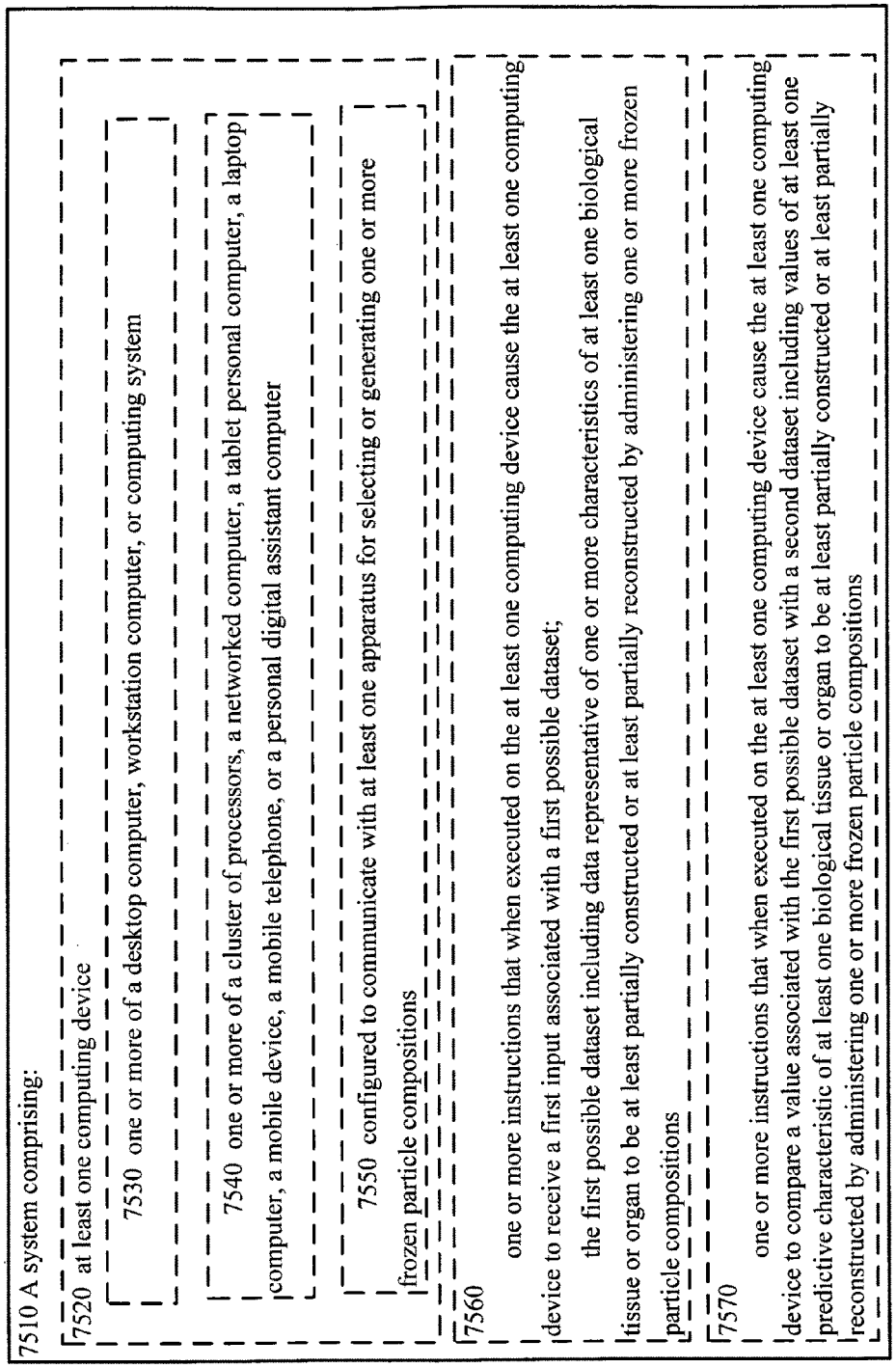
FIG. 75 illustrates a partial view of a system 7510 in which embodiments may be implemented.

As indicated in FIG. 75, a system 7510 comprises at least one computing device 7520; one or more instructions 7560 that when executed on the at least one computing device cause the at least one computing device to receive a first input associated with a first possible dataset, the first possible dataset including data representative of one or more characteristics of at least one biological tissue or organ to be at least partially constructed or at least partially reconstructed by administering one or more frozen particle compositions (or frozen piercing implements). In one embodiment 7570, the system further comprises one or more instructions that when executed on the at least one computing device cause the at least one computing device to compare a value associated with the first possible dataset with a second dataset including values of at least one predictive characteristic of at least one biological tissue or organ to be at least partially constructed or at least partially reconstructed by administering one or more frozen particle compositions (or frozen piercing implements).

In one embodiment 7530, the at least one computing device includes one or more of a desktop computer, workstation computer, or computing system. In one embodiment 7540, the at least one computing system includes one or more of a cluster of processors, a networked computer, a tablet personal computer, a laptop computer, a mobile device, a mobile telephone, or a personal digital assistant computer. In one embodiment 7550, the at least one computing device is configured to communicate with at least one apparatus for selecting or generating one or more frozen particle compositions (or frozen piercing implements).

As indicated in FIG. 76, the system further comprises one or more instructions 7610, that when executed on the at least one computing device cause the at least one computing device to determine a graphical illustration of the second possible dataset. In one embodiment 7620, the system further comprises one or more instructions that when executed on the at least one computing device cause the at least one computing device to determine from the comparison at least one characteristic of the at least one biological tissue or organ to be at least partially constructed or at least partially reconstructed by administering one or more frozen particle compositions (or frozen piercing implements). In one embodiment 7630, the system further comprises one or more instructions that when executed on the at least one computing device cause the at least one computing device to generate at least one response based on the determination.

In one embodiment 7640, the system further comprises one or more instructions that when executed on the at least one computing device cause the at least one computing device to access the first possible dataset in response to the first input. In one embodiment 7650, the system further comprises one or more instructions that when executed on the at least one computing device cause the at least one computing device to generate the first possible dataset in response to the first input. In one embodiment 7660, the system further comprises one or more instructions that when executed on the at least one computing device cause the at least one computing device to determine a graphical illustration of the first possible dataset.

Figure 77:
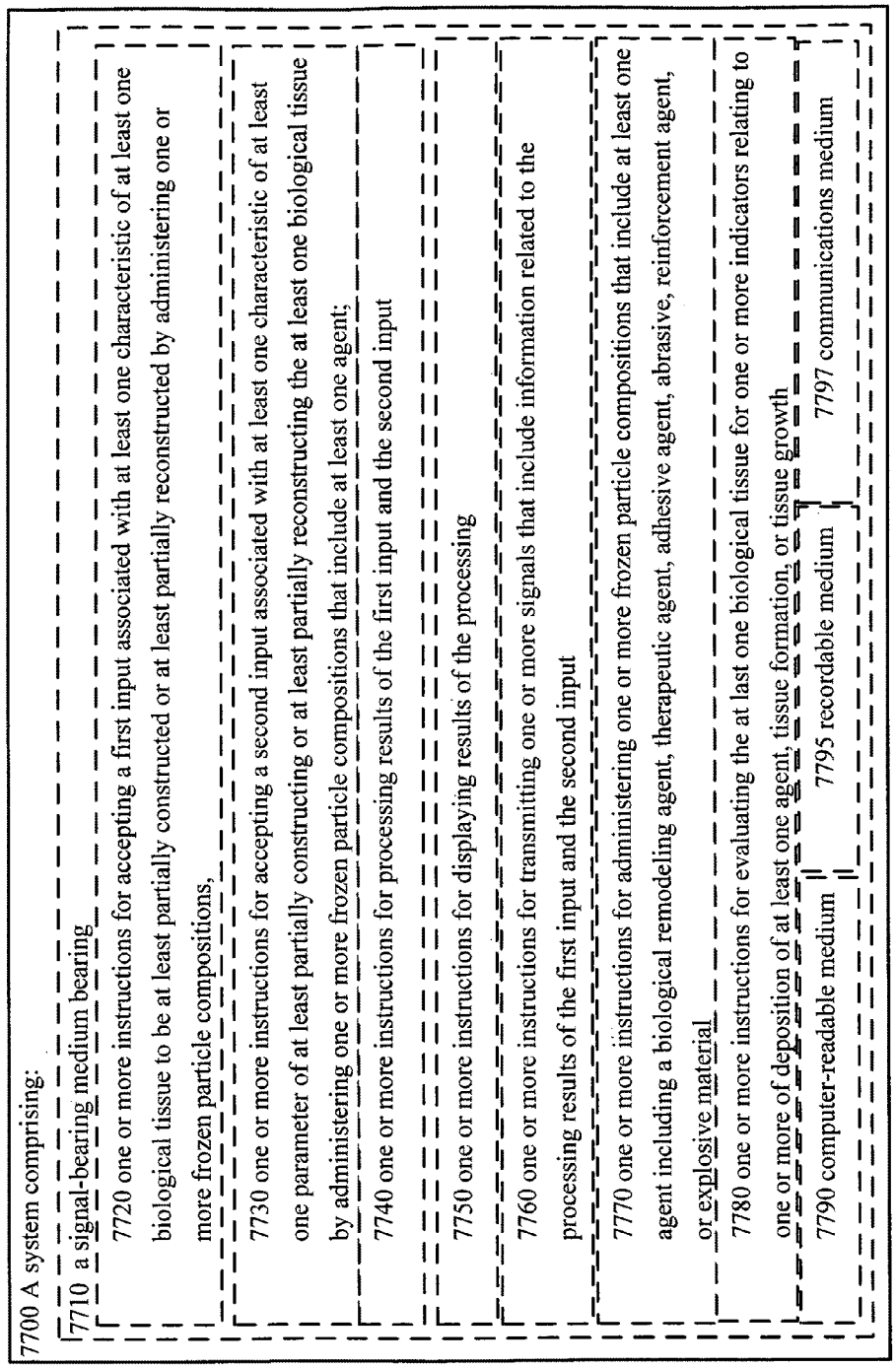
FIG. 77 illustrates a partial view of a system 7700 in which embodiments may be implemented.

As indicated in FIG. 77, a system 7700 comprises a signal-bearing medium 7710 bearing one or more instructions 7720 for accepting a first input associated with at least one characteristic of at least one biological tissue to be at least partially constructed or at least partially reconstructed by administering one or more frozen particle compositions (or frozen piercing implements); one or more instructions 7730 for accepting a second input associated with at least one characteristic of at least one parameter of at least partially constructing or at least partially reconstructing the at least one biological tissue by administering one or more frozen particle compositions (or frozen piercing implements) that include at least one agent; and one or more instructions 7740 for processing results of the first input and the second input. In one embodiment 7750, the system further comprising one or more instructions for displaying results of the processing.

In one embodiment 7760, the system further comprises one or more instructions for transmitting one or more signals that include information related to the processing results of the first input and the second input. In one embodiment 7770, the system further comprises one or more instructions for administering one or more frozen particle compositions (or frozen piercing implements) that include at least one agent including: biological remodeling agent, therapeutic agent, adhesive agent, abrasive, reinforcement agent, or explosive material. In one embodiment, the system 7780 further comprises one or more instructions for evaluating the at least one biological tissue for one or more indicators relating to one or more of: deposition of at least one agent, tissue formation, or tissue growth.

In one embodiment 7790, the signal-bearing medium includes a computer-readable medium. In one embodiment 7795, the signal-bearing medium includes a recordable medium. In one embodiment 7797, the signal-bearing medium includes a communications medium.

Figure 78:
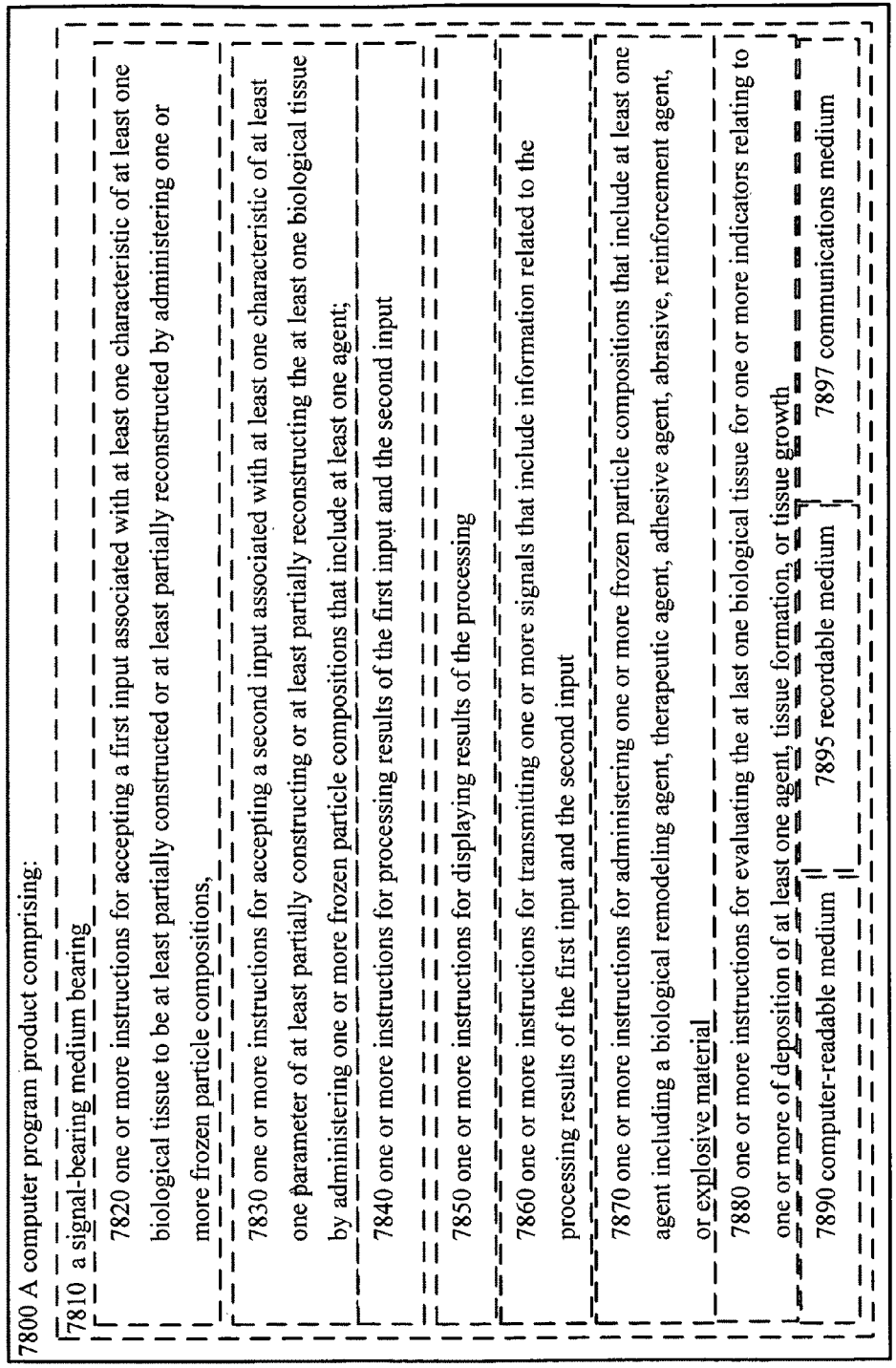
FIG. 78 illustrates a partial view of a computer program product 7800 in which embodiments may be implemented.

As indicated in FIG. 78, a computer program product 7800 comprises a signal-bearing medium 7810 bearing one or more instructions 7820 for accepting a first input associated with at least one characteristic of at least one biological tissue to be at least partially constructed or at least partially reconstructed by administering one or more frozen particle compositions (or frozen piercing implements); one or more instructions 7830 for accepting a second input associated with at least one characteristic of at least one parameter of at least partially constructing or at least partially reconstructing the at least one biological tissue by administering one or more frozen particle compositions (or frozen piercing implements) that include at least one agent; and one or more instructions 7840 for processing results of the first input and the second input.

In one embodiment 7850, the computer program product further comprises one or more instructions for displaying results of the processing. In one embodiment 7860, the computer program product further comprises one or more instructions for transmitting one or more signals that include information related to the processing results of the first input and the second input. In one embodiment 7870, the computer program product further comprises one or more instructions for administering one or more frozen particle compositions (or frozen piercing implements) that include at least one agent including biological remodeling agent, therapeutic agent, adhesive agent, abrasive, reinforcement agent, or explosive material.

In one embodiment 7880, the computer program product further comprises one or more instructions for evaluating the at least one biological tissue for one or more indicators relating to one or more of deposition of at least one agent, tissue formation, or tissue growth.

In one embodiment 7890, the signal-bearing medium includes a computer-readable medium. In one embodiment 7895, the signal-bearing medium includes a recordable medium. In one embodiment 7897, the signal-bearing medium includes a communications medium.

Figure 79:
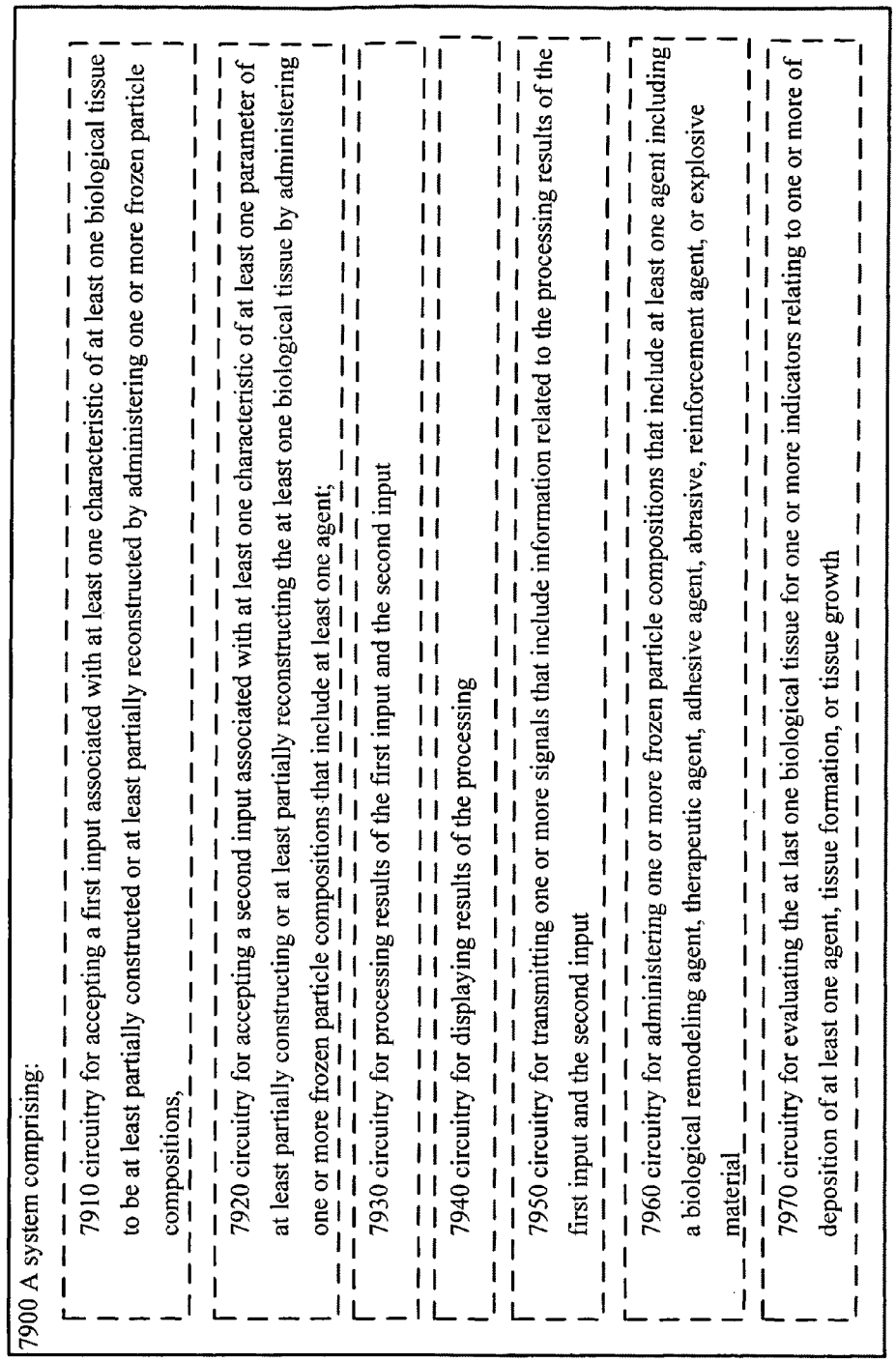
FIG. 79 illustrates a partial view of a system 7900 in which embodiments may be implemented.

As indicated in FIG. 79, a system 7900 comprises circuitry 7910 for accepting a first input associated with at least one characteristic of at least one biological tissue to be at least partially constructed or at least partially reconstructed by administering one or more frozen particle compositions (or frozen piercing implements); circuitry 7920 for accepting a second input associated with at least one characteristic of at least one parameter of at least partially constructing or at least partially reconstructing the at least one biological tissue by administering one or more frozen particle compositions (or frozen piercing implements) that include at least one agent; and circuitry 7930 for processing results of the first input and the second input. In one embodiment 7940, the system further comprises circuitry for displaying results of the processing. In one embodiment 7950, the system further comprises circuitry for transmitting one or more signals that include information related to the processing results of the first input and the second input. In one embodiment 7960, the system further comprises circuitry for administering one or more frozen particle compositions (or frozen piercing implements) that include at least one agent including at least one biological remodeling agent, therapeutic agent, adhesive agent, abrasive, reinforcement agent, or explosive material. In one embodiment 7970, the system further comprises circuitry for evaluating the at least one biological tissue for one or more indicators relating to one or more of deposition of at least one agent, tissue formation, or tissue growth.

As indicated in FIG. 80, a system 8000 comprises at least at least one computer program 8010, configured with a computer-readable medium, for use with at least one computer system and wherein the computer program includes a plurality of instructions including but not limited to: one or more instructions 8020 for accepting a first input associated with at least one characteristic of at least one biological tissue to be at least partially constructed or at least partially reconstructed by administering one or more frozen particle compositions (or frozen piercing implements); one or more instructions 8030 for accepting a second input associated with at least one characteristic of at least one parameter of at least partially constructing or at least partially reconstructing the at least one biological tissue by administering one or more frozen particle compositions (or frozen piercing implements) that include at least one agent; and one or more instructions 8040 for processing results of the first input and the second input.

In one embodiment 8050, the system further comprises one or more instructions for displaying results of the processing. In one embodiment 8060, the system further comprises one or more instructions for transmitting one or more signals that include information related to the processing results of the first input and the second input.

In one embodiment 8070, the system further comprises one or more instructions for administering one or more frozen particle compositions (or frozen piercing implements) that include at least one agent including biological remodeling agent, therapeutic agent, adhesive agent, abrasive, reinforcement agent, or explosive material. In one embodiment 8080, the system further comprises one or more instructions for evaluating the at least one biological tissue for one or more indicators relating to one or more of deposition of at least one agent, tissue formation, or tissue growth.

Figure 81:
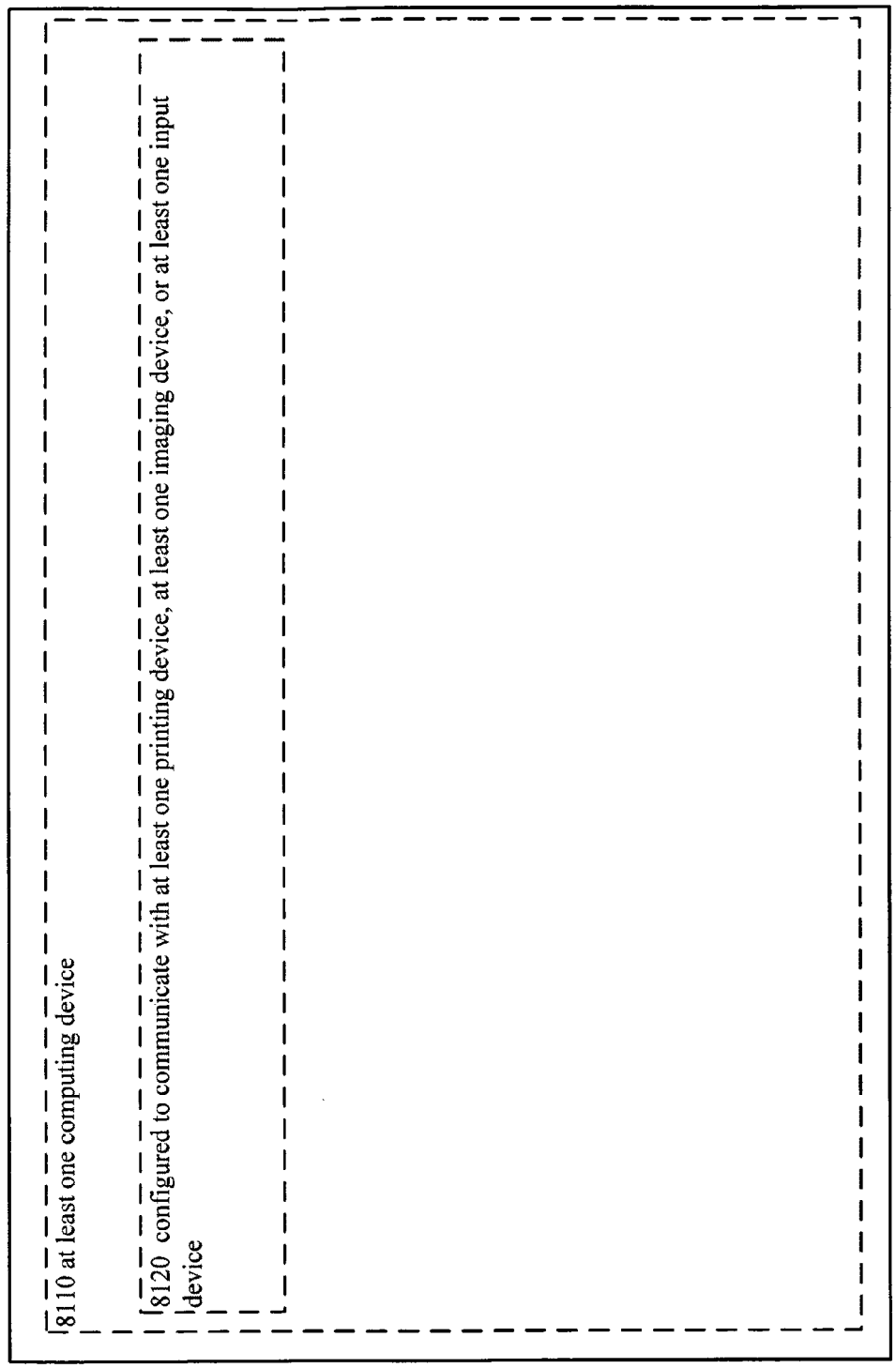
FIG. 81 illustrates a partial view of FIG. 80 in which embodiments may be implemented.

As indicated in FIG. 81, the system further comprises at least one computing device 8110. In one embodiment 8120, the at least one computing device is configured to communicate with at least one printing device, at least one imaging device, or at least one input device.

As indicated in FIG. 82, a system 8200 comprises means 8210 for accepting a first input associated with at least one characteristic of at least one biological tissue to be at least partially constructed or at least partially reconstructed; means 8220 for accepting a second input associated with at least one parameter of at least partially constructing or at least partially reconstructing the at least one biological tissue by administering one or more frozen particle compositions (or frozen piercing implements) including at least one agent; and means 8260 for processing results of the first input and the second input. In one embodiment 8230 the at least one agent includes one or more of a therapeutic agent, adhesive agent, abrasive, reinforcement agent, explosive material, or biological remodeling agent. In one embodiment 8240 the administering one or more frozen particle compositions (or frozen piercing implements) includes administering the one or more frozen particle compositions (or frozen piercing implements) to at least one substrate. In one embodiment 8250 the at least one substrate includes one or more of a cell, tissue, organ, structure, or device. In one embodiment 8270 means for processing results of the first input and the second input include means for electronically processing results of the first input and the second input. In one embodiment 8280 means for electronically processing results of the first input and the second input by utilizing one or more of Gaussian smoothing, scaling, homorphic filtering, parametric estimation techniques, Boolean operations, Monte Carlo simulations, wavelet based techniques, mirroring, smoothing, gradient weighted partial differential equation smoothing, NURBS, polygonal modeling, splines and patches modeling, algorithmic execution, logical decision-making, result prediction, Finite Element Analysis, or modification of a CAD design.

As indicated in FIG. 83, the first input 8310 includes one or more values related to the at least one characteristic of at least one biological tissue. In one embodiment 8320, the first input includes one or more spatial addresses associated with the at least one characteristic of at least one biological tissue. In one embodiment 8330, the first input includes one or more of x, y, or z coordinates associated with the at least one characteristic of at least one biological tissue.

In one embodiment, the at least one characteristic 8340 of at least one biological tissue to be at least partially constructed or at least partially reconstructed includes one or more of: morphological feature, anatomical feature, histological feature, tissue hierarchical level, scaffold feature, vascular structure feature, heterogenous tissue feature, mechanical feature, volumetric feature, geometric feature, volumetric representation, mechanical feature, deformation, kinematic feature, surface contour feature, cytometric feature, cell aggregation, cell growth, cell-cell interaction, cell-tissue interaction, biomimetic design, cell pattern, cell deposition, organ hierarchical level, tissue microstructure, cellular microstructure, cell junction feature, tissue junction feature, cell-tissue classification, hard tissue classification, soft tissue classification, tumor diagnosis, or other feature.

In one embodiment, the at least one characteristic 8350 of at least one biological tissue includes one or more of cellular type, cellular function, cellular size, cellular constitution, cellular architecture, cellular durability, cellular source, tissue type, tissue constitution, tissue size, tissue shape, tissue function, tissue architecture, tissue source, tissue durability, organ type, organ constitution, organ size, organ shape, organ function, organ architecture, organ source, or organ durability. In one embodiment, the first input 8360 includes one or more temporal addresses associated with the at least one characteristic of at least one biological tissue.

As indicated in FIG. 84, in one embodiment 8410, the first input includes one or more values derived from at least one image of the at least one biological tissue. In one embodiment 8420, the at least one image includes one or more images acquired by one or more of optical coherence tomography, computer-assisted tomography scan, computed tomography, magnetic resonance imaging, positron-emission tomography scan, ultrasound, x-ray, laser, holography, x-ray crystallography, electrical-impedance monitoring, microscopy, spectrometry, flow cytommetry, radioisotope imaging, thermal imaging, multiphoton calcium-imaging, photography, or in silico generation.

In one embodiment 8430, the at least one biological tissue is located in at least one of in situ, in vitro, in vivo, in utero, in planta, in silico, or ex vivo. In one embodiment 8440, the at least one biological tissue is at least partially located in at least one subject. In one embodiment 8450, the system further comprises means for accepting a third input associated with at least one feature of the at least one subject. In one embodiment 8460, the at least one feature of the at least one subject includes one or more of age, gender, genotype, phenotype, proteomic profile, or health condition.

As indicated in FIGS. 85-86, in one embodiment 8510 the means for processing results of the first input and the second input include means for determining at least one parameter of at least partially constructing or at least partially reconstructing the at least one biological tissue with one or more frozen particle compositions (or frozen piercing implements) from one or more values derived from at least one image of the at least one biological tissue. In one embodiment 8520, the second input includes one or more values related to the at least one parameter of at least partially constructing or at least partially reconstructing the at least one biological tissue by administering one or more frozen particle compositions (or frozen piercing implements) to the at least one substrate. In one embodiment 8530, the one or more values related to the at least one parameter of constructing or reconstructing the at least one biological tissue includes one or more predictive values.

In one embodiment 8540, the at least one parameter of at least partially constructing or at least partially reconstructing the at least one biological tissue includes one or more of porosity of the at least one substrate, pore size of the at least one substrate, interconnectivity of the pores of the at least one substrate, transport properties of the at least one substrate, cell-tissue formation of the at least one substrate, mechanical strength of the at least one substrate, ability for attachment or distribution of the at least one agent included in the one or more frozen particle compositions (or frozen piercing implements) to the at least one substrate, ability for attachment or distribution of one or more cells or tissues to the at least one substrate, facilitation of at least one nutrient, or tissue formation or tissue growth associated with the at least one substrate.

In one embodiment 8610, the at least one parameter of at least partially constructing or at least partially reconstructing the at least one biological tissue by administering one or more frozen particle compositions (or frozen piercing implements) includes one or more of: design of plot or model for administration of one or more frozen particle compositions (or frozen piercing implements), constitution of the one or more frozen particle compositions (or frozen piercing implements), formulation of the one or more frozen particle compositions (or frozen piercing implements), size of the one or more frozen particle compositions (or frozen piercing implements), shape of the one or more frozen particle compositions (or frozen piercing implements), angle of administration of the one or more frozen particle compositions (or frozen piercing implements), velocity of administration of the one or more frozen particle compositions (or frozen piercing implements), quantity of frozen particle compositions (or frozen piercing implements) administered, rate of administration of more than one frozen particle composition (or frozen piercing implement), spatial location for administration of one or more frozen particle compositions (or frozen piercing implements), temporal location for administration of one or more frozen particle compositions (or frozen piercing implements), method of administration of one or more frozen particle compositions (or frozen piercing implements), timing of administration of one or more frozen particle compositions (or frozen piercing implements), modulation of administration of one or more frozen particle compositions (or frozen piercing implements), deposition of one or more frozen particle compositions (or frozen piercing implements), or rate of deposition of at least one agent.

In one embodiment 8620, the at least one parameter of at least partially constructing or at least partially reconstructing the at least one biological tissue by administering one or more frozen particle compositions (or frozen piercing implements) includes at least one parameter relating to at least partially ablating or at least partially abrading one or more surfaces of the at least one biological tissue with the one or more frozen particle compositions (or frozen piercing implements).

In one embodiment 8630, the at least one parameter of at least partially constructing or at least partially reconstructing the at least one biological tissue by administering one or more frozen particle compositions (or frozen piercing implements) includes at least one parameter relating to administering at least one of a therapeutic agent, adhesive agent, biological remodeling agent, reinforcement agent, abrasive, or explosive material with the one or more frozen particle compositions (or frozen piercing implements).

In one embodiment 8640, the spatial location for administration of one or more frozen particle compositions (or frozen piercing implements) includes one or more of x, y, or z coordinates. In one embodiment 8650, the means for processing results include means for comparing at least one value related to the first input associated with the at least one characteristic of at least one biological tissue to be at least partially constructed or at least partially reconstructed with at least one value related to at least one image of a target biological tissue. In one embodiment 8660, the image of a target biological tissue includes an image of a similar biological tissue, or an image of a dissimilar biological tissue.

As indicated in FIG. 87, the means 8710 for processing results include means for comparing at least one value related to the second input associated with the at least one parameter of at least partially constructing or at least partially reconstructing the at least one biological tissue with at least one value related to another administration of one or more frozen particle compositions (or frozen piercing implements). In one embodiment 8720, the means for processing results include means for determining one or more differences in at least one value related to the first input and at least one value related to at least one image of the at least one biological tissue or a similar biological tissue. In one embodiment 8730, the means for processing results include means for determining one or more differences in at least one value related to the second input associated with the at least one parameter of at least partially constructing or at least partially reconstructing the at least one biological tissue and at least one value related to another administration of one or more frozen particle compositions (or frozen piercing implements) to the at least one substrate.

In one embodiment 8740, the means for processing results include means for generating one or more protocols for administering the one or more frozen particle compositions (or frozen piercing implements). In one embodiment 8750, the means for processing results include generating one or more blueprints for administering the one or more frozen particle compositions (or frozen piercing implements). In one embodiment 8760, the one or more blueprints include at least one of a two-dimensional plot or a three-dimensional model. In one embodiment 8770, the one or more blueprints include at least one representation of at least one of organ anatomy, morphology, tissue heterogeneity, scale of vascular system, geometry, internal architecture of an organ or tissue, internal or external boundary distinction of a tissue or organ, topology, or tomography.

As indicated in FIG. 88, the means for processing results include: means for comparing one or more values related to the one or more characteristics of the at least one biological tissue that are determined at two or more different times to obtain one or more characteristic comparisons; means for comparing one or more values related to the at least one parameter of at least partially constructing or at least partially reconstructing the at least one biological tissue at two or more different times to obtain one or more parameter comparisons; means for comparing the one or more characteristic comparisons with the one or more parameter comparisons to obtain one or more characteristic-characteristic/parameter-parameter comparisons; and means for comparing the one or more characteristic-characteristic/parameter-parameter comparisons to one or more substantially similar results obtained for one or more other at least partially constructed or at least partially reconstructed biological tissues. In one embodiment 8820, the administering one or more frozen particle compositions (or frozen piercing implements) includes depositing the at least one agent on the at least one substrate.

Figure 89:
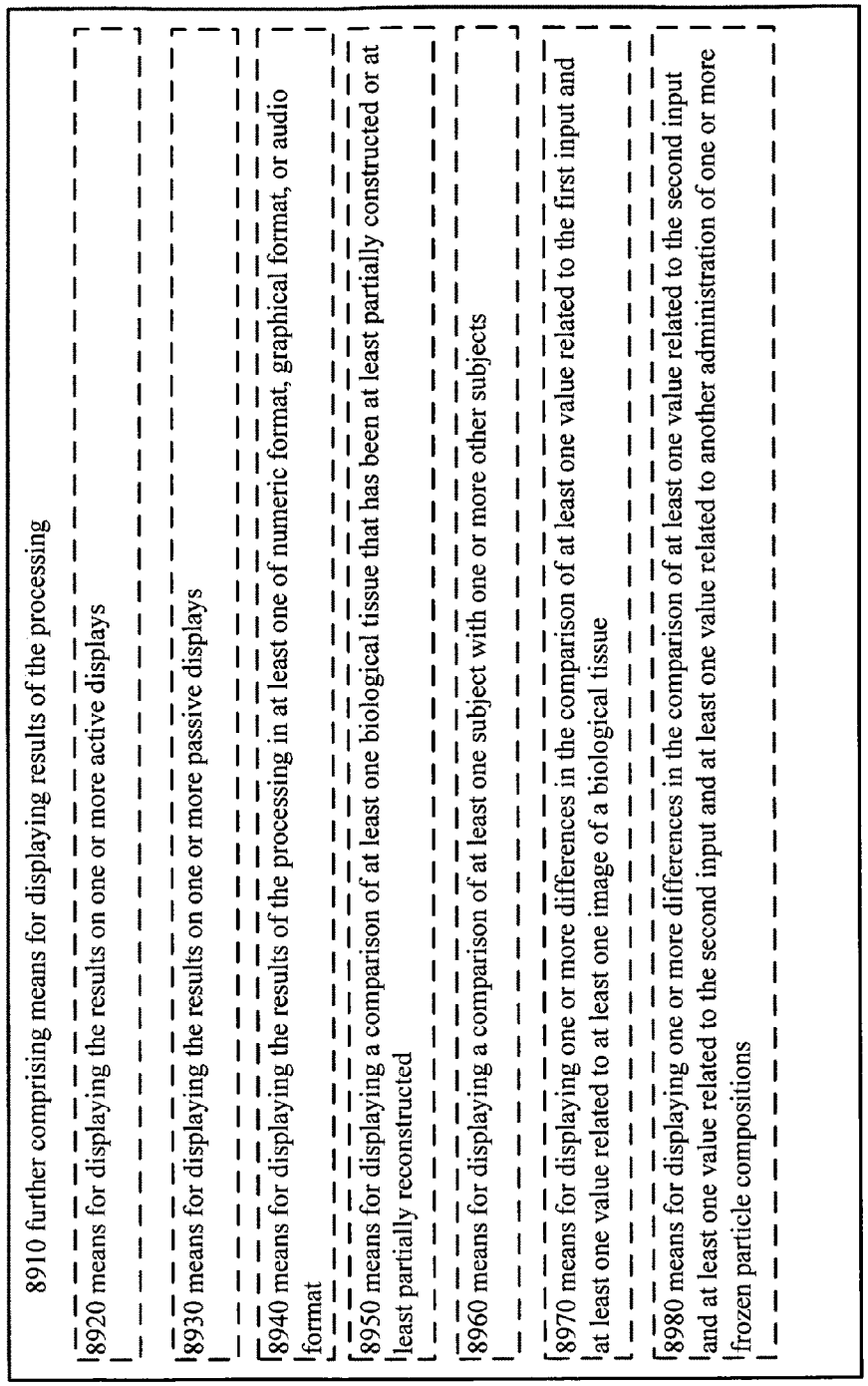
FIG. 89 illustrates a partial view of FIG. 82 in which embodiments may be implemented.

As indicated in FIG. 89, the system further comprises means 8910 for displaying results of the processing. In one embodiment 8920, the means for displaying the results of the processing include means for displaying the results on one or more active displays. In one embodiment 8930, the means for displaying results of the processing include means for displaying the results on one or more passive displays. In one embodiment 8940, the means for displaying results of the processing includes means for displaying the results of the processing in at least one of numeric format, graphical format, or audio format.

In one embodiment 8950, the means for displaying results of the processing include means for displaying a comparison of at least one biological tissue that has been at least partially constructed or at least partially reconstructed. In one embodiment 8960, the means for displaying results of the processing include means for displaying a comparison of at least one subject with one or more other subjects. In one embodiment 8970, the means for displaying results of the processing include means for displaying one or more differences in the comparison of at least one value related to the first input and at least one value related to at least one image of a biological tissue. In one embodiment 8980, the means for displaying results of the processing include means for displaying one or more differences in the comparison of at least one value related to the second input and at least one value related to another administration of one or more frozen particle compositions (or frozen piercing implements).

Figure 90:
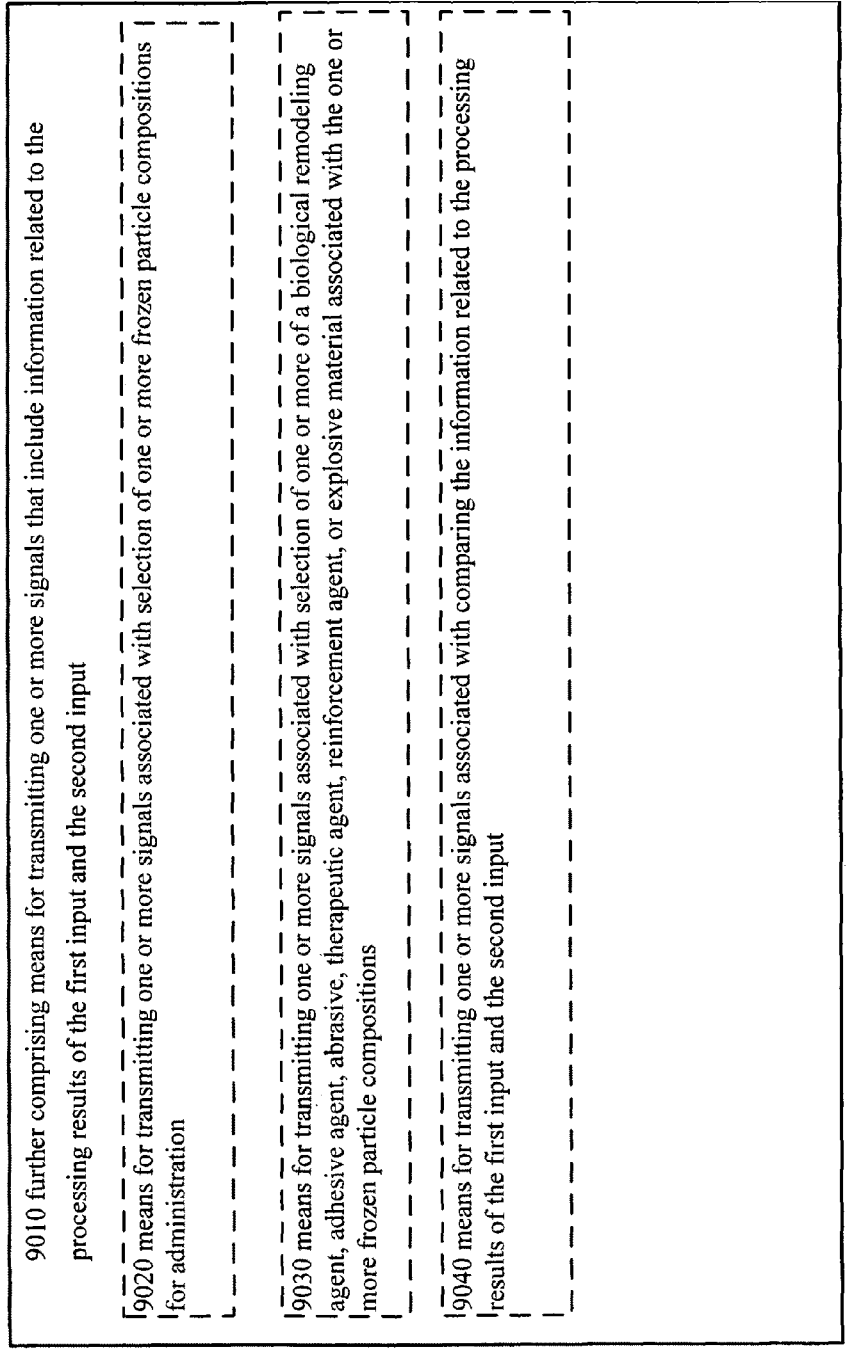
FIG. 90 illustrates a partial view of FIG. 82 in which embodiments may be implemented.

As indicated in FIG. 90, the system further comprises means 9010 for transmitting one or more signals that include information related to the processing results of the first input and the second input. In one embodiment 9020, the means for transmitting one or more signals include means for transmitting one or more signals associated with selection of one or more frozen particle compositions (or frozen piercing implements) for administration. In one embodiment 9030, the means for transmitting one or more signals include means for transmitting one or more signals associated with selection of one or more of a biological remodeling agent, adhesive agent, abrasive, therapeutic agent, reinforcement agent, or explosive material associated with the one or more frozen particle compositions (or frozen piercing implements). In one embodiment 9040, the means for transmitting one or more signals include means for transmitting one or more signals associated with comparing the information related to the processing results of the first input and the second input.

As indicated in FIG. 91, the one or more frozen particle compositions (or frozen piercing implements) 9110 include one or more frozen particles including at least one of: hydrogen oxide, nitrogen, oxygen, air, helium, neon, argon, xenon, chlorine, bromine, carbon dioxide, acetone, ethyl acetate, dimethyl sulfoxide, dimethyl formamide, dioxane, tetrahydrofuran, acetonitrile, acetic acid, n-butanol, isopropanol, n-propanol, hexamethylphosphorotriamide, perfluorohydrocarbon, methanol, ethanol, tert-butyl alcohol, formic acid, hydrogen fluoride, ammonia, benzene, carbon tetrachloride, hexane, dichloromethane, methylene chloride, carboxylic acid, saline, standard saline citrate, methane, toluene, chloroform, polyethylene glycol, acetic acid, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, or diethyl ether.

In one embodiment 9120, the at least one agent includes one or more of an adhesive agent, therapeutic agent, reinforcement agent, abrasive, explosive material, or biological remodeling agent. In one embodiment 9130, at least one of the adhesive agent, therapeutic agent, reinforcement agent, abrasive, explosive material, or biological remodeling agent is substantially in the form of at least one of an organic or inorganic small molecule, clathrate or caged compound, protocell, coacervate, microsphere, Janus particle, proteinoid, laminate, helical rod, liposome, macroscopic tube, niosome, sphingosome, toroid, vesicular tube, vesicle, small unilamellar vesicle, large unilamellar vesicle, large multilamellar vesicle, multivesicular vesicle, lipid layer, lipid bilayer, micelle, organelle, cell, membrane, nucleic acid, peptide, polypeptide, protein, oligosaccharide, polysaccharide, glycopeptide, glycolipid, sphingolipid, glycosphingolipid, glycoprotein, peptidoglycan, lipid, carbohydrate, metalloprotein, proteoglycan, chromosome, cell nucleus, acid, base, buffer, protic solvent, aprotic solvent, nitric oxide, nitric oxide synthase, nitrous oxide, amino acid, micelle, polymer, bone cement, copolymer, cell receptor, adhesion molecule, cytokine, chemokine, immunoglobulin, antibody, antigen, platelet, extracellular matrix, blood, plasma, cell ligand, zwitterionic material, cationic material, oligonucleotide, nanotube, or piloxymer.

As indicated in FIG. 92, the one or more explosive materials 9210 include at least one of a carbonate, carbon dioxide, nitroglycerine, acid, base, epoxy, acrylic polymer or copolymer, acrylamide polymer or copolymer, urethane, hypoxyapatite, or reactive metal. In one embodiment 9220, the at least one adhesive agent includes one or more of an acrylic polymer or copolymer, acrylamide polymer or copolymer polymer or copolymer, acrylamide polymer or copolymer, polyacrylic acid, epoxy, urethane, gum arabic, polyester, polyhydroxyalkanoate, poly(L-lactic acid), polyglycolide, polylactic acid, polyether, polyol, polyvinylpyrrolidone, pyroxylin, polymethylacrylate-isobutene-monoisopropylmaleate, siloxane polymer, polylactic-co-glycolic-acid, poly-3-hydroxybutyrate, poly-4-hydroxybutyrate, polyhydroxyvalerate, polydydroxyhexanoate, polydyroxyoctanoate, polycaprolactone, poly(e-caprolactone), sialyl Lewis$^x$, heme group, hemoglobin, healon, carboxymethylcellulose, hydroxyapatite, silicone, cadherin; integrin, hydroxyapatite, polyelectrolyte, maleic polyelectrolyte, cellulose, resilin, cyanoacrylate, isocyanate, 2-octyl cyanoacrylate, 2-butyl-n-cyanoacrylate, n-butyl-2-cyanoacrylate, butyl-2-cyanoacrylate, methyl 2-cyanoacrylate, polyisohexylcyanoacrylate, fibrin, thrombin, fibrinogen, hyaluronate, chitin, Factor XIII, Factor XII, silk, nylon, collagen, glycosaminoglycan, selectin, polyurethane, methacrylate, or polysulfide, polyanhydride, polydioxanone, poly-p-dioxanone, silicone, albumin, glutaraldehyde, polyethylene glycol, or gelatin.

In at least one embodiment 9230, the one or more reinforcement agents include one or more of polyaramid, vinylester matrix, metal, ceramic, fiberglass, cellulose, broad carbide, aromatic polyamide, nylon, silk, rayon, acetate, modacrylic, olefin, acrylic, polyester, aromatic polyester, poly-lactic acid, vinyon, saran, spandex, vinalon, aromatic nylon, vinylidene chloride, modal, polybenzimidazole, sulfur, lyocell, orlon, zylon, high-performance polyethylene, polypyridobenzimidazole, vectran; acrylonitrile rubber, glass, copper, iron, steel, sodium, potassium, calcium, zinc, manganese, carbon, magnesium, silicon, silica, frozen hydrogen oxide ice, plant matter, animal matter, or mineral matter.

As indicated in FIG. 93, the therapeutic agent 9310 includes at least one of an anti-tumor agent, antimicrobial agent, anti-viral agent, analgesic, antiseptic, anesthetic, diagnostic agent, anti-inflammatory agent, vaccine, cell growth inhibitor, cell growth promoter, immunogen, antigen, radioactive agent, apoptosis promoting factor, enzymatic agent, angiogenic factor, anti-angiogenic factor, hormone, vitamin, mineral, nutraceutical, cytokine, chemokine, probiotic, coagulant, anti-coagulant, phage, prodrug, prebiotic, blood sugar stabilizer, smooth muscle cell activator, epinephrine, adrenaline, neurotoxin, neuro-muscular toxin, Botulinum toxin type A, microbial cell or component thereof, or virus or component thereof.

In one embodiment 9320 the at least one biological remodeling agent includes one or more of a blood cell, chondrocyte, endothelial cell, hepatocyte, keratinocyte, myocyte, osteoblast, osteoclast, osteocyte, mesenchymal cell, stem cell, progenitor cell, or fibroblast. In one embodiment 9330, the at least one biological remodeling agent includes one or more of calcium phosphate, albumin, cytokine, pegylated cytokine, bone, cartilage, globulin, fibrin, thrombin, glutaraldehyde-crosslinked pericardium, hide powder, hyaluronic acid, hydroxylapatite, keratin, ligament, nitinol, nucleic acid polymers, polyethylene, polyethylene glycol, polyethylene glycol diacrylate, polyethylene terephthalate fiber, polyglycol, polylactate, polytetrafluoroethylene, polylactic acid, polyglycolic acid, polycaprolactone, PURAMATRIX™ self-assembly peptide hydrogel fibers, linear aliphatic polyester, tendon, fibrinogen, hyaluronate, chitin, chitosan, methylcellulose, alginate, hyaluronic acid, agarose, cellulose, polyaldehyde gluronate, Factor XIII, Factor XII, silk, nylon, collagen, silicone, polyurethane, ceramic powder, elastin, pectin, wax, glycosaminoglycan, poly(α-hydroxyacid), selectin, glutaraldehyde, hydrophobic non-glycosylated protein, hydrogel, peptide hydrogel, or gelatin. In one embodiment 9340, the at least one biological remodeling agent includes one or more of Type I collagen, Type II collagen, Type III collagen, Type VII collagen, Type X collagen, elastin fibers, or soluble elastin. In one embodiment 9350, the at least one biological remodeling agent is included as part of a carrier that assists in synthesis or activation of the at least one biological remodeling agent.

Figure 96:
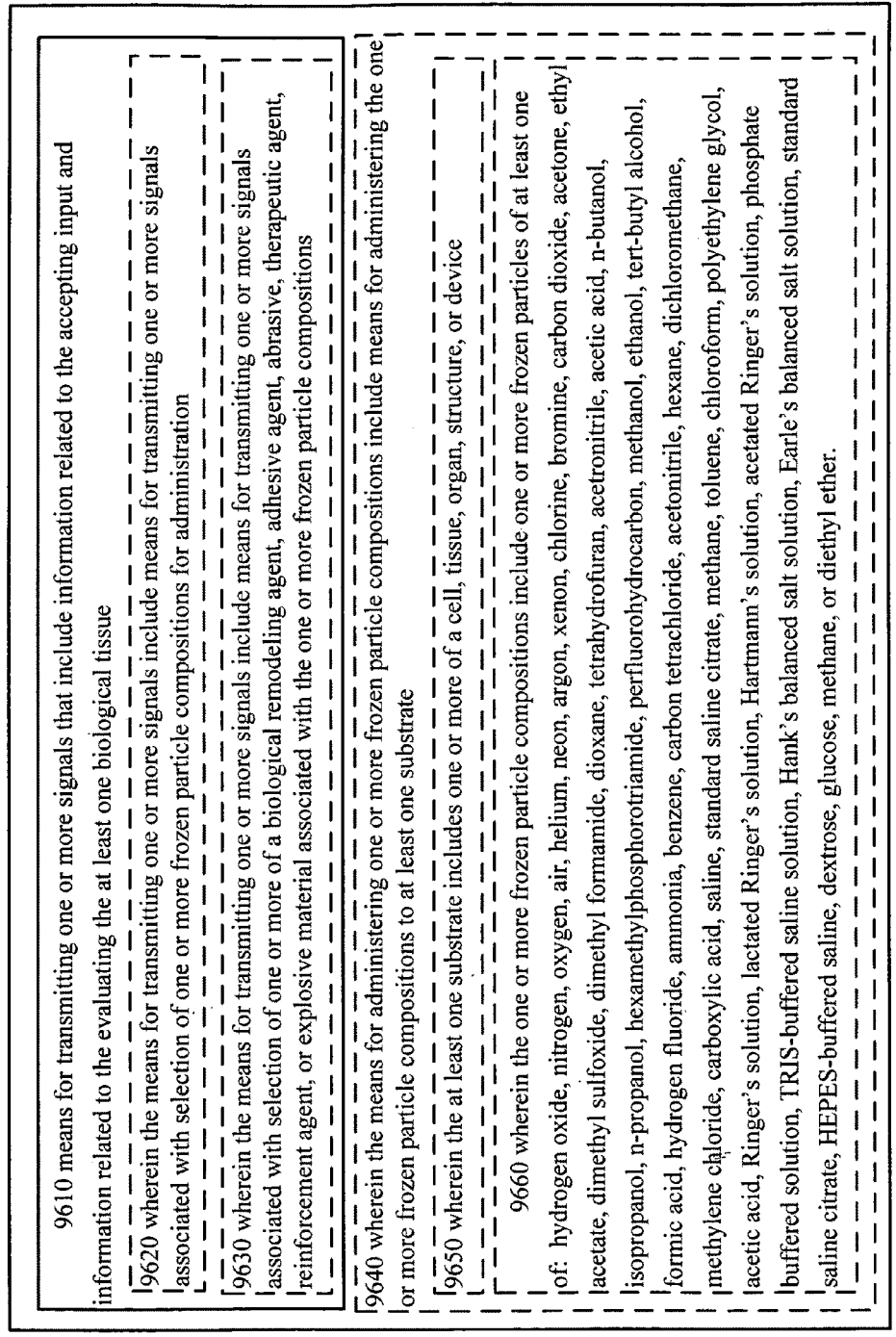
FIG. 96 illustrates a partial view of FIG. 94 in which embodiments may be implemented.

As indicated in FIGS. 94-96, a system 9400 comprises means 9410 for accepting input associated with at least one parameter of at least partially constructing or at least partially reconstructing at least one biological tissue by administering one or more frozen particle compositions (or frozen piercing implements); means 9420 for administering one or more frozen particle compositions (or frozen piercing implements) including at least one agent; wherein 9430 the at least one agent includes one or more of a biological remodeling agent, therapeutic agent, reinforcement agent, explosive material, abrasive, or adhesive agent; means 9440 for evaluating the at least one biological tissue for one or more indicators related to deposition of at least one agent, tissue formation, or tissue growth; and means 9610 for transmitting one or more signals that include information related to the accepting input and information related to the evaluating the at least one biological tissue.

In one embodiment 9450, the means for evaluating at least one biological tissue for one or more indicators includes evaluating at least one of an assay, image, or gross assessment of the at least one biological tissue prior to, during, or subsequent to at least one administration of the one or more frozen particle compositions (or frozen piercing implements). In one embodiment 9460, the assay includes at least one technique that includes spectroscopy, microscopy, electrochemical detection, polynucleotide detection, histological examination, biopsy analysis, fluorescence resonance energy transfer, electron transfer, enzyme assay, electrical conductivity, isoelectric focusing, chromatography, immunoprecipitation, immunoseparation, aptamer binding, filtration, electrophoresis, immunoassay, or radioactive assay.

In one embodiment 9520, the image includes at least one image acquired by one or more of optical coherence tomography, computer-assisted tomography scan, computed tomography, magnetic resonance imaging, positron-emission tomography scan, ultrasound, x-ray, x-ray crystallography, laser, holography, electrical-impedance monitoring, microscopy, spectrometry, flow cytommetry, radioisotope imaging, thermal imaging, multiphoton calcium-imaging, photography, or in silico generation. In one embodiment 9530, the one or more indicators of tissue formation or growth include at least one of cell migration, cell attachment, cell retention, cell differentiation, cell proliferation, apoptosis, diffusion of materials, angiogenesis, nucleic acid expression, protein translation, protein modification, carbohydrate production, carbohydrate secretion, fat production, fat secretion, or protein secretion.

In one embodiment 9540, the input associated with at least one parameter of at least partially constructing or at least partially reconstructing the at least one biological tissue by administering one or more frozen particle compositions (or frozen piercing implements) includes one or more of: constitution of the one or more frozen particle compositions (or frozen piercing implements), formulation of the one or more frozen particle compositions (or frozen piercing implements), size of the one or more frozen particle compositions (or frozen piercing implements), shape of the one or more frozen particle compositions (or frozen piercing implements), angle of administration of the one or more frozen particle compositions (or frozen piercing implements), velocity of administration of the one or more frozen particle compositions (or frozen piercing implements), quantity of frozen particle compositions (or frozen piercing implements) administered, rate of administration of more than one frozen particle composition (or frozen piercing implement), spatial location for administration of one or more frozen particle compositions (or frozen piercing implements), temporal location for administration of one or more frozen particle compositions (or frozen piercing implements), method of administration of one or more frozen particle compositions (or frozen piercing implements), timing of administration of one or more frozen particle compositions (or frozen piercing implements), modulation of administration of one or more frozen particle compositions (or frozen piercing implements), deposition of one or more frozen particle compositions (or frozen piercing implements), or rate of deposition of at least one agent.

In one embodiment 9620, the means for transmitting one or more signals include means for transmitting one or more signals associated with selection of one or more frozen particle compositions for administration. In one embodiment 9630, the means for transmitting one or more signals include means for transmitting one or more signals associated with selection of one or more of a biological remodeling agent, adhesive agent, abrasive, therapeutic agent, reinforcement agent, or explosive material associated with the one or more frozen particle compositions (or frozen piercing implements). In one embodiment 9640, the means for administering one or more frozen particle compositions (or frozen piercing implements) include means for administering the one or more frozen particle compositions (or frozen piercing implements) to at least one substrate. In one embodiment 9650, the at least one substrate includes one or more of a cell, tissue, organ, structure, or device. In one embodiment 9660, the one or more frozen particle compositions (or frozen piercing implements) include one or more frozen particles including at least one of hydrogen oxide, nitrogen, oxygen, air, helium, neon, argon, xenon, chlorine, bromine, carbon dioxide, acetone, ethyl acetate, dimethyl sulfoxide, dimethyl formamide, dioxane, tetrahydrofuran, acetonitrile, acetic acid, n-butanol, isopropanol, n-propanol, hexamethylphosphorotriamide, perfluorohydrocarbon, methanol, ethanol, tert-butyl alcohol, formic acid, hydrogen fluoride, ammonia, benzene, carbon tetrachloride, hexane, dichloromethane, methylene chloride, carboxylic acid, saline, standard saline citrate, methane, toluene, chloroform, polyethylene glycol, acetic acid, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, or diethyl ether.

As indicated in FIG. 97, the at least one agent 9710 includes one or more of an adhesive agent, therapeutic agent, reinforcement agent, abrasive, explosive material, or biological remodeling agent. In one embodiment 9720, the adhesive agent, therapeutic agent, reinforcement agent, abrasive, explosive material, or biological remodeling agent is substantially in the form of at least one of an organic or inorganic small molecule, clathrate or caged compound, protocell, coacervate, microsphere, Janus particle, proteinoid, laminate, helical rod, liposome, macroscopic tube, niosome, sphingosome, toroid, vesicular tube, vesicle, small unilamellar vesicle, large unilamellar vesicle, large multilamellar vesicle, multivesicular vesicle, lipid layer, lipid bilayer, micelle, organelle, cell, membrane, nucleic acid, peptide, polypeptide, protein, oligosaccharide, polysaccharide, glycopeptide, glycolipid, sphingolipid, glycosphingolipid, glycoprotein, peptidoglycan, lipid, carbohydrate, metalloprotein, proteoglycan, chromosome, cell nucleus, acid, base, buffer, protic solvent, aprotic solvent, nitric oxide, nitric oxide synthase, nitrous oxide, amino acid, micelle, polymer, bone cement, copolymer, cell receptor, adhesion molecule, cytokine, chemokine, immunoglobulin, antibody, antigen, platelet, extracellular matrix, blood, plasma, cell ligand, zwitterionic material, cationic material, oligonucleotide, nanotube, or piloxymer.

In one embodiment 9730, the one or more explosive materials include at least one of a carbonate, carbon dioxide, nitroglycerine, acid, base, epoxy, acrylic polymer or copolymer, acrylamide polymer or copolymer, urethane, hypoxyapatite, or reactive metal. In one embodiment 9740, the at least one adhesive agent includes one or more of an acrylic polymer or copolymer, acrylamide polymer or copolymer polymer or copolymer, acrylamide polymer or copolymer, polyacrylic acid, epoxy, urethane, gum arabic, polyester, polyhydroxyalkanoate, poly(L-lactic acid), polyglycolide, polylactic acid, polyether, polyol, polyvinylpyrrolidone, pyroxylin, polymethylacrylate-isobutene-monoisopropylmaleate, siloxane polymer, polylactic-co-glycolic-acid, poly-3-hydroxybutyrate, poly-4-hydroxybutyrate, polyhydroxyvalerate, polydydroxyhexanoate, polydyroxyoctanoate, polycaprolactone, poly(e-caprolactone), sialyl Lewis$^x$, heme group, hemoglobin, healon, carboxymethylcellulose, hydroxyapatite, silicone, cadherin, integrin, hydroxyapatite, polyelectrolyte, maleic polyelectrolyte, cellulose, resilin, cyanoacrylate, isocyanate, 2-octyl cyanoacrylate, 2-butyl-n-cyanoacrylate, n-butyl-2-cyanoacrylate, butyl-2-cyanoacrylate, methyl 2-cyanoacrylate, polyisohexylcyanoacrylate, fibrin, thrombin, fibrinogen, hyaluronate, chitin, Factor XIII, Factor XII, silk, nylon, collagen, glycosaminoglycan, selectin, polyurethane, methacrylate, or polysulfide, polyanhydride, polydioxanone, poly-p-dioxanone, silicone, albumin, glutaraldehyde, polyethylene glycol, or gelatin.

As indicated in FIG. 98, the one or more reinforcement agents 9810 include one or more of polyaramid, vinylester matrix, metal, ceramic, fiberglass, cellulose, broad carbide, aromatic polyamide, nylon, silk, rayon, acetate, modacrylic, olefin, acrylic, polyester, aromatic polyester, poly-lactic acid, vinyon, saran, spandex, vinalon, aromatic nylon, vinylidene chloride, modal, polybenzimidazole, sulfur, lyocell, orlon, zylon, high-performance polyethylene, polypyridobenzimidazole, vectran, acrylonitrile rubber, glass, copper, iron, steel, sodium, potassium, calcium, zinc, manganese, carbon, magnesium, silicon, silica, frozen hydrogen oxide ice, plant matter, animal matter, or mineral matter.

In one embodiment 9820, the therapeutic agent includes at least one of an anti-tumor agent, antimicrobial agent, antiviral agent, analgesic, antiseptic, anesthetic, diagnostic agent, anti-inflammatory agent, vaccine, cell growth inhibitor, cell growth promoter, immunogen, antigen, radioactive agent, apoptosis promoting factor, enzymatic agent, angiogenic factor, anti-angiogenic factor, hormone, vitamin, mineral, nutraceutical, cytokine, chemokine, probiotic, coagulant, anti-coagulant, phage, prodrug, prebiotic, blood sugar stabilizer, smooth muscle cell activator, epinephrine, adrenaline, neurotoxin, neuro-muscular toxin, Botulinum toxin type A, microbial cell or component thereof, or virus or component thereof. In one embodiment 9830, the at least one biological remodeling agent includes one or more of a blood cell, chondrocyte, endothelial cell, hepatocyte, keratinocyte, myocyte, osteoblast, osteoclast, osteocyte, mesenchymal cell, stem cell, progenitor cell, or fibroblast.

In one embodiment 9840, the at least one biological remodeling agent includes one or more of calcium phosphate, albumin, cytokine, pegylated cytokine, bone, cartilage, globulin, fibrin, thrombin, glutaraldehyde-crosslinked pericardium, hide powder, hyaluronic acid, hydroxylapatite, keratin, ligament, nitinol, nucleic acid polymers, polyethylene, polyethylene glycol, polyethylene glycol diacrylate, polyethylene terephthalate fiber, polyglycol, polylactate, polytetrafluoroethylene, polylactic acid, polyglycolic acid, polycaprolactone, PURAMATRIX™ self-assembly peptide hydrogel fibers, linear aliphatic polyester, tendon, fibrinogen, hyaluronate, chitin, chitosan, methylcellulose, alginate, hyaluronic acid, agarose, cellulose, polyaldehyde gluronate, Factor XIII, Factor XII, silk, nylon, collagen, silicone, polyurethane, ceramic powder, elastin, pectin, wax, glycosaminoglycan, poly(α-hydroxyacid), selectin, glutaraldehyde, hydrophobic non-glycosylated protein, hydrogel, peptide hydrogel, or gelatin.

In one embodiment 9850, the at least one biological remodeling agent includes one or more of Type I collagen, Type II collagen, Type III collagen, Type VII collagen, Type X collagen, elastin fibers, or soluble elastin.

As indicated in FIG. 99, a system 9900 comprises means 9910 for receiving one or more signals that include information related to accepting input associated with at least one parameter of at least partially constructing or at least partially reconstructing the at least one biological tissue by administering one or more frozen particle compositions (or frozen piercing implements); means 9920 for receiving one or more signals that include information related to evaluating the at least one biological tissue for one or more indicators of tissue formation or growth; and means for 9930 processing the information related to the input associated with at least one parameter of at least partially constructing or at least partially reconstructing the at least one biological tissue and the information related to the evaluating the at least one biological tissue. In one embodiment 9940, the evaluating at least one biological tissue for one or more indicators includes evaluating at least one of an assay, image, or gross assessment of the at least one biological tissue prior to, during, or subsequent to at least one administration of one or more frozen particle compositions (or frozen piercing implements).

In one embodiment 9950, the assay includes at least one technique that includes spectroscopy, microscopy, electrochemical detection, polynucleotide detection, histological examination, biopsy analysis, fluorescence resonance energy transfer, electron transfer, enzyme assay, electrical conductivity, isoelectric focusing, chromatography, immunoprecipitation, immunoseparation, aptamer binding, filtration, electrophoresis, immunoassay, or radioactive assay. In one embodiment 9960, the image includes at least one image acquired by one or more of optical coherence tomography, computer-assisted tomography scan, computed tomography, laser, holography, x-ray crystallography, magnetic resonance imaging, positron-emission tomography scan, ultrasound, x-ray, electrical-impedance monitoring, microscopy, spectrometry, flow cytommetry, radioisotope imaging, thermal imaging, multiphoton calcium-imaging, photography, or in silico generation.

As indicated in FIG. 100, the one or more indicators 10010 of tissue formation or growth include at least one of: cell migration, cell attachment, cell retention, cell differentiation, cell proliferation, apoptosis, diffusion of materials, angiogenesis, nucleic acid expression, protein translation, protein modification, carbohydrate production, carbohydrate secretion, fat production, fat secretion, or protein secretion.

In one embodiment 10020, the input associated with at least one parameter of at least partially constructing or at least partially reconstructing the at least one biological tissue includes one or more of: constitution of the one or more frozen particle compositions (or frozen piercing implements), formulation of the one or more frozen particle compositions (or frozen piercing implements), size of the one or more frozen particle compositions (or frozen piercing implements), shape of the one or more frozen particle compositions (or frozen piercing implements), angle of administration of the one or more frozen particle compositions (or frozen piercing implements), velocity of administration of the one or more frozen particle compositions (or frozen piercing implements), quantity of frozen particle compositions (or frozen piercing implements) administered, rate of administration of more than one frozen particle composition (or frozen piercing implement), spatial location for administration of one or more frozen particle compositions (or frozen piercing implements), temporal location for administration of one or more frozen particle compositions (or frozen piercing implements), method of administration of one or more frozen particle compositions (or frozen piercing implements), timing of administration of one or more frozen particle compositions (or frozen piercing implements), modulation of administration of one or more frozen particle compositions (or frozen piercing implements), deposition of one or more frozen particle compositions (or frozen piercing implements), or rate of deposition of at least one agent.

In one embodiment 10030, the means for receiving one or more signals include means for receiving one or more signals associated with selection of one or more frozen particle compositions (or frozen piercing implements) for administration. In one embodiment 10040, the means for receiving one or more signals include means for receiving one or more signals associated with the selection of at least one of a biological remodeling agent, adhesive agent, abrasive, therapeutic agent, reinforcement agent, or explosive material associated with the one or more frozen particle compositions (or frozen piercing implements).

As indicated in FIG. 101, in one embodiment 10110, the means for administering one or more frozen particle compositions (or frozen piercing implements) include means for administering the one or more frozen particle compositions (or frozen piercing implements) to at least one substrate. In one embodiment 10120, the at least one substrate includes one or more of a cell, tissue, organ, structure, or device. In one embodiment 10130, the one or more frozen particle compositions (or frozen piercing implements) include one or more frozen particles including at least one of hydrogen oxide, nitrogen, oxygen, air, helium, neon, argon, xenon, chlorine, bromine, carbon dioxide, acetone, ethyl acetate, dimethyl sulfoxide, dimethyl formamide, dioxane, tetrahydrofuran, acetonitrile, acetic acid, n-butanol, isopropanol, n-propanol, hexamethylphosphorotriamide, perfluorohydrocarbon, methanol, ethanol, tert-butyl alcohol, formic acid, hydrogen fluoride, ammonia, benzene, carbon tetrachloride, hexane, dichloromethane, methylene chloride, carboxylic acid, saline, standard saline citrate, methane, toluene, chloroform, polyethylene glycol, acetic acid, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, or diethyl ether.

In one embodiment 10140, the at least one agent includes one or more of an adhesive agent, therapeutic agent, reinforcement agent, abrasive, explosive material, or biological remodeling agent. In one embodiment 10150, the adhesive agent, therapeutic agent, reinforcement agent, abrasive, explosive material, or biological remodeling agent is substantially in the form of at least one of an organic or inorganic small molecule, clathrate or caged compound, protocell, coacervate, microsphere, Janus particle, proteinoid, laminate, helical rod, liposome, macroscopic tube, niosome, sphingosome, toroid, vesicular tube, vesicle, small unilamellar vesicle, large unilamellar vesicle, large multilamellar vesicle, multivesicular vesicle, lipid layer, lipid bilayer, micelle, organelle, cell, membrane, nucleic acid, peptide, polypeptide, protein, oligosaccharide, polysaccharide, glycopeptide, glycolipid, sphingolipid, glycosphingolipid, glycoprotein, peptidoglycan, lipid, carbohydrate, metalloprotein, proteoglycan, chromosome, cell nucleus, acid, base, buffer, protic solvent, aprotic solvent, nitric oxide, nitric oxide synthase, nitrous oxide, amino acid, micelle, polymer, bone cement, copolymer, cell receptor, adhesion molecule, cytokine, chemokine, immunoglobulin, antibody, antigen, platelet, extracellular matrix, blood, plasma, cell ligand, zwitterionic material, cationic material, oligonucleotide, nanotube, or piloxymer.

As indicated in FIG. 102, the one or more explosive materials 10210 include at least one of a carbonate, carbon dioxide, nitroglycerine, acid, base, epoxy, acrylic polymer or copolymer, acrylamide polymer or copolymer, urethane, hypoxyapatite, or reactive metal. In one embodiment 10220, the at least one adhesive agent includes one or more of an acrylic polymer or copolymer, acrylamide polymer or copolymer polymer or copolymer, acrylamide polymer or copolymer, polyacrylic acid, epoxy, urethane, gum arabic, polyester, polyhydroxyalkanoate, poly(L-lactic acid), polyglycolide, polylactic acid, polyether, polyol, polyvinylpyrrolidone, pyroxylin, polymethylacrylate-isobutene-monoisopropylmaleate, siloxane polymer, polylactic-co-glycolic-acid, poly-3-hydroxybutyrate, poly-4-hydroxybutyrate, polyhydroxyvalerate, polydydroxyhexanoate, polydyroxyoctanoate, polycaprolactone, poly(e-caprolactone), sialyl Lewis$^x$, heme group, hemoglobin, healon, carboxymethylcellulose, hydroxyapatite, silicone, cadherin, integrin, hydroxyapatite, polyelectrolyte, maleic polyelectrolyte, cellulose, resilin, cyanoacrylate, isocyanate, 2-octyl cyanoacrylate, 2-butyl-n-cyanoacrylate, n-butyl-2-cyanoacrylate, butyl-2-cyanoacrylate, methyl 2-cyanoacrylate, polyisohexylcyanoacrylate, fibrin, thrombin, fibrinogen, hyaluronate, chitin, Factor XIII, Factor XII, silk, nylon, collagen, glycosaminoglycan, selectin, polyurethane, methacrylate, or polysulfide, polyanhydride, polydioxanone, poly-p-dioxanone, silicone, albumin, glutaraldehyde, polyethylene glycol, or gelatin. In one embodiment 10230, the one or more reinforcement agents include one or more of polyaramid, vinylester matrix, metal, ceramic, fiberglass, cellulose, broad carbide, aromatic polyamide, nylon, silk, rayon, acetate, modacrylic, olefin, acrylic, polyester, aromatic polyester, poly-lactic acid, vinyon, saran, spandex, vinalon, aromatic nylon, vinylidene chloride, modal, polybenzimidazole, sulfur, lyocell, orlon, zylon, high-performance polyethylene, polypyridobenzimidazole, vectran, acrylonitrile rubber, glass, copper, iron, steel, sodium, potassium, calcium, zinc, manganese, carbon, magnesium, silicon, silica, frozen hydrogen oxide ice, plant matter, animal matter, or mineral matter. In one embodiment 10240, the therapeutic agent includes at least one of an anti-tumor agent, antimicrobial agent, antiviral agent, analgesic, antiseptic, anesthetic, diagnostic agent, anti-inflammatory agent, vaccine, cell growth inhibitor, cell growth promoter, immunogen, antigen, radioactive agent, apoptosis promoting factor, enzymatic agent, angiogenic factor, anti-angiogenic factor, hormone, vitamin, mineral, nutraceutical, cytokine, chemokine, probiotic, coagulant, anti-coagulant, phage, prodrug, prebiotic, blood sugar stabilizer, smooth muscle cell activator, epinephrine, adrenaline, neurotoxin, neuro-muscular toxin, Botulinum toxin type A, microbial cell or component thereof, or virus or component thereof.

As indicated in FIG. 103, in one embodiment 10310, the at least one biological remodeling agent includes one or more of a blood cell, chondrocyte, endothelial cell, hepatocyte, keratinocyte, myocyte, osteoblast, osteoclast, osteocyte, mesenchymal cell, stem cell, progenitor cell, or fibroblast. In one embodiment 10320, the at least one biological remodeling agent includes one or more of calcium phosphate, albumin, cytokine, pegylated cytokine, bone, cartilage, globulin, fibrin, thrombin, glutaraldehyde-crosslinked pericardium, hide powder, hyaluronic acid, hydroxylapatite, keratin, ligament, nitinol, nucleic acid polymers, polyethylene, polyethylene glycol, polyethylene glycol diacrylate, polyethylene terephthalate fiber, polyglycol, polylactate, polytetrafluoroethylene, polylactic acid, polyglycolic acid, polycaprolactone, PURAMATRIX™ self-assembly peptide hydrogel fibers, linear aliphatic polyester, tendon, fibrinogen, hyaluronate, chitin, chitosan, methylcellulose, alginate, hyaluronic acid, agarose, cellulose, polyaldehyde gluronate, Factor XIII, Factor XII, silk, nylon, collagen, silicone, polyurethane, ceramic powder, elastin, pectin, wax, glycosaminoglycan, poly($\alpha$-hydroxyacid), selectin, glutaraldehyde, hydrophobic non-glycosylated protein, hydrogel, peptide hydrogel, or gelatin. In one embodiment 10330, the at least one biological remodeling agent includes one or more of Type I collagen, Type II collagen, Type III collagen, Type VII collagen, Type X collagen, elastin fibers, or soluble elastin.

In one embodiment 10340, the at least one biological remodeling agent is included as part of a carrier that assists in synthesis or activation of the at least one biological remodeling agent.

As indicated in FIG. 104, a system 10400 comprises means for comparing information 10410 regarding at least one parameter for at least partially constructing or at least partially reconstructing at least one biological tissue of a subject by administering one or more frozen particle compositions (or frozen piercing implements) to the at least one subject and information regarding at least one clinical outcome following receipt by the at least one subject of one or more frozen particle compositions (or frozen piercing implements); and means for providing output information 10420. In one embodiment 10430, the output information is based on the comparison. In one embodiment 10440, the system further comprises means for determining at least one statistical correlation. In one embodiment 10450, the system further comprises means for counting the occurrence of at least one clinical outcome. In one embodiment 10460, the information regarding at least one parameter of at least partially constructing or at least partially reconstructing at least one biological tissue of a subject includes information regarding quantity of cells or tissue at least partially constructed or at least partially reconstructed. In one embodiment 10470, the information regarding at least one parameter of at least partially constructing or at least partially reconstructing at least one biological tissue of a subject includes information regarding at least one cellular or tissue source. In one embodiment 10480, the information regarding at least one parameter of at least partially constructing or at least partially reconstructing at least one biological tissue of a subject includes information regarding at least one abnormal cellular or tissue source. In one embodiment 10490, the information regarding at least one parameter of at least partially constructing or at least partially reconstructing at least one biological tissue of a subject includes information regarding at least one type of cell or tissue.

As indicated in FIG. 105, the at least one agent 10510 includes at least one agent including at least one adhesive agent, abrasive, reinforcement agent, therapeutic agent, biological remodeling agent, or explosive material. In one embodiment 10520, the information regarding at least one parameter of at least partially constructing or at least partially reconstructing at least one biological tissue of a subject includes information regarding at least one dimension of at least one agent deposited. In one embodiment 10530, the information regarding at least one parameter of at least partially constructing or at least partially reconstructing at least one biological tissue of at least one subject includes information regarding at least one dimension of at least one depth, width, or breadth of cellular, tissue, or other material removal or destruction. In one embodiment 10540, the information regarding at least one clinical outcome following receipt by the at least one subject of one or more frozen particle compositions (or frozen piercing implements) includes information regarding two or more subjects with one or more common attributes.

In one embodiment 10550, the one or more common attributes include one or more of genetic attributes, mental attributes, proteomic attributes, phenotypic attributes, or psychological attributes. In one embodiment 10560, the one or more common attributes include one or more of height, weight, medical diagnosis, familial background, results on one or more medical tests, ethnic background, body mass index, age, presence or absence of at least one disease or condition, species, ethnicity, race, allergies, gender, thickness of tissue, blood vessel condition, hair or fur condition, skin condition, tissue condition, muscle condition, organ condition, nerve condition, brain condition, presence or absence of at least one biological, chemical, or therapeutic agent in the subject, pregnancy status, lactation status, genetic profile, proteomic profile, partial or whole genetic sequence, partial or whole proteomic sequence, medical condition, medical history, or blood condition.

As indicated in FIG. 106, the output information 10610 includes at least one of a response signal, comparison code, comparison plot, diagnostic code, treatment code, test code, code indicative of at least one treatment received, code indicative of at least one prescribed treatment step, code indicative of at least one vaccination administered, code indicative of at least one therapeutic agent administered, code indicative of at least one diagnostic agent administered, code indicative of at least one interaction of an administered agent and at least one biological or chemical agent in the subject; a code indicative of at least one dispertion or location of at least one administered agent; code indicative of at least one detection material administered; code indicative of the depth of penetration of an administered agent, code indicative of the depth of deposition of an administered agent, or a code indicative of the condition of at least one location of an administered frozen particle composition (or frozen piercing implement).

In one embodiment 10620, receipt by the at least one subject of one or more frozen particle compositions (or frozen piercing implements) is pursuant to at least one clinical trial. In one embodiment 10630, the method further comprises determining at least one correlation before the administration of the one or more frozen particle compositions (or frozen piercing implements) to the at least one subject.

In one embodiment 10640, the method further comprises creating at least one inclusion criterion and at least one exclusion criterion for a clinical trial involving the one or more frozen particle compositions (or frozen piercing implements). In one embodiment 10650, the method further comprises suggesting the inclusion of one or more of the at least one subject in at least one clinical trial. In one embodiment 10660, the method further comprises suggesting the exclusion of one or more of the at least one subject in at least one clinical trial.

As indicated in FIG. 107, the system further comprises means for using one or more of the at least one correlation 10710 to predict at least one clinical outcome regarding at least one second subject. In one embodiment 10720, the at least one second subject has not received the one or more frozen particle compositions (or frozen piercing implements). In one embodiment 10730, the system further comprises means for predicting at least one clinical outcome involving the at least one second subject, wherein the at least one second subject is a plurality of people; and means for segregating subject identifiers associated with the plurality of people in reference to the predicted at least one clinical outcome. In one embodiment 10740, the system further comprises means for determining the eligibility of the at least one second subject for the at least one clinical trial.

In one embodiment 10750, the one or more frozen particle compositions (or frozen piercing implements) include one or more frozen particles including at least one of hydrogen oxide, nitrogen, oxygen, air, helium, neon, argon, xenon, chlorine, bromine, carbon dioxide, acetone, ethyl acetate, dimethyl sulfoxide, dimethyl formamide, dioxane, tetrahydrofuran, acetronitrile, acetic acid, n-butanol, isopropanol, n-propanol, hexamethylphosphorotriamide, perfluorohydrocarbon, methanol, ethanol, tert-butyl alcohol, formic acid, hydrogen fluoride, ammonia, benzene, carbon tetrachloride, hexane, dichloromethane, methylene chloride, carboxylic acid, saline, standard saline citrate, methane, toluene, chloroform, polyethylene glycol, acetic acid, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, or diethyl ether.

As indicated in FIG. 108, the at least one agent 10810 includes one or more of an adhesive agent, therapeutic agent, reinforcement agent, abrasive, explosive material, or biological remodeling agent. In one embodiment 10820, the adhesive agent, therapeutic agent, reinforcement agent, abrasive, explosive material, or biological remodeling agent is substantially in the form of at least one of an organic or inorganic small molecule, clathrate or caged compound, protocell, coacervate, microsphere, Janus particle, proteinoid, laminate, helical rod, liposome, macroscopic tube, niosome, sphingosome, toroid, vesicular tube, vesicle, small unilamellar vesicle, large unilamellar vesicle, large multilamellar vesicle, multivesicular vesicle, lipid layer, lipid bilayer, micelle, organelle, cell, membrane, nucleic acid, peptide, polypeptide, protein, oligosaccharide, polysaccharide, glycopeptide, glycolipid, sphingolipid, glycosphingolipid, glycoprotein, peptidoglycan, lipid, carbohydrate, metalloprotein, proteoglycan, chromosome, cell nucleus, acid, base, buffer, protic solvent, aprotic solvent, nitric oxide, nitric oxide synthase, nitrous oxide, amino acid, micelle, polymer, bone cement, copolymer, cell receptor, adhesion molecule, cytokine, chemokine, immunoglobulin, antibody, antigen, platelet, extracellular matrix, blood, plasma, cell ligand, zwitterionic material, cationic material, oligonucleotide, nanotube, or piloxymer. In one embodiment 10830, the one or more explosive materials include at least one of a carbonate, carbon dioxide, nitroglycerine, acid, base, epoxy, acrylic polymer or copolymer, acrylamide polymer or copolymer, urethane, hypoxyapatite, or reactive metal. In one embodiment 10840, the at least one adhesive agent includes one or more of an acrylic polymer or copolymer, acrylamide polymer or copolymer polymer or copolymer, acrylamide polymer or copolymer, polyacrylic acid, epoxy, urethane, gum arabic, polyester, polyhydroxyalkanoate, poly(L-lactic acid), polyglycolide, polylactic acid, polyether, polyol, polyvinylpyrrolidone, pyroxylin, polymethylacrylate-isobutene-monoisopropylmaleate, siloxane polymer, polylactic-co-glycolic-acid, poly-3-hydroxybutyrate, poly-4-hydroxybutyrate, polyhydroxyvalerate, polydydroxyhexanoate, polydyroxyoctanoate, polycaprolactone, poly(e-caprolactone), sialyl Lewis$^x$, heme group, hemoglobin, healon, carboxymethylcellulose, hydroxyapatite, silicone, cadherin, integrin, hydroxyapatite, polyelectrolyte, maleic polyelectrolyte, cellulose, resilin, cyanoacrylate, isocyanate, 2-octyl cyanoacrylate, 2-butyl-n-cyanoacrylate, n-butyl-2-cyanoacrylate, butyl-2-cyanoacrylate, methyl 2-cyanoacrylate, polyisohexylcyanoacrylate, fibrin, thrombin, fibrinogen, hyaluronate, chitin, Factor XIII, Factor XII, silk, nylon, collagen, glycosaminoglycan, selectin, polyurethane, methacrylate, or polysulfide, polyanhydride, polydioxanone, poly-p-dioxanone, silicone, albumin, glutaraldehyde, polyethylene glycol, or gelatin.

Figure 109:
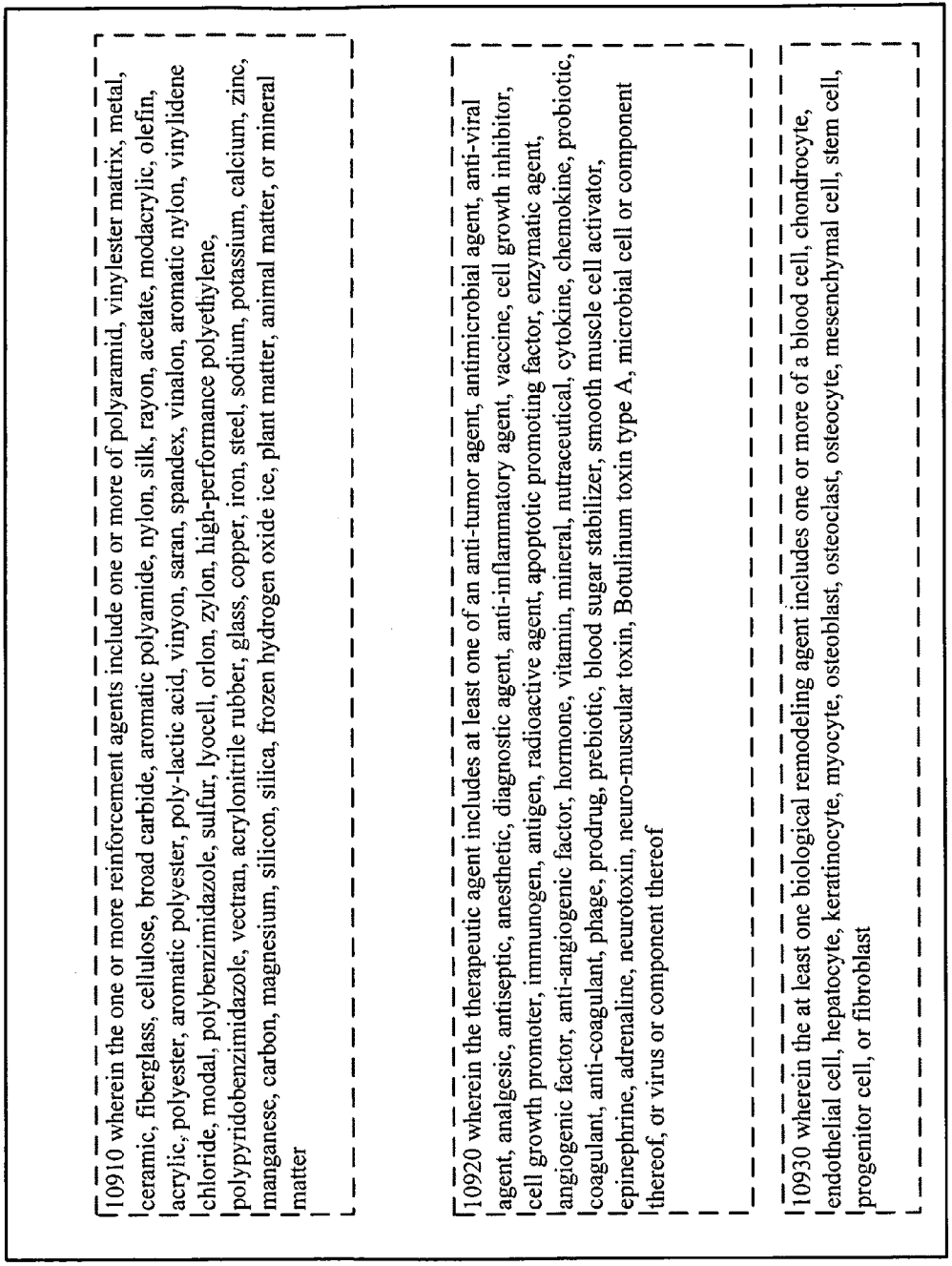
FIG. 109 illustrates a partial view of FIG. 104 in which embodiments may be implemented.

As indicated in FIG. 109, the one or more reinforcement agents 10910 include one or more of polyaramid, vinylester matrix, metal, ceramic, fiberglass, cellulose, broad carbide, aromatic polyamide, nylon, silk, rayon, acetate, modacrylic, olefin, acrylic, polyester, aromatic polyester, poly-lactic acid, vinyon, saran, spandex, vinalon, aromatic nylon, vinylidene chloride, modal, polybenzimidazole, sulfur, lyocell, orlon, zylon, high-performance polyethylene, polypyridobenzimidazole, vectran, acrylonitrile rubber, glass, copper, iron, steel, sodium, potassium, calcium, zinc, manganese, carbon, magnesium, silicon, silica, frozen hydrogen oxide ice, plant matter, animal matter, or mineral matter.

In one embodiment 10920, the therapeutic agent includes at least one of an anti-tumor agent, antimicrobial agent, antiviral agent, analgesic, antiseptic, anesthetic, diagnostic agent, anti-inflammatory agent, vaccine, cell growth inhibitor, cell growth promoter, immunogen, antigen, radioactive agent, apoptosis promoting factor, enzymatic agent, angiogenic factor, anti-angiogenic factor, hormone, vitamin, mineral, nutraceutical, cytokine, chemokine, probiotic, coagulant, anti-coagulant, phage, prodrug, prebiotic, blood sugar stabilizer, smooth muscle cell activator, epinephrine, adrenaline, neurotoxin, neuro-muscular toxin, Botulinum toxin type A, microbial cell or component thereof, or virus or component thereof In one embodiment 10930, the at least one biological remodeling agent includes one or more of a blood cell, chondrocyte, endothelial cell, hepatocyte, keratinocyte, myocyte, osteoblast, osteoclast, osteocyte, mesenchymal cell, stem cell, progenitor cell, or fibroblast.

As indicated in FIG. 110, the at least one biological remodeling agent 11010 includes one or more of calcium phosphate, albumin, cytokine, pegylated cytokine, bone, cartilage, globulin, fibrin, thrombin, glutaraldehyde-crosslinked pericardium, hide powder, hyaluronic acid, hydroxylapatite, keratin, ligament, nitinol, nucleic acid polymers, polyethylene, polyethylene glycol, polyethylene glycol diacrylate, polyethylene terephthalate fiber, polyglycol, polylactate, polytetrafluoroethylene, polylactic acid, polyglycolic acid, polycaprolactone, PURAMATRIX™ self-assembly peptide hydrogel fibers, linear aliphatic polyester, tendon, fibrinogen, hyaluronate, chitin, chitosan, methylcellulose, alginate, hyaluronic acid, agarose, cellulose, polyaldehyde gluronate, Factor XIII, Factor XII, silk, nylon, collagen, silicone, polyurethane, ceramic powder, elastin, pectin, wax, glycosaminoglycan, poly($\alpha$-hydroxyacid), selectin, glutaraldehyde, hydrophobic non-glycosylated protein, hydrogel, peptide hydrogel, or gelatin. In one embodiment 11020, the at least one biological remodeling agent includes one or more of Type I collagen, Type II collagen, Type III collagen, Type VII collagen, Type X collagen, elastin fibers, or soluble elastin. In one embodiment 11030, the at least one biological remodeling agent is included as part of a carrier that assists in synthesis or activation of the at least one biological remodeling agent.

As indicated in FIGS. 111-113, one embodiment relates to a system 11100 comprising means for predicting a clinical outcome of one or more frozen particle composition (or frozen piercing implement) treatments for at least one first subject, including means 11120 for determining a similarity or a dissimilarity in information regarding at least one parameter for at least partially constructing or at least partially reconstructing at least one biological tissue of at least one first subject by administering one or more frozen particle compositions (or frozen piercing implements) to the at least one first subject with information regarding at least one parameter of at least partially constructing or at least partially reconstructing at least one biological tissue of at least one second subject; wherein 11130 the at least one second subject attained a clinical outcome following receipt of the one or more frozen particle compositions (or frozen piercing implements); and 11140 means for providing output information. In one embodiment 11150, the output information is based on the determination.

In one embodiment 11160, the information regarding at least one parameter of at least partially constructing or at least partially reconstructing at least one biological tissue of at least one second subject includes information regarding quantity of cells or tissue at least partially constructed or at least partially reconstructed. In one embodiment 11170, the information regarding at least one parameter of at least partially constructing or at least partially reconstructing at least one biological tissue of at least one first subject includes information regarding at least one cellular or tissue source. In one embodiment 11180, the information regarding at least one parameter of at least partially constructing or at least partially reconstructing at least one biological tissue of at least one first subject includes information regarding at least one abnormal cellular or tissue source.

As indicated in FIG. 112, in one embodiment 11210, the information regarding at least one parameter of at least partially constructing or at least partially reconstructing at least one biological tissue of at least one first subject includes information regarding at least one type of cell or tissue. In one embodiment 11220 the information regarding at least one parameter of at least partially constructing or at least partially reconstructing at least one biological tissue of at least one second subject includes information regarding at least one type of cell or tissue. In one embodiment 11230 the at least one agent includes one or more of an adhesive agent, abrasive, reinforcement agent, therapeutic agent, biological remodeling agent, or explosive material. In one embodiment 11240 the information regarding at least one parameter of at least partially constructing or at least partially reconstructing at least one biological tissue of at least one first subject includes information regarding at least one dimension of at least one agent deposited. In one embodiment 11250 the information regarding at least one parameter of at least partially constructing or at least partially reconstructing at least one biological tissue of at least one second subject includes information regarding at least one dimension of at least one agent deposited. In one embodiment 11260, the information regarding at least one parameter of at least partially constructing or at least partially reconstructing at least one biological tissue of at least one second subject includes information regarding at least one dimension of at least one depth, width, or breadth of cellular, tissue, or other material removal or destruction. In one embodiment 11270, the information regarding at least one parameter of at least partially constructing or at least partially reconstructing at least one biological tissue of at least one first subject includes information regarding at least one dimension of at least one depth, width, or breadth of cellular, tissue, or other material removal or destruction.

As indicated in FIG. 113, in one embodiment 11310, the information regarding at least one clinical outcome following receipt by the at least one second subject of one or more frozen particle compositions (or frozen piercing implements) includes information regarding two or more subjects with one or more common attributes. In one embodiment 11320, the one or more common attributes include but are not, limited to genetic attributes, mental attributes, proteomic attributes, phenotypic attributes, or psychological attributes. In one embodiment 11330, the one or more common attributes include at least one of height; weight; medical diagnosis; familial background; results on one or more medical tests; ethnic background; body mass index; age; presence or absence of at least one disease or condition; species; ethnicity; race; allergies; gender; thickness of epidermis; thickness of dermis; thickness of stratum corneum; keratin deposition; collagen deposition; blood vessel condition; skin condition; hair or fur condition; muscle condition; tissue condition; organ condition; nerve condition; brain condition; presence or absence of at least one biological, chemical, or therapeutic agent in the subject; pregnancy status; lactation status; medical history; genetic profile; proteomic profile; partial or whole genetic sequence; partial or whole proteomic sequence; lymph condition, medical history, or blood condition.

In one embodiment 11340, the output information includes at least one of a response signal, a comparison code, a comparison plot, a diagnostic code, a treatment code, a test code, a code indicative of at least one treatment received, a code indicative of at least one prescribed treatment step, a code indicative of at least one vaccination delivered; a code indicative of at least one therapeutic agent delivered; a code indicative of at least one diagnostic agent delivered; a code indicative of at least one interaction of a delivered agent and at least one biological or chemical agent in the subject; a code indicative of at least one dispersion or location of at least one delivered agent; a code indicative of at least one detection material delivered; a code indicative of the depth of penetration of a delivered agent; or a code indicative of the condition of at least one location of a delivered or administered frozen particle composition (or frozen piercing implement) 2700.

As indicated in FIG. 114, in one embodiment 11410, receipt by the at least one second subject of one or more frozen particle compositions (or frozen piercing implements) is pursuant to at least one clinical trial. In one embodiment 11420, the system further comprises means for determining at least one correlation before the administration of the one or more frozen particle compositions (or frozen piercing implements) to the at least one first subject. In one embodiment 11430, the system further comprises means for creating at least one inclusion criterion and at least one exclusion criterion for a clinical trial involving the one or more frozen particle compositions (or frozen piercing implements). In one embodiment 11440, the system further comprises means for suggesting the inclusion of one or more of the at least one first subject in at least one clinical trial.

In one embodiment 11450, the system further comprises means for suggesting the exclusion of one or more of the at least one first subject in at least one clinical trial. In one embodiment 11460, the system further comprises means for using one or more of the at least one first subject in at least one clinical trial. In one embodiment 11470, the at least one second subject has not received the one or more frozen particle compositions (or frozen piercing implements). In one embodiment 11480, the system further comprises means for predicting at least one clinical outcome involving the at least one second subject, wherein the at least one second subject is a plurality of people; and means for segregating subject identifiers associated with the plurality of people in reference to the predicted at least one clinical outcome.

As indicated in FIG. 115, in one embodiment 11510, the one or more frozen particle compositions (or frozen piercing implements) include at least one of hydrogen oxide, nitrogen, oxygen, air, helium, neon, argon, xenon, chlorine, bromine, carbon dioxide, acetone, ethyl acetate, dimethyl sulfoxide, dimethyl formamide, dioxane, tetrahydrofuran, acetonitrile, acetic acid, n-butanol, isopropanol, n-propanol, hexamethylphosphorotriamide, perfluorohydrocarbon, methanol, ethanol, tert-butyl alcohol, formic acid, hydrogen fluoride, ammonia, benzene, carbon tetrachloride, hexane, dichloromethane, methylene chloride, carboxylic acid, saline, standard saline citrate, methane, toluene, chloroform, polyethylene glycol, acetic acid, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, or diethyl ether.

In one embodiment 11520, the one or more frozen particle compositions (or frozen piercing implements) include one or more of an adhesive agent, therapeutic agent, reinforcement agent, abrasive, explosive material, or biological remodeling agent.

In one embodiment 11530, the adhesive agent, therapeutic agent, reinforcement agent, abrasive, explosive material, or biological remodeling agent includes at least one of an organic or inorganic small molecule, clathrate or caged compound, protocell, coacervate, microsphere, Janus particle, proteinoid, laminate, helical rod, liposome, macroscopic tube, niosome, sphingosome, toroid, vesicular tube, vesicle, small unilamellar vesicle, large unilamellar vesicle, large multilamellar vesicle, multivesicular vesicle, lipid layer, lipid bilayer, micelle, organelle, cell, membrane, nucleic acid, peptide, polypeptide, protein, oligosaccharide, polysaccharide, glycopeptide, glycolipid, sphingolipid, glycosphingolipid, glycoprotein, peptidoglycan, lipid, carbohydrate, metalloprotein, proteoglycan, chromosome, cell nucleus, acid, base, buffer, protic solvent, aprotic solvent, nitric oxide, nitric oxide synthase, nitrous oxide, amino acid, micelle, polymer, bone cement, copolymer, cell receptor, adhesion molecule, cytokine, chemokine, immunoglobulin, antibody, antigen, platelet, extracellular matrix, blood, plasma, cell ligand, zwitterionic material, cationic material, oligonucleotide, nanotube, or piloxymer.

In one embodiment 11540, the one or more explosive materials include at least one of a carbonate, carbon dioxide, nitroglycerine, acid, base, epoxy, acrylic polymer or copolymer, acrylamide polymer or copolymer, urethane, hypoxyapatite, or reactive metal.

In one embodiment 11610, the at least one adhesive agent includes one or more of an acrylic polymer or copolymer, acrylamide polymer or copolymer polymer or copolymer, acrylamide polymer or copolymer, polyacrylic acid, epoxy, urethane, gum arabic, polyester, polyhydroxyalkanoate, poly (L-lactic acid), polyglycolide, polylactic acid, polyether, polyol, polyvinylpyrrolidone, pyroxylin, polymethylacrylate-isobutene-monoisopropylmaleate, siloxane polymer, polylactic-co-glycolic-acid, poly-3-hydroxybutyrate, poly-4-hydroxybutyrate, polyhydroxyvalerate, polydydroxyhexanoate, polydyroxyoctanoate, polycaprolactone, poly(e-caprolactone), sialyl Lewis$^x$, heme group, hemoglobin, healon, carboxymethylcellulose, hydroxyapatite, silicone, cadherin, integrin, hydroxyapatite, polyelectrolyte, maleic polyelectrolyte, cellulose, resilin, cyanoacrylate, isocyanate, 2-octyl cyanoacrylate, 2-butyl-n-cyanoacrylate, n-butyl-2-cyanoacrylate, butyl-2-cyanoacrylate, methyl 2-cyanoacrylate, polyisohexylcyanoacrylate, fibrin, thrombin, fibrinogen, hyaluronate, chitin, Factor XIII, Factor XII, silk, nylon, collagen, glycosaminoglycan, selectin, polyurethane, methacrylate, or polysulfide, polyanhydride, polydioxanone, poly-p-dioxanone, silicone, albumin, glutaraldehyde, polyethylene glycol, or gelatin.

In one embodiment 11620, the one or more reinforcement agents include one or more of polyaramid, vinylester matrix, metal, ceramic, fiberglass, cellulose, broad carbide, aromatic polyamide, nylon, silk, rayon, acetate, modacrylic, olefin, acrylic, polyester, aromatic polyester, poly-lactic acid, vinyon, saran, spandex, vinalon, aromatic nylon, vinylidene chloride, modal, polybenzimidazole, sulfur, lyocell, orlon, zylon, high-performance polyethylene, polypyridobenzimidazole, vectran, acrylonitrile rubber, glass, copper, iron, steel, sodium, potassium, calcium, zinc, manganese, carbon, magnesium, silicon, silica, frozen hydrogen oxide ice, plant matter, animal matter, or mineral matter

11630 wherein the therapeutic agent includes at least one of an anti-tumor agent, antimicrobial agent, anti-viral agent, analgesic, antiseptic, anesthetic, diagnostic agent, anti-inflammatory agent, vaccine, cell growth inhibitor, cell growth promoter, immunogen, antigen, radioactive agent, apoptosis promoting factor, enzymatic agent, angiogenic factor, anti-angiogenic factor, hormone, vitamin, mineral, nutraceutical, cytokine, chemokine, probiotic, coagulant, anti-coagulant, phage, prodrug, prebiotic, blood sugar stabilizer, smooth muscle cell activator, epinephrine, adrenaline, neurotoxin, neuro-muscular toxin, Botulinum toxin type A, microbial cell or component thereof, or virus or component thereof.

In one embodiment 11710, the at least one biological remodeling agent includes one or more of a blood cell, chondrocyte, endothelial cell, hepatocyte, keratinocyte, myocyte, osteoblast, osteoclast, osteocyte, mesenchymal cell, stem cell, progenitor cell, or fibroblast.

In one embodiment 11720, the at least one biological remodeling agent includes one or more of calcium phosphate, albumin, cytokine, pegylated cytokine, bone, cartilage, globulin, fibrin, thrombin, glutaraldehyde-crosslinked pericardium, hide powder, hyaluronic acid, hydroxylapatite, keratin, ligament, nitinol, nucleic acid polymers, polyethylene, polyethylene glycol, polyethylene glycol diacrylate, polyethylene terephthalate fiber, polyglycol, polylactate, polytetrafluoroethylene, polylactic acid, polyglycolic acid, polycaprolactone, PURAMATRIX™ self-assembly peptide hydrogel fibers, linear aliphatic polyester, tendon, fibrinogen, hyaluronate, chitin, chitosan, methylcellulose, alginate, hyaluronic acid, agarose, cellulose, polyaldehyde gluronate, Factor XIII, Factor XII, silk, nylon, collagen, silicone, polyurethane, ceramic powder, elastin, pectin, wax, glycosaminoglycan, poly($\alpha$-hydroxyacid), selectin, glutaraldehyde, hydrophobic non-glycosylated protein, hydrogel, peptide hydrogel, or gelatin.

In one embodiment 11730, the at least one biological remodeling agent includes one or more of Type I collagen, Type II collagen, Type III collagen, Type VII collagen, Type X collagen, elastin fibers, or soluble elastin.

In one embodiment 11740, the at least one biological remodeling agent is included as part of a carrier that assists in synthesis or activation of the at least one biological remodeling agent.

Figure 118:
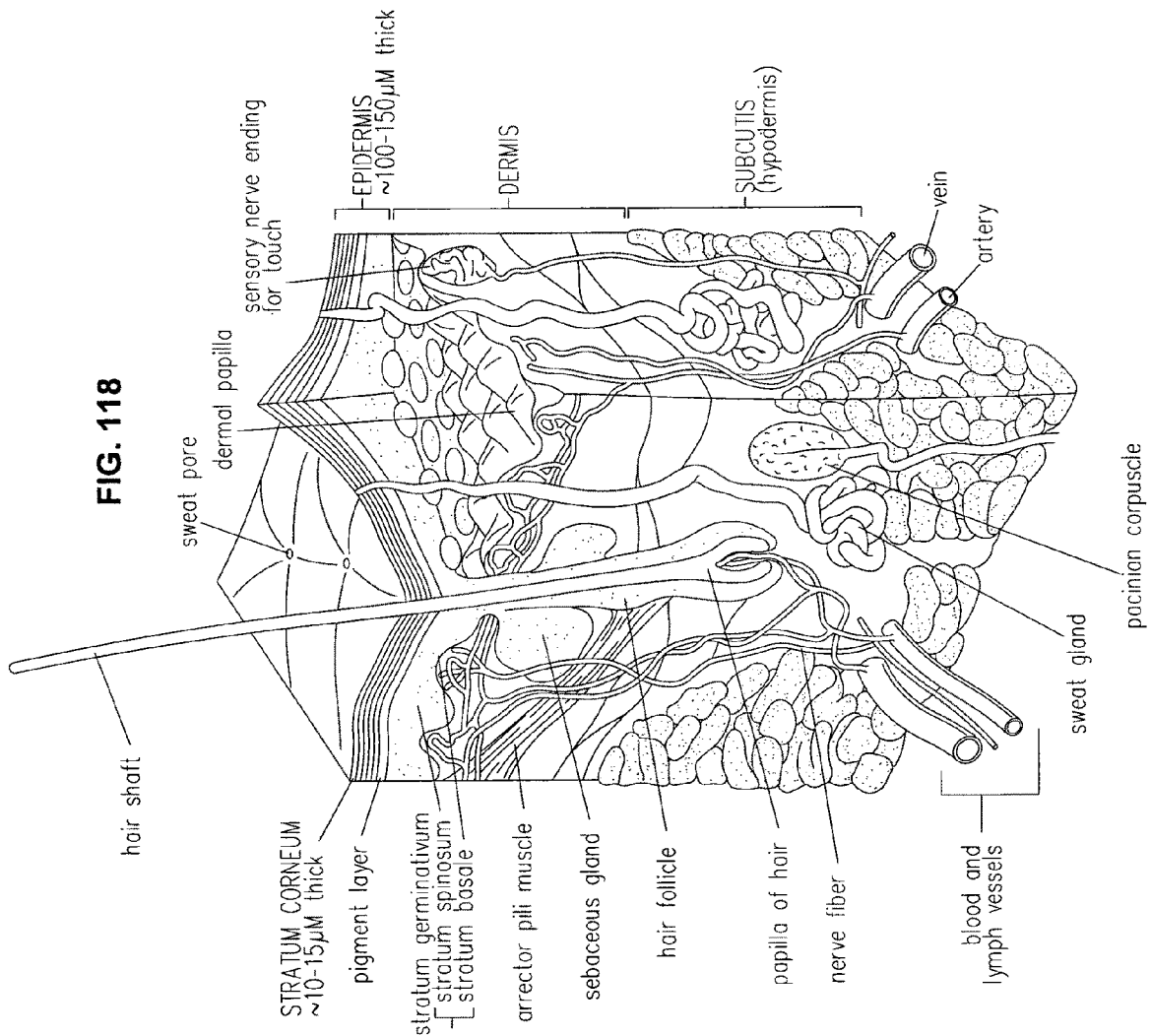
FIG. 118 illustrates a partial cross-sectional view of mammalian skin.

As illustrated in FIG. 118, a cross-section of animal skin (e.g., human skin, as shown) has multiple layers, including but not limited to the stratum corneum (approximately 10-15 microns thick) as part of the epidermis (approximately 100-150 microns thick). In one embodiment, at least one frozen particle composition, at least one frozen piercing implement, or at least one frozen piercing implement device is administered to a substrate, such as skin, and is configured to penetrate the stratum corneum or entire epidermis, without reaching the underlying nerves (e.g., "sensory nerve ending for touch," of FIG. 118). In one embodiment, at least one agent (e.g., an anesthetic) is included in the at least one frozen particle composition, at least one frozen piercing implement, or at least one frozen piercing implement device that at least partially disrupts nerve function in such a manner that even if further frozen particle compositions, frozen piercing implements, or frozen piercing implement devices are administered, pain is reduced or eliminated regardless of the depth of penetration.

Figure 119:
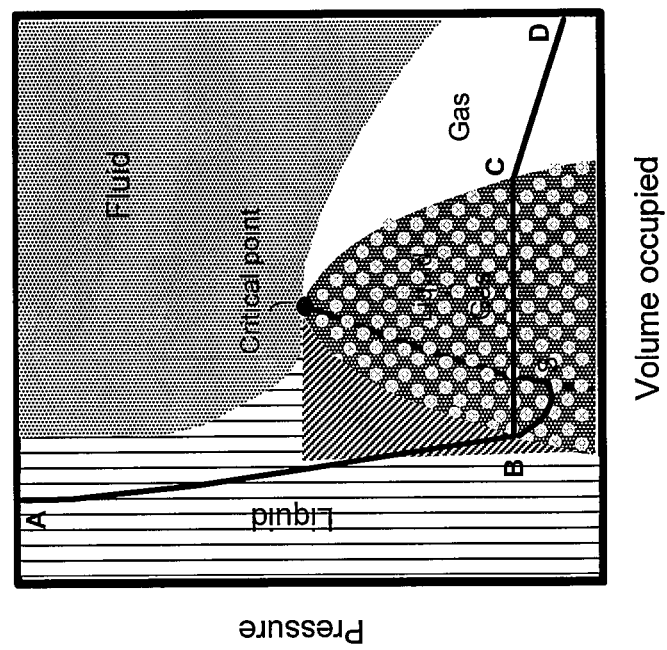
FIG. 119 illustrates a general phase diagram, including the critical point and sinodal curve.

As illustrated in FIG. 119, in one embodiment, at least one frozen particle composition, frozen piercing implement, or frozen piercing implement device is administered by propelling under a rapid expansion force (e.g., by way of at least one outlet) which may be the result of at least one explosion. In one embodiment, the explosion includes flash-boiling the at least one cooling liquid. In one embodiment, the explosion includes a boiling liquid expanding vapor explosion (BLEVE) of the at least one cooling liquid.

The BLEVE of the cooling liquid can be calculated according to standard techniques. For example, in FIG. 119, a diagram of the relationship between the pressure for a substance in various phases of liquid and gas, and the volume occupied by that substance. See, for example, the worldwide web at: criticalprocesses.com/BLEVE.htm, the subject matter of which is incorporated herein by reference. The line from point A to B indicates the substance is in liquid form and as the volume the substance occupies expands, the pressure falls until it reaches the vapor pressure of the liquid (B) for a particular temperature. Id. The liquid then evaporates to become a liquid-gas mixture, and the pressure stays constant at the vapor pressure. Eventually the substance reaches point C, where the liquid has been converted to gas phase, and the pressure drops with further expansion. Id.

If the pressure falls suddenly, the substance can become unstable liquid along the line from point B to point S. Id. S is known as a spinodal point, and the slope of the line at this point is zero (i.e. $(\partial p/\partial V)_\tau=0$). Id. The dotted line connects spinodal points at different temperatures, forming the spinodal curve, and ending at the critical point. Id. During a BLEVE, density variations develop spontaneously and homogenously into liquid and gas regions. Id. The rise in pressure on the vapor pressure line from point B to C occurs rapidly, and a BLEVE results. Id.

Figure 120:
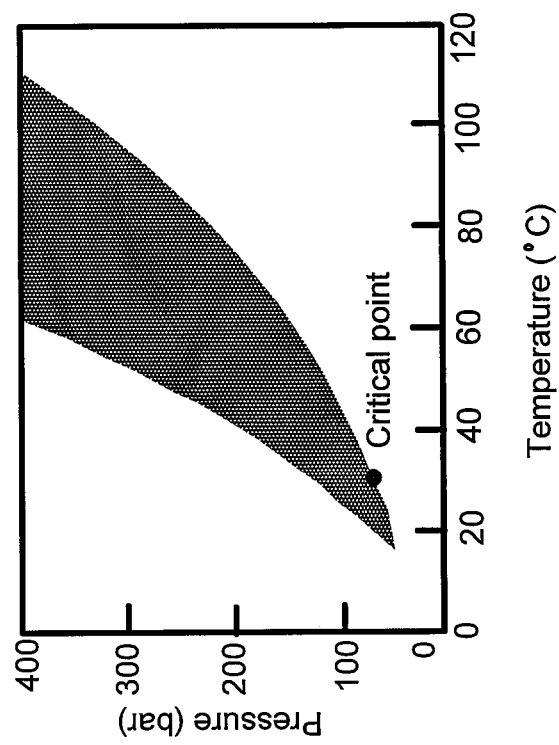

As illustrated in FIG. 120, for carbon dioxide, conditions for inducing a BLEVE can be calculated for a particular substance since the entropy of the system remains constant. Id. Thus, conditions that induce a BLEVE for any particular substance are found along the spinodal curve for that substance, between 1 bar and the critical point where the curve ends. Id.

As illustrated in FIG. 121, various embodiments of frozen particle compositions or frozen piercing implements (alone, or as part of a device), include different sizes, shapes, or configurations. In one embodiment (as depicted in FIG. 121A), the frozen particle composition or frozen piercing implement includes a tip (or distal end), a shaft, and a base (or proximal end). As indicated in FIG. 121A, the height, width, or breadth can vary according to particular parameters for making or administering the at least one frozen particle composition or frozen piercing implement. In one embodiment, multiple different frozen particle compositions or frozen piercing implements are included in a device, wherein multiple different parameters (including but not limited to size, shape, density, height, width, breadth, or configuration) are included.

In one embodiment, FIG. 121B includes a frozen particle composition or frozen piercing implement with at least one cavity. As disclosed herein, in one embodiment, the at least one cavity includes at least one solid, liquid, gas, or other form of substance. In one embodiment, the at least one cavity includes at least one agent. Various non-limiting examples of agents are described herein. In one embodiment, the at least one frozen particle composition or frozen piercing implement includes at least one channel. In one embodiment, as indicated in FIG. 121B, the at least one frozen particle composition or frozen piercing implement includes multiple cavities. As illustrated in FIG. 121C, in one embodiment, the at least one frozen particle composition or frozen piercing implement includes at least one of a tapered, mushroom shaped, beveled, serated, or other configuration (respectively from left to right in the figure).

Figure 122:
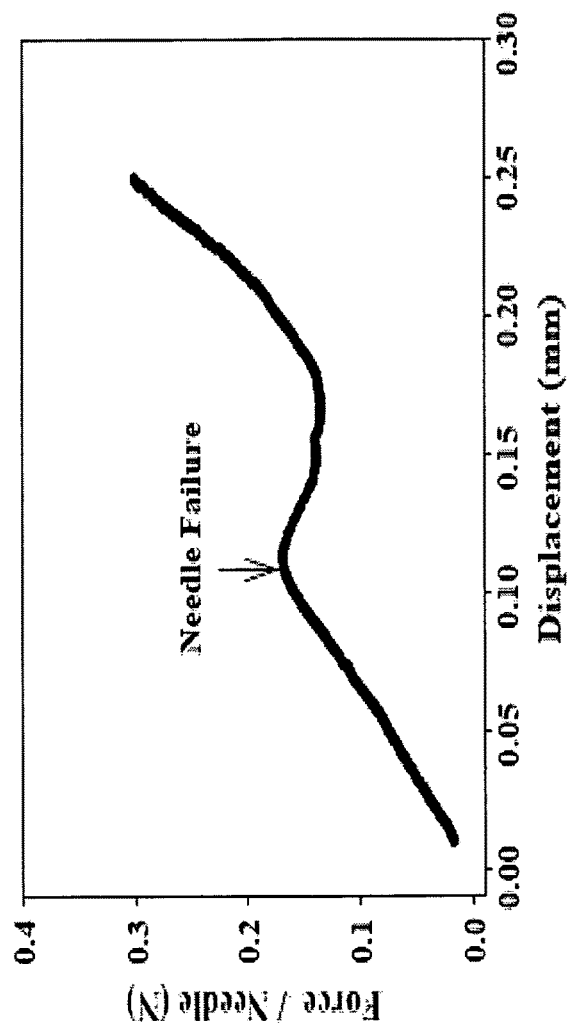

As illustrated in FIG. 122, strength of frozen piercing implements is indicated by a sudden drop in force at the point of failure. See, for example, Park et al., Ibid. The maximum force just prior to the sudden drop defines the force of the piercing implement failure. As shown in FIG. 122, according to the published study, microneedles containing polylactic acid with a height of approximately 800 μm and a base diameter of approximately 200 μm display a failure force of approximately 0.50 Newtons/needle, which is approximately three times greater than the force needed for insertion into skin. See, for example, Park et al, J. Contr. Rel., vol. 104, pp. 51-66 (2005), which is incorporated herein by reference.

Figure 123:
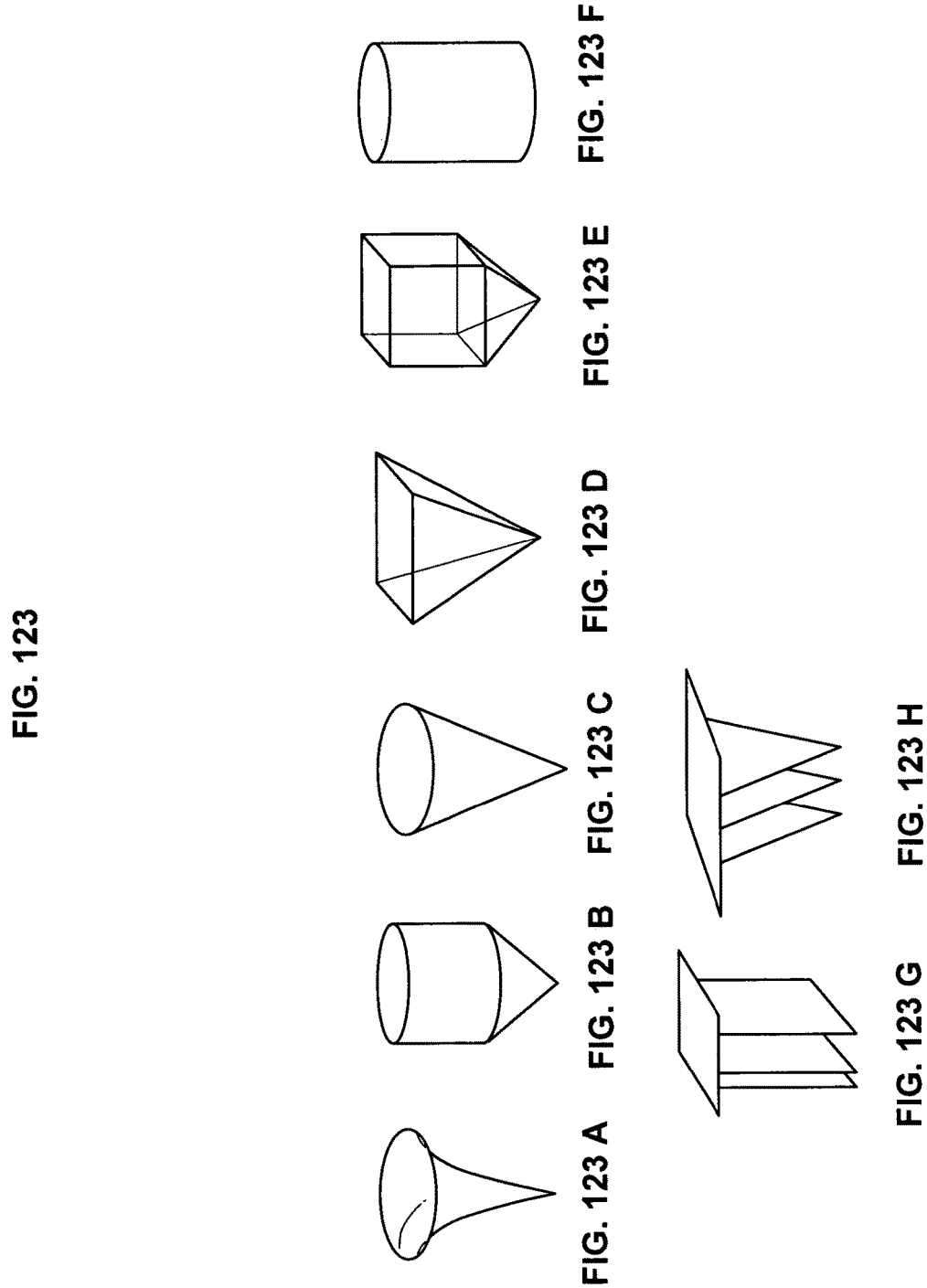

As illustrated in FIG. 123, in one embodiment, at least one frozen particle composition, frozen piercing implement, or frozen piercing implement device includes at least one shape or configuration illustrated. In one embodiment, the at least one frozen particle composition, or frozen piercing implement includes at least one cavity or channel. For example, FIG. 123A illustrates a conical shape, FIG. 123B illustrates a cylindrical and conical hybrid, FIG. 123C indicates another conical shape, FIG. 123D illustrates a pyramidal shape, FIG. 123E illustrates a cuboidal and pyramidal hybrid, FIG. 123F illustrates a cylindrical shape, FIG. 123G illustrates several planar rectangular shapes attached to a support structure (e.g., for a frozen piercing implement device), and FIG. 123H illustrates several planar triangular shapes attached to a support structure (e.g., for a frozen piercing implement device).

As illustrated in FIG. 124, in one embodiment at least one frozen piercing implement device 12400 includes multiple frozen piercing implements contacting a support structure. In one embodiment, at least one frozen piercing implement is made by contacting at least one fluid 12420 with at least one frame 12430 defining at least one projection, raising the at least one frame approximately vertically from the at least one fluid, such that the surface tension of the at least one fluid is maintained, forming at least one fluid extension 12420 (FIGS. 124D-G); exposing the at least one fluid extension to conditions for a time sufficient to solidify the at least one fluid extension 12420 (FIGS. 124D-G) in the form of at least one frozen particle composition or frozen piercing implement. In one embodiment, the fluid 12420 is located on at least one support structure 12410. Subsequent to making the at least one frozen piercing implement from the fluid extension, the implement can remain on the support structure, or be removed.

Figure 125:
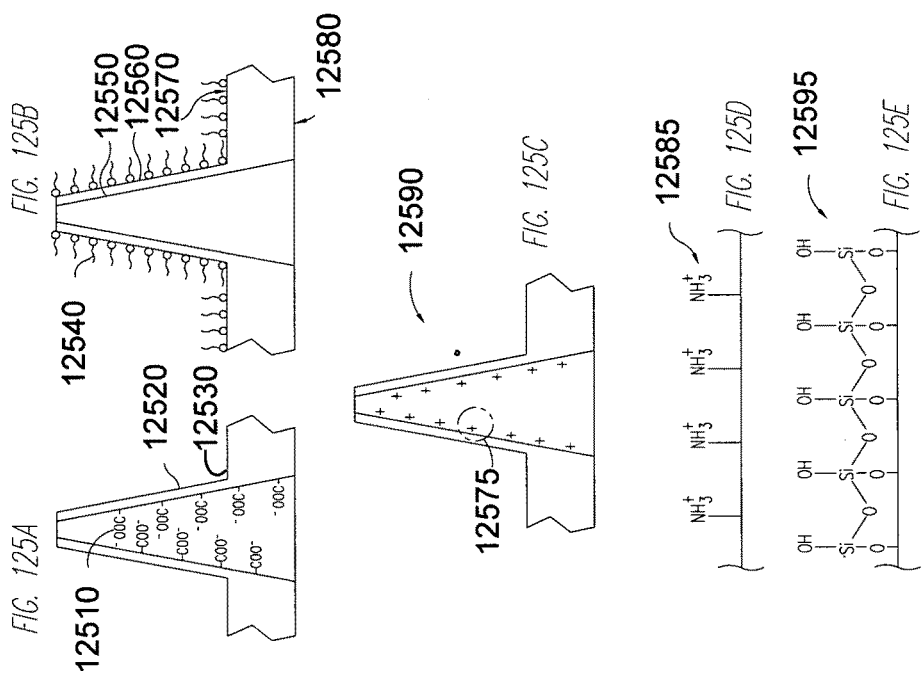

As illustrated in FIG. 125, at least one frozen piercing implement includes at least one functionalized surface 12560. In one embodiment (FIG. 125 A) at least one inner surface 12550 of the at least one frozen piercing implement 12590 is functionalized. For example, the inner surface may include at least one carboxylic group 12510, capable of providing a surface tending toward a hydrophilic, or anionic surface. In one embodiment (FIG. 125 B) at least one outer surface 12560 of the at least one frozen piercing implement is functionalized. For example, the outer surface may include at least one lipid group 12540, capable of providing a surface tending toward a hydrophobic, or lipophilic surface. In one embodiment (FIGS. 125 C and 125 D) at least one inner surface of the at least one frozen piercing implement is functionalized. For example, the inner surface may include at least one amino group 12585, capable of providing a surface tending toward a hydrophilic, cationic surface. In one embodiment (FIG. 125 E) at least one surface of the frozen piercing implement includes at least one silane group 12595. For example, the surface may be modified to include at least one alkoxysilane of Formula I: $(R^2)Si(R^1)_3$ (Formula I), wherein $R^1$ includes at least one of a chlorine, acetoxy, or alkoxy, and $R^2$ includes at least one of an organofunctional group (e.g. methyl, phenyl, isobutyl, octyl, $-NH(CH_2)_3NH_2$, epoxy, methacryl, etc.), alkyl, aryl, amino, methacryloxy, or epoxy. In one embodiment, the Formula I silanized surface may be capable of imparting at least one property of nonpolar, hydrophilic, hydrophobic, organophilic, lipophilic, lipophobic, acidic, basic, neutral, increased or decreased permeability, or combinations thereof. See, for example, U.S. Patent Application Publication No. 2008/0078376, which is incorporated herein by reference.

In one embodiment, the inner surface 12550 is functionalized with a charged group 12575. In one embodiment, the underside of the support structure 12580 is in fluid communication with at least one compartment (not shown). In one embodiment, the topside of the support structure 12530 can also be functionalized 12570.

In one embodiment, the at least one functionalized surface 12560 includes one or more functionalities including one or more of charge functionality, hydrophobic functionality, hydrophilic functionality, chemically reactive functionality, organo functionality, or wetability. In one embodiment, the at least one functionalized surface 12560 includes one or more functional groups including at least one of an agent, alcohol, hydroxyl, amine, aldehyde, dye, ketone, carbonyl, thiol, alkoxysilane, phosphate, carboxyl, carboxylic acid, carboxylate, nucleic acid, amino acid, polypeptide, protein, lipid, carbohydrate, metal, $-NH_3^+$, $-COOH$, $-COO-$, $-SO_3$, $CH_2N^{+(CH_3)}{}_3$, $-(CH_2)_xCH_3$, $-C((CH_2)_xCF_3)_3$, $-CH_2N(C_2H_5)_2$, $-NH_2$, $-(CH_2)_xCOOH$, $-(OCH_2CH_2)_xCH_3$, $-SiOH$, or $-OH$.

In one embodiment, the at least one functionalized surface 12560 includes at least part of an outer surface. In one embodiment, the at least one functionalized surface includes at least part of an inner surface 12550.

As illustrated in FIG. 126, in one embodiment, at least one frozen particle composition, frozen piercing implement, or component of a frozen piercing implement device 12600 includes at least one distal end, or tip, 12810, and a proximal end, or base end, 12820. In one embodiment, the frozen particle composition or frozen piercing implement includes at least one channel 12800. In one embodiment, the at least one channel includes at least one inner surface 12830 and at least one outer surface 12860. In one embodiment, the frozen particle composition or frozen piercing implement are substantially solid in form. As indicated by FIGS. 126A through 126G, the frozen particle compositions or frozen piercing implements can take a variety of forms, shapes, or configurations. For example, FIGS. 126C-126D illustrate at least one frozen piercing implement including at least one beveled end. In another example, FIG. 126G illustrates at least one frozen piercing implement including at least one jagged end. In another example, FIG. 126D includes at least one frozen piercing implement including at least one blunt or substantially flattened end. In another example, FIGS. 126A, 126B, and 126F illustrate at least one frozen piercing implement including at least one tapered end.

As illustrated in FIG. 127 A, in one embodiment, an array device comprises a body portion 12720, including a support structure having a surface 12725; and a plurality of piercing implements 12750 extending substantially outward from the support structure 12725. In one embodiment, the plurality of piercing implements 12750 includes at least one frozen piercing implement 12755. In one embodiment, the device includes at least one compartment 12700 configured to hold at least one agent to be administered to the at least one substrate, or at least one material extracted from the at least one substrate. In one embodiment, at least one piercing implement 12755 is in fluid communication with the at least one compartment 12700, and includes a distal end opening (e.g., a port) 12740 from which at least one agent can be administered to the at least one substrate, or at least one material can be extracted from the at least one substrate. In one embodiment, the device includes at least one backing member 12710, which can be a portion of the overall support structure 12725, and can function as an outer portion of the support structure (e.g., in at least one embodiment, the compartment is disposable and the backing member and/or remaining support structure is recyclable or reusable). In one embodiment, the backing member is an outer shell. In one embodiment, the backing member is multi-layered (e.g., polymeric or paper-based materials). In one embodiment, a fastening mechanism (e.g., adhesive, VELCRO®, etc.) 12730 is included to attach the device to the at least one substrate (e.g., the surface of a subject or device, etc.). In one embodiment, the fastening mechanism 12730 is at least temporarily covered by a device cover 12760.

In one embodiment, the plurality of sterile frozen piercing implements 12750 have at least one major dimension of approximately one centimeter or less, approximately one millimeter or less, approximately one micrometer or less, approximately one nanometer, or any value therebetween.

In one embodiment, the plurality of sterile frozen piercing implements 12750 extends substantially perpendicular to the support structure. In one embodiment, the plurality of sterile frozen piercing implements 12750 extends through the surface of the support structure 12725. In one embodiment, the plurality of sterile frozen piercing implements 12750 extends from the surface of the support structure 12725. In one embodiment, the support structure 12725 includes at least one frozen composition. In one embodiment, the support structure 12725 includes at least one frozen composition also included in at least one frozen piercing implement 12755. In one embodiment, the support structure 12725 is at least partially frozen. In one embodiment, the support structure 12725 and at least one frozen piercing implement 12755 of the plurality of frozen piercing implements 12750 include at least one common constituent. In one embodiment, the plurality of frozen piercing implements 12750 are positioned substantially parallel to each other.

In one embodiment, the plurality of frozen piercing implements 12750 are positioned substantially in a predetermined spatial pattern. In one embodiment, the predetermined spatial pattern is at least partially periodic. See FIG. 131 for various non-limiting examples of spatial patterns for array devices, including at least partially periodic patterns.

In one embodiment, the plurality of frozen piercing implements 12750 includes an area density of implements greater than or approximately equal to 1 µm, greater than or approximately equal to 10 µm, greater than or approximately equal to 50 µm, greater than or approximately equal to 100 µm, greater than or approximately equal to 500 µm, greater than or approximately equal to 1 mm, greater than or approximately equal to 10 mm, greater than or approximately equal to 50 mm, greater than or approximately equal to 100 mm, greater than or approximately equal to 500 mm, greater than or approximately equal to 1 cm, or any value there between. In one embodiment, the plurality of frozen piercing implements 12750 includes approximately the same length.

In one embodiment, the length of a frozen piercing implement is associated with the position or location of the frozen piercing implement in the array device. For some non-limiting examples, longer or taller implements may be in the center, while shorter implements are around the periphery; longer or taller implements may be in a particular pattern within the spatial pattern of the array device, while shorter implements are in a different particular pattern; implements in the center may include different agents that extend their length (e.g. reinforcement agents); or implements along one particular side may be longer than implements along another particular side. In one embodiment, the length of a frozen piercing implement is actuatable, or controllable.

In one embodiment, the at least one frozen piercing implement is configured to be deactivated. In one embodiment, the at least one frozen piercing implement is configured to be deactivated by at least one component of the array device or the frozen piercing implement. In one embodiment, the at least one frozen piercing implement configured to be deactivated by thermal transfer to the at least one frozen piercing implement.

In one embodiment, the plurality of frozen piercing implements 12750 is positioned as at least a portion of a fluidic or injection device. See FIGS. 127B, 129, and 130, for various non-limiting examples of devices.

As illustrated in FIG. 127, in one embodiment, the plurality of frozen piercing implements 12750 is positioned in fluid communication with at least one compartment 12700 configured to be mechanically regulated. In one embodiment, the plurality of frozen piercing implements 12750 is positioned on at least one surface 12725.

In one embodiment, a fluidic device comprises a support structure 12725 at least partially defining at least one compartment 12700, and at least one frozen piercing implement 12755 in fluid communication with the at least one compartment 12700.

In one embodiment, at least one frozen piercing implement of the plurality of frozen piercing implements includes one or more of hydrogen oxide, nitrogen, oxygen, air, helium, neon, argon, xenon, chlorine, bromine, carbon dioxide, acetone, ethyl acetate, dimethyl sulfoxide, dimethyl formamide, dioxane, tetrahydrofuran, acetonitrile, acetic acid, n-butanol, isopropanol, n-propanol, hexamethylphosphorotriamide, perfluorohydrocarbon, methanol, ethanol, tert-butyl alcohol, formic acid, hydrogen fluoride, ammonia, benzene, carbon tetrachloride, hexane, dichloromethane, methylene chloride, carboxylic acid, saline, standard saline citrate, methane, toluene, chloroform, polyethylene glycol, acetic acid, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, or diethyl ether.

In one embodiment, at least one frozen piercing implement 12755 of the plurality of frozen piercing implements 12750 is configured to deliver at least one agent, and further comprises at least one agent. In one embodiment, the at least one major dimension includes at least one of the radius, diameter, length, width, height, or perimeter.

In one embodiment, each frozen piercing implement 12755 of the plurality 12750 includes at least one agent different than the agent of every other frozen piercing implement of the plurality 12750. In one embodiment, at least one frozen piercing implement 12755 of the plurality 12750 includes at least two different agents. In one embodiment, the device includes at least two different agents. In one embodiment, the at least one agent includes at least one antigen. In one embodiment, each frozen piercing implement 12755 of the plurality 12750 includes at least one antigen. In one embodiment, the at least one antigen includes at least one allergen. In one embodiment, the frozen piercing implement 12755 is configured for delivering the at least one agent. Various non-limiting examples of agents are described herein. In one embodiment, the at least one agent includes at least one of a nontoxic, biocompatible, bioresorbable, or biodegradable agent. In one embodiment, at least two frozen piercing implements of the plurality of frozen piercing implements have at least one agent in common. In one embodiment, each frozen piercing implement 12755 of the plurality of frozen piercing implements 12750 has at least one agent in common. In one embodiment, each frozen piercing implement 12755 of the plurality of frozen piercing implements 12750 is different from every other piercing implement by varying one or more of: size of implement, shape of implement, or constitution of implement.

In one embodiment, at least two frozen piercing implements of the plurality 12750 of frozen piercing implement differ in one or more of size of implement, shape of implement, or constitution of implement. In one embodiment, at least one frozen piercing implement of the plurality of frozen piercing implements 12750 includes hydrogen oxide in one or more phases including at least one of amorphous solid water, low density amorphous ice, high density amorphous ice, very high density amorphous ice, clathrate ice, hyperquenched glassy water, ice Ic, ice II, ice III, ice IV, ice V, ice VI, ice VII, ice VIII, ice IX, ice X, ice XI, ice XII, ice XIII, ice XIV, or ice XV. In one embodiment, at least one of the plurality of frozen piercing implements is substantially solid at approximately 0° C., approximately −10° C., approximately −20° C., approximately −30° C., approximately −40° C., approximately −50° C., approximately −60° C., approximately −70° C., approximately −75° C., approximately −80° C., approximately −85° C., approximately −90° C., approximately −95° C., approximately −100° C., approximately −120° C., approximately −150° C., approximately −180° C., approximately −200° C., approximately −220° C., approximately −250° C., or any value less than or therebetween. In one embodiment, the array device has at least one major dimension of approximately one centimeter or less, approximately one millimeter or less, approximately one micrometer or less, approximately one nanometer, or any value therebetween.

In one embodiment, the plurality of frozen piercing implements 12750 includes a two dimensional array, or a three dimensional array. In one embodiment, the plurality of frozen piercing implements are arranged in at least one configuration including a regular or irregular shape. See for example, FIG. 130 for various non-limiting examples of array device shapes. In one embodiment, the plurality of frozen piercing implements are arranged in at least one configuration including at least one of a rectangle, square, circle, triangle, or polygon. See for example, FIG. 130.

In one embodiment, at least one frozen piercing implement of the plurality 12750 of frozen piercing implements includes at least one functionalized surface. See, for example, FIG. 125, for various non-limiting examples of functionalized surfaces.

In one embodiment, the array device includes at least one attachment component 12730 configured to secure the array device to at least one substrate. In one embodiment, the at least one attachment component 12730 includes at least one adhesive material. In one embodiment, the device is configured to substantially form a patch. In one embodiment, the array device further comprising at least one compartment 12700. In one embodiment, the at least one compartment includes, for example, at least one syringe or valve. See, for example, FIG. 130 for various non-limiting examples of a syringe and valve. In one embodiment, the at least one compartment 12700 is configured to hold at least one material extracted from at least one substrate. In one embodiment, the at least one compartment 12700 is in fluid communication with at least one frozen piercing implement of the plurality of frozen piercing implements. In one embodiment, the at least one compartment 12700 is configured for holding at least one agent. In one embodiment, the at least one compartment 12700 is configured for holding at least one cryogenic substance.

In one embodiment, the frozen piercing implement is configured to pierce at least one substrate to a depth of approximately 1 µm, approximately 5 µm, approximately 10 µm, approximately 15 µm, approximately 20 µm, approximately 50 µm, approximately 100 µm, approximately 120 µm, approximately 150 µm, approximately 200 µm, approximately 250 µm, approximately 300 µm, approximately 350 µm, approximately 400 µm, approximately 450 µm, approximately 500 µm, approximately 600 µm, approximately 700 µm, approximately 800 µm, approximately 900 µm, approximately 1 mm, approximately 2 mm, approximately 3 mm, approximately 4 mm, approximately 5 mm, or any value therebetween. In one embodiment, the at least one frozen piercing implement is configured to abrade or ablate at least one substrate surface 12895. In one embodiment, the plurality of frozen piercing implements 12750 is positioned such that each frozen piercing implement of the array device contacts a single cell of at least one biological tissue. In one embodiment, at least one implement of the plurality of frozen piercing implements includes at least one sensor.

In one embodiment, at least one implement of the plurality of frozen piercing implements 127500 is configured for extracting at least one material from at least one substrate 12895. Specific non-limiting examples of materials that are capable of being sensed or extracted from at least one substrate are provided herein.

In one embodiment, at least one implement of the plurality of frozen piercing implements further includes at least one of an organic or inorganic small molecule, clathrate or caged compound, protocell, coacervate, microsphere, Janus particle, proteinoid, laminate, helical rod, liposome, macroscopic tube, niosome, sphingosome, toroid, vesicular tube, vesicle, small unilamellar vesicle, large unilamellar vesicle, large multilamellar vesicle, multivesicular vesicle, lipid layer, lipid bilayer, micelle, organelle, cell, membrane, nucleic acid, peptide, polypeptide, protein, glycopeptide, glycolipid, lipoprotein, sphingolipid, glycosphingolipid, glycoprotein, peptidoglycan, lipid, carbohydrate, metalloprotein, proteoglycan, chromosome, nucleus, acid, support structure, buffer, protic solvent, aprotic solvent, nitric oxide, nitrous oxide, nitric oxide synthase, amino acid, micelle, polymer, copolymer, monomer, prepolymer, cell receptor, adhesion molecule, cytokine, chemokine, immunoglobulin, antibody, antigen, platelet, extracellular matrix, blood, plasma, cell ligand, zwitterionic material, cationic material, oligonucleotide, nanotube, piloxymer, transfersome, gas, element, contaminant, radioactive particle, hormone, microorganism, bacteria, virus, quantum dot, contrast agent, or any part thereof.

In one embodiment, the plurality of frozen piercing implements 12750 includes at least approximately 2 implements, approximately 5 implements, approximately 10 implements, approximately 20 implements, approximately 50 implements, approximately 100 implements, approximately 200 implements, approximately 300 implements, approximately 400 implements, approximately 500 implements, approximately 600 implements, approximately 700 implements, approximately 800 implements, approximately 900 implements, approximately 1000 implements, approximately 5000 implements, approximately 10000 implements, or any value therebetween or greater.

In one embodiment, the spacing between two or more frozen piercing implements includes at least approximately 1 nm, approximately 5 nm, approximately 10 nm, approximately 20 nm, approximately 50 nm, approximately 80 nm, approximately 100 nm, approximately 200 nm, approximately 300 nm, approximately 400 nm, approximately 500 nm, approximately 600 nm, approximately 700 nm, approximately 800 nm, approximately 900 nm, approximately 1 µm, approximately 5 µm, approximately 10 µm, approximately 15 µm, approximately 20 µm, approximately 50 µm, approximately 100 µm, approximately 120 µm, approximately 150 µm, approximately 200 µm, approximately 500 µm, approximately 1 mm, approximately 5 mm, approximately 10 mm, approximately 100 mm, approximately 500 mm, approximately 1 cm, approximately 5 cm, approximately 10 cm, or any value therebetween or greater.

As illustrated in FIG. 127 B, in on embodiment, the frozen piercing implement includes at least one distal end 12775, at least one frozen piercing implement shaft 12735, which may include at least one channel 12755, or port (e.g., outlet or inlet ports at the distal end 12765 or proximal end 12705). In one embodiment, the device includes at least one sensor, valve, gate, transducer, actuator, detector, heater, circuit, on-chip electronics, or other features 12745 are located in the body of the device 12725. In one embodiment, at least one electrode contact site 12715 serves as an outside connection to at least one resistor 12785, which may be utilized to form a thermally driven, cascaded bubble pump or heater. In one embodiment, the device includes at least one compartment 12705 configured to hold at least one agent or at least one material extracted from at least one substrate. Such devices may include a micro- or nano-scale, as well as larger scales.

In one embodiment, the at least one frozen piercing implement includes at least one port (e.g., 12765, 12705). The at least one port can be an inlet port, or an outlet port, and may vary according to the relative use of the device. For example, in one embodiment, a first port 12705 functions as an inlet port when administering at least one agent to at least one substrate by way of a second port 12765 functioning as an outlet port. In another example, in one embodiment a first port 12765 functions as an inlet port when extracting at least one material from at least one substrate. In one embodiment, the at least one material is analyzed or manipulated while still in the device (according to at least one feature 12745), or the at least one material exits the device by way of at least one port 12705 functioning as an outlet port. In one embodiment, at least one outlet port is in fluid communication with at least one inlet port.

Figure 128:
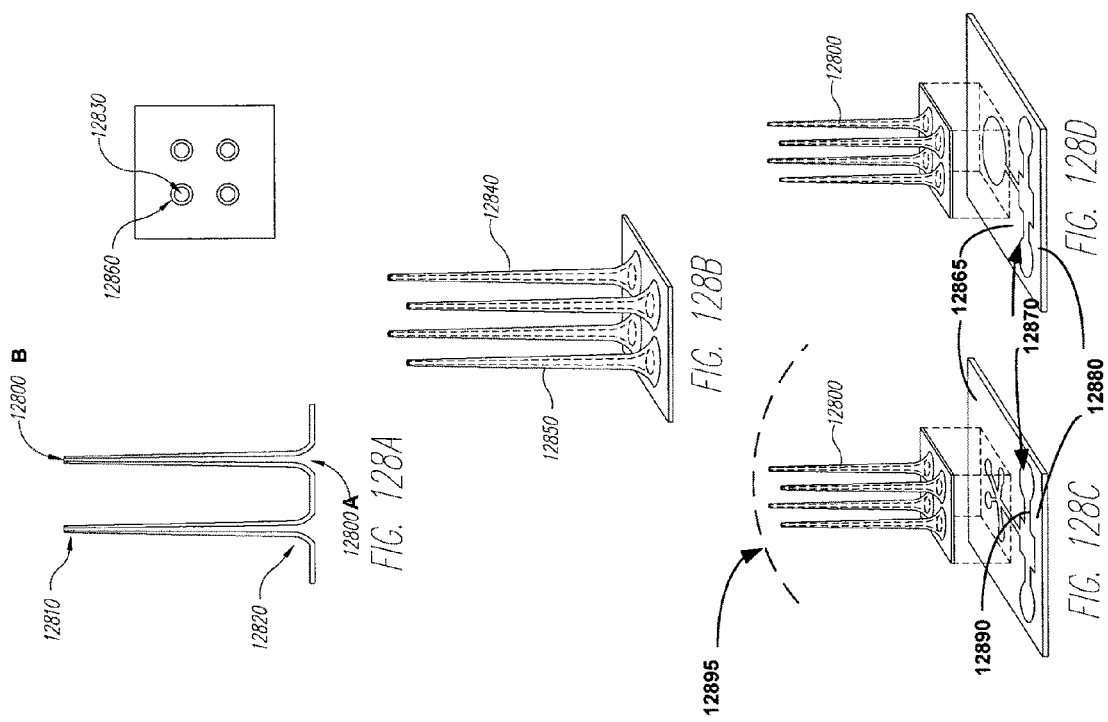

As illustrated in FIG. 128, in one embodiment, the plurality of implements is included in an array positioned on a support structure 12865 that has a surface 12880. In one embodiment, the at least one frozen piercing implement 12840 includes at least one channel 12850 that includes at least one inner surface 12830 and at least one outer surface 12860. In one embodiment, the frozen piercing implement includes a distal end 12810 and a proximal end 12820. In one embodiment, the frozen piercing implement 12840 includes a channel 12850 that includes at least one opening 12800. In one embodiment, the at least one channel 12850 is in fluid communication with at least one fluidics device (FIGS. 128C-128D).

In one embodiment, the array device includes at least one channel 12890. In one embodiment, the at least one channel 12890 includes at least one cross-coupling flow channel 12890. In one embodiment, the array device includes at least one compartment 12870. In one embodiment, the at least one compartment 12870 is in fluid communication with the at least one channel 12890. In one embodiment, the array device includes at least one agent. In one embodiment, the agent is included in the at least one compartment 12870. In one embodiment, the at least one compartment is configured to hold at least one agent, or at least one material extracted from at least one substrate 12895.

In one embodiment, at least one frozen piercing implement of the plurality of frozen piercing implements includes at least one inlet port 12800A or 12800B. In one embodiment, the at least one inlet port 12800A or 12800B is in fluid communication with at least one channel 12890 of at least one frozen piercing implement. In one embodiment, the at least one inlet port 12800A or 12800B is in fluid communication with at least one channel 12890 of the array device. In one embodiment, at least one frozen piercing implement of the plurality of frozen piercing implements includes a plurality of inlet ports. In one embodiment, at least one frozen piercing implement of the plurality of frozen piercing implements includes at least one outlet port 12800B or 12800A. In one embodiment, the at least one outlet port 12800B or 12800A is in fluid communication with at least one channel 12890 of at least one frozen piercing implement. In one embodiment, the at least one outlet port 12800B or 12800A is in fluid communication with at least one channel 12890 of the array device. In one embodiment, at least one frozen piercing implement of the plurality of frozen piercing implements includes a plurality of outlet ports 12800B or 12800A.

In one embodiment, the array device further comprises at least one of a nanoparticle, microparticle, sensor, valve, gate, channel, transducer, actuator, detector, heater, circuit, or detection material. The location of these features may vary according to the device (e.g., the distal end 12810, the proximal end 12820, any location along the shaft or channel of the implement 12800, 12830). See, for particular non-limiting examples, FIGS. 128, and 129.

As illustrated in FIG. 129, in one embodiment, the frozen piercing implement device includes at least one actuator structure 12910, optionally integral with the at least one support structure 12925 of the frozen piercing implement(s). In one embodiment, a fluidic device comprises at least one frozen piercing implement, and at least one actuator 12910 configured to actuate the at least one frozen piercing implement 12800.

In one embodiment, the at least one actuator 12910 includes at least one of a piezoelectric actuator, electrostatic actuator, thermal actuator, shape-memory alloy actuator, bioactuator, or magnetic actuator. In one embodiment, the actuator includes a microactuator or a nanoactuator. In one embodiment, at least one feature 12940 or 12930 (e.g., channel, pump, sensor, injector, actuator, heater, detector, controller, transducer, receiver, cooler, transmitter, circuit, lens, tunablelens, valve, gate, nanoparticle, microparticle, power source, or detection material, etc.) is located in the body 12900 of the device. In one embodiment, the valve includes at least one of a one-way valve, or pressure settable valve.

In one embodiment, the at least compartment 12920 is configured to hold at least one material extracted from at least one substrate 12970. In one embodiment, the fluidic device includes at least one means for drawing up the at least one material from the at least one substrate 12970. In one embodiment, at least one piercing implement 12800 is in fluid communication with at least one compartment 12920. In one embodiment, the sensor is configured to respond to at least one material collected in the at least one compartment 12920. In one embodiment, the at least one compartment 12920 is configured for displacement of at least one fluid as the at least one material is extracted from the at least one substrate 12970. In at least one embodiment, the at least one compartment 12920 is substantially rigid. See, FIG. 130 for other non-limiting examples of compartments. In one embodiment, the at least one compartment 12920 is substantially deformable. See FIGS. 133-134 for other non-limiting examples of compartments. In one embodiment, the fluidic device includes at least one cantilever 12955. In one embodiment, the at least one cantilever 12955 is integral with the at least one actuator 12910. In one embodiment, the at least one cantilever 12955 is supported by the body 12900, or other structures within the body 12900 of the device.

As described herein for other embodiments of frozen piercing implements or frozen piercing implement devices, in one embodiment, the at least one frozen piercing implement or device includes at least one agent. Various non-limiting examples of agents are provided herein. In particular, in one embodiment, the agent includes at least one of an antimicrobial, citrate, EDTA, anticoagulant, or other agent.

As described herein for other embodiments of frozen piercing implements or frozen piercing implement devices, in one embodiment, the at least one frozen piercing implement is configured to transform to another phase state upon the occurrence of at least one inducible event. In one embodiment, the at least one inducible event includes one or more of: administration of the device to at least one substrate, contacting the at least one frozen piercing implement with at least one substrate, increasing the temperature of the at least one frozen piercing implement, increasing the temperature of the at least one substrate, increasing the pressure on the at least one frozen piercing implement, increasing the pressure on the at least one substrate, altering a magnetic field on the at least one frozen piercing implement, altering a magnetic field on the at least one substrate, administering at least one additional agent to the at least one frozen piercing implement, administering at least one additional agent to the substrate, administering at least one electric field to the at least one frozen piercing implement, administering at least one electric field to the at least one substrate, administering ultrasound to the at least one frozen piercing implement, administering ultrasound to the at least one substrate.

As illustrated in FIG. 129, in one embodiment, the fluidic device including at least one frozen piercing implement 12800, includes at least one actuator 12910. In one embodiment, at least one controller 12960 is configured to control the at least one actuator 12910. The controller 12960 may include, for example, a mechanical or electrical controller. In one embodiment, the controller 12960 includes a wireless controller. In one embodiment, the device includes at least one sensor 12950 configured to sense at least one material extracted from the at least one substrate 12970 (e.g., the material passes through the at least one piercing implement 12800 or is extracted by force from the at least one piercing implement changing phase and retreating). In one embodiment, the at least one frozen piercing implement 12800 is integral with the at least one actuator 12910. In one embodiment, the at least one sensor is configured to detect at least one material from the at least one substrate 12970. Several non-limiting examples of materials capable of being sensed are disclosed herein.

In various embodiments disclosed herein, the support structure (e.g., 12880, 12925, 13030, etc.) includes at least one frozen composition. In one embodiment, the support structure (12900) includes at least one of a metal, ceramic, polymer, organic or inorganic compound, semiconductor, other material, or composite thereof.

In one embodiment, the at least one compartment 12920 expands as at least one material is extracted. See FIG. 134 for other non-limiting examples of compartments. In one embodiment, the at least one compartment 12920 is substantially fabricated from one or more of a polymer, metal, ceramic, semiconductor, frozen composition, other material, or composite thereof.

In one embodiment, the at least one actuator 12910 includes at least one of a piezoelectric actuator, electrostatic actuator, thermal actuator, shape-memory alloy actuator, bioactuator, or magnetic actuator. In one embodiment, the at least one frozen piercing implement is integral with one or more of the at least one of a channel, pump, sensor, injector, actuator, heater, detector, controller, transducer, receiver, transmitter, circuit, lens, cooler, tunablelens, valve, gate, channel, nanoparticle, microparticle, power source, or detection material. See, for example, FIGS. 127-131 for various non-limiting examples of particular embodiments.

Figure 130:
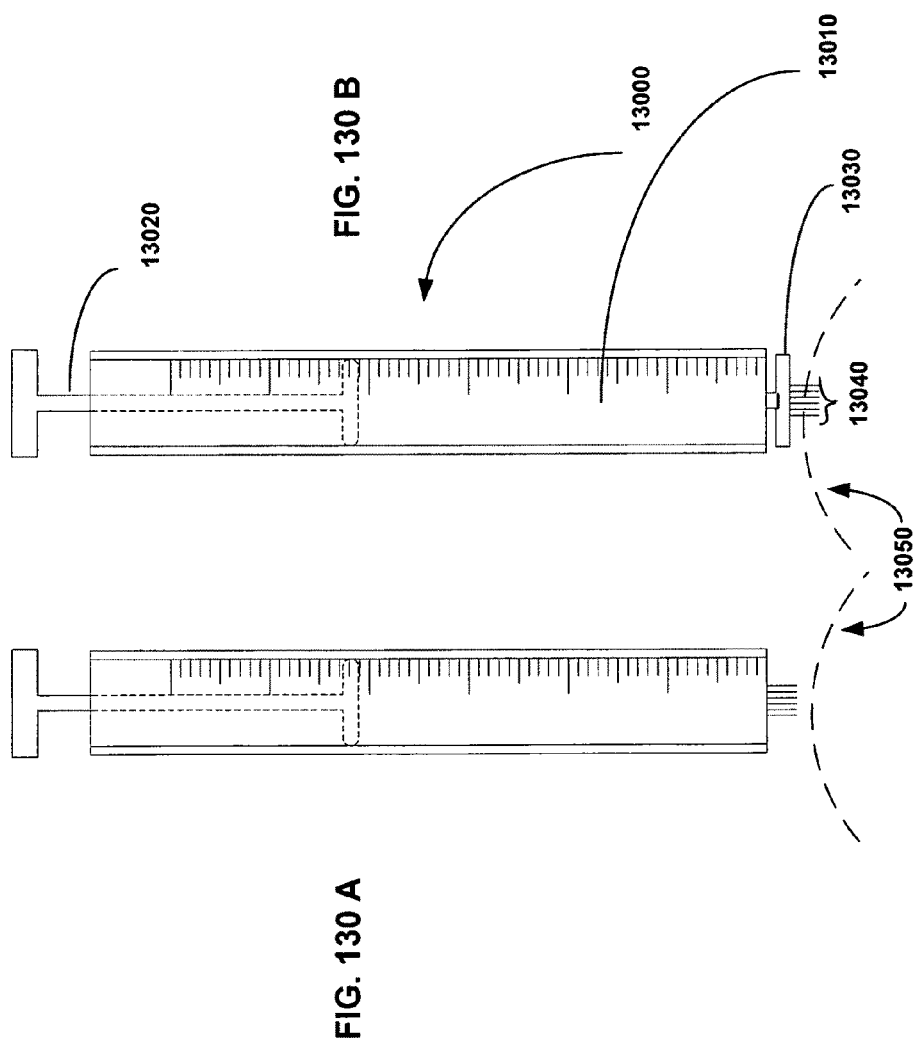

As illustrated in FIG. 130, in one embodiment, a frozen piercing implement device includes at least one injection or fluidic device 13000. In one embodiment, the injection device 13000 includes at least one auto-injection device. In one embodiment, a plurality of piercing implements 13040, including at least one frozen piercing implement, is employed in the injection device. In one embodiment, a single frozen piercing implement is employed (not shown). In one embodiment, the plurality of piercing implements 13040 are positioned on at least one support structure 13030. In one embodiment, the piercing implement(s) 13040 are in fluid communication with at least one compartment 13010 configured to hold at least one agent for administration to at least one substrate, or at least one material extracted from at least one substrate. In one embodiment, the piercing implement(s) 13040 can be contracted (FIG. 130A) or extended (FIG. 130B). In one embodiment, a mechanical controller (e.g., plunger) 13020 is configured to control at least one of the position of the piercing implement(s) 13040, or the level of contents of the at least one compartment 13010.

In one embodiment, at least one first implement of the plurality of implements 13040 is configured to deliver at least one agent, and at least one second implement of the plurality of implements 13040 is configured to sense or extract at least one material from the at least one substrate 13050: In one embodiment, the at least one first implement is configured to deliver an agent that is different than the at least one second implement.

In one embodiment, the fluidic device includes at least one of a channel, pump, sensor, injector, actuatory, heater, detector, controller, transducer, receiver, cooler, transmitter, circuit, lens, tunablelens, valve, gate, nanoparticle, microparticle, power source, or detection material (e.g., in the compartment, in the support structure, in at least one frozen piercing implement, etc.). The location of these various features can vary, depending on the particular embodiment. For example, such features may be found in the at least one compartment 13010, in or near the mechanical controller 13020, near the proximal or distal end of the at least one compartment 13010, in or near the at least one support structure 13030, or in or near the at least one frozen piercing implement 13040. See FIG. 129 for other non-limiting examples of particular embodiments.

Figure 131:
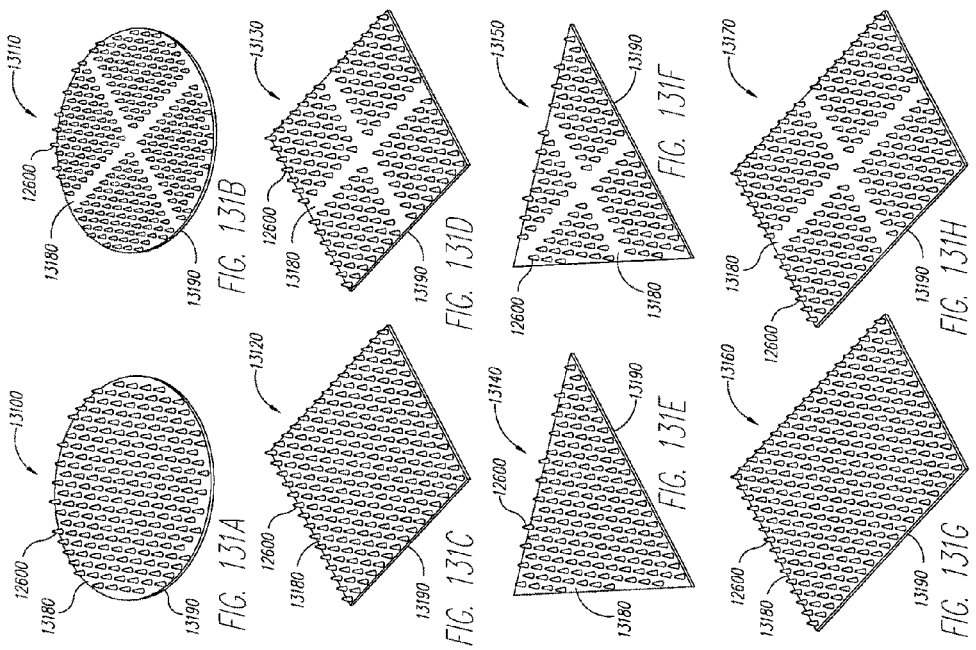

As illustrated in FIG. 131, a frozen piercing implement device including a plurality of piercing implements, including at least one frozen piercing implement 12600, includes at least one topside of a support structure 13180, and at least one underside of the at least one support structure 13190. In one embodiment, the frozen piercing implement device can be fabricated into various shapes (13100, 13120, 13140, 13160) or configurations (13110, 13130, 13150, 13170).

As illustrated in FIG. 132, a frozen piercing implement device 13205 is included in at least one system 13200 for administration to at least one substrate 13250, or extraction of at least one material from at least one substrate 13250. In one embodiment, the device includes at least two electrode assemblies (13210, 13212) and an integrated power source 13220. In one embodiment, the device includes at least one frozen piercing implement 13230, and at least one support structure 13240.

As illustrated in FIGS. 133-134, in one embodiment, the array device includes a plurality of compartments 13370 in fluid communication with at least one frozen piercing implement 13360 of the plurality of frozen piercing implements 13380. In one embodiment, the plurality of compartments 13370 includes at least one first compartment (e.g., 13370A) configured to hold at least one different substance from at least one second compartment (e.g., 13370B or 13370C).

In one embodiment, the plurality of compartments 13370 includes at least one first compartment (e.g., 13370A) configured to hold at least one first agent, wherein the at least one first agent is different from at least one other agent located in at least one second compartment (e.g., 13370B or 13370C). In one embodiment, the plurality of compartments 13370 includes at least one first compartment configured to hold at least one first agent, and at least one second compartment configured to hold a pharmaceutically acceptable carrier or excipient.

In one embodiment, two or more compartments (e.g., 13370A, 13370B, or 13370C) are configured to interact with at least one means for intermixing the contents of the two or more compartments prior to or during administration of the array device to at least one substrate. In one embodiment, the at least one means for intermixing includes mechanical disruption of at least one compartment, altering porosity of at least one compartment, electrochemical degradation of at least one compartment, valve opening of at least one compartment, chemical degradation of at least one compartment, or altering magnetic field of at least one compartment. In one embodiment, the contents of the two or more compartments are intermixed during administration by way of contact of the one or more piercing implements 13380 with the at least one substrate.

In one embodiment, the array device is in electronic communication with at least one computing device.

In one embodiment, a composition comprises a plurality of piercing implement array devices joined together, the piercing implement array devices including at least one frozen piercing implement. See, for example, FIGS. 131-132 for various non-limiting examples of arrays that can be joined together in particular embodiments.

As illustrated in FIG. 133, in one embodiment, the frozen piercing implement device 13300, includes at least one frozen piercing implement 13360. In one embodiment, the at least one frozen piercing implement 13360 includes at least one channel 13310. In one embodiment, the at least one channel 13310 is in fluid communication with at least one compartment 13320, or plurality of compartments 13370. In one embodiment, the at least one compartment is configured to hold at least one agent to be administered to the at least one substrate, or at least one material extracted from the at least one substrate. In one embodiment, the plurality of compartments can include multiple compartments for administration or extraction. In one embodiment, the same compartment can be utilized for both administration of at least one agent, and for collection of extracted material from the at least one substrate. In one embodiment, the at least one frozen piercing implement 13360 is positioned on at least one support structure 13330. In one embodiment, the at least one support structure includes at least one frozen fluid or frozen composition. In one embodiment, the at least one compartment 13320 is configured to at least partially deflate (thereby expelling any contents) or at least partially inflate (thereby extracting or collecting at least one material from at least one substrate) by way of a separate component 13340, including an expandable component. In one embodiment, the frozen piercing implement device includes at least one backing member, such as a rim or shell 13350 of the support structure configured to secure the at least one component 13340 or at least one compartment 13320. In one embodiment, the at least one compartment 13320 is configured to at least partially deflate or inflate by way of direct pressure on the compartment.

In one embodiment, a composition comprises a support means for an array device, wherein the array device includes one or more frozen piercing implements. See, for example, FIGS. 132-134 for various non-limiting examples of support means for various array device embodiments (e.g., 13330). In one embodiment, the support means 13330 is separable from the one or more frozen piercing implements. In one embodiment, at least part of the support means 13330 is at least partially frozen. In one embodiment, the at least partially frozen support means 13330 and the one or more frozen piercing implements include at least one frozen constituent in common. In one embodiment, the one or more frozen piercing implements have at least one major dimension of approximately one centimeter or less, approximately one millimeter or less, approximately one micrometer or less, approximately one nanometer, or any value therebetween.

In one embodiment, a method of administering at least one array device to at least one substrate comprises contacting at least one array device to at least one substrate, wherein the array device includes at least one frozen piercing implement.

In one embodiment, a method of vaccinating a subject comprises administering to a subject at least one frozen piercing implement array device; wherein the at least one frozen piercing implement array device includes at least one frozen piercing implement including at least one vaccine.

As illustrated in FIG. 140, in one embodiment, the frozen piercing implement device (FIG. 140A-C), includes at least one frozen piercing implement 14090. In one embodiment, the device includes at least one valve 14070. In one embodiment, the valve maintains a sealed compartment 14060. In one embodiment, the valve maintains air pressure equilibrium between the at least one compartment 14060 and the surrounding area during actuation of the bridge 14000.

In one embodiment, the device includes at least one compartment 14060 configured to hold at least one agent to be administered to at least one substrate 14080, or configured to hold at least one material extracted or collected from at least one substrate 14080. In one embodiment, the device includes at least one actuator bridge 14000 supported by at least one support structure 14010. In one embodiment, the device includes at least one sensor 14020 located in the at least one compartment 14060, or sidewall 14030. In one embodiment, the device includes at least one fastening or adhesive mechanism 14040 for adhering the device to the at least one substrate 14080. In one embodiment, the actuator bridge 14000 is configured to cause the at least one frozen piercing implement 14090 to contact the at least one substrate 14080 when at least one vertical force 14050 is placed on the bridge of the actuator 14000.

In one embodiment, the actuator is driven by at least one of mechanical, magnetic, electric, or electromagnetic force. See, for example, Zhao, et al., Abstract, Information Acquisition, 2005 IEEE Int'l Conf, Jun. 27-Jul. 3, 2005, which is incorporated herein by reference.

In on embodiment, the amount of force needed to pierce the at least one substrate is approximately 1 mN, approximately 10 mN, approximately 20 mN, approximately 30 mN, approximately 40 mN, approximately 50 mN, approximately 60 mN, approximately 70 mN, approximately 80 mN, approximately 90 mN, approximately 100 mN, approximately 150 mN, approximately 200 mN, approximately 250 mN, approximately 300 mN, approximately 350 mN, approximately 400 mN, approximately 450 mN, approximately 500 mN, approximately 550 mN, approximately 600 mN, approximately 650 mN, approximately 700 mN, approximately 750 mN, approximately 800 mN, approximately 850 mN, approximately 900 mN, approximately 1 N, approximately 2 N, approximately 3 N, approximately 4 N, approximately 5 N, or any value less than or therebetween. In one embodiment, the amount of force needed to pierce the at least one substrate includes at least one predetermined value. In one embodiment, the amount of force needed to pierce the at least one substrate is calculated based on at least one characteristic or property of the substrate. In one embodiment, the amount of force needed to pierce the at least one substrate depends on at least one characteristic or property of the frozen piercing implement, or frozen piercing implement device. Examples of such properties are disclosed herein.

For example, the vertical force F, which is required to penetrate the substrate, can be calculated by multiplying the lateral force $F_1$ on the bridge upon deflection, with the sine of the deflection angle a relative to resting. In one embodiment, by increasing the horizontal width w increases the actuation force at the tip of the cantilever bridge. Likewise, in one embodiment, an electrical voltage can be applied to actuate the cantilever-tip.

In one embodiment, the frozen piercing implement device includes at least one sensor. In one non-limiting example, the sensor includes an electrochemical transducer in which current is converted from chemical to electrical energy through oxidation or reduction at the electrode surface. See, for example, U.S. Patent Application Publication No. 20050228313, which is incorporated herein by reference. In one embodiment, the at least one sensor includes at least one sensor to monitor at least one material in the at least one substrate (e.g., glucose, insulin, etc.). Some non-limiting examples of materials that can be detected or analyzed are disclosed herein.

In one embodiment, the transducer includes a small metal electrode that is insulated except at a particular location where the chemical reaction occurs. At the reaction location, several electrochemical analytical and synthetic systems are implemented. The type of electrode sensor utilized with the device can be varied according to the electrical parameter being measured. For example, in the case of glucose measurement, potentiometric and emperometric sensors can be utilized. Id.

The output signal from the at least one sensor can be displayed, for example, on an active or passive display. In one embodiment, the frozen piercing implement device includes at least one power source for operation of, for example, the actuator, sensor, corresponding transceiver or electronics. As described herein, in one embodiment, the power source includes, for example, a battery, fuel cell, capacitor, or DC power supply.

As illustrated in FIGS. 135-139, a computer-implemented method 13500, comprises: 13510 receiving one or more signals that include information related to accepting input associated with at least one parameter for making or administering at least one frozen particle composition, frozen piercing implement, or frozen piercing implement device to at least one substrate; 13520 wherein the at least one frozen particle composition or frozen piercing implement includes at least one agent; 13530 receiving one or more signals that include information related to evaluating the at least one substrate for one or more indicators of administration of the at least one frozen particle composition, frozen piercing implement, or frozen piercing implement device; 13540 processing the information related to the input associated with at least one parameter for making or administering the at least one frozen particle composition, frozen piercing implement, or frozen piercing implement device to at least one substrate and the information related to the evaluating the at least one substrate; and 13550 generating an output to a user readable display. In one embodiment 13560, evaluating at least one substrate for one or more indicators includes evaluating at least one of an assay, image, or gross assessment of the at least one substrate prior to, during, or subsequent to at least one administration of at least one frozen particle composition, frozen piercing implement, or frozen piercing implement device. In one embodiment 13570, the assay includes at least one technique that includes spectroscopy, microscopy, electrochemical detection, polynucleotide detection, histological examination, biopsy analysis, fluorescence resonance energy transfer, electron transfer, enzyme assay, electrical conductivity, isoelectric focusing, chromatography, immunoprecipitation, immunoseparation, aptamer binding, filtration, electrophoresis, immunoassay, or radioactive assay.

In one embodiment 13610, the image includes at least one image acquired by one or more of x-ray crystallography, laser, holography, optical coherence tomography, computer-assisted tomography scan, computed tomography, magnetic resonance imaging, positron-emission tomography scan, ultrasound, x-ray, electrical-impedance monitoring, microscopy, spectrometry, flow cytometry, radioisotope imaging, thermal imaging, infrared visualization, multiphoton calcium-imaging, photography, or in silico generation. In one embodiment 13620 receiving one or more signals includes receiving one or more signals associated with selection of at least one parameter for making or administering the at least one frozen particle composition, frozen piercing implement, or frozen piercing implement device.

In one embodiment 13630, wherein the at least one parameter for making the at least one frozen piercing implement device includes one or more of: constitution of the at least one frozen piercing implement of the frozen piercing implement device, constitution of the at least one frozen piercing implement device, formulation of the at least one frozen piercing implement of the frozen piercing implement device, formulation of the at least one frozen piercing implement device, size of the at least one frozen piercing implement of the frozen piercing implement device, size of the at least one frozen piercing implement device, shape of the at least one frozen piercing implement of the frozen piercing implement device, shape of the at least one frozen piercing implement device, physical structure of the at least one frozen piercing implement of the frozen piercing implement device, physical structure of the at least one frozen piercing implement device, physical or chemical integrity of the at least one frozen piercing implement of the frozen piercing implement device, physical or chemical integrity of the at least one frozen piercing implement device, or presence or absence of at least one microparticle, nanoparticle, lens, tunable lens, sensor, transducer, actuator, detector, heater, valve, gate, channel, detection material, pump, energy source, injector, controller, receiver, transmitter, or circuit, in the at least one frozen piercing implement or frozen piercing implement device.

In one embodiment 13710, at least one parameter for administering the at least one frozen particle composition or frozen piercing implement includes one or more of: substrate type; substrate function; substrate size; substrate constitution; substrate architecture; substrate durability; substrate temperature; temperature of administration conditions; depth of administration of the at least one frozen particle composition or frozen piercing implement; substrate source; one or more temporal coordinates; one or more spatial coordinates; presence or absence of at least one agent; presence or absence of at least one microparticle, nanoparticle, lens, tunablelens, sensor, transducer, actuator, detector, heater, valve, gate, channel, detection material, pump, power source, injector, controller, receiver, transmitter, or circuit; angle of administration of the at least one frozen piercing implement device; force of administration of the at least one frozen piercing implement device; velocity of administration of the at least one frozen piercing implement device; quantity of frozen piercing implements of the device; quantity of frozen piercing implement devices administered; rate of administration of more than one frozen piercing implement devices; method of administration of at least one frozen piercing implement device; timing of administration of at least one frozen piercing implement; or rate of delivery of at least one agent of the device.

In one embodiment 13720, the input associated with at least one parameter for making the at least one frozen particle composition or frozen piercing implement includes one or more property including: constitution of the at least one frozen particle composition or frozen piercing implement, configuration of the at least one frozen particle composition or frozen piercing implement, formulation of the at least one frozen particle composition or frozen piercing implement, size of the at least one frozen particle composition or frozen piercing implement, density of the at least one frozen particle composition or frozen piercing implement, shape of the at least one frozen particle composition or frozen piercing implement, physical structure of the at least one frozen particle composition or frozen piercing implement, physical or chemical integrity of the at least one frozen particle composition or frozen piercing implement.

In one embodiment 13730, the at least one agent includes one or more of an adhesive agent, therapeutic agent, reinforcement agent, abrasive, explosive material, or biological remodeling agent.

In one embodiment 13810, the input associated with at least one parameter for administering at least one frozen particle composition or frozen piercing implement to at least one substrate includes one or more of: substrate type; substrate function; substrate size; substrate constitution; substrate architecture; substrate durability; substrate temperature; temperature of administration conditions; depth of administration of the at least one frozen particle composition or frozen piercing implement; substrate source; one or more temporal coordinates; one or more spatial coordinates; presence or absence of at least one agent; presence or absence of at least one microparticle, nanoparticle, lens, tunablelens, sensor, transducer, actuator, detector, heater, valve, gate, channel, detection material, pump, power source, injector, controller, receiver, transmitter, or circuit; angle of administration of the at least one frozen particle composition or frozen piercing implement; force of administration of the at least one frozen particle composition or frozen piercing implement; velocity of administration of the at least one frozen particle composition or frozen piercing implement; quantity of frozen particle compositions or frozen piercing implements administered; rate of administration of more than one frozen particle compositions or frozen piercing implements; method of administration of at least one frozen particle composition or frozen piercing implement; timing of administration of at least one frozen particle composition or frozen piercing implement; or rate of delivery of at least one agent.

In one embodiment 13820, the at least one substrate includes one or more of a cell, tissue, organ, structure, device, or food product. In one embodiment 13830, the at least one frozen particle composition, frozen piercing implement, or frozen piercing implement device includes one or more of hydrogen oxide, nitrogen, oxygen, air, helium, neon, argon, xenon, chlorine, bromine, carbon dioxide, acetone, ethyl acetate, dimethyl sulfoxide, dimethyl formamide, dioxane, tetrahydrofuran, acetonitrile, acetic acid, n-butanol, isopropanol, n-propanol, hexamethylphosphorotriamide, perfluorohydrocarbon, methanol, ethanol, tert-butyl alcohol, formic acid, hydrogen fluoride, ammonia, benzene, carbon tetrachloride, hexane, dichloromethane, methylene chloride, carboxylic acid, saline, methane, toluene, chloroform, polyethylene glycol, acetic acid, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, or diethyl ether.

In one embodiment 13910, the output includes one or more instructions for making the at least one frozen particle composition, frozen piercing implement, or frozen piercing implement device. In one embodiment 13920, the output includes at least one graphical description of the at least one frozen particle composition, frozen piercing implement, or frozen piercing implement device. In one embodiment 13930, the user includes at least one entity. In one embodiment 13940, the entity includes at least one person, or computer. In one embodiment 13950, the user readable display includes a human readable display. In one embodiment 13960, the user readable display includes one or more active displays. In one embodiment 13970, the user readable display includes one or more passive displays. In one embodiment 13980, the user readable display includes one or more of a numeric format, graphical format, or audio format. In one embodiment 13990, the user readable display includes one or more of a display of one or more differences in the comparison of at least one value related to the first input and at least one value related to at least one property of the at least one frozen particle composition, frozen piercing implement, or frozen piercing implement device. In one embodiment 13995, the user readable display includes one or more of a display of one or more differences in the comparison of at least one value related to the second input and at least one value related to at least one parameter for administration of the at least one frozen particle composition, frozen piercing implement, or frozen piercing implement device.

As illustrated in FIGS. 141-147, a computer-implemented method 14100 comprises 14110 accepting a first input associated with at least one parameter for making at least one frozen particle composition or frozen piercing implement; 14120 accepting a second input associated with at least one parameter for administering the at least one frozen particle composition or frozen piercing implement to at least one substrate; and 14160 processing results of the first input and the second input. In one embodiment, 14130 wherein the at least one frozen particle composition or frozen piercing implement includes at least one agent. In one embodiment, 14140 wherein the at least one agent includes one or more of a therapeutic agent, adhesive agent, abrasive, reinforcement agent, explosive material, or biological remodeling agent. In one embodiment, 14150 the at least one substrate includes one or more of a cell, tissue, organ, structure, or device.

In one embodiment, 14170 processing results of the first input and the second input includes electronically processing results of the first input and the second input. In one embodiment, 14180 electronically processing results of the first input and the second input by utilizing one or more of Gaussian smoothing, scaling, homomorphic filtering, parametric estimation techniques, Boolean operations, Monte Carlo simulations, wavelet based techniques, mirroring, smoothing, gradient weighted partial differential equation smoothing, NURBS, polygonal modeling, splines and patches modeling, algorithmic execution, logical decision-making, result prediction, Finite Element Analysis, or modification of a CAD design.

In one embodiment, 14210 the first input includes one or more values related to the at least one parameter for making the at least one frozen particle composition or frozen piercing implement. In one embodiment, 14220 the first input includes one or more values derived from at least one image of at least one frozen particle composition or frozen piercing implement. In one embodiment, 14230 the at least one image includes one or more images acquired by at least one of laser, holography, x-ray, crystallography, optical coherence tomography, computer-assisted tomography scan, computed tomography, magnetic resonance imaging, positron-emission tomography scan, ultrasound, x-ray, electrical-impedance monitoring, microscopy, spectrometry, flow cytometry, radioisotope imaging, thermal imaging, infrared visualization, multiphoton calcium-imaging, photography, or in silico generation. In one embodiment, 14250 the at least one parameter for making the at least one frozen particle composition or frozen piercing implement includes one or more property including: constitution of the at least one frozen particle composition or frozen piercing implement, configuration of the at least one frozen particle composition or frozen piercing implement, formulation of the at least one frozen particle composition or frozen piercing implement, size of the at least one frozen particle composition or frozen piercing implement, density of the at least one frozen particle composition or frozen piercing implement, shape of the at least one frozen particle composition or frozen piercing implement, physical structure of the at least one frozen particle composition or frozen piercing implement, or physical or chemical integrity of the at least one frozen particle composition or frozen piercing implement. In one embodiment, 14310 the at least one parameter for administering at least one frozen particle composition or frozen piercing implement to at least one substrate includes one or more of substrate type; substrate function; substrate size; substrate constitution; substrate architecture; substrate durability; substrate temperature; temperature of administration conditions; depth of administration of the at least one frozen particle composition or frozen piercing implement; substrate source; one or more temporal coordinates; one or more spatial coordinates; presence or absence of at least one agent; presence or absence of one or more sensors, valves, gates, channels, transducers, circuits, nanoparticles, microactuators, microdetectors, microheaters, or detection materials; angle of administration of the at least one frozen particle composition or frozen piercing implement; velocity of administration of the at least one frozen particle composition or frozen piercing implement; quantity of frozen particle compositions or frozen piercing implements administered; rate of administration of more than one frozen particle compositions or frozen piercing implements; method of administration of at least one frozen particle composition or frozen piercing implement; timing of administration of at least one frozen particle composition or frozen piercing implement; or rate of delivery of at least one agent.

In one embodiment, 14330 the at least one biological tissue is located in at least one of in situ, in vitro, in vivo, in utero, in planta, in silico, or ex vivo. In one embodiment, 14340 the at least one substrate is at least partially located in at least one subject. In one embodiment, 14350 the method further comprises accepting a third input associated with at least one feature of the at least one subject. In one embodiment, 14360 the at least one feature of the at least one subject includes one or more of age, gender, genotype, phenotype, proteomic profile, lipidomic profile, glycomic profile, system biology profile, circulatory condition, respiratory condition, blood condition, lymph condition, anatomic landscape, body contour, or health condition.

In one embodiment, 14410 the at least one parameter for administering at least one frozen particle composition or frozen piercing implement includes at least one parameter relating to administering at least one of a therapeutic agent, adhesive agent, biological remodeling agent, reinforcement agent, abrasive, or explosive material by way of the at least one frozen particle composition or frozen piercing implement.

In one embodiment, 14420 the at least one parameter for administering at least one frozen particle composition or frozen piercing implement includes at least one parameter relating to at least partially ablating or at least partially abrading one or more surfaces of the at least one substrate with the at least one frozen particle composition or frozen piercing implement. In one embodiment, 14430 the processing results of the first input and the second input includes determining at least one parameter for administering at least one frozen particle composition or frozen piercing implement from one or more values derived from at least one image of the at least one frozen particle composition or frozen piercing implement. In one embodiment, 14440 the second input includes one or more values related to the at least one parameter for administering at least one frozen particle composition or frozen piercing implement. In one embodiment, 14450 the one or more values related to the at least one parameter for administering at least one frozen particle composition or frozen piercing implement includes one or more predictive values.

In one embodiment, 14460 the processing results includes comparing at least one value related to the first input associated with the at least one parameter for making the at least one frozen particle composition or frozen piercing implement with at least one value related to at least one property of the frozen particle composition or frozen piercing implement. In one embodiment, 14470 the processing results includes determining one or more differences in at least one value related to the first input and at least one value related to at least one image of the at least one frozen particle composition or frozen piercing implement.

In one embodiment, 14510 the processing results includes determining one or more differences in at least one value related to the second input associated with the at least one parameter for administering at least one frozen particle composition or frozen piercing implement. In one embodiment, 14520 the processing results includes generating one or more protocols for administering the at least one frozen particle composition or frozen piercing implement. In one embodiment, 14530 the administering at least one frozen particle composition or frozen piercing implement to at least one substrate includes delivering at least one agent to at least one substrate.

In one embodiment, 14550, the output includes one or more instructions for making the at least one frozen particle composition or frozen piercing implement. In one embodiment, 14560 the output includes at least one graphical description of the at least one frozen particle composition or frozen piercing implement.

In one embodiment, 14570 the user includes at least one entity. In one embodiment 14575, the entity includes at least one person, or computer. In one embodiment 14580, the user readable display includes a human readable display. In one embodiment 14590, the user readable display includes one or more active displays. In one embodiment 14595, the user readable display includes one or more passive displays. In one embodiment, 14598 the user readable display includes one or more of a numeric format, graphical format, or audio format.

In one embodiment, 14610 the user readable display includes one or more of a display of one or more differences in the comparison of at least one value related to the first input and at least one value related to at least one property of the at least one frozen particle composition or frozen piercing implement. In one embodiment, 14615 the user readable display includes one or more displays of one or more differences in the comparison of at least one value related to the second input and at least one value related to at least one parameter for administration of the at least one frozen particle composition or frozen piercing implement.

In one embodiment 14618, the method further comprises transmitting one or more signals that include information related to the processing results of the first input and the second input. In one embodiment, 14620 the transmitting one or more signals includes transmitting one or more signals associated with selection of at least one parameter for making at least one frozen particle composition or frozen piercing implement. In one embodiment, 14630 the transmitting one or more signals includes transmitting one or more signals associated with selection of at least one parameter for making the at least one frozen particle composition or frozen piercing implement. In one embodiment, 14640 the transmitting one or more signals includes transmitting one or more signals associated with comparing the information related to the processing results of the first input and the second input. In one embodiment, 14650 the at least one frozen particle composition or frozen piercing implement includes one or more of hydrogen oxide, nitrogen, oxygen, air, helium, neon, argon, xenon, chlorine, bromine, carbon dioxide, acetone, ethyl acetate, dimethyl sulfoxide, dimethyl formamide, dioxane, tetrahydrofuran, acetonitrile, acetic acid, n-butanol, isopropanol, n-propanol, hexamethylphosphorotriamide, perfluorohydrocarbon, methanol, ethanol, tert-butyl alcohol, formic acid, hydrogen fluoride, ammonia, benzene, carbon tetrachloride, hexane, dichloromethane, methylene chloride, carboxylic acid, saline, standard saline citrate, methane, toluene, chloroform, polyethylene glycol, acetic acid, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, or diethyl ether.

In one embodiment 14710, the method further comprises making at least one frozen particle composition or frozen piercing implement. In one embodiment, the method 14720 further comprises administering at least one frozen particle composition or frozen piercing implement to at least one substrate. In one embodiment, 14730 the method further comprises evaluating the at least one substrate for one or more indicators related to at least one parameter for administering the at least one frozen particle composition or frozen piercing implement. In one embodiment, 14740 wherein the evaluating at least one substrate for one or more indicators includes evaluating at least one of an assay, image, or gross assessment of the at least one substrate prior to, during, or subsequent to at least one administration of the at least one frozen particle composition or frozen piercing implement. In one embodiment, 14750 the assay includes at least one technique including spectroscopy, microscopy, electrochemical detection, polynucleotide detection, histological examination, biopsy analysis, fluorescence resonance energy transfer, electron transfer, enzyme assay, electrical conductivity, isoelectric focusing, chromatography, immunoprecipitation, immunoseparation, aptamer binding, filtration, electrophoresis, immunoassay, or radioactive assay.

In one embodiment 14755 the at least one image includes one or more images acquired by at least one of a laser, holography, x-ray crystallography, optical coherence tomography, computer-assisted tomography scan, computed tomography, magnetic resonance imaging, positron-emission tomography scan, ultrasound, x-ray, electrical-impedance monitoring, microscopy, spectrometry, flow cytommetry, radioisotope imaging, thermal imaging, infrared visualization, multiphoton calcium-imaging, photography, or in silico generation.

In one embodiment, 14760 the method further comprises transmitting one or more signals that include information relating to the accepting a first input or a second input and information related to the evaluating the at least one substrate. In one embodiment, 14770 the transmitting one or more signals includes transmitting one or more signals associated with selection of at least one parameter for making the at least one frozen particle composition or frozen piercing implement. In one embodiment, 14780 the transmitting one or more signals includes transmitting one or more signals associated with selection of at least one parameter for administering the at least one frozen particle composition or frozen piercing implement.

As illustrated in FIGS. 148-150, in one embodiment, a computer-implemented method 14800, comprises 14810 receiving one or more signals that include information related to accepting input associated with at least one parameter for making or administering at least one frozen particle composition or frozen piercing implement to at least one substrate; 14820 receiving one or more signals that include information related to evaluating the at least one substrate for one or more indicators of administration of the at least one frozen particle composition, or frozen piercing implement; and 14830 processing the information related to the input associated with at least one parameter for making or administering the at least one frozen particle composition or frozen piercing implement to at least one substrate and the information related to the evaluating the at least one substrate.

In one embodiment, 14840 the at least one frozen particle composition or frozen piercing implement includes at least one agent. In one embodiment, 14850 wherein the evaluating at least one substrate for one or more indicators includes evaluating at least one of an assay, image, or gross assessment of the at least one substrate prior to, during, or subsequent to at least one administration of at least one frozen particle composition or frozen piercing implement. In one embodiment, 14860 wherein the assay includes at least one technique that includes spectroscopy, microscopy, electrochemical detection, polynucleotide detection, histological examination, biopsy analysis, fluorescence resonance energy transfer, electron transfer, enzyme assay, electrical conductivity, isoelectric focusing, chromatography, immunoprecipitation, immunoseparation, aptamer binding, filtration, electrophoresis, immunoassay, or radioactive assay. In one embodiment, 14870 wherein the image includes at least one image acquired by one or more of x-ray crystallography, laser, holography, optical coherence tomography, computer-assisted tomography scan, computed tomography, magnetic resonance imaging, positron-emission tomography scan, ultrasound, x-ray, electrical-impedance monitoring, microscopy, spectrometry, flow cytommetry, radioisotope imaging, thermal imaging, infrared visualization, multiphoton calcium-imaging, photography, or in silico generation.

In one embodiment, 14910 wherein the input associated with at least one parameter for administering at least one frozen particle composition or frozen piercing implement to at least one substrate includes one or more of: substrate type; substrate function; substrate size; substrate constitution; substrate architecture; substrate durability; substrate temperature; temperature of administration conditions; depth of administration of the at least one frozen particle composition or frozen piercing implement; substrate source; one or more temporal coordinates; one or more spatial coordinates; presence or absence of at least one agent; presence or absence of at least one microparticle, nanoparticle, lens, tunable lens, sensor, regulator, transducer, actuator, detector, heater, valve, gate, channel, detection material, pump, energy source, injector, controller, receiver, transmitter, or circuit; angle of administration of the at least one frozen particle composition or frozen piercing implement; velocity of administration of the at least one frozen particle composition or frozen piercing implement; quantity of frozen particle compositions or frozen piercing implements administered; rate of administration of more than one frozen particle compositions or frozen piercing implements; method of administration of at least one frozen particle composition or frozen piercing implement; timing of administration of at least one frozen particle composition or frozen piercing implement; or rate of delivery of at least one agent.

In one embodiment, 14920 wherein the input associated with at least one parameter for making the at least one frozen particle composition or frozen piercing implement includes one or more property including: constitution of the at least one frozen particle composition or frozen piercing implement, formulation of the at least one frozen particle composition or frozen piercing implement, size of the at least one frozen particle composition or frozen piercing implement, density of the at least one frozen particle composition or frozen piercing implement, shape of the at least one frozen particle composition or frozen piercing implement, physical structure of the at least one frozen particle composition or frozen piercing implement, or physical or chemical integrity of the at least one frozen particle composition or frozen piercing implement.

In one embodiment, 15010 the at least one agent includes one or more of an adhesive agent, therapeutic agent, reinforcement agent, abrasive, explosive material, or biological remodeling agent. In one embodiment, 15020 the receiving one or more signals includes receiving one or more signals associated with selection of at least one parameter for making or administering the at least one frozen particle composition or frozen piercing implement. In one embodiment, 15030 wherein the at least one substrate includes one or more of a cell, tissue, organ, structure, device, or food product. In one embodiment, 15040 wherein the at least one frozen particle composition or frozen piercing implement includes one or more of hydrogen oxide, nitrogen, oxygen, air, helium, neon, argon, xenon, chlorine, bromine, carbon dioxide, acetone, ethyl acetate, dimethyl sulfoxide, dimethyl formamide, dioxane, tetrahydrofuran, acetronitrile, acetic acid, n-butanol, isopropanol, n-propanol, hexamethylphosphorotriamide, perfluorohydrocarbon, methanol, ethanol, tert-butyl alcohol, formic acid, hydrogen fluoride, ammonia, benzene, carbon tetrachloride, hexane, dichloromethane, methylene chloride, carboxylic acid, saline, standard saline citrate, methane, toluene, chloroform, polyethylene glycol, acetic acid, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, or diethyl ether.

In one embodiment 15050, the output includes one or more instructions for making the at least one frozen particle composition or frozen piercing implement. In one embodiment 15055 the output includes at least one graphical description of the at least one frozen particle composition or frozen piercing implement. In one embodiment 15060, the user includes at least one entity. In one embodiment 15065, the entity includes at least one person, or computer. In one embodiment 15070, the user readable display includes a human readable display. In one embodiment 15080, the user readable display includes one or more active displays. In one embodiment 15090, the user readable display includes one or more passive displays. In one embodiment 15095, the user readable display includes one or more of a numeric format, graphical format, or audio format. In one embodiment 15096 the user readable display includes one or more of a display of one or more differences in the comparison of at least one value related to the first input and at least one value related to at least one property of the at least one frozen particle composition or frozen piercing implement. In one embodiment 15097, the user readable display includes one or more of a display of one or more differences in the comparison of at least one value related to the second input and at least one value related to at least one parameter for administration of the at least one frozen particle composition or frozen piercing implement.

As illustrated in FIGS. 151-157, in one embodiment, a computer-implemented method 15100 comprises 15110 accepting a first input associated with at least one parameter for making at least one frozen piercing implement device; 15120 accepting a second input associated with at least one parameter for administering the at least one frozen piercing implement device to at least one substrate; 15180 processing results of the first input and the second input; and 15198 generating an output to a user readable display. In one embodiment, 15125 the at least one substrate includes one or more of a cell, tissue, organ, structure, device or food product. In one embodiment, 15130 the at least one frozen piercing implement device includes at least one of a frozen piercing implement array device, frozen piercing implement fluidic device, or frozen piercing implement injection device. In one embodiment, 15140 the frozen piercing implement injection device includes a frozen piercing implement auto-injection device. In one embodiment, 15150 wherein the at least one frozen piercing implement device includes at least one agent. In one embodiment, 15160 wherein the at least one agent includes one or more of a therapeutic agent, adhesive agent, abrasive, reinforcement agent, explosive material, or biological remodeling agent. In one embodiment, 15170 wherein the at least one agent is located in at least one frozen piercing implement of the device. In one embodiment, 15190 processing results of the first input and the second input includes electronically processing results of the first input and the second input. In one embodiment, 15195 electronically processing results of the first input and the second input by utilizing one or more of Gaussian smoothing, scaling, homomorphic filtering, parametric estimation techniques, Boolean operations, Monte Carlo simulations, wavelet based techniques, mirroring, smoothing, gradient weighted partial differential equation smoothing, NURBS, polygonal modeling, splines and patches modeling, algorithmic execution, logical decision-making, result prediction, Finite Element Analysis, or modification of a CAD design.

In one embodiment, 15210 the first input includes one or more values related to the at least one parameter for making the at least one frozen piercing implement device. In one embodiment, 15220 wherein the at least one parameter for making the at least one frozen piercing implement device includes one or more of: constitution of the at least one frozen piercing implement of the frozen piercing implement device, constitution of the at least one frozen piercing implement device, formulation of the at least one frozen piercing implement of the frozen piercing implement device, formulation of the at least one frozen piercing implement device, size of the at least one frozen piercing implement of the frozen piercing implement device, size of the at least one frozen piercing implement device, shape of the at least one frozen piercing implement of the frozen piercing implement device, shape of the at least one frozen piercing implement device, physical structure of the at least one frozen piercing implement of the frozen piercing implement device, physical structure of the at least one frozen piercing implement device, physical or chemical integrity of the at least one frozen piercing implement of the frozen piercing implement device, physical or chemical integrity of the at least one frozen piercing implement device, or presence or absence of at least one microparticle, nanoparticle, lens, tunable lens, sensor, transducer, actuator, detector, heater, valve, gate, channel, detection material, pump, energy source, injector, controller, receiver, transmitter, or circuit, in the at least one frozen piercing implement or frozen piercing implement device. In one embodiment, 15230 the at least one parameter for administering at least one frozen piercing implement device to at least one substrate includes one or more of: substrate type; substrate function; substrate size; substrate constitution; substrate architecture; substrate durability; substrate temperature; temperature of administration conditions; depth of administration of the at least one frozen particle composition or frozen piercing implement; substrate source; one or more temporal coordinates; one or more spatial coordinates; presence or absence of at least one agent; presence or absence of at least one microparticle, nanoparticle, lens, tunable lens, sensor, regulator, transducer, actuator, detector, heater, valve, gate, channel, detection material, pump, energy source, injector, controller, receiver, transmitter, or circuit; angle of administration of the at least one frozen piercing implement device; velocity of administration of the at least one frozen piercing implement device; quantity of frozen piercing implements of the device; quantity of frozen piercing implement devices administered; rate of administration of more than one frozen piercing implement devices; method of administration of at least one frozen piercing implement device; timing of administration of at least one frozen piercing implement; or rate of delivery of at least one agent of the device.

In one embodiment, 15310 the one or more values related to the at least one parameter for administering at least one frozen piercing implement device includes one or more predictive values. In one embodiment, 15320 the at least one parameter for administering at least one frozen piercing implement device includes at least one parameter relating to at least partially ablating or at least partially abrading one or more surfaces of the at least one substrate with the at least one frozen piercing implement device. In one embodiment, 15330 the first input includes one or more values derived from at least one property of at least one frozen piercing implement device. In one embodiment, 15340 the at least one substrate is located in at least one of in situ, in vitro, in vivo, in utero, in planta, in silico, or ex vivo. In one embodiment, 15350 the at least one substrate is at least partially located in at least one subject. In one embodiment, the method 15360 further comprises accepting a third input associated with at least one feature of the at least one subject. In one embodiment, the at least one feature of the at least one subject includes one or more of age, gender, genotype, phenotype, proteomic profile, anatomic landscape, body contour, or health condition. In one embodiment 15370, the at least one feature of the at least one subject includes one or more of age, gender, genotype, phenotype, proteomic profile, lipidomic profile, glycomic profile, system biology profile, lymph condition, circulatory condition, respiratory condition, blood condition, anatomic landscape, body contour, or health condition. In one embodiment, 15380 the output includes one or more instructions for making the at least one frozen particle composition or frozen piercing implement. In one embodiment, 15390 the output includes at least one graphical description of the at least one frozen particle composition or frozen piercing implement.

In one embodiment 15407, the user readable display includes one or more of a display of one or more differences in the comparison of at least one value related to the first input and at least one value related to at least one property of the at least one frozen particle composition or frozen piercing implement. In one embodiment 15408, the user readable display includes one or more of a display of one or more differences in the comparison of at least one value related to the second input and at least one value related to at least one parameter for administration of the at least one frozen particle composition or frozen piercing implement. In one embodiment, 15410 the processing results of the first input and the second input includes determining at least one parameter for making at least one frozen piercing implement device from one or more values derived from at least one characteristic of at least one frozen piercing implement of the frozen piercing implement device. In one embodiment, 15420 the second input includes one or more values related to the at least one parameter for administering at least one frozen piercing implement device to the at least one substrate. In one embodiment, 15430 the processing results includes comparing at least one value related to the first input associated with the at least one parameter for making the frozen piercing implement device with at least one value related to at least one property of the at least one frozen piercing implement. In one embodiment, 15440 the processing results includes determining one or more differences in at least one value related to the first input and at least one value related to at least one property of the at least one frozen piercing implement device. In one embodiment, 15450 the processing results includes determining one or more differences in at least one value related to the second input associated with the one or more parameters of administering at least one frozen piercing implement device to the at least one substrate. In one embodiment, 15460 the processing results includes generating one or more protocols for administering the at least one frozen piercing implement device. In one embodiment, 15510 the administering at least one frozen piercing implement device includes delivering at least one agent to the at least one substrate by way of the at least one frozen piercing implement device.

In one embodiment 15518, the user includes at least one entity. In one embodiment 15520, the entity includes at least one person, or computer. In one embodiment 15530, the user readable display includes a human readable display. In one embodiment 15540, the user readable display includes one or more active displays. In one embodiment 15550, the user readable display includes one or more passive displays. In one embodiment 15560, the user readable display includes one or more of a numeric format, graphical format, or audio format. In one embodiment 15570 the user readable display includes one or more of a display of one or more differences in the comparison of at least one value related to the first input and at least one value related to at least one property of the at least one frozen particle composition or frozen piercing implement. In one embodiment 15580, the user readable display includes one or more of a display of one or more differences in the comparison of at least one value related to the second input and at least one value related to at least one parameter for administration of the at least one frozen particle composition or frozen piercing implement.

In one embodiment, the method 15610 further comprises transmitting one or more signals that include information related to the processing results of the first input and the second input. In one embodiment, 15620 the transmitting one or more signals includes transmitting one or more signals associated with selection of at least one parameter for making the at least one frozen piercing implement device. In one embodiment, 15630 the transmitting one or more signals includes transmitting one or more signals associated with selection of one or more agents to be delivered by the at least one frozen piercing implement device. In one embodiment, 15640 wherein the transmitting one or more signals includes transmitting one or more signals associated with comparing the information related to the processing results of the first input and the second input. In one embodiment, 15650 wherein the at least one frozen piercing implement device includes one or more frozen piercing implements that include at least one of hydrogen oxide, nitrogen, oxygen, air, helium, neon, argon, xenon, chlorine, bromine, carbon dioxide, acetone, ethyl acetate, dimethyl sulfoxide, dimethyl formamide, dioxane, tetrahydrofuran, acetonitrile, acetic acid, n-butanol, isopropanol, n-propanol, hexamethylphosphorotriamide, perfluorohydrocarbon, methanol, ethanol, tert-butyl alcohol, formic acid, hydrogen fluoride, ammonia, benzene, carbon tetrachloride, hexane, dichloromethane, methylene chloride, carboxylic acid, saline, standard saline citrate, methane, toluene, chloroform, polyethylene glycol, acetic acid, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, or diethyl ether.

In one embodiment, the method 15710 further comprises making at least one frozen piercing implement device. In one embodiment, the method 15720 further comprises administering at least one frozen piercing implement device to at least one substrate. In one embodiment, the method 15730 further comprises evaluating the at least one substrate for one or more indicators related to at least one parameter for administering the at least one frozen piercing implement device. In one embodiment, 15740 the evaluating at least one substrate for one or more indicators includes evaluating at least one of an assay, image, or gross assessment of the at least one substrate prior to, during, or subsequent to at least one administration of the at least one frozen piercing implement device. In one embodiment, 15750 the assay includes at least one technique including spectroscopy, microscopy, electrochemical detection, polynucleotide detection, histological examination, biopsy analysis, fluorescence resonance energy transfer, electron transfer, enzyme assay, electrical conductivity, isoelectric focusing, chromatography, immunoprecipitation, immunoseparation, aptamer binding, filtration, electrophoresis, immunoassay, or radioactive assay. In one embodiment, 15755 wherein the at least one image includes one or more images acquired by at least one of laser, holography, x-ray, crystallography, optical coherence tomography, computer-assisted tomography scan, computed tomography, magnetic resonance imaging, positron-emission tomography scan, ultrasound, x-ray, electrical-impedance monitoring, microscopy, spectrometry, flow cytommetry, radioisotope imaging, thermal imaging, infrared visualization, multiphoton calcium-imaging, photography, or in silico generation In one embodiment, the method 15760 further comprises transmitting one or more signals that include information relating to the accepting a first input or a second input and information related to the evaluating the at least one substrate. In one embodiment, 15770 the transmitting one or more signals includes transmitting one or more signals associated with selection of at least one parameter for making the at least one frozen piercing implement device. In one embodiment, 15780 wherein the transmitting one or more signals includes transmitting one or more signals associated with selection of at least one parameter for administering the at least one frozen piercing implement device.

As illustrated in FIGS. 158-160 a computer-implemented method 15800 comprises 15810 receiving one or more signals that include information related to accepting input associated with at least one parameter for making or administering at least one frozen particle composition, frozen piercing implement, or frozen piercing implement device to at least one substrate; wherein the at least one frozen particle composition, frozen piercing implement, or frozen piercing implement device includes at least one agent; 15820 receiving one or more signals that include information related to evaluating the at least one substrate for one or more indicators of administration of the at least one frozen particle composition, frozen piercing implement, frozen piercing implement device, or agent; and 15830 processing the information related to the input associated with at least one parameter for making or administering the at least one frozen piercing implement device to at least one substrate and the information related to the evaluating the at least one substrate. In one embodiment, 15840 wherein the evaluating at least one substrate for one or more indicators includes evaluating at least one of an assay, image, or gross assessment of the at least one substrate prior to, during, or subsequent to at least one administration of at least one frozen piercing implement device. In one embodiment, 15850 the assay includes at least one technique that includes spectroscopy, microscopy, electrochemical detection, polynucleotide detection, histological examination, biopsy analysis, fluorescence resonance energy transfer, electron transfer, enzyme assay, electrical conductivity, isoelectric focusing, chromatography, immunoprecipitation, immunoseparation, aptamer binding, filtration, electrophoresis, immunoassay, or radioactive assay. In one embodiment, 15860 wherein the image includes at least one image acquired by one or more of x-ray crystallography, laser, holography, optical coherence tomography, computer-assisted tomography scan, computed tomography, magnetic resonance imaging, positron-emission tomography scan, ultrasound, x-ray, electrical-impedance monitoring, microscopy, spectrometry, flow cytommetry, radioisotope imaging, thermal imaging, infrared visualization, multiphoton calcium-imaging, photography, or in silico generation. In one embodiment, 15870 wherein the receiving one or more signals includes receiving one or more signals associated with selection of at least one parameter for making or administering the at least one frozen particle composition, frozen piercing implement, or frozen piercing implement device.

In one embodiment, 15910 the at least one parameter for making the at least one frozen piercing implement device includes one or more of: constitution of the at least one frozen piercing implement of the frozen piercing implement device, constitution of the at least one frozen piercing implement device, formulation of the at least one frozen piercing implement of the frozen piercing implement device, formulation of the at least one frozen piercing implement device, size of the at least one frozen piercing implement of the frozen piercing implement device, size of the at least one frozen piercing implement device, shape of the at least one frozen piercing implement of the frozen piercing implement device, shape of the at least one frozen piercing implement device, physical structure of the at least one frozen piercing implement of the frozen piercing implement device, physical structure of the at least one frozen piercing implement device, physical or chemical integrity of the at least one frozen piercing implement of the frozen piercing implement device, physical or chemical integrity of the at least one frozen piercing implement device, or presence or absence of at least one microparticle, nanoparticle, lens, tunable lens, sensor, transducer, actuator, detector, heater, valve, gate, channel, detection material, pump, energy source, injector, controller, receiver, transmitter, or circuit, in the at least one frozen piercing implement or frozen piercing implement device.

In one embodiment, 15920 wherein the at least one parameter for administering at least one frozen piercing implement device to at least one substrate includes one or more of: substrate type; substrate function; substrate size; substrate constitution; substrate architecture; substrate durability; substrate temperature; temperature of administration conditions; depth of administration of the at least one frozen particle composition or frozen piercing implement; substrate source; one or more temporal coordinates; one or more spatial coordinates; presence or absence of at least one agent; presence or absence of at least one microparticle, nanoparticle, lens, tunable lens, sensor, regulator, transducer, actuator, detector, heater, valve, gate, channel, detection material, pump, energy source, injector, controller, receiver, transmitter, or circuit; angle of administration of the at least one frozen piercing implement device; velocity of administration of the at least one frozen piercing implement device; quantity of frozen piercing implements of the device; quantity of frozen piercing implement devices administered; rate of administration of more than one frozen piercing implement devices; method of administration of at least one frozen piercing implement device; timing of administration of at least one frozen piercing implement; or rate of delivery of at least one agent of the device.

In one embodiment, 16010 the at least one agent includes one or more of an adhesive agent, therapeutic agent, reinforcement agent, abrasive, explosive material, or biological remodeling agent. In one embodiment, 16020 wherein the at least one substrate includes one or more of a cell, tissue, organ, structure, device, or food product. In one embodiment, 16030 wherein the at least one frozen particle composition, frozen piercing implement, or frozen piercing implement device includes one or more of hydrogen oxide, nitrogen, oxygen, air, helium, neon, argon, xenon, chlorine, bromine, carbon dioxide, acetone, ethyl acetate, dimethyl sulfoxide, dimethyl formamide, dioxane, tetrahydrofuran, acetronitrile, acetic acid, n-butanol, isopropanol, n-propanol, hexamethylphosphorotriamide, perfluorohydrocarbon, methanol, ethanol, tert-butyl alcohol, formic acid, hydrogen fluoride, ammonia, benzene, carbon tetrachloride, hexane, dichloromethane, methylene chloride, carboxylic acid, saline, standard saline citrate, methane, toluene, chloroform, polyethylene glycol, acetic acid, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, or diethyl ether.

In one embodiment 16035, the output includes one or more instructions for making the at least one frozen particle composition, frozen piercing implement, or frozen piercing implement device. In one embodiment 16040, the output includes at least one graphical description of the at least one frozen particle composition, frozen piercing implement, or frozen piercing implement device.

In one embodiment 16050, the user includes at least one entity. In one embodiment 16055, the entity includes at least one person, or computer. In one embodiment 16060, the user readable display includes a human readable display. In one embodiment 16065, the user readable display includes one or more active displays. In one embodiment 16070, the user readable display includes one or more passive displays. In one embodiment 16075, the user readable display includes one or more of a numeric format, graphical format, or audio format. In one embodiment 16076 the user readable display includes one or more of a display of one or more differences in the comparison of at least one value related to the first input and at least one value related to at least one property of the at least one frozen particle composition or frozen piercing implement. In one embodiment 16077, the user readable display includes one or more of a display of one or more differences in the comparison of at least one value related to the second input and at least one value related to at least one parameter for administration of the at least one frozen particle composition or frozen piercing implement.

In one embodiment 16110, at least one parameter for making the at least one frozen particle composition or frozen piercing implement includes one or more of: constitution of the at least one frozen particle composition or frozen piercing implement, formulation of the at least one frozen particle composition or frozen piercing implement, size of the at least one frozen particle composition or frozen piercing implement, density of the at least one frozen particle composition or frozen piercing implement, shape of the at least one frozen particle composition or frozen piercing implement, physical structure of the at least one frozen particle composition or frozen piercing implement, physical or chemical integrity of the at least one frozen particle composition or frozen piercing implement, or presence or absence of a microparticle, nanoparticle, lens, tunable lens, sensor, transducer, actuator, detector, heater, valve, gate, channel, detection material, pump, energy source, injector, controller, receiver, transmitter, or circuit.

In one embodiment 16120, at least one parameter for administering the at least one frozen particle composition or frozen piercing implement includes one or more of: substrate type; substrate function; substrate size; substrate constitution; substrate architecture; substrate durability; substrate temperature; temperature of administration conditions; depth of administration of the at least one frozen particle composition or frozen piercing implement; substrate source; one or more temporal coordinates; one or more spatial coordinates; presence or absence of at least one agent; presence or absence of at least one microparticle, nanoparticle, lens, tunablelens, sensor, transducer, actuator, detector, heater, valve, gate, channel, detection material, pump, power source, injector, controller, receiver, transmitter, or circuit; angle of administration of the at least one frozen piercing implement device; force of administration of the at least one frozen piercing implement device; velocity of administration of the at least one frozen piercing implement device; quantity of frozen piercing implements of the device; quantity of frozen piercing implement devices administered; rate of administration of more than one frozen piercing implement devices; method of administration of at least one frozen piercing implement device; timing of administration of at least one frozen piercing implement; or rate of delivery of at least one agent of the device.

As illustrated in FIG. 162, in one embodiment, a method 16200 comprises 16210 making at least one frozen particle composition, frozen piercing implement, or frozen piercing implement device; and 16220 administering at least one frozen particle composition, frozen piercing implement, or frozen piercing implement device to at least one substrate. In one embodiment, the method 16200 includes a computer-implemented method.

As illustrated in FIGS. 163-166, a system 16300 comprises: 16310 means for receiving one or more signals that include information related to accepting input associated with at least one parameter for making or administering at least one frozen particle composition or frozen piercing implement to at least one substrate, the frozen particle composition or frozen piercing implement including at least one agent; 16320 means for receiving one or more signals that include information related to evaluating the at least one substrate for one or more indicators of administration of the at least one frozen particle composition, frozen piercing implement, or agent; 16330 means for processing the information related to the input associated with at least one parameter for making or administering the at least one frozen particle composition or frozen piercing implement to at least one substrate and the information related to the evaluating the at least one substrate; and 16340 means for generating an output to a user readable display. In one embodiment 16350, evaluating at least one substrate for one or more indicators includes evaluating at least one of an assay, image, or gross assessment of the at least one biological tissue prior to, during, or subsequent to at least one administration of the at least one frozen particle composition or frozen piercing implement. In one embodiment 16360, the assay includes at least one technique that includes spectroscopy, microscopy, electrochemical detection, polynucleotide detection, histological examination, biopsy analysis, fluorescence resonance energy transfer, electron transfer, enzyme assay, electrical conductivity, isoelectric focusing, chromatography, immunoprecipitation, immunoseparation, aptamer binding, filtration, electrophoresis, immunoassay, or radioactive assay.

In one embodiment 16370, the image includes at least one image acquired by one or more of x-ray crystallography, laser, holography, optical coherence tomography, computer-assisted tomography scan, computed tomography, magnetic resonance imaging, positron-emission tomography scan, ultrasound, x-ray, electrical-impedance monitoring, microscopy, spectrometry, flow cytommetry, radioisotope imaging, thermal imaging, infrared visualization, multiphoton calcium-imaging, photography, or in silico generation. In one embodiment 16410, the input associated with at least one parameter for administering at least one frozen particle composition or frozen piercing implement to at least one substrate includes one or more of: substrate type; substrate function; substrate size; substrate constitution; substrate architecture; substrate durability; substrate temperature; temperature of administration conditions; depth of administration of the at least one frozen particle composition or frozen piercing implement; substrate source; one or more temporal coordinates; one or more spatial coordinates; presence or absence of at least one agent; presence or absence of at least one microparticle, nanoparticle, lens, tunablelens, sensor, transducer, actuator, detector, heater, valve, gate, channel, detection material, pump, power source, injector, controller, receiver, transmitter, or circuit; angle of administration of the at least one frozen particle composition or frozen piercing implement; force of administration of the at least one frozen particle composition or frozen piercing implement; velocity of administration of the at least one frozen particle composition or frozen piercing implement; quantity of frozen particle compositions or frozen piercing implements administered; rate of administration of more than one frozen particle compositions or frozen piercing implements; method of administration of at least one frozen particle composition or frozen piercing implement; timing of administration of at least one frozen particle composition or frozen piercing implement; or rate of delivery of at least one agent.

In one embodiment 16420, the at least one agent includes one or more of an adhesive agent, therapeutic agent, reinforcement agent, abrasive, explosive material, or biological remodeling agent. In one embodiment 16430, the means for receiving one or more signals includes means for receiving one or more signals associated with selection of at least one parameter for making the at least one frozen particle composition or frozen piercing implement. In one embodiment 16440, the at least one parameter for making the at least one frozen particle composition or frozen piercing implement includes one or more property including: constitution of the at least one frozen particle composition or frozen piercing implement, configuration of the at least one frozen particle composition or frozen piercing implement, formulation of the at least one frozen particle composition or frozen piercing implement, size of the at least one frozen particle composition or frozen piercing implement, density of the at least one frozen particle composition or frozen piercing implement, shape of the at least one frozen particle composition or frozen piercing implement, physical structure of the at least one frozen particle composition or frozen piercing implement, physical or chemical integrity of the at least one frozen particle composition or frozen piercing implement.

In one embodiment 16510, the at least one substrate includes one or more of a cell, tissue, organ, structure, device, or food product. In one embodiment 16520, the at least one frozen particle composition or frozen piercing implement includes one or more of hydrogen oxide, nitrogen, oxygen, air, helium, neon, argon, xenon, chlorine, bromine, carbon dioxide, acetone, ethyl acetate, dimethyl sulfoxide, dimethyl formamide, dioxane, tetrahydrofuran, acetonitrile, acetic acid, n-butanol, isopropanol, n-propanol, hexamethylphosphorotriamide, perfluorohydrocarbon, methanol, ethanol, tert-butyl alcohol, formic acid, hydrogen fluoride, ammonia, benzene, carbon tetrachloride, hexane, dichloromethane, methylene chloride, carboxylic acid, saline, methane, toluene, chloroform, polyethylene glycol, acetic acid, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, or diethyl ether.

In one embodiment 16530, the output includes one or more instructions for making the at least one frozen particle composition or frozen piercing implement. In one embodiment 16540, the output includes at least one graphical description of the at least one frozen particle composition or frozen piercing implement. In one embodiment 16550, the user includes at least one entity. In one embodiment 16560, the entity includes at least one person, or computer. In one embodiment 16570, the user readable display includes a human readable display. In one embodiment 16580, the user readable display includes one or more active displays. In one embodiment 16590, the user readable display includes one or more passive displays. In one embodiment 16595, the user readable display includes one or more of a numeric format, graphical format, or audio format. In one embodiment 16610, the user readable display includes one or more of a display of one or more differences in the comparison of at least one value related to the first input and at least one value related to at least one property of the at least one frozen particle composition or frozen piercing implement. In one embodiment 16620, the user readable display includes one or more of a display of one or more differences in the comparison of at least one value related to the second input and at least one value related to at least one parameter for administration of the at least one frozen particle composition or frozen piercing implement.

As illustrated in FIGS. 167-174, a system 16700 comprises: 16710 means for accepting a first input associated with at least one parameter for making at least one frozen piercing implement device; 16720 means for accepting a second input associated with at least one parameter for administering the at least one frozen piercing implement device to at least one substrate; 16730 means for processing the first input and the second input; and 16740 means for generating an output to a user readable display.

In one embodiment 16750, the at least one frozen piercing implement device includes at least one of a frozen piercing implement array device, frozen piercing implement fluidic device, or frozen piercing implement injection device. In one embodiment 16760, the frozen piercing implement injection device includes a frozen piercing implement auto-injection device.

In one embodiment 16770, the means for processing the first input and the second input includes means for electronically processing the first input and the second input. In one embodiment 16780, the means for processing the first input and the second input includes means for electronically processing the first input and the second input by utilizing one or more of Gaussian smoothing, scaling, homomorphic filtering, parametric estimation techniques, Boolean operations, Monte Carlo simulations, wavelet based techniques, mirroring, smoothing, gradient weighted partial differential equation smoothing, NURBS, polygonal modeling, splines and patches modeling, algorithmic execution, logical decision-making, result prediction, Finite Element Analysis, or modification of a CAD design.

In one embodiment 16810, the frozen piercing implement device includes at least one agent. In one embodiment 16820, the at least one agent is located in at least one frozen piercing implement of the device. In one embodiment 16830, the at least one agent includes one or more of a therapeutic agent, adhesive agent, abrasive, reinforcement agent, explosive material, or biological remodeling agent. In one embodiment 16840, the at least one substrate includes one or more of a cell, tissue, organ, structure, device, or food product. In one embodiment 16850, the first input includes one or more values related to the at least one parameter for making the at least one frozen piercing implement device. In one embodiment 16860, the at least one parameter for making the at least one frozen piercing implement device includes one or more of: constitution of the at least one frozen piercing implement of the frozen piercing implement device, constitution of the at least one frozen piercing implement device, configuration of the at least one frozen piercing implement, configuration of the at least one frozen piercing implement or frozen piercing implement device, formulation of the at least one frozen piercing implement of the frozen piercing implement device, formulation of the at least one frozen piercing implement device, size of the at least one frozen piercing implement of the frozen piercing implement device, size of the at least one frozen piercing implement device, shape of the at least one frozen piercing implement of the frozen piercing implement device, shape of the at least one frozen piercing implement device, physical structure of the at least one frozen piercing implement of the frozen piercing implement device, physical structure of the at least one frozen piercing implement device, physical or chemical integrity of the at least one frozen piercing implement of the frozen piercing implement device, or physical or chemical integrity of the at least one frozen piercing implement device.

In one embodiment 16910, the at least one parameter for administering at least one frozen piercing implement device to at least one substrate includes one or more of: substrate type; substrate function; substrate size; substrate constitution; substrate architecture; substrate durability; substrate temperature; temperature of administration conditions; depth of administration of the at least one frozen particle composition or frozen piercing implement; substrate source; one or more temporal coordinates; one or more spatial coordinates; presence or absence of at least one agent; presence or absence of at least one microparticle, nanoparticle, lens, tunablelens, sensor, transducer, actuator, detector, heater, valve, gate, channel, detection material, pump, power source, injector, controller, receiver, transmitter, or circuit; angle of administration of the at least one frozen piercing implement device; force of administration of the at least one frozen piercing implement device; velocity of administration of the at least one frozen piercing implement device; quantity of frozen piercing implements of the device; quantity of frozen piercing implement devices administered; rate of administration of more than one frozen piercing implement devices; method of administration of at least one frozen piercing implement device; timing of administration of at least one frozen piercing implement; or rate of delivery of at least one agent of the device.

In one embodiment 16920, the at least one parameter for administering at least one frozen piercing implement device includes at least one parameter relating to at least partially ablating or at least partially abrading one or more surfaces of the at least one substrate with the at least one frozen piercing implement device. In one embodiment 16930, the first input includes one or more values derived from at least one property of at least one frozen piercing implement device. In one embodiment 16940, the at least one substrate is located in at least one of in situ, in vitro, in vivo, in utero, in planta, in silico, or ex vivo. In one embodiment 16950, the at least one substrate is at least partially located in at least one subject.

In one embodiment 16960, the system further comprises means for accepting a third input associated with at least one feature of the at least one subject. In one embodiment 17010, the at least one feature of the at least one subject includes one or more of age, gender, genotype, phenotype, proteomic profile, lipidomic profile, glycomic profile, system biology profile, lymph condition, circulatory condition, respiratory condition, blood condition, anatomic landscape, body contour, or health condition. In one embodiment 17020, the means for processing the first input and the second input includes means for determining at least one parameter for administering at least one frozen piercing implement device from one or more values derived from at least one image of at least one frozen piercing implement of the device, or at least one image of at least one frozen piercing implement device. In one embodiment 17030, the second input includes one or more values related to the at least one parameter for administering at least one frozen piercing implement device to the at least one substrate.

In one embodiment 17040, the one or more values related to the at least one parameter for administering at least one frozen piercing implement device includes one or more predictive values. In one embodiment 17050, the means for processing the first input and the second input includes means for comparing at least one value related to the first input associated with the at least one parameter for making the frozen piercing implement device with at least one value related to at least one property of at least one frozen piercing implement of the device, or at least one frozen piercing implement device. In one embodiment 17060, the means for processing the first input and the second input includes means for determining one or more differences in at least one value related to the first input and at least one value related to at least one property of at least one frozen piercing implement device or at least one frozen piercing implement of the device. In one embodiment 17070, the means for processing the first input and the second input includes means for determining one or more differences in at least one value related to the second input associated with the one or more parameters of administering at least one frozen piercing implement device to the at least one substrate.

In one embodiment 17110, the means for processing the first input and the second input includes means for generating one or more protocols for administering the at least one frozen piercing implement device. In one embodiment 17120, the output includes one or more instructions for making the at least one frozen particle composition or frozen piercing implement. In one embodiment 17130, the output includes at least one graphical description of the at least one frozen particle composition or frozen piercing implement.

In one embodiment 17140, the user includes at least one entity. In one embodiment 17150, the entity includes at least one person, or computer. In one embodiment 17160, the user readable display includes a human readable display. In one embodiment 17170, the user readable display includes one or more active displays. In one embodiment 17180, the user readable display includes one or more passive displays. In one embodiment 17185, the user readable display includes one or more of a numeric format, graphical format, or audio format. In one embodiment 17190, the user readable display includes one or more of a display of one or more differences in the comparison of at least one value related to the first input and at least one value related to at least one property of the at least one frozen particle composition or frozen piercing implement.

In one embodiment 17210, the user readable display includes one or more of a display of one or more differences in the comparison of at least one value related to the second input and at least one value related to at least one parameter for administration of the at least one frozen particle composition or frozen piercing implement. In one embodiment 17220, the system further comprises means for transmitting one or more signals that include information related to the means for processing the first input and the second input. In one embodiment 17230, the means for transmitting one or more signals includes means for transmitting one or more signals associated with selection of at least one parameter for making the at least one frozen piercing implement device. In one embodiment 17240, the means for transmitting one or more signals includes means for transmitting one or more signals associated with selection of one or more agents to be delivered by the at least one frozen piercing implement device.

In one embodiment 17250, the at least one agent includes one or more of an adhesive agent, therapeutic agent, reinforcement agent, abrasive, explosive material, or biological remodeling agent. In one embodiment 17310, the means for transmitting one or more signals includes means for transmitting one or more signals associated with at least one parameter for making or administering at least one frozen piercing implement device. In one embodiment 17320, means for transmitting one or more signals includes means for transmitting one or more signals associated with means for comparing the information related to the means for processing the first input and the second input. In one embodiment 17330, the at least one frozen piercing implement device includes one or more frozen piercing implements that include at least one of hydrogen oxide, nitrogen, oxygen, air, helium, neon, argon, xenon, chlorine, bromine, carbon dioxide, acetone, ethyl acetate, dimethyl sulfoxide, dimethyl formamide, dioxane, tetrahydrofuran, acetonitrile, acetic acid, n-butanol, isopropanol, n-propanol, hexamethylphosphorotriamide, perfluorohydrocarbon, methanol, ethanol, tert-butyl alcohol, formic acid, hydrogen fluoride, ammonia, benzene, carbon tetrachloride, hexane, dichloromethane, methylene chloride, carboxylic acid, saline, methane, toluene, chloroform, polyethylene glycol, acetic acid, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, or diethyl ether.

In one embodiment 17340, the system further comprises means for making at least one frozen piercing implement device. In one embodiment 17350, the system further comprises means for administering at least one frozen piercing implement device to at least one substrate. In one embodiment 17360, the system further comprises means for evaluating the at least one substrate for one or more indicators related to at least one parameter for administering the at least one frozen piercing implement device. In one embodiment 17370, the means for evaluating at least one substrate for one or more indicators includes means for evaluating at least one of an assay, image, or gross assessment of the at least one substrate prior to, during, or subsequent to at least one administration of the at least one frozen particle composition or frozen piercing implement.

In one embodiment 17410, the assay includes at least one technique including spectroscopy, microscopy, electrochemical detection, polynucleotide detection, histological examination, biopsy analysis, fluorescence resonance energy transfer, electron transfer, enzyme assay, electrical conductivity, isoelectric focusing, chromatography, immunoprecipitation, immunoseparation, aptamer binding, filtration, electrophoresis, immunoassay, or radioactive assay. In one embodiment 17420, the at least one image includes one or more images acquired by at least one of laser, holography, x-ray crystallography, optical coherence tomography, computer-assisted tomography scan, computed tomography, magnetic resonance imaging, positron-emission tomography scan, ultrasound, x-ray, electrical-impedance monitoring, microscopy, spectrometry, flow cytommetry, radioisotope imaging, thermal imaging, infrared visualization, multiphoton calcium-imaging, photography, or in silico generation.

In one embodiment 17430, the system further comprises means for transmitting one or more signals that include information relating to the accepting a first input or a second input and information related to the evaluating the at least one substrate. In one embodiment 17440, the means for transmitting one or more signals includes means for transmitting one or more signals associated with selection of at least one parameter for making the at least one frozen particle composition or frozen piercing implement. In one embodiment 17460, the means for transmitting one or more signals includes means for transmitting one or more signals associated with selection of at least one parameter for administering the at least one frozen particle composition or frozen piercing implement.

As illustrated in FIGS. 175-181, a system 17500, comprises: 17510 means for accepting a first input associated with at least one parameter for making at least one frozen particle composition or frozen piercing implement; 17520 means for accepting a second input associated with at least one parameter for administering the at least one frozen particle composition or frozen piercing implement to at least one substrate; 17530 means for processing the first input and the second input; and 17540 means for generating an output to a user readable display. In one embodiment 17550, the at least one parameter for administering at least one frozen particle composition or frozen piercing implement includes at least one parameter relating to at least partially ablating or at least partially abrading one or more surfaces of the at least one substrate with the at least one frozen particle composition or frozen piercing implement. In one embodiment 17560, the means for processing the first input and the second input includes means for electronically processing the first input and the second input. In one embodiment 17570, the means for processing the first input and the second input includes means for electronically processing the first input and the second input by utilizing one or more of Gaussian smoothing, scaling, homomorphic filtering, parametric estimation techniques, Boolean operations, Monte Carlo simulations, wavelet based techniques, mirroring, smoothing, gradient weighted partial differential equation smoothing, NURBS, polygonal modeling, splines and patches modeling, algorithmic execution, logical decision-making, result prediction, Finite Element Analysis, or modification of a CAD design.

In one embodiment 17580, the first input includes one or more values related to the at least one parameter for making the at least one frozen particle composition or frozen piercing implement. In one embodiment 17610, the at least one parameter for making the at least one frozen particle composition or frozen piercing implement includes one or more property including: constitution of the at least one frozen particle composition or frozen piercing implement, configuration of the at least one frozen particle composition or frozen piercing implement, formulation of the at least one frozen particle composition or frozen piercing implement, size of the at least one frozen particle composition or frozen piercing implement, density of the at least one frozen particle composition or frozen piercing implement, shape of the at least one frozen particle composition or frozen piercing implement, physical structure of the at least one frozen particle composition or frozen piercing implement, physical or chemical integrity of the at least one frozen particle composition or frozen piercing implement, or presence or absence of a microparticle, nanoparticle, lens, tunablelens, sensor, transducer, actuator, detector, heater, valve, gate, channel, detection material, pump, power source, injector, controller, receiver, transmitter, or circuit. In one embodiment 17620, the at least one parameter for administering at least one frozen particle composition or frozen piercing implement to at least one substrate includes one or more of: substrate type; substrate function; substrate size; substrate constitution; substrate architecture; substrate durability; substrate temperature; temperature of administration conditions; depth of administration of the at least one frozen particle composition or frozen piercing implement; substrate source; one or more temporal coordinates; one or more spatial coordinates; presence or absence of at least one agent; presence or absence of one or more sensors, valves, gates, channels, transducers, circuits, nanoparticles, microactuators, microdetectors, microheaters, or detection materials; angle of administration of the at least one frozen particle composition or frozen piercing implement; force of administration of the at least one frozen particle composition or frozen piercing implement velocity of administration of the at least one frozen particle composition or frozen piercing implement; quantity of frozen particle compositions or frozen piercing implements administered; rate of administration of more than one frozen particle compositions or frozen piercing implements; method of administration of at least one frozen particle composition or frozen piercing implement; timing of administration of at least one frozen particle composition or frozen piercing implement; or rate of delivery of at least one agent.

In one embodiment 17630, the at least one agent includes one or more of an adhesive agent, therapeutic agent, reinforcement agent, abrasive, explosive material, or biological remodeling agent. In one embodiment 17710, the at least one substrate includes one or more of a cell, tissue, organ, structure, device, or food product. In one embodiment 17720, the first input includes one or more values derived from at least one property of the at least one frozen particle composition or frozen piercing implement.

In one embodiment 17730, the at least one substrate is located in at least one of in situ, in vitro, in vivo, in utero, in planta, in silico, or ex vivo. In one embodiment 17740, the at least one substrate is at least partially located in at least one subject. In one embodiment 17750, the system further comprises means for accepting a third input associated with at least one feature of the at least one subject. In one embodiment 17760, the at least one feature of the at least one subject includes one or more of age, gender, genotype, phenotype, proteomic profile, lipidomic profile, glycomic profile, system biology profile, lymph condition, circulatory condition, respiratory condition, blood condition, anatomic landscape, body contour, or health condition. In one embodiment 17770, the means for processing the first input and the second input includes means for determining at least one parameter for administering at least one frozen particle composition or frozen piercing implement from one or more values derived from at least one parameter for administering the at least one frozen particle composition or frozen piercing implement. In one embodiment 17780, the means for processing the first input and the second input includes means for determining one or more differences in at least one value related to the second input and at least one value related to at least one parameter for administering of at least one frozen particle composition or frozen piercing implement to at least one substrate.

In one embodiment 17810, the second input includes one or more values related to the at least one parameter for administering at least one frozen particle composition or frozen piercing implement to the at least one substrate. In one embodiment 17820, the one or more values related to the at least one parameter for administering at least one frozen particle composition or frozen piercing implement includes one or more predictive values. In one embodiment 17830, the means for processing the first input and the second input includes means for comparing at least one value related to the first input associated with the at least one parameter for making the at least one frozen particle composition or frozen piercing implement with at least one value related to at least one property of the frozen particle composition or frozen piercing implement.

In one embodiment 17840, the means for processing the first input and the second input includes means for determining one or more differences in at least one value related to the first input and at least one value related to at least one property of the at least one frozen particle composition or frozen piercing implement. In one embodiment 19950, the means for processing the first input and the second input includes means for generating one or more protocols for administering the at least one frozen particle composition or frozen piercing implement. In one embodiment 17860, the output includes one or more instructions for making the at least one frozen particle composition or frozen piercing implement. In one embodiment 17870, the output includes at least one graphical description of the at least one frozen particle composition or frozen piercing implement. In one embodiment 17880, the user includes at least one entity.

In one embodiment 17910, the entity includes at least one person, or computer. In one embodiment 17920, the user readable display includes a human readable display. In one embodiment 17930, the user readable display includes one or more active displays. In one embodiment 17940, the user readable display includes one or more passive displays. In one embodiment 17950, the user readable display includes one or more of a numeric format, graphical format, or audio format. In one embodiment 17960, the user readable display includes one or more of a display of one or more differences in the comparison of at least one value related to the first input and at least one value related to at least one property of the at least one frozen particle composition or frozen piercing implement. In one embodiment 17970, the user readable display includes one or more of a display of one or more differences in the comparison of at least one value related to the second input and at least one value related to at least one parameter for administration of the at least one frozen particle composition or frozen piercing implement.

In one embodiment 17980, the system further comprises means for transmitting one or more signals that include information related to the processing of the first input and the second input. In one embodiment 17990, the means for transmitting one or more signals includes means for transmitting one or more signals associated with selection of at least one parameter for making the at least one frozen particle composition or frozen piercing implement.

In one embodiment 18010, the means for transmitting one or more signals includes means for transmitting one or more signals associated with comparing the information related to the processing of the first input and the second input. In one embodiment 18020, the means for transmitting one or more signals includes means for transmitting one or more signals associated with comparing the information related to the processing of the first input and the second input. In one embodiment 18030, the at least one frozen particle composition or frozen piercing implement includes one or more of hydrogen oxide, nitrogen, oxygen, air, helium, neon, argon, xenon, chlorine, bromine, carbon dioxide, acetone, ethyl acetate, dimethyl sulfoxide, dimethyl formamide, dioxane, tetrahydrofuran, acetonitrile, acetic acid, n-butanol, isopropanol, n-propanol, hexamethylphosphorotriamide, perfluorohydrocarbon, methanol, ethanol, tert-butyl alcohol, formic acid, hydrogen fluoride, ammonia, benzene, carbon tetrachloride, hexane, dichloromethane, methylene chloride, carboxylic acid, saline, methane, toluene, chloroform, polyethylene glycol, acetic acid, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, or diethyl ether. In one embodiment 18040, the system further comprises means for making at least one frozen particle composition or frozen piercing implement. In one embodiment 18050, the system further comprises means for administering at least one frozen particle composition or frozen piercing implement to at least one substrate. In one embodiment 18060, the system further comprises means for evaluating the at least one substrate for one or more indicators related to at least one parameter for administering the at least one frozen particle composition or frozen piercing implement. In one embodiment 18070, evaluating at least one substrate for one or more indicators includes evaluating at least one of an assay, image, or gross assessment of the at least one substrate prior to, during, or subsequent to at least one administration of the at least one frozen particle composition or frozen piercing implement.

In one embodiment 18110, the assay includes at least one technique including spectroscopy, microscopy, electrochemical detection, polynucleotide detection, histological examination, biopsy analysis, fluorescence resonance energy transfer, electron transfer, enzyme assay, electrical conductivity, isoelectric focusing, chromatography, immunoprecipitation, immunoseparation, aptamer binding, filtration, electrophoresis, immunoassay, or radioactive assay. In one embodiment 18120, the at least one image includes one or more images acquired by at least one of laser, holography, x-ray crystallography, optical coherence tomography, computer-assisted tomography scan, computed tomography, magnetic resonance imaging, positron-emission tomography scan, ultrasound, x-ray, electrical-impedance monitoring, microscopy, spectrometry, flow cytommetry, radioisotope imaging, thermal imaging, infrared visualization, multiphoton calcium-imaging, photography, or in silico generation. In one embodiment 18130, the system further comprises means for transmitting one or more signals that include information relating to the accepting a first input or a second input and information related to the evaluating the at least one substrate. In one embodiment 18140, the means for transmitting one or more signals includes means for transmitting one or more signals associated with selection of at least one parameter for making the at least one frozen particle composition or frozen piercing implement. In one embodiment 18150, the means for transmitting one or more signals includes means for transmitting one or more signals associated with selection of at least one parameter for administering the at least one frozen particle composition or frozen piercing implement.

As illustrated in FIGS. 182-185, a system 18200 comprises: 18210 means for receiving one or more signals that include information related to accepting input associated with at least one parameter for making or administering at least one frozen particle composition, frozen piercing implement, or frozen piercing implement device to at least one substrate; wherein the at least one frozen particle composition, frozen piercing implement, or frozen piercing implement device includes at least one agent; 18220 means for receiving one or more signals that include information related to evaluating the at least one substrate for one or more indicators of administration of at least one frozen particle composition, frozen piercing implement, frozen piercing implement device, or agent; 18230 means for processing the information related to the input associated with at least one parameter for making or administering the at least one frozen particle composition, frozen piercing implement, or frozen piercing implement device to at least one substrate and the information related to the evaluating the at least one substrate; and 18240 means for generating an output to a user readable display. In one embodiment 18250, the at least one frozen piercing implement device includes at least one of a frozen piercing implement device, frozen piercing implement fluidic device, or frozen piercing implement injection device. In one embodiment 18260, the frozen piercing implement injection device includes a frozen piercing implement auto-injection device. In one embodiment 18270, evaluating at least one substrate for one or more indicators includes means for evaluating at least one of an assay, image, or gross assessment of the at least one biological tissue prior to, during, or subsequent to at least one administration of one or more frozen piercing implement devices. In one embodiment 18280, the assay includes at least one technique that includes spectroscopy, microscopy, electrochemical detection, polynucleotide detection, histological examination, biopsy analysis, fluorescence resonance energy transfer, electron transfer, enzyme assay, electrical conductivity, isoelectric focusing, chromatography, immunoprecipitation, immunoseparation, aptamer binding, filtration, electrophoresis, immunoassay, or radioactive assay.

In one embodiment 18310, the image includes at least one image acquired by one or more of x-ray crystallography, laser, holography, optical coherence tomography, computer-assisted tomography scan, computed tomography, magnetic resonance imaging, positron-emission tomography scan, ultrasound, x-ray, electrical-impedance monitoring, microscopy, spectrometry, flow cytommetry, radioisotope imaging, thermal imaging, infrared visualization, multiphoton calcium-imaging, photography, or in silico generation. In one embodiment 18320, the means for receiving one or more signals includes means for receiving one or more signals associated with selection of at least one parameter for making or administering the at least one frozen piercing implement. In one embodiment 18330, the at least one parameter for making the at least one frozen piercing implement device includes one or more of: constitution of the at least one frozen piercing implement of the frozen piercing implement device, constitution of the at least one frozen piercing implement device, formulation of the at least one frozen piercing implement of the frozen piercing implement device, formulation of the at least one frozen piercing implement device, configuration of the at least one frozen piercing implement of the device, configuration of the at least one frozen piercing implement device, size of the at least one frozen piercing implement of the frozen piercing implement device, size of the at least one frozen piercing implement device, shape of the at least one frozen piercing implement of the frozen piercing implement device, shape of the at least one frozen piercing implement device, physical structure of the at least one frozen piercing implement of the frozen piercing implement device, physical structure of the at least one frozen piercing implement device, physical or chemical integrity of the at least one frozen piercing implement of the frozen piercing implement device, or physical or chemical integrity of the at least one frozen piercing implement device.

In one embodiment 18340, the at least one parameter for administering at least one frozen piercing implement device to at least one substrate includes one or more of: substrate type; substrate function; substrate size; substrate constitution; substrate architecture; substrate durability; substrate temperature; temperature of administration conditions; depth of administration of the at least one frozen particle composition or frozen piercing implement; substrate source; one or more temporal coordinates; one or more spatial coordinates; presence or absence of at least one agent; presence or absence of at least one microparticle, nanoparticle, lens, tunablelens, sensor, transducer, actuator, detector, heater, valve, gate, channel, detection material, pump, power source, injector, controller, receiver, transmitter, or circuit; angle of administration of the at least one frozen piercing implement device; force of administration of the at least one frozen piercing implement device velocity of administration of the at least one frozen piercing implement device; quantity of frozen piercing implements of the device; quantity of frozen piercing implement devices administered; rate of administration of more than one frozen piercing implement devices; method of administration of at least one frozen piercing implement device; timing of administration of at least one frozen piercing implement; or rate of delivery of at least one agent of the device.

In one embodiment 18410, the at least one agent includes one or more of an adhesive agent, therapeutic agent, reinforcement agent, abrasive, explosive material, or biological remodeling agent. In one embodiment 18420, the at least one substrate includes one or more of a cell, tissue, organ, structure, device, or food product. In one embodiment 18430, the at least one frozen piercing implement device includes one or more frozen piercing implements that include at least one of hydrogen oxide, nitrogen, oxygen, air, helium, neon, argon, xenon, chlorine, bromine, carbon dioxide, acetone, ethyl acetate, dimethyl sulfoxide, dimethyl formamide, dioxane, tetrahydrofuran, acetonitrile, acetic acid, n-butanol, isopropanol, n-propanol, hexamethylphosphorotriamide, perfluorohydrocarbon, methanol, ethanol, tert-butyl alcohol, formic acid, hydrogen fluoride, ammonia, benzene, carbon tetrachloride, hexane, dichloromethane, methylene chloride, carboxylic acid, saline, methane, toluene, chloroform, polyethylene glycol, acetic acid, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, or diethyl ether.

In one embodiment 18440, the output includes one or more instructions for making the at least one frozen particle composition, frozen piercing implement, or frozen piercing implement device. In one embodiment 18450, the output includes at least one graphical description of the at least one frozen particle composition, frozen piercing implement, or frozen piercing implement device. In one embodiment 18460, the user includes at least one entity. In on embodiment 18470, the entity includes at least one person, or computer. In one embodiment 18480, the user readable display includes a human readable display. In one embodiment 18490, the user readable display includes one or more active displays. In one embodiment 18495, the user readable display includes one or more passive displays. In one embodiment 18510, the user readable display includes one or more of a numeric format, graphical format, or audio format. In one embodiment 18520, the user readable display includes one or more of a display of one or more differences in the comparison of at least one value related to the first input and at least one value related to at least one property of the at least one frozen particle composition, frozen piercing implement, or frozen piercing implement device. In one embodiment 18530, the user readable display includes one or more of a display of one or more differences in the comparison of at least one value related to the second input and at least one value related to at least one parameter for administration of the at least one frozen particle composition or frozen piercing implement.

In one embodiment 18540, the at least one parameter for making the at least one frozen particle composition or frozen piercing implement includes one or more of: constitution of the at least one frozen particle composition or frozen piercing implement, formulation of the at least one frozen particle composition or frozen piercing implement, size of the at least one frozen particle composition or frozen piercing implement, density of the at least one frozen particle composition or frozen piercing implement, shape of the at least one frozen particle composition or frozen piercing implement, physical structure of the at least one frozen particle composition or frozen piercing implement, or physical or chemical integrity of the at least one frozen particle composition or frozen piercing implement. In one embodiment 18550, at least one parameter for administering the at least one frozen particle composition or frozen piercing implement includes one or more of: substrate type; substrate function; substrate size; substrate constitution; substrate architecture; substrate durability; substrate temperature; temperature of administration conditions; depth of administration of the at least one frozen particle composition or frozen piercing implement; substrate source; one or more temporal coordinates; one or more spatial coordinates; presence or absence of at least one agent; presence or absence of at least one microparticle, nanoparticle, lens, tunablelens, sensor, transducer, actuator, detector, heater, valve, gate, channel, detection material, pump, power source, injector, controller, receiver, transmitter, or circuit; angle of administration of the at least one frozen piercing implement device; force of administration of the at least one frozen piercing implement device; velocity of administration of the at least one frozen piercing implement device; quantity of frozen piercing implements of the device; quantity of frozen piercing implement devices administered; rate of administration of more than one frozen piercing implement devices; method of administration of at least one frozen piercing implement device; timing of administration of at least one frozen piercing implement; or rate of delivery of at least one agent of the device.

As illustrated in FIGS. 186-189, in one embodiment, a system 18600 comprises: 18610 at least one computing device; 18620 one or more instructions that when executed on the at least one computing device cause the at least one computing device to receive a first input associated with a first possible dataset, 18630 the first possible dataset including data representative of at least one parameter for making or administering at least one frozen particle composition or frozen piercing implement; and 18640 one or more instructions that when executed generate an output to a user readable display.

In one embodiment 18650, the system further comprises one or more instructions that when executed on the at least one computing device cause the at least one computing device to compare a value associated with the first possible dataset with a second dataset including values of at least one predictive parameter for making the at least one frozen particle composition or frozen piercing implement.

In one embodiment 18660, the system further comprises one or more instructions that when executed on the at least one computing device cause the at least one computing device to determine a graphical illustration of the second possible dataset.

In one embodiment 18670, the at least one parameter for making the at least one frozen particle composition or frozen piercing implement includes one or more of: constitution of the at least one frozen particle composition or frozen piercing implement, formulation of the at least one frozen particle composition or frozen piercing implement, size of the at least one frozen particle composition or frozen piercing implement, density of the at least one frozen particle composition or frozen piercing implement, shape of the at least one frozen particle composition or frozen piercing implement, physical structure of the at least one frozen particle composition or frozen piercing implement, or physical or chemical integrity of the at least one frozen particle composition or frozen piercing implement. In one embodiment 18710, at least one parameter for administering the at least one frozen particle composition or frozen piercing implement includes one or more of: substrate type; substrate function; substrate size; substrate constitution; substrate architecture; substrate durability; substrate temperature; temperature of administration conditions; depth of administration of the at least one frozen particle composition or frozen piercing implement; substrate source; one or more temporal coordinates; one or more spatial coordinates; presence or absence of at least one agent; presence or absence of at least one microparticle, nanoparticle, lens, tunablelens, sensor, transducer, actuator, detector, heater, valve, gate, channel, detection material, pump, power source, injector, controller, receiver, transmitter, or circuit; angle of administration of the at least one frozen piercing implement device; force of administration of the at least one frozen piercing implement device; velocity of administration of the at least one frozen piercing implement device; quantity of frozen piercing implements of the device; quantity of frozen piercing implement devices administered; rate of administration of more than one frozen piercing implement devices; method of administration of at least one frozen piercing implement device; timing of administration of at least one frozen piercing implement; or rate of delivery of at least one agent of the device.

In one embodiment 18720, the system further comprises one or more instructions that when executed on the at least one computing device cause'the at least one computing device to determine from the comparison at least one parameter for making or administering at least one frozen particle composition or frozen piercing implement to at least one substrate. In one embodiment 18730, the system further comprises one or more instructions that when executed on the at least one computing device cause the at least one computing device to generate at least one response support structured on the determination.

In one embodiment 18740, the system further comprises one or more instructions that when executed on the at least one computing device cause the at least one computing device to access the first possible dataset in response to the first input. In one embodiment 18750, the system further comprises one or more instructions that when executed on the at least one computing device cause the at least one computing device to generate the first possible dataset in response to the first input. In one embodiment 18760, the system further comprises one or more instructions that when executed on the at least one computing device cause the at least one computing device to determine a graphical illustration of the first possible dataset.

In one embodiment 18810, the at least one computing device includes one or more of a desktop computer, workstation computer, or computing system. In one embodiment 18820, the at least one computing system includes one or more of a cluster of processors, a networked computer, a tablet personal computer, a laptop computer, a mobile device, a mobile telephone, or a personal digital assistant computer. In one embodiment 18830, the output includes one or more instructions for making the at least one frozen particle composition or frozen piercing implement. In one embodiment 18840, the output includes at least one graphical description of the at least one frozen particle composition or frozen piercing implement.

In one embodiment 18850, the user includes at least one entity. In one embodiment 18860, the entity includes at least one person, or computer. In one embodiment 18870, the user readable display includes a human readable display. In one embodiment 18880, the user readable display includes one or more active displays. In one embodiment 18890, the user readable display includes one or more passive displays. In one embodiment 18895, the user readable display includes one or more of a numeric format, graphical format, or audio format. In one embodiment 18898, the user readable display includes one or more of a display of one or more differences in the comparison of at least one value related to the first input and at least one value related to at least one property of the at least one frozen particle composition or frozen piercing implement.

In one embodiment 18910, the user readable display includes one or more of a display of one or more differences in the comparison of at least one value related to the second input and at least one value related to at least one parameter for administration of the at least one frozen particle composition or frozen piercing implement.

As illustrated in FIGS. 190-192, one embodiment includes a system 19000 comprising: 19010 circuitry for accepting a first input associated with one or more parameters for making at least one frozen particle composition or frozen piercing implement; 19020 circuitry for accepting a second input associated with one or more parameters for administering at least one frozen particle composition or frozen piercing implement to at least one substrate; 19030 circuitry for processing the first input and the second input; and 19040 circuitry for generating an output to a user readable display.

In one embodiment 19050, the one or more parameters for making at least one frozen particle composition or frozen piercing implement include at least one value derived from an image. In one embodiment 19060, the image includes a 2-dimensional or 3-dimensional image. In one embodiment 19070, the image includes at least one image acquired by one or more of x-ray crystallography, laser, holography, optical coherence tomography, computer-assisted tomography scan, computed tomography, magnetic resonance imaging, positron-emission tomography scan, ultrasound, x-ray, electrical-impedance monitoring, microscopy, spectrometry, flow cytommetry, radioisotope imaging, thermal imaging, infrared visualization, multiphoton calcium-imaging, photography, or in silico generation.

In one embodiment 19080, the image includes at least one CAD drawing. In one embodiment 19090, the image includes at least one characteristic of the at least one frozen particle composition or frozen piercing implement. In one embodiment 19095, the at least one characteristic includes one or more of inner diameter, outer diameter, shape, at least one major dimension, or constitution.

In one embodiment 19110, the system further comprises circuitry for displaying results of the processing. In one embodiment 19120, the system further comprises circuitry for transmitting one or more signals that include information related to the processing the first input and the second input. In one embodiment 19130, the system further comprises circuitry for evaluating the at least one substrate for one or more indicators relating to one or more of: quantitative delivery of at least one agent; depth of piercing the at least one substrate; spatial coordinates for administration of at least one frozen particle composition; at least one frozen piercing implement or at least one agent; temporal coordinates for administration of at least one frozen particle composition, at least one frozen piercing implement, or at least one agent; substrate type; substrate function; substrate size; substrate constitution; substrate architecture; substrate durability; substrate temperature; temperature of administration conditions; depth of administration of the at least one frozen particle composition or frozen piercing implement; substrate source; any substrate response to administration of at least one frozen piercing implement, at least one frozen particle composition, or at least one agent.

In one embodiment 19140, the at least one agent includes at least one therapeutic agent, reinforcement agent, abrasive, explosive material, adhesive agent, or biological remodeling agent. In one embodiment 19150, the output includes one or more instructions for making the at least one frozen particle composition or frozen piercing implement. In one embodiment 19160, the output includes at least one graphical description of the at least one frozen particle composition or frozen piercing implement.

In one embodiment 19170, the user includes at least one entity. In one embodiment 19180, the entity includes at least one person, or computer. In one embodiment 19210, the user readable display includes a human readable display. In one embodiment 19220, the user readable display includes one or more active displays. In one embodiment 19230, the user readable display includes one or more passive displays. In one embodiment 19240, the user readable display includes one or more of a numeric format, graphical format, or audio format. In one embodiment 19250, the user readable display includes one or more of a display of one or more differences in the comparison of at least one value related to the first input and at least one value related to at least one property of the at least one frozen particle composition or frozen piercing implement. In one embodiment 19260, the user readable display includes one or more of a display of one or more differences in the comparison of at least one value related to the second input and at least one value related to at least one parameter for administration of the at least one frozen particle composition or frozen piercing implement.

As illustrated in FIGS. 193-195, in one embodiment a computer program product 19300 comprises: 19310 a recordable medium bearing one or more instructions for accepting a first input associated with at least one parameter for making at least one frozen particle composition or frozen piercing implement to at least one substrate; 19320 one or more instructions for accepting a second input associated with at least one parameter for administering the at least one frozen particle composition or frozen piercing implement; 19330 one or more instructions for processing the first input and the second input; and 19340 one or more instructions for generating an output to a user readable display. In one embodiment

19350, the recordable medium includes a computer-readable medium. In one embodiment 19360, the recordable medium includes a communications medium.

In one embodiment 19370, the computer program product further comprises one or more instructions for displaying results of the processing. In one embodiment 19380, the computer program product further comprises one or more instructions for transmitting one or more signals that include information related to the processing the first input and the second input. In one embodiment 19390, the computer program product further comprises one or more instructions for evaluating the at least one substrate for one or more indicators relating to one or more of: quantitative delivery of at least one agent, depth of piercing the at least one substrate, spatial location of delivery of at least one agent, or temporal location of delivery of at least one agent. In one embodiment 19395, the at least one agent includes at least one therapeutic agent, reinforcement agent, abrasive, explosive material, adhesive agent, or biological remodeling agent.

In one embodiment 19410, the first input includes at least one parameter for making the at least one frozen particle composition or frozen piercing implement includes one or more of: constitution of the at least one frozen particle composition or frozen piercing implement, formulation of the at least one frozen particle composition or frozen piercing implement, configuration of the at least one frozen particle composition or frozen piercing implement, size of the at least one frozen particle composition or frozen piercing implement, density of the at least one frozen particle composition or frozen piercing implement, shape of the at least one frozen particle composition or frozen piercing implement, physical structure of the at least one frozen particle composition or frozen piercing implement, or physical or chemical integrity of the at least one frozen particle composition or frozen piercing implement.

In one embodiment 19420, the second input includes at least one parameter for administering the at least one frozen particle composition or frozen piercing implement includes one or more of: substrate type; substrate function; substrate size; substrate constitution; substrate architecture; substrate durability; substrate temperature; temperature of administration conditions; depth of administration of the at least one frozen particle composition or frozen piercing implement; substrate source; one or more temporal coordinates; one or more spatial coordinates; presence or absence of at least one agent; presence or absence of at least one microparticle, nanoparticle, lens, tunablelens, sensor, transducer, actuator, detector, heater, valve, gate, channel, detection material, pump, power source, injector, controller, receiver, transmitter, or circuit; angle of administration of the at least one frozen piercing implement device; force of administration of the at least one frozen piercing implement device; velocity of administration of the at least one frozen piercing implement device; quantity of frozen piercing implements of the device; quantity of frozen piercing implement devices administered; rate of administration of more than one frozen piercing implement devices; method of administration of at least one frozen piercing implement device; timing of administration of at least one frozen piercing implement; or rate of delivery of at least one agent of the device.

In one embodiment 19430, the output includes one or more instructions for making the at least one frozen particle composition or frozen piercing implement. In one embodiment 19440, the output includes at least one graphical description of the at least one frozen particle composition or frozen piercing implement.

In one embodiment 19510, the user includes at least one entity. In one embodiment 19520, the entity includes at least one person, or computer. In one embodiment 19530, the user readable display includes a human readable display. In one embodiment 19540, the user readable display includes one or more active displays. In one embodiment 19550, the user readable display includes one or more passive displays. In one embodiment 19560, the user readable display includes one or more of a numeric format, graphical format, or audio format. In one embodiment 19570, the user readable display includes one or more of a display of one or more differences in the comparison of at least one value related to the first input and at least one value related to at least one property of the at least one frozen particle composition or frozen piercing implement. In one embodiment 19580, the user readable display includes one or more of a display of one or more differences in the comparison of at least one value related to the second input and at least one value related to at least one parameter for administration of the at least one frozen particle composition or frozen piercing implement.

As illustrated in FIGS. 196-198, in one embodiment a system 19600 comprises: 19610 a recordable medium bearing one or more instructions for accepting a first input associated with at least one parameter for making at least one frozen particle composition or frozen piercing implement; 19620 one or more instructions for accepting a second input associated with at least one parameter for administering at least one frozen particle composition or frozen piercing implement; 19630 one or more instructions for processing the first input and the second input; and 19640 one or more instructions for generating an output to a user readable display.

In one embodiment 19650 the recordable medium includes a computer-readable medium. In one embodiment 19660, the recordable medium includes a communications medium. In one embodiment 19670, the system further comprises one or more instructions for transmitting one or more signals that include information related to the processing the first input and the second input.

In one embodiment 19680, the system further comprises one or more instructions for evaluating the at least one substrate for one or more indicators relating to one or more of: quantitative delivery of at least one agent, depth of piercing the at least one substrate, spatial location of delivery of at least one agent, or temporal location of delivery of at least one agent. In one embodiment 19690, the at least one agent includes at least one therapeutic agent, reinforcement agent, abrasive, explosive material, adhesive agent, or biological remodeling agent.

In one embodiment 19710 the first input includes at least one parameter for making the at least one frozen particle composition or frozen piercing implement includes one or more of: constitution of the at least one frozen particle composition or frozen piercing implement, configuration of the at least one frozen particle composition or frozen piercing implement, formulation of the at least one frozen particle composition or frozen piercing implement, size of the at least one frozen particle composition or frozen piercing implement, density of the at least one frozen particle composition or frozen piercing implement, shape of the at least one frozen particle composition or frozen piercing implement, physical structure of the at least one frozen particle composition or frozen piercing implement, or physical or chemical integrity of the at least one frozen particle composition or frozen piercing implement.

In one embodiment 19720, the second input includes at least one parameter for administering the at least one frozen particle composition or frozen piercing implement includes one or more of: substrate type; substrate function; substrate size; substrate constitution; substrate architecture; substrate durability; substrate temperature; temperature of administration conditions; depth of administration of the at least one frozen particle composition or frozen piercing implement; substrate source; one or more temporal coordinates; one or more spatial coordinates; presence or absence of at least one agent; presence or absence of at least one microparticle, nanoparticle, lens, tunablelens, sensor, transducer, actuator, detector, heater, valve, gate, channel, detection material, pump, power source, injector, controller, receiver, transmitter, or circuit; angle of administration of the at least one frozen piercing implement device; force of administration of the at least one frozen piercing implement device velocity of administration of the at least one frozen piercing implement device; quantity of frozen piercing implements of the device; quantity of frozen piercing implement devices administered; rate of administration of more than one frozen piercing implement devices; method of administration of at least one frozen piercing implement device; timing of administration of at least one frozen piercing implement; or rate of delivery of at least one agent of the device. In one embodiment 19730, the output includes one or more instructions for making the at least one frozen particle composition or frozen piercing implement.

In one embodiment 19810, the output includes at least one graphical description of the at least one frozen particle composition or frozen piercing implement. In one embodiment 19820, the user includes at least one entity. In one embodiment 19830, the entity includes at least one person, or computer. In one embodiment 19840, the user readable display includes a human readable display. In one embodiment 19850, the user readable display includes one or more active displays. In one embodiment 19860, the user readable display includes one or more passive displays. In one embodiment 19870, the user readable display includes one or more of a numeric format, graphical format, or audio format.

In one embodiment 19880, the user readable display includes one or more of a display of one or more differences in the comparison of at least one value related to the first input and at least one value related to at least one property of the at least one frozen particle composition or frozen piercing implement. In one embodiment 19890, the user readable display includes one or more of a display of one or more differences in the comparison of at least one value related to the second input and at least one value related to at least one parameter for administration of the at least one frozen particle composition or frozen piercing implement.

As illustrated in FIGS. 199-200, in one embodiment a system 19900 comprises: 19910 at least one computer program, configured with a computer-readable medium, for use with at least one computer system and wherein the computer program includes a plurality of instructions including but not limited to: one or more instructions for accepting a first input associated with one or more parameters for making one or more frozen particle compositions or frozen piercing implements to at least one substrate; one or more instructions for accepting a second input associated with one or more parameters for administering one or more frozen particle compositions or frozen piercing implements; one or more instructions for processing the first input and the second input; and one or more instructions for generating an output to a user readable display.

In one embodiment 19920, the system further comprises one or more instructions for transmitting one or more signals that include information related to the processing the first input and the second input. In one embodiment 19930, the system further comprises one or more instructions for evaluating the at least one biological tissue for one or more indicators relating to one or more of: quantitative delivery of at least one agent, depth of piercing the at least one substrate, spatial location of delivery of at least one agent, or temporal location of delivery of at least one agent.

In one embodiment 19940, the at least one agent includes at least one therapeutic agent, reinforcement agent, abrasive, explosive material, adhesive agent, or biological remodeling agent. In one embodiment 19950, the system further comprises at least one computing device. In one embodiment 19960, the at least one computing device is configured to communicate with at least one printing device, at least one imaging device, or at least one input device.

In one embodiment 19970, the first input includes at least one parameter for making the at least one frozen piercing implement device includes one or more of: constitution of the at least one frozen piercing implement of the frozen piercing implement device, constitution of the at least one frozen piercing implement device, configuration of the at least one frozen piercing implement or frozen piercing implement device, formulation of the at least one frozen piercing implement of the frozen piercing implement device, formulation of the at least one frozen piercing implement device, size of the at least one frozen piercing implement of the frozen piercing implement device, size of the at least one frozen piercing implement device, shape of the at least one frozen piercing implement of the frozen piercing implement device, shape of the at least one frozen piercing implement device, physical structure of the at least one frozen piercing implement of the frozen piercing implement device, physical structure of the at least one frozen piercing implement device, physical or chemical integrity of the at least one frozen piercing implement of the frozen piercing implement device, or physical or chemical integrity of the at least one frozen piercing implement device.

In one embodiment 20010, the first input includes at least one parameter for making the at least one frozen particle composition or frozen piercing implement includes one or more of: constitution of the at least one frozen particle composition or frozen piercing implement, configuration of the at least one frozen particle composition or frozen piercing implement, formulation of the at least one frozen particle composition or frozen piercing implement, size of the at least one frozen particle composition or frozen piercing implement, density of the at least one frozen particle composition or frozen piercing implement, shape of the at least one frozen particle composition or frozen piercing implement, physical structure of the at least one frozen particle composition or frozen piercing implement, or physical or chemical integrity of the at least one frozen particle composition or frozen piercing implement.

In one embodiment 20020, the second input includes at least one parameter for administering the at least one frozen particle composition or frozen piercing implement includes one or more of: substrate type; substrate function; substrate size; substrate constitution; substrate architecture; substrate durability; substrate temperature; temperature of administration conditions; depth of administration of the at least one frozen particle composition or frozen piercing implement; substrate source; one or more temporal coordinates; one or more spatial coordinates; presence or absence of at least one agent; presence or absence of at least one microparticle, nanoparticle, lens, tunablelens, sensor, transducer, actuator, detector, heater, valve, gate, channel, detection material, pump, power source, injector, controller, receiver, transmitter, or circuit; angle of administration of the at least one frozen piercing implement device; force of administration of the at least one frozen piercing implement device; velocity of administration of the at least one frozen piercing implement device; quantity of frozen piercing implements of the device; quantity of frozen piercing implement devices administered; rate of administration of more than one frozen piercing implement devices; method of administration of at least one frozen piercing implement device; timing of administration of at least one frozen piercing implement; or rate of delivery of at least one agent of the device.

In one embodiment 20030, the second input includes at least one parameter for administering at least one frozen piercing implement device to at least one substrate includes one or more of: substrate type; substrate function; substrate size; substrate constitution; substrate architecture; substrate durability; substrate temperature; temperature of administration conditions; depth of administration of the at least one frozen particle composition or frozen piercing implement; substrate source; one or more temporal coordinates; one or more spatial coordinates; presence or absence of at least one agent; presence or absence of at least one microparticle, nanoparticle, lens, tunablelens, sensor, transducer, actuator, detector, heater, valve, gate, channel, detection material, pump, power source, injector, controller, receiver, transmitter, or circuit; angle of administration of the at least one frozen piercing implement device; force of administration of the at least one frozen piercing implement device; velocity of administration of the at least one frozen piercing implement device; quantity of frozen piercing implements of the device; quantity of frozen piercing implement devices administered; rate of administration of more than one frozen piercing implement devices; method of administration of at least one frozen piercing implement device; timing of administration of at least one frozen piercing implement; or rate of delivery of at least one agent of the device.

As illustrated in FIGS. 201-204, a system 20100, comprises: 20110 at least one computing device; 20120 one or more instructions that when executed on the at least one computing device cause the at least one computing device to receive a first input associated with a first possible dataset, 20130 the first possible dataset including data representative of at least one parameter for making or administering at least one frozen particle composition, frozen piercing implement, or frozen piercing implement device to at least one substrate; and 20140 one or more instructions for generating an output to a user readable display.

In one embodiment 20150, the at least one frozen piercing implement device includes at least one frozen piercing implement array device, frozen piercing implement fluidic device, or frozen piercing implement injection device. In one embodiment 20160, the frozen piercing implement injection device includes a frozen piercing implement auto-injection device.

In one embodiment 20170, the system further comprises one or more instructions that when executed on the at least one computing device cause the at least one computing device to compare a value associated with the first possible dataset with a second dataset including values of at least one predictive parameter for administering at least one frozen particle compositions or frozen piercing implements to at least one substrate. In one embodiment 20180, the first input includes at least one parameter for making the at least one frozen piercing implement device includes one or more of: constitution of the at least one frozen piercing implement of the frozen piercing implement device, constitution of the at least one frozen piercing implement device, configuration of the at least one frozen piercing implement or frozen piercing implement device, formulation of the at least one frozen piercing implement of the frozen piercing implement device, formulation of the at least one frozen piercing implement device, size of the at least one frozen piercing implement of the frozen piercing implement device, size of the at least one frozen piercing implement device, shape of the at least one frozen piercing implement of the frozen piercing implement device, shape of the at least one frozen piercing implement device, physical structure of the at least one frozen piercing implement of the frozen piercing implement device, physical structure of the at least one frozen piercing implement device, physical or chemical integrity of the at least one frozen piercing implement of the frozen piercing implement device, or physical or chemical integrity of the at least one frozen piercing implement device.

In one embodiment 20210, the second input includes at least one parameter for administering at least one frozen piercing implement device to at least one substrate includes one or more of: substrate type; substrate function; substrate size; substrate constitution; substrate architecture; substrate durability; substrate temperature; temperature of administration conditions; depth of administration of the at least one frozen particle composition or frozen piercing implement; substrate source; one or more temporal coordinates; one or more spatial coordinates; presence or absence of at least one agent; presence or absence of at least one microparticle, nanoparticle, lens, tunablelens, sensor, transducer, actuator, detector, heater, valve, gate, channel, detection material, pump, power source, injector, controller, receiver, transmitter, or circuit; angle of administration of the at least one frozen piercing implement device; force of administration of the at least one frozen piercing implement device; velocity of administration of the at least one frozen piercing implement device; quantity of frozen piercing implements of the device; quantity of frozen piercing implement devices administered; rate of administration of more than one frozen piercing implement devices; method of administration of at least one frozen piercing implement device; timing of administration of at least one frozen piercing implement; or rate of delivery of at least one agent of the device.

In one embodiment 20220, the system further comprises one or more instructions that when executed on the at least one computing device cause the at least one computing device to determine a graphical illustration of the second possible dataset. In one embodiment 20230, the system further comprises one or more instructions that when executed on the at least one computing device cause the at least one computing device to determine from the comparison at least one parameter for administering at least one frozen particle composition, frozen piercing implement, or frozen piercing implement device to at least one substrate.

In one embodiment 20240, the system further comprises one or more instructions that when executed on the at least one computing device cause the at least one computing device to generate at least one response support structured on the determination.

In one embodiment 20250, the system further comprises one or more instructions that when executed on the at least one computing device cause the at least one computing device to access the first possible dataset in response to the first input.

In one embodiment 20310, the system further comprises one or more instructions that when executed on the at least one computing device cause the at least one computing device to generate the first possible dataset in response to the first input. In one embodiment 20320, the system further comprises one or more instructions that when executed on the at least one computing device cause the at least one computing device to determine a graphical illustration of the first possible dataset. In one embodiment 20330, the at least one computing device includes one or more of a desktop computer, workstation computer, or computing system.

In one embodiment 20340, the at least one computing system includes one or more of a cluster of processors, a networked computer, a tablet personal computer, a laptop computer, a mobile device, a mobile telephone, or a personal digital assistant computer. In one embodiment 20350, the output includes one or more instructions for making the at least one frozen particle composition or frozen piercing implement. In one embodiment 20360, the output includes at least one graphical description of the at least one frozen particle composition or frozen piercing implement.

In one embodiment 20370, the user includes at least one entity. In one embodiment 20380, the entity includes at least one person, or computer. In one embodiment 20390, the user readable display includes a human readable display. In one embodiment 20410, the user readable display includes one or more active displays. In one embodiment 20420, the user readable display includes one or more passive displays. In one embodiment 20430, the user readable display includes one or more of a numeric format, graphical format, or audio format. In one embodiment 20440, the user readable display includes one or more of a display of one or more differences in the comparison of at least one value related to the first input and at least one value related to at least one property of the at least one frozen particle composition or frozen piercing implement. In one embodiment 20450, the user readable display includes one or more of a display of one or more differences in the comparison of at least one value related to the second input and at least one value related to at least one parameter for administration of the at least one frozen particle composition or frozen piercing implement.

As illustrated in FIGS. 205-208, a system 20500 comprises: 20510 circuitry for accepting a first input associated with at least one parameter for making at least one frozen piercing implement device; 20520 circuitry for accepting a second input associated with at least one parameter for administering at least one frozen piercing implement device to at least one substrate; 20530 circuitry for processing the first input and the second input; and 20540 circuitry for generating an output to a user readable display. In one embodiment 20550, the at least one frozen piercing implement device includes at least one frozen piercing implement array device, frozen piercing implement fluidic device, or frozen piercing implement injection device. In one embodiment 20560, the frozen piercing implement injection device includes a frozen piercing implement auto-injection device. In one embodiment 20570, the first input includes at least one value derived from at least one image. In one embodiment 20580, the at least one image includes at least one 2-dimensional or 3-dimensional image. In one embodiment 20590, the image includes at least one image acquired by one or more of x-ray crystallography, laser, holography, optical coherence tomography, computer-assisted tomography scan, computed tomography, magnetic resonance imaging, positron-emission tomography scan, ultrasound, x-ray, electrical-impedance monitoring, microscopy, spectrometry, flow cytometry, radioisotope imaging, thermal imaging, infrared visualization, multiphoton calcium-imaging, photography, or in silico generation.

In one embodiment 20610, the at least one image includes at least one CAD drawing. In one embodiment 20620, the at least one image includes at least one characteristic of the at least one frozen piercing implement of the device or the frozen piercing implement device. In one embodiment 20630, the at least one characteristic of the one or more frozen piercing implement device includes one or more of number of frozen piercing implements, number of total piercing implements, size of at least one frozen piercing implement, constitution of at least one frozen piercing implement, shape of at least one frozen piercing implement, shape of the device, configuration of the device, spacing of at least two components of the device, spacing of at least two frozen piercing implements of the device, or presence or absence of at least one microparticle, nanoparticle, lens, tunablelens, sensor, transducer, actuator, detector, heater, valve, gate, channel, detection material, pump, power source, injector, controller, receiver, transmitter, or circuit.

In one embodiment 20640, the first input includes at least one parameter for making the at least one frozen piercing implement device includes one or more of: constitution of the at least one frozen piercing implement of the frozen piercing implement device, constitution of the at least one frozen piercing implement device, configuration of the at least one frozen piercing implement or frozen piercing implement device, formulation of the at least one frozen piercing implement of the frozen piercing implement device, formulation of the at least one frozen piercing implement device, size of the at least one frozen piercing implement of the frozen piercing implement device, size of the at least one frozen piercing implement device, shape of the at least one frozen piercing implement of the frozen piercing implement device, shape of the at least one frozen piercing implement device, physical structure of the at least one frozen piercing implement of the frozen piercing implement device, physical structure of the at least one frozen piercing implement device, physical or chemical integrity of the at least one frozen piercing implement of the frozen piercing implement device, physical or chemical integrity of the at least one frozen piercing implement device, or presence or absence of at least one microparticle, nanoparticle, lens, tunablelens, sensor, transducer, actuator, detector, heater, valve, gate, channel, detection material, pump, power source, injector, controller, receiver, transmitter, or circuit, in the at least one frozen piercing implement or frozen piercing implement device.

In one embodiment 20710, the second input includes at least one parameter for administering the at least one frozen piercing implement device includes one or more of: substrate type; substrate function; substrate size; substrate constitution; substrate architecture; substrate durability; substrate temperature; temperature of administration conditions; depth of administration of the at least one frozen particle composition or frozen piercing implement; substrate source; one or more temporal coordinates; one or more spatial coordinates; presence or absence of at least one agent; presence or absence of at least one microparticle, nanoparticle, lens, tunablelens, sensor, transducer, actuator, detector, heater, valve, gate, channel, detection material, pump, power source, injector, controller, receiver, transmitter, or circuit; angle of administration of the at least one frozen piercing implement device; force of administration of the at least one frozen piercing implement device; velocity of administration of the at least one frozen piercing implement device; quantity of frozen piercing implements of the device; quantity of frozen piercing implement devices administered; rate of administration of more than one frozen piercing implement devices; method of administration of at least one frozen piercing implement device; timing of administration of at least one frozen piercing implement; or rate of delivery of at least one agent of the device.

In one embodiment 20720, the system further comprises circuitry for transmitting one or more signals that include information related to the processing the first input and the second input. In one embodiment 20730, the system further comprises circuitry for evaluating the at least one substrate for one or more indicators relating to one or more of: quantitative delivery of at least one agent, depth of piercing the at least one substrate, spatial location of delivery of at least one agent, or temporal location of delivery of at least one agent. In one embodiment 20740, the at least one agent includes at least one therapeutic agent, reinforcement agent, abrasive, explosive material, adhesive agent, or biological remodeling agent. In one embodiment 20750, the output includes one or more instructions for making the at least one frozen particle composition or frozen piercing implement. In one embodiment 20760, the output includes at least one graphical description of the at least one frozen particle composition or frozen piercing implement.

In one embodiment 20810, the user includes at least one entity. In one embodiment 20820, the entity includes at least one person, or computer. In one embodiment 20830, the user readable display includes a human readable display. In one embodiment 20840, the user readable display includes one or more active displays. In one embodiment 20850, the user readable display includes one or more passive displays. In one embodiment 20860, the user readable display includes one or more of a numeric format, graphical format, or audio format. In one embodiment 20870, the user readable display includes one or more of a display of one or more differences in the comparison of at least one value related to the first input and at least one value related to at least one property of the at least one frozen particle composition or frozen piercing implement. In one embodiment 20880, the user readable display includes one or more of a display of one or more differences in the comparison of at least one value related to the second input and at least one value related to at least one parameter for administration of the at least one frozen particle composition or frozen piercing implement.

As illustrated in FIGS. 209-211, a computer program product 20900 comprises: 20910 a recordable medium bearing one or more instructions for accepting a first input associated with at least one parameter for making at least one frozen piercing implement device; 20920 one or more instructions for accepting a second input associated with at least one parameter for administering the at least one frozen piercing implement device to at least one substrate; 20930 one or more instructions for processing the first input and the second input; and 20940 one or more instructions for generating an output to a user readable display.

In one embodiment 20950 the recordable medium includes a computer-readable medium. In one embodiment 20960 the recordable medium includes a communications medium. In one embodiment 20970 the computer program product further comprises one or more instructions for displaying results of the processing. In one embodiment 20980 the computer program product further comprises one or more instructions for transmitting one or more signals that include information related to the processing the first input and the second input. In one embodiment 20990 the first input includes at least one parameter for making the at least one frozen piercing implement device includes one or more of: constitution of the at least one frozen piercing implement of the frozen piercing implement device, constitution of the at least one frozen piercing implement device, configuration of the at least one frozen piercing implement or frozen piercing implement device, formulation of the at least one frozen piercing implement of the frozen piercing implement device, formulation of the at least one frozen piercing implement device, size of the at least one frozen piercing implement of the frozen piercing implement device, size of the at least one frozen piercing implement device, shape of the at least one frozen piercing implement of the frozen piercing implement device, shape of the at least one frozen piercing implement device, physical structure of the at least one frozen piercing implement of the frozen piercing implement device, physical structure of the at least one frozen piercing implement device, physical or chemical integrity of the at least one frozen piercing implement of the frozen piercing implement device, physical or chemical integrity of the at least one frozen piercing implement device, or presence or absence of at least one microparticle, nanoparticle, lens, tunablelens, sensor, transducer, actuator, detector, heater, valve, gate, channel, detection material, pump, power source, injector, controller, receiver, transmitter, or circuit, in the at least one frozen piercing implement or frozen piercing implement device.

In one embodiment 21010, the at least one parameter for administering at least one frozen piercing implement device to at least one substrate includes one or more of: substrate type; substrate function; substrate size; substrate constitution; substrate architecture; substrate durability; substrate temperature; temperature of administration conditions; depth of administration of the at least one frozen particle composition or frozen piercing implement; substrate source; one or more temporal coordinates; one or more spatial coordinates; presence or absence of at least one agent; presence or absence of at least one microparticle, nanoparticle, lens, tunablelens, sensor, transducer, actuator, detector, heater, valve, gate, channel, detection material, pump, power source, injector, controller, receiver, transmitter, or circuit; angle of administration of the at least one frozen piercing implement device; force of administration of the at least one frozen piercing implement device; velocity of administration of the at least one frozen piercing implement device; quantity of frozen piercing implements of the device; quantity of frozen piercing implement devices administered; rate of administration of more than one frozen piercing implement devices; method of administration of at least one frozen piercing implement device; timing of administration of at least one frozen piercing implement; or rate of delivery of at least one agent of the device.

In one embodiment 21020, the computer program product further comprises one or more instructions for evaluating the at least one substrate for one or more indicators relating to one or more of: quantitative delivery of at least one agent, depth of piercing the at least one substrate, spatial location of delivery of at least one agent, or temporal location of delivery of at least one agent. In one embodiment 21030, the at least one agent includes at least one therapeutic agent, reinforcement agent, abrasive, explosive material, adhesive agent, or biological remodeling agent. In one embodiment 21040, the at least one frozen piercing implement device includes at least one frozen piercing implement array device, frozen piercing implement fluidic device, or frozen piercing implement injection device. In one embodiment 21050, the frozen piercing implement injection device includes a frozen piercing implement auto-injection device. In one embodiment 21060, the output includes one or more instructions for making the at least one frozen particle composition or frozen piercing implement.

In one embodiment 21110, the output includes at least one graphical description of the at least one frozen particle composition or frozen piercing implement. In one embodiment 21120, the user includes at least one entity. In one embodiment 21130, the entity includes at least one person, or computer. In one embodiment 21140, the user readable display includes a human readable display. In one embodiment 21150, the user readable display includes one or more active displays. In one embodiment 21160, the user readable display includes one or more passive displays. In one embodiment 21170, the user readable display includes one or more of a numeric format, graphical format, or audio format. In one embodiment 21180, the user readable display includes one or more of a display of one or more differences in the comparison of at least one value related to the first input and at least one value related to at least one property of the at least one frozen particle composition or frozen piercing implement. In one embodiment 21190, the user readable display includes one or more of a display of one or more differences in the comparison of at least one value related to the second input and at least one value related to at least one parameter for administration of the at least one frozen particle composition or frozen piercing implement.

As illustrated in FIGS. 212-214, a system 21200 comprises: 21210 a recordable medium bearing one or more instructions for accepting a first input associated with at least one parameter for making at least one frozen piercing implement device; 21220 one or more instructions for accepting a second input associated with at least one parameter for administering at least one frozen piercing implement device; 21230 one or more instructions for processing the first input and the second input; and 21240 one or more instructions for generating an output to a user readable display. In one embodiment 21250, the at least one frozen piercing implement device includes at least one frozen piercing implement array device, frozen piercing implement fluidic device, or frozen piercing implement injection device. In one embodiment 21260, the frozen piercing implement injection device includes a frozen piercing implement auto-injection device.

In one embodiment 21270, the recordable medium includes a computer-readable medium. In one embodiment 21280, the recordable medium includes a communications medium. In one embodiment 21290, the system further comprises one or more instructions for transmitting one or more signals that include information related to the processing the first input and the second input. In one embodiment 21310, the first input includes at least one parameter for making the at least one frozen piercing implement device includes one or more of: constitution of the at least one frozen piercing implement of the frozen piercing implement device, constitution of the at least one frozen piercing implement device, configuration of the at least one frozen piercing implement or frozen piercing implement device, formulation of the at least one frozen piercing implement of the frozen piercing implement device, formulation of the at least one frozen piercing implement device, size of the at least one frozen piercing implement of the frozen piercing implement device, size of the at least one frozen piercing implement device, shape of the at least one frozen piercing implement of the frozen piercing implement device, shape of the at least one frozen piercing implement device, physical structure of the at least one frozen piercing implement of the frozen piercing implement device, physical structure of the at least one frozen piercing implement device, physical or chemical integrity of the at least one frozen piercing implement of the frozen piercing implement device, physical or chemical integrity of the at least one frozen piercing implement device, or presence or absence of at least one microparticle, nanoparticle, lens, tunablelens, sensor, transducer, actuator, detector, heater, valve, gate, channel, detection material, pump, power source, injector, controller, receiver, transmitter, or circuit, in the at least one frozen piercing implement or frozen piercing implement device.

In one embodiment 21320, the second input includes at least one parameter for administering the at least one frozen piercing implement device includes one or more of: substrate type; substrate function; substrate size; substrate constitution; substrate architecture; substrate durability; substrate temperature; temperature of administration conditions; depth of administration of the at least one frozen particle composition or frozen piercing implement; substrate source; one or more temporal coordinates; one or more spatial coordinates; presence or absence of at least one agent; presence or absence of at least one microparticle, nanoparticle, lens, tunablelens, sensor, transducer, actuator, detector, heater, valve, gate, channel, detection material, pump, power source, injector, controller, receiver, transmitter, or circuit; angle of administration of the at least one frozen piercing implement device; force of administration of the at least one frozen piercing implement device; velocity of administration of the at least one frozen piercing implement device; quantity of frozen piercing implements of the device; quantity of frozen piercing implement devices administered; rate of administration of more than one frozen piercing implement devices; method of administration of at least one frozen piercing implement device; timing of administration of at least one frozen piercing implement; or rate of delivery of at least one agent of the device.

In one embodiment 21410, the system further comprises one or more instructions for evaluating the at least one substrate for one or more indicators relating to one or more of: quantitative delivery of at least one agent, depth of piercing the at least one substrate, spatial location of delivery of at least one agent, or temporal location of delivery of at least one agent. In one embodiment 21420, the at least one agent includes at least one therapeutic agent, reinforcement agent, abrasive, explosive material, adhesive agent, or biological remodeling agent. In one embodiment 21430, the output includes one or more instructions for making the at least one frozen particle composition or frozen piercing implement. In one embodiment 21440, the output includes at least one graphical description of the at least one frozen particle composition or frozen piercing implement.

In one embodiment 21450, the user includes at least one entity. In one embodiment 21460, the entity includes at least one person, or computer. In one embodiment 21470, the user readable display includes a human readable display. In one embodiment 21480, the user readable display includes one or more active displays. In one embodiment 21485, the user readable display includes one or more passive displays. In one embodiment 21490, the user readable display includes one or more of a numeric format, graphical format, or audio format. In one embodiment 21495, the user readable display includes one or more of a display of one or more differences in the comparison of at least one value related to the first input and at least one value related to at least one property of the at least one frozen particle composition or frozen piercing implement. In one embodiment 21498, the user readable display includes one or more of a display of one or more differences in the comparison of at least one value related to the second input and at least one value related to at least one parameter for administration of the at least one frozen particle composition or frozen piercing implement.

As illustrated in FIGS. 215-218, a system 21500 comprises: 21510 at least one computer program, configured with a computer-readable medium, for use with at least one computer system and wherein the computer program includes a plurality of instructions including but not limited to: one or more instructions for accepting a first input associated with at least one parameter for making at least one frozen piercing implement device; one or more instructions for accepting a second input associated with at least one parameter for administering at least one frozen piercing implement device; one or more instructions for processing the first input and the second input; and one or more instructions for generating an output to a user readable display. In one embodiment 21520, the system further comprises one or more instructions for transmitting one or more signals that include information related to the processing the first input and the second input. In one embodiment 21530, the system further comprises one or more instructions for evaluating the at least one biological tissue for one or more indicators relating to one or more of: quantitative delivery of at least one agent, depth of piercing the at least one substrate, spatial location of delivery of at least one agent, or temporal location of delivery of at least one agent.

In one embodiment 21540, the at least one agent includes at least one therapeutic agent, reinforcement agent, abrasive, explosive material, adhesive agent, or biological remodeling agent. In one embodiment 21650, the system further comprises at least one computing device. In one embodiment 21660, the at least one computing device is configured to communicate with at least one printing device, at least one imaging device, or at least one input device. In one embodiment 21670, the at least one frozen piercing implement device includes at least one frozen piercing implement array device, frozen piercing implement fluidic device, or frozen piercing implement injection device. In one embodiment 21680, the frozen piercing implement injection device includes a frozen piercing implement auto-injection device.

In one embodiment 21710, the output includes one or more instructions for making the at least one frozen particle composition or frozen piercing implement. In one embodiment 21720, the output includes at least one graphical description of the at least one frozen particle composition or frozen piercing implement. In one embodiment 21730, the user includes at least one entity. In one embodiment 21740, the entity includes at least one person, or computer. In one embodiment 21750, the user readable display includes a human readable display. In one embodiment 21760, the user readable display includes one or more active displays. In one embodiment 21770, the user readable display includes one or more passive displays. In one embodiment 21780, the user readable display includes one or more of a numeric format, graphical format, or audio format. In one embodiment 21790, the user readable display includes one or more of a display of one or more differences in the comparison of at least one value related to the first input and at least one value related to at least one property of the at least one frozen particle composition or frozen piercing implement. In one embodiment 21795, the user readable display includes one or more of a display of one or more differences in the comparison of at least one value related to the second input and at least one value related to at least one parameter for administration of the at least one frozen particle composition or frozen piercing implement.

In one embodiment 21810, the first input includes at least one parameter for making the at least one frozen piercing implement device includes one or more of: constitution of the at least one frozen piercing implement of the frozen piercing implement device, constitution of the at least one frozen piercing implement device, configuration of the at least one frozen piercing implement or frozen piercing implement device, formulation of the at least one frozen piercing implement of the frozen piercing implement device, formulation of the at least one frozen piercing implement device, size of the at least one frozen piercing implement of the frozen piercing implement device, size of the at least one frozen piercing implement device, shape of the at least one frozen piercing implement of the frozen piercing implement device, shape of the at least one frozen piercing implement device, physical structure of the at least one frozen piercing implement of the frozen piercing implement device, physical structure of the at least one frozen piercing implement device, physical or chemical integrity of the at least one frozen piercing implement of the frozen piercing implement device, physical or chemical integrity of the at least one frozen piercing implement device, or presence or absence of at least one microparticle, nanoparticle, lens, tunablelens, sensor, transducer, actuator, detector, heater, valve, gate, channel, detection material, pump, power source, injector, controller, receiver, transmitter, or circuit, in the at least one frozen piercing implement or frozen piercing implement device.

In one embodiment 21820, the second input includes at least one parameter for administering the at least one frozen piercing implement device includes one or more of: substrate type; substrate function; substrate size; substrate constitution; substrate architecture; substrate durability; substrate temperature; temperature of administration conditions; depth of administration of the at least one frozen particle composition or frozen piercing implement; substrate source; one or more temporal coordinates; one or more spatial coordinates; presence or absence of at least one agent; presence or absence of at least one microparticle, nanoparticle, lens, tunablelens, sensor, transducer, actuator, detector, heater, valve, gate, channel, detection material, pump, power source, injector, controller, receiver, transmitter, or circuit; angle of administration of the at least one frozen piercing implement device; force of administration of the at least one frozen piercing implement device; velocity of administration of the at least one frozen piercing implement device; quantity of frozen piercing implements of the device; quantity of frozen piercing implement devices administered; rate of administration of more than one frozen piercing implement devices; method of administration of at least one frozen piercing implement device; timing of administration of at least one frozen piercing implement; or rate of delivery of at least one agent of the device.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof In one embodiment, several portions of the subject matter described herein can be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

For any of the various aspects and embodiments disclosed herein, one or more kits can be developed with the components described herein. In one embodiment, a kit includes one or more frozen particle compositions as described herein. In one embodiment, a kit includes one or more frozen particle compositions and at least one therapeutic agent as disclosed herein. In one embodiment, a kit includes one or more frozen particle compositions and one or more reinforcement agents. In one embodiment, a kit includes one or more frozen particle compositions and one or more explosive materials.

PROPHETIC EXAMPLES

Example 1

Compositions and Methods of Making Frozen Particles

Frozen particle compositions suitable for various embodiments described herein can be produced by controlling the pressure and temperature of hydrogen oxide that is introduced as a liquid, gas or solid. Frozen particle compositions, including frozen hydrogen oxide ice Ic, are produced by cooling small hydrogen oxide droplets (~6 μm diameter) below approximately −38° C. (See e.g., Murray, et al., Phys. Chem. Chem. Phys. vol. 8, pp. 186-192 (2006), which is incorporated herein by reference). Emulsions of 30-40% by weight of distilled and de-ionized hydrogen oxide in paraffin oil (Fisher Scientific) are agitated to produce hydrogen oxide droplets of mean diameters ranging from 5 to 35 μm as determined by optical microscopy. The droplets are cooled to approximately −100° C. at a rate of approximately 10° C./min by using a cryostat cooled with liquid nitrogen and containing a heater and temperature controller. Freezing liquid droplets with a median diameter of approximately 5.6 μm or smaller can provide approximately 80% frozen ice Ic and approximately 20% frozen ice Ih. Following the procedures of Murray et al, selective production of ice Ic in pellet form produces quantities suitable for use in various embodiments described herein.

Frozen particles generated in this manner are utilized for abrasion of at least one biological tissue, including but not limited to skin. The frozen particle composition is administered to at least one biological tissue by, for example, accelerating, ejecting, or propelling the frozen particles by way of a carrier gas under pressure (e.g., air, carbon dioxide, nitrogen, neon, argon, etc.) through a tube, or other device directed toward at least one biological tissue, such as skin. Microdermabrasion, microscissuining, or other surface abrasion techniques are carried out in a similar fashion.

Example 2

Compositions and Methods of Making Frozen Particles

Frozen particles, including frozen hydrogen oxide ice Ic, are produced by depositing hydrogen oxide vapor onto a copper plate held at low temperatures in vacuo. Purified (deionized) hydrogen oxide is added to a vessel at approximately 25° C. and the hydrogen oxide vapor is condensed onto a metal plate held at approximately −196° C. in vacuo. The deposited amorphous ice is heated (at 10° C./min) to approximately −93° C. and is converted to crystalline cubic ice (ice Ic). Ice Ic is stable when stored under liquid nitrogen (See e.g., Johari, et al., J. Phys. Chem, vol. 94, pp. 1212-1214 (1990), which is incorporated herein by reference). An example of an apparatus that is used to produce frozen hydrogen oxide ice Ic is described in Hallbrucker et al (J. Phys. Chem., vol. 93, pp. 4986-4990 (1989), which is incorporated herein by reference).

Example 3

Compositions and Methods of Making Frozen Particles

Frozen hydrogen oxide ice Ic particles are produced from small hydrogen oxide droplets in an example of a "pelletizer" apparatus similar to those described by, for example, U.S. Pat. Nos. 4,617,064; or 6,306,119, each of which is incorporated herein by reference. Frozen hydrogen oxide ice Ic particles are formed by spraying hydrogen oxide droplets of the desired size into a compartment filled with a cold inert gas maintained at the desired temperature, for example, nitrogen gas maintained at approximately −100° C. to promote formation of ice Ic. Spray droplet size is maintained by variation of nozzle/aperature size and hydrogen oxide pressure to yield droplet diameters ranging from nanometers to centimeters. Frozen hydrogen oxide ice Ic, ice Ih, amorphous low density ice, amorphous high density ice, and other forms are produced by controlling the temperature and pressure of the compartment. Cubic hydrogen oxide ice Ic particles are formed in a step-wise process, by maintaining the chamber at a very low temperature (approximately −196° C.) with increased pressure, which first promotes formation of amorphous hydrogen oxide ice. Next, the chamber is heated to approximately −93° C., which results in transformation to cubic hydrogen oxide ice (ice Ic) particles.

The hydrogen oxide ice particles are propelled into a delivery system (such as tubing and nozzle) by nitrogen gas under pressure. The delivery system is maintained at the appropriate temperature for preservation of the hydrogen oxide particle structure, (e.g., approximately −93° C. for ice Ic structure).

Example 4

Compositions and Methods of Making Frozen Carbon Dioxide Particles

Carbon dioxide frozen particles are produced from small carbon dioxide droplets in a "pelletizer" similar to those described by, for example, U.S. Pat. Nos. 4,617,064; and 6,306,119; each of which is incorporated herein by reference. Carbon dioxide frozen particles are formed by spraying liquid carbon dioxide droplets into a compartment maintained at low temperatures (e.g., approximately −100° C.). Droplet size is regulated by varying nozzle or aperature size, and pressure. Carbon dioxide droplet diameters range, for example, from nanometers to centimeters. The frozen carbon dioxide particles are propelled into a delivery system (e.g., tubing and nozzle) by carrier gas, (e.g., air or nitrogen) under pressure. The carbon dioxide particles are maintained while in the delivery system at the appropriate temperature, (e.g., approximately −100° C.). Frozen carbon dioxide particles sublimate, or transition to a gas phase, at approximately −78.5° C. and 1 atm pressure.

Example 5

Compositions and Methods of Making Frozen DMSO Particles

Dimethyl sulfoxide (DMSO) frozen particles are produced from DMSO droplets, for example, in a "pelletizer" apparatus similar to those described by, for example, U.S. Pat. Nos. 4,617,064; 6,306,119, each of which is incorporated herein by reference. DMSO frozen particles are formed from spraying liquid DMSO droplets of the desired size into a compartment that is maintained at low temperature, for example, less than approximately 18.5° C. Droplet size is regulated by varying nozzle or aperature size, and DMSO pressure, with compressed air as a carrier gas. DMSO droplet diameters range, for example, from nanometers to centimeters. The DMSO frozen particles are propelled by a carrier gas (e.g., air or nitrogen) under pressure to enter a delivery system (e.g., tubing and nozzle). In order to preserve DMSO particle structure, the delivery system is maintained at low temperature (e.g., less than approximately 18.5° C.).

Example 6

Methods of Assessment or Selection of Frozen Particles

According to various embodiments described herein, at least one frozen particle is made by lowering the temperature of liquid droplets of a selected material. Droplet and particle sizes are measured by imaging a spray or particle stream upon a background screen. The background screen is illuminated with a short pulse of light, for example, from an infrared laser beam (at approximately 805 nm), which is capable of pulsing at frequencies of approximately 1000 Hz.

A digital camera captures high resolution images of the droplets or particles. High-speed, real-time particle sizing software analyses the images to assess the diameter distribution for the particles and to determine the shape. The diameter of each droplet is determined automatically by referencing the number of dark pixels in the droplet image to the pixel area of a calibration circle. Droplet diameters between approximately 100 μm (±3.2%) and approximately 2000 μm (±0.03%) were measured with 95% confidence (See e.g., Ireland et al., 6th ASME-JSME Thermal Engineering Joint Conference (2003), which is incorporated herein by reference). Instruments, computer programs and protocols for measuring particle and droplet size are available, for example, from Oxford Lasers, Shirley, Mass. (e.g., world wide web at oxfordlasers.com, which is incorporated herein by reference).

Example 7

Methods of Assessment or Selection of Frozen Particles

According to various embodiments described herein, at least one frozen particle is made by lowering the temperature of liquid droplets of a selected material. Droplet and particle sizes are measured by laser diffraction. Laser diffraction based particle size analysis relies on particles passing through a laser beam and scattering light at an angle that is directly related to their size. As particle size decreases, the observed scattering angle increases logarithmically. Scattering intensity is also dependent on particle size, and decreases with decreasing particle volume. Thus, large particles scatter light at narrow angles with high intensity whereas small particles scatter at wider angles but with low intensity. Laser diffraction is used for the non-destructive analysis of wet or dry samples, to measure particles in the size range 0.02 to 2000 micrometers (e.g., world wide web at chemie.de/articles/e/61205/, which is incorporated herein by reference). A laser diffraction instrument, protocols and analysis software are available, for example, from Malvern Instruments Ltd. (Malvern, Worcestershire, WR14 1XZ United Kingdom).

Example 8

Compositions and Methods of Making Frozen Particles Including a Reinforcement Agent One or more reinforcement agents are added to the frozen particles during the formation process. Among other things, reinforcement agents can increase the strength of frozen particles (e.g., increase the modulus of rupture of ice) and decrease the deformation of frozen particles (e.g., decrease the beam deflection of ice). As indicated in Table A below, glass fibers present at 9% (wt./vol.), for example, increase the modulus of rupture of ice by approximately 7-fold relative to ice derived from unreinforced hydrogen oxide ice (See e.g., Kingery, Science, vol. 134, pp. 164-168 (1960), which is incorporated herein by reference).

TABLE A

Strength of fresh ice with sawdust and Fiberglass, respectively, added. Additions were % wt./vol. (Kingery, Ibid).

| | Modulus of rupture ($kg/cm^2$) | |
|---|---|---|
| Addition (%) | Sawdust (−17° C.) | Fiberglass (−20° C.) |
| 0 | 22.5 | 24.1 |
| 0.8 | 22.7 | 24.0 |
| 2.5 | 35 | 65.4 |
| 9.0 | 60 | 161 |
| 14.0 | 66.7 | N/A |

As indicated in FIG. 5, the beam deflection is less than 0.005 inches for hydrogen oxide ice that is reinforced with approximately 9.0% glass fibers and increases over time for hydrogen oxide ice that is reinforced with approximately 0.8% glass fibers (Kingery, Ibid). Furthermore, hydrogen oxide ice with approximately 9% (w/v) of glass fibers is not deformed over 23 hours under an applied force of approximately 24.5 in.lbs. As described in Kingery, et al, and as indicated in FIG. 5, beam deflection of hydrogen oxide ice with approximately 0.8% glass fibers is approximately 0.16 inches after 23 hours under 25.3 in.lbs. of force. Likewise, as indicated in FIG. 5, and according to Kingery et al, hydrogen oxide ice without reinforcement agents is deformed approximately 0.05 inches after 4 hours under approximately 26.6 in.lbs. of force. Additionally, aluminum and silica carbonate particles can be mixed at various volume fractions and co-milled under an argon atmosphere to produce nanocrystalline composites as reinforcement agents for frozen particle compositions. (See e.g., Kamrani, et al., Powder Met. vol. 50, pp. 276-282(7) (2007), which is incorporated herein by reference).

Example 9

Compositions and Methods of Making Frozen Particles

Frozen particles (e.g., carbon dioxide, DMSO, gelatin) are reinforced by incorporating one or more reinforcement agents, including but not limited to silica beads, fiberglass, polyethylene glycol, kaolin, or wood fibers.

Silica beads approximately 1 micrometer in diameter are mixed with hydrogen oxide at approximately 0° C. to make volume fractions including the approximate ranges, but not limited to, 0, 0.004, 0.04, 0.15, 0.29, 0.49 and 0.63 volume fraction. The volume fractions, or one or more particular volume fraction, are frozen in, for example, a cylindrical mold, at low temperatures (e.g., approximately −10° C.). Unconfined coaxial compression tests are used to determine the maximum stress (also known as the failure point) of the one or more frozen particles at defined temperatures and strain rates (See e.g., Yasui et al, Geophys. Res. Lett., vol. 35, L12206, (2008), which is incorporated herein by reference).

As indicated in FIG. 6, maximum stress values (MPa) increase for mixtures with an increased volume fraction of silica beads relative to the maximum stress for unreinforced hydrogen oxide ice. (See e.g., Yasui et al, Ibid.) φ=silica volume fraction The strength of specific frozen particles is altered by varying the composition of frozen particle mixtures containing one or more reinforcement agents. For example, Table B indicates the frozen particle strength of frozen particles including hydrogen oxide, DMSO, carbon dioxide, and gelatin, which contain at least one reinforcement agent. As indicated, the reinforced frozen particles exhibited increased strength compared to their unreinforced counterparts. As indicated in Table B, frozen particles containing at least one reinforcement agent at the volume fractions shown in the table displayed maximal strength in compression tests. (See also, FIGS. 5 and 6, as well as Table A herein for hydrogen oxide frozen particle strength).

TABLE B

Frozen particles and reinforcement agents leading to increased particle strength

| Particle Base | Fiber Glass | Saw Dust | Silica Beads | PEG | Kaolin |
|---|---|---|---|---|---|
| Ice | 0.15* | 0.14 | 0.63 | ND | 0.15 |
| DMSO | 0.15 | 0.14 | 0.63 | ND | 0.15 |
| carbon dioxide | 0.15 | 0.14 | 0.63 | ND | 0.15 |
| gelatin | 0.15 | 0.14 | 0.63 | ND | 0.15 |

Volume fraction for reinforcement agents in frozen particle base materials is given. ND = Not Determined. (Yasui, et al.)

Example 10

Vaccine Compositions and Methods of Making Frozen Particles

As described herein, immunization of a subject with a vaccine is accomplished by way of introduction of the vaccine through, for example, subcutaneous, transcutaneous or intramuscular administration. (See e.g., Berzofsky et al, Nat. Rev. Immunol. vol. 1, pp. 209-219, (2001), which is incorporated herein by reference). Non-limiting examples of frozen particle vaccines are described herein, and include one or more immunogens. The immunogen therapeutic compositions are made, for example, in solution or as a solid in suspension or as a colloid created from, for example, buffered solutions (e.g., phosphate, citrate, lactate, pyruvate or an organic acid buffer) that optimize the stability and immunogenicity of the vaccine.

Storage stability of vaccines depends upon many factors, including vaccine formulation and storage temperature. For example, an influenza subunit vaccine formulated with trehalose, and Hepes buffered saline, is stable at room temperature for approximately 26 weeks (See e.g., Amorij et al, Pharm. Res. vol. 25, pp. 1256-1273 (2008), which is incorporated herein by reference).

Vaccines with adjuvants such as: N-acetyl muramyl-1-alanyl-d-isoglutamine, also called muramyl dipeptide (MDP) or monophosphoryl lipid A (MPL) elicit enhanced cellular and humoral immunity (See e.g., Aguilar et al Vaccine vol. 25, pp. 3752-62 (2007), which is incorporated herein by reference).

Furthermore, stable genetic transformation and vaccination of intact plant cells has been achievable by particle bombardment processes (See e.g., Klein et al PNAS vol. 85, pp. 8502-8505 (1988), and Klein et al BioTech vol. 24, pp. 384-386 (1992); each of which is incorporated herein by reference).

One or more hydrogen oxide frozen particle vaccine compositions, including, for example, one or more buffers, one or more immunogens (e.g., viral protein subunits) and one or more adjuvants, as a solution or suspension, are made by spraying the compositions through an aperature or nozzle. Each vaccine composition is propelled by a pressurized gas (e.g., compressed air) into a compartment maintained at, for example, approximately −40° C.

The vaccine composition is delivered to at least one biological tissue of a subject, for example, by propelling the particles via a carrier gas under pressure (e.g., air, carbon dioxide, nitrogen) through a tube directed toward at least one biological tissue (including but not limited to plant callus, plant leaves, plant roots, plant stems, vasculature, lymphatic, lymph node, epidermis, subcutaneous, intramuscular, oral, nasal, pulmonary, intraperitoneal or rectal tissue).

Alternatively, the vaccine composition is delivered to at least one biological tissue of a subject, for example, by first forming the frozen particle vaccine compositions through spraying composition droplets into a cryogen bath (e.g., liquid nitrogen). The frozen particle compositions are subsequently delivered to at least one biological tissue by flash boiling liquid nitrogen, and propelling the frozen particle compositions through a tube or barrel, for example, to at least one biological tissue of a subject.

Frozen particle vaccine compositions containing one or more reinforcement agents (e.g., silica beads) and of the appropriate size and shape (e.g., bullet, spheroid, high aspect ratio shape) penetrate the at least one biological tissue when propelled to high velocity by a carrier gas. In one non-limiting example, a vaccine composition approximately 20-70 μm in size penetrates the epidermis when the composition is accelerated to high speed with a powder jet injector (PowderJect, PowderJect Pharmaceuticals) (Amorij et al, Ibid.).

Similarly, one group found that using the Bio-Rad HELIOS Gene Gun® and microparticle-delivery of pCMV-S DNA vaccination in mice resulted in greater numbers of animals achieving immunity than those receiving intramuscular injection. (See, e.g., Conn et al, Bio-Rad Tech Note 2726, available on the worldwide web at bio-rad. com/LifeScience/pdf/Bulletin_2726.pdf, accessed Feb. 12, 2009, the content of which is incorporated herein by reference.)

For plant leaves, a high rate of infection with a Potyviridae virus was obtained by another group using the Bio-Rad HELIOS Gene Gun® and microparticle-delivery of the virus. (See, e.g., Kekarainen and Valkonen, Bio-Rad Tech Note 2531, available on the worldwide web at bio-rad.com/LifeScience/pdf/Bulletin_2531.pdf, accessed Feb. 12, 2009, the content of which is incorporated herein by reference.) The authors found optimal infection rates in plant leaves under a helium pressure of 150 psi or 200 psi, at a distance of 0 cm from the delivery device to the tissue. (Id. at page 2).

Example 11

Vaccine Compositions and Methods of Making Frozen Particles

Frozen particle vaccine compositions containing multiple immunogens, for example, toxoids (chemically modified toxins) from bacteria such as *Clostridium tetani, Cornybacterium diphtheriae* or *Bordetella pertussis*, stimulate immunity to multiple bacteria or toxins in a single vaccine composition.

Alternatively, multiple distinct immunogens, proteins, or peptides that are derived from a single pathogen are combined in a single frozen particle vaccine composition that immunizes a subject against a pathogenic virus or bacteria that mutates frequently. For example, multiple hemagglutinin or neuraminidase proteins, (e.g., H1N1, H3N2) from different viral strains (e.g., A/New Caledonia/H1N1, or A/Wellington/H3N2) or viral species of influenza (e g , influenza A or influenza B) are combined in a single frozen particle vaccine composition and provides immunity to multiple strains or species. (See e.g., Kamps et al, Influenza Report, pp. 127-149 (2006); world wide web at influenzareport.com/ir/vaccines; each of which is incorporated herein by reference).

Alternatively, frozen particle vaccine compositions including one or more immunogens, antigens or proteins (e.g., influenza A/New Caledonia/(H1N1)) are combined with one or more frozen particle vaccine compositions containing one or more different antigens (e.g., influenza B/Shanghai or influenza A/Wellington/(H3N2)). Such a frozen particle vaccine composition combination provides immunity against seasonal variants of viral pathogens.

In one non-limiting example, combinations of frozen particle vaccine compositions including specific antigens from selected influenza variants or strains target a seasonal flu epidemic. (Kamps et al, Ibid.) Combination of frozen particle compositions are made containing one or more different antigens or epitopes, wherein the one or more different antigens or epitopes are derived from mutant or variant HIV proteins that evolve during HIV infection (See e.g., Berzofsky et al, J. Clin. Inv. vol. 114, pp. 450-462 (2004)). Such combination compositions immunize a subject against existing HIV mutants and anticipate the emergence of new HIV mutants or variants.

Alternatively, one or more frozen particle vaccine compositions are delivered to one or more mucosal tissues (e.g., nasal, oral, rectal, pulmonary) via propulsion using a "pellet gun," via inhalation, or ingestion by a subject. For example, an influenza vaccine lyophilized and delivered nasally as spherical particles, approximately 26.9 mm (mean diameter), induces mucosal (e.g., nasal IgA response) and systemic immunity (e.g., serum antibody response) to influenza virus (See e.g., Garmise et al, AAPS Pharm Sci Tech. vol. 8:E81 (2007); Huang et al, Vaccine. vol. 23(6), pp. 794-801 (2004); each of which is incorporated herein by reference).

Alternatively, the one or more frozen particle vaccine compositions are delivered to one or more pulmonary surfaces of the subject via propulsion by way of a "pellet gun," by using flash boiled liquid nitrogen as a propellant, or by inhalation. Frozen particle influenza vaccine compositions administered to one or more pulmonary surfaces of a subject elicit mucosal and systemic humoral, as well as cell-mediated immune responses to influenza (See e.g., Amorij et al Vaccine. vol. 25, pp. 8707-8717 (2007), which is incorporated herein by reference).

Example 12

Compositions and Methods of Making Frozen Particles

Frozen particle compositions of the appropriate size and shape, including botulinum toxin, an optimal buffer (e.g., Hepes buffer), one or more stabilizing agents, and one or more reinforcement agents are administered through the skin of a subject to neuromuscular junctions. Botulinum toxin inhibits acetylcholine release, which blocks synapse formation, and temporarily paralyzes the corresponding musculature.

Frozen particle compositions containing a recommended dose of botulinum toxin (See e.g., Borodic, U.S. Pat. No. 5,183,462, which is incorporated herein by reference), and at least one reinforcement agent (e.g., polymer) are administered to skeletal muscles using a delivery system derived from inkjet printer technology that sprays picoliter quantities of the frozen particle compositions at high velocity (e.g., 50 m/sec) toward the skin of the subject. Botulinum toxin is typically administered by subcutaneous injection (generally with a 26 gauge hypodermic needle). Botulinum toxin is approved by the FDA for therapy of strabismus (crossed-eyes), blepharospasm (uncontrolled blinking), and other facial nerve disorders including hemifacial spasm. It is also approved for treatment of cervical dystonia and glabellar (frown) lines (See e.g., Jankovic, J. Neurol. Neurosurg. Psychiatry vol. 75, pp. 951-957 (2004), which is incorporated herein by reference).

In addition, botulinum toxin is included in the treatment of focal or segmental dystonia (e.g., oromandibular-facial-lingual dystonia, laryngeal dystonia, limb dystonia). Dystonias are neurological disorders with repetitive and patterned contractions of muscles that cause abnormal movements and postures. For example, cervical dystonia subjects are injected with, for example, approximately 100 I.U of botulinum toxin, distributed over 3-5 injection sites, spaced 5-15 mm apart, across the length of the sternomastoid muscle. (Borodic, Ibid.)

Frozen particle compositions containing botulinum toxin are administered to facial muscles that underlie frown lines, wrinkles, and "crow's feet." For example, botulinum toxin is targeted to: 1) the corrugator and procerus muscles to treat vertical glabellar eyebrow furrows; 2) to multiple sites in the frontalis muscle to eliminate horizontal lines in the forehead; or 3) to the lateral orbicularis oculi to treat crow's feet.

Frozen particle compositions containing an optimal dose of botulinum toxin (e.g., 0.2-0.4 I.U./kg) are administered over the length of a specific facial muscle (e.g., orbicularis oculi) by use of a delivery system with an inkjet nozzle. As described herein, picoliter volumes of one or more frozen particle compositions are sprayed at a velocity that achieves a desired or predetermined depth (for example, 5-8 mm; Borodic, Ibid.). The velocity is also altered according to the size, shape, and constituents of the frozen particle composition.

Example 13

Methods of Administering Frozen Particle Therapeutic Compositions

Frozen hydrogen oxide particles of ice Ic form and at least one therapeutic agent or at least one diagnostic agent are formulated for treatment of hematological cancers (e.g., leukemia or lymphoma) or solid tumors (e.g., carcinoma, sarcoma). For example, at least one of neo-adjuvant therapy, adjuvant therapy, chemotherapy, antibody therapy, or immunotherapy are employed.

In one non-limiting embodiment, frozen particle compositions are used for adjuvant therapy of cancers treated with surgery such as colon cancer, lung cancer, and breast cancer. At least one frozen particle hydrogen oxide therapeutic composition containing one or more reinforcement agents (e.g., silica beads, Kevlar®), one or more buffers, one or more stabilizing agents (e.g., one or more saccharides), and one or more cancer therapeutic agents (such as one or more chemotherapy drugs, antibodies, biological agents (e.g., antibodies, cytokines or peptides), or one or more chemotherapeutic agents) are administered to an area proximal to a region of at least one biological tissue where a tumor is present or believed to be present. Optionally, resection of at least a part of a tumor can be performed, with or without additional administration of the at least one frozen particle therapeutic composition.

The at least one frozen particle therapeutic composition is administered in such a manner as described herein, that allows for desired depth of penetration of the at least one biological tissue. In one embodiment, the at least one frozen particle therapeutic composition is administered to a depth that allows for at least one of intracellular or intercellular delivery. For example, the at least one frozen particle therapeutic composition is administered to a depth that allows for delivery to at least one of epithelium, endothelium, vasculature, lymphatic vessels, lymph nodes or mucosa.

Specifically, if metastasis is present or believed to be present in the subject, administration of the at least one frozen particle therapeutic composition is delivered to such region of metastases or micro-metastases are believed to be present.

Frozen particle hydrogen oxide therapeutic compositions provided as an adjuvant therapy are administered by spraying at least one composition under pressure with a carrier gas through a nozzle designed to uniformly distribute particles over at least one biological tissue at sufficient velocity to penetrate the tissue exposed during tumor resection.

Advanced colon cancer (e.g., stage II, III) is treated surgically by removal of sections of colon containing tumor with margins of "normal" colon tissue and often includes removal of associated lymph nodes and mesentery (colectomy). Standard adjuvant therapy following surgery is systemic administration of a combination of chemotherapy drugs (e.g., 5-fluorouracil, leucovorin or oxaliplatin (FOLFOX)), (See e.g., Wolpin et al, CA Cancer J. Clin. vol. 57, pp. 168-185 (2007)). Systemic FOLFOX adjuvant therapy is associated with significant toxicities including gastrointestinal toxicity, neutropenia and neurotoxicity (Wolpin et al, Ibid.). Localized in situ delivery of FOLFOX by administration of frozen particle therapeutic compositions permits delivery of a lower dose.

Administration of at least one frozen particle hydrogen oxide therapeutic composition containing at least one therapeutic antibody includes, for example, bevacizumab (an anti-vascular endothelial growth factor) or cetuximab (an anti-epidermal gowth factor receptor). Bevacizumab and cetuximab both target the tumor-associated vasculature and tumor cells in the remaining colon sections and the surrounding tissues, mesentery and lymph nodes. Localized administration of therapeutic antibodies provides sustained protection from recurrence of colon tumors at the site of tumor resection and in the surrounding tissues. (Wolpin et al, Ibid.). Following surgery and adjuvant therapy with one or more frozen particle hydrogen oxide therapeutic compositions, including at least one of one or more chemotherapy drugs, or one or more antibodies, the remaining colon sections are spliced together (i.e. anastomosis) or an artificial orifice (i.e. stoma) is inserted to restore a functional colon.

Example 14

Methods of Administering Frozen Particle Therapeutic Compositions

Frozen particle hydrogen oxide therapeutic compositions including one or more cancer therapeutics or one or more cancer diagnostics are used to treat cancers in distal locations from the primary tumor or initial tumor site treated with surgery or radiation. For example, colon cancer cells often metastasize to the liver ((Wolpin et al, Ibid.). At the time of surgical resection of colon cancer tumors, one or more frozen particle hydrogen oxide therapeutic compositions including at least one cancer therapeutic, such as one or more cytotoxic drugs (e.g., fluouracil), antibodies (e.g., cetuximab), radioisotopes conjugated to antibodies (e.g., $^{131}$I-cetuximab), or one or more mixtures of at least one cytotoxic drug and at least one biological-based therapeutic agent are administered to the liver and surrounding tissues.

Administration of the at least one frozen particle hydrogen oxide therapeutic composition is accomplished by traditional surgery or laparoscopic surgery that allows access to the liver (or other organs to be treated). Administration of at least one frozen particle hydrogen oxide therapeutic composition directly to the liver and the surrounding vasculature allows for intracellular or intercellular penetration and release of at least one anti-cancer therapeutic for treatment of any existing or suspected colon cancer mestastases or micro-metastases.

As described herein, the at least one frozen particle hydrogen oxide therapeutic composition including one or more cancer therapeutics are administered by way of a spraying device. Such a spraying device includes an insulated tube and nozzle, as well as a valve that controls the flow of particles. In the case of traditional surgery for tumor or tissue resection, the at least one frozen particle hydrogen oxide therapeutic composition is sprayed directly onto the target tissue or tissues. Whereas in the case of laparoscopic surgery for tumor or tissue resection, the at least one frozen particle hydrogen oxide therapeutic composition is sprayed through a trocar (a hollow tube approximately 10 millimeters in diameter).

In certain spraying devices, the at least one frozen particle hydrogen oxide therapeutic composition is administered by way of a carrier gas. The depth of penetration by the at least one therapeutic composition is controlled by regulating the carrier gas pressure as well as the consequent particle velocity. The at least one therapeutic composition optionally includes one or more tracer agents or is delivered simultaneously with one or more tracer agents. Some non-limiting examples of tracer agents include dyes, stains or fluorescent compounds that mark the tissue area sprayed. The one or more tracer agents can optionally monitor or provide feedback as to the quantity or quality (in the case of multiple therapeutic compositions administered simultaneously or over time) of the at least one therapeutic composition administered to a specific site.

In one embodiment, the at least one frozen particle hydrogen oxide therapeutic composition including at least one cancer therapeutic further includes hematoxylin and eosin stains mixed at a known ratio (e.g., 1:10). Alternatively, a batch of the at least one frozen particle hydrogen oxide therapeutic composition is administered in a mixture or in separate applications frozen particles including hematoxylin and eosin stains. Staining of tissues is visualized by inspection with a low power microscope (e.g., dissection microscope) or with a laparoscope, which allows for assessment of the relative quantity or quality of the at least one therapeutic composition administered to the tissue. Staining of the tissues further provides a guide as to the region that received the at least one therapeutic composition.

Example 15

Methods of Administering Frozen Particle Therapeutic Compositions

Frozen particle hydrogen oxide therapeutic compositions including carbon dioxide and at least one cancer therapeutic are administered to at least one tumor or tissue suspected of being cancerous. Upon administration, the frozen particle hydrogen oxide therapeutic compositions penetrate one or more tumor cells, warm to ambient temperature, and undergo rapid sublimation and gaseous expansion of the carbon dioxide. This rapid reaction produces a small explosion that destroys at least one tumor cell as well as one or more adjacent cells. In addition, administration of the frozen particle therapeutic compositions at low temperatures (e.g., lower than approximately $-78.5°$ C., which is the approximate sublimation temperature for carbon dioxide at 1 atm pressure), freezes cells and tissues, causing tumor cell death (See e.g., Vergnon et al, Eur. Respir. J. vol. 28 pp. 200-218 (2006); incorporated herein by reference).

Alternatively, carbon dioxide gas is entrapped in frozen particles by placing the liquid phase (e.g., hydrogen oxide) under high pressure in the presence of carbon dioxide gas. (See e.g., U.S. Pat. Nos. 4,289,794; 4,289,790; 4,262,029; 5,439,698, each of which is incorporated herein by reference). Administration of the at least one therapeutic composition is conducted as described herein. In one embodiment, the use of a tube and nozzle is used that sprays the frozen particle therapeutic compositions under pressure in a carrier gas (e.g., carbon dioxide, nitrogen). Administration of the at least one therapeutic composition is carried out as an adjuvant therapy in conjunction with tumor resection, or as an alternative when tumor resection is not favored. For example lung cancer tumors are generally inoperable when such tumors are adjacent to airways, or infiltrate central airways including the trachea, main stem bronchi or multiple lung lobes. Additionally, subjects with compromised respiration (e.g., those with lung disease, heart disease or advanced age) are generally not candidates for surgery (See e.g., Spiro et al, Amer. J. Respir. Crit. Care Med., vol. 172, pp. 523-529 (2005); which is incorporated herein by reference).

Carbon dioxide frozen particle therapeutic compositions including one or more chemotherapeutic drugs (e.g., cisplatin, docetaxel, vinorelbine), targeted drugs (e.g., gefitnib, erlotnib), or biological-based agents (e.g., cetuximab, panitumumab, bevacizumab) are administered directly onto lung cancer tumors. Administration is conducted via endoluminal bronchoscopy or by video-assisted thoracoscopy by means of an insulated tube and nozzle integral to the endoscopic device. Frozen particle composition velocities and spray rate are controlled by a valve between the spray head and the compartment of the "pelletizer." (See e.g., U.S. Pat. Nos. 6,306,119, or 6,764,493, each of which is incorporated herein by reference). Precise localization and administration of the frozen particle therapeutic compositions are accomplished by bronchoscopy and endoscopy with fluoroscopy used to mark the field(s) of interest.

Methods for endoscopic targeting of tumors are described, for example, in Huber et al (Chest vol. 107, pp. 463-470 (1995); which is incorporated herein by reference). Moreover, computed tomography, magnetic resonance imaging, positron emission tomography or other techniques are used to locate lung cancer tumors.

Frozen particle therapeutic composition administration by using endoscopic procedures or as an adjuvant therapy in conjunction with traditional surgery is used for various regions of existing or potential carcinogenesis, including mediastinal lymph nodes, vasculature, chest wall and other thoracic sites.

Alternatively, frozen particle therapeutic compositions are delivered during traditional surgery for lung cancer and used to treat inoperable tumors remaining following lobectomy, wedge resection, and pneumonectomy, as well as to treat margins of lobe, wedge or lung excisions to reduce recurrence of lung cancer (See e.g., the worldwideweb at en.wikipedia.org/wiki/Lung_cancer#Surgery; which is incorporated herein by reference). Without wishing to be bound by any particular theory, frozen particle carbon dioxide therapeutic compositions maintained at approximately $-80°$ C. while administered to tumors rapidly freeze the tumor cells leading to formation of ice crystals in tumor cells that destroy cell organelles (e.g., mitochondria) leading to death of the tumor cells. (Vergnon et al, Ibid.)

Similarly, frozen particle therapeutic compositions containing at least one radioactive element deliver radiation to lung cancer tumor cells. One non-limiting example utilizes frozen particle therapeutic compositions including $^{192}$Iridium for irradiating lung tumors that obstruct major airways. Administration of the frozen particle therapeutic compositions is conducted using an endoscope and a wire to place the radioactive compositions in at least one lung tumor. Without wishing to be bound to any theory, tumor cell irradiation results in single-stranded DNA breaks that induce apoptosis and reduce rates of cell division (Vergnon et, Ibid.).

Example 16

Compartmentalized Frozen Particle Therapeutic Compositions

Frozen particles formed in a bullet-shaped mold with hollow cores or cavities that can be filled with therapeutics are useful for delivering at least one therapeutic agent to a variety of specific tissues, cells and organ or body locations. Hollow bullet-shaped frozen particles can be filled with a therapeutic agent such as one or more of an antibody, cytokine, DNA, small interfering RNA, microRNA, aptamer, cytotoxic agent (e.g. a xenobiotic, synthetic, or radioactive agent) that are in aqueous solution (e.g. sodium phosphate buffer) or form a suspension. Alternatively, hollow frozen bullets can be filled with one or more liquid or solid polymers or nanoparticles that contain at least one therapeutic agent (e.g. at least one prodrug) that requires activation.

In one particular embodiment, at least one therapeutic agent is frozen in carbon dioxide. The frozen carbon dioxide/therapeutic agent mixture or solution is used to fill pre-formed hollow bullet-shaped frozen particles. In certain embodiments, the hollow bullet-shaped frozen particles are formed and filled simultaneously. The temperature and pressure of the frozen particles are adjusted according to the particular constituents and specific parameters of the desired frozen particle.

Administration of at least one compartmentalized therapeutic frozen particle composition with a spraying device allows for localized delivery of at least one therapeutic agent to specific cells or tissues, such as one or more tumors. In certain embodiments, administration of at least one compartmentalized therapeutic frozen particle composition is directed to one or more adjacent, metastatic, or affected tissues including lymph nodes, lymphatic vessels, blood vessels, and organs (e.g. liver, lung, and kidney).

The size, shape or delivery velocity of the at least one compartmentalized frozen particle composition can be controlled in order to deliver the at least one particle composition to a desired location or penetration depth. In certain embodiments, the compartmentalized frozen particle composition includes at least one therapeutic agent (e.g. a cytotoxic agent) that is delivered intracellularly, intercellularly, or into the lumen of vasculature, lymphatics, alveoli, bladder, intestine, lungs or into a specific tissue (e.g. endoderm, smooth muscle, skeletal muscle, prostate).

In one example, hollow bullet-shaped frozen particle compositions containing a prodrug, such as capecitabine, can be delivered intracellularly to tumor cells (e.g. colon carcinoma) where capecitabine is metabolized to 5-fluorouracil, an active cytotoxic agent. Administration of at least one frozen particle composition including capecitabine specifically to tumor cells and optionally to proximal tissues allows for the potential to increase the therapeutic dose to tumor cells, while reducing systemic exposure (which can lead to toxicity and side effects, including angina and myocardial infarction, diarrhea, nausea, neutropenia, anemia and thrombocytopenia).

Alternatively, in one embodiment, intracellular delivery of at least one frozen particle composition including capecitabine that is encapsulated in biodegradable polymeric nanoparticles, releases capecitabine in a pH-dependent manner. (See for example, Shenoy et al, Pharm. Res. vol. 22, pp. 2107-2114 (2005), which is incorporated herein by reference). Since tumor cells generally have a lower pH than non-tumor cells, the capecitabine is released in higher amounts in the tumor environment.

Alternatively, in one embodiment, at least one frozen particle includes capecitabine and one or more polymeric nanoparticles composed of at least poly (ϵ-caplactone) (PCL), a non-pH sensitive polymer that is able to release capecitabine as the frozen particle melts or sublimates. (See, for example, Shenoy et al, Ibid.).

Example 17

Compartmentalized Frozen Particle Therapeutic Compositions Including Reinforcement Agents for Transdermal Administration Frozen particle compositions that include at least one therapeutic agent in one or more distinct regions of the particles are useful for transdermal administration of at least one therapeutic to various layers of the skin or to underlying tissues, organs and structures. For example, treatment of certain skin disorders, such as psoriasis, is currently limited to topical administration of a therapeutic agent (e.g. coal tar, corticosteroids, vitamin $D_3$ analogs, or retinoids), systemic treatments (e.g. methotrexate, cyclosporin and retinoids), or UV irradiation (e.g. phototherapy) (See, for example, en.wikipedia/wiki/psoriasis2008, which is incorporated herein by reference). None of these current treatments are fully effective.

In one embodiment, at least one frozen particle composition including one or more psoriasis therapeutic agents located in one or more gradation layers of concentration, or as a coating on the particle is administered to the epidermis, dermis or hypodermis layer by controlling specific parameters, such as particle hardness, size, shape, reinforcement agent, or velocity. For example, frozen particle compositions including reinforced hydrogen oxide are propelled toward at least one biological tissue by "flash-boiling" liquid nitrogen to create nitrogen gas and propel the particle compositions by explosive force. The frozen particle compositions are reinforced with plant matter (such as silk fibers, or collagen fibers), or spun metallic fibers (such as tungsten, iron, manganese, carbon, titanium, or steel). The one or more frozen particle compositions are directed with a hose and nozzle device onto psoriatic skin. In addition, the frozen therapeutic particle compositions can be delivered to the dermis to further impact any pathogenic T cells or cytokines associated with the condition.

In one embodiment, hollow bullet-shaped frozen particle compositions containing one or more biological agent, for example etanercept (as an anti-TNF-α therapy), are administered to the dermal layer underlying areas of psoriatic skin. One or more other therapeutic agents can be combined with the one or more biological agent on the same frozen particle, or on different frozen particles for administration. For example, cytotoxic or cytostatic agents are administered to cells associated with psoriasis, including T1 cells, $T_H17$ cells, dendritic cells, neutrophils or keratinocytes. (See, for example, Sabat et al, Exp. Derm. vol. 16, pp. 779-798 (2007), which is incorporated herein by reference). For example, therapeutic agents such as anti-CD3, anti-IL-23, anti-IL-17 or cyclosporin are included in one or more frozen particles to further treat psoriasis in the dermis or epidermis.

Example 18

Compartmentalized Frozen Particle Therapeutic Compositions Including Explosive Materials Hollow frozen particle compositions including one or more reinforcement agents and hydrogen oxide are filled with solid carbon dioxide. The hollow frozen particle compositions are useful for destroying, debriding, ablating, or eliminating unwanted cells or tissues such as fat, bone or tumor cells. In one embodiment, the hollow frozen particle compositions containing a solid carbon dioxide core produces an explosive force as the particle sublimates or melts during administration of the frozen particle compositions. The explosive force fragments, abrades, or destroys cells or tissues.

At least one sub-group of the frozen particle composition treatment course includes one or more of an antibiotic or other anti-microbial agent; one or more anti-inflammatory drugs; one or more anesthetics or analgesics; or one or more vasoconstrictors. Targeted delivery of hollow frozen particle compositions to unwanted cells or tissues is regulated by controlling, for example, frozen particle hardness, size, shape, reinforcement agents or explosive agents, and velocity. One or more frozen particle compositions are administered to at least one biological tissue by external (e.g. transdermal) methods, or internal (e.g. laparoscopic) methods. In one embodiment, a device (e.g. tube and spray nozzle) is integrated for administration of the one or more frozen particle compositions.

Compartmentalizd frozen particle compositions are useful for destroying adipocytes or fatty tissue. Present treatments include liposuction, which is performed with a cannula attached to an aspirator that is inserted through small incisions proximal to unwanted fat and the cannula are drawn over the fat to dislodge it and aspirate it (See, for example, en.wikipedia.org/wiki/Liposuction2008, which is incorporated herein by reference).

In one embodiment, a tube and spray nozzle is integrated with the cannula for administration of frozen particles containing a solid carbon dioxide core and optionally, one or more therapeutic agents. For example, the operator sprays frozen particle compositions containing carbon dioxide toward the adipocytes or fatty tissue in order to remove or destroy the tissue. Next, the treated tissue is aspirated with the cannula.

In one embodiment, a laparoscope can be used with the delivery device to allow visualization of the fatty tissue as well as precise delivery of the one or more frozen particle compositions. In certain embodiments, the frozen particle compositions also include lidocaine or ibuprofen in order to minimize pain and inflammation often associated with liposuction. In certain embodiments, at least one vasoconstrictor, such as epinephrine, is included in the one or more frozen particles in order to minimize bleeding. In certain embodiments, antibiotics, such as penicillin or sulfonamide, are included to reduce infection.

Alternatively, frozen particle compositions including a solid carbon dioxide core, one or more antibiotics, analgesics, anti-inflammatory drugs or vasoconstrictors are delivered transdermally to adipose tissue by spraying the particle compositions as described herein, at the appropriate velocity to penetrate the epidermis, dermis or hypodermis. Following treatment of adipocytes or fatty tissue with the one or more frozen particles, liposuction is performed to remove the treated cells or tissues. In one embodiment, adipocytes are selectively treated with minimal effect on the underlying muscle cells, which reduces bruising or bleeding.

Example 19

Compositions and Methods of Administering Frozen Particles Including One or More Adhesive Agents and One or More Biological Remodeling Agents Frozen particles including hydrogen oxide, carbon dioxide, dimethylsulfoxide or a buffer (e.g. HEPES, Ringer's solution, sodium citrate, sodium phosphate, etc.) are formulated with at least one adhesive agent such as cyanoacrylate, polyethylene glycol polymers or albumin plus glutaraldehyde.

Frozen particle compositions including at least one adhesive agent are utilized in conjunction with standard methods to achieve hemostasis in patients undergoing surgery, for example, to repair large blood vessels such as the aorta, femoral or carotid arteries. Frozen particle compositions including bovine albumin and glutaraldehyde (BIOGLUE®, CryoLife, Inc., Kennesaw, Ga.) are utilized, for example, in repair of an aortic dissection or other blood vessel repair.

Frozen particle compositions including hydrogen oxide, glutaraldehyde, and bovine albumin are produced as described herein at other sections. In an embodiment, various different subsets of frozen particle compositions are produced, for example, one subset includes frozen hydrogen oxide particles including glutaraldehyde, while another subset is produced that includes frozen hydrogen oxide particles including bovine albumin.

In an embodiment, a single set of frozen particle compositions are produced, for example, including frozen hydrogen oxide particles including both glutaraldehyde and bovine albumin.

In an embodiment, a set of frozen particle compositions are produced, for example, that includes compartmentalized particles wherein both glutaraldehyde and bovine albumin are present on a particular particle, but each is partially or wholly sequestered in a separate compartment of the particular particle. Some examples of compartmentalized frozen particles are described herein at other sections.

In an embodiment, frozen particles include bovine albumin in a mass ratio of weight per volume of approximately 5%, approximately 10%, approximately 15%, approximately 20%, approximately 25%, approximately 30%, approximately 35%, approximately 40%, approximately 45%, approximately 50%, approximately 55%, approximately 60%, approximately 65%, approximately 70%, approximately 75%, or any value therebetween.

In an embodiment, frozen particles include glutaraldehyde in a mass ratio of weight per volume of approximately 1%, approximately 2%, approximately 3%, approximately 4%, approximately 5%, approximately 6%, approximately 7%, approximately 8%, approximately 9%, approximately 10%, approximately 11%, approximately 12%, approximately 15%, approximately 16%, approximately 17%, approximately 18%, approximately 19%, approximately 20%, or any value therebetween.

One or more sets of frozen particle compositions including hydrogen oxide, glutaraldehyde, and/or bovine albumin, as described herein, are administered to the false lumen of the dissected aorta or other blood vessel in need of repair, at the distal and proximal anastomotic sites.

In an embodiment, a set of frozen particle compositions including bovine albumin and glutaraldehyde is administered alone or in conjunction with (sequentially or simultaneously with) other frozen particle compositions that optionally include, for example, one or more of at least one therapeutic agent, at least one reinforcement agent, at least one explosive material.

In an embodiment, multiple sets of frozen particle compositions, including bovine albumin and glutaraldehyde on separate particles are administered simultaneously or sequentially to the biological tissue. These multiple sets of frozen particle compositions are optionally administered simultaneously or sequentially with other frozen particle compositions that include, for example, one or more of at least one therapeutic agent, at least one reinforcement agent, or at least one explosive material.

Depending on the thickness of the blood vessel to be repaired, as well as other factors, an adhesive layer is administered with a thickness of approximately 0.1 mm, approximately 0.2 mm, approximately 0.3 mm, approximately 0.4 mm, approximately 0.5 mm, approximately 0.6 mm, approximately 0.7 mm, approximately 0.8 mm, approximately 0.9 mm, approximately 1.0 mm, approximately 1.5 mm, approximately 2.0 mm, approximately 2.5 mm, approximately 3.0 mm, approximately 3.5 mm, approximately 4.0 mm, approximately 4.5 mm, approximately 5.0 mm, approximately 6.0 mm.

Optionally, subsequent to repair of the distal and proximal ends of the blood vessel, one or more support structural materials are inserted to replace damaged blood vessel sections. Some examples of structural material that can be utilized are described herein at other sections. For example, some non-limiting examples of structural material include one or more of tubing (such as plastic or rubber tubing, e.g. polyethylene terephthalate or polytetrafluoroethylene), a stent (optionally including one or more therapeutic agents), a matrix (such as extracellular matrix components, or an artificial or synthetic matrix), a rod or other physical support.

Following insertion of the optional support structure, one or more sets of frozen particle compositions are administered to the repaired blood vessel to secure the structure or assist in modulating hemostasis. One or more sets of frozen particle compositions are also optionally administered to the junctions between the support structure and the vasculature.

Example 20

Compositions and Methods of Administering Frozen Particles Including One or More Adhesive Agents and One or More Biological Remodeling Agents Surgical incisions, burns, and other traumatic injuries result in damage to the dermis or hypodermis skin layers. Frozen particles including at least one adhesive agent, and optionally one or more of a growth factor, an anesthetic, or an antibiotic are administered to the biological tissue to secure would closure, including securing skin grafts. The frozen particles are administered alone or in conjunction with surgical staples or sutures.

In an embodiment, one or more frozen particles including thrombin (e.g., activated thrombin) or fibrinogen are administered. As described in other sections herein, thrombin and fibrinogen can be included as part of a single frozen particle (including, for example, provided in compartments of a single frozen particle), a single set of frozen particles, or separately as part of different frozen particles or different sets of frozen particles. As described herein, if multiple sets of frozen particles are administered, the sets can be administered simultaneously or sequentially.

In an embodiment, one or more frozen particles including at least one adhesive agent include a biodegradable polymer that encapsulates at least one therapeutic agent (such as a growth factor, antibiotic, anesthetic or other agent). For example, poly (ε-caprolactone) (PCL) allows for controlled or sustained release of a therapeutic agent for a specific location (See, for example, Shenoy et al, Ibid., which is incorporated herein by reference).

In an embodiment, one or more frozen particles include activated thrombin at a concentration of approximately 0.5 IU/mL, approximately 1.0 IU/mL, approximately 1.5 IU/mL, approximately 2.0 IU/mL, approximately 2.5 IU/mL, approximately 3.0 IU/mL, approximately 3.5 IU/mL, approximately 4.0 IU/mL, approximately 4.5 IU/mL, approximately 5.0 IU/mL, approximately 5.5 IU/mL, approximately 6.0 IU/mL, approximately 6.5 IU/mL, approximately 7.0 IU/mL, approximately 7.5 IU/mL, approximately 8.0 IU/mL, approximately 8.5 IU/mL, approximately 9.0 IU/mL, or any value therebetween.

In an embodiment, one or more frozen particles include fibrinogen at a concentration of approximately 20 mg/mL, 30 mg/mL, 40 mg/mL, 50 mg/mL, 60 mg/mL, 70 mg/mL, 80 mg/mL, 90 mg/mL, 100 mg/mL, 110 mg/mL, 115 mg/mL, 120 mg/mL, 130 mg/mL, 140 mg/mL, 150 mg/mL, or any value therebetween.

Since activated thrombin reacts with fibrinogen by way of proteolysis to form a fibrin adhesive, the concentration of either fibrinogen or thrombin can be increased or decreased, depending on the desired goal of wound closure. (See, e.g., Spotnitz et al. Transfusion, vol. 48, pp. 1502-1516 (2008); Evans et al., Braz. J. Urol. vol. 32, pp. 131-141 (2006), each of which is incorporated herein by reference.) For example, if a skin graft is involved in the wound repair and a slow rate of adherence is desired in order to accurately place the graft on the wound, the concentration of either thrombin or fibrinogen can be reduced. Alternatively, separate sets of one or more frozen particles can be administered, wherein the concentration of at least one adhesive agent varies within a set or between the separate sets of frozen particles. Optionally, one or more frozen particles can include at least one proteolytic inhibitor, such as aprotinin, in order to prolong the fibrin adhesive effect. (See, e.g., Spotnitz et al, Ibid., which is herein incorporated by reference).

Optionally, one or more of the frozen particles includes at least one detection material (e.g., a non-reactive, biodegradable dye or non-toxic contrast agent) that allows for visual detection of application of the one or more frozen particles. In an embodiment, the one or more frozen particles including at least one detection material also include at least one other agent (e.g., at least one adhesive agent, or at least one therapeutic agent). (See, e.g., worldwide web at kolorjectchemicals.com/natural-food-color.html, visited on Nov. 25, 2008, which is incorporated herein by reference.)

Optionally, frozen particles are administered that include one or more growth factor (e.g., keratinocyte growth factor, vascular endothelial growth factor A, epidermal growth factor, fibroblast growth factor, or hepatocyte growth factor) to promote engraftment. (See, for example, Nolte et al, Cells Tissue Organs, vol. 187, pp. 165-176 (2008); Boateng et al., J Pharm. Sci. vol. 97, pp. 2892-2923 (2008), each of which is incorporated herein by reference). In addition or instead of these growth factors, one or more frozen particles include one or more of collagen, hyaluronic acid, glycosaminoglycans, or other extracellular matrix components, at least one of which is encapsulated in a PCL polymer. (See, for example, Boateng et al., Ibid, which is incorporated herein by reference.)

In an embodiment, compartmentalized frozen particles including one or more of activated thrombin, fibrinogen, antibiotic (e.g., minocycline, gentamycin, oxoflacin, or tetracycline), or PCL-encapsulated extracellular matrix or growth factor are administered to a wound.

In an embodiment, one or more frozen particles include one or more cells (e.g., pluripotent stem cells, mesenchymal stem cells, fibroblasts, keratinocytes, dermal progenitor cells) to assist in wound repair, including skin engraftment. For example, dermal fibroblasts suspended in cryogenic media (e.g., containing 10% dimethylsulfoxide) are included in one or more frozen particles. In the same or different frozen particle, one or more of at least one growth factor, at least one extracellular matrix component, or at least one adhesive agent are included. Optionally, one or more of the agents included in the frozen particles are encapsulated by PCL or another polymer. The frozen particles can be administered simultaneously or sequentially.

In an embodiment, several different sets of frozen particles are administered in order to establish layers of, for example, extracellular matrix, fibroblasts, fibrin sealant, and keratinocytes can be administered in multiple layers with or without an additional skin graft. In an embodiment, the skin graft itself has been derived artificially or synthetically, at least in part, by administration of frozen particles including various skin components to at least one biological tissue or a synthetic matrix (e.g., biodegradable sponge or polymer matrix).

Optionally, as in the case of burns or other wounds in which necrotic tissue is present, frozen particles are administered to debride tissue prior to would closure or skin engraftment. Frozen particles including one or more of at least one antibiotic (e.g., neomycin, polymixin B, or gramicidin), or at least one anesthetic (e.g., lidocaine). As described herein at other sections, debridement of cells or tissue is regulated by several factors, including characteristics of the one or more frozen particles (e.g., size, shape, or constitution of any particular frozen particle), as well as characteristics of administration of the one or more frozen particles (e.g., velocity of delivery, angle of delivery, quantity of particles delivered, or rate of delivery).

In an embodiment in which tissue is debrided, a device is utilized to administer the one or more frozen particles, as described herein at other sections. In an embodiment, a tube and nozzle is utilized to administer the one or more frozen particles, with an optional aspirator tube to remove liquid and tissue as debridement occurs.

Example 21

Compositions and Methods of Administering Frozen Particles Including One or More Biological Remodeling Agents, One or More Therapeutic Agents, One or More Adhesive Agents, and One or More Reinforcement Agents for Tissue Reconstruction Frozen particle compositions including one or more of a reinforcement agent, antibiotic, therapeutic agent, polymer, adhesive, stem cell, or progenitor cell are utilized for debriding damaged or necrotic tissue, such as bone and cartilage. Subsequently, one or more frozen particle compositions as described are utilized for reconstructing the tissue, in addition to or instead of one or more frozen particle compositions including one or more of a growth factor, progenitor cell or stem cell.

For example, joint restructuring or replacement is a common surgical procedure for joints such as knee or hip joints. Knee replacement surgery is performed as a partial or total knee joint replacement. Standard knee replacement generally includes replacing or supplementing diseased or damaged joint surfaces with bone grafts (e.g., autologous or cadaveric bone grafts) or synthetic materials (e.g., metal, plastic, or rubber substrates).

Optionally, computer systems are used to model the bone defect, based on imaging studies (e.g., x-ray, computed tomography (CT), or other imaging). Among other things, imaging the bone or other tissue (e.g., cartilage), allows for assessment of the defect, or analysis of the present joint structure, allows for assistance in designing repair or replacement of the joint, and provides guidance for delivery of the frozen particle compositions. In certain instances, the frozen particle compositions are delivered by way of a piezoelectric or inkjet printer device that is directly or indirectly under the control of a computer system.

In an embodiment, a CT scan is used to develop a three-dimensional image of the joint to be reconstructed. For a knee joint, for example, regions from the distal femur and proximal tibia, including synovial and cartilage, can be imaged for assessment. Computer systems and methods for designing and repairing the joint(s) can also be used for comparing the present state of the subject's joint with that of a healthy individual. Thus, the repair may include reconstructing or restructuring the joint according to healthy or undamaged joints.

Optionally, a computer system also controls a robotic arm or other automated instrument containing a piezoelectric or inkjet printer device, or sprayer for administration of one or more frozen particle compositions in the reconstruction of the joint. In certain instances, the subject's damaged or diseased joint is ablated or debrided with one or more frozen particle compositions in addition to or instead of reconstructing the joint. In certain instances, one or more frozen particles are delivered to a substrate (e.g., natural, artificial, or synthetic materials) used in reconstructing the subject's knee joint. In certain instances, the substrate includes an artificial knee joint or a cadaveric knee joint.

In the case where the subject's joint is ablated or debrided, one or more frozen particle compositions are administered to the subject's joint (optionally with assistance of a computer system). The ablation or debridement may be performed before, during, or subsequent to the administration of one or more frozen particle compositions related to stabilizing the joint or reconstructing the joint. For example, frozen particle compositions including reinforcement agents (e.g., silica beads, fiberglass, polyethylene glycol) are propelled toward the subject's knee joint at or to a predetermined velocity that allows for delivery of the compositions into the various layers of the joint (i.e., skin, subcutaneous layers, synovial membrane, etc.).

In an embodiment, an arthroscopic device is utilized for delivery of one or more frozen particle compositions to the knee joint. A computer system can assist a surgeon in ablating or debriding the cartilage and/or bone to the proper depth by delivering the frozen particle compositions at a predetermined or preselected set of parameters. The predetermined or preselected parameters include, but are not limited to, size of frozen particle compositions, shape of frozen particle compositions, constitution of frozen particle compositions, velocity at which frozen particle compositions are delivered, angle at which frozen particle compositions are delivered, timing for delivery of specific frozen particle compositions, or programs for cycling any one or more parameters. In an embodiment, ablation is performed on a knee joint with guidance provided by a computer system or imaging apparatus. During or subsequent to ablation, frozen particle compositions containing therapeutic agents (such as at least one antibiotic or anti-inflammatory agent) are administered to the joint.

In an embodiment, the joint is reconstructed by utilizing a computer system for imagine or modeling the joint. Optionally, the computer system is directly or indirectly linked to a sprayer or piezoelectric or inkjet printer device capable of administering one or more frozen particle compositions. In certain instances, the frozen particle compositions administered to reconstruct the joint include scaffolding materials of natural, artificial, or synthetic origin (examples of specific agents include, but are not limited to, antibodies; growth factors; e.g., bone morphogenic protein; polymers; e.g., polylactic acid, polylactic acid-co-glycolic acid; or adhesives; e.g., polyethylmethacrylate/tetrahydrofurfuryl methacrylate, hydroxyapatite, etc.), or an amphiphilic polymer. In one embodiment, the delivery of one or more adhesive agents or at least one biological remodeling agents, includes at least one temporally-regulated method. (See, e.g., Davies, et al. Advanced Drug Delivery Reviews, vol. 60, pp. 373-387 (2008); or Kanczler et al. Biomaterials, vol. 29, pp. 1892-1900 (2008), each of which is incorporated herein by reference.)

In an embodiment, scaffolding materials solidify in situ at physiological temperature and pH, and may include, but not be limited to, calcium phosphate cement with a biocompatible gelling agent and scaffold materials for cartilage regeneration (e.g., oligopoly-ethylene glycol fumarate, polyN-isopropylacrylamideco-acrylic acid, polyN-isopropylacrylamide-grafted gelatin, polyethylene oxide, alginate, fibrin, PLGA-g-PEG, pluronics, calcium phosphate/hyaluronic acid composites, hyaluronic acid gel and chitosan. See, e.g., Hou et al., J. Mat. Chem. vol. 14, pp. 1915-1923 (2004), which is incorporated by reference herein.

Optionally, one or more frozen particle compositions including scaffolding materials that promote adhesion of cell types that produce bone or cartilage are administered to assist in reconstructing the subject's joint. For example, integrin peptides with the arginine-glycine-aspartic acid (RGD) sequence can be covalently coupled with other scaffolding materials administered to the joint. Integrins are capable of promoting adhesion of cells, including osteoblasts, via their integrin receptors. See, e.g., Hou, et al., Ibid.

Optionally, one or more frozen particle compositions including antibodies or antibody fragments are chemically coupled with scaffold polymers that among other things, promote binding and retention of specific cell types within the scaffold, are administered to the subject's knee or a substrate used in reconstructing the knee. For example, anti-integrin $\alpha_v\beta_3$ antibodies recognize endothelial cells, and anti-integrin $a_5$ antibodies recognize chondrocytes, both of which cell types can assist in reconstructing the joint. See, e.g., Hou et al, Ibid.

Optionally, one or more frozen particle compositions including one or more growth factors that are capable, for example, of promoting cell growth and/or cell differentiation are administered in reconstructing the knee joint. For example, bone morphogenic proteins, fibroblast growth factors, vascular endothelial growth factors, or other factors are encapsulated in polymer particles (e.g., vesicles) that form at least part of a scaffold to support reconstruction of the joint. See, e.g., Davies et al., Ibid. In an embodiment, one or more growth factors support the infiltration or growth of osteocytes, chondrocytes, or vascular cells.

In an embodiment, one or more frozen particle compositions including one or more of a progenitor cell, stem cell, osteoblast, chondrocyte, or endothelial cell are administered. In an embodiment, one or more subsets of frozen particle compositions include, but are not limited to compositions containing one or more of a scaffolding material, adhesive agent, or growth factor. In an embodiment, one or more subsets of frozen particle compositions are administered to the subject's joint simultaneously, sequentially, or cyclically.

In an embodiment, reconstruction of the joint is conducted by administering one or more subsets of frozen particle compositions through interaction or consultation with a computer system. In an embodiment, administration of one or more frozen particle compositions or one or more subsets of frozen particle compositions occurs in a stepwise fashion according to one or more parameters including, but not limited to, size of frozen particle compositions, shape of frozen particle compositions, constitution of frozen particle compositions, velocity at which frozen particle compositions are delivered, angle at which frozen particle compositions are delivered, timing for delivery of specific frozen particle compositions, or programs for cycling any one or more parameters.

In an embodiment, the joint is debrided, and the surface is prepared for reconstruction. Additionally, one or more frozen particle compositions or one or more subsets of frozen particle compositions are administered containing one or more of a scaffolding material, an adhesive agent, a therapeutic agent, a reinforcement agent, or an explosive agent. For example, calcium phosphate cement with a biocompatible gelling agent are included with one or more frozen particle compositions. In the same or different frozen particle compositions, growth factors (such as vascular endothelial growth factors or bone morphogenic factors) are included. In addition, in the same or different frozen particle compositions, osteoblast cells or osteoblast precursor cells are administered to the subject's joint or a substrate used for reconstructing the joint. In the same or different frozen particle compositions, at least one scaffold material, such as a polymer, is administered to the joint or a substrate used for reconstructing the joint. For example, oligopoly-ethylene glycol fumarate optionally with a chondrocyte growth factor (e.g., fibroblast growth factor) are included in one or more frozen particle compositions. In the same or different frozen particle compositions, frozen particle compositions including chondrocytes or condrocyte progenitor cells (e.g., mesenchymal stem cells) are administered to the joint.

In an embodiment, one or more steps of assessing the joint, preparing the joint, debriding or abrading the joint, or reconstructing the joint are aided by use of a computer system, including but not limited to CT imaging, computer-aided design (CAD), or computer-aided surgery (CAS). See, e.g., Bradley et al., Arch. Otolaryngol. Head Neck Surg. Vol. 34, pp. 1080-1084 (2008), which is incorporated by reference herein.

Example 22

Compositions and Methods of Administering Frozen Particles Including One or More Biological Adhesive Agents and One or More Biological Remodeling Agents Frozen particles containing one or more biological adhesive agents (for example, bispecific antibodies or bispecific proteins), are used to bind cells or tissues specifically to therapeutic targets, such as endothelial cells, leukocytes, epithelial cells, cancer cells, extracellular matrices, vasculature, lymphatics, tumors, and other tissues. For example, one or more frozen particles containing at least one bispecific receptor, antibody, ligand, or fusion proteins of one or more of receptors, antibodies, or ligands are used to selectively bind or adhere leukocytes, such as macrophages, monocytes, T cells, natural killer cells (NK cells), granulocytes, or other cells to target tissues, extracellular matrices, or other cell types (e.g., cancer cells, endothelial cells, or epithelial cells).

Moreover, one or more frozen particles optionally contain at least one biological adhesive agent and at least one leukocyte in separate sectors. In one embodiment, the sector includes a compartment.

In one embodiment, one or more biological adhesive agent is bound to a leukocyte (or other cell) in vitro prior to incorporation of the cell plus biological adhesive into the one or more frozen particle compositions. Optionally, one or more frozen particle compositions including at least one biological adhesive or at least one cell are delivered sequentially to a target tissue, matrix, or cell type.

Examples of one or more biological adhesive agents are disclosed herein at other sections, and include but are not limited to mammalian cell surface proteins, and glycoproteins. For example, adhesion molecules include CD44, immunoglobulin (Ig) superfamily members, integrins, cadherins, and selectins. These or other factors that are included in the disclosure specifically bind to protein or macromolecule ligands (e.g., intercellular adhesion molecule (ICAM), vascular cell adhesion molecule (VCAM), fibronectin, and hyaluronate), MADCAM, LFA-1, and others. Other cell surface receptors are included as biological adhesive agents, including but not limited to immunoglobulin Fc receptors (FcR), complement receptors (CR), and surface immunoglobulin (sIg).

Example 23

Compositions and Methods of Administering Frozen Particles Including One or More Biological Adhesive Agents for Administration to Tumor Tissue Frozen particles containing one or more biological-based adhesive agents are used to deliver and bind immune effector cells to primary or metastatic tumor cells, as well as tumor-associated stroma or extracellular matrices. Macrophages or monocytes that have the potential to kill tumor cells, and present tumor-associated antigens are recognized by antibodies that bind integrin receptors, such as VLA-4, $\beta$-1, $\beta$-2, F$c\gamma$ receptor I (CD64) or by cell adhesion peptides (e.g., YRGDS, YEILDV). (See, for example, Martin-Manso et al., Cancer Res., vol. 68, pp. 7090-7099 (2008); Wagner et al., Biomat., vol. 25, pp. 2247-2263 (2006); each of which is incorporated herein by reference). In addition, lymphocytes (such as T cells or B cells), as well as natural killer cells are capable of directed killing of tumor cells, and are included in specific embodiments disclosed herein.

Biological adhesive agents, including a bispecific antibody, such as anti-CD64 binding domain (e.g., single chain Fv (SCFv)) is fused to a second binding domain that recognizes a tumor-associated antigen (e.g., CA-125 (mucin 16), or melanoma-associated antigen (MAGE)). Mucin 16 binds macrophages to ovarian cancer cells, while MAGE binds macrophages to melanoma cancer cells. Generation, including design, construction, and production, of bispecific antibodies is generally known in the art. (See, for example, USPTO Application Publication No. 20080305105; Kufer et al., Trends in Biotech., vol. 22, pp. 238-244 (2004); each of which is incorporated herein by reference.)

Macrophage or monocyte cells are obtained from the peripheral blood of cancer patients or subjects. Monocytes are purified from peripheral blood leukocytes (standard reagents and protocols are available from, for example, Stem-Cell Tech., Inc., Vancouver, B.C., Canada). Monocytes are activated by treatment in vitro with cytokines, such as interferon-$\gamma$. (See, for example, Kufer et al., Ibid.) Production of macrophage cells that are cytotoxic for tumor cells is described, for example, in Martin-Manso et al., Ibid. Cytotoxic macrophage cells are bound in vitro to a bispecific antibody (e.g., antibody that recognizes CD64 or MAGE), prior to incorporation into one or more frozen particle compositions for administration to a melanoma tumor.

Briefly, bispecific antibodies at 10-100 micrograms/mL in RPMI 1640 media, pH 7.4 (Invitrogen Corp., Carlsbad, Calif.), are incubated with monocyte cells for 1-4 hours at 5°-37° C. Monocyte cells with bound bispecific antibodies are washed by centrifugation and incorporated into one or more frozen particle compositions containing dimethylsulfoxide (10% vol/vol), RPMI 1640 media, and human serum (20% vol/vol).

One or more frozen particle compositions containing one or more monocyte cells, one or more biological adhesive agents, and media are delivered directly to tumor tissue by a device (for example, a spray device). Depending on various factors, including but not limited to, size of tumor, presence of metastatic tumor tissue, extent of any metastatic tissue, type of tissue of origin for the tumor, location of tumor, condition of the subject, or other factors, the depth of frozen particle penetration can be predicted or determined through design or alteration of frozen particle composition velocity, size, shape, and constituency of the one or more frozen particles.

Example 24

Compositions and Methods of Administering Frozen Particles Including One or More Biological Adhesive Agents for Administration to Tumor Tissue Immune effector cells (including monocytes, macrophages, natural killer cells, or lymphocytes) plus bound bispecific antibodies are delivered to tumor tissue, for example, at a site or organ (e.g. lung, liver) using a device (such as an endoscope, incluindg a laparascope or thoracoscope). In one embodiment, a particle spraying device is introduced through a trocar and guided by way of an endoscope, delivers the frozen particle compositions including at least one immune effector cell with at least one biological adhesive to the target site. In one embodiment, the target site includes tumor tissue. In at least on embodiment, the target site includes tissue surrounding a tumor. In one embodiment, the target site includes tissue suspected of being cancerous. In one embodiment, the target site includes primary tumor tissue. In one embodiment, the target site includes metastatic cancer tissue.

In one embodiment, frozen particle compositions including at least one biological adhesive and at least one immune effector cell are administered as an adjunct therapy following surgery to resect diseased tissue, chemotherapy, radiation treatment, or other therapy. For example, frozen particle compositions including at least one biological adhesive that recognizes monocytes (e.g., anti-CD64) and MAGE are administered to tissue surrounding the surgical site, including lymph nodes or sites of suspected or anticipated metastasis.

Example 25

Compositions and Methods of Administering Frozen Particles Including One or More Biological Adhesive Agents to Melanoma Cells and Tumor-Associated Endothelial Cells At least one biological adhesive recognizing one or more integrin present on melanoma cells or tumor endothelial cells is used to bind immune effector cells to melanoma cells or tumor-associated endothelial cells. For example, one or more antibodies specific for the integrin $\alpha_v\beta_3$ and CD3 (a signaling part of the T cell antigen receptor) can be used in conjunction with cytotoxic T cells derived from melanoma subjects. See, for example, Berger et al., J. Clin. Invest. vol. 118, pp. 294-305 (2008), which is incorporated herein by reference.

One or more frozen particle compositions containing anti-$\alpha_v\beta_3$, anti-CD3, or cytotoxic T cells bind to melanoma cells directly or indirectly following binding to tumor neovasculature endothelium and extravasation. See, for example, Mahabeleshwar et al., Ibid. In one embodiment, the one or more frozen particle compositions are administered in multiple dimensions (e.g., x, y, z coordinates) to melanoma cells, neovasculature, and adjacent tissues (which may or may not be malignant). In one embodiment, primary tumor cells, metastatic tumor cells, neovasculature, and adjacent lymphatic ducts and lymph nodes are targeted. One or more frozen particle compositions delivered to the epidermis, dermis, and subcutaneous layers of a subject target melanoma cells in radial, vertical, and metastatic modes of growth. See, for example, Mahabeleshwar et al, Ibid.

In one embodiment, administration of the one or more frozen particle compositions in three dimensions is conducted with a computer-guided spraying device. The computer-guided device uses one or more computer systems, or one or more computer programs to derive or obtain data to predict or generate one or more frozen particle compositions based on specific characteristics. For example, the one or more frozen particle compositions are predicted or generated based on particle hardness, shape, size, constituency, or other factors. The one or more frozen particle composition administration is predicted or generated based on number of frozen particle compositions administered for any particular round of delivery, the velocity of delivery, the angle of delivery, the number of rounds of delivery of the same or different frozen particle compositions, the type of tissue receiving the frozen particle compositions, the condition of the tissue receiving the frozen particle compositions, and other factors. In this manner, the one or more frozen particle compositions are administered to a particular target tissue, and to a particular desired depth or breadth.

Example 26

Compositions and Methods of Administering Frozen Particles Including One or More Biological Adhesive Agents to Melanoma Cells One or more frozen particle compositions including one or more biological adhesive agents capable of specifically binding melanoma tumor cell surface receptors, including at least one receptor capable of signaling or initiating apoptosis are administered to melanoma cells. For example, at least one biological adhesive agent including at least one bispecific protein that recognizes melanoma tumor cell antigens (e.g., MAGE), as well as a pro-apoptotic cell surface receptor (e.g., death receptor 5 (DR5)) is delivered to melanoma cells for induction of apoptosis.

In one embodiment, binding of DR5 by an agonistic monoclonal antibody or apoptosis ligand 2/TNF-related apoptosis-inducing ligand (e.g., Apo2L/TRAIL) initiates signaling that leads to apoptotic death of the tumor cell. See, for example, Ashkenazi, Nat. Rev. Drug Discov., vol. 7, pp. 1001-1012 (2008). Some examples of agonistic antibodies that are capable of inducing apoptosis on tumor cells include, but are not limited to, mapatumumab and lexatumumab (Human Genome Sciences, Inc., Rockville, Md.; HGS), Apomab (Genentech Inc., South San Francisco, Calif.), AMG655 (Amgen, Inc., Thousand Oaks, Calif.), CS-1008 (Daiichi Sankyo Co., Ltd., Tokyo), and LBY-135 (Novartis Int'l AG, Basel).

In one embodiment, a bispecific protein including anti-MAGE binding domains (e.g., single chain Fv (SCFv)) and at least one agonistic anti-DR5 binding domain (e.g., SCFv from Apomab; Ashkenazi, Ibid) is administered in one or more frozen particle compositions directly to melanoma cells, or delivered to subcutaneous layers surround the melanoma cells.

In one embodiment, in addition to targeting primary tumor cells, tissue known to be metastatic, or suspected to be metastatic due to the epidemiology of the disease, are targeted. For example, melanoma is known to metastasize to the brain. In one embodiment, the brain receives one or more frozen particles alone or in combination with surgery (e.g., craniotomy), based on imaging studies done with computer-assisted tomography or magnetic resonance imaging. Frozen particle compositions including pro-apoptotic agonists or anti-MAGE binding proteins are used as adjuvant therapy following surgery (e.g., open surgery, stereotactic surgery, or stereotactic radiosurgery to remove or destroy melanoma metastatic cells.

In one embodiment, minimally invasive computer assisted surgery is used to remove tumor cells and tumor tissue, followed by administration of one or more frozen particle compositions as adjuvant therapy. For example, computer-aided surgery (CAS) is used with stereotactic surgery systems to target tumor cells that have infiltrated essential and/or highly vascularized brain tissues that are considered inaccessible or inoperable by standard methods.

Example 27

Frozen Piercing Implements Utilized for Transdermal Delivery

In one embodiment, frozen hydrogen oxide piercing implements, including microneedles, are utilized for transdermal delivery of at least one agent.

In one embodiment, frozen microneedles with dimensions ranging from approximately nanometers (nm) to approximately millimeters (mm) can be made from hydrogen oxide ice Ic, and optionally include one or more reinforcement agents. Frozen microneedles can contain at least one therapeutic agent, including but not limited to at least one antigen, vaccine, antibiotic, analgesic, or other agent. The use of microneedles has been reported to induce minor skin irritation. See, for example, Wermeling, et al., Ibid. Such minor irritation may be desirable in certain instances (i.e. for vaccination).

In one embodiment, microneedles made of frozen hydrogen oxide, and optionally reinforced with at least one of polylactic acid (L-PLA from BPI at Birmingham, Ala.) or polyvinyl pyrrolidone (PVP), are cast in a first micromold fabricated using standard photolithography and molding processes. For example, a frozen microneedle mastermold is created in SU-8 photoresist (SU-8 2025, Microchem, Newton, Mass.) by UV exposure to mold, for example, pyramidal (square cross-section) piercing implements tapering from a base measuring approximately 4 µm to approximately 300 µm in width to a tip of approximately 0.33 µm to approximately 25 µm in width over a length of approximately 10 µm to approximately 2.0 mm. Next a frozen piercing implement second mold is made, for example, from polydimethylsiloxane (PDMS, Sylgard 184, Dow Corning, Midland, Mich.) by using the first micromold. Multiple replicate molds can be produced by layering PDMS on the second mold. (See Lee et al, Biomaterials, vol. 29, pp. 2113-2124 (2008) which is incorporated herein by reference.) Finally, frozen piercing implements are made, for example, by contacting liquid hydrogen oxide optionally containing L-PLA and at least one therapeutic or other agent in the molds, and freezing at −20° C. to −250° C. to form frozen hydrogen oxide piercing implements, such as microneedles.

In one embodiment, the frozen hydrogen oxide piercing implements, such as microneedles, are in one or more phases including at least one of: amorphous solid water, low density amorphous ice, high density amorphous ice, very high density amorphous ice, clathrate ice, hyperquenched glassy water, ice Ic, ice II, ice III, ice IV, ice V, ice VI, ice VII, ice VIII, ice IX, ice X, ice XI, ice XII, ice XIII, ice XIV, or ice XV.

In one embodiment, multiple micromolds contain one or more arrays of multiple piercing implements, including one or more microneedles. For example, in one embodiment, an array containing 120 microneedles in rows is made in a 9×9 mm configuration. See, for example, Park et al, J. Control. Rel., vol. 104, pp. 51-66 (2005) which is incorporated herein by reference.

In one embodiment, frozen piercing implement arrays, including microneedle arrays, are made by contacting, for example, hydrogen oxide, one or more polymers, and at least one therapeutic agent. For example, frozen piercing implement arrays, including microneedle arrays, are made by utilizing at least one support structure fabricated by patterning SU-8 epoxy photoresist onto glass substrates and defining piercing implement shapes by lithography. In one embodiment, at least one frozen piercing implement includes at least one side-opening hollow implement. In one embodiment, piercing implement tips are sharpened by reactive ion etching. See, for example, Martanto et al, "Side-Opening Hollow Microneedles for Transdermal Drug Delivery," 32nd Annual Meeting of the Controlled Release Society, Florida, June, 2005 on the worldwide web at: mems.mirc.gatech.edu/msmawebsite_2006/publications/publication_list.html#c05, the content of which is incorporated herein by reference.

In one embodiment, hydrogen oxide frozen piercing implements, such as microneedles, include an optional reinforcement agent, such as L-PLA, as well as at least one therapeutic or other agent (including but not limited to bovine serum albumin (BSA) or lysozyme). For example, reinforced hydrogen oxide solutions with approximately 20% (weight %) bovine serum albumin (Sigma, St. Louis, Mo.) are frozen at approximately 0° C. to approximately −250° C. or lower in the micromolds to form at least one array of frozen piercing implements, such as microneedles.

In one embodiment, an array with 100 piercing implements, including microneedles, delivers about 2000 µg of BSA transdermally. See, for example, Lee et al, Ibid. In one embodiment, at least one piercing implement of the array includes a frozen piercing implement. In one embodiment, all of the piercing implements of the array include frozen piercing implements.

In one embodiment, frozen piercing implement arrays, such as microneedle arrays, including BSA are inserted by hand into the skin, then taped in place and left for time sufficient to deliver at least part of the at least one agent (e.g., BSA). In one embodiment, the array is allowed to stay in contact with the substrate for at least approximately 1 second, approximately 5 seconds, approximately 10 seconds, approximately 20 seconds, approximately 30 seconds, approximately 45 seconds, approximately 1 minute, approximately 2 minutes, approximately 5 minutes, approximately 10 minutes, approximately 30 minutes, approximately 1 hour, approximately 2 hours, approximately 5 hours, approximately 24 hours, or any value therebetween or greater.

In one embodiment, frozen piercing implements, such as microneedles, are inserted and ejected or released into the skin by at least one mechanism including, but not limited to, breaking, applying shear force, for example with a blade, or applying axial force, for example, with plungers or pressure through the base of the array.

In one embodiment, frozen piercing implements, including microneedles, in an array define at last one cavity including at least one therapeutic or other agent (e.g. a protein, nucleic acid, cell, viral vector, or pharmaceutical). In one embodiment, both the support structure and at least one frozen piercing implement, such as a microneedle, define at least one cavity including at least one therapeutic or other agent. In one embodiment, the support structure includes at least one reservoir in fluid communication with at least one frozen piercing implement, or other piercing implement of the array that includes at least one frozen piercing implement. In one embodiment, at least one frozen piercing implement is hollow and is in fluid communication with at least one external reservoir.

Cavitized or hollow frozen microneedles can be created by laser drilling holes extending the length of the microneedles projecting away from the support structure. See, for example, Martanto et al, Ibid.

In one embodiment, the one or more frozen piercing implements are utilized for delivery of at least one therapeutic agent or other agent, diagnostic or detection materials or devices, or sensing, or collecting one or more materials from the substrate (e.g. blood, interstitial fluid, one or more cells or biological materials). In one embodiment, at least one pump, syringe, or other material transfer device is included in the frozen piercing implement array. In one embodiment, a frozen piercing implement array, such as a microneedle array, includes a manifold for connection to a pump. See, for example, Martanto et al, Ibid.

In one embodiment, hollow frozen piercing implements, such as microneedles, are utilized to deliver at least one therapeutic or other agent in vivo. For example, McAllister et al, Proc. Natl. Acad. Sci. USA, vol. 100, pp. 13755-13760 (2003), which is incorporated herein by reference. As reported, hollow microneedles interfaced with a pump providing 10-14 pounds/square inch of pressure to deliver 32 µl of insulin solution (100 units/ml Humulin-R, Eli Lilly Co., Indianapolis, Ind.) to diabetic rats. As reported, microneedle delivery of insulin is effective, as indicated by the reduction in blood glucose levels in diabetic rats following treatment. Id. As reported, microneedle injection delivery of insulin is comparable in efficacy to subcutaneous injection of insulin with a conventional hypodermic syringe (McAllister et al, Ibid.).

Further, as reported, solid microneedles with tapered and beveled tips and feature sizes from 1 to 1,000 µm provide increased skin permeability by orders of magnitude for macromolecules and particles up to 50 nm in radius. Id.

In one embodiment, frozen hydrogen oxide microneedles are coated with at least one therapeutic or other agent configured for rapid release subsequent to piercing a substrate, such as skin. For example, frozen piercing implements, such as microneedles, and the corresponding arrays, are dip-coated by immersing them in stable aqueous solutions of at least one therapeutic, adhesive, biological remodeling, or other agent. For example, an agent such as sulforhodamine (Invitrogen-Molecular Probes, Eugene, Oreg.), FITC-labeled BSA ((Invitrogen-Molecular Probes, Eugene, Oreg.), YOYO-3-labeled plasmid DNA (Invitrogen-Molecular Probes, Eugene, Oreg.), sodium fluorescein (Sigma-Aldrich, St. Louis, Mo.), or pilocarpine hydrochloride (Sigma-Aldrich, St. Louis, Mo.) are dip-coated onto microneedles or other piercing implements. See, for example, Jiang et al, Invest. Opthal. Vis. Sci., vol. 48, pp. 4038-4043 (2007), which is incorporated herein by reference.

In one embodiment, aqueous coating solutions containing approximately 10% (wt/vol) polyvinylpyrrolidone (Sigma-Aldrich, St. Louis, Mo.) and one or more therapeutic agents at concentrations ranging from approximately 0.05% (wt/vol) to approximately 10% (wt/vol) are coated on one or more frozen piercing implements, such as microneedles. Id. As reported, microneedles coated with approximately 280 ng of fluorescein or approximately 1.1 µg of pilocarpine, with dimensions of approximately 500 µm in length, approximately 100 µm in width, and approximately 50 µm in thickness, are effective at delivering at least some of each agent to the eye. Id.

In one embodiment, the strength of one or more frozen piercing implements, such as microneedles, is measured by subjecting the one or more frozen piercing implements to an axial force (i.e. force parallel to the long dimension of the microneedle (e.g., approximately 600 µm) by using a displacement force test station (Model 921 A, Tricor Systems, Elgin, Ill.). For example, a stress versus strain curve is generated by measuring displacement while the test station presses an array of microneedles or other piercing implements against a rigid metal surface at a rate of approximately 1.1 mm/sec.

As shown in FIG. 122, strength of microneedle or other piercing implements is indicated by a sudden drop in force at the point of failure. See, for example, Park et al., Ibid. The maximum force just prior to the sudden drop defines the force of the piercing implement failure. Piercing implements, including microneedles, with failure forces greater than the force required for penetration of the stratus corneum are suitable for transdermal delivery. According to published studies, microneedles containing polylactic acid with a height of approximately 800 µm and a base diameter of approximately 200 µm display a failure force of approximately 0.50 Newtons/needle, which is approximately three times greater than the force needed for insertion into skin. See, for example, Park et al, J. Contr. Rel., vol. 104, pp. 51-66 (2005), which is incorporated herein by reference.

In one embodiment, experimental data and theoretical models are utilized to predict the failure force, or fracture force, of piercing implements, including microneedles, which depends in part on the implement geometry. See, for example, Davis et al, J. Biomech., vol. 37, pp. 1155-1163 (2004) which is incorporated herein by reference. For example, experiments to measure microneedle fracture force can be done using an axial load test station (Scope Test 1, EnduraTEC, Minnetonka, Minn.) to drive microneedles against a flat block of aluminum at a rate of approximately 0.01 mm/sec until a preset displacement of approximately 500 µm is reached. Id. Based on this test, force and displacement data are used to determine the fracture force. Id.

For example, microneedles or other piercing implements approximately 500 µm in length with: 1) variable tip radii and constant wall thickness of approximately 12 µm, and wall angle of 78.5°; or 2) variable wall thickness and constant tip radius of approximately 43 µm and wall angle of 78.5°; or 3) variable wall angle and constant tip radius of approximately 30 µm and wall thickness of approximately 10 µm can be used to measure fracture force variation with piercing implement geometry. Id. As reported, the fracture force does not necessarily depend on microneedle tip radius, but tends to increase with increasing wall thickness and wall angle. Id. The geometry of any particular piercing implement can be imaged by scanning electron microscopy, for example, in order to determine at least the base radius, tip radius, and wall thickness. Id. The interfacial area (i.e. the effective area of contact between the needle and the skin) can be calculated in at least two ways: (i) annular surface area, Aa, of the piercing implement tip can be represented as $Aa=\pi(r_t t - t^2/4)$ where $r_t$=outer tip radius, and t=wall thickness, or (ii) the full cross-sectional area, Af, at the needle tip $Af=\pi r_t^2$, while needle wall angle $\alpha$, can be calculated as $\alpha=\tan^{-1}[(r_b-r_t)/h]$, where $r_t$=outer tip radius, $r_b$=outer radius at the needle base, t is the wall thickness, and h is the height. Id.

Moreover, analytical models or finite element models can be developed using standard techniques, and are capable of predicting the fracture force of a microneedle, or other piercing implement, with a given geometry. Id. As reported, both systems predict an increase in fracture force with increase in wall thickness or wall angle. Id. Accordingly, analytic or finite element models can be developed for a particular frozen piercing implement, including a microneedle, in such a way that the fracture force exceeds the force required for administration to at least one substrate.

In one embodiment, the penetration of dermal layers or the location of delivery of at least one agent is visualized by using fluorescent molecules as tracers, followed by fluorescence microscopy and bright field microscopy. For example, according to published studies, delivery of sulforhodamine B (Molecular Probes, Eugene, Oreg.) with microneedle arrays into pig cadaver skin is assessed qualitatively by histological analysis, which includes fluorescence microscopy, to establish the distribution of sulforhodamine in the epidermis and dermis. See, for example, Lee et al., Ibid.

In one embodiment, epidermis from cadaver skin sections are placed in a diffusion chamber (Permegear, Hellertown, Pa.) and the amount of sulforhodamine passing through the epidermis following delivery with microneedle arrays is measured by spectrofluorimetry (Lee et al, Ibid.). For example, in vivo delivery of agents, such as therapeutic agents, adhesive agents, biological remodeling agents, reinforcement agents, or other agents, by microneedle arrays can be measured by evaluating local concentrations of the agent, or plasma concentrations of the agent, i.e. pharmacokinetic analysis.

In one embodiment, at least one agent is administered as a component of the frozen piercing implement (or array). In one embodiment, at least one agent is administered in conjunction with the frozen piercing implement (or array), including sequentially, serially, continuously, or other mode.

For example, delivery of naltrexone by a frozen piercing implement array, such as a microneedle array, can be monitored by analyzing plasma samples obtained at various time points following administration. In one embodiment, plasma naltrexone concentrations are determined by an assay, for example, employing high pressure liquid chromatography and mass spectrometry.

For example, pharmacokinetic parameters for naltrexone (NTX) (and its primary metabolite naltrexol (NTXOL)), following permeation with a microneedle array and NTX delivery with a transdermal patch are shown in Table C, adapted from Wermeling et al, Proc. Natl. Acad. Sci. USA, vol. 105, pp. 2058-2063 (2008), which is incorporated herein by reference. For example, pharmacokinetic analysis includes calculation of particlar values, such as the steady state concentration (Css), the area under the curve (AUC), and the time to reach steady state concentration (Tlag), some of which can be done with computer programs. See, for example, WinNonlin Professional, version 4.0; Pharsight, the subject matter of which is incorporated herein by reference.

Additionally, the pharmacokinetic parameters obtained following microneedle-enhanced transdermal delivery of NTX are comparable to the pharmacokinetics obtained following oral administration of NTX. See, for example, Wermeling et al, Ibid.

TABLE C

NTX and NTXOL exposure after microneedle-enhanced transdermal delivery

| Parameters | NTX | NTXOL |
|---|---|---|
| Css, ng/ml | 2.5 (1.0) | 0.6 (0.5) |
| Tlag, h | 1.8 (1.1) | 1.4 (1.4) |
| Cmax, ng/ml | 4.5 (2.4) | 1.9 (1.3) |
| Tmax, h | 8.8 (7.6) | 37.5 (31.3) |

TABLE C-continued

NTX and NTXOL exposure after microneedle-enhanced transdermal delivery

| Parameters | NTX | NTXOL |
|---|---|---|
| AUC, ng h/ml | 142.9 (43.9) | 39.7 (25.9) |
| Clast, ng/ml | 1.8 (1.0) | 0.4 (0.6) |

Results are expressed as means ± SD (in parentheses) for six MN-treated subjects. $C_{ss}$ = concentration at steady-state condition; $T_{lag}$ = time to reach steady-state condition; $C_{max}$ = maximum concentration achieved; $T_{max}$ = time to achieve maximum concentration; $AUC_{0-t}$ = area under the concentration-time curve from time 0 to 72 h; $C_{last}$ = concentration at time of patch removal after 72 h of application.

As reported, pretreatment with microneedle arrays, removal of the microneedles, and application of transdermal patches containing NTX results in efficient delivery of NTX and achievement of pharmacologically active blood concentrations of NTX (2.5 ng/ml) within two hours after applying the patch. Id. The Css is maintained for 48 hours. Id. Without microneedle pretreatment NTX is not detected in the plasma following application of transdermal patches. Id. Furthermore pretreatment of cadaver epidermis samples with microneedle arrays followed by application of test drugs such as calcein (Sigma Chemical Co., St. Louis, Mo.), or fluorescent BSA (Texas Red conjugated-BSA, Molecular Probes, Eugene, Oreg.) increases the skin permeability by more than 100-fold relative to untreated epidermis. See, for example, Park et al, Ibid.

In one embodiment, frozen piercing implement arrays, or microneedle arrays, are fabricated to include a support structure that acts as a reservoir for sustained agent release. For example, sustained release of at least one agent can occur even after removal, sublimation, or melting of the frozen piercing implements, and be delivered via microchannels created by the piercing implement administration. For example, as published in Lee et al, Ibid., an array of microneedles has a support structure that contains a test drug, such as sulforhodamine. In one embodiment, the frozen piercing implements, such as microneedles, include sulforhodamine and an optional reinforcement agent, such as PLA. In one embodiment, the base of the piercing implement contains frozen sulforhodamine, buffers and water. Accordingly, frozen piercing implements can be made that include channels, cavities, layers or other areas.

In one embodiment, the tip of the frozen piercing implement includes at least one constituent in common with the base of the implement. In one embodiment, the tip of the frozen piercing implement is different than the base of the implement. In one embodiment, the support structure of the microarray is also frozen. In one embodiment, the frozen piercing implement includes at least one component that is not frozen. In one embodiment, the frozen piercing implement array includes at least one implement that is not frozen. In one embodiment, the frozen piercing implement array includes at least one implement that is frozen.

In one embodiment, a large surface area is utilized for the base of the piercing implement. For example, a piercing implement with a base of approximately 81 mm$^2$ and approximately 300 μm thick, can accomodate milligram quantities of drug. See, for example, Lee et al., Ibid. A relatively small piercing implement array, such as a microneedle array, (for example, 7×7 implements) with a base composed of approximately 30% (wt %) solution of sulforhodamine contains approximately 3 mg of sulforhodamine. Administration of a piercing implement array with amylopectin needles and base, and containing sulforhodamine, results in sustained delivery of sulforhodamine across the epidermis for about 12 hours. See, for example, Lee et al, Ibid.

Example 28

Frozen Piercing Implements Utilized for Transdermal Delivery

In one embodiment, frozen piercing implements, such as microneedles, include at least one non-aqueous constituent, including but not limited to dimethyl sulfoxide, ethanol, isopropanol, dimethyl formamide, or formaldehyde, as well as at least one therapeutic agent. For example, using the methods described in Lee et al, Ibid. micromolds can be constructed to allow casting arrays of piercing implements derived from solutions or suspensions of at least one agent in a non-aqueous solvent. For example, in one embodiment, a therapeutic agent, such as a small molecule (e.g. sulforhodamine (Molecular Probes, Eugene, Oreg.)), a protein (e.g. bovine serum albumin (BSA) conjugated to Texas Red (Molecular Probes, Eugene, Oreg.)), a nucleic acid (e.g. gWiz™ luciferase plasmid DNA (6732 base pairs, Aldevron, Fargo, N.Dak., USA)), a viral particle (e.g. modified vaccinia virus—Ankara (Emory University Vaccine Center, Atlanta, Ga., USA)) is suspended or dissolved in dimethyl sulfoxide (DMSO) (freezing temperature is approximately 18.5° C. See, for example, Gill et al, J. Control. Release, vol. 117, pp. 227-237 (2007), which is incorporated herein by reference herein. In one embodiment, the suspension or solution is cast in a piercing implement array mold by using centrifugation. See, for example, Lee et al, Ibid. In one embodiment, the piercing implements are frozen prior to, during, or subsequent to centrifugation. Optionally, multiple layers can be fabricated in the frozen piercing implements by repeating the process of centrifuging/freezing and layering, then centrifuging/freezing again.

In one embodiment, frozen piercing implement arrays, such as microneedle arrays, with at least one frozen piercing implement including, for example, DMSO and at least one agent, optionally includes at least one reinforcement agent (e.g., a polymer, ceramic particle (e.g. silica, alumina, hydroxyapatite), metal or fiber) to increase the fracture strength of the frozen piercing implements.

One example of a freezing method for a composite piercing implement with increased fracture strength is described in Deville et al, Science, vol. 311, pp. 515-518 (2006), which is incorporated herein by reference. In one embodiment, frozen piercing implements, including frozen microneedles, wherein at least one frozen piercing implement includes DMSO, at least one reinforcement agent, such as PLA, and at least one therapeutic agent, such as BSA. In one embodiment, DMSO assists to disrupt the lipid bilayer of the stratum corneum. Id. In one embodiment, other solvents or chemical enhancers of skin permeability are utilized to increase efficiency of administration of the at least one agent. See, for example, Prausnitz et al, Nature Biotech., vol. 26, pp. 1261-1268 (2008), which is incorporated herein by reference.

In one embodiment, frozen piercing implements, such as frozen microneedles, include at least one frozen piercing implement including DMSO, are utilized for delivery of viable mammalian cells, with DMSO providing a cryoprotectant. For example, other cryopreservatives for mammalian cells are available from Sigma-Aldrich, St. Louis, Mo.

In one embodiment, frozen piercing implement arrays, or frozen microneedle arrays, including at least one frozen piercing implement that includes DMSO, is used for localized subcutaneous or intradermal delivery of cytotoxic T cells to skin tumors for treatment of metastatic melanoma or other skin disorders. See, for example, Morgan et al, Science vol. 314, pp. 126-130 (2006), which is incorporated herein by reference.

In one embodiment, frozen piercing implements, including frozen microneedles, optionally include at least one abrasive or explosive material. In one embodiment, the at least one abrasive or explosive material provides additional capability for debriding bone or other tissue, or abrading or ablating skin or other tissue. In one embodiment, the at least one abrasive or explosive material promotes transdermal delivery of at least one agent. For example, frozen piercing implement arrays, such as frozen microneedle arrays, include at least one frozen piercing implement including carbon dioxide ($CO_2$). In one embodiment, liquid $CO_2$ can be cast in microneedle molds maintained at approximately −100° C., the freezing temperature of $CO_2$.

Some non-limiting examples of methods for measuring the insertion force of microneedle arrays into human skin are described by Davis et al, Ibid. In one embodiment, frozen piercing implements including $CO_2$ sublimate upon administration to the at least one substrate. In one embodiment, the at least one substrate includes skin.

In one embodiment, transdermal patches, including at least one agent, is administered in conjunction with the frozen piercing implement array, including the frozen microneedle array. In one embodiment, pores or microchannels are created by frozen piercing implements, which is amplified, for example, if the frozen piercing implement includes at least one explosive material, such as carbon dioxide. For example, the rapid sublimation of carbon dioxide during administration of the frozen piercing implement array results in a small "explosion" near the at least one substrate to which the frozen piercing implement array is administered, which can assist in delivery of at least one agent. For example, as reported, transdermal delivery of naltrexone (a skin-impermeant hydrophilic molecule) by transdermal patch remains undetected, unless administered following administration of microneedles, when pharmacologically active steady state levels of naltrexone are detected. See, for example, Wermeling et al, Ibid.

Example 29

Frozen Piercing Implements, Including Surgical Blades, Blade Handles, and Scalpels In one embodiment, at least one of a macroneedle (e.g., hypodermic needle), surgical blade, blade handle, scalpel, scalpel blade, or other frozen cutting instrument (including detachable blade and/or detachable blade handle) is fashioned by utilizing at least one frozen composition (e.g., sterile hydrogen oxide, a frozen solution including at least one fluid and at least one agent, at least one frozen gas, or other frozen composition). In one embodiment, the at least one fluid composition is frozen according to methods described herein. In one embodiment, at least one cutting instrument changes shape as it is used with at least one substrate. In one embodiment, at least one cutting instrument deposits at least one agent (such as a therapeutic agent, biological remoding agent, adhesive agent, abrasive, explosive material, or reinforcement agent) as it is used with at least one substrate.

In one embodiment, the frozen composition includes sterile hydrogen oxide including at least one agent, and is frozen at approximately −196° C., then raised to a temperature of approximately −93° C. to favor formation of ice Ic. See, for example, Halbrucker et al, Ibid. In one embodiment, macroneedles, surgical blades, or scalpels made from at least one frozen composition, includes at least one reinforcement agents to increase hardness and fracture strength. For example, glass fibers, silica beads, alumina, calcium phosphate and calcium carbonate can be added to hydrogen oxide to increase the hardness, modulus of rupture and fracture force of frozen hydrogen oxide. See, for example, Kingery et al, Ibid.; Kamrani et al, Ibid.; and Delville et al, Science vol. 311, pp. 515-518 (2006), each of which is incorporated herein by reference. In one embodiment, frozen cutting instruments are coated with or include at least one therapeutic agent. In one embodiment, the at least one therapeutic agent is released into the substrate during use of the frozen cutting instrument. In one embodiment, the substrate includes a surgical site.

For example, in one embodiment, the frozen cutting instrument is utilized in a procedure to transplant skin on burn patients. In one embodiment, frozen surgical blades, or other frozen cutting instruments, are coated with or otherwise include at least one antibiotic. Some non-limiting examples include neomycin, polymixin B, or gramicidin. In one embodiment, at least one other agent, such as an adhesive agent or biological remodeling agent, is included in the frozen cutting instrument. In one embodiment, the at least one other agent includes at least one biological remodeling agent, such as a growth factor, (e.g. keratinocyte growth factor, vascular endothelial growth factor A, epidermal growth factor, fibroblast growth factors and hepatocyte growth factor) to promote the growth, vascularization or engraftment of skin grafts, or avoid scarring or contraction of the graft(s). See, for example, Nolte et al, Cells Tissue Organs, vol. 187, pp. 165-176 (2008); and Colwell et al, Plast. Reconstr. Surg., vol. 115, pp. 204-212 (2005), each of which is incorporated herein by reference. Non-limiting examples of methods for coating frozen cutting instruments are reported in Jiang et al, Ibid.

In one embodiment, frozen surgical blades are made in lengths ranging from approximately 1-10 mm to approximately 10-50 mm. In one embodiment, the frozen surgical blades have at least one surgical knife handle that includes at least one frozen composition, such as hydrogen oxide, and an optional reinforcement agent, such as metal filings or polymer fibers approximately 5 cm to 13 cm long. Methods for casting handles of surgical knives using two part molds are described in U.S. Pat. No. 4,846,250, which is incorporated herein by reference.

In one embodiment, frozen surgical blades, or other frozen cutting instruments, are made such that they terminate in at least one of a point, rounded tip, jagged edge, serated edge, or other configuration. In one embodiment, at least part of the length of the entire cutting instrument includes a jagged or serated edge. In one embodiment, at least one configuration includes one or more of a single sharp edge, multiple sharp edges, or a continuous sharp edge. In one embodiment, the frozen cutting instrument, such as a frozen blade, includes at least one of a beveled edge, symmetric or asymmetric double beveled edges, or curvilinear cutting edges. In one embodiment, a smaller cutting edge radius is utilized, and forms a sharper instrument.

In one embodiment, at least one abrasive or explosive material is utilized in forming at least one surface of the cutting instrument, in order to fabricate a rough surface.

In one embodiment, a surgical blade is made with cutting edge radii that are approximately 5 nm to approximately 1000 nm. See, for example, U.S. Pat. No. 6,386,952, which is incorporated herein by reference. In one embodiment, the edges of a frozen cutting instrument is sharpened by, for example, grinding, mechanical abrasion, or lapping. Id. For example, various blade or other cutting instrument profiles can be made, including but not limited to single edge chisel, three edge chisel, slit, two edges sharp, four edges sharp, stab, one edge sharp, keratome, one edge sharp or crescent, curvilinear sharp edge, as well as others. See, for example, U.S. Pat. No. 7,396,484, which is incorporated herein by reference.

In one embodiment, frozen surgical blades or other cutting instruments are made for specific purposes, such as opthalmic surgery, arthroscopic, endoscopic, laparoscopic, diagnostic, orthopedic, or plastic surgeries. See, for example, U.S. Pat. No. 6,547,802, which is incorporated herein by reference.

In one embodiment, frozen cutting instruments, such as frozen surgical blades, are manufactured using methods that include at least one of: machining trenches (or V-grooves) in wafers or slabs of frozen compositions, or etching the trenches to produce sharp cutting edges. For example, a frozen composition slab or section can be secured on a mounting assembly and one or more trenches (e.g. V-groove) can be machined with a router to create a groove with any desired angle.

In one embodiment, trenches are made, for example, with a dicing saw blade, laser system, ultrasonic machining tool, or a hot forging process. See, for example, U.S. Pat. No. 7,396,484, Ibid. In one embodiment, the machined frozen slab is etched with a laser etching system to sublimate away layers of molecules from the V-groove and to create a sharp cutting edge of uniform radius.

In one embodiment, etching is done with a laser etching system that includes at least one of: a laser for producing a laser beam (e.g. $CO_2$ laser and an Er:YAG laser); a laser aiming system adapted to aim and direct a laser beam onto the frozen slabs (optionally including a lens to focus the laser beam and mirrors coupled to drive devices such as servo-galvanometers); and has an optional controller operatively coupled to the laser and laser aiming system. See, for example, U.S. Patent Appl. Publ. No. 20080290065, which is incorporated herein by reference. In one embodiment, the system includes a user interface such as a USB port, a wireless network device, a CD-ROM drive or any combination thereof, which is optionally coupled to the controller and allows input of programmed designs or lines for etching the frozen composition slabs. Id.

In one embodiment, one or more fluids are allowed to flow over a cooled (including super cooled) surface (such as a metal plate), where the fluid freezes. Prior to, during, or subsequent to such freezing, the frozen composition can be etched, for example, with a laser. As an optional next step, at least one agent or other composition is allowed to flow over the frozen etched composition (which may be in the form of frozen piercing implements, for example), and optionally, the frozen composition is etched again.

In one embodiment, one or more frozen surgical blades are made by casting hydrogen oxide, or another fluid composition, optionally with one or more reinforcements or one or more therapeutic agents in a mold. As discussed herein at other sections, molds for casting surgical blades are made by standard techniques, such as for example, photolithography or molding processes. For example, a first surgical blade mastermold is created in SU-8 photoresist (SU-8 2025, Microchem, Newton, Mass.) by UV exposure to create a surgical blade with a sharp point and single cutting edge. In one embodiment, sharp point surgical blades are formed with approximately 10 mm to approximately 50 mm in length and approximately 4.65 mm to approximately 7.65 mm in width. See, for example, U.S. Pat. No. 7,396,484, Ibid. and the worldwide web at ribbil.com/fitting-dimensions.html, the content of each of which is incorporated herein by reference.

In one embodiment, a second surgical blade master-structure is made, for example, of polydimethylsiloxane (PDMS, Sylgard 184, Dow Corning, Midland, Mich.) by using the first mastermold. Additionally, multiple replicate molds are produced, for example, by layering PDMS on the second master-structure. See, for example, Lee et al, Biomaterials, vol. 29, pp. 2113-2124 (2008) which is incorporated herein by reference. Finally, in one embodiment, fluid hydrogen oxide, or another fluid composition, including at least one reinforcement agent, such as silica, and including at least one therapeutic agent, such as neomycin, is added to the molds and frozen to create frozen piercing implements, such as frozen surgical blades. In one embodiment, the cutting edge of the frozen surgical blade can be sharpened by etching or by grinding to form small edge radii, including approximately 5 nm to approximately 1000 nm. See, for example, U.S. Patent Appl. Publ. No. 20080290065, Ibid.; U.S. Pat. No. 6,386,952, Ibid.; and U.S. Pat. No. 7,396,484, Ibid., each of which is incorporated herein by reference.

In one embodiment, frozen surgical blades are die-cut, coined or imprinted from slabs or sections of frozen hydrogen oxide, or other frozen composition. For example, in one embodiment, surgical blades are stamped from frozen hydrogen oxide, or other frozen composition, by utilizing dies or stamping devices configured to apply sufficient pressure to impress a negative image of the die into the frozen composition. Some non-limiting examples of imprinting methods are described, for example, in U.S. Pat. No. 7,105,103, which is incorporated herein by reference. Frozen surgical blades manufactured by die-cutting or imprinting can be sharpened using grinding, lapping, or etching. See, for example, U.S. Patent Appl. Pub. No. 20080290065, Ibid.; U.S. Pat. No. 6,386,952, Ibid.; and U.S. Pat. No. 7,396,484, Ibid., each of which is incorporated herein by reference.

In one embodiment, the frozen cutting instrument (such as a blade) is sharpened, for example, by using cylindrical abrasive wheels interlocked to form a nip. In one embodiment, the cutting instrument is sharpened, for example, by utilizing grinding assemblies mounted for rotation about parallel axes. See, for example, U.S. Pat. No. 6,386,952, Ibid.

Example 30A

Method of Making Frozen Particle Compositions or Frozen Piercing Implements

Frozen particle compositions, including at least one frozen or deposited fluid, are produced from small droplets in a nonlinear channel including at least one super hydrophobic surface. For example, at least one fluid is sprayed as droplets, a mist, etc. into a nonlinear channel maintained at low temperature (e.g., approximately −100° C.), or high pressure (e.g., approximately 2000 bar). For example, at 2100 bar, hydrogen oxide is 1500 times more viscous than at atmospheric pressure, which reduces the nucleation and crystal growth rate. See, for example, product guide for HPM 010 High Pressure Freezing Machine, available at the worldwide web at: rmcproducts.com, the subject matter of which is incorporated herein by reference. Droplet size is regulated by varying nozzle or aperature size, and pressure. Fluid droplet diameters range, for example, from nanometers to centimeters. In one embodiment, the fluid droplets freeze or deposit along the nonlinear channel, forming frozen particle compositions.

In one embodiment, the frozen fluid particle compositions are translocated to at least one compartment that contains at least one cooling fluid with a triple point lower than the triple point of the frozen fluid particle compositions, such that the frozen fluid compositions are retained in solid form. In one embodiment, the fluid droplets are translocated along the nonlinear channel, where at least one other fluid or at least one agent is added by way of at least one inlet. In one embodiment, the fluid compositions are translocated to at least one compartment, wherein they combine to form frozen particle compositions.

In one embodiment, the fluid compositions are cycled through multiple stages of freezing or deposition, in order to layer multiple fluids or agents, or in order to attain a particular state (e.g., crystalline state). In one embodiment, fluid compositions are subjected to conditions in the nonlinear channel that favor crystalline states, thereby forming at least one frozen piercing implement.

In one embodiment, the cooling fluid includes at least one refrigerant or cryogenic fluid. In one embodiment, the cooling fluid includes at least one fluid included in the frozen particle composition or frozen piercing implement.

Example 30B

Method of Propelling or Administering Frozen Particle Compositions or Frozen Piercing Implements At least one frozen particle composition or frozen piercing implement is received or retained in at least one compartment containing one or more cooling fluids. In one embodiment, the at least one frozen particle composition or frozen piercing implement is formed prior to being received in the at least one compartment. In one embodiment, the at least one frozen particle composition or frozen piercing implement is formed by way of extrudation, embossing, cutting, splintering, etching, molding, electrospinning, electrospraying, gel-casting, spin-casting, or other method, and subsequently translocated to at least one compartment.

In one embodiment, the at least one frozen particle composition or frozen piercing implement is formed while residing in the at least one compartment.

In one embodiment, the cooling fluid includes at least one refrigerant or cryogenic fluid. In one embodiment, the cooling fluid includes at least one fluid included in the frozen particle composition or frozen piercing implement.

In one embodiment, the cooling fluid includes at least one cooling liquid. In one embodiment, the frozen particle compositions or frozen piercing implements are propelled out of the compartment (e.g., by way of at least one outlet) by inducing at least one explosion in the cooling fluid. In one embodiment, the explosion includes flash-boiling the at least one cooling liquid. In one embodiment, the explosion includes a boiling liquid expanding vapor explosion (BLEVE) of the at least one cooling liquid.

The BLEVE of the cooling liquid can be calculated according to standard techniques. For example, in FIG. 119, a diagram of the relationship between the pressure for a substance in various phases of liquid and gas, and the volume occupied by that substance. See, for example, the worldwide web at: criticalprocesses.com/BLEVE.htm, the subject matter of which is incorporated herein by reference. The line from point A to B indicates the substance is in liquid form and as the volume the substance occupies expands, the pressure falls until it reaches the vapor pressure of the liquid (B) for a particular temperature. Id. The liquid then evaporates to become a liquid-gas mixture, and the pressure stays constant at the vapor pressure. Eventually the substance reaches point C, where the liquid has been converted to gas phase, and the pressure drops with further expansion. Id.

If the pressure falls suddenly, the substance can become unstable liquid along the line from point B to point S. Id. S is known as a spinodal point, and the slope of the line at this point is zero (i.e. $(\partial p/\partial V)_T=0$). Id. The dotted line connects spinodal points at different temperatures, forming the spinodal curve, and ending at the critical point. Id. During a BLEVE, density variations develop spontaneously and homogenously into liquid and gas regions. Id. The rise in pressure on the vapor pressure line from point B to C occurs rapidly, and a BLEVE results. Id.

As illustrated in FIG. 120, for carbon dioxide, conditions for inducing a BLEVE can be calculated for a particular substance since the entropy of the system remains constant. Id. Thus, conditions that induce a BLEVE for any particular substance are found along the spinodal curve for that substance, between 1 bar and the critical point where the curve ends. Id.

In one embodiment, the cooling fluid is flash boiled. In one embodiment, the cooling fluid is a liquid. As with all liquids, vapor pressure increases with temperature approximately exponentially. For example, the boiling point of nitrogen at 1 bar is approximately 77 K (−196° C.), whereas the boiling point of nitrogen at 10 bar is approximately 103.8 K (−169.2° C.). Accordingly, pressure can be used to control reaction temperature, and controlling pressure above a cryogenic bath, for example, via regulators and pumps can maintain accurate temperature control. See, for example, Downie, Industrial Gases, pp. 445-446, Blackie Academic and Prof. (1996).

In one embodiment, the size of the outlet assists in dispersion by altering spray cone angles, altering particle size, altering depressurization rates, and altering mass flow rates. See, for example, Nutter, J. Energy Res. Technol. vol. 119, no. 3 (1997), which is incorporated herein by reference.

In one embodiment, the frozen particle compositions or frozen piercing implements are directionally propelled for administration to at least one substrate. For example, a handheld device, or a hose and nozzle system can be used, with or without a carrier gas, (e.g., air or nitrogen) under pressure, to administer the frozen particle compositions or frozen piercing implements to at least one substrate.

In one embodiment, the substrate includes at least one cell, tissue, organ, structure, or device. In one embodiment, the substrate includes at least one food product (e.g., fruit juice, cereals, grains, sugar, soda, meat, vegetables, canned goods, baked goods, fruits, etc.). In one embodiment, the substrate includes at least part of a subject.

While particular aspects of the present subject matter described herein have been shown and described, it will be apparent to those skilled in the art that, based upon the teachings herein, changes and modifications can be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., " a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations can be performed in other orders than those which are illustrated, or can be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

All publications and patent applications cited in this specification are incorporated herein by reference to the extent not inconsistent with the description herein and for all purposes as if each individual publication or patent application were specifically and individually indicated to be incorporated by reference for all purposes.

What is claimed is:

1. A frozen piercing implement array, comprising:
a support structure having a surface; a plurality of frozen piercing implements extending substantially outward from the surface of the support structure, each frozen piercing implement including at least one sterile frozen solvent and at least one therapeutic agent including one or more of a vitamin, mineral, antioxidant, antibiotic, antifungal, preservative, antiviral, or anti-worming agent, frozen in an elongated piercing implement form of a high aspect shape having a ratio of greater than or approximately equal to 1.5;
and at least one reinforcement agent including one or more of vinyon, saran, spandex, vinalon, aromatic nylon, vinylidene chloride, modal, polybenzimidazole, lyocell, orlon, zylon, high-performance polyethylene, polypyridobenzimidazole, vectran, acrylonitrile rubber, alluvium, calcite, emery, diamond, novaculite, pumice, rouge, borazon, corundum, zirconia, or alumina
wherein each of the plurality of frozen piercing implements is approximately 250 microns or smaller in length; and
wherein the plurality of frozen piercing implements is configured for piercing at least one biological tissue.

2. The frozen piercing implement array of claim 1, wherein the plurality of frozen piercing implements is configured for delivering the at least one agent to the at least one biological tissue.

3. The frozen piercing implement array of claim 1, wherein the at least one agent includes at least one of a nontoxic, biocompatible, bioresorbable, or biodegradable agent.

4. The frozen piercing implement array of claim 1, wherein the at least one agent includes at least one sterile or sterilizing agent.

5. The frozen piercing implement of claim 4, wherein the at least one sterilizing agent includes at least one antimicrobial compound.

6. The frozen piercing implement of claim 4, wherein the at least one sterilizing agent includes at least one antiseptic.

7. The frozen piercing implement of claim 1, wherein the at least one agent is included as an outer coating of the frozen piercing implement.

8. The frozen particle composition of claim 1, wherein the at least one agent includes one or more of a prodrug or precursor compound.

9. The frozen piercing implement array of claim 1, wherein the plurality of frozen piercing implements further comprises at least one detection material.

10. The frozen piercing implement of claim 9, wherein the at least one detection material includes at least one of a contrast agent, sensor, or electronic identification device.

11. The frozen piercing implement of claim 10, wherein the at least one electronic identification device includes at least one radio frequency identification device.

12. The frozen piercing implement of claim 9, wherein the at least one detection material includes at least one temperature-sensitive substance.

13. The frozen piercing implement array of claim 1, wherein at least one frozen piercing implement of the plurality includes at least one channel.

14. The frozen piercing implement array of claim 13, wherein at least one surface of the at least one channel is substantially hydrophobic.

15. The frozen piercing implement array of claim 1, wherein the at least one frozen piercing implement includes one or more layers including at least one first layer including at least one vitamin, at least one second layer including at least one anesthetic, and at least one third layer including at least one antibiotic.

16. The frozen piercing implement array of claim 1, wherein at least one frozen piercing implement is configured to melt within the at least one biological tissue.

17. The frozen piercing implement array of claim 1, wherein at least one frozen piercing implement is configured to be substantially removed from the at least one biological tissue.

18. The frozen piercing implement array of claim 1, wherein the plurality of frozen piercing implements is formulated to be administered to the at least one biological tissue.

19. The frozen piercing implement array of claim 1, wherein the at least one biological tissue includes one or more of a plant or animal cell, tissue, or organ.

20. The frozen piercing implement array of claim 1, wherein at least one frozen piercing implement includes at least one sensor.

21. The frozen piercing implement of claim 1, wherein the at least one frozen piercing implement is configured to extract at least one material from the at least one biological tissue.

22. The frozen piercing implement array of claim 1, wherein at least one of the plurality of frozen piercing implements is substantially in the form of at least one blade.

23. The frozen piercing implement of claim 1, wherein the at least one biological tissue includes one or more of a stalk, stem, leaf, root, or tendril of a plant.

24. The frozen piercing implement of claim 1, wherein the at least one biological tissue includes one or more of meristem tissue, plant embryo tissue, cotyledon tissue, shoot apex tissue, scutellum tissue, epicotyl tissue, hypocotyl tissue, stamen tissue, receptacle tissue, anther tissue, stigma tissue, plant ovary tissue, carpel tissue, endosperm tissue, or seed germ tissue.

25. The frozen piercing implement of claim 1, wherein the at least one biological tissue includes at least one tissue from a fruit, vegetable, meat, or grain.

* * * * *